US007655777B2

(12) United States Patent
Bhat et al.

(10) Patent No.: US 7,655,777 B2
(45) Date of Patent: Feb. 2, 2010

(54) NUCLEIC ACID MOLECULES ASSOCIATED WITH THE TOCOPHEROL PATHWAY

(75) Inventors: Barkur G. Bhat, St. Louis, MO (US); Sekhar S. Boddupalli, Manchester, MO (US); Ganesh M. Kishore, Creve Coeur, MO (US); Jingdong Liu, Ballwin, MO (US); Shaukat H. Rangwala, Ballwin, MO (US); Mylavarapu Venkatramesh, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 656 days.

(21) Appl. No.: 11/329,160

(22) Filed: Jan. 11, 2006

(65) Prior Publication Data

US 2007/0143878 A1 Jun. 21, 2007

Related U.S. Application Data

(63) Continuation of application No. 09/267,199, filed on Mar. 12, 1999, now abandoned, which is a continuation-in-part of application No. 09/198,779, filed on Nov. 24, 1998, now abandoned, said application No. 09/267,199 is a continuation-in-part of application No. 09/229,413, filed on Jan. 12, 1999, now abandoned, said application No. 09/267,199 is a continuation-in-part of application No. 09/252,974, filed on Feb. 19, 1999, now abandoned, said application No. 09/267, 199 is a continuation-in-part of application No. 09/262,979, filed on Mar. 4, 1999, now abandoned, said application No. 09/267,199 is a continuation-in-part of application No. 09/233,218, filed on Jan. 20, 1999, now abandoned, which is a continuation-in-part of application No. 09/198,779, filed on Nov. 24, 1998, now abandoned, said application No. 09/198,779, said application No. 09/267,199 is a continuation-in-part of application No. 09/233,218, filed on Jan. 20, 1999, now abandoned, said application No. 09/198,779, said application No. 09/267,199 is a continuation-in-part of application No. 09/227,586, filed on Jan. 8, 1999, now abandoned, said application No. 09/233,218 is a continuation-in-part of application No. 09/227,586, filed on Jan. 8, 1999, now abandoned, said application No. 09/233,218 is a continuation-in-part of application No. 09/229,413, filed on Jan. 12, 1999, now abandoned, said application No. 09/229,413, said application No. 09/267,199 is a continuation-in-part of application No. 09/237,183, filed on Jan. 26, 1999, which is a continuation-in-part of application No. 09/198,779, filed on Nov. 24, 1998, now abandoned, said application No. 09/198,779, said application No. 09/237,183 is a continuation-in-part of application No. 09/233,218, filed on Jan. 20, 1999, now abandoned, which is a continuation-in-part of application No. 09/198,779, filed on Nov. 24, 1998, now abandoned, said application No. 09/233,218 is a continuation-in-part of application No. 09/227,586, filed on Jan. 8, 1999, now abandoned, said application No. 09/233,218 is a continuation-in-part of application No. 09/229,413, filed on Jan. 12, 1999, now abandoned, said application No. 09/229,413.

(60) Provisional application No. 60/067,000, filed on Nov. 24, 1997, provisional application No. 60/066,873, filed on Nov. 25, 1997, provisional application No. 60/069,472, filed on Dec. 9, 1997, provisional application No. 60/074,201, filed on Feb. 10, 1998, provisional application No. 60/074,282, filed on Feb. 10, 1998, provisional application No. 60/074,280, filed on Feb. 10, 1998, provisional application No. 60/074,281, filed on Feb. 10, 1998, provisional application No.

(Continued)

(51) Int. Cl.
*C07H 21/02* (2006.01)
*C12Q 1/66* (2006.01)
(52) U.S. Cl. .......................... 536/23.1; 536/24.1; 435/6
(58) Field of Classification Search ...................... None
See application file for complete search history.

(56) References Cited

U.S. PATENT DOCUMENTS 4,784,949 A 11/1988 Gelfand et al.

(Continued)

FOREIGN PATENT DOCUMENTS

WO    WO-9749816 A1 * 12/1997
WO    WO 00/18922      4/2000

OTHER PUBLICATIONS

Everett et al., Nature Genetics, vol. 17, pp. 411-422, 1997.*
Scott et al., Nature Genetics, vol. 21, pp. 440-443, 1999.*

(Continued)

*Primary Examiner*—Shubo (Joe) Zhou
(74) *Attorney, Agent, or Firm*—Matthew Madsen; Ying-Horng Liu; Arnold & Porter LLP

(57) ABSTRACT

The present invention is in the field of plant biochemistry. More specifically the invention relates to nucleic acid sequences from plant cells, in particular, nucleic acid sequences from maize and soybean associated with the tocopherol synthesis pathway enzymes. The invention encompasses nucleic acid molecules that encode proteins and fragments of proteins. In addition, the invention also encompasses proteins and fragments of proteins so encoded and antibodies capable of binding these proteins or fragments. The invention also relates to methods of using the nucleic acid molecules, proteins and fragments of proteins and antibodies, for example for genome mapping, gene identification and analysis, plant breeding, preparation of constructs for use in plant gene expression and transgenic plants.

6 Claims, No Drawings

Related U.S. Application Data

60/074,566, filed on Feb. 12, 1998, provisional application No. 60/074,567, filed on Feb. 12, 1998, provisional application No. 60/074,565, filed on Feb. 12, 1998, provisional application No. 60/074,789, filed on Feb. 19, 1998, provisional application No. 60/075,459, filed on Feb. 19, 1998, provisional application No. 60/075,460, filed on Feb. 19, 1998, provisional application No. 60/092,036, filed on Jul. 8, 1998, provisional application No. 60/071,479, filed on Jan. 13, 1998, provisional application No. 60/085,533, filed on May 15, 1998, provisional application No. 60/089,806, filed on Jun. 18, 1998, provisional application No. 60/089,807, filed on Jun. 18, 1998, provisional application No. 60/089,811, filed on Jun. 18, 1998, provisional application No. 60/089,808, filed on Jun. 18, 1998, provisional application No. 60/089,812, filed on Jun. 18, 1998, provisional application No. 60/089,813, filed on Jun. 18, 1998, provisional application No. 60/091,247, filed on Jun. 30, 1998, provisional application No. 60/091,405, filed on Jun. 30, 1998, provisional application No. 60/099,697, filed on Sep. 9, 1998, provisional application No. 60/100,963, filed on Sep. 17, 1998, provisional application No. 60/101,343, filed on Sep. 22, 1998, provisional application No. 60/101,344, filed on Sep. 22, 1998, provisional application No. 60/101,347, filed on Sep. 22, 1998, provisional application No. 60/101,508, filed on Sep. 22, 1998, provisional application No. 60/101,707, filed on Sep. 25, 1998, provisional application No. 60/104,124, filed on Oct. 13, 1998, provisional application No. 60/104,126, filed on Oct. 13, 1998, provisional application No. 60/104,127, filed on Oct. 13, 1998, provisional application No. 60/104,128, filed on Oct. 13, 1998, provisional application No. 60/111,981, filed on Dec. 11, 1998, provisional application No. 60/076,709, filed on Jun. 9, 1998, provisional application No. 60/084,684, filed on May 8, 1998, provisional application No. 60/076,912, filed on Mar. 6, 1998, provisional application No. 60/075,461, filed on Feb. 19, 1998, provisional application No. 60/075,462, filed on Feb. 19, 1998, provisional application No. 60/075,463, filed on Feb. 19, 1998, provisional application No. 60/075,464, filed on Feb. 19, 1998, provisional application No. 60/077,229, filed on Mar. 9, 1998, provisional application No. 60/077,230, filed on Mar. 9, 1998, provisional application No. 60/077,231, filed on Mar. 9, 1998, provisional application No. 60/078,031, filed on Mar. 16, 1998, provisional application No. 60/078,368, filed on Mar. 18, 1998, provisional application No. 60/080,844, filed on Apr. 7, 1998, provisional application No. 60/083,386, filed on Apr. 29, 1998, provisional application No. 60/083,387, filed on Apr. 29, 1998, provisional application No. 60/083,388, filed on Apr. 29, 1998, provisional application No. 60/083,389, filed on Apr. 29, 1998, provisional application No. 60/084,684, filed on May 8, 1998, provisional application No. 60/085,245, filed on May 13, 1998, provisional application No. 60/085,224, filed on May 13, 1998, provisional application No. 60/085,223, filed on May 13, 1998, provisional application No. 60/085,222, filed on May 13, 1998, provisional application No. 60/086,186, filed on May 21, 1998, provisional application No. 60/086,339, filed on May 21, 1998, provisional application No. 60/086,187, filed on May 21, 1998, provisional application No. 60/086,185, filed on May 21, 1998, provisional application No. 60/086,184, filed on May 21, 1998, provisional application No. 60/086,183, filed on May 21, 1998, provisional application No. 60/086,188, filed on May 21, 1998, provisional application No. 60/089,524, filed on Jun. 16, 1998, provisional application No. 60/089,810, filed on Jun. 18, 1998, provisional application No. 60/089,814, filed on Jun. 18, 1998, provisional application No. 60/099,667, filed on Sep. 9, 1998, provisional application No. 60/100,674, filed on Sep. 16, 1998, provisional application No. 60/100,673, filed on Sep. 16, 1998, provisional application No. 60/100,672, filed on Sep. 16, 1998, provisional application No. 60/101,132, filed on Sep. 21, 1998, provisional application No. 60/101,130, filed on Sep. 21, 1998, provisional application No. 60/108,996, filed on Nov. 18, 1998, provisional application No. 60/109,018, filed on Nov. 19, 1998, provisional application No. 60/071,064, filed on Jan. 9, 1998, provisional application No. 60/090,170, filed on Jun. 22, 1998, provisional application No. 60/083,067, filed on Apr. 27, 1998, provisional application No. 60/072,027, filed on Jan. 21, 1998, provisional application No. 60/072,888, filed on Jan. 27, 1998, provisional application No. 60/083,390, filed on Apr. 29, 1998, provisional application No. 60/085,057, filed on May 12, 1998, provisional application No. 60/085,429, filed on May 14, 1998, provisional application No. 60/085,940, filed on May 19, 1998, provisional application No. 60/086,594, filed on May 22, 1998, provisional application No. 60/086,608, filed on May 22, 1998, provisional application No. 60/087,422, filed on Jun. 1, 1998, provisional application No. 60/087,631, filed on Jun. 2, 1998, provisional application No. 60/087,762, filed on Jun. 2, 1998, provisional application No. 60/087,972, filed on Jun. 4, 1998, provisional application No. 60/087,973, filed on Jun. 4, 1998, provisional application No. 60/088,441, filed on Jun. 8, 1998, provisional application No. 60/089,627, filed on Jun. 16, 1998, provisional application No. 60/089,789, filed on Jun. 18, 1998, provisional application No. 60/090,856, filed on Jun. 26, 1998, provisional application No. 60/090,928, filed on Jun. 26, 1998, provisional application No. 60/090,035, filed on Jun. 29, 1998, provisional application No. 60/110,108, filed on Nov. 25, 1998, provisional application No. 60/110,109, filed on Nov. 25, 1998, provisional application No. 60/111,033, filed on Dec. 4, 1998, provisional application No. 60/111,742, filed on Dec. 10, 1998.

(56) References Cited

U.S. PATENT DOCUMENTS

| | | | |
|---|---|---|---|
| 4,956,282 | A | 9/1990 | Goodman et al. |
| 5,011,912 | A | 4/1991 | Hopp et al. |
| 6,093,545 | A | 7/2000 | Goodearl et al. |
| 2003/0066102 | A1* | 4/2003 | Maxwell et al. ............. 800/278 |

OTHER PUBLICATIONS

Database sequence, GenBank Accession No. AJ000693 (GI: 2695709), Dec. 16, 1997.*

IUBMB Enzyme Nomenclature for enzyme EC 1.13.11.27, retrieved from the internet at http://www.chem.qmul.ac.uk/iubmb/enzyme/EC1/13/11/27.html on Nov. 16, 2006.*

U.S. Appl. No. 09/815,254, Boukharov et al., filed Mar. 23, 2001.
U.S. Appl. No. 10/425,114, Liu et al., filed Mar. 28, 2003.
U.S. Appl. No. 11/329,175, CaJacob et al., filed Jan. 11, 2006.
U.S. Appl. No. 11/329,388, Andersen et al., filed Jan. 11, 2006.
U.S. Appl. No. 11/330,082, Buehler et al., filed Jan. 12, 2006.
U.S. Appl. No. 11/330,083, Byrum et al., filed Jan. 12, 2006.
U.S. Appl. No. 11/330,364, Abad et al., filed Jan. 12, 2006.
U.S. Appl. No. 11/331,019, Fincher et al., filed Jan. 13, 2006.
U.S. Appl. No. 11/331,032, Fincher et al., filed Jan. 13, 2006.
U.S. Appl. No. 11/352,295, Andersen et al., filed Feb. 13, 2006.
U.S. Appl. No. 11/353,150, Andersen et al., filed Feb. 14, 2006.
U.S. Appl. No. 11/486,299, Byrum, filed Jul. 14, 2006.
U.S. Appl. No. 11/490,207, Brown et al., filed Jul. 21, 2006.
U.S. Appl. No. 11/491,125, Boukharov et al., filed Jul. 24, 2006.
U.S. Appl. No. 11/491,178, Hinkle et al., filed Jul. 24, 2006.
U.S. Appl. No. 11/491,371, Byrum, filed Jul. 24, 2006.
U.S. Appl. No. 11/497,489, Byrum et al., filed Aug. 2, 2006.
U.S. Appl. No. 11/503,243, Kovalic et al., filed Aug. 14, 2006.
U.S. Appl. No. 11/520,715, Liu et al., filed Sep. 14, 2006.
U.S. Appl. No. 11/521,349, Byrum et al., filed Sep. 15, 2006.
U.S. Appl. No. 11/595,983, Boukharov et al., filed Nov. 13, 2006.
AA501409, EST Database (Aug. 19, 1997).
Aach et al., "*ent*-Kaurene Biosynthesis in a Cell-Free System From Wheat (*Triticum aestivum* L.) Seedlings and the Localisation of *ent*-Kaurene Synthetase in Plastids of Three Species", *Planta* 197(2), 333-342 (1995).
Adams et al., "Complementary DNA Sequencing: Expressed Sequence Tags and Human Genome Project", *Science* 252(5013), 1651-1656 (1991).
Ait-Ali et al., "The *LS* Locus of Pea Encodes the Gibberellin Biosynthesis Enzyme *ent*-Kaurene Synthase A", *Plant J.* 11(3), 443-454 (1997).
Anaviev et al., "Oat-Maize Chromosome Addition Lines: A New System for Mapping the Maize Genome", *Proc. Natl. Acad. Sci. USA* 94, 3524-3529 (1997).
Anton et al., "Sequencing and Overexpression of the *Escherichia coli aroE* Gene Encoding Shikimate Dehydrogenase", *Biochem. J.* 249, 319-326 (1988).
Attwood, "The Babel of Bioinoformatics", *Science* 290(5491), 471-473 (2000).
Bentley, "The Shikimate Pathway—A Metabolic Tree with Many Branches," *Critical Rev. Biochem. Mol. Biol.* 25(5), 307-384 (1990).
Birkenbihl et al., "Cosmid-Derived Map of *E.coli* Strain BHE2600 in Comparison to the Map of Strain W3110", *Nucleic Acids Res.* 17(13), 5057-5069 (1989).
Bishop et al., "The Tomato *Dwarf* Gene Isolated by Heterologous Transposon Tagging Encodes the First Member of a New Cytochrome P450 Family", *Plant Cell* 8, 959-969 (1996).
Bonner et al., "Cloning of cDNA Encoding the Bifunctional Dehydroquinase-Shikimate Dehydrogenease of Aromatic-Amino-Acid Biosynthesis in *Nicotiana tabacum*", *Biochem J.* 362, 11-14 (1994).
Bork, "Powers and Pitfalls in Sequence Analysis: The 70% Hurdle", *Genome Res.*, 10, 398-400 (2000).
Bougri et al., "Members of a Low-Copy Number Gene Family Encoding Glutamyl-tRNA Reductase are Differentially Expressed in Barley," *Plant J.* 9(6), 867-878 (1996).
Broun et al., "Catalytic Plasticity of Fatty Acid Modification Enzymes Underlying Chemical Diversity of Plant Lipids", *Science* 282, 1315-1317 (1998).
Bukanov et al., "Ordered Cosmid Library and High-Resolution Physical-Genetic Aap of *Helicobacter pylori* Strain NCTC11638", *Mol. Microbiol.* 11(3), 509-523 (1994).
Charles et al., "Isolation, Characterization and Nucleotide Sequences of the *aroC* Genes encoding Chorismate Synthase from *Salmonella typhi* and *Escherichia coli*", *J. Gen. Microbiol.* 136, 353-358 (1990).
Chen et al., "Microcolinearity in *sh2*-Homologous Regions of the Maize, Rice, and Sorghum Genomes", *Proc. Natl. Acad. Sci. USA* 94, 3431-3435 (1997).
Coulson et al., "Toward a Physical Map of the Genome of the Nematode *Caenorhabditis elegans*", *Proc. Natl. Acad. Sci. USA* 83, 7821-7825 (1986).

Day et al., "Cloning of the cDNA for Glutamyl-tRNA Synthetase from *Arabidopsis thaliana*", *Biochim. Biophys. Acta* 1399(2-3):219-224 (1998).
Duncan et al., "The Overexpression and Complete Amino Acid Sequence of *Escherichia coli* 3-Dehydroquinase", *Biochem. J.* 238, 475-483 (1986).
Eberhard et al., "Cloning and Expression in Yeast of a Higher Plant Chorismate Mutase", *FEBS Lett.* 334(2), 233-236 (1993).
Ebert et al., "Identification of an Essential Upstream Element in the Nopaline Synthase Promoter by Stable and Transient Assays", *Proc. Natl. Acad. Sci. USA* 84(16), 5745-5749 (1987).
Efstratiadis et al., "Enzymatic in Vitro Synthesis of Globin Genes", *Cell* 7, 279-288 (1976).
Eiglmeier et al., "Use of an Ordered Cosmid Library to Deduce the Genomic Organization of *Mycobacterium leprae*", *Mol. Microbiol.* 7(2), 197-206 (1993).
Evans et al., "Immunodetection of Recombinant Proteins Based on Antibodies Directed Against a Metal Binding Peptide Engineered for Purification by Immobilized Metal Affinity Chromatography," *J. Immunol. Meth.* 156(2), 231-238 (1992) (Abstract Only).
Entrez Accession No. M21071 J03227 (Sep. 15, 1989).
Entrez Accession No. 170374 (Sep. 15, 1989).
Entrez Accession No. M27715 (Jun. 15, 1990).
Entrez Accession No. 153878 (Jun. 15, 1990).
Entrez Accession No. X59509 S55160 (Jun. 30, 1993).
Entrez Accession No. 48906 (Jun. 30, 1993).
Entrez Accession No. Y00710 (Sep. 12, 1993).
Entrez Accession No. 40978 (Sep. 12, 1993).
Entrez Accession No. Z26519 (Dec. 2, 1993).
Entrez Accession No. 429153 (Dec. 2, 1993).
Entrez Accession No. 551666 (Jan. 25, 1995).
Entrez Accession No. X81413 (Jan. 25, 1995).
Entrez Accession No. M87280 M99707 (Apr. 12, 1995).
Entrez Accession No. 551855 (Apr. 12, 1995).
Entrez Accession No. 313150 (Jun. 13, 1995).
Entrez Accession No. X73535 (Jun. 13, 1995).
Entrez Accession No. X04306 (Jul. 12, 1995).
Entrez Accession No. 40973 (Jul. 12, 1995).
Entrez Accession No. D63474 D16312 (Jul. 27, 1995).
Entrez Accession No. 474964 (Jul. 27, 1995).
Entrez Accession No. 987267 (Jul. 31, 1995).
Entrez Accession No. U32579 (Sep. 16, 1995).
Entrez Accession No. X82831 (Mar. 1, 1996).
Entrez Accession No. 1213067 (Mar. 1, 1996).
Entrez Accession No. 1220402 (Mar. 5, 1996).
Entrez Accession No. M63245 (Mar. 11, 1996).
Entrez Accession No. W49458 (May 28, 1996).
Entrez Accession No. 1421741 (Oct. 17, 1996).
Entrez Accession No. U54770 (Oct. 18, 1996).
Entrez Accession No. X86101 (Nov. 8, 1996).
Entrez Accession No. 520943 (Feb. 26, 1997).
Entrez Accession No. 2160544 (Jun. 5, 1997).
Entrez Accession No. U63652 (Jun. 6, 1997).
Entrez Accession No. 2257714 (Jul. 15, 1997).
Entrez Accession No. U93215 (Jul. 15, 1997).
Entrez Accession No. 2224890 (Jul. 31, 1997).
Entrez Accession No. 2224892 (Jul. 31, 1997).
Entrez Accession No. U61385 (Aug. 1, 1997).
Entrez Accession No. U61386 (Aug. 1, 1997).
Entez Accession No. 2316104 (Aug. 8, 1997).
Entrez Accession No. AF010169 (Aug. 9, 1997).
Entrez Accession No. 1524045 (Aug. 20, 1997).
Entrez Accession No. X96943 (Aug. 20, 1997).
Entrez Accession No. Y12809 (Dec. 2, 1997).
Entrez Accession No. D88382 (Mar. 17, 1998).
Entrez Accession No. 3068709 (Apr. 2, 1998).
Entrez Accession No. AF058763 (Aug. 16, 1998).
Entrez Accession No. 3420233 (Apr. 20, 1998).
Entrez Accession No. AF049236 (Apr. 22, 1998).
Entrez Accession No. AF038152 (May 7, 1998).
Entrez Accession No. 2708690 (May 7, 1998).
Entrez Accession No. AC003058 (May 16, 1998).
Entrez Accession No. 3135277 (May 16, 1998).

Entrez Accession No. 3288821 (Jul. 20, 1998).
Entrez Accession No. AF063901 (Jul. 21, 1998).
Entrez Accession No. 3435196 (Sep. 21, 1998).
Entrez Accession No. AF067773 (Sep. 22, 1998).
Entrez Accession No. 3694811 (Sep. 24, 1998).
Entrez Accession No. AJ225107 (Oct. 1, 1998).
Entrez Accession No. 3093410 (Oct. 1, 1998).
Entrez Accession No. AF060481 (Oct. 4, 1998).
Entrez Accession No. 3925407 (Nov. 24, 1998).
Entrez Accession No. AF083948 (Nov. 25, 1998).
Entrez Accession No. AB015492 (Dec. 11, 1998).
Entrez Accession No. 4001680 (Dec. 11, 1998).
Entrez Accession No. AF017431 (Jan. 2, 1999).
Entrez Accession No. 3080490 (Jan. 12, 1999).
Entrez Accession No. AL022602 (Jan. 12, 1999).
Entrez Accession No. AB011416 (Feb. 5, 1999).
Entrez Accession No. AAC17095 GI:315616 (Apr. 5, 1999).
Entrez Accession No. AP000836; GI:6539551 (Aug. 12, 2000).
Entrez Accession No. AY013245 (May 7, 2002).
Fiedler et al., "The Formation of Homogentisate in the Biosynthesis of Tocopherol and Plastoquinone in Spinach Chloroplasts", *Planta* 155, 511-515 (1982).
Garbe et al., "The *Mycobacterium tuberculosis* Shikimate Pathway Genes: Evolutionary Relationship Between Biosynthetic and Catabolic 3-Dehydroquinases", *Mol. Gen. Genet.* 228, 385-392 (1991).
Gasser et al., "Structure, Expression, and Evolution of the 5-Enolpyruvylshikimate-3-Phosphate Synthase Genes of Petunia and Tomato", *J. Biol. Chem.* 263, 4280-4289 (1988).
Gaubier et al., "A Chlorophyll Synthetase Gene from *Arabidopsis thaliana*", *Mol. Gen. Genet.* 249, 58-64 (1995).
GenBank Accession No. U03774 (Jun. 22, 1994).
GenBank Accession No. L37750 (Aug. 3, 1995).
GenBank Accession No. H30177 (Aug. 16, 1995).
GenBank Accession No. W21756 (May 6, 1996).
GenBank Accession No. X80265 (Feb. 26, 1997).
GenBank Accession No. E03435 (Sep. 29, 1997).
GenBank Accession No. AF015462 (Jul. 16, 1998).
Genbank Accession No. AC005922 (Nov. 14, 1998).
GenBank Accession No. X74737 (Jan. 21, 1999).
GenBank Accession No. AU033328 (Apr. 28, 1999).
GenBank Accession No. AQ402486 (Mar. 13, 1999).
GenBank Accession No. AI861202 (Jul. 19, 1999).
GenBank Accession No. AC018632 (Dec. 15, 1999).
GenBank Accession No. AI834598 (Feb. 2, 2000).
GenBank Accession No. AZ134591 (Jun. 2, 2000).
GenBank Accession No. BE428765 (Jul. 26, 2000).
GenBank Accession No. BF542512 (Dec. 11, 2000).
GenBank Accession No. AW871780 (Dec. 11, 2001).
GenBank Accession No. BQ603510 (Jun. 24, 2002).
GenBank Accession No. DR37H4T (Nov. 22, 2002).
GenBank Accession No. BX513761 (May 27, 2003).
GenEMBL Accession No. AF096555 (Jul. 22, 1999).
GenEMBL Accession No. AL096768 (Dec. 12, 1999).
GenSeq Accession No. AAZ35275 (Mar. 27, 2000).
Gerhold et al., "It's the genes! EST access to human genome content", *BioEssays* 18(2), 973-981 (1996).
Gibson et al., "The Bacteriochlorophyll Biosynthesis Gene, *bchM*, of *Rhodobacter sphaeroides* Encodes S-Adenosyl-1-Methionine: Mg Protoporphyrin IX Methyltransferase", *FEBS Lett.* 352, 127-130 (1994).
Goers et al., "The Differential Allosteric Regulation of Two Chorismate-Mutase Isoenzymes of *Nicotiana silvestris*", *Planta* 162, 117-124 (1984).
Goff, "Rice as a Model for Cereal Genomics", *Curr. Opin. Plant Biol.* 2, 86-89 (1999).
Hedden et al., "Gibberellin Biosynthesis: Enzymes, Genes and Their Regulation", *Annu. Rev. Plant Physiol. Plant Mol. Biol.* 48, 431-460 (1997).
Herrmann, "The Shikimate Pathway as an Entry to Aromatic Secondary Metabolism," *Plant Physiol.* 107, 7-12 (1995).
Hong, "A Rapid and Accurate Strategy for Rice Contig Map Construction by Combination of Fingerprinting and Hybridization", *Plant Mol. Biol.* 35,129-133 (1997).

Hundle et al., "Functional Assignment of *Erwinia herbicola* Eho10 Carotenoid Genes Expressed in *Escherichia coli*", *Mol. Gen. Genet.* 245, 406-416 (1994).
Ibba, "Biochemistry and Bioinformatics: When Worlds Collide," *Trends in Biochem. Sci.* 27(2), 64 (2000).
Iyer et al.,"*Quod erat demonstrandum*? The Mystery of Experimental Validation of Apparently Erroneous Computational Analysis of Protein Aequences", *Genome Biol.* 2(12), 1-11 (2001).
Johnston et al., "Cloning and Characterization of Potato cDNAs Involved in Tetrapyrrole Biosynthesis: Ferrochelatase (Accession No. AJ005802), Chloroplatic Protoporphyrinogen IX Oxidase (Accession No. AJ225107), and Mitochondrial Protoporphyrinogen IX Oxidase (Accession No. AJ225108)", *Plant Physiol.* 118, 329-331 (1998).
Keon et al., "Isolation and Heterologous Expression of a Gene Encoding 4-Hydroxyphenylpyruvate Dioxygenase from the Wheat Leaf-Spot Pathogen, *Mycosphaerella graminicola*", *FEMS Microbiol. Lett.* 161, 337-343 (1998).
Kidwell et al., "Transposable Elements as Sources of Variation in Animals and Plants", *Proc. Natl. Acad. Sci. USA* 94, 7704-7711(1997).
Kim et al., "Construction and Characterization of a Human Bacterial Artificial Chromosome Library", *Genomics* 34, 213-218 (1996).
Knott et al., "Randomly Picked Cosmid Clones Overlap the *pyr*B and *ori*C gap in the Physical Map of the *E.coli* Chromosome", *Nucleic Acids Res.* 16, 2601-2612 (1988).
Ko et al, "An 'Equalized cDNA' Library by the Reassociation of Short Double-Stranded cDNAs", *Nucleic Acids Res.* 18(19), 5705-5711 (1990).
Kyrpides et al., "Whole-Genome Sequence Annotation: 'Going Wrong With Confidence'", *Mol. Microbiol.* 32, 886-887 (1999).
Kurata et al., "A 300 Kilobase Interval Genetic Map of Rice Including 883 Expressed Sequences," *Nature Gen.* 8(4), 362-372 (1994).
Lange et al., "Cloning and Expression of a Gibberellin 2β,3β-Hydroxylase cDNA from Pumpkin Endosperm," *Plant Cell* 9(8), 1459-1467 (1997).
Lange "Cloning Gibberellin Dioxygenase Genes from Pumpkin Endosperm by Heterologous Expression of Enzyme Activities in *Escherichia coli*", *Proc. Natl. Acad. Sci. USA* 94(12), 6553-6558 (1997).
Lange et al., "Expression Cloning of a Gibberellin 20-Oxidase, a Multifunctional Enzyme Involved in Gibberellin Biosynthesis", *Proc. Natl. Acad. Sci. USA* 91(18), 8552-8556 (1994).
Liepman et al., "Sequence Analysis of a cDNA Encoding Alanine:Glyoxylate Amino Transferase from *Arabidopsis* (Accession No. AF063901) ", *Plant Physiol.* 117, 1125-1127 (1998).
Lim et al., "Porphobilinogen Deaminase is Encoded by a Single Gene in *Arabidopsis thaliana* and Is Targeted to the Chloroplasts," *Plant Mol. Biol.* 26, 863-872 (1994).
Mahairas et al., "Sequence-Tagged Connectors: A Sequence Approach to Mapping and Scanning the Human Genome", *Proc. Natl. Acad. Sci. USA* 96, 9739-9744 (1999).
Martin et al., "MYB Transcription Factors in Plants", *Trends Genet.* 13(2), 67-73 (1997).
Martin et al., "Mendel's Dwarfing Gene: cDNAs from the *Le* Alleles and Function of the Expressed Proteins", *Proc. Natl. Acad. Sci. USA*, 94(16):8907-8911 (1997).
McCombie et al.,"*Caenorhabditis elegans* Expressed Sequence Tags Identify Gene Families and Disease Gene Homologues," *Nature Gen.* 1, 124-131 (1992).
Meinkoth et al., "Hybridization of Nucleic Acids Immobilized on Solid Supports", *Anal. Biochem.* 138, 267-284 (1984).
Mende et al., "The Geranylgeranyl Diphosphate Synthase Gene of *Gibberella fujikuroi*: Isolation and Expression", *Mol. Gen. Genet.* 255(1), 96-105 (1997).
Mohan et al., "Genome Mapping, Molecular Markers and Marker-Assisted Selection Crop Plants", *Mol. Breed.* 3, 87-103 (1997).
Nakane et al., "Nucleotide Sequence of the Shikimate Kinase Gene (*aro*I) of *Bacillus subtilis*", *J. Ferment. Bioeng.* 77, 312-314 (1994).
Nakayashiki et al., "Nucleotide Sequence of a cDNA Clone Encoding Glutamyl-tRNA Reductase from Rice (Accession No. AB011416)", *Plant Physiol.* 117, 332 (1998).
NCBI Accession No. S42508 (May 8, 1993).

NCBI Accession No. D23883 (Nov. 29, 1993).
NCBI Accession No. AAA34069, corresponding to gi:535771 (Sep. 11, 1994).
Norris et al., "Complementation of the *Arabidopsis pds* I Mutation with the Gene Encoding *p*-Hydroxyphenylpuruvate Dioxygenase", *Plant Physiol.* 117, 1317-1323 (1998).
Oka et al., "Replication Origin of the *Escherichia coli* K-12 Chromosome: The Size and Structure of the Minimum DNA Segment Carrying the Information for Autonomous Replication", *Mol. Gen. Genet.* 178(1), 9-20 (1980).
Okubo et al., "Large Scale cDNA Sequencing for Analysis of Quantitative and Qualitative Aspects of Gene Expression", *Nature Gen.* 2, 173-179 (1992).
Phillips et al., "Isolation and Expression of Three Gibberellin 20-Oxidase cDNA Clones from *Arabidopsis*", *Plant Physiol.* 108(3), 1049-1057 (1995).
Porra, "Recent Progress in Porphyrin and Chlorophyll Biosynthesis", *Photochem. Photobiol.* 65(3), 492-516 (1997).
Russell et al., "Structural Features can be Unconserved in Proteins with Similar Folds. An Analysis of Side-Chain to Side-Chain Contacts Secondary Structure and Accessibility", *J. Mol. Biol.* 244, 332-350 (1994).
Sakamoto et al., "An Overview of Gibberellin Metabolism Enzyme Genes and Their Related Mutants in Rice", *Plant Physiol.* 134, 1642-1653 (2004).
Schmitz et al., "The Tomato *Blind* Gene Encodes a MYB Transcription Factor that Controls the Formation of Lateral Meristems", *Proc. Nat. Acad. Sci.* 99(2), 1064-1069 (2002).
Schünmann et al., "Identification of Three cDNA Clones Expressed in the Leaf Extension Zone and with Altered Patterns of Expression in the *Slender* Mutant of Barley: A Tonoplast Intrinsic Protein, a Putative Structural Protein and Protochlorophylide Oxidoreductase," *Plant Mol. Biol.* 31, 529-537 (1996).
Seffernick et al., "Melamine Deaminase and Atrazine Chlorohydrolase: 98 Percent Identical but Functionally Different", *J. Bacteriol.* 183(8), 2405-2410 (2001).
SIGMA Chemical Catalogue (Sigma Chemical Co.; P.O. Box 14508, St. Louis MO 63178) 1993, product Nos. 01256, 03628, 04375, pp. 736-737.
Smith et al., "Partial Purification and Characterization of the Gibberellin $A_{20}$ 3β-Hydroxylase from Seeds of *Phaseolus vulgaris*", *Plant Physiol.* 94:1390-1401 (1990).
Smith et al., "The First Step of Gibberellin Biosynthesis in Pumpkin is Catalyzed by at Least Two Copalyl Diphosphate Synthases Encoded by Differentially Regulated Genes", *Plant Physiol.* 118, 1411-1419 (1998).
Stammers et al., "Rapid Purification and Characterization of HIV-1 Reverse Transcriptase and RNaseH Engineered to Incorporate a C-terminal Tripeptide α-Tubulin Epitope", *FEBS Lett.* 283(2), 298-302 (1991).

Tanaka et al., "The Third Member of the *hemA* gene Family Encoding Glutamyl-tRNA Reductase is Primarily Expressed in Roots in *Hordeum vulgare*", *Photosynthesis Res.* 53, 161-171 (1997).
Tanksley et al., "Chromosome landing: a paradigm for map-based gene cloning in plants with large genomes", *Trends in Genet.* 11(2), 63-68 (1995).
Tikhonov et al., "Colinearity and its Exceptions in Orthologous *adh* Regions of Maize and Sorghum", *Proc. Natl. Acad. Sci. USA* 96, 7409-7414 (1999).
van de Loo et al., "An Oleate 12-Hydroxylase from *Ricirus communis* L. is a Fatty Acyl Desaturase Homolog", *Proc. Nat. Acad. Sci.* 92, 6743-6747 (1995).
Venter et al., "A New Strategy for Genome Sequencing", *Nature* 381, 364-366 (1996).
Venter et al., "The Sequence of the Human Genome" *Science* 291, 1304-1351 (2001).
Wang et al., "Construction of a Rice Bacterial Artificial Chromosome Library and Identification of Clones Linked to the Xa-21 Disease Resistance Locus", *Plant J.* 7(3), 525-533 (1995).
Wells et al., "The Chemokine Information Source: Identification and Characterization of Novel Chemokines Using the WorldWideWeb and Expressed Sequence Tag Databases", *J. Leukocyte Biol.* 61(5), 545-550 (1997).
Wendel et al., "New Isozyme Systems for Maize (*Zea mays* L.): Aconitate Hydratase, Adenylate Kinase, NADH Dehydrogenase, and Shikimate Dehydrogenase", *Biochem. Genet.* 26(5-6), 421-446 (1988) (Abstract Only).
Wenzel et al., "Physical mapping of the *Mycoplasma pneumoniae* genome", *Nucleic Acids Res.* 16(17), 8323-8336 (1988).
Winkler et al., "The Maize *Dwarf3* Gene Encodes a Cytochrome P450-Mediated Early Step in Gibberellin Biosynthesis", *Plant Cell* 7(8), 1307-1317 (1995).
Woese et al., "Conservation of Primary Structure in 16S Ribosomal RNA", *Nature* 254, 83-85 (1975).
Yomo et al., "Histochemical Studies on Protease Formation in the Cotyledons of Germinating Bean Seeds," *Planta* 112(1), 35-43 (1973).
Zhang et al., "Physical Mapping of the Rice Genome with BACs", *Plant Mol. Biol.* 35, 115-127 (1997).
Zhang et al., "Construction and Characterization of Two Rice Bacterial Artificial Chromosome Libraries from the Parents of a Permanent Recombinant Inbred Mapping Population", *Mol. Breeding* 2, 11-24 (1996).
Zwick et al., "Physical Mapping of the *liguleless* Linkage Group in *Sorghum bicolor* Using Rice RFLP-Selected Sorghum BACs", *Genetics* 248, 1983-1992 (1998).
Benson et al., "Cloning and Characterization of the Maize An1 Gene," *Plant Cell*, 7:75-84 (Jan. 1995).
Written Description Training Material, Example 7, pp. 30-32 (Dec. 21, 1999).

\* cited by examiner

SEQUENCE LISTING

<160> NUMBER OF SEQ ID NOS: 627

<210> SEQ ID NO 1
<211> LENGTH: 252
<212> TYPE: DNA
<213> ORGANISM: Zea mays

<400> SEQUENCE: 1

```
ggagttcaac gccaacaaca tcagggacac cttccgcgtc ctcctgcaaa tgtccgttgt      60
gctcatgttc ggaggccaga tgcctgtcgt caaggtggga agaatggcag gtcagtttgc     120
gaaccaaggt cagatggttt tgaggagcgg gatggattga agttgccaag ctatagaggg     180
gacaatatca atggggatgc attcaatggg gagtcaaggt tgccagatcc acaccgcatg     240
ataagggcgt ac                                                         252
```

<210> SEQ ID NO 2
<211> LENGTH: 123

```
<212> TYPE: DNA
<213> ORGANISM: Zea mays

<400> SEQUENCE: 2
ttctggacag attgtcacat ggattacaga tcgtatgcat ggaaacacca tcaaggcccc    60
ttgtggcctg aagacgcgtc catttgactc cattctggct gaagtgcgtg cctgcttcga   120
tgt                                                                 123

<210> SEQ ID NO 3
<211> LENGTH: 287
<212> TYPE: DNA
<213> ORGANISM: Zea mays

<400> SEQUENCE: 3
gtcaagcaac gtcaccttcg acaacctgag agaccgctac cacacgcaat gcgaccccag    60
gctgaacgcg tcccagtccc tggagctcgc cttcatactc gccgagaagc ttaggaagcg   120
gaggatgcgg cggtcgtcgg tggcgtctgg gctcggcggc agcatcttgc ccttgccgcc   180
ctttggcttt tgatgtcttg cacgctggct gtgtgcatgc agggtgcagt gcaggggtgt   240
ggtaggagaa tcttacgttg tcgtttgcct tgctatgtag tatgtaa                 287

<210> SEQ ID NO 4
<211> LENGTH: 268
<212> TYPE: DNA
<213> ORGANISM: Zea mays

<400> SEQUENCE: 4
cggtgacctt cgatgatctg gggtcacgct accacacgca ctgcgaccca aggctcaatg    60
cctcacagtc tctggagatg gcatttaaca tcgccgagcg ccttaggaaa aggaggatgg   120
cctcgtcgcc tttgtacacg aaccagctgg gttccattcc atcaatgggt caaaaagcac   180
aactaggttc actgtcaagg actagtcctt gggttttgtt tcagctgctg tgtcaaactt   240
tgctggcatg cactggtaaa ctagatag                                      268

<210> SEQ ID NO 5
<211> LENGTH: 341
<212> TYPE: DNA
<213> ORGANISM: Zea mays

<400> SEQUENCE: 5
ctgacttctg gacctcacac gagtgccttc tcttacccta cgagcagtct cttacccgta    60
aagactccac cagtggcctt ttctacgatt gttcggccca catgctgtgg gttggtgagc   120
gcactcgtca actcgatgga gcgcatgttg aattccttcg tggtgttgcc aatcctcttg   180
gcataaaggt gagcgacaaa atgaacccca gtgacttggt gaagctgatt gagattctga   240
acccttcaaa caaacctgga aggatcacca taattacaag gatgggggca gagaacatga   300
gagtgaagtt gcctcatctc atccgtgctg ttcgcaatgc t                       341

<210> SEQ ID NO 6
<211> LENGTH: 299
<212> TYPE: DNA
<213> ORGANISM: Zea mays

<400> SEQUENCE: 6
agcaagtggc ctttctatg attgttcggc ccacatgttg tgggttggtg agcgcactcg    60
acaactcgat ggagctcatg ttgaattcct ccgtggtgtt gccaaccctc tgggcataaa   120
```

```
ggtgagcgac aaaatgaacc ccagtgagtt ggtgaagctg attgatattc tgaacccttc    180
aaacaaacct ggaaggatca ccataattac aaggatgggg cagagaaca tgagggtgaa    240 gttgcctcat ctcatccgtg ctgttcgcaa tgctggactg attgtcacat ggattactg    299

<210> SEQ ID NO 7
<211> LENGTH: 269
<212> TYPE: DNA
<213> ORGANISM: Zea mays

<400> SEQUENCE: 7
ggtgagcgca ctcgtcaact cgatggagcg catgttgaat ccttcgtgg tgttgccaat     60 cctcttggca taaaggtgag cgacaaaatg aaccccagtg acttggtgaa gctgattgag    120
attctgaacc cttcaaacaa acctggaagg atcaccataa ttacaaggat gggggcagag    180
aacatggagt gaagttgcct catctcatcc gtgctgttcg caatgctgga ttaattgtca    240
catggattac tgatcctatg catggaaac                                      269

<210> SEQ ID NO 8
<211> LENGTH: 310
<212> TYPE: DNA
<213> ORGANISM: Zea mays

<400> SEQUENCE: 8
gggcttacag ttgaccaccc gataatgacg actactgact tctggacctc acacgagtgc     60
cttctcttac cctacgagca gtctcttacc cgtaaagact ccaccagtgg ccttttctac    120
gattgttcgg cccacatgct gtgggttggt gagcgcactc gtcaactcga tggagcgcat    180
gttgaattcc ttcgtggtgt tgccaatcct cttggcataa agtgagcgac aaaatgaacc    240
ccagtgactt ggtgaagctg attgagattc tgaacccttc aacaaacct ggaaggatca    300 ccataattac                                                           310

<210> SEQ ID NO 9
<211> LENGTH: 292
<212> TYPE: DNA
<213> ORGANISM: Zea mays

<400> SEQUENCE: 9
gtcgaccacc cgataatgac gactactgac ttctggacct cgcacgagtg ccttctctta     60
ccctacgagc aggctcttac ccgtgaggat tccaccagtg ccttttctat gattgttcg     120 gcccacatgt tgtgggttgg tgagcgcact cgacaactcg atgagctca tgttgaattc    180 ctccgtggtg ttgccaaccc tctgggcata aggtgagcg acaaaatgaa ccccagtgag    240
ttggtgaagc tgattgatat tctgaacccct tcaaacaaac tggaaggat ca            292

<210> SEQ ID NO 10
<211> LENGTH: 332
<212> TYPE: DNA
<213> ORGANISM: Zea mays

<400> SEQUENCE: 10
aagcgcactc gtcaactcga tggagcgcat gttgaattcc ttcgtggtgt tgccaatcct     60
cttggcataa aggtgagcga caaaatgaac cccagtgact tggtgaagct gattgagatt    120 ctgaacccctt caaacaaacc tggaaggatc accataatta caaggatggg ggcagagaac    180
atgagagtga agttgcctca tctcatccgt gctgttcgca atgctggatt aattgtcaca    240
tggattactg atcctatgca tggaaacacc atcaaggcgc cttgtggcct gaagactcgt    300
```

-continued

```
ccattcgact caattctggc tgaagtgcgc gc                                    332

<210> SEQ ID NO 11
<211> LENGTH: 277
<212> TYPE: DNA
<213> ORGANISM: Zea mays

<400> SEQUENCE: 11
ggtgagcgca ctcgtcaact cgatggagcg catgttgaat tccttcgtgg tgttgccaat      60
cctcttggca taaggtgagc gacaaaatg aacccagtg acttggtgaa gctgattgag       120
attctgaacc cttcaaacaa acctggaagg atcaccataa ttacaaggat ggggcagag      180 aacatgagag tgaagttgcc tcatctcatc cgtgctgttc gcaatgctgg attaattgtc    240
acatggatta ctgatcctat gcatggaaac accatca                              277

<210> SEQ ID NO 12
<211> LENGTH: 272
<212> TYPE: DNA
<213> ORGANISM: Zea mays

<400> SEQUENCE: 12
attctggacc tcgcacgagt gccttctctt accctacgag caggatctga cccgtgagga      60
ttccagcagt ggccttttct atgattgttc ggcccagatg ttgtgggttg gtgagcgcac    120
tcgacaactc gatggagctc atgttgaatt cctccgttgt gttgccaagc ctctgggcat    180
aaaggtgagc gagaaaatga agccgagtga gttggtgaag ctgattgata gtctgaaccc    240
ttgaaacaaa gctggaagga tcagcatatt ac                                    272

<210> SEQ ID NO 13
<211> LENGTH: 218
<212> TYPE: DNA
<213> ORGANISM: Zea mays
<220> FEATURE:
<223> OTHER INFORMATION: unsure at all n locations

<400> SEQUENCE: 13
gttcggccca catgctgtgg gttggtgagc gcactcgtca actcgatgga gcgcatgttg      60
aattccttcg tggtgttgcc aatcctcttg gcataaaggt gagcgacaaa atgaacccca    120
gtgacttggt gaagctgatt gagattctga acccttcaaa caaacctgga aggatcaccn    180
ataatacaag gactggggca gagaacanta gagtgtaa                             218

<210> SEQ ID NO 14
<211> LENGTH: 227
<212> TYPE: DNA
<213> ORGANISM: Zea mays

<400> SEQUENCE: 14
acatgttgtg ggttggtgag cgcactcgac aactcgatgg agctcatgtt gaattcctcc      60
gtggtgttgc caaccctctg gcataaaggt gagcgacaa aatgaacccc agtgagttgg     120
tgaagctgat tgatattctg aaccctccaa acaaacctgg aaggatcacc ataattacaa    180 ggatggggc agagaacatg agggtgaagt tgcctcatct catccgt                    227

<210> SEQ ID NO 15
<211> LENGTH: 267
<212> TYPE: DNA
<213> ORGANISM: Zea mays
```

<400> SEQUENCE: 15

```
cgcacgagtg ccttctctta ccctacgagc agtctcttac ccgtaaagac tccaccagtg    60
gccttttcta cgattgttct gcccacatgt tgtgggatgt agagcgcact cgtaaactcg   120
atgtagcgca tgttgaattc cttcgtggtg ttgccaatcc tcttggcata aaggtgagcg   180
acaaaatgaa ccccagtgac ttggtgaagc tgattgagat tctgaaccct tcaaacaaac   240
ctggaaggat caccataatt acaagga                                        267
```

<210> SEQ ID NO 16
<211> LENGTH: 309
<212> TYPE: DNA
<213> ORGANISM: Zea mays

<400> SEQUENCE: 16

```
aaattggccc atagggtgga tgaggctctt gggttcatga ctgcagcagg gcttacagtt    60
gaccacccga taatgacgac tactgacttc tggacctcgc acgagtgcct tctcttaccc   120
tacgagcagt ctcttacccg taaagactcc accagtggcc ttttctacga ttgttcggcc   180
cacatgttgt gggttggtga gcgcactcgt caactcgatg gagcgcatgt tgaattcctc   240
cgtggtgttg ccaaccctct tggcataaag gcgagcgaca aaatgaaccc cagtgacttg   300
gtgaagctg                                                            309
```

<210> SEQ ID NO 17
<211> LENGTH: 296
<212> TYPE: DNA
<213> ORGANISM: Zea mays

<400> SEQUENCE: 17

```
cccacgcgtc cgatgggggc agagaacatg agggtgaagt tgcctcatct catccgtgct    60
gttcgcaatg ctggactgat tgtcacatgg attactgatc ctatgcatgg aaacaccatc   120
aaggcccctt gtggcctgaa gactcgtcca tttgactcca ttctggctga agtgcgtgcc   180
ttcttcgatg tgcatgacca agaaggaagc caccctgggg cgtccaccct tgaaatgact   240
gggcagaacg tgaccgagtg catcggtgga tcacggaccg tgaccttcga cgatct       296
```

<210> SEQ ID NO 18
<211> LENGTH: 272
<212> TYPE: DNA
<213> ORGANISM: Zea mays

<400> SEQUENCE: 18

```
ggaaacacca tcaaggcccc ttgtggcctg aagactcgtc cattcgactc aattctggct    60
gaagtgcgcg cattcttcga cgtgcatgat caagaaggaa gtcacccagg aggcatccac   120
cttgaaatga ctgggcagaa cgtgaccgag tgcattggtg gatcacggac tgtgaccttc   180
gatgacctta gtgaccgcta ccacacccac tgtgacccaa ggctgaacgc ctcccagtcc   240
ctggagctcg ccttcatcat tgcagagagg ct                                  272
```

<210> SEQ ID NO 19
<211> LENGTH: 328
<212> TYPE: DNA
<213> ORGANISM: Zea mays

<400> SEQUENCE: 19

```
gcgtcactca gtggaacctc gatttcatgg atcacaacga gcaaggtgat aggtaccgtg    60
aataggccca tagggtggat gatgctcttg ggttcatgac tgcatcgggg cttacagtcg   120
```

```
accacccgat aatgacgact actgacttct ggacctcgca cgagtgcctt ctcttaccct      180
acgagcaggc tcttacccgt gaggattcca ccagtggcct tttctatgat tgttcggccc      240
acatgttgtg ggttggtgag cgcactcgac aactcgatgg agctcatgtt gaattcctcc      300
gtggtgttgc caaccctctg ggcataaa                                         328
```

<210> SEQ ID NO 20
<211> LENGTH: 265
<212> TYPE: DNA
<213> ORGANISM: Zea mays

<400> SEQUENCE: 20

```
gggttcatga ctgcagcagg gcttacagtt gaccacccga taatgacgac tactgacttc      60
tggacctcgc acgagtgcct tctcttaccc tacgagcagt ctcttacccg taaagactcc     120
accagtggcc ttttctacga ttgttcggcc cacatgttgt gggttggtga gcgcactcgt     180
caactcgatg gagcgcatgt tgaattcctc cgttgtgttg ccaaccctct tggcataaag     240
gtgagcgaca aaatgaaccc cagtg                                            265
```

<210> SEQ ID NO 21
<211> LENGTH: 232
<212> TYPE: DNA
<213> ORGANISM: Zea mays

<400> SEQUENCE: 21

```
cccacgcgtc cggacgacta ctgacttctg gacctcgcac gagtgccttc tcttacccta      60
cgagcagtct cttacccgta aagactccac cagtggcctt ttctacgatt gttcggccca     120
catgttgtgg gttggtgagc gcactcgtca actcgatgga gcgcatgttg aattcctccg     180
tggtgttgcc aaccctcttg gcataaaggt gagcgacaaa atgaacccca gt             232
```

<210> SEQ ID NO 22
<211> LENGTH: 320
<212> TYPE: DNA
<213> ORGANISM: Zea mays

<400> SEQUENCE: 22

```
agcaaggtga taggtaccgt gaattggccc atagggtgga tgatgctctt gggttcatga      60
ctgcatcggg gcttacagtc gaccacccga taatgacgac tactgacttc tggacctcgc     120
acgagtgcct tctcttaccc tacgagcagg ctcttacccg tgaggattcc accagtggcc     180
ttttctatga ttgttcggcc cacatgttgt gggttggtga gcgcactcga caactcgatg     240
gagctcatgt tgaattcctc cgtggtgttg ccaaccctct gggcataaag gtgagcgaca     300
aaatgaaccc cagtgagttg                                                  320
```

<210> SEQ ID NO 23
<211> LENGTH: 309
<212> TYPE: DNA
<213> ORGANISM: Zea mays

<400> SEQUENCE: 23

```
tgcaatttgt ggaatttagg tgagcgacaa aatgaacccc agtgagttgg tgaagctgat      60
tgatattctg aacccttcaa acaaacctgg aaggatcacc ataattacaa ggatggggc      120 agagaacatg agggtgaagt tgcctcatct catccgtgct gttcgcaatg ctggactgat     180
tgtcacatgg attactgatc ctatgcatgg aaacaccatc aaggccccct tgtggcctgaa    240
```

```
gactcgtcca tttgactcca ttctggctga agtgcgtgcc ttcttcgatg tgcatgacca      300
agaaggaag                                                              309

<210> SEQ ID NO 24
<211> LENGTH: 336
<212> TYPE: DNA
<213> ORGANISM: Zea mays

<400> SEQUENCE: 24
gtgctgttcg caatgctgga ttaattgtca catgattact gatcctatgc atggatacac      60
catcaaggcc ccttgtggtc tgaagactcg tccattcgac tcaattctgg ctgaagtgcg     120
cgcattcttc gacgtgcatg atcaagaagg aagtcaccca ggaggcatcc accttgaaat     180
gactgggcag aacgtgaccg agtgcattgg tggatcacgg actgtgacct tcgatgacct     240
tagtgaccgc taccacaccc actgtgaccc aatgctgaac gcctcccagt ccctggagct     300
cgccttcatc attgcagaga gtcaggaaga ggaggt                               336

<210> SEQ ID NO 25
<211> LENGTH: 303
<212> TYPE: DNA
<213> ORGANISM: Zea mays

<400> SEQUENCE: 25
agcgagcaag gtgataggta ccgtgaattg gcccataggg tggatgaggc tcttgggttc      60
atgactgcag cagggcttac agttgaccac ccgataatga cgactactga cttctggacc     120
tcgcacgagt gccttctctt accctacgag cagtctctta cccgtaaaga ctccaccagt     180
ggccttttct acgattgttc ggcccacatg ttgtgggttg gtgagcgcac tcgtcaactc     240
gatggagcgc atgttgaatt ccttcgtggt gttgccaatc ctcttggcat aaaggtgagc     300
gac                                                                   303

<210> SEQ ID NO 26
<211> LENGTH: 248
<212> TYPE: DNA
<213> ORGANISM: Zea mays

<400> SEQUENCE: 26
gacaaaatga accccagtga gttggtgaag ctgattgata ttctgaaccc ttcaaacaaa      60
cctggaagga tcaccataat tacaaggatg ggggcagaga acatgagggt gaagttgcct     120
catctcatcc gtgctgttcg caatgctgga ctgattgtca catggattac tgatcctatg     180
catggaaaca ccatcaaggc cccttgtggc ctgaagactc gtccatttga ctccattctg     240
gctgaagt                                                              248

<210> SEQ ID NO 27
<211> LENGTH: 262
<212> TYPE: DNA
<213> ORGANISM: Zea mays

<400> SEQUENCE: 27
ggatcaccat aattacaagg atgggggcag agaacatgag ggtgaagttg cctcatctca      60
tccgtgctgt tcgcaatgct ggactgattg tcacatggat tactgatcct atgcatggaa     120
acaccatcaa ggccccttgt ggcctgaaga ctcgtccatt tgactccatt ctggctgaag     180
tgcgtgcctt cttcgatgtg catgaccaag aaggaagcca ccctgggggc gtccaccttg     240
aaatgactgg gcagaacgtg ac                                              262
```

<210> SEQ ID NO 28
<211> LENGTH: 291
<212> TYPE: DNA
<213> ORGANISM: Zea mays

<400> SEQUENCE: 28

```
tgagcgacaa aatgaacccc agtgactttg tgaagctgaa tgagattctg aacccttcaa      60
acaaacctgg aaggatcacc ataattacaa ggatggggc agagaacatg agagtgaagt     120
tgcctcatct catccgtgct gttcgcaatg ctggattaat tgtcacatgg attactgatc     180
ctatgcatgg aaacaccatc aaggcccctt gtgagctgaa gactcgtcca ttcgactcat     240
tctggctgaa gtgcgcgcat tcttcgacgt gcatgatcaa gaaggaagtc a             291
```

<210> SEQ ID NO 29
<211> LENGTH: 313
<212> TYPE: DNA
<213> ORGANISM: Zea mays

<400> SEQUENCE: 29

```
ctggccagtt tgccaagcca aggtccgaac cgttggagga gagggacggc gtcaagctgc      60
caagctacag gggcgacaac gtcaacggcg acgacttcac cgagaagagc cgcgtgccag     120
acccgcagag gatgatccgc gcctactcgc agtcggtggc gacgctcaac ctgctccgcg     180
cgttggcgac cggagggtac gctgccatgc agcgcgtcac acagtggaac ctcgatttca     240
tggatcacag cgagcaaggt gataggtacc gtgaattggc ccatagggtg gatgaggctc     300
ttgggttcat gac                                                        313
```

<210> SEQ ID NO 30
<211> LENGTH: 305
<212> TYPE: DNA
<213> ORGANISM: Zea mays

<400> SEQUENCE: 30

```
gcgagcaagg tgataggtac cgtgaattgg cccatagggt ggatgaggct cttgggttca      60
tgactgcagc agggcttaca gttgaccacc cgataatgac gactactgac ttctggacct     120
cgcacgagtg ccttctctta ccctacgagc agtctcttac ccgtaaagac tccaccagtg     180
gccttttcta cgattgttcg gcccacatgt tgtgggttgg tgagcgcact cgtcaactcg     240
atggagcgca tgttgaattc cttcgtggtg ttgccaatcc tcttggcata aaggtgagcg     300
acaaa                                                                  305
```

<210> SEQ ID NO 31
<211> LENGTH: 258
<212> TYPE: DNA
<213> ORGANISM: Zea mays

<400> SEQUENCE: 31

```
ctggattact gatcctatgc atggaaacac catcaaggcc ccttgtggcc tgaagactcg      60
tccattcgac tcaattctgg ctgaagtgcg cgcattcttc gacgtgcatg atcaagaagg     120
aagtcaccca ggaggcatcc accttgacat gactgggcag aacgtgaccg agtgcattgg     180
tggatcacgg actgtgacct tcgatgacct gagcgaccga taccacaccc actgtgaccc     240
aaggctgaac gcctccca                                                   258
```

<210> SEQ ID NO 32

```
<211> LENGTH: 250
<212> TYPE: DNA
<213> ORGANISM: Zea mays

<400> SEQUENCE: 32
gtcgaccacc cgataatgac gactactgac ttctggacct cgcacgagtg ccttctctta      60
ccctacgagc tggctcttac acgtgaggat tccaccagtg ccttttctca tgattgttcg     120
gcccacatgt tgtgggttgg tgagcgcact cgacaactcg ctcgagctca tgttgaattc     180
ctccgtggtg ttgccaatcc tctgggcata aggtgagcg acaaaatgaa ccccagtgag      240
ttggtgaagc                                                            250

<210> SEQ ID NO 33
<211> LENGTH: 290
<212> TYPE: DNA
<213> ORGANISM: Zea mays

<400> SEQUENCE: 33
catgcagcgc gtcacacagt ggaacctcga tttcatggat cacagcgagc aaggtgatag      60
gtaccgtgaa ttggcccata gggtggatga ggctcttggg ttcatgactg cagcagggct     120
tacagttgac cacccgataa tgacgactac tgacttctgg acctcgcacg agtgccttct     180
cttaccctac gagcagtctc ttacccgtaa agactccacc agtggccttt tctacgattg     240
ttcggcgcac atgttgtggg ttggtgagcg cactcgtcaa ctcgatggag                290

<210> SEQ ID NO 34
<211> LENGTH: 239
<212> TYPE: DNA
<213> ORGANISM: Zea mays

<400> SEQUENCE: 34
tgctggatta attgtcacat ggattactga tcctatgcat ggaaacacca tcaaggcccc      60
ttgtggcctg aagactcgtc cattcgactc aattctggct gaagtgcgcg cattcttcga     120
cgtgcatgat caagaaggaa gtcacccagg aggcatccac cttgaaatga ctgggcagaa     180
cgtgaccgag tgcattggtg gatcacggac tgtgaccttc gatgacctta gtgaccgct      239

<210> SEQ ID NO 35
<211> LENGTH: 220
<212> TYPE: DNA
<213> ORGANISM: Zea mays

<400> SEQUENCE: 35
ggccccttgt ggcctgaaga ctcgtccatt cgactcaatt ctggctgaag tgcgcgcatt      60
cttcgacgtg catgatcaag aaggaagtca cccaggaggc atccaccttg aaatgactgg     120
gcagaacgtg accgagtgca ttggtggatc acggactgtg accttcgatg accttagcga     180
ccgctaccac acccactgtg acccaaggct gaacgcctcc                           220

<210> SEQ ID NO 36
<211> LENGTH: 228
<212> TYPE: DNA
<213> ORGANISM: Zea mays

<400> SEQUENCE: 36
gcacgagtga agactcgtcc atttgactcc attctggctg aagtgcgtgc cttcttcgat      60
gtgcatgacc aagaaggaag ccaccctggg ggcgtccacc ttgaaatgac tgggcagaat     120
gtgaccgagt gcatcggtgg atcacggacc gtgaccttcg acgatctgag cgaccgctac     180
```

```
cacacccact gcgacccaag gctgaatgcc tcccagtccc tggagctc        228

<210> SEQ ID NO 37
<211> LENGTH: 263
<212> TYPE: DNA
<213> ORGANISM: Zea mays

<400> SEQUENCE: 37
gagttggtga agctgattga tattctgaac ccttcaaaca aacctggaag gatcaccata    60
attacaagga tgggggcaga gaacatgagg gtgaagttgc tcatctcat ccgtgctgtt   120 cgcaatgctg gactgattgt cacatggatt actgatccta tgcatggaaa caccatcaag   180
gccccttgtg gcctgaagac tcgtccattt gactccattc tggctgaagt gcgtgccttc   240
ttcgatgtgc atgaccaaga agg                                            263

<210> SEQ ID NO 38
<211> LENGTH: 241
<212> TYPE: DNA
<213> ORGANISM: Zea mays

<400> SEQUENCE: 38
cgatttcatg gatcacaacg agcaaggtga taggtaccgt gaattggccc atagggtgga    60
tgatgctctt gggttcatga ctgcatcggg gcttacagtc gaccacccga taatgacgac   120
tactgacttc tggacctcgc acgagtgcct tctcttaccc tacgagcagg ctcttacccg   180
tgaggattcc accagtggcc ttttctatga ttgttcggcc cacatgttgt gggttggtga   240
g                                                                    241

<210> SEQ ID NO 39
<211> LENGTH: 225
<212> TYPE: DNA
<213> ORGANISM: Zea mays

<400> SEQUENCE: 39
aaacaaacct ggaaggatca ccataattac aaggatgggg gcagagaaca tgagggtgaa    60
gttgcctcat ctcatccgtg ctgttcgcaa tgctggactg attgtcacat ggattactga   120
tcctatgcat ggaaacacca tcaaggcccc ttgtggcctg aagactcgtc catttgactc   180
cattctggct gaagtgcgtg ccttcttcga tgtgcatgac caaga                    225

<210> SEQ ID NO 40
<211> LENGTH: 248
<212> TYPE: DNA
<213> ORGANISM: Zea mays

<400> SEQUENCE: 40
atcgaccacc cgataatgac gactactgac ttctggacct cgcacgagtg ccttctctta    60
ccctacgagc aggctcttac ccgtgaggat tccaccagtg gcctttctca tgattgttcg   120
gtccacatgt tgtgggttgg tgagcgcact cgacaactcg atggagctca tgttgaatac   180
ctccgtggtg ttgccaaccc tctgggcata aggtgagcg acaaaatgca ccccagtgag   240
ttggtgaa                                                             248

<210> SEQ ID NO 41
<211> LENGTH: 227
<212> TYPE: DNA
<213> ORGANISM: Zea mays
```

```
<400> SEQUENCE: 41
tcttgggttc atgactgcag cagggcttac agttgaccac ccgataatga cgactactga      60
cttctggacc tcgcacgagt gccttctctt accctacgag cagtctctta cccgtaaaga     120
ctccaccagt ggccttttct acgattgttc ggcccacatg ttgtgggttg gtgagcgcac     180
tcgtcaactc gatggagcgc atgttgaatt ccttcgtggt gttgcca                    227

<210> SEQ ID NO 42
<211> LENGTH: 170
<212> TYPE: DNA
<213> ORGANISM: Zea mays

<400> SEQUENCE: 42
agctgattga gattctgaac ccttcaaaca aacctggaag gatcaccata attacaagga      60
tgggggcaga gaacatgaga gtgaagttgc ctcatctcat ccgtgctgtt cgcaatgctg     120
gattgattgt cacatggatt actgatccta tgcatggaaa caccatcaag                 170

<210> SEQ ID NO 43
<211> LENGTH: 277
<212> TYPE: DNA
<213> ORGANISM: Zea mays

<400> SEQUENCE: 43
gcgcgcattc ttcgacgtgc atgatcaaga aggaagtcac ccaggaggca tccaccttga      60
aatgactggg cagaacgtga ccgagtgcat tggtggatca cggactgtga ccttcgatga     120
cctgatcgac cgctaccaca cccacgtgac ccaaggctga acgcctccca gtccctggag     180
ctcgccttca tcattgcaga gaggctcagg aagaggagga tgcggtcggg gctcaacaac     240
agcctgcctc tgccaccact ggctttctaa gtagccg                               277

<210> SEQ ID NO 44
<211> LENGTH: 281
<212> TYPE: DNA
<213> ORGANISM: Zea mays

<400> SEQUENCE: 44
ccaagaatga accaccctgg gggcgtccac cttgaaatga ctgggcagaa cgtgaccgag      60
tgcatcggtg gatcacggac cgtgaccttc gacgatctga gcgaccgcta ccacacccac     120
tgcgacccaa ggctgaatgc ctcccagtcc ctggagctcg cctttatcat cgcagagagg     180
ctgaggaaga ggaggatgcg atcggggctc aacagcagcc tgccactgcc gccactggct     240
ttctgagtag ccggagccaa acacaaagga gggtaggaat a                          281

<210> SEQ ID NO 45
<211> LENGTH: 273
<212> TYPE: DNA
<213> ORGANISM: Zea mays

<400> SEQUENCE: 45
ggctacttag aaagccagtg gtggcagagg caggctgttg ttgagccccg accgcatcct      60
cctcttcctg agcctctctg caatgatgaa ggcgagctcc agggactggg aggcgttcag     120
ccttgggtca cagtgggtgt ggtagcggtc gctcaggtca tcgaaggtta cagtccgtga     180
tctaccaatg cactcggtca cgttctgccc agtcatttca aggtggatgc ctcctgggtg     240
acttccttct tgatcatgca cgtcgaagaa tgc                                   273
```

<210> SEQ ID NO 46
<211> LENGTH: 201
<212> TYPE: DNA
<213> ORGANISM: Zea mays

<400> SEQUENCE: 46

| | |
|---|---|
| ggcccttgt ggcctgaaga ctcgtccatt tgactccatt ctggctgaag tgcgtgcctt | 60 |
| cttcgatgtg catgaccaag aaggaagcca ccctgggggc gtccaccttg aaatgactgg | 120 |
| gcagaacgtg accgagtgca tcggtggatc acggaccgtg accttcgacg atctgagcga | 180 |
| ccgctaccac acccactgcg a | 201 |

<210> SEQ ID NO 47
<211> LENGTH: 228
<212> TYPE: DNA
<213> ORGANISM: Zea mays

<400> SEQUENCE: 47

| | |
|---|---|
| ccacgcgtcc ggtgaagttg cctcatctca tccgtgctgt tcgcaatgct ggattaattg | 60 |
| tcacatggat tactgatcct atgcatggaa acaccatcaa ggcccttgt ggcctgaaga | 120 |
| ctcgtccatt cgactcaatt ctggctgaag tgcgcgcatt cttcgacgtg catgatcaag | 180 |
| aaggaagtca cccaggaggc atccaccttg aaatgactgg gcagaacg | 228 |

<210> SEQ ID NO 48
<211> LENGTH: 301
<212> TYPE: DNA
<213> ORGANISM: Zea mays

<400> SEQUENCE: 48

| | |
|---|---|
| cgtgaattgg cccatagggt ggatgatgct cttggggtca tgactgcatc ggggcttaca | 60 |
| gtcgaccacc cgataatgac gactactgac ttctggacct cgaacgaggt gccttcgctt | 120 |
| accctacgag caggctctta cccgtgagga ttccaccagt ggccttttct atgattgtta | 180 |
| cgcccacatg ttgtgggttg gtgagcgcac tcgacaactc gatggagctc atgttgaatt | 240 |
| cctccgtggt gttgccaacc ctctgggcat aaaggtgagc gacaaaatga accccagtga | 300 |
| g | 301 |

<210> SEQ ID NO 49
<211> LENGTH: 332
<212> TYPE: DNA
<213> ORGANISM: Zea mays

<400> SEQUENCE: 49

| | |
|---|---|
| gccaccctgg gggcgtccac cttgaaatga ctgggcagac gtgaccgagt gcatcggtgg | 60 |
| atcacggacc gtgaccttcg acgatctgag cgaccgctac cacacccact gcgacccaag | 120 |
| gctgaatgcc tcccagtccc tggagctcgc ctttatcatc gcagagaggc tgaggaagag | 180 |
| gaggatgcga tcggggctca acagcagcct gccactgccg ccactggctt tctgagtagc | 240 |
| cggagccaaa cacaaaggag ggtaggaata gctgtggtga ctcggaagag aaagagacag | 300 |
| tcgacgcctt gttttgttga tgctagtgtg gt | 332 |

<210> SEQ ID NO 50
<211> LENGTH: 310
<212> TYPE: DNA
<213> ORGANISM: Zea mays
<220> FEATURE:
<223> OTHER INFORMATION: unsure at all n locations

```
<400> SEQUENCE: 50
cgacgacttc accgagaaga gccgcgtgcc ggacccgcag aggatgatcc gcgcctacgc      60
acagtcggtg gcgacactca acctgctccg cgcgttcgcc accggagggt acgctgccat     120
gcacgcgtca ctcagtggaa cctcgatttc atggatcaca acgagcaagg tgataggtac     180
cgtgaattgg cccatagggt ggatgatgct cttgggttca tgactgcatc ggggcttaca     240
gtcgaccacc cgataatgac gactactgac ttctggacct cgcacgagtg cncttctctt     300
acctacgagc                                                            310

<210> SEQ ID NO 51
<211> LENGTH: 227
<212> TYPE: DNA
<213> ORGANISM: Zea mays

<400> SEQUENCE: 51
cgacgacttc accgagaaga gccgcgtgcc agacccgcag aggatgatcc gcgcctactc      60
gcagtcggtg gcgacgctca acctgctccg cgcgttggcg accggagggt acgctgccat     120
gcacgcgtca cacagtggaa cctcgatttc atggatcaca gcgagcaagg tgataggtac     180
cgtgaattgg cccatagggt ggatgaggct cttgggttca tgactgc                   227

<210> SEQ ID NO 52
<211> LENGTH: 215
<212> TYPE: DNA
<213> ORGANISM: Zea mays

<400> SEQUENCE: 52
aggcttacag ttgaacaccc gataatgacg actactgact tctggacctc acacgagtgc      60
cttctcatac actaagaaaa gtctcttacc cgtaaagact ccaccagtgg ccttttctac     120
gattgttcgg cccacatgct gtgggttggt gagcgcactc gtcaactcga tggagcgcat     180
gtatgaattc cttcgtggtg ttgcaatcct cttgg                                215

<210> SEQ ID NO 53
<211> LENGTH: 249
<212> TYPE: DNA
<213> ORGANISM: Zea mays

<400> SEQUENCE: 53
gagaagagcc gcgtgccgga cccgcagagg atgatccgcg cctacgcaca gtcggtggcg      60
acactcaacc tgctccgcgc gttcgccacc ggagggtacg ctgccatgca cgcgtcactc     120
agtggaacct cgatttcatg gatcacaacg agcaaggtga taggtaccgt gaattggccc     180
atagggtgga tgatgctctt gggttcatga ctgcatcggg gcttacagtc gaccacccga     240
taatgacga                                                             249

<210> SEQ ID NO 54
<211> LENGTH: 184
<212> TYPE: DNA
<213> ORGANISM: Zea mays

<400> SEQUENCE: 54
ctccatcgag ttgacgagtg cgctcaccaa cccacaacat gtgggccgaa caatcgtaga      60
aaaggccact ggtggagtct ttacgggtaa gagactgctc gtagggtaag agaaggcact     120
cgtgcgaggt ccagaagtca gtagtcgtca ttatcgggtg gtcaactgta agccctgctg     180
cagt                                                                  184
```

<210> SEQ ID NO 55
<211> LENGTH: 202
<212> TYPE: DNA
<213> ORGANISM: Zea mays

<400> SEQUENCE: 55

| | |
|---|---|
| gaagttgcct catctcatcc gtgctgttcg caatgctgga ttaattgtca catggattac | 60 |
| tgatcctatg catggaaaca ccatcaaggc cccttgtggc ctgaagactc gtccattcga | 120 |
| ctcaattctg gctgaagtgc gcgcattctt cgacgtgcat gatcaagaag gaagtcaccc | 180 |
| aggaggcatc caccttgaaa tg | 202 |

<210> SEQ ID NO 56
<211> LENGTH: 279
<212> TYPE: DNA
<213> ORGANISM: Zea mays

<400> SEQUENCE: 56

| | |
|---|---|
| cggctcgagg ccaccctggg ggcgtccacc ttgaaatgac tgggcagaat gtgaccgaga | 60 |
| ccatcggtgg atcacggacc gtgaccttcg acgatctgag cgaccgctac cacacccact | 120 |
| gcgacccaag gctgaatgcc tcccagtccc tggagctcgc ctttatcatc gcagagaggc | 180 |
| tgaggaagag gaggatgcga tcggggctca acagcagcct gccactgccg ccactggctt | 240 |
| tctgagtagc cggagccaaa cacaaaggag ggtaggaat | 279 |

<210> SEQ ID NO 57
<211> LENGTH: 205
<212> TYPE: DNA
<213> ORGANISM: Zea mays

<400> SEQUENCE: 57

| | |
|---|---|
| tctgaaccgt tggaggagag ggacggcgtc aagctgccaa gctacagggg cgacaacgtc | 60 |
| aacggcgacg acttcaccga aagagccgc gtgccagacc cgcagaggat gatccgcgcc | 120 |
| tactcgcagt cggtggcgac gctcaacctg ctccgcgcgt tggcgaccgg agggtacgct | 180 |
| gccatgcagc gcgtcacaca gtgga | 205 |

<210> SEQ ID NO 58
<211> LENGTH: 124
<212> TYPE: DNA
<213> ORGANISM: Zea mays

<400> SEQUENCE: 58

| | |
|---|---|
| tgtgctgttc gcaatgctgg attaattgtc acatggatta ctgatcctat gcatggaaac | 60 |
| accatcaagg ccccttgtgg cctgaagact cgtccattcg actcaattct ggctgaagtg | 120 |
| cgcg | 124 |

<210> SEQ ID NO 59
<211> LENGTH: 272
<212> TYPE: DNA
<213> ORGANISM: Zea mays

<400> SEQUENCE: 59

| | |
|---|---|
| caaggttagt gacaagatgg acccagcaga acttgtgcgg ttgattgata tattgaatcc | 60 |
| cgaaaacagg gctgggagaa taaccatcat cacaagaatg ggacctgaaa acatgagggt | 120 |
| gaaacttcca cacctgatac gcgctgtccg tggggccggt cagatagtaa catgggttac | 180 |

```
tgacccaatg catgggaaca ctatgaaggc cccttgcgga ctcaaaaccc gctcgttcga      240
caggattttg ggtgaggtgc gtgcgttctt tg                                   272

<210> SEQ ID NO 60
<211> LENGTH: 237
<212> TYPE: DNA
<213> ORGANISM: Zea mays

<400> SEQUENCE: 60
tggacacggt gctcaaaacc atcgagacgt tcccgccggt ggtgttcgcc ggagaggcgc      60
gccacctcga ggagcgcatg gccgaggccg ccatgggccg cgccttcatc ctccagggcg     120
gcgactgcgc cgagagcttc aaggagttcc acgccaacaa catccgtgac accttccgta     180
tcctgctgca gatgggcgcc gtgctcatgt tcggtggtca ggtgccggtc gtcaagg        237

<210> SEQ ID NO 61
<211> LENGTH: 215
<212> TYPE: DNA
<213> ORGANISM: Zea mays

<400> SEQUENCE: 61
accaggagga gctggacacg gtgctcaaaa ccatcgagac gttcccgccg gtggtgttcg      60
ccggagaggc gcgccacctc gaggagcgca tggccgaggc cgccatgggc gcgccttca     120 tcctccaggg cggcgactgc gccgagagct caaggagta ccacgccaac aacatccatg     180
acaccttccg tatcctgctg cagatgggcg ccgtg                                215

<210> SEQ ID NO 62
<211> LENGTH: 125
<212> TYPE: DNA
<213> ORGANISM: Zea mays

<400> SEQUENCE: 62
tggacacggt gctcaagatc atcgagacgt tcccgccggt ggtgttcgcc ggagaagcgc      60
gtcacctcga ggagcgcatg gccgaagccg ccattggccg cgccttcatc ctccatgacg     120
gcgac                                                                 125

<210> SEQ ID NO 63
<211> LENGTH: 287
<212> TYPE: DNA
<213> ORGANISM: Zea mays

<400> SEQUENCE: 63
gtgctgcgga cggtgggaac gttcccgccc atcgtcttcg ccggcgaggc gcgcaccctc      60
gaggagcgcc tcgcggaggc cgccgtcggc cgggccttcc tcctccaggg cggcgactgc     120
gccgagagct tcaaggagtt caacgccaac aacatcaggg acaccttccg cgtcctcatg     180
caaatgtccg ttgtgctcat gttcggaggc cagatgcctg tcgtcaaggt gggaagaatg     240
gcaggtcagt ttgcgaagca aggtcagatg gttttgagga gcgggat                   287

<210> SEQ ID NO 64
<211> LENGTH: 305
<212> TYPE: DNA
<213> ORGANISM: Zea mays

<400> SEQUENCE: 64
cccacgcgtc cgcccacgcg tccggtcagc tgctgggctc cctttagatc accctataat      60
gacaacagca gaattttgga cgtcacatga gtgtcttctt ctaccttatg agcaagcgct     120
```

```
cactcgtgag gattccacca cgggcctcta ttatgactgc tctgcccact tcctatgggt    180
cggagagcgc actcgccagc ttgatggtgc tcacgttgag ttccttcgag gcattgccaa    240
ccctcttggt atcaaggtta gtgacaagat ggacccagca gaacttgtgc ggttgattga    300
tatat                                                                305

<210> SEQ ID NO 65
<211> LENGTH: 311
<212> TYPE: DNA
<213> ORGANISM: Zea mays

<400> SEQUENCE: 65
ggccgcgcct tcatcctcca gggcggcgac tgcgccgaga gcttcaagga gttccacgcc    60
aacaacatcc gtgacacctt ccgtattctg cttcagatgg gcgccgtgct catgttcggt    120
ggtcaggtgc cggtcgtcaa cgtggggagg atggctggcc agtttgccaa gccaaggtcc    180
gaaccgttgg aggagaggga cggcgtcaag ctgccaagct acaggggcga caacgtcaac    240
ggcgacgact tcaccgagaa gagccgcgtg ccagacccgc agaggatgat ccgcgcctac    300
tcgcagtcgg t                                                         311

<210> SEQ ID NO 66
<211> LENGTH: 271
<212> TYPE: DNA
<213> ORGANISM: Zea mays

<400> SEQUENCE: 66
gcgccgagag tttcaaggag ttccacgcca acaacatccg tgacaccttc cgcgtccttc    60
tccagatggg cgtcgtgctc atgttcggtg gccagatgcc ggtcgtcaag gtggggagga    120
tggctggcca gttcgccaag ccaaggtctg agccgttcga ggagaaggac ggagttaagc    180
tgccgagctc caggggcgac aacgtcaacg gcgacgactt caccgagaag agccgcgtgc    240
cggacccgca gaggatgatc cgcgcctacg c                                   271

<210> SEQ ID NO 67
<211> LENGTH: 264
<212> TYPE: DNA
<213> ORGANISM: Zea mays

<400> SEQUENCE: 67
cacgccaaca acatccgtga caccttccgt attctgcttc agatgggcgc cgtgctcatg    60
ttcggtggtc aggtgccggt cgtcaaggtg gggaggatgg ctggccagtt tgccaagcca    120
aggtccgaac cgttggagga gggacggc gtcaagctgc caagctacag ggcgacaac    180 gtcaacggcg acgacttcac cgagaagagc cgcgtgccag acccgcagag gatgatccgc    240
gcctactcgc agtcggtggc gacg                                           264

<210> SEQ ID NO 68
<211> LENGTH: 265
<212> TYPE: DNA
<213> ORGANISM: Zea mays

<400> SEQUENCE: 68
cccacgcgtc cgagatgggc gtcgtgctca tgttcggtgg ccagatgccg gtcgtcaagg    60
tggggaggat ggctggccag ttcgccaagc caaggtctga gccgttcgag gagaaggacg    120
gagttaagct gccgagctac aggggcgaca acgtcaacgg cgacgacttc accgagaaga    180
```

| | |
|---|---:|
| gccgcgtgcc ggacccgcag aggatgatcc gcgcctacgc acagtcggtg gcgacactca | 240 |
| acctgctccg cgcgttcgcc accgg | 265 |

<210> SEQ ID NO 69
<211> LENGTH: 315
<212> TYPE: DNA
<213> ORGANISM: Zea mays

<400> SEQUENCE: 69

| | |
|---|---:|
| caaggagttc cacgccaaca acatccgtga caccttccgc gtccttctcc agatgggcgt | 60 |
| cgtgctcatg ttcggtggca agatgccggt cgtcaaggtg gggaggatgg ctggccagtt | 120 |
| cgccaagcca aggtctgagc cgttcgagga aaggacgga gttaagctgc cgagctacag | 180 |
| gggcgacaac gtcaacggcg acgacttcac cgagaagagc cgcgtgccgg acccgcagag | 240 |
| gatgatccgc gcctacgcac agtcggtggc gacactcaac ctgctccgcg cgttcgccac | 300 |
| cggagggtac gctgc | 315 |

<210> SEQ ID NO 70
<211> LENGTH: 286
<212> TYPE: DNA
<213> ORGANISM: Zea mays

<400> SEQUENCE: 70

| | |
|---|---:|
| gacccgagag tttcaaggag ttccacgcca acaacatccg ggagcccttc cgcgtcgttc | 60 |
| tccagatggg cgtcgtgctc atgttcggtg gccagatgcc ggtcgtcaag gtggggagga | 120 |
| tggctggcca gttcgccaag ccaaggtctg agccgttcga ggagaaggac ggagttaagc | 180 |
| tgccgagcta caggggcgac aacgtcaacg gcgacgactt caccgagaag agccgcgtgc | 240 |
| cggacccgca gaggatgatc gcgcctaca gcacatcggt ggcgac | 286 |

<210> SEQ ID NO 71
<211> LENGTH: 284
<212> TYPE: DNA
<213> ORGANISM: Zea mays

<400> SEQUENCE: 71

| | |
|---|---:|
| catgaccta gtgaccgcta ccacacccac tgtgacccaa ggctgaacgc ctcccagtcc | 60 |
| ctggagctcg ccttcatcat tgcagagagg ctcaggaaga ggaggatgcg gtcggggctc | 120 |
| aacaacagcc tgcctctgcc accactggct ttctaagtag ccgaagctga acagagaagg | 180 |
| tagaggggat agttgcggcg actcgaaaga ttacgcctgt ttatttgttg atgcttggtg | 240 |
| tggaggcctg gtgggtgctc ttggcacaag ttacatgctg ggga | 284 |

<210> SEQ ID NO 72
<211> LENGTH: 390
<212> TYPE: DNA
<213> ORGANISM: Zea mays

<400> SEQUENCE: 72

| | |
|---|---:|
| acccacgcgt ccgccggcg ctcccttgc cgtggtgggg gcgggccggc cgcggtgcgc | 60 |
| tcgtccgcgc ccgcgcccgc gccgtccgcg cggcgctacg gccccgagc cagtggtccg | 120 |
| tcgggagctg gcggggccgc ccggcgcagc agcagcccga gtaccggac aaggcggacc | 180 |
| tggaagacgt gctgcggacg gtgggaacgt tcccgcccat cgtcttcgcc ggcgaggcgc | 240 |
| gcaccctcga ggagcgcctc gcggaggccg ccgtcggccg ggccttcctc ctccagggcg | 300 |
| gcgactgcgc cgagagcttc aaggagttca acgccaacaa catcagggac accttccgcg | 360 |

```
tcctcctgca aatgtccgtt gtgctcatgt                                      390

<210> SEQ ID NO 73
<211> LENGTH: 322
<212> TYPE: DNA
<213> ORGANISM: Zea mays
<220> FEATURE:
<223> OTHER INFORMATION: unsure at all n locations

<400> SEQUENCE: 73
gtttataaat tctcatgntt ccgacccttg catgctatcg ctcttatccc acgtagtatc     60
atgcccgcaa ttatacatat attttttttt ccctccaatt catgaatcca tctggaggac    120
attttaaagc ctgtcataca ataatctatt tctatacctc acataattac cttctcctac    180
cttactagca atccttaacc cttcaagact ccaccaccga tcttttctac tactgctcct    240
tccacatgct ctcattcgac gagctcaccc tgcaacttga tacctcccat ctacagttcc    300
tgatggagat cgccaacccc ct                                             322

<210> SEQ ID NO 74
<211> LENGTH: 439
<212> TYPE: DNA
<213> ORGANISM: Zea mays

<400> SEQUENCE: 74
gcatgactga gtttgtaggt accgtgaatt ggcacatcgg gttgatgatg cccttggatt     60
catgggtgca actgggctga caatggacca gcctttgacg acgatgatcg agtttctgga    120
cctaacatga gtgcttcctc ctaccttaca agcaagcctt aacccggcag gattccacca    180
ccggcctttc tataaatggt tcggccacat actcttggtt cggagagcga cacccgaact    240
tgaatggccc atatgtagag tctctgaggg agatcgcaaa ccctcttggt atcaaggtga    300
gccacaatat ggagcccgga gagctggaaa atctgatcga catactgaac ccgacgaaca    360
agcccgagag gatcaccgtc atcacaggga tgggcgcaga gcacatcagg gtcaagttac    420
ctcaccttat ccgcgcggt                                                 439

<210> SEQ ID NO 75
<211> LENGTH: 434
<212> TYPE: DNA
<213> ORGANISM: Zea mays

<400> SEQUENCE: 75
cccacacatc cacatttcca ataacacatt tcatcgcaac ataccatc cttcactggt      60 ggcatcatga acacatgtgg gtgaaactta cacacctgat acccgctgtc cattctgccc    120
gtcagatagt aacatgggtt actgacccaa tgcatgggaa cactattaag gcccattgcg    180
gactcaaaac cctctcgttc gacaggattt tgggtcacgt gcgtgcgttc tttgatgtcc    240
acgaacaaga agggagccac cctggaggag tgcatctaga gatgactgga caaaatgtta    300
cacagtgcat cggcggttca cgtactgtta ccttcgatga tctggggtca cgctaccaca    360
cgcactgcta cccaaggctc aatgccttac agtctctgga gattgcattt atcatcgccg    420
aacgccttat gaaa                                                      434

<210> SEQ ID NO 76
<211> LENGTH: 437
<212> TYPE: DNA
<213> ORGANISM: Zea mays
```

```
<400> SEQUENCE: 76
cggacgcgtg ggcgagcaag ccttaacccg gcaagactcc accaccggtc ttttctacga      60
ctgctccgcc cacatgctct gggtcggcga gcgcacccgg cagcttgatg cgtccatgt      120 ggagttcctg aggggatcg ccaaccccct tggcatcaag gtgagcgaca agatggagcc      180
cggcgagctg gtgaagctga tcgacatact gaacccgacg aacaagcccg ggaggatcac      240
cgtcatcaca aggatggggg cagagaacat cagggtcaag ttacctcacc ttatccgcgc      300
ggtccgccag gctggacaga gtgtcacctg atcactgac ccgatgcacg gaacaccat      360 caagactcct tgcggacgaa agactcggcc atttgactcc attctggccg aggtacgggc      420
cttcttcgac gtgcacg                                                     437

<210> SEQ ID NO 77
<211> LENGTH: 347
<212> TYPE: DNA
<213> ORGANISM: Zea mays

<400> SEQUENCE: 77
ggcacgccta cgcttccgcc tacgcgttgt ctgactcgtg ggctttcgcg tggtcggacg       60
cgtgggccga cgctggtgcc gtagaagaag ccggtagcgc acgggaagtg tgcggtctac      120
agctggaggt ccaagaaggc tttgcagctc cccgagtacc cgaacgcgga tgagctggac      180
gctgtgctga agaccatcga gacgttcccg ccggtggtgt tcgtcggaga ggctcgccgt      240
ctcgaggagc gcatggccga ggccggcatg ggccgcgcct tcgtcctcca aggtggcgac      300
tgctccgaga gtttcaagga gttccacgcc aacaacatgc gtgacac                   347

<210> SEQ ID NO 78
<211> LENGTH: 258
<212> TYPE: DNA
<213> ORGANISM: Zea mays

<400> SEQUENCE: 78
tcgcccacgc gtacgcccac gcgtacgccc acgcgtccgt ccacgcgtcc ggcaaggtga       60
taagtaccgg gaattggccc atacggtgga tgatgctctt gggttcatga ctgcatcggg      120
gcttacaggc gaacaaccgg ttatgaccac tactgacttc tggaccttgg accaatggct      180
tttcttaccc tacgagcagg ctcttacccg tgaggattcc accagtggcc ttttctatga      240
atggtcgggc cacaatgt                                                    258

<210> SEQ ID NO 79
<211> LENGTH: 448
<212> TYPE: DNA
<213> ORGANISM: Zea mays

<400> SEQUENCE: 79
acgctgactt ctggacctcg cacgagtgcc gtctcttacc ctacgagcag gctcttgccc       60
gtggggattc caccaggggc ctttctatg attgttcggc ccacatgttg tgggttggtg      120
agcgcactcg acaactcgat ggagctcatg ttgaattcct ccgtggtgtt gccaacccta      180
tgggcataaa ggtgagcgac aaaatgaacc ccagtgagtt ggtgaagctg attgatattc      240
tgaacccttc aaacaaacct ggaaggatca ccataattac aaggatgggg gcagagaaca      300
tgagggtgaa gttgcctcat ctcatccgtg ctgttcgcaa tgctggactg attgtcacat      360
ggattactga tcctatgcat ggaaacacca tcaaggcccc ttgtggcctg aagactcgtc      420
catttgactc cattctggct gaagtgcg                                         448
```

<210> SEQ ID NO 80
<211> LENGTH: 459
<212> TYPE: DNA
<213> ORGANISM: Zea mays
<220> FEATURE:
<223> OTHER INFORMATION: unsure at all n locations

<400> SEQUENCE: 80

```
cggtaatgtt gacttctggc cgcctagtcc gaagcagggc cgcccccact nccgagtaca      60
ctagttgnaa tcctccgtgg tgttgccaac cctctgggca taaaggtgag tcgacaacaa     120
tgaatcccca gtgagttggt gaagctgatt gatattctga acccttcaaa caaacctgga     180
aggatcacca taattacaag gatggggca gagaacatga gggtgaagtt gcctcatctc     240
atccgtgctg ttcgcaatgc tggactgatt gtcacatgga ttactgatcc tatgcatgga     300
aacaccatca aggccccttg tggcctgaag actcgtccat ttgactccat tctggctgaa     360
gtgcgtgcct tcttcgatgt gcatgaccaa gaatgaagcc accctgggg cgtccacctt     420
gaaatgactg ggcagaacgt gaccgagtgc atcggtgga                           459
```

<210> SEQ ID NO 81
<211> LENGTH: 369
<212> TYPE: DNA
<213> ORGANISM: Zea mays
<220> FEATURE:
<223> OTHER INFORMATION: unsure at all n locations

<400> SEQUENCE: 81

```
cacatgttgt gggttggtga gcgcactcgt taactcgatg gagcgcatgt tgaattcctt      60
ggtggtgtgg ccaatcctct tggcataaag gtgagcgaca aaatgaaccc cagtgacttg     120
gtgaagctga ttgagattct gaaccctca aacaaacctg aaggatcac cataattaca      180
aggatggggg cagagaacat gagagtgaag ttgcctcatc ttatccgtgc tgttcgcaat     240
gctggattaa ttgtcacatg gattactgat cctatgcatg gaaacaccat caaggcccct     300
tgtggccctg agactcgtnc atttgactca attctggctg aagtgcgcgc attcttcgat     360
gtgcatgat                                                             369
```

<210> SEQ ID NO 82
<211> LENGTH: 455
<212> TYPE: DNA
<213> ORGANISM: Zea mays

<400> SEQUENCE: 82

```
ggggtgagac gttactatgc actgtcggct caggactagc gggtcgatgc aagcctctag      60
atgcagtctc acaaccgtgc tgttcgcaat gctggactga ttgtcacatg gattactgat     120
cctatgcatg gaaacaccat caaggcccct tgtggcctga agactcgtcc atttgactcc     180
attctggctg aagtgcgtgc cttcttcgat gtgcatgacc aagaaggaag ccaccctggg     240
ggcgtccacc ttgaaatgac tgggcagaac gtgaccgagt gcatcggtgg atcacggacc     300
gtgaccttcg acgatctgag cgaccgctac cacacccact gcgacccaag gctgaatgcc     360
tcccagtccc tggagctcgc ctttatcatc gcagagaggc tgaggaagag gacgatgcga     420
tcggggctca acagcagcct gccactgccg ccact                                455
```

<210> SEQ ID NO 83
<211> LENGTH: 405
<212> TYPE: DNA

<213> ORGANISM: Zea mays

<400> SEQUENCE: 83

```
cccacgcgtt cgcccacgcg tccgcccacg cgtccgccca cgcgtccggc aaggtgatag      60
gtaccgtgaa ttggcccata gggtggatga tgctcttggg ttcatgactg catcggggct     120
tacagtcgac cacccgataa tgacgactac tgacttctgg acctcgcacg agtgccttct     180
cttaccctac gagcaggctc ttaccgtgta ggattccacc agtggccttt tctatgattg     240
ttcggcccac atgttgtggg ttggtgagcg cactcgacaa ctcgatggag ctcatgttga     300
attcctccgt ggtgttgcca accctctggg cataaaggtg agcgacaaaa tgaacccag      360
tgagttggtg aagctgattg atattctgaa cccttcaaac aaacc                     405
```

<210> SEQ ID NO 84
<211> LENGTH: 444
<212> TYPE: DNA
<213> ORGANISM: Zea mays

<400> SEQUENCE: 84

```
gtgccggacc cgcagaggat gatccgcgcc tacgcacagt cggtggcgac actcaacctg      60
gtccgggcgt cgccaccgg agggtacgct gccatgcagc gcgtcactca gtggaacctc     120
gatttcatgg atcacaacga gcaaggtgat aggtaccgtg aattggccca tagggtggat     180
gatgctcttg ggttcatgac tgcatcgggg cttacagtcg accacccgat aatgacgact     240
actgacttct ggacctcgca cgagtgcctt ctcttaccct acgagcaggc tcttaccgt      300
gaggattcca ccagtggcct tttctatgat tgttcggccc acatgttgtg ggttggtgag     360
cgcactcgac aactcgatgg agctcatgtt gaattcctcc gtggtgttgc caaccctctg     420
ggcataaagg tgagcgacaa aatg                                            444
```

<210> SEQ ID NO 85
<211> LENGTH: 371
<212> TYPE: DNA
<213> ORGANISM: Zea mays
<220> FEATURE:
<223> OTHER INFORMATION: unsure at all n locations

<400> SEQUENCE: 85

```
ctgaacccctt caaacaaacc tggaaggatc accataatta caaggatggg ggcagagaac      60
atgagagtga agttgcctca tcttatccgt gctgttcgca atgctggatt aattgtcaca     120
tggattactg atcctatgca tggaaacacc atcaaggccc cttgtggcct gaagactcgt     180
ncatttgact caattctggc tgaagtgcgc gcattcttcg atgtgcatga tcaagaaaga     240
agtcaccca gaggcatcca ccttgaaatg actgngcaga acgtgaccga gtgcattggt     300
ggatcacgga ctgtgacctt cgatgacctg acgaccgcta ccacacccac tgtgacccaa     360
ggctgaacgc c                                                         371
```

<210> SEQ ID NO 86
<211> LENGTH: 474
<212> TYPE: DNA
<213> ORGANISM: Zea mays

<400> SEQUENCE: 86

```
gggcgtgggt aggtcacgag caggctcggt cagcactcgc gggctgacac acgcgtcaag      60
acttcatcga gaaaagccgc gtgccggacc cgcagaggat gatccgcgcc tacgcacagt     120
cggtggcgac actcaacctg ctccgcgcgt cgccaccgg agggtacgct gccatgcagc     180
```

```
gcgtcactca gtggaacctc gatttcatgg atcacaacga gcaaggtgat aggtaccgtg      240
aattggccca taaggtggat gatgctcttg ggttcatgac tgcatcgggg cttacagtcg      300
accacccgat aatgacgact actgacttct ggacctcgca cgagtgcctt ctcttaccct      360
acgagcaggc tcttacccgt gaggattcca ccagtggcct tttctatgat tgttcggccc      420
acatgttgtg ggttggtgaa gcgaatcgac aactcgatgg acctcatgtt gaat            474
```

<210> SEQ ID NO 87
<211> LENGTH: 423
<212> TYPE: DNA
<213> ORGANISM: Zea mays

<400> SEQUENCE: 87

```
gaagactcgt ccatttgact ccattctggc tgaagtgcgt gccttcttcg atgtgcatga      60
ccaagaagga agccaccctg ggggcgtcca ccttgaaatg actgggcaga acgtgaccga     120
gtgcatcggt ggatcacgga ccgtgacctt cgacgatctg agcgaccgct accacaccca     180
ctgcgaccca aggctgaatg cctcccagtc cctggagctc gcctttatca tcgcagagag     240
gctgaggaag aggaggatgc gatcggggct caacagcagc ctgccactgc cgccactggc     300
tttctgagta gccggagcca acacaaagg agggtaggaa tagctgtggt gactcggaag      360
agaaagagac agtcgacgcc ttggtttgtt gatgcttagt gtggtgacct ggtggtggtg     420
gtg                                                                   423
```

<210> SEQ ID NO 88
<211> LENGTH: 369
<212> TYPE: DNA
<213> ORGANISM: Zea mays
<220> FEATURE:
<223> OTHER INFORMATION: unsure at all n locations

<400> SEQUENCE: 88

```
ctggctgaag tgcgtgcctt cttcgatgtg catgaccaag aaggaagcca ccctgggggc      60
gtccaccttg aaatgactgg gcagaacgtg accgagtgca tcggtggatc acggaccgtg     120
accttcgacg atctgagcga ccgctaccac ccactgcg acccaaggct gaatgcctcc       180
cagtccctgg agctcgcctt tatcatcgca gagaggctga ggaagaggag gatgcgatcg     240
gggctcaaca gcagcctgcc actgccgnca ctggcttttct gagtagccgg agccaaacac    300
aaagggaggt aggaatagct gtggtgacct cggaggagaa gagacagtcg acgccttgtt     360
tggtgatgc                                                             369
```

<210> SEQ ID NO 89
<211> LENGTH: 376
<212> TYPE: DNA
<213> ORGANISM: Zea mays

<400> SEQUENCE: 89

```
aattaagctg ccgagctaca ggggcgacaa cgtcaacggc gacgacttca ccgagaagag      60
ccgcgtgccg gacccgcaga ggatgatccg cgcctacgca cagtcggtgg cgacactcaa     120
cctgctccgc gcgttcgcca ccggagggta cgctgccatg cagcgcgtca ctcagtggaa     180
cctcgatttc atggatcaca acgagcaagg tgataggtac cgtgaattgg cccataggt      240 ggatgatgct cttgggttca tgactgcatc ggggcttaca gtcgaccacc cgataatgac      300
aactactgac tttctggact ccgcacaatt gcctccccta acccaacgaa caaggtccta     360
```

| | |
|---|---|
| acccttaagg atccaa | 376 |

<210> SEQ ID NO 90
<211> LENGTH: 205
<212> TYPE: DNA
<213> ORGANISM: Zea mays

<400> SEQUENCE: 90

| | |
|---|---|
| gaagttgcct catcttatcc gtgctgttcg caatgctgga ttaattgtca catggatggc | 60 |
| tgatcctatg catggaaaca ccatcaaggc cccttgtggc ctgaagactc gtccatttga | 120 |
| ctcaattctg gctgaagtgc gcgcattctt cgatgtgcat gatcaagaat gaagtcaccc | 180 |
| aggaggcatc caccttgaaa tgact | 205 |

<210> SEQ ID NO 91
<211> LENGTH: 391
<212> TYPE: DNA
<213> ORGANISM: Zea mays

<400> SEQUENCE: 91

| | |
|---|---|
| gagtcgctct gcactgcacg actcctcccc catctaccac tacctgtcta cctaccgagc | 60 |
| ccatcgactg cccctcgcaa cgcaatggcg ctcgccacca actccgccgc tgccgcagca | 120 |
| gctgccgtat ccggcggcgc ggcatcccag ccgcaccgcg cggccacgtt cctcccgctg | 180 |
| aagaggcgca ccatctccgc catccacgcc gccgacccgt ctaagaacaa cgggcccgcc | 240 |
| gtccccgcgg ccgccgccgc taagtcatct gcctctgcgg tggccacgcc ggagaagaat | 300 |
| ccggcggcgc cggtaaagtg gcggtcgac agctggaagt cgaagaaggc actgcagctc | 360 |
| ccagagtacc cgaaccagga ggagctggac a | 391 |

<210> SEQ ID NO 92
<211> LENGTH: 438
<212> TYPE: DNA
<213> ORGANISM: Zea mays

<400> SEQUENCE: 92

| | |
|---|---|
| gcggttgatt gatatattga atcccgaaaa cagggctggg agaataacca tcatcacaag | 60 |
| aatgggacct gaaaacatga gggtgaaact tccacacctg atacgcgctg tccgtggggc | 120 |
| cggtcagata gtaacatggg ttactgaccc aatgcatggg aacactatga aggccccttg | 180 |
| cggactcaaa acccgctcgt tcgacaggat tttgggtgag gtgcgtgcgt tctttgatgt | 240 |
| ccacgaacaa gaagggagcc accctggagg agtgcatcta gagatgactg acaaaatgt | 300 |
| tacagagtgc atcggcggtt cacgtacggt gaccttcgat gatctggggt cacgctacca | 360 |
| cacgcactgc gacccaaggc tcaatgcctc acagtctctg gagatggcat ttatcatcgc | 420 |
| cgagcgcctt aagaaaag | 438 |

<210> SEQ ID NO 93
<211> LENGTH: 335
<212> TYPE: DNA
<213> ORGANISM: Zea mays

<400> SEQUENCE: 93

| | |
|---|---|
| gtgacaagat ggacccagca gaacttgtgc ggttgattga tatattgaat cccgaaaaca | 60 |
| gggctgggag aataaccatc atcacaagaa tgggacctga aaacatgagg gtgaaacttc | 120 |
| cacacctgat acgcgctgtc cgtggggccg gtcagatagt aacatgggtt actgacccaa | 180 |
| tgcatgggaa cactatgaag gccccttgcg gactcaaaac ccgctcgttc gataggattt | 240 |

```
tgggtgaggt gcgtgcgttc tttgatgttc aacggaaaa cccaaaaaaa ggggaaaaaa    300 aaggggggggg gggggaaaaa aagggggcccc ccccc                             335

<210> SEQ ID NO 94
<211> LENGTH: 462
<212> TYPE: DNA
<213> ORGANISM: Zea mays

<400> SEQUENCE: 94
gcgggcgcta cgcgcaactt agctgcagtg cggtcagatt acgggcgagc acgcgtcgag    60
ccggacccgg tcccccgtc gccccggcc ccgccccctt cgccccggcc aacggcccc      120 cgaaccaatt ggccgttcgg aaccgggcgg ggcccccgg cgcaacagca gcccgagtac   180
ccggaacaag cggacctgga agacgtgctg cggacggtgg gaacgttccc gcccatcgtc   240
ttcgccggcg aggcgcgcac cctcgaggag cgcctcgcgg aggccgccgt cggccgggcc   300
ttcctcctcc agggcggcga ctgcgccgag agcttcaagg agttcaacgc caacaacatc   360
agggacacct tccgcgtcct cctgcaaatg tccgttgtgc tcatgttcgg aggccagatg   420
cctgtcgtca aggtgggaag aatggcaagt cagtttgcga ag                      462

<210> SEQ ID NO 95
<211> LENGTH: 436
<212> TYPE: DNA
<213> ORGANISM: Zea mays

<400> SEQUENCE: 95
cagagaacag cgaacaaggt gataggtaca tggagttggc tcaccgagtt gacgaagctt   60
tggggttcat gtcagctgct gggctcccctt tagatcaccc tataatgaca acagcagaat  120
tttggacgtc acatgagtgt cttcttctac cttatgagca agcgctcact cgtgaggatt   180
ccaccacggg cctctattat gactgctctg cccacttcct atgggtcgga gagcgcactc   240
gccagcttga tggtgctcac gttgagttcc ttcgaggcat tgccaaccct cttggtatca   300
aggttagtga caagatggac ccagcagaac ttgtgcggtt gattgatata ttgaatcccg   360
aaaacagggc tgggagaata accatcatca caagaatggg acctgaaaac atgagggtga   420
aacttccaca cctgat                                                    436

<210> SEQ ID NO 96
<211> LENGTH: 472
<212> TYPE: DNA
<213> ORGANISM: Zea mays

<400> SEQUENCE: 96
ggttaatagg tacatggagt tggctcaccg agttgacgaa gctttggggt tcatgtcagg   60
tgctgggctc cctttagatc accctataat gacaacagca gaattttgga cgtcacatga   120
gtgtcttctt ctaccttatg agcaagcgct cactcgtgag gattccacca cgggcctcta   180
ttatgactgc tctgcccact tcctatgggt cggagagcgc actcgccagc ttgatggtgc   240
tcacgttgag ttccttcgag gcattgccaa ccctcttggt atcaaggtta gtgacaagat   300
ggacccagca gaacttgtgc ggttgattga tatattgaat cccgaaaaca gggctgggag   360
aataaccatc atcacaagaa tgggacctga aaacatgagg gtgaaacttc cacacctgat   420
acgcgctgtc ccgtgggccg gtcagatagg tacatggggtt actgacccaa tg           472

<210> SEQ ID NO 97
```

<211> LENGTH: 427
<212> TYPE: DNA
<213> ORGANISM: Zea mays

<400> SEQUENCE: 97

```
tgacctgagc gaccgctacc acacccactg tgacccaagg ctgaacgcct cccagtcgct      60
ggagctcgcc ttcatcattg cagagaggct caggaagagg acgatgccgt cggggctcaa     120
caacagcctg cctctgccac cactggcttt ctaagtagcc gaagctgaac agagaaggta     180
gagggatagt tgcggcgact cgaaagatta cgcctgttta tttgctgatg cttggtgtgg     240
aggcctggcg ggcgctcttg gcacaagtta catgctgggg agctatagga gggtacctgt     300
tgcgttgtgg aagacagtag ctagtattat gtgttgtaat tgtatgcctt cgattcatgt     360
tctgagtgcg tgacttgtcg actttgctgc ttctggggtt ctgaccttgg taaggagaga     420
atataga                                                              427
```

<210> SEQ ID NO 98
<211> LENGTH: 220
<212> TYPE: DNA
<213> ORGANISM: Zea mays

<400> SEQUENCE: 98

```
cggagaatga gctgcttgtc ccactgaagg ctgctctcct agatattggg aaagaaagga      60
aggaagcatg gattagttgg gtacagactt atattgaaga gctggtggag agcggcgttc     120
ctgatgaaga aaggaaagcc gcgatgaact ctgttaatcc aaagtatatt ctccgcaact     180
atctctgcca gtacactatc gacgcagctg cagcaggcga                           220
```

<210> SEQ ID NO 99
<211> LENGTH: 293
<212> TYPE: DNA
<213> ORGANISM: Zea mays

<400> SEQUENCE: 99

```
acctggtgca atagtttgtc gtgtagcacc gtcttttta cgttttggtt cgtatcagat       60
acacgcttca aggggcaaag aggacattga gattgttcgt cgtttggcag actacacgat     120
acatcatcac tttccacatc ttgaaaatat gaaaaagagt gaaggtttgt cattcgagac     180
agctatagga gattccccaa caatagatct cacatcaaac aaatatgcag cttgggcagt     240
tgaggtggcg gagaggactg cttacttgat agctagatgg caaggtgttg gct            293
```

<210> SEQ ID NO 100
<211> LENGTH: 261
<212> TYPE: DNA
<213> ORGANISM: Glycine max

<400> SEQUENCE: 100

```
ccgacaagcc caagccccaa gcccaacaat ctgcatcccc ggccgcggcc cgtgcaacca      60
aatgggccgt ggacagctgg aagtccaaga aggccctgca gctgcccgaa taccccaacc     120
aggaggatct cgaggccgtc ctccgcaccc tcgacgcttc cgctcacatc gtcttcgccg     180
gcgaggcccg gacactcgag gagcacctcg ccgatgccgc catgggaaat gccttcttcc     240
tcaatggcgg agactgtgcc g                                               261
```

<210> SEQ ID NO 101
<211> LENGTH: 257
<212> TYPE: DNA
<213> ORGANISM: Glycine max

```
<400> SEQUENCE: 101
caccttcatc atggctgagt tcttcttccc aaacaagtcg gtcggcgacc agaacagtgt      60
cgaggattgg cgcatccgcg gcatgactcc tttgactcct cccgatctcc tccagcatga     120
aattcgccag acagacaagt caagagagac tgtcgtcaag tcccgcaaag aggctgtcga     180
ggtcgtacac ggcgtggacg agaagaggag actcatggtt tcattggtcc ttgctccatc     240
cacgaccctg ccatggc                                                    257

<210> SEQ ID NO 102
<211> LENGTH: 236
<212> TYPE: DNA
<213> ORGANISM: Glycine max

<400> SEQUENCE: 102
ctcccttatg agcaagcact tactagggag gattctacta ctgggcttca ttatgattgc      60
tcagctcaca tgctatgggt tggggaacgt acccgccaac ttgatggtgc tcatgttgaa     120
ttcttgagag gagttgctaa tccacttggc atcaaggtga gtgataagat ggttcccgat     180
gaacttgtta agctgataga tattctgaac cctaaaaaca gcctggaag aattac          236

<210> SEQ ID NO 103
<211> LENGTH: 245
<212> TYPE: DNA
<213> ORGANISM: Glycine max

<400> SEQUENCE: 103
cgccggtgag gccaggacat tggaggagca tctcgccgag gccgccatgg gaaatgcctt      60
cctcctccag ggcggagact gtgctgagag cttcaaggag ttcaatgcca acaacatccg     120
tgacaccttc cgcatcatcc tccagatgag cgtcgtcatg atgttcggcg gccaaatgcc     180
tgtcatcaag gtggggagaa tggcggggca atttgcaaag cctcgttcgg attcgtttga     240
ggagc                                                                 245

<210> SEQ ID NO 104
<211> LENGTH: 255
<212> TYPE: DNA
<213> ORGANISM: Glycine max

<400> SEQUENCE: 104
ttttagaact ttaatctcaa aatgtattca atattctttt gaaatataa ttcataaacg       60 attttaaaac accacctcgc cgaggccgcc atgggaaatg ccttcctcct ccagggcgga     120
gactgtgccg agagcttcaa ggagttcaat gccaacaaca tccgtgacac cttccgcatc     180
atcctccaga tgagcgtcgt catgatgttc ggcggccaaa tgcccgtcat caaggtgggg     240
agaatggcgg ggcaa                                                      255

<210> SEQ ID NO 105
<211> LENGTH: 254
<212> TYPE: DNA
<213> ORGANISM: Glycine max

<400> SEQUENCE: 105
aagatgacgg gtcagaatgt gaccgagtgc attggtgggt caaggacggt cacatttgat      60
gacttgagct cacgtaccca cacacactgt gacccaaggc tcaatgcttc acaatctctt     120
gagcttgcta tcatcatcgc cgagcgtttg agaaagagca ggatcagatc gcagcaacct     180
```

```
cttgcccctc taggagtgta aaagtgcctt caaaaccaac aagagaaaga tattttgtt      240 cttttttttt tttg                                                        254

<210> SEQ ID NO 106
<211> LENGTH: 278
<212> TYPE: DNA
<213> ORGANISM: Glycine max

<400> SEQUENCE: 106
ggagaatggc ggggcaattt gcaaagcctc gttcggattc gtttgaggag aagaatggcg      60
tgaagcttcc gagttacaga ggggataaca ttaacgagac tctttcgac gagaagtcga      120 ggattccgga tccgcagagg atgattaggg cttattgcca agccgcggcc acgctgaatc      180
ttctcagagc ttttgccacc ggtggttatg ctgctatgca gagggttact cagtggaatt      240
tggacttcac ggatcacagc gaacaggag ataggtac                              278

<210> SEQ ID NO 107
<211> LENGTH: 267
<212> TYPE: DNA
<213> ORGANISM: Glycine max

<400> SEQUENCE: 107
attcgtttga ggagaagaat ggcgtgaagc ttccgagtta cagaggggat aacattaacg      60
gagactcttt cgacgagaag tcgaggattc cggatccgca gaggatgatt agggcttatt      120
gccaagccgc ggccacgctg aatcttctca gagcttttgc caccggtggt tatgctgcta      180
tgcagagggt tactcagtgg aatttggact tcacggatca cagcgaacag ggagataggt      240
accgagagct tgctaaccga gttgatg                                          267

<210> SEQ ID NO 108
<211> LENGTH: 267
<212> TYPE: DNA
<213> ORGANISM: Glycine max

<400> SEQUENCE: 108
tcggcggcca aatgcccgtc atcaaggtgg ggagaatggc ggggcaattt gcgaagcgag      60
gtcggattcg tttgaggaga gaacggcgt gaagcttccg agttacagag gggacaacat      120
taacggagac tcctttgacg agaagtcgag gattccggat ccgcagagga tgattagggc      180
ttattgccaa gccgcggcga cgctgaatct tctcagagct ttcgccaccg gtggttatgc      240
tgctatgcag agggttactc agtggaa                                          267

<210> SEQ ID NO 109
<211> LENGTH: 247
<212> TYPE: DNA
<213> ORGANISM: Glycine max

<400> SEQUENCE: 109
gggagaatgg cggggcaatt tgcaaagcct cgttcggatt cgtttgagga gaagaatggc      60
gtgaagcttc cgagttacag aggggataac attaacggag actctttcga cgagaagtcg      120
aggattccgg atccgcagag gatgattagg gcttattgcc aagccgcggc cacgctgaat      180
cttctcagag cttttgccac cggtggttat gctgctatgc agagggttac tcagtggaat      240
ttggact                                                                247

<210> SEQ ID NO 110
<211> LENGTH: 263
```

```
<212> TYPE: DNA
<213> ORGANISM: Glycine max

<400> SEQUENCE: 110
catccgtgac accttccgca tcatcctcca gatgagcgtc gtcatgatgt tcggcggcca      60
aatgcccgtc atcaaggtgg ggagaatggc ggggcaattt gcgaaccgag gtcggattcg     120
tttgaggaga gaacggcgt gaagcttccg agttacagag gggacaacat taacggagac     180
tcctttgacg agaagtcgag gattccggat ccgcagagga tgattagggc ttattgccaa    240
gccgcggcga cgctgaatct tct                                             263

<210> SEQ ID NO 111
<211> LENGTH: 247
<212> TYPE: DNA
<213> ORGANISM: Glycine max

<400> SEQUENCE: 111
ctcgagccga ttcggctcga ggaggggata acattaacgg agactacttt cgacgagaag      60
tcgcggattc cggatccgca gaagatgatt agggcttatt gccaagccgc ggccacgctg    120
aatcttctca gagcttttgc caccggtggt tatgctgcta tgcagagggt tactcagtgg    180
aatttggact tcacggatca cagcgaacag ggagataggt accgagagct tgctaaccga    240
gttgatg                                                               247

<210> SEQ ID NO 112
<211> LENGTH: 217
<212> TYPE: DNA
<213> ORGANISM: Glycine max
<220> FEATURE:
<223> OTHER INFORMATION: unsure at all n locations

<400> SEQUENCE: 112
aatttgtaaa gctctcgact cggtattcgt tttgaggaga agtaatggtc gtgaagcttt      60
ccgagttaca gaggtggata actgttaacg tgtagactct ttcgacgtat tagtcgagtg    120
attccggatc cgcataggat gatnagggct tatcgccatt ccgcggctac gctgaatctt    180
ctcatagctt tttccaccgg tggttatgct gctatgc                              217

<210> SEQ ID NO 113
<211> LENGTH: 228
<212> TYPE: DNA
<213> ORGANISM: Glycine max

<400> SEQUENCE: 113
cgaggtcgga ttcgtttgag gagaagaacg gcgtgaagct tccgagttac agatgggaca      60
acattaacgg agactcgttt gacgataagt cgaggattcc ggatccgcag aggatgatta    120
gggcttattg ccaagccgcg cgacgctga atcttctcag agctttcgcc accggtggtt     180
atgctgctat gcacacggtt actcagtgga atttggactt cacggatc                 228

<210> SEQ ID NO 114
<211> LENGTH: 310
<212> TYPE: DNA
<213> ORGANISM: Glycine max
<220> FEATURE:
<223> OTHER INFORMATION: unsure at all n locations

<400> SEQUENCE: 114
tccaaacaca ccaattgcat ttgcattacc attcacaatg gcaatctcct ccacttccaa      60
```

```
ctccctcatt cccaccaaat ctctantccc ccaatcccac cccctcattc ccaacaccag      120
gcccgccctc cggcccaagc ccggcccatc accttccatc ntcgccgttc acgccgccga      180
gcccgccaaa aaccccgtcg tcaccgacaa gcccaagccc caagcccaac aacctccccc      240
ggcctcggcc cgggcaacga aatgggccgt ggacagctgg aagtnccaga aagccctgca      300
gctgcccgaa                                                            310
```

<210> SEQ ID NO 115
<211> LENGTH: 284
<212> TYPE: DNA
<213> ORGANISM: Glycine max

<400> SEQUENCE: 115

```
aaacacacca attgcatttg cattaccatt cacaatggca atctcctcca cttccaactc       60
cctcattccc accaaatctc taatccccca atcccacccc ctcattccca acaccaggcc      120
cgccctccgg cccaagcccg gcccatcccc ttccatcttc gccgttcacg ccgccgagcc      180
cgccaaaaac cccgtcgtca ccgacaagcc caagccccaa gccaacaac ctcccccggc      240 ctcggcccgg gcaacgaaat gggccgtgga cagctggaag tcaa                      284
```

<210> SEQ ID NO 116
<211> LENGTH: 286
<212> TYPE: DNA
<213> ORGANISM: Glycine max

<400> SEQUENCE: 116

```
cacaatggca atctcctcca cttccaactc cctcattccc accaaatctc taatccccca       60
atcccacccc ctcattccca acaccaggcc cgccctccgg cccaagcccg gcccatcccc      120
ttccatcttc gccgttcacg ccgccgagcc cgccaaaaac cccgtcgtca ccgacaagcc      180
caagccccaa gccaacaac ctcccccggc ctcggcccgg gcaacgaaat gggccgtgga      240
cagctggaag tcaaagaaag ccctgcagct gcccgaatac ccgagc                    286
```

<210> SEQ ID NO 117
<211> LENGTH: 285
<212> TYPE: DNA
<213> ORGANISM: Glycine max

<400> SEQUENCE: 117

```
gggagaagct cgctcaggct gccatgggga acgcttttct ccttcagggc ggtgattgcg       60
ccgagagctt caaggaattc actgccaaca acatccgtga caccttccgt gtcatccttc      120
aaatgggtgt ggtcctcatg ttcggtggcc aaatgcccgt tatcaaggtg gggagaatgg      180
caggtcaatt tgcaaagccg agatccgatt catttgagga gaagaatgga gtgacgctcc      240
cgattacagg ggtgataatg tgaatggcga tgcatttgac gcggc                     285
```

<210> SEQ ID NO 118
<211> LENGTH: 176
<212> TYPE: DNA
<213> ORGANISM: Glycine max

<400> SEQUENCE: 118

```
atccttcaaa tgggtgtggt cctcatgttc ggtggccaaa tgcccgttat caaggtgggg       60
agaatggcag gtcaatttgc aaagccgaga tccgattcat ttgaggagaa gaatggagtg      120
acgctcccga gttacagggg tgataatgtg aatggcgatg catttgacgc ggcatc         176
```

<210> SEQ ID NO 119
<211> LENGTH: 249
<212> TYPE: DNA
<213> ORGANISM: Glycine max

<400> SEQUENCE: 119

```
cagatgcgaa tgaattggac ctagtcctcc aaaccctctc ttcttttccc ccaatcgtct      60
tcgccggcga ggcgaggaat ctggaggaga agctcgctca ggctgccatg gggaacgctt     120
ttctccttca gggcggtgat tgcgccgaga gcttcaagga attcactgcc aacaacatcc     180
gtgacaccta ccgtgtcatc cttcaaatgg gtgtggtcct catgttcggt ggccaaatgc     240
ccgttatca                                                              249
```

<210> SEQ ID NO 120
<211> LENGTH: 269
<212> TYPE: DNA
<213> ORGANISM: Glycine max

<400> SEQUENCE: 120

```
cccagatgcg aatgaattgg acctagtcct ccacaccctc tcttcttttc ccccaatcgt      60
cttcgccggc gaggcgagga atctggagga gaagctcgct caggctgcca tcgggaacgc     120
ttttctcctt cagggcggtg attgcgccga gagcttcaag gaattcactg ccaacaacat     180
ccgtgacacc ttccgtgtca tccttcaaat gggtgtggtc tcatgttcg gtggccaaat      240 gcccgttatc aaggtgggga gaatggcag                                       269
```

<210> SEQ ID NO 121
<211> LENGTH: 270
<212> TYPE: DNA
<213> ORGANISM: Glycine max
<220> FEATURE:
<223> OTHER INFORMATION: unsure at all n locations

<400> SEQUENCE: 121

```
gaacgtaccc gccaacttga tggtgctcat gttgaattct tgagaggagt tgctaatcca      60
cttggcatca aggtgagtga taagatggtt cccgatgaac ttgttaagct gatagatatt     120
ctgaacccta aaaacaagcc tggaagaatt acagtcattg ttagaatggg agctgagaat     180
atgcgagtga agcttccaca tcttatcagg gcagttcgca gagcaggtca attgtcactt     240
gggttagtga cnccatgcat gggaacacca                                      270
```

<210> SEQ ID NO 122
<211> LENGTH: 255
<212> TYPE: DNA
<213> ORGANISM: Glycine max
<220> FEATURE:
<223> OTHER INFORMATION: unsure at all n locations

<400> SEQUENCE: 122

```
aatccacttg gcatcaaggt gagtgataag atggttcccg atgaacttgt taagctgata      60
gatattctga accctaaaaa caagcctgga agaattacag ttattgttag aatgggagct     120
gagaatatgc gagtgaagct tccacatctt atcagggcag ttcgcagagc aggtcaaatt     180
gtcacttggg ttagtgaccc catgcatggg aacaccatta agctccatc tggacttaaa      240 accgctcttt tgang                                                      255
```

<210> SEQ ID NO 123
<211> LENGTH: 266
<212> TYPE: DNA

<213> ORGANISM: Glycine max
<220> FEATURE:
<223> OTHER INFORMATION: unsure at all n locations

<400> SEQUENCE: 123

| | |
|---|---|
| tgaaccctaa aaacaagcct ggaagaatta cagtcattgt tagaatggga gctgagaata | 60 |
| tgcgagtgaa gcttcncaca tcttatcagg gcngttcgca gagcaggtca aattgtcact | 120 |
| tggtnnagtg accccatgca tgggaacacc attaaagctc catctggact taaaacccgc | 180 |
| tnttntgatg caataagggc tgagctgagg gcnttnnncn nngtgcagat caagaaggaa | 240 |
| gctacccagg aggggttcat tagaga | 266 |

<210> SEQ ID NO 124
<211> LENGTH: 258
<212> TYPE: DNA
<213> ORGANISM: Glycine max

<400> SEQUENCE: 124

| | |
|---|---|
| ggttactcag tggaatttgg acttcacgga tcacagcgaa cagggagata ggtaccgaga | 60 |
| gcttgctaac cgagttgatg aggctcttgg attcatggct gctgctgggc tcacagtgga | 120 |
| ccatcccata atgagaacaa ctgaattctg acatctcat gagtgcttat tgttgcctta | 180 |
| tgaacaatcc ctcaccaggt tggattcaac ttctggtctc tactatgact gttcagccca | 240 |
| tatgctctgg gttgggga | 258 |

<210> SEQ ID NO 125
<211> LENGTH: 241
<212> TYPE: DNA
<213> ORGANISM: Glycine max

<400> SEQUENCE: 125

| | |
|---|---|
| ggttactcag tggaatttgg acttcacgga tcacagcgaa cagggagata ggtaccgaga | 60 |
| gcttgctaac cgagttgatg aggctcttgg attcatggct gctgctgggc tcacagtgga | 120 |
| ccatcccata atgagaacaa ctgaattctg acatctcat gagtgcttat tgttgcctta | 180 |
| tgaacaatcc ctcaccaggt tggattcaac ttctggtctc tactatgact gttcagccca | 240 |
| t | 241 |

<210> SEQ ID NO 126
<211> LENGTH: 228
<212> TYPE: DNA
<213> ORGANISM: Glycine max

<400> SEQUENCE: 126

| | |
|---|---|
| agtatcgaga gcttgctaac cgagttgatg aggctcttgg attcatggct gctgctgggc | 60 |
| tcacagtgga ccatcccata atgagaacaa ctgaattctg acatctcat gagtgcttat | 120 |
| tgttgcctta tgaacaatcc ctcaccaggt tggattcaac ttctggtctc tactatgact | 180 |
| gttcagccca tatgctctgg gttggggaac gaaccaggca gcttgatg | 228 |

<210> SEQ ID NO 127
<211> LENGTH: 253
<212> TYPE: DNA
<213> ORGANISM: Glycine max

<400> SEQUENCE: 127

| | |
|---|---|
| ttcagtggaa tttggacttc acggatcaca gcgaacaggg agataggtac cgagagcttg | 60 |
| ctaaccgagt tgatgaggcc cttggattca tggctgctgc tgggctcacg gtggaccatc | 120 |

```
ccataatgag aacaactgaa ttctggacat ctcatgagtg cttattgttg ccttatgaac      180
aatccctcac aaggttggat tcaacttctg gtctctacta tgactgttca gcccatatga      240
tctgggttgg aga                                                         253

<210> SEQ ID NO 128
<211> LENGTH: 289
<212> TYPE: DNA
<213> ORGANISM: Glycine max

<400> SEQUENCE: 128
tacggctgcg agaagacgac agaaagggag gtaccgagag cttgctaacc gagttgatga      60
ggcccttgga ttcatggctg ctgctgggct cacggtggac catcccataa tgagaacaac      120
tgaattctgg acatctcatg agtgcttatt gttgcattat gaacaatccc tcacaaggtt      180
ggattcaact tctggtctct actatgactg ttcagcccat atgatctggg ttggagaacg      240
aaccaggcag cttgatggtg cccatgttga gtttctaaga ggagttgct                  289

<210> SEQ ID NO 129
<211> LENGTH: 295
<212> TYPE: DNA
<213> ORGANISM: Glycine max
<220> FEATURE:
<223> OTHER INFORMATION: unsure at all n locations

<400> SEQUENCE: 129
gaaccaggca gcttgatggt gcccatgttg agtttctaag aggagttgct aatcccttgg      60
gaattaaggt aagtgacaag atggatccaa atgagctagt taaactcatt gagatcttga     120
atcctcaaaa caaagcagga agaattactg tgatcacgng atgggagctg aaaatatgag     180
ggtgaagctt ccacatctca tcagggcagt gcgcagagca ggccaaattg tcacttgggt     240
cagtgatcct atgcatggaa acaccattaa ggctccctgt ggtcttaaaa ctcgc          295

<210> SEQ ID NO 130
<211> LENGTH: 269
<212> TYPE: DNA
<213> ORGANISM: Glycine max

<400> SEQUENCE: 130
ttccacatct catcagggca gtgcgcagag caggccaaat tgtcacttgg gtcagtgatc      60
ctatgcatgg aaacaccatt aaggctccct gtggtcttaa aactcgcccc ttcgattcca     120
tcagggccga agtgagagca ttcttcgacg tacacgagca agaggaagc cacccaggag      180 gggttcatct agagatgacg ggtcagaatg tgaccgagtg cattggtggg tcaaggacgg     240
tcacatttga tgacttgagc tcacgttac                                       269

<210> SEQ ID NO 131
<211> LENGTH: 269
<212> TYPE: DNA
<213> ORGANISM: Glycine max

<400> SEQUENCE: 131
gaacaactga attctggaca tctcatgagt gcttattgtt gccttatgaa caatccctca      60
ccaggttgga ttcaacttct ggtctctact atgactgttc agcccatatg ctctgggttg     120
gggaacgaac caggcagctt gatggtgccc atgtcgagtt tctaagagga gttgctaatc     180
ccttgggaat taaggtaagt gacaagatgg atccaaatga gcttgttaga ctcattgaga     240
```

```
tcttgaatcc ccaaaacaaa ccagggaga                                       269
```

<210> SEQ ID NO 132
<211> LENGTH: 259
<212> TYPE: DNA
<213> ORGANISM: Glycine max

<400> SEQUENCE: 132

```
cggctcgagt gaaatatga gggtgaagct tccacatctc atcagggcag tgcgcagagc        60
aggccaaatt gtcacttggg tcagtgatcc tatgcatgga acaccatta aggctccctg       120 tggtcttaaa actcgcccct tcgattccat cagggccgaa gtgagagcat tcttcgacgt      180
acacgatcaa gaaggaagcc acccaggagg ggttcatcta gagatgacgg gtcagaatgt      240
gacctagtgc attggtggg                                                   259
```

<210> SEQ ID NO 133
<211> LENGTH: 243
<212> TYPE: DNA
<213> ORGANISM: Glycine max

<400> SEQUENCE: 133

```
tggacatctc atgagtgctt attgttgcct tatgaacaat ccctcaccag gttggattca       60
acttctggtc tctactatga ctgttcagcc catatgctct gggttgggga acgaaccagg      120
cagcttgatg gtgcccatgt cgagtttcta agaggagttg ctaatccctt gggaattaag      180
gtaagtgaca agatggatcc aaatgagctt gttagactca ttgagatctt gaatccccaa      240
aac                                                                    243
```

<210> SEQ ID NO 134
<211> LENGTH: 294
<212> TYPE: DNA
<213> ORGANISM: Glycine max
<220> FEATURE:
<223> OTHER INFORMATION: unsure at all n locations

<400> SEQUENCE: 134

```
gagcttgtta gactcantgn natcttgaat ccccaaaaca aaccaggag nataactgtg        60 attacnanga tgggagctgn aaatatgagg gtgaagcttc acatcttca tcagggcagt      120 gcgcagagca gggcaaattg tcacctgggt cagtgatcta tgcatggaaa caccattaag     180
gctccatgng gtcttaaaac ttcgcccctt cgattcatca gggctgaagt gagagcattc     240
tttgnngtgc acgagcaaga aggaagccac ccaggangg ttcatctaga gatg            294
```

<210> SEQ ID NO 135
<211> LENGTH: 278
<212> TYPE: DNA
<213> ORGANISM: Glycine max

<400> SEQUENCE: 135

```
gttgagaaga gagaatggct gtggcgtcgt catcatccct tatcacgttg aaggtgaaac       60
cttgcatttt cgggtctcct cggagatccg cggtggttcg gaattgtgcg aagtcaacgg     120
cggggacaat atcgacgagt tggagcctgg acagctggag ggcgaagaag gcgcttcagc     180
ttccggagta cccagatgcg aatgaattgg acctagtcct ccaaaccctc tcttcttttc     240
ccccaatcgt cttcgccggc gaggcgagga atctggag                             278
```

<210> SEQ ID NO 136
<211> LENGTH: 254

```
<212> TYPE: DNA
<213> ORGANISM: Glycine max

<400> SEQUENCE: 136
attttgttga gaagagagaa tggctgtggc gtcgtcatca tcccttatca cgttgaaggt      60
gaaaccttgc attttcgggt ctcctcggag atccgcggtg gttcggaatt gtgcgaagtc    120
aacggcgggg acaatatcga cgagttggag cctggacagc tggagggcga agaaggcgct    180
tcagcttccg gagtacccag atgcgaatga attggaccta gtcctccaaa ccctctcttc    240 ttttcccca atcg                                                        254

<210> SEQ ID NO 137
<211> LENGTH: 256
<212> TYPE: DNA
<213> ORGANISM: Glycine max

<400> SEQUENCE: 137 tgttttttg ttgagaagag agaatggctg tggcgtcgtc atcatcccct tatcacgttga     60 aggtgaaacc ttgcattttc gggtctcctc ggagatccgc ggtggttcgg aattgtgcga    120
agtcaacggc ggggacaata tcgacgagtt ggagcctgga cagctggagg gcgaagaagg    180
cgcttcagct tccggagtac ccagatgcga atgaattgga cctagtcctc caaaccctct    240 cttctttttcc cccaat                                                    256

<210> SEQ ID NO 138
<211> LENGTH: 245
<212> TYPE: DNA
<213> ORGANISM: Glycine max

<400> SEQUENCE: 138
ttttgttgag aagagagaat ggctgtggcg tcgtcatcat cccttatcac gttgaaggtg     60
aaaccttgca ttttcgggtc ctcggaga tccgcggtgg ttcggaattg tgcgaagtca      120
acggcgggga caatatcgat cagttggagc ctggacagct ggagggcgaa gaaggcgctt    180
cagcttccgg agtacccaga tgcgaatgaa ttggacctag tcctccaaac cctctcttct    240
tttcc                                                                 245

<210> SEQ ID NO 139
<211> LENGTH: 240
<212> TYPE: DNA
<213> ORGANISM: Glycine max

<400> SEQUENCE: 139
tttgtttttt tgttgagaag agaatggctg tggcgtcgtc atcatccc ttatcacgtt       60 gaaggtgaaa ccttgcattt tcgggtctcc tcggagatcc gcggtggttc ggaattgtgc    120
gaagtcaacg gcggggacaa tatcgacgag ttggagcctg gacagctgga gggcgaagaa    180
ggcgcttcag cttccggagt acccagatgc gaatgaattg gacctagtcc tccaaaccct    240

<210> SEQ ID NO 140
<211> LENGTH: 258
<212> TYPE: DNA
<213> ORGANISM: Glycine max
<220> FEATURE:
<223> OTHER INFORMATION: unsure at all n locations

<400> SEQUENCE: 140
gtttttttgt tgagaagaga gaatggctgt ggcgtcgtca tcatcccta tcacgttgaa      60
```

```
ggtgaaacct tgcatttcg ggtctcctcg gagatccgcg gtggttcgga attgtggcga      120
agtcaacggc ggggacaata tcgacgagtt ggagcctgga cagctggagg gcgaagaagg    180
cgcttcagct tccggagtac ccagatgcga atgaattgga ctaatncttc aaaacnctct    240
cttctttccc ccaatngt                                                    258

<210> SEQ ID NO 141
<211> LENGTH: 247
<212> TYPE: DNA
<213> ORGANISM: Glycine max

<400> SEQUENCE: 141
gttggtttgt ttttttgttg agaagagaga atggctgtgg cgtcgtcatc atcccttatc     60
acgttgaagg tgaaacttgc attttcgggt ctcctcggag atccgcggtg gttcggaatt    120
gtgcgaagtc aacggcgggg acaatatcga cgagttggag cctggacagc tggagggcga    180
agaaggcgct tcagcttccg gagtacccag atgcgaatga attggaccta gtcctccaaa    240
ccctctc                                                                247

<210> SEQ ID NO 142
<211> LENGTH: 251
<212> TYPE: DNA
<213> ORGANISM: Glycine max

<400> SEQUENCE: 142
ctcgagccga atcggctcga ggttttttg ttgagaagag agaacggctg tggcgtcgtc      60 atcatcccctt atcacgttga cggtgaaacc ttgcattttc gggtctcctc ggagatccgc   120
ggtggttcgg aattgtgcga agtcaacggc ggggacaata tcgacgagtt ggagcctgga   180
cagctggagg gcgaagaagg cgcttcagct tccggagtac ccagatgcga atgaattgga   240
cctagtcctc c                                                          251

<210> SEQ ID NO 143
<211> LENGTH: 352
<212> TYPE: DNA
<213> ORGANISM: Glycine max

<400> SEQUENCE: 143
gaatggagtg acgctcccga gttacagggg tgataatgtg aatggcgatg catttgacgc     60
ggcatctaga atccccgatc cacagaggat gataagagcc tactgccaat ctgtgtctac   120
tctgaacctt ttgcgggcat ttgccacggg aggttatgct gccatgcaaa gggttaatca   180
atggaatctt gatttcatgg agcatagtga acagggagac aggtaccgtg aattagccca   240
tagagtggat gaggctcttg gcttcatgaa tgttgctggg ctcacagccg accatcccat   300
catgagtaca acagactttt ggacctccca tgagtgtttg cttctccctt at             352

<210> SEQ ID NO 144
<211> LENGTH: 239
<212> TYPE: DNA
<213> ORGANISM: Glycine max

<400> SEQUENCE: 144
caaagggtta atcaatggaa tcttgatttc atggagcata gtgaacaggg agacaggtac     60
cgtgaattag cccatagagt ggatgaggct cttggcttca tgaatgttgc tgggctcaca   120
gccgaccatc ccatcatgag tacaacagac ttttggacct cccatgagtg tttgcttctc   180
ccttatgagc aagcacttac tagggaggat tctactactg ggcttcatta tgattgctc     239
```

<210> SEQ ID NO 145
<211> LENGTH: 264
<212> TYPE: DNA
<213> ORGANISM: Glycine max

<400> SEQUENCE: 145
cagctggaag tcaaagaaag ccctgcagct gcccgaatac ccgagccagg aggagctgga      60
gtccgtcctc aaaaccctcg aggcttttcc tccaatcgtc ttcgccggtg aggccaggac     120
attggaggag catctcgccg aggccgccat gggaaatgcc ttcctcctcc agggcggaga     180
ctgtgctgag agcttcaagg agttcaatgc caacaacatc cgtgacacct tccgcatcat     240
cctccagatg agcgtcgtca tgat                                            264

<210> SEQ ID NO 146
<211> LENGTH: 223
<212> TYPE: DNA
<213> ORGANISM: Glycine max

<400> SEQUENCE: 146
acgaaatggg ccgtggacag ctggaagtca agacagccc tgcagctgcc cgaatacccg       60
agccaggagg agctggagtc cgtcctcaaa accctcgagg cttttcctcc aatcgtcttc     120
gccggtgagg ccaggacatt ggaggagcat ctcgccgagg ccgccatggg aaatgccttc     180
ctcctccagg gcggagactg tgctgagagc ttcaaggagt cat                       223

<210> SEQ ID NO 147
<211> LENGTH: 224
<212> TYPE: DNA
<213> ORGANISM: Glycine max

<400> SEQUENCE: 147
ccactaaagt ctgtactgtt agatattggt aaagagcgta aggaagcatg gaccagttgg      60
ttgaaagctt atatacatga ggtctctacc agtgggatac ctgatgacga aggaagatc     120 tcgatggatt cagtgaatcc taaatatata ctgaggaact atctctgcca gactgcaatt     180
gatgctgcag aaataggtga ttttggagag gttcgcagcc tgct                      224

<210> SEQ ID NO 148
<211> LENGTH: 265
<212> TYPE: DNA
<213> ORGANISM: Glycine max

<400> SEQUENCE: 148
acggaagacg acagaagggg acgaaaggaa gatctcgatg gattcagtga atcctaaata      60
tatactgagg aactatctct gccagactgc aattgatgct gcagaaatag gtgattttgg     120
agaggttcgc agcctgctca aattagtgga gcatccgtat gatgagcaac aggaatgga     180 aaaatatgct cgcttgcccc cagcttgggc atatcgacca ggtgtatgca tgctttcttg     240
ttcttcatga ggctcccatt taggt                                           265

<210> SEQ ID NO 149
<211> LENGTH: 276
<212> TYPE: DNA
<213> ORGANISM: Glycine max
<220> FEATURE:
<223> OTHER INFORMATION: unsure at all n locations

<400> SEQUENCE: 149

```
cccaggtcga agatactgtt ttccnaacca gcctgacatt ggtttgtgga atattgcaca      60
gttcacaaca acactacaan ctgctcattt aataaatgan aaagaggcca actatgctat    120
ggaaagatat ggaacgagat ttatggatga ttatcaggtt acaatgacca aaaagcttgg    180
cctccctaag tataataagc agatgattaa taaacttctt agcaatatgg ctgttgacaa    240
agttgattac acanacttct ttcgtacgct ttcaac                              276
```

<210> SEQ ID NO 150
<211> LENGTH: 266
<212> TYPE: DNA
<213> ORGANISM: Glycine max

<400> SEQUENCE: 150

```
gttttgcaaa ccagcctgac attggtttgt ggaatattgc acagttcaca acaacactac     60
aagctgctca tttaataaat gaaaagagg ccaactatgc tatggaaaga tatggaacga    120
gatttatgga tgattatcag gttacaatga ccaaaaagct tggcctccct aagtataata    180
agcagatgat taataaactt cttagcagta tggctgttga caagttgat tacacaaact    240 tctttcgtac gctttcaaat gttaaa                                         266
```

<210> SEQ ID NO 151
<211> LENGTH: 392
<212> TYPE: DNA
<213> ORGANISM: Glycine max

<400> SEQUENCE: 151

```
gttcccgatg aacttgttaa gctgatagat attctgaacc ctaaaacaa gcctggaaga     60 attacagtca ttgttagaat gggagctgag aatatgcgag tgaagcttcc acatcttatc   120
agggcagttc gcagagcagg tcaaattgtc acttgggtta gtgaccccat gcatgggaac   180
accattaaag ctccatctgg acttaaaacc cgctcttttg atgcaataag ggctgagctg   240
agggcattct ttgatgtgca tgatcaagaa ggaagctacc caggagggt tcatttagag    300 atgacagggc agaacgtgac agaatgtgtt ggaggctcaa ggactattac ttatgatgac   360
ttgagctcac gctaccacac acattgtgat cc                                  392
```

<210> SEQ ID NO 152
<211> LENGTH: 359
<212> TYPE: DNA
<213> ORGANISM: Glycine max

<400> SEQUENCE: 152

```
ctgttttttt gctgagaaga gagaatggct gtggcgtggt catcatccct tatcacgttg     60
aaggtgaaac cttgcatttt cgggtctcct cggagatccg cggtggatcg gaattgtgcg   120
aagtcaacgg cggggacaat atcgacgagt tggagcctgg acagttggag ggcgaagaag   180
gcgcttcagc ttccggagta cccagatgcg gaaagatgaa ttggacctag tccttcaaac   240
cctatgttct tttcccccaa tcgtcttcgg cggcgaggcg aggaatctgg aggagaagct   300
agctcaggct gccatgggga acgcttatct gcttcagggc ggtgattgcg ccgagagct    359
```

<210> SEQ ID NO 153
<211> LENGTH: 167
<212> TYPE: DNA
<213> ORGANISM: Zea mays

<400> SEQUENCE: 153

```
gcggattcat ctgtaggcgg gaaaacgggg attaaccacc cactagggaa gaacttgatt     60
```

```
ggacgattct catcagccac aatgtgttct aattgacaca gctacactga acacattgcc    120
tgacagggag ctagcctcag gcattgccga ggtagtgaag tatgggc                  167

<210> SEQ ID NO 154
<211> LENGTH: 235
<212> TYPE: DNA
<213> ORGANISM: Zea mays

<400> SEQUENCE: 154
cggatatgga gcatggctcc atggggaggc tgtcgcagct ggaacagtta tggcaactga    60
catgtctcac cgcctggggt ggatagatga ctccatcaga aaacgtgtgg ttgacatact   120
aaagcaagcc aaacttccca ttgcacctcc tgagaccatg accgtagaga agtttaaaaa   180
catcatggct gttgacaaga aggttgctga tggtctgttg agactcatcc ttctg        235

<210> SEQ ID NO 155
<211> LENGTH: 248
<212> TYPE: DNA
<213> ORGANISM: Zea mays

<400> SEQUENCE: 155
aagagggttc tggtggtgac caacacgacc gtcgcgccgc tttacctgga caaggtgaca    60
tgggcactca cccacaacaa cctgaatgta tcagtggaaa gcgtgatcct gcccgacggt   120
gaaaagtaca aaatatgga cacgctgatg aaggtgtttg acaaggcagt cgagtcccgt   180
tttgaccgcc ggtgcacatt tgtagcactg ggtggtggtg tcattgggga catgtgtggt   240
tttgcagc                                                            248

<210> SEQ ID NO 156
<211> LENGTH: 284
<212> TYPE: DNA
<213> ORGANISM: Zea mays

<400> SEQUENCE: 156
ggcatgttca tggtaagagg gttctggtgg tgaccaacac gaccgtcgcg ccgctttacc    60
tggacaaggt gacatgggca ctcacccaca acaacctgaa tgtatcagtg gaaagcgtga   120
tcctgcccga cggtgaaaag tacaaaaata tggacacgct gatgaaggtg tttgacaagg   180
cagtcgagtc ccgttttgac cgccggtgca catttgtagc actgggtggt ggtgtcattg   240
gggacatgtg tggttttgca gctgctgcat tcctccgggg cgtc                    284

<210> SEQ ID NO 157
<211> LENGTH: 473
<212> TYPE: DNA
<213> ORGANISM: Zea mays
<220> FEATURE:
<223> OTHER INFORMATION: unsure at all n locations

<400> SEQUENCE: 157
gtggagttgc acgtcttcgc agccacggtc tagtaatccg gctcgccnca cgcgtcaggc    60
tgaagtggtg gcacaagatg agaaggaaag tggccttcga gcaacactaa acctgggtca   120
cacatttggc catgctattg agactgggac aggatatgga gcatggctcc atggggaggc   180
tgtcgcagct ggaacagtta tggcaactga catgtctcac cgcctggggt ggatagatga   240
ctccatcaga aaacgtgtgg ttgacatact aaagcaagcc aaacttccca ttgcacctcc   300
tgagaccatg accgtagaga agtttaaaaa catcatggct gttgacaaga aggttgctga   360
```

```
tggtctgttg agactcatcc ttctgaaagg accgctangg tgctgtgtat ttacggggga        420
ttatgacggg aatgcactcg atgaaaccta catgcattct gcgacaactg aga              473

<210> SEQ ID NO 158
<211> LENGTH: 182
<212> TYPE: DNA
<213> ORGANISM: Zea mays

<400> SEQUENCE: 158
cggacgctgg gcggacgcgt gggggcagat agggccagac actaaggtct ttggtataat        60
tggtaaacca gttggccata gcaaaagccc aattttgcat aatgaagctt tcagatcagt       120
gggtttcaac gctgtgtatg ttccattttt ggtggatgac ttggctaaat ttcttgatac       180
at                                                                     182

<210> SEQ ID NO 159
<211> LENGTH: 251
<212> TYPE: DNA
<213> ORGANISM: Zea mays

<400> SEQUENCE: 159
gcttaaggtg gctgacaaat ttatgaaact tatttctggg aggaaacctg ataactgtaa        60
acttatagtt tcatcccaca actatgagac cactccatcg tccgaggaac ttgcaaattt       120
ggtggctcag attcaagcaa cgggggctga tatcgtgaaa atagctacaa ccgctactga       180
aattgttgat gtggcaaaaa tgtttcaaat acttgttcac tgccaggaaa agcaggtgcc       240
aatcattggg c                                                           251

<210> SEQ ID NO 160
<211> LENGTH: 251
<212> TYPE: DNA
<213> ORGANISM: Glycine max

<400> SEQUENCE: 160
caacgctttg tctaccgctc cggcagcggg tagtaggaag aacgcgacgc taatttgcgt        60
cccaataatg ggagaatcag ttgaaaagat ggagattgac gtggacaaag cgaaagccgg       120
aggcgcggac cttgttgaaa ttcgattgga ttctttgaaa acctttgacc cctatcgaga       180
tctcaacgct ttcattcaac accgttcttt acccttgttg ttcacttaca ggcccaaatg       240
ggagggtggt a                                                           251

<210> SEQ ID NO 161
<211> LENGTH: 225
<212> TYPE: DNA
<213> ORGANISM: Zea mays

<400> SEQUENCE: 161
attgttggaa tgatgggttc aggcaaaact acagttggga agatattatc cgaagtgtta        60
ggttattcgt tcttcgacag tgataagttg gtagagaagg ctgttggtat ttcatctgtt       120
gctgagatct ttcagctcca tagcgaaaca ttcttcagag ataatgagga gttacatgaa       180
gaaagggctg accgtatggt tagatgtccc actggatgca cttgc                      225

<210> SEQ ID NO 162
<211> LENGTH: 297
<212> TYPE: DNA
<213> ORGANISM: Zea mays

<400> SEQUENCE: 162
```

```
cagttgccca aatattcaag gtccatagtg aagccttctt tcgggataat gagagtagtg      60
tcttgagaga tttgtcctcc atgcgacgat tagttgttgc caccggaggt gatgctgtta    120
tccgaccaat taactggaga tatatgaaga ggggcctatc tgtttggtta gatgtgccct    180
tggatgctct tgctaggcgt attgctaaag tgggaactgc ctctcgtcct cttctggacc    240
aaccatctgg tgatccgtac gcaatggtag ctacttgttc ttgttccttc aaattct       297
```

<210> SEQ ID NO 163
<211> LENGTH: 249
<212> TYPE: DNA
<213> ORGANISM: Zea mays

<400> SEQUENCE: 163

```
ttcacaagct gttggaatcc cttcagttgc tcaaatattc aaagttcaca gtgaagcctt     60
ctttcgggat aattggagta gcgtcttcag ggatctgtcc tccatgcgac gattagttgt    120
tgccacggag gtgttctgtc atccgaccag ttaactggac atatatgaag atgggcctat    180
ccgtttggtt agatgtgccc ttagatgctc ttgctaggcg tattactaaa gtgggaccgc    240
ttctcgtcc                                                            249
```

<210> SEQ ID NO 164
<211> LENGTH: 334
<212> TYPE: DNA
<213> ORGANISM: Zea mays

<400> SEQUENCE: 164

```
gaaatatatg aagaagggcc tatccgtttg gttagatgtg cccttggatg ctcttgctag     60
gcgcattgct aaagtgggaa ccgcttctcg tcctcttctg gaccaaccgt ccggtgatcc    120
atacacaatg gtagctactt attctttcaa tattctttca tgctcgtgaa acggaattgt    180
ttcttttttc tatttggaca aagaactgct catagatcca cttgagcctt gaagccctat    240
cctggattcc agtcctttac ttgtggtagc aaatgctcag acttcttatg ctagttctaa    300
tatggatcac tcactgggtt ccttattgtt atag                                334
```

<210> SEQ ID NO 165
<211> LENGTH: 273
<212> TYPE: DNA
<213> ORGANISM: Zea mays

<400> SEQUENCE: 165

```
atttacctag taggaatgat gggttctgga aaaagtactg tggggaagat tatgtctgaa     60
gtcttgggtt attcgttctt tgatagtgac aagttagtgg agcaagctgt tggaatgcca    120
tcagttgccc aaatattcaa ggtccatagt gaagccttct ttcgggataa tgagagtagt    180
gtcttgagag atttgtcctc catgcgacga ttagttgttg ccaccggagt ggtgcctgtt    240
atccgaccaa ttaactggag atatatgaag agg                                 273
```

<210> SEQ ID NO 166
<211> LENGTH: 298
<212> TYPE: DNA
<213> ORGANISM: Zea mays

<400> SEQUENCE: 166

```
gatgggttct ggaaaaagta ctgtggggaa gatcatgtct gaagtcttgg gttattcgtt     60
ctttgatagt gacaaattag tggagcaagc tgttggaatg ccttcagttg ctcaaatatt    120
```

-continued

| | |
|---|---|
| caaagttcac agtgaagcct tctttcggga taatgagagt agcgtcttga gggatctgtc | 180 |
| ctccatgcga cgattagttg ttgccaccgg agtggtgctg tcatccgacc agttaactgg | 240 |
| aaatatatga agaagggcct atccgtttgg ttagatgtgc ccttggatgc tcttgcta | 298 |

<210> SEQ ID NO 167
<211> LENGTH: 297
<212> TYPE: DNA
<213> ORGANISM: Zea mays

<400> SEQUENCE: 167

| | |
|---|---|
| agaagttctg ttctacttaa acgggaggtg tatttactta gtgggaatga tgggttctgg | 60 |
| aaaaagtact gtggggaaga tcatgtctga agtcttgggt tattcgttct ttgatagtga | 120 |
| caaattagtg gagcaagctg ttggaatgcc ttcagttgct caaatattca agttcacag | 180 |
| tgaagccttc tttcgggata atgagagtag cgtcttgagg gatctgtcct ccatgcgacg | 240 |
| attagttgtt gccaccggag gtggtgctgt catccgacca gttaaactgg aatatat | 297 |

<210> SEQ ID NO 168
<211> LENGTH: 231
<212> TYPE: DNA
<213> ORGANISM: Zea mays

<400> SEQUENCE: 168

| | |
|---|---|
| gaagctctcc tgttgaagag aaaatcagaa gaagttctgt tctacttaaa cgggaggtgt | 60 |
| atttacttag tgggaatgat gggttctgga aaaagtactg tggggaagat catgtctgaa | 120 |
| gtcttgggtt attcgttctt tgatagtgac aaattagtgg agcaagctgt tggaatgcct | 180 |
| tcagttgctc aaatattcaa agttcacagt gaagccttct ttcgggataa t | 231 |

<210> SEQ ID NO 169
<211> LENGTH: 274
<212> TYPE: DNA
<213> ORGANISM: Zea mays

<400> SEQUENCE: 169

| | |
|---|---|
| cccacgcgtc cgcccacgcg tccgggaaga tcatgtctga agtcttgggt tattcgttct | 60 |
| ttgatagtga caaattagtg gagcaagctg ttggaatgcc ttcagttgct caaatattca | 120 |
| aagttcacag tgaagccttc tttcgggata atgagagtag cgtcttgagg gatctgtcct | 180 |
| ccatgcgacg attagttgtt gccaccggag gggtgctgt catccgacca gttaactgga | 240 |
| aatatatgaa gaagggccta tccgtttggt taga | 274 |

<210> SEQ ID NO 170
<211> LENGTH: 294
<212> TYPE: DNA
<213> ORGANISM: Zea mays

<400> SEQUENCE: 170

| | |
|---|---|
| tgttcaggca aaactacagt tgggaagata ctatccgaag tgttaggtta ttcgttcttc | 60 |
| gacagtgata agttggtaga gaaggctgtt ggtatttcat ctgttgctga gatctttcag | 120 |
| ctccatagcg aaacattctt cagagataat gagagtgagg tcctgacgga tctgtcatca | 180 |
| atgcatcggt tggttgttgc aacctggagt ggtgcagtga tccgaccaat caattggagt | 240 |
| tacatgaaga aagggctgac cgtatggtta gatgtcccac tggatgcact tgca | 294 |

<210> SEQ ID NO 171
<211> LENGTH: 261

```
<212> TYPE: DNA
<213> ORGANISM: Zea mays

<400> SEQUENCE: 171
atccgaccaa tcaattggag ttacatgaag aaagggctga ccgtatggtt agatgtccca      60
ctggatgcac ttgcaagaag aatcgctgct gtaggaaccg cgtctcgacc actcttgcat     120
caggaatccg gtgatcctta tgcaaaggct tatgcaaaac ttacgtcact ttttgagcaa     180
agaatggact cgtatgctaa tgctgatgcc agagtttcac ttgaacatat tgcattaaaa     240
caaggccata atgatgtcac t                                                261

<210> SEQ ID NO 172
<211> LENGTH: 289
<212> TYPE: DNA
<213> ORGANISM: Zea mays

<400> SEQUENCE: 172
agtgaggtcc tgacggatct gtcatcaatg catcggttgg ttgttgcaac cggaggtggt      60
gcagtgatcc gaccaatcaa ttggagttac atgaagaaag gctgaccgt atggttagat     120 gtcccactgg atgcacttgc aagaagaatc gctgctgtag gaaccgcgtc tcgaccactc     180
ttgcatcagg aatccggtga tccttatgca aaggcttatg caaaacttac gtcactttt    240 gagcaaagaa tggactcgta tgctaatgct gatgccagag tttcacttg                289

<210> SEQ ID NO 173
<211> LENGTH: 317
<212> TYPE: DNA
<213> ORGANISM: Zea mays

<400> SEQUENCE: 173
ctatccgaag tgttaggtta ttcgttcttc gacagtgata agttggtaga gaaggctgtt      60
ggtatttcat ctgttgctga gatctttcag ctccatagcg aaacattctt cagagataat     120
gaggagttac atgaagaaag gctgaccgt atggttagat gtcccactgg atgcacttgc     180
aagaagaatc gctgctgtag gaaccgcgtc tcgaccactc ttgcatcagg aatccggtga     240
tccttatgca aaggcttatg caaaacttac gtcactttt gagcaaagaa tggactcgta     300
tgctaatgct gatgcca                                                     317

<210> SEQ ID NO 174
<211> LENGTH: 231
<212> TYPE: DNA
<213> ORGANISM: Zea mays

<400> SEQUENCE: 174
ggcatgacta cagttgggaa gatactatcc gaagtgttag gttattcgtt cttcgacagt      60
gataagttgg tagagaaggc tttggtattt catctgttgc tgagatcttt cagctccata     120
gcgaaacatt cttcagagat aatgagagtg aggtcctgac ggatctgtca tcaatgcatc     180
ggttggttgt tgcaaccgga ggtggtgcag tgatccgacc aatcattgga g              231

<210> SEQ ID NO 175
<211> LENGTH: 241
<212> TYPE: DNA
<213> ORGANISM: Zea mays

<400> SEQUENCE: 175
gtcccactgg atgcacttgc aagaagaatc gctgctgtag gaaccgcgtc tcgaccactc      60
```

```
ttgcatcagg aatccggtga tccttatgca aaggcttatg caaaacttac gtcactttt      120 gagcaaagaa tggactcgta tgctaatgct gatgccagag tttcacttga acatattgca    180
ttaaaacaag gccataatga tgtcactata cttacaccta gtaccatcgc cattgaggca    240
t                                                                    241

<210> SEQ ID NO 176
<211> LENGTH: 337
<212> TYPE: DNA
<213> ORGANISM: Zea mays
<220> FEATURE:
<223> OTHER INFORMATION: unsure at all n locations

<400> SEQUENCE: 176
cctccatgcg acgattagtt gttgccaccg gaggtgtgct gttatccgac caattaactg     60
gagatatatg aagaggggcc tatctgtttg gttagatgtg cccttggatg ctcttgctag    120
gcgtattgct aaagtgggaa ctgcctctcg tcctcttctg gaccaaccat ctggtgatcc    180
gtacgcaatg gccttttcta agctcagcat gcttgcacag caaggggtg atgcttatgc     240 aaatgcagat gtaagggttt ctctggaaga gattgcatgt anacaaggtc atgatgatgt    300
ctctaagctg acacctactg atattgcaat tgagtca                             337

<210> SEQ ID NO 177
<211> LENGTH: 360
<212> TYPE: DNA
<213> ORGANISM: Zea mays

<400> SEQUENCE: 177
gaagggccta ccgtttggt tagatgtgcc cttggatgct cttgctaggc gcattgctaa       60
agtgggaacc gcttctcgtc ctcttctgga ccaaacgtcc ggtgatccat acacaatggc    120
cttttctaag ctcagcatgc ttgcagagca aaggggtgat gcttatgcaa atgcggatgt    180
aagggtttct ctggaagaga ttgcatctaa acaaggtcat ggcgatgtct ctaagctgat    240
gccgactgat atcgcaattg agtcacttca taagatcgag agtttcgtca tcgagcacgc    300
tgctgataat ccagctagcg actcgcaagc tgagtcacag atccaaggat acagacttgt    360

<210> SEQ ID NO 178
<211> LENGTH: 460
<212> TYPE: DNA
<213> ORGANISM: Zea mays

<400> SEQUENCE: 178
agggtgtgag aatggctcat ggagcacggt cggtatccgg gtcagccccg cgtctgcgca     60
gaagtctgcc gacgcgtggg ggaaaacgcc aatctatatt gttggtacgg attgcacagc    120
caagcgcaac atcgccaagc tgcttgcgaa ttccataata taccgctacc tcagcagtga    180
ggaactgctt gaggatgttc ttggtggcaa ggacgccctc agagccttca aggaatctga    240
tgagaacggt tatcttgaag tcgagacgga agggttaaag cagctcacgt ccatgggtag    300
ccttgtactg tgctgtggag atggcgccgt tatgaactca accaatctag gctgctgag     360 gcatggtgtc tccatttgga ttgatgttcc tcttgaaatg gcagcaaatg acatgttgaa    420
gagcactgga acacaagcta ctacagatcc agactctttt                          460

<210> SEQ ID NO 179
<211> LENGTH: 434
<212> TYPE: DNA
<213> ORGANISM: Zea mays
```

<400> SEQUENCE: 179

```
aaggtccact actctgctga tgacgctctc atactacagc aaaaagccca ggatgttctg      60
ccttacttgg atggccgttg cgtttatctt gttggaatga tgggttcagg caaaactaca     120
gttgggaaga tactatccga agtgttaggt tattcgttct tcgacagtga aagttggta      180
gagaaggctg ttggtatttc atctgttgct gagatctttc agctccatag cgaaacattc    240
ttcagagata atgagagtga ggtcctgagg atctgtcat caatgcatcg gttggttgtt     300
gcaaccggag gtggtgcagt gatccgacca atcaattgga gttacatgaa gaaagggctg    360
accgtatggt tagatgtccc actggatgca cttgcaagaa gaattgctgc tgtaggaacc    420
gcgtctcgac cact                                                      434
```

<210> SEQ ID NO 180
<211> LENGTH: 281
<212> TYPE: DNA
<213> ORGANISM: Glycine max
<220> FEATURE:
<223> OTHER INFORMATION: unsure at all n locations

<400> SEQUENCE: 180

```
cttgttgnta atgatggcct ctgggaagac aactngggac gganattgtc agaggcgctt      60
tcttattcgt tttannatag tgatgcattg gtggtgaagg aggttggtgg aatatctgta    120
actgatatat tcaagcacta tggagagcct ttttttcgtaa taaggagatn gaggtgttgc    180
agaaggtgtc aataatggca tagacatctt atttctactg gtggangtgc gtcgtgaggc    240
ccatcattgg aaatatatgc agcaggggat tagtgtttgg t                        281
```

<210> SEQ ID NO 181
<211> LENGTH: 271
<212> TYPE: DNA
<213> ORGANISM: Glycine max

<400> SEQUENCE: 181

```
ttcaagcact atgagagcc ttttttttcgt aataaggaga ctgaggtgtt gcagaaggtg      60
tcaataatgc atagacatct tatttctact ggtggaggtg ctgtcgtgag gcccatcaat    120
tggaaatata tgcagcaggg gattagtgtt tggttggatg tacctgtaga agtcttgact    180
cagagaataa cagctgaagg aactgattct cgcccacttc tacattatga aggaggagat    240
gcatacacaa agactatcac gcatttgtct t                                    271
```

<210> SEQ ID NO 182
<211> LENGTH: 283
<212> TYPE: DNA
<213> ORGANISM: Glycine max
<220> FEATURE:
<223> OTHER INFORMATION: unsure at all n locations

<400> SEQUENCE: 182

```
cagtatcaga cggcaccgtt tcgtcttcgc ttggtgccac ggactcgtct cttgcggtga      60
agtttttgtt cagaagaaag cagcagaggt gtcttctgag ctcaaaggga cctccatatt    120
tctggttggt ttgaagagct ctcttaaact agtttgggga agctgctggc tgatgcattg    180
cggtattatt atttcgacag tgatagtttg gtggaagaag cngtaggtgg tgcactggct    240
gcaaaatcat tcagagagag tgacgaaaaa ggcttctatg agt                       283
```

<210> SEQ ID NO 183

```
<211> LENGTH: 414
<212> TYPE: DNA
<213> ORGANISM: Glycine max

<400> SEQUENCE: 183
aatcgccctt ccaattttct tcaattcaag caccaaaact gcttcctgaa gttcccgaac      60
ccaaacctcc atcgactgcg caggctcaat tgctcagtat cagacggcac cgtttcgtct     120
tcgcttggtg ccacggactc gtctcttgcg gtgaagaaga aagcagcaga ggtgtcttct     180
gagctcaaag ggacctccat atttctggtt ggtttgaaga gctctcttaa aactagtttg     240
gggaagctgc tggctgatgc attgcggtat tattatttcg acagtgatag tttggtggaa     300
gaagctgtac gtggtgcact ggctgcaaaa tcattcagag agagtgacga aaaaggcttc     360
tatgagtctg agactgaagt actgaagcaa ttatcgttca tgggtcgact agtg           414

<210> SEQ ID NO 184
<211> LENGTH: 244
<212> TYPE: DNA
<213> ORGANISM: Glycine max

<400> SEQUENCE: 184
tgcttttgtt gaaggtgatg cttcaagtgc cagttacttc ctagctggtg cagcagtaac      60
tggtgggact atcactgtta atggctgtgg cacaagcagt ttacagggag atgtaaaatt     120
tgctgaagtt cttgaaaaga tgggagctaa ggttacatgg tcagagaaca gtgtcaccgt     180
tactggaccg ccacaagatt cttctggtca aaaagtcttg caaggcattg atgtcaatat     240
gaac                                                                 244

<210> SEQ ID NO 185
<211> LENGTH: 262
<212> TYPE: DNA
<213> ORGANISM: Glycine max

<400> SEQUENCE: 185
ggtttctgca tcggtcgccg ccgcagagaa gccgtcaacg tcgccggaga tcgtgctgga      60
acccatcaaa gacttctcgg gtaccatcac attgccaggg tccaagtctc tgtccaatcg     120
aattttgctt cttgctgctc tctctgaggg aacaactgtt gtagacaact tgttgtatag     180
tgaggatatt cattacatgc ttggtgcatt aaggacccct ggactgcgtg tggaagatga     240
caaaacaacc aaacaagcaa tt                                             262

<210> SEQ ID NO 186
<211> LENGTH: 234
<212> TYPE: DNA
<213> ORGANISM: Glycine max

<400> SEQUENCE: 186
tgctgtacag cgaggatatt cattacatgc ttggtgcatt aaggacccct ggactgcgtg      60
tggaagacga ccaaacaacc aaacaagcaa ttgtggaagg ctgtggggga ttgtttccca     120
ctattaaaga atctaaagat gaaatcaatt tattccttgg aagtgctggt actgcgatgc     180
gtccctttga cagcagctgta gttgctgcag gtggaaatgc aagctacgta cttg          234

<210> SEQ ID NO 187
<211> LENGTH: 280
<212> TYPE: DNA
<213> ORGANISM: Glycine max

<400> SEQUENCE: 187
```

```
gttgggaacc tatcaaagac atctcgggta ccatcacatt gccagggtct aagtctctgt    60
ccaatcgaat tttgcttctt gctgctctct ctgagggaac aactgttgta gacaacttgc   120
tgtacagcga ggatattcat tacatgcttg gtgcattaag gacccttgga ctgcgtgtgg   180
aagacgacca acaaccaaa caagcaattg tggaaggctg tggggattg tttcccacta    240 ttaaagaatc taaagatgaa atcaatttat tccttggaaa                        280

<210> SEQ ID NO 188
<211> LENGTH: 239
<212> TYPE: DNA
<213> ORGANISM: Glycine max

<400> SEQUENCE: 188
cccacgcctt tgggggggcct caaaatctcg catcccgatg cataaaaatg gaagctttat    60
gggaaatttt aatgtgggga acggaaattc cggcgtgttt aaggtttctg catcggtcgc   120
cgccgcagag aagccgtcaa cgtcgccgga gatcgtgttg aacccatca aagacttctc   180 gggtaccatc acattgccag gtccaagtc tctgtccaat cgaattttgc ttcttgctg    239

<210> SEQ ID NO 189
<211> LENGTH: 256
<212> TYPE: DNA
<213> ORGANISM: Glycine max

<400> SEQUENCE: 189
cagctcggtg cagatgttga ttgctttctt ggcacaaact gtccacctgt tcgtgtaaat    60
gggaagggag gacttcctgg cggaaaggtg aaactgtctg gatcaattag cagtcaatac   120
ctaactgctt tgcttatggc agctccttta gctcttggcg acgtggaaat tgagattgtt   180
gataaactga tttctgttcc atatgttgaa atgactctga agttgatgga gcgttttgga   240
gtttctgtgg aacaca                                                  256

<210> SEQ ID NO 190
<211> LENGTH: 263
<212> TYPE: DNA
<213> ORGANISM: Glycine max
<220> FEATURE:
<223> OTHER INFORMATION: unsure at all n locations

<400> SEQUENCE: 190
caggttcaaa ccggagcaaa aaaacttgtt acgatggttt cttccgacaa ggatccaccn    60
ttgacancan ctgtggttgc tgcaggtgga aatgcaagct acgtacttga tggggtgccc   120
cgaatgagag agaggccaat tgggatttg gttgctggtc ttaanccgtt atnactcaaa    180
ccgagaccga aactgacgga gccaccatcg tcgacgtcgc cgtcgccgtc aacgtcaacg   240
tcaacgtnaa cgacgagaat tac                                          263

<210> SEQ ID NO 191
<211> LENGTH: 255
<212> TYPE: DNA
<213> ORGANISM: Glycine max

<400> SEQUENCE: 191
ctgcaatgcg tcctttgaca gcagctgtgg ttgctgcagg tggaaatgca agctacgtac    60 ttgatgggt gccccgaatg agagagaggc caattgggga tttggttgct ggtcttaagc   120
aacttggtgc agatgttgat tgcttttcttg gcacaaactg tccacctgtt cgtgtaaatg   180
```

```
ggaagggagg acttcctggc ggaaaggtga aactgtctgg atcagttagc agtcaatact    240
tgactgcttt gctta                                                   255

<210> SEQ ID NO 192
<211> LENGTH: 262
<212> TYPE: DNA
<213> ORGANISM: Glycine max

<400> SEQUENCE: 192
gcaatgcgtc ctttgacagc agctgtggtt gctgcaggtg gaaatgcaag ctacgtactt    60 gatgggtgc cccgaatgag agagaggcca attgggatt tggtagctgg tcttaagcaa    120
cttggtgcag atgttgattg ctttcttggc acaaactgtc cacctgttcg tgtaaatggg    180
aagggaggac ttcctggcgg aaaggtgaaa ctgtctggat cagttagcag tcaatacttg    240
actgctttgc ttatggcagc tc                                           262

<210> SEQ ID NO 193
<211> LENGTH: 260
<212> TYPE: DNA
<213> ORGANISM: Glycine max

<400> SEQUENCE: 193
gggagctaag gttacatggt cagagaacag tgtcactgtt tctggaccac cacgagattt    60
ttctggtcga aaagtcttgc gaggcattga tgtcaatatg aacaagatgc agatgttgc    120 catgacactt gctgttgttg cactatttgc taatggtccc actgctataa agatgtggc    180 aagttggaga gttaaagaga ctgagaggat datagcaatc tgcacagaac tcagaaagct    240
aggagcaaca gttgaagaag                                              260

<210> SEQ ID NO 194
<211> LENGTH: 271
<212> TYPE: DNA
<213> ORGANISM: Glycine max

<400> SEQUENCE: 194
gggagctaag gttacatggt cagagaacag tgtcactgtt tctggaccac cacgagattt    60
ttctggtcga aaagtcttgc gaggcattga tgtcaatatg aacaagatgc agatgttac    120 catgacactt gctgttgttg actatttgct aatggtccca ctgctataag agatgtggca    180
agttggagag ttaaagagac tgagaggatg atagcaatct gcacagaact cagaaagcta    240
ggagcaacag ttgaagaagg tcctgattac t                                 271

<210> SEQ ID NO 195
<211> LENGTH: 305
<212> TYPE: DNA
<213> ORGANISM: Glycine max
<220> FEATURE:
<223> OTHER INFORMATION: unsure at all n locations

<400> SEQUENCE: 195
ctgatttctg ttccatatgt tganatgact ctgaagttga tggagcgttt tggagtttct    60
gtggaacaca gtggtaattg ggataggttc ttggtccatg gaggtcaaaa gtacaagtct    120
cctggcaatg cttttgttga aggtgatgct tcaagtgcca ttatttacta gctggtgcag    180
caattactgg tgggactatc actgttaatg gctgtggcac aagcagttta cagggagatg    240
taaaatttgc tgaagttctt gaaaagatgg gagctaaggt tacatggtca gagaacagtg    300
tcact                                                              305
```

<210> SEQ ID NO 196
<211> LENGTH: 280
<212> TYPE: DNA
<213> ORGANISM: Glycine max
<220> FEATURE:
<223> OTHER INFORMATION: unsure at all n locations

<400> SEQUENCE: 196

| | |
|---|---|
| gaaattgaga ttgttgataa actgatttct gttccatatg ttgaaatgac tctgaagntg | 60 |
| atggagcgtt ttngagtttc tgtggaacac agtggtaatt gggataggtt cttggtccat | 120 |
| ggaggtcana agtacaagtc tcctggnaat gcttttgttg aaggtgatgc ttcaagtgcn | 180 |
| agttatttac tanctggtgc agcaantact gnngggacta tcactgtnna tggctgtggc | 240 |
| acaaacagtt tacagggaga tgtaaaattt gcngnagttc | 280 |

<210> SEQ ID NO 197
<211> LENGTH: 280
<212> TYPE: DNA
<213> ORGANISM: Glycine max

<400> SEQUENCE: 197

| | |
|---|---|
| gttagcagtc aatacttgac tgctttgctt atggcagctc ctttagctct tggtgatgtg | 60 |
| gaaattgagc attgttgata aactgatacc tgttccatat gttgaacatg actctgaagt | 120 |
| tgatggagcg ttttggagtt tctgtggaac acagtggtaa ttgggatagg ttcttggtcc | 180 |
| atggaggtca aaagtacaag tctcctggca atgcttttgt tgaaggtgat gcttcaagtg | 240 |
| ccagttcttt actagctggt gcagcaatta ctggtgggat | 280 |

<210> SEQ ID NO 198
<211> LENGTH: 136
<212> TYPE: DNA
<213> ORGANISM: Glycine max

<400> SEQUENCE: 198

| | |
|---|---|
| gttgaaatga ctctgaagtt gatggagcgt tttggagttt ctgtggaaca cagtcgtaat | 60 |
| tgggataagt tcttggtcca tggaggtcaa aagtacaagt ctcctggcaa tgcttttgtt | 120 |
| gaaggtgatg cttcaa | 136 |

<210> SEQ ID NO 199
<211> LENGTH: 331
<212> TYPE: DNA
<213> ORGANISM: Zea mays

<400> SEQUENCE: 199

| | |
|---|---|
| atcccagcct cggtcgtatc atcaactgca agctccggca tccccaggat ttgatcctat | 60 |
| ctcttctaaa tagccgtgtt cctccatttt acgctcaccg atcatcaaat tatctccaag | 120 |
| ccatcatgtc gaccttcgga acactctttc gcgttactac ctacggtgaa tctcactgtg | 180 |
| cctcggtcgg ctgcattgtc gacggcgttc ctccaggcct caaactcact gctcctgaca | 240 |
| ttcaagtgca gcttagccgt cgacgacctg gtcagagcaa tttgaccact ccccgaaacg | 300 |
| agaaggacct tgtcaacatc cagtccggag t | 331 |

<210> SEQ ID NO 200
<211> LENGTH: 305
<212> TYPE: DNA
<213> ORGANISM: Zea mays

```
<400> SEQUENCE: 200
cttcattagc tcatccaatc tattccgatg acgaccgtgc ccacgccaca gcaggtggcg    60
cactcacggg ctcggctcgc accccgcgcg atcggcgcct tgctggagtt tgccccagcc   120
tcctcctccc tccgcttcgc cgtgcaccgc tgccgcactg ctcgcctaga ggtgaaggca   180
tctggaaaca cgtttggaaa ctactttcag gttgcaacct atggtgaatc tcatgggggt   240
ggtgttggtt tgttatcag tggttgccac ctagaattca ctcactgagg cagactacaa   300
gttga                                                               305

<210> SEQ ID NO 201
<211> LENGTH: 303
<212> TYPE: DNA
<213> ORGANISM: Zea mays

<400> SEQUENCE: 201
cagcttcgtc tctctcgccg gcgcggcaac tatcatcact tcattagctc atccaatcta    60
ttccgatgac gaccgtgccc acgccacagc aggtgggtac tcacgggcac ggctcgcacc   120
ccgcgcgatc ggcgccttgc tggagtttgc cccagcctcc tcctcctcc gcttcgccgt   180 gcaccgctgc cgcactgctc gcctagaggt gaaggcatct ggaaacacgt ttggaaacta   240
ctttcaggtt gcaacttatg gtgaatctca tggggtggt gttggctgtg ttatcagtgg   300
ttg                                                                 303

<210> SEQ ID NO 202
<211> LENGTH: 285
<212> TYPE: DNA
<213> ORGANISM: Zea mays

<400> SEQUENCE: 202
ctcagcttcg tctctctcgc cggcgcggca actatcatca cttcattagc tcatccaatc    60
tattccgatg acgaccgtgc tcacgccaca gcaggtggcg tactcacggg cacggctcgc   120
accccgcgcg atcggcgcct tgctggagtt tgccccagcc tcctcctccc tccgcttcgc   180
cgtgcaccgc tgccgcactg ctcgcctaga ggtgaaggca tctggaaaca cgtatggaaa   240
ctactttcag gttgcaactt atggtgaatc tcatggggt ggtgt                    285

<210> SEQ ID NO 203
<211> LENGTH: 302
<212> TYPE: DNA
<213> ORGANISM: Zea mays

<400> SEQUENCE: 203
gatgggatga ctactggtac accaattcac gtctttgtcc caaacacaga tcaaaggggt    60
ggtgattaca gtgaaatgtc taaggcgtac agaccatccc atgcagatgc aacctatgac   120
ttcaagtatg gagttagagc tgtgcaggga ggtgaaggt catcagccag agaaaccatt   180
ggcagggtgg ctgcaggagc tcttgcaaag aaaattctaa agctcaaatc aggagtggag   240
atcttggcat ttgtttctaa agtgcaccaa gtcgtacttc cagaagatgc agttgattat   300
ga                                                                  302

<210> SEQ ID NO 204
<211> LENGTH: 304
<212> TYPE: DNA
<213> ORGANISM: Zea mays

<400> SEQUENCE: 204
```

```
cggaccgtgg ggcgaggtgg aaggtcatca gccagagaaa ccattggcag ggtggctgca        60
ggagctcttg caaagaaaat tctaaagctc aaatcatcag tggagatctt ggcatttgtt       120
tctaaagtgc accaagtcgt acttccagaa gatgcagttg attatgagac tgtaaccttg       180
gaacatatag agagcaacat cgttagatgt cctgatccag aatatgcaga aagatgatt        240 gctgccattg atacggtacg agttagagga gattcaattg gtggggtcgt cacatgcatt       300
gcaa                                                                    304

<210> SEQ ID NO 205
<211> LENGTH: 301
<212> TYPE: DNA
<213> ORGANISM: Zea mays

<400> SEQUENCE: 205
tggagatctt ggcatttgtt tctaaagtgc accaagtcgt acttccagaa gatgcagttg        60
attatgagac tgtaaccttg gaacatatag agagcaacat cgttagatgt cctgatccag       120
aatatgcaga gaagatgatt gctgccattg atacggtacg agttagagga gattcaattg       180
gtggggtcgt cacatgcatt gcaagaaatg ttcctcgtgg tcttggctct cctgttttg        240 acaaacttga agctgaactg gctaaagcca tgctttctct tcctgcaagc aaggggttg        300 a                                                                       301

<210> SEQ ID NO 206
<211> LENGTH: 334
<212> TYPE: DNA
<213> ORGANISM: Zea mays

<400> SEQUENCE: 206
caataagctc gagctcgagc cgctcgagcc gtgcagatgc aacctatgac ttcaagtatg        60
gagttagagc tgtagcaggg agacggaagg tcatcagcca gagaaaccat ggcagggtg       120 gctgcaggag ctcttgcaaa gaaaattcta aagctcaaat caggagtgga gatcttggca      180
tttgtttcta aagtgcacca agtcgtactt ccagaagatg cagttgatta tgagactgta      240
accttggaac atatagagag caacatcgtt agatgtcctg atccagaata tgcagagaag      300
atgattgctg ccattgatac ggtacgagtt agag                                  334

<210> SEQ ID NO 207
<211> LENGTH: 301
<212> TYPE: DNA
<213> ORGANISM: Zea mays

<400> SEQUENCE: 207
cggacgcgtg gatcaggaaa tgtgttcggg aactacttcc aggttgcaac ctatggcgaa        60
tcccatggag ggggtgttgg ttgcgttatc agtggctgcc cacccagaat tcctctcact       120
gaggcagaca tgcaagtaga actcgataga agacgtccgg gtcaaagtag aattacaacc       180
ccaagaaagg agactgatac atgcaaaatt ctatcaggga cacatgatgg gatgactact       240
ggtacaccaa ttcacgtctt tgtcccaaac acagatcaaa ggggtggtga ttacagtgaa       300
a                                                                       301

<210> SEQ ID NO 208
<211> LENGTH: 254
<212> TYPE: DNA
<213> ORGANISM: Zea mays
```

```
<400> SEQUENCE: 208
cacacgcatc cggtagaatt acaaccccaa gaaaggagac tgatacatgc aaaattctat      60
cagggacaca tgatgggatg actactggta caccaattca cgtctttgtc ccaaacacag     120
atcaaagggg tggtgattac agtgaaatgt ctaaggcgta cagaccatcc catgcagatg     180
caacctatga cttcaagtat ggagttagag ctgtgcaggg aggtggaagg tcatcagcca     240
gagaaaccat tggc                                                       254

<210> SEQ ID NO 209
<211> LENGTH: 232
<212> TYPE: DNA
<213> ORGANISM: Zea mays

<400> SEQUENCE: 209
ctaaagctca aatcaggagt ggagatcttg gcatttgttt ctaaagtgca ccaagtcgta      60
cttccagaag atgcagttga ttatgagact gtaaccttgg aacatataga gagcaacatc     120
gttagatgtc ctgatccaga atatgcagag aagatgattg ctgccattga tacggtacga     180
gttagaggag attcaattgg tggggtcgtc acatgcattg caagaaatgt tc             232

<210> SEQ ID NO 210
<211> LENGTH: 277
<212> TYPE: DNA
<213> ORGANISM: Zea mays

<400> SEQUENCE: 210
cttccaggtt gcaacctatg gcgaatccat ggaggggtg ttggttgcgt tatcagtggc       60
tgcccaccca gaattcctct cactgaggca gacatgcaag tagaactcga tagaagacgt     120
ccgggtcaaa gtagaattac aaccccaaga aaggagactg atacatgcaa aattctatca     180
gggacacatg atgggatgac tactggtaca ccagttcacg tctttgtccc aaacacagat     240
caaaggggtg gtgattacag tgaaatgtct aaagcgt                              277

<210> SEQ ID NO 211
<211> LENGTH: 196
<212> TYPE: DNA
<213> ORGANISM: Zea mays

<400> SEQUENCE: 211
cactcgatag aagacgtccg ggtcaaagta gaattacaac cccaagaaag gagactgata      60
catgcaaaat tctatcaggg acacatgatg ggatgactac tggtacacca attcacgtct     120
ttgtcccaaa cacagatcaa aggggtggtg attacagtga aatgtctaag gcgtacagac     180
catcccatgc agatgc                                                     196

<210> SEQ ID NO 212
<211> LENGTH: 309
<212> TYPE: DNA
<213> ORGANISM: Zea mays

<400> SEQUENCE: 212
ggcaaccaaa ccttctccga tggccgcgcc cgtgtcgcag ccgccggtgt ccgccagggc      60
gtccacacgg tttctccccc gcgggatagg cgcgctcccg gagtccgctc ccacgtccct     120
ccggttatcc gtcggccgcc gtcgccgggc cgccagccta gaggtgaagg catcgggaaa     180
tgtgttcggg aactacttcc aggttgcaac ctatggcgaa tcccatggag ggggtgttgg     240
ttgcgttatc agtggctgcc cacccagaat tcctctcact gaggcagaca tgcaagtaga     300
```

```
actcgatag                                                           309

<210> SEQ ID NO 213
<211> LENGTH: 285
<212> TYPE: DNA
<213> ORGANISM: Zea mays

<400> SEQUENCE: 213
ccttctccga tggccgcgcc cgtgtcgcag ccgccggtgt acgacagggc gtccacacag     60
tttctccccc gcgggatagg cgcgctcccg gagtccgctc ccacgtccct ccggttatcc    120
gtcggacgcc gtcgccgggc cgccagcata gatgtgaagg catcgggaaa tgtgttcggg    180
aactacttcc aggttgcaac ctatggcgaa tcccatggag ggggtgttgg ttgcgttatc    240
agtggctgcc cacccagaat tcctctcact gaggcagaca tgcaa                    285

<210> SEQ ID NO 214
<211> LENGTH: 317
<212> TYPE: DNA
<213> ORGANISM: Zea mays

<400> SEQUENCE: 214
ctcagaccct caccaaccag gcaaccaaac cttctccgat ggccgcgccc gtgtcgcagc     60
cgccggtgtc cgccagggcg tccacacggt ttctcccccg cgggataggc gcgctcccgg    120
agtccgctcc cacgtccctc cggttatccg tcggccgccg tcgccgggcc gccagcctag    180
aggtgaaggc atcgggaaat gtgttcggga actacttcca ggttgcaacc tatggcgaat    240
ctcatggagg gggtgttggt tgcgttatca gtggctgccc acccagaatt cctctcactg    300
aggcagacat gcaagta                                                   317

<210> SEQ ID NO 215
<211> LENGTH: 286
<212> TYPE: DNA
<213> ORGANISM: Zea mays

<400> SEQUENCE: 215
ggacctgggc tcagaccctc accaaccagg caaccaaacc ttctccgatg gccgcgcccg     60
tgtcgcagcc gccggtgtcc gccaggactt ccacacggtt tctcccccgc gggataggcg    120
cgctcccgga gtccgccccc acgtccctcc ggttatccgt cggccgccgt cgccgcgcct    180
ccagcctaga ggtgaaggca tcaggaaatg tgttcgggaa ctacttccag gttgcaacct    240
atggcgaatc ccatggaggg ggtgttggtt gcgttatcag tggctg                   286

<210> SEQ ID NO 216
<211> LENGTH: 274
<212> TYPE: DNA
<213> ORGANISM: Zea mays

<400> SEQUENCE: 216
ctcagaccct caccaaccag gcaaccaaac cttctccgat ggccgcgccc gtgtcgcagc     60
cgccggtgtc cgccagggcg tccacacggt ttctcccccg cgggataggc gcgctcccgg    120
agtccgcccc cacgtccctc cggttatccg tcggccgccg tcgccgcgcc tccagcctag    180
aggtgaaggc atcaggaaat gtgttcggga actacttcca ggttgcaacc tatggcgaat    240
cccatggagg gggtgttggt tgcgttatca gtgg                                274

<210> SEQ ID NO 217
```

<211> LENGTH: 255
<212> TYPE: DNA
<213> ORGANISM: Zea mays

<400> SEQUENCE: 217
ggcaaccaaa ccttctccga tggccgcgcc cgtgtcgcag ccgccggtgt ccgccagggc    60
gtccacacgg tttctccccc gcgggatagg cgcgctcccg gagtccgctc ccacgtccct   120
ccggttatcc gtcggccgcc gtcgccgggc cgccagccta gaggtgaagg catcgggaaa   180
tgtgttcggg aactacttcc aggttgcaac ctatggcgaa tcccatggag ttggtgttgg   240
ttgcggtatc agtgg                                                    255

<210> SEQ ID NO 218
<211> LENGTH: 299
<212> TYPE: DNA
<213> ORGANISM: Zea mays

<400> SEQUENCE: 218 ctgttttga caaacttgaa gctgaactgg caaaagccat gctttctctt cctgcaagca     60
aggggtttga gattggcagt gggttcgctg gtacggactt tactggaagt gagcataatg   120
atgagttcta tatggatgag gctggaaatg tgaggacacg aactaatcgc tcaggcggtg   180 ttcaggagg gatatcaaat ggtgaaatta tttacttcaa agtggctttt aagccaacag    240
caactatcgg aaagaagcaa atactgtgt caagggagca tgaggatgtt gaacttttg    299

<210> SEQ ID NO 219
<211> LENGTH: 310
<212> TYPE: DNA
<213> ORGANISM: Zea mays

<400> SEQUENCE: 219
acataatgat gagttctata tggatgaggc tggaaatgtg aggacacgaa ctaatcgctc    60
aggcggtgtt cagggaggga tatcaaatgg tgaaattatt tacttcaaag tggcttttaa   120
gccaacagca actatcggaa agaagcaaaa tactgtgtca agggagcatg aggatgttga   180
acttttggca aggggcgcc atgacccctg tgttgtccct cgagctgttc ctatggtggt    240
atccatggct gctctggtcc tgatggacca gctcatggcg catattgccc agtgtgagat   300
gtttccgctg                                                          310

<210> SEQ ID NO 220
<211> LENGTH: 267
<212> TYPE: DNA
<213> ORGANISM: Zea mays

<400> SEQUENCE: 220
acggacttta ctggaagtga gcataatgat gagttctata tggatgaggc tggaaatgtg    60
aggacacgaa ctaatcgctc aggcggtgtt cagggaggga tatcaaatgg tgaaattatt   120
tacttcaaag tggcttttaa gccaacagca actatcggaa agaagcaaaa tactgtgtca   180
agggagcatg aggatgttga acttttggca agggggcgcc atgacccctg tgttgtccct   240
cgagctgttc ctatggtgga atccatg                                       267

<210> SEQ ID NO 221
<211> LENGTH: 241
<212> TYPE: DNA
<213> ORGANISM: Zea mays

<400> SEQUENCE: 221

```
gtttgagatt ggcagtgggt tcgctggtac ggactttact ggaagtgagc ataatgatga    60
gttctatatg gatgaggctg aaatgtgag acacgaact aatcgctcag gcggtgttca   120
gggagggata tcaaatggtg aaattattta cttcaaagtg gcttttaagc caacagcaac   180
tatcggaaag aagcaaaata ctgtgtcaag ggagcatgag gtgttgaact tttggcaagg   240
g                                                                   241

<210> SEQ ID NO 222
<211> LENGTH: 231
<212> TYPE: DNA
<213> ORGANISM: Zea mays

<400> SEQUENCE: 222
ggctggaaat gtgaggacac gaactaatcg ctcaggcggt gttcagggag ggatatcaaa    60
tggtgaaatt atttacttca aagtggcttt taagccaaca gcaactatcg gaaagaagca   120
aaatactgtg tcaagggagc atgaggatgt tgaacttttg gcaggggggc gccatgaccc   180
ctgtgttgtc cctcgaggta atgtctccaa aaatttccta ccttttatca t            231

<210> SEQ ID NO 223
<211> LENGTH: 241
<212> TYPE: DNA
<213> ORGANISM: Zea mays

<400> SEQUENCE: 223
caacagcaac tatcggaaag aagcaaaata ctgtgtcaag ggagcatgag gatgttgaac    60
ttttggcaag ggggcgccat gaccctgtg ttgtccctcg agctgttcct atggtggaat   120
ccatggctgc gctggtcctg atggaccact catggcgcat attgcccagt gtgagatgtt   180
tccgctgaac cttgccctac aagagcccat ggctctgct agcagtgcat ctgaactgtc   240
a                                                                   241

<210> SEQ ID NO 224
<211> LENGTH: 218
<212> TYPE: DNA
<213> ORGANISM: Zea mays

<400> SEQUENCE: 224
cccctgtgtt gtccctcgag ctgttcctat ggtggaatcc atggctgcac tggtcctgat    60
ggaccagctc atggcgcata ttgcccagtg tgagatgttt ccgctgaacc ttgccctaca   120
agagcccatt ggctctgcta gcagtgcatc tgaactgtca ccaaacctat cataatgttt   180
gtcgtggaac atgtcccagc tttccttcga ccgaaatt                            218

<210> SEQ ID NO 225
<211> LENGTH: 282
<212> TYPE: DNA
<213> ORGANISM: Zea mays

<400> SEQUENCE: 225
ctgtttttta ttctattact tctgtagctg ttcctatggt ggaatccatg gctgctttgg    60
tcctgatgga ccagctcatg gcgcatattg cccagtgtga gatgtttccg ctgaaccttg   120
ccctacaaga gcccattggc tctgctagca gtgcatctga actgtcacca aacctatcat   180
aatgactgtc gtggaacatg tcccagcttt ccttctatcg aaattctggt ctttgctaag   240
cagtttgcaa ttcggaaccc ccataaaccc tcgactattg ta                      282
```

<210> SEQ ID NO 226
<211> LENGTH: 397
<212> TYPE: DNA
<213> ORGANISM: Zea mays

<400> SEQUENCE: 226

```
acggacgcgt gggtatcgaa tggtgagatt gtgcacttca aagttgcttt taagccgaca    60
ccatctatcg gggtgaaaca gaacactgtg tcaagggagc gtcagaacgt tgagcttctg   120
gcaagagggc gccatgaccc atgcgtcgcc cctcgagctg ttcctgtggt ggaatccatg   180
gccgcgttgg tcctcgtgga ccagctgatg gcgcacgtgg cccagtgcga gatgttcgcg   240
ctcaatgctg cacttcaaga accagttggc tctttctagc agaggcagag cacacctgat   300
gagctcgcgc caaattttat catttatcat agtaataagt agctcaagcg tggcttggtt   360
tgcttgtctc ttgcaccgta gttttgtttt ttttccc                            397
```

<210> SEQ ID NO 227
<211> LENGTH: 420
<212> TYPE: DNA
<213> ORGANISM: Zea mays

<400> SEQUENCE: 227

```
aggggtgact actggcacgc caattgttgg tattgtccca aacacagatc agataggcag    60
tgatcaccgt gaaatagcca atgtgtaccg accttctcat gcagacgcaa cttatgactt   120
caagtacggc gttagagctg tacagggagg tgggaggtcg tttggcacag aaaccgtagg   180
aagggtggct gcaggtgccc tcgccaagaa aattcttaag ctcaaatgtg gattagagat   240
ctcgtcgttt gtttacaaag tgcatcacgt tgtgctccca aagacgcgg ttgattatgg    300
atctgtaact ttggaacata tagagagcaa catcgttaga tgtgctgatc cagagtacgc   360
agagatgatt atagacgcaa tcgacagagt tcgagttcca agggattcgg acggtggaat   420
```

<210> SEQ ID NO 228
<211> LENGTH: 406
<212> TYPE: DNA
<213> ORGANISM: Zea mays

<400> SEQUENCE: 228

```
aaaggggtgg tgattacagt gaaatgtcta aggcgtacag accattccat gcagatgcaa    60
cggatgactt caagtatgga gttagagctg tgcatggagg tggaaggtca tcagccagag   120
aaaccattgg cagggtggct gcaggagctc ttgcaaagaa aattctaaag ctcaaatcag   180
gagtggagat cttggcattt gtttctaaag tgcaccaagt cgtactttca gaagatgcag   240
ttgattatga gactgtaacc ttggaacata tagagagcaa catcgttaga tgtcctgatc   300
cataatatgc acagaagatg attgctgcca ttgatacggt acgagttata ggagattcaa   360
ttggtggggt cgtcacatgc attgcaagaa atgttcctcg tggtct                  406
```

<210> SEQ ID NO 229
<211> LENGTH: 453
<212> TYPE: DNA
<213> ORGANISM: Zea mays
<220> FEATURE:
<223> OTHER INFORMATION: unsure at all n locations

<400> SEQUENCE: 229

```
cccacgcgtc cgagtgaaat gtctaaggtg tacagaccat cccatgcaga tgcaacctgt    60
gacttcaagt atggagttag agctgtgcag ggaggtggaa ggtcatcagc cagagaaacc   120
```

```
attggcaggg tggctgcagg agctcttgca agaaaaattc taaagctcaa atcaggagtg    180
gagatcttgg catttgtttc taaagtgcac caagtcgtac ttccagaaga tgcagttgat    240
tatgagactg taaccttgga acatatagag agcaacatcg ttagatgtcc tgatccagaa    300
tatgcagaga agatgattgc tgccattgat acggtacgag ttagaggaga ttcaattggt    360
ggggtcgtca catgcattgc angaaatgtt cctcgtggtc ttggctctcc tgttttgac    420 aaacttgaag ctgaactggg caaagccatg ctt                                 453

<210> SEQ ID NO 230
<211> LENGTH: 385
<212> TYPE: DNA
<213> ORGANISM: Zea mays

<400> SEQUENCE: 230
agaccatccc atgcagatgc aacctatgac ttcaagtatg gagttagagc tgtgcaggga     60
ggtggaaggt catcagccag agaaaccatt ggcagggtgg ctgcaggagc tcttgcaaag    120
aaaattctaa agctcaaatc acgagtggag atcttggcat tgtttctaa agtgcaccaa    180 gtcgtacttc cagaagatgc agttgattat gagactgtaa ccttggaaca tatagagagc    240
aacatcctta gatgtcctga tccagaatat gcagagaaga tgattgctgc cattgatacc    300
gtacgagtta gaggagattc aattggtggg gtcgtcacat gcattggaag aaatgttcct    360
cgtggtcgtg gatcccctgt ttttg                                          385

<210> SEQ ID NO 231
<211> LENGTH: 400
<212> TYPE: DNA
<213> ORGANISM: Zea mays

<400> SEQUENCE: 231
aggatgttga actttggca aggggcgcc atgacccctg tgttgtccct cgagctgttc      60
ctatggtgga atccatggct gcgctggtcc tgatggacca gctcatggcg catattgccc    120
agtgtgagat gtttccgctg aaccttgccc tacaagagcc cattggctct gctagcagtg    180
catctgaact gtcaccaaac ctatcataat gtttgtcgtg aacatgttc cagcttctcct    240 tctatcgaaa ttctggtctt tgctaagcag tttgcaattc ggaaccccca taaaccctcg    300
actattgtac ctagagataa agtgaacgga tatcatgata gaaatgcatt tatgtttttg    360
tgatgtggta ttttactgtt attttacccc tttttttttt                          400

<210> SEQ ID NO 232
<211> LENGTH: 245
<212> TYPE: DNA
<213> ORGANISM: Glycine max
<220> FEATURE:
<223> OTHER INFORMATION: unsure at all n locations

<400> SEQUENCE: 232
ttctcttcca atggcgtctt ctcttttccac ccaaccttcg actctagacg ctctctccgn    60
cttcgcttct ctcaattccg atctctcatc cctccacccc gcctacctcc gactctcact    120
ccgtcctcgt cttcccaaga gacttcacat acaggcggct gggagtacct atggaaatca    180
ctttcgtgtt acaacatatg gggaatcaca tggaggaggt gttggttgtg ttattgatgg    240
atgtc                                                                245

<210> SEQ ID NO 233
```

```
<211> LENGTH: 254
<212> TYPE: DNA
<213> ORGANISM: Glycine max

<400> SEQUENCE: 233
atttgacaaa cttgaagctg aactagctaa agctgctatg tcattgcctg caaccaaggg      60
ctttcagttt ggtagtgggt atgcaggcac cttttttgact gggagtgaac acaatgatga    120
gttctatata gatgaacatg gaaacacaag aacaagaaca aatcgctctg gtgggataca    180
gggtggaatt ccaatggggg aaatcattaa tatgagaata gctttcaggc caacatcaac    240
aattggaaag aagc                                                      254

<210> SEQ ID NO 234
<211> LENGTH: 247
<212> TYPE: DNA
<213> ORGANISM: Glycine max

<400> SEQUENCE: 234
ccggttcaaa acgaggaaat tctagccaag aagtatagga ttcggttaag gggaattgat      60
gcaccagaaa gtgcaatgcc atatggaaag gaagctaaaa ctgaactgac caagattgtt    120
caaggcaagc ctttgaggat ccttgtttat gaggaagatc gttatggtcg ttctgtaggt    180
gatatctatt gtaatggcat ttttgtacag gaaatgatgt taaagaaagg tttagcatgg    240
cactacg                                                              247

<210> SEQ ID NO 235
<211> LENGTH: 255
<212> TYPE: DNA
<213> ORGANISM: Glycine max
<220> FEATURE:
<223> OTHER INFORMATION: unsure at all n locations

<400> SEQUENCE: 235
gtacccaata ctgatcaaag aggacatgac tatagcgaga tggcagtagc ttataggcct      60
cccatgcaga tgctacctat gacatgaagt atggtgtcag atcagttcag ggtggtggta    120
gatcttctgc aagagaaaca attggnaggg ttgcttctgg tgctgttgct aagaaaatcc    180
ttaaagaatt ttctggaact gagattctgg cctatgtctc tcaagttcat aagattgttc    240
ttccagagga cctga                                                     255

<210> SEQ ID NO 236
<211> LENGTH: 249
<212> TYPE: DNA
<213> ORGANISM: Glycine max

<400> SEQUENCE: 236
actcgagccg attcggctcg agggcttagt gaaattatta taggcaccctt tttgactggg      60 agtgcccaca atgatgagtt ctaaatagat gaacatgaa acactagaac aagaacaaat    120
cgctctgtgg gatacaggta tttgtgctgt tctgtaatta ctaattagtt gtttctagat    180
atgcactata tcagtcacat gtctatattt gtcttactta tattatctgt attgacaatc    240
agggtggaa                                                            249

<210> SEQ ID NO 237
<211> LENGTH: 201
<212> TYPE: DNA
<213> ORGANISM: Glycine max

<400> SEQUENCE: 237
```

```
gcactttatg actgggagtg aacacaatga tgagttctat atagatgaac atggaaacac    60
aagaacaaga acaaatcgct ctcgtgggat acagggtgga atttccaatg ggaaatcat    120 taatatagaa tagcttttcaa gccaacatca acaattggat taagtcttaa tctcttctct   180
ttctgtcttc atcactatct c                                              201

<210> SEQ ID NO 238
<211> LENGTH: 274
<212> TYPE: DNA
<213> ORGANISM: Glycine max

<400> SEQUENCE: 238
tctctcccaa tttctctcat caaagtttca acctttgata agattgaatc atggggaacg    60
ccctgagatt cctctacagc cattgctgca agcccacagc agctggtgat tctgaatcac   120
ttggaccaca cggtgtttcc tctgccaccg ttggtgtttc aacacttgcc catgatctct   180
ttcactttga catcacctcc caggtcccgg aaggactcag caagcatgtt gtgtcttcta   240
agaaggctca ggctaattgg tatagaaagt tagt                                274

<210> SEQ ID NO 239
<211> LENGTH: 270
<212> TYPE: DNA
<213> ORGANISM: Glycine max

<400> SEQUENCE: 239
catttctctc atcaaagttt caacctttga taagattgaa tcatggggaa cgccctgaga    60
ttcctctaca gccattgctg caagcccaca gcagctggtg attctgaatc acttggccca   120
cacggtgttt cctctgccac cgttggtgtt tcaacacttg cccatgatct ctttcacttt   180
gacatcacct cccaggtccc ggaaggactc agcaagcatg ttgtgtcttc taagaaggct   240
caggctaatt ggtatagaga gttagtagtg                                     270

<210> SEQ ID NO 240
<211> LENGTH: 254
<212> TYPE: DNA
<213> ORGANISM: Glycine max

<400> SEQUENCE: 240
aatgttttta ggtcccggaa ggactcagca agcatgttgt gtcttctaag aaggctcagg    60
ctaattggta tagaaagtta gtagatgctt ggaaagaggc aaaacctcct cctaagacac   120
ctgaagaagc agctagactt gtcattcaga ccttgagaag acatcaaaaa gcagatgttg   180
agggattgtt ggcttttctat ggtcttcctc taccacacac actggttcaa ggaactaccc   240
aacccctttc atcc                                                      254

<210> SEQ ID NO 241
<211> LENGTH: 276
<212> TYPE: DNA
<213> ORGANISM: Glycine max
<220> FEATURE:
<223> OTHER INFORMATION: unsure at all n locations

<400> SEQUENCE: 241
atcacctccc aggtcccgga aggactcagc aagcatgttg tgtcttctaa gaaggctcag    60
gctaattggt atagaaagtt agtagatgct tggaaagagg caaaacctcc tcctaagaca   120
cctgaagaag cagctagact tgtcattcag accttgagaa gacatgcaaa agcagatgt    180
```

```
tgagggattg ttggctttct atggtctcct ctaccacaca cactggttca aggaatacccc    240 aaccccttc atccttgcct gatggagttc anttga                                276

<210> SEQ ID NO 242
<211> LENGTH: 337
<212> TYPE: DNA
<213> ORGANISM: Glycine max

<400> SEQUENCE: 242
tcggaatcgg tcgtagaatt tctggaactg agattctggc ctatgtctct caagttcata     60
agattgttct tccagaggac cttattgatc atgacactct gactcttgat cagattgaga    120
gtaacattgt tcgatgtcca gacccggagt atgcagagaa gatgatatct gcaattgatg    180
ctgtgcgagt gagaggtgat tctgttggtg tgttgtgac atgcattgtg aggaactgtc     240
cacgaggtct cggttcacca gtatttgaca aacttgaagc tgagctggct aaagctgcaa    300
tgtcattgcc tgcaaccaag ggctttcagt ttggtag                              337

<210> SEQ ID NO 243
<211> LENGTH: 256
<212> TYPE: DNA
<213> ORGANISM: Glycine max

<400> SEQUENCE: 243
tgatcatgac actctgactc ttgatcagat tgagagtaac attgttcgat gtccagaccc     60
ggagtatgca gagaagatga tatctgcaat tgatgctgtg cgagtgagag gtgattctgt    120
tggtggtgtt gtgacatgca ttgtgaggaa ctgtccacga ggtctcggtt caccagtatt    180
tgacaaactt gaagctgagc tggctaaagc tgcaatgtca ttgcctgcaa ccaagggctt    240
tcagtttggt agtggg                                                     256

<210> SEQ ID NO 244
<211> LENGTH: 357
<212> TYPE: DNA
<213> ORGANISM: Glycine max
<220> FEATURE:
<223> OTHER INFORMATION: unsure at all n locations

<400> SEQUENCE: 244
gagacttcag atacgggctg ctgggagnnt ctatggaaat cactttcgtg tttcaacata     60
tggncgaatc acatggagga ggtgttggtt gtattattga tggatgtcct cctcaccttc    120
ctctctccga agctgatatg caattggatc ttgacagaag gaggcaggt cagagccgaa     180 ttacaactcc tagaaaggag actgatacat gtaaaatatt ttcaggagtt tctgaaggac    240
ttactactgg aactccaatt catgtatttg tacccatact gatcaaagag gacatgacta    300
tactgagatg gcagtagctt ataggccttc ccatgcagat ntactatgac atgagta       357

<210> SEQ ID NO 245
<211> LENGTH: 252
<212> TYPE: DNA
<213> ORGANISM: Glycine max

<400> SEQUENCE: 245
ctgaagctga tatgcaagtg gatcttgaca gaaggaggcc aggtcagagc cgaattacaa     60
ctcctagaaa ggagactgat acatgtaaaa tattttcagg agtttccgac agaatcacta    120
ctggaactca attcatgtat ctgtacccaa tactgatcaa agaggacatg actatagcga    180
gatggcagta gcttataggc cctcccatgc agatgctacc tatgacatga agtatggtgt    240
```

<210> SEQ ID NO 246
<211> LENGTH: 265
<212> TYPE: DNA
<213> ORGANISM: Glycine max

<400> SEQUENCE: 246

```
ggaaatcact ttcgtgttac aacatatggg gaatcacatg gaggaggtgt tggttgtgtt      60
attgatggat gtcctcctcg ccttcctctc tctgaagctg atatgcaagt ggatcttgac     120
agaaggaggc caggtcagag ccgaattaca actcctagaa aggagactga tacatgtaaa     180
atattttcag gagtttccga agaatcacta ctggaactcc aattcatgta tctgtaccca     240
atactgatca aagaggacat gacta                                           265
```

<210> SEQ ID NO 247
<211> LENGTH: 181
<212> TYPE: DNA
<213> ORGANISM: Glycine max
<220> FEATURE:
<223> OTHER INFORMATION: unsure at all n locations

<400> SEQUENCE: 247

```
agagacttca gatacgggct gctgggagta tctatggaaa tcactttcgt gtttcaacat      60
atggagaatc acatggagga ggtgttggtt gtattattga tgnatgtcct cctcaccttc     120
ctctctccga agctgatatg caattggatc ttgacagaag gaggccaggt caganccgaa     180
t                                                                     181
```

<210> SEQ ID NO 248
<211> LENGTH: 274
<212> TYPE: DNA
<213> ORGANISM: Glycine max
<220> FEATURE:
<223> OTHER INFORMATION: unsure at all n locations

<400> SEQUENCE: 248

```
ctctttccac caaaccattc acacccgncg ctctctccgg cttcgcttct ctcaattccg      60
atctcggacc cctctccccc gcctacctcc gactctcact ccgtcctcgt cttcccaaga     120
gacttcacat acaggcggct gggagtacct atggaaatca ctttcgtgtt acaacatatg     180
gggaatcaca tggaggaggt gttggttgtg ttattgatgg atgtcctcct cgccttcctc     240
tctctgaagc tgatatgcaa gtggatcttg acag                                 274
```

<210> SEQ ID NO 249
<211> LENGTH: 248
<212> TYPE: DNA
<213> ORGANISM: Glycine max

<400> SEQUENCE: 249

```
gacgctctct ccgccttcgc ttctctcaat cccgatctcc gatccttctc ccccggctac      60
ctccgtctct cactccgtcc tcgtcttccc aagatacttc agatacgggc ttctgggagt     120
atctatggaa atcactttcg tgtttcaaca tatggagaat cgcatggagg aggtgttggt     180
tgtattattg atggatgtcc tcctcacctt cctctctccg aagctgatat gcaattggat     240
cttgacag                                                              248
```

<210> SEQ ID NO 250

<211> LENGTH: 302
<212> TYPE: DNA
<213> ORGANISM: Glycine max
<220> FEATURE:
<223> OTHER INFORMATION: unsure at all n locations

<400> SEQUENCE: 250

```
tctaattctc ccatttctct tccaatggcg tcttctcttt ccaccaaacc attctacanc      60
cgacgctctc tccgccttcg cttctctcaa ttccgatctc ggatccctct ccccgccta     120
cctccgactc tcactccgtc ctcgtcttcc aagaacttc gcatacaggc ggctgggagt     180
acctatggaa atcactttcg tgttacaaca tggggaat cacatggagg aggtgttggt     240
tgtgttattg atggagtctc ctcgccttct tctctctgaa gctgatatgc aagtggannct     300
tc                                                                   302
```

<210> SEQ ID NO 251
<211> LENGTH: 246
<212> TYPE: DNA
<213> ORGANISM: Glycine max

<400> SEQUENCE: 251

```
ctccaccaaa ccattctcat caaccgacgc tctctccgcc ttcgcttctc tcaatcccga      60
tctccgatcc ttctccccg gctacctccg tctctcactc cgtcctcgtc ttcccaagag     120
acttcagata cgggctgctg ggagtatcta tggaaatcac tttcgtgttt caacatatgg     180
agaatcgcat ggaggaggtg ttggttgtat tattgatgga gtcctcctc accttccctc     240
tccgaa                                                               246
```

<210> SEQ ID NO 252
<211> LENGTH: 275
<212> TYPE: DNA
<213> ORGANISM: Glycine max

<400> SEQUENCE: 252

```
gttcctcaat caatctaatt ctcccatttc tcttccaatg gcgtcttctc tttccaccaa      60
accattctca tccgacgctc tctccgcctt cgcttctctc aattccgatc tcggatccct     120
ctccccgcc tacctccgac tctcactccg tcctcgtctt cccaagagac ttcacataca     180
ggcggctggg agtacctatg gaaatcactt tcgtgttaca acatatgggg aatcacatgg     240
aggaggtgtt ggttgtgtta ttgatggatg tcctc                               275
```

<210> SEQ ID NO 253
<211> LENGTH: 262
<212> TYPE: DNA
<213> ORGANISM: Glycine max

<400> SEQUENCE: 253

```
gcgttcttct ctctccacca aaccattctc atcaaccgac gctctctccg ccttcgcttc      60
tctccttccc gatctccgat ccttctcccc cggctacctc cgtctctcac tccgtcctcg     120
tcttcccaag agacttcaga tacgggctgc tgggagtatc tatggaaatc actttcgtgt     180
ttcaacatat ggagaatcca tggaggaggt gttggttgta ttattgatgg atgtcctcct     240
caccttcctc tctccggagc tg                                             262
```

<210> SEQ ID NO 254
<211> LENGTH: 263
<212> TYPE: DNA
<213> ORGANISM: Glycine max

```
<220> FEATURE:
<223> OTHER INFORMATION: unsure at all n locations

<400> SEQUENCE: 254
agatactgtg agtgtttttn ttcctcaatc aatctaattc tctcaatggc ttcttctctc      60
tccaccaaac cattctcatc aaccgacgct ctctccgcct tcgcttctct caatcccgat     120
ctccgatcct tctcccccgg ctacctccgt ctctcactcc gtcctcgtct tcccaagaga     180
cttcagatac gggctgctgg gagtatctat ggaaatcact ttcgtgtttc aacatatgga     240
gaatcgcatg gaggaggtgt tgg                                             263

<210> SEQ ID NO 255
<211> LENGTH: 374
<212> TYPE: DNA
<213> ORGANISM: Glycine max

<400> SEQUENCE: 255
tctctttcca ccaaaccatt ctcagccgac gctctctccg ccttcgcttc tctcaattcc      60
gatctcggat ccctctcccc cgcctacctc cgactctcac tccgtcctcg tcttcccaag     120
agacttcgca tacaggcggc tgggagtacc tatggaaatc actttcgtgt tacaacatat     180
ggggaatcac atggaggagg tgttggttgt gttattgatg gatgtcctcc tcgccttcct     240
ctctctgaag ctgatatgca agtggatctt gacagaagga ggccaggtca gagccgaatt     300
acaactccta gaaaggagac tgatacatgt aaaatatttt caggagtttc gaaggaatc      360 actactggaa ctcc                                                       374

<210> SEQ ID NO 256
<211> LENGTH: 222
<212> TYPE: DNA
<213> ORGANISM: Zea mays

<400> SEQUENCE: 256
cttttggaga gagcacagtt ttgttacaat gctgatacat atgatagcaa tgctttccac      60
atggatggtt ttggcggctc tttggttgaa tatatggtta gagaaactga aaagctccat     120
gcacatgttg ggagatacaa gagccagatg agcacctttc tttccgagga tctgcctgag     180
cccggttgca gctatgatac caaggtttgc accatgcgat ct                        222

<210> SEQ ID NO 257
<211> LENGTH: 267
<212> TYPE: DNA
<213> ORGANISM: Zea mays

<400> SEQUENCE: 257
gtacccgctc aaccggccgg cctacgaccc cctccactcc gccgccggcc gccgcctcaa      60
cgcctctttc gtcgagctct tcatccgcga gtccgaggcc gttcagtcca aggccggaag     120
gtaccaaagc ctacaggaga ttccattctt cgcttacaga gttccttctg ctctggcgcc     180
tccatacaac ttcacaagcg atctgtatcc cgctgccgcg tcagtcaacg ttaacgacgc     240
catatggagc atgtacttcg acgagct                                         267

<210> SEQ ID NO 258
<211> LENGTH: 346
<212> TYPE: DNA
<213> ORGANISM: Zea mays

<400> SEQUENCE: 258
```

```
ccggcatttt ccttgcacaa cgtgctctcc ctcccatttc ctgcgaggtg gttggtagcg    60
atggccttca agctgatcac caagcccgcg gcggcgtcgc ccgctgctgc ttactgggga   120
gatctcgccc aacaactccg caacgccat  agctaaggta gagagggttg atcgaagtga   180
catattgaca ttggatagca tcagacaagt tttgattaga ctagaagaca gcatcatatt   240 tggcctttg  gagagagcac agttttgtta caatgctgat acatatgata gcaatgcctt   300
tcacatggat ggttttggag gatctttggt ctgatatata gttaga               346
```

<210> SEQ ID NO 259
<211> LENGTH: 258
<212> TYPE: DNA
<213> ORGANISM: Zea mays

<400> SEQUENCE: 259

```
gttgggagat acaagagccc agatgagcac cctttctttt ccaaggatct gcctgagccc    60
cggttgccac ctatgcaata cccaagggtt ttgcatccca ttgctgattc tatcaatatc   120
aacaaagaga tttggaaaat gtattttgat gaacttcttc caagattggt gaaagaagga   180
agtgatggta atgctggatc cagtgctctt tgtgacacaa cctgcttgca ggcactctcc   240
agaaggatcc actatggg                                                 258
```

<210> SEQ ID NO 260
<211> LENGTH: 254
<212> TYPE: DNA
<213> ORGANISM: Zea mays

<400> SEQUENCE: 260

```
ctatgggaag tttgtggcag aggctaagtt tcaggagtcc ccggaagctt acatgccagc    60
cataatagct caggaccgtg atcaactcat gcaccttctc acatatgaaa cggtggagcg   120
tgctatcgaa catagggtgg aagccaaagc caagatcttc gggcaagagg tgaacatcgg   180
tgtggaggac aacggcagcc caccggtgta caagatcgtt ccgagcttgg tcgccgagct   240
gtacagctac agaa                                                     254
```

<210> SEQ ID NO 261
<211> LENGTH: 216
<212> TYPE: DNA
<213> ORGANISM: Zea mays

<400> SEQUENCE: 261

```
accgtgatca actcatgcgc cttctcacat atgaaacggt ggagcgtgct gtcgaacaca    60
gggtggaagc caaagccaag atcttcgggc aagaggtgaa cattggtgct aaggacaacg   120
gcagccaacc agtctacaaa atcaggccga gcttggtcgc cgagctgtac agctacagaa   180
tcatgccgct aaccaaggag gttgaggtcg cgtact                             216
```

<210> SEQ ID NO 262
<211> LENGTH: 308
<212> TYPE: DNA
<213> ORGANISM: Zea mays

<400> SEQUENCE: 262

```
cccattcgtt ctagccctcc ctccgacact ccgatccatt actcgctatg gacgcggcgg    60
gcggcgacca gctaagcctg gccgcggtgc gcgacgcgct ggtgcggctg gaggactccg   120
tggtgttcgc gctcatcgag cggccccggc atccgcggaa ccgccagcct acgcgcccgc   180
cgccaccgct ggagaacatt cgctcgtgga gttcttcgtc cgggaagcag aggccctcaa   240
```

```
cgcaaaggct ggacattatc aaaagccaga agatgttcca ttcttccctc aagatctacc    300
ctcacctc                                                             308
```

<210> SEQ ID NO 263
<211> LENGTH: 178
<212> TYPE: DNA
<213> ORGANISM: Zea mays

<400> SEQUENCE: 263

```
ctcaatacaa atgtgagttc ttgtaggctg gacattatca aaagccagaa gatgttccat    60
tcttccctca agatctaccc tcacctctct ttcctacaaa gccttccgca aaggtcttgc    120
acccttttgc ttcattggtc accgtgaatg atgcaatatg gaaaatgtat tttgatga     178
```

<210> SEQ ID NO 264
<211> LENGTH: 232
<212> TYPE: DNA
<213> ORGANISM: Zea mays

<400> SEQUENCE: 264

```
cttttattag ggaagagagg gttgatcgaa gtgaaatatt gacattggat agcattagac    60
aagttttgat tagactagaa gacagcatca tatttggcct tttggagaga gcacagtttt    120
gttacagtgc tgatacatat gatagcaatg ctttccacat ggatggtttt ggcggctttt    180
tggttgaata tatggttaga gaaactgaaa agctccatgc acaggttggg ag           232
```

<210> SEQ ID NO 265
<211> LENGTH: 304
<212> TYPE: DNA
<213> ORGANISM: Zea mays

<400> SEQUENCE: 265

```
agctggccac caaggccgcg gcggcgtcgc ccgctgctgc tcaccgcggg ggtctcgccc    60
gggggccgga gggtacgatc cgcgttgcct tcggaccagc gcctagaaac aaggggctcc    120
gcgcggccaa caactccgcg acgcccgtgg ctacggaaga gagggttgat cgaagtgaaa    180
tattgacatt ggatagcatt agacaagttt tgattagact agaagacagc atcatatttg    240
gccttttgga gagagcacag ttttgttaca atgctgatac atatgatagc aatgcttttcc   300 acat                                                                304
```

<210> SEQ ID NO 266
<211> LENGTH: 260
<212> TYPE: DNA
<213> ORGANISM: Zea mays

<400> SEQUENCE: 266

```
tggccttcaa gctggccacc aaggccgcgg cggcgtcgcc cgctgctgct caccgcgggg    60
gtctcgcccg ggggccggag ggtacgagcc gcgttgcctt cggaccagcg cctagaaaca    120
aggggctccg cgcggccaac aactccgcga cgcccgtggc taaggaagag agggttgatc    180
gaagtgaaat attgacattg gatagcatta gacaagtttt gattagacta gaagacagca    240
tcatatttgg ccttttggag                                               260
```

<210> SEQ ID NO 267
<211> LENGTH: 281
<212> TYPE: DNA
<213> ORGANISM: Zea mays

```
<400> SEQUENCE: 267
gtcgactaat aaaagaaaag gacaccgatt ctctgatgga tatgctgaca ttcaaggctg    60
tggaagagaa ggtcaagaag agagtagaga agaaggccag gacgttcggg cagaacgtca   120
ccttggagga caatgccact gctggtgaca gcgagtgcaa ggtcgatccc aaagtgctct   180
ccaagctgta tgatcagtgg gtgatgccac tgaccaagga tgtcgaagtc gagtatctcc   240
tgcgccgcct cgattgatca cccgattagt tgtagctgcg a                       281

<210> SEQ ID NO 268
<211> LENGTH: 227
<212> TYPE: DNA
<213> ORGANISM: Zea mays

<400> SEQUENCE: 268
caagaagaga gtagagaaga aggccaggac gttcgggcag aacgtcacct tggaggacaa    60
tgccactgct ggtgacagcg agtgcaaggt cgatcccaaa gtgctctcca agctgtatga   120
tcagtgggtg atgccactga ccaaggatgt cgaagtcgag tatctcctgc gccgcctcga   180
ttgatcaccc gattagttgt agctgcgaac tttatgtacg cgtggtt                 227

<210> SEQ ID NO 269
<211> LENGTH: 451
<212> TYPE: DNA
<213> ORGANISM: Zea mays
<220> FEATURE:
<223> OTHER INFORMATION: unsure at all n locations

<400> SEQUENCE: 269
aggggnnnna aatttagctg atatcattgc atgtctgtcc ggttccaatt cgacccacgc    60
gtacgaagag cccagatgag caccctttct ttcctgagga tctgcctgag cccggttgc    120 cagctatgca gtacccaagg gttttgcatc ccattgccga ttctatcaat atcaacaaag   180
agatttggaa aatgtatttt gatgaacttc ttccaagatt ggtgaaaaaa ggaagtgatg   240
gtaatgctgg atccagtgct ctttgtgaca cgacctgctt gcaggcgctc tccaaaagga   300
tccactatgg gaagtttgtg gcagaagcta gtttcagga gtccccggaa gcttacatgc    360
catccataat agctcaagac cgtgatcaac tcatgcacct tctcacatat gaaacggtgg   420
aacgtgctat cgaacacagg gtggaaacca a                                  451

<210> SEQ ID NO 270
<211> LENGTH: 453
<212> TYPE: DNA
<213> ORGANISM: Zea mays

<400> SEQUENCE: 270
atgctttcca catggatggt tttggcggct ctttggttga atatatggtt agagaaactg    60
aaaagctcca tgcacaggtt gggagataca agagcccaga tgagcaccct ttctttcctg   120
aggatctgcc tgagccccgg ttgccaccta tgcagtaccc aagggttttg catcccattg   180
ccgattctat caatatcaac aaagagattt ggaaaatgta ttttgatgaa cttcttccaa   240
gattggtaaa aaaggaagt gatggtaatg ctggatccag tgctctttgt gacacgacct    300
gcttgcaagc gctctccaaa aggatccact atgggaagtt tgtggcagag ctaagtttc    360 aggagtcccc ggaagcttac atgccagcca taatagctca agaccgtgat caactcatgc   420
accttctcac atatgaaacg gtggagcgtg cta                                453
```

<210> SEQ ID NO 271
<211> LENGTH: 403
<212> TYPE: DNA
<213> ORGANISM: Zea mays

<400> SEQUENCE: 271

| | | | | | |
|---|---|---|---|---|---|
| aagagcccag | atgagcaccc | tttcttttcc | aaggatctgc | ctgagcccg | gttgccaggt | 60 |
| atgcggtacc | caaaggtttt | gcatcccatt | gctgattcta | tcaatatcaa | caaagagatt | 120 |
| tggaaaatgt | attttgatga | acttctacca | agattggtga | agaaggaag | tgatggtaat | 180 |
| gctggatcca | gtgctctttg | tgacacaacc | tgcttgcagg | cactctccag | aaggatccac | 240 |
| tatgggaagt | atgtggcaga | cgcctagttt | caagagtccc | ctgaagctta | cacgccagcc | 300 |
| ataatagccc | aagtctgctt | ttgttccaac | tattagtatt | tctagtacta | ctattttcat | 360 |
| ttattttta | atctaattcc | aaagtttcag | aaccaaattg | ttt | | 403 |

<210> SEQ ID NO 272
<211> LENGTH: 426
<212> TYPE: DNA
<213> ORGANISM: Zea mays

<400> SEQUENCE: 272

| | | | | | |
|---|---|---|---|---|---|
| cggacgcgtg | ggcggacgcg | tgggcacata | tgaaacggtg | gagcgtgcta | tcgaacacag | 60 |
| ggtggaggcc | aaagccaaga | tcttcgggca | agaggtgaac | attggtgcta | aggacaacgg | 120 |
| cagcccaccg | gtctacaaaa | tcaggccgag | cttggtcgcc | gagctgtaca | gctacagaat | 180 |
| catgccgcta | accaaggagg | ttgaggtcgc | gtacttgctt | aagaggctgg | attgagtgtg | 240 |
| tttacgtagc | tgtaaaactg | ccagatccga | actcctggta | ttaaaccata | acatcggtaa | 300 |
| gtacccattt | ctgtgaagag | gatgatccga | actcctgtca | ttaaaccaga | acatcagtaa | 360 |
| gtacccagtt | ttggggaaag | gatggaaaat | ataccatgtg | tggcaagcaa | catgcataat | 420 |
| atcatc | | | | | | 426 |

<210> SEQ ID NO 273
<211> LENGTH: 363
<212> TYPE: DNA
<213> ORGANISM: Zea mays

<400> SEQUENCE: 273

| | | | | | |
|---|---|---|---|---|---|
| cgcagttcac | gcttggctga | cgaccgaccc | ccattcgttc | tagccctccc | tccgacactc | 60 |
| cgatccatta | ctcgctatgg | acggcgggg | cggcgaccag | ctaagcctgg | ccgcggtgcg | 120 |
| cgacgcgctg | gtgcggctgg | aggactccgt | ggtgttcgcg | ctcatcgagc | gcgcccggca | 180 |
| tccgcggaac | gcgccagcct | acgcgcccgc | cgccaccgct | ggagaacatt | cgctcgtgga | 240 |
| gttcttcgtc | cgggaagcag | aggccctcaa | cgcaaaggct | ggacattatc | aaaagccaga | 300 |
| agatgttcca | ttcttccctc | aagatctacc | ctcacctctc | tttcctacaa | agccttcccc | 360 |
| aaa | | | | | | 363 |

<210> SEQ ID NO 274
<211> LENGTH: 426
<212> TYPE: DNA
<213> ORGANISM: Zea mays

<400> SEQUENCE: 274

| | | | | | |
|---|---|---|---|---|---|
| cggacgcgtg | ggcggacgcg | tgggtggcct | tcaagctggc | caccaaggcc | gcggcggcgt | 60 |
| cgcccgctgc | tgctcaccgc | gggggtctcg | cccgggggcc | ggagggtacg | agccgcgttg | 120 |

-continued

```
ccttcggacc agcgcctaga aacaagggc tccgcgcggc caacaactcc gcgacgcccg    180
tggctaagga agagagggtt gatcgaagtg aaatattgac attggatagc attagacaag    240
ttttgattag actagaagac agcatcatat tcggccttt ggagagagca cagttttgtt     300
acaacgctga tacatatgat agcaatgctt tccacatgga tggttttggc ggctctttgg    360
ttgaatatat ggttagagaa actgaaaagc tccatgcaca ggttgggaga tacaagagcc    420
cagatg                                                               426
```

<210> SEQ ID NO 275
<211> LENGTH: 435
<212> TYPE: DNA
<213> ORGANISM: Zea mays

<400> SEQUENCE: 275

```
ccttcaagct ggtcaccaag cccgcggcgg cgtcgcccgc tgctgctcac tggggagagc    60
tcgcccgggg gccgcagggt accagccgcg ttggctcttg acacaagccc acaaacacag    120
ggcgctccgc acggacaaaa tctccgaaac gcccatggct aaggaagaga gggttgatcg    180
aagtgaaata ttgacatggg atagcatcag acaagttttg attagactag aagacagcat    240
catatttgga cttttggaga gagcacagtt tgttacaac gctgacacat atgatagcaa     300
tgcttttcca catgatggtt ttggagggtc ttttggttgaa tatatggtta gagaaactga    360
aaagctccat gcacaggttg ggaggtacaa gagcccagat gagcacccttt tctttccaa    420 ggatctgcct gagcc                                                     435
```

<210> SEQ ID NO 276
<211> LENGTH: 379
<212> TYPE: DNA
<213> ORGANISM: Zea mays

<400> SEQUENCE: 276

```
cctcccactt cgtgcgagcg tcccgaacta agttgctcgt ggtggaggtg gtttgtggcg    60
atggccttca agctggtcac caagcccgcg cggcgtcgc cgctgctgc tcactgggga     120 gatctcgccc ggtggccgca gggtacgagc cgcgttgcct tcggaccagc gcccaggaac    180
aaggggctcc gcacgggcaa caactccgca acgcccatgg ctaaggaaga gagggttgat    240
cgaagtgaaa tattgacatt ggatagcatc agacaagttt tgattagact agaagacagc    300
atcatatttg acttttgga gagagcacag ttttgttaca acgctgacac atatgatagc     360
aatgctatcc acatggatg                                                  379
```

<210> SEQ ID NO 277
<211> LENGTH: 405
<212> TYPE: DNA
<213> ORGANISM: Zea mays

<400> SEQUENCE: 277

```
aaagaattca tattggtaaa tatgttgctg aggtgaagtt caaagacgct cctcaagagt    60
atagtcgact aataaaagaa aaggacagca attctctgat ggatatgctg acattcaagg    120
ctgtggaaga gaaggtcaag aagagagtag agaagaaggc taggacgttc gggcagaacg    180
tcaccttgga tgacaatgcc actgctggtg acagcgagtg caaggtcgat cccaaagtgc    240
tctccaagct gtatgatcag tgggtgatgc cactgaccaa ggatgtcgaa gtcgagtatc    300
tcctgcgccg cctcgactga tcagtgatca cccgattagc tgtagctgct aactttatgt    360
acgcgtgggt atcagattgc tttgcacatg ctctttatgg cttta                    405
```

<210> SEQ ID NO 278
<211> LENGTH: 322
<212> TYPE: DNA
<213> ORGANISM: Glycine max

<400> SEQUENCE: 278

| | | | | | |
|---|---|---|---|---|---|
| agctgaggca | aaatatcaag | ctagtccaga | ttcatataaa | gatgccatta | tagcacagga | 60 |
| caaggacaag | ttgatggaat | tgctaacata | tcctgaagtt | gaagaggcaa | ttaagaggag | 120 |
| agttgacatg | aagaccaaga | cttatgggca | agaactggtt | gtaactacga | aggaacatcg | 180 |
| aactgaacct | gtctacaaaa | taaatccaag | cttggttgct | gatctataca | gtgattggat | 240 |
| catgccattg | acaaaggaag | ttcaagttgc | ctatctgttg | agaaggttgg | attgaacata | 300 |
| acaaaaagta | ccttttcaat | ta | | | | 322 |

<210> SEQ ID NO 279
<211> LENGTH: 262
<212> TYPE: DNA
<213> ORGANISM: Glycine max

<400> SEQUENCE: 279

| | | | | | |
|---|---|---|---|---|---|
| cccacaaata | gtcaaacaag | gggatgatgg | taactctgga | tccagtgctg | tttgtgatgt | 60 |
| aatatgcttg | caggctctct | caaagagaat | tcattatgga | aaatatgtag | ctgaggcaaa | 120 |
| ataccaagct | agtccagatt | catataaaga | tgccattata | gcacaggaca | aggacaagtt | 180 |
| gatggaattg | ctaacatatc | ctgaagttga | agaggcaatt | aagaggagag | ttgacatgaa | 240 |
| gaccaagact | tatgggcaag | aa | | | | 262 |

<210> SEQ ID NO 280
<211> LENGTH: 263
<212> TYPE: DNA
<213> ORGANISM: Glycine max

<400> SEQUENCE: 280

| | | | | | |
|---|---|---|---|---|---|
| aagacgacag | aaggggaaaa | agtatggagt | ttatacttca | gagttcttat | tccacaaata | 60 |
| gtccaagcaa | ggagatgatg | gtaactctgg | atccagtgct | gtttgtgatg | taatatgctt | 120 |
| gcaggctctc | tcaaagagaa | ttcattatgg | caaatatgta | gctgaggcaa | attatcaagc | 180 |
| tagtccagat | tcatataaag | atgccattat | agcacaggac | aaggacattg | ttatggaatt | 240 |
| gctaacatat | cgtgaagttg | aag | | | | 263 |

<210> SEQ ID NO 281
<211> LENGTH: 299
<212> TYPE: DNA
<213> ORGANISM: Glycine max

<400> SEQUENCE: 281

| | | | | | |
|---|---|---|---|---|---|
| tgttggttct | ctttcaatgg | agtctaagct | tttaagagcc | accaccatct | cagtcccttc | 60 |
| aacaccctca | tgcgctttcc | atcgcacaac | tcgcaaggct | tcgatttcct | tcaaccccac | 120 |
| ctcggatttc | gccccaaaaa | gcaatctttc | tctccaggca | catgcggctt | ccatcgagtc | 180 |
| agtgccaaca | agaaaagaa | ttgatgagag | tgacaacctg | accttgatc | atataagacg | 240 |
| ttctttagtt | cgtcaagagg | atagcataat | cttcagtctc | atcggcgagc | acaatactg | 299 |

<210> SEQ ID NO 282
<211> LENGTH: 388
<212> TYPE: DNA

<213> ORGANISM: Glycine max

<400> SEQUENCE: 282

```
gccattttag cccaggacaa ggataggttg atggatatgc taacatatcc gaaagttgaa      60
gaggaaaaca tgataagagt agaggaaaag gccaaaaaat ttggcctagt agtggattta     120
aatgcaaaga agcctcgagc tgagccactg tacataataa atccaagtgt ggtttctgat     180
ctgtatggcc attgggtcat gccattgaca aaggaagtgc aagttgcata tttattgagg     240
aggctggact aaacatatag taagagttct tggttatgtt ggtggtagag aaccaataat     300
tcatgtatat aaataaagct tagactgagt aataatgtct tgaatggac ttgaatttga      360
tagaaattaa caaacaccgt tttcttc                                         388
```

<210> SEQ ID NO 283
<211> LENGTH: 319
<212> TYPE: DNA
<213> ORGANISM: Glycine max

<400> SEQUENCE: 283

```
acgcgtcagt acggctgcga aagacgaca gaaggggta gaatttgttg ttaagaatac       60
agaggccatt caagctaagg ctggaagata caaaaccct gaagaaaacg ccttcttccc     120
agaaaattta ccaccatcaa ttgtgccatc ttactccttc aaacagtttt tgcatcctgg     180
agctgcttca attaacatta acaagtccat ctggaaaatg tatttccaag agttacttcc     240
attggttgct acttcggggg atgatggaaa ctatgcacaa actgcagcta atgatctttc     300
attagtgcag gccatctct                                                  319
```

<210> SEQ ID NO 284
<211> LENGTH: 424
<212> TYPE: DNA
<213> ORGANISM: Glycine max

<400> SEQUENCE: 284

```
cccacgcgtc cgtacggctg cgagaagacg acagaagggg ggcaagaact ggttgtaact     60
acgaaggaac atcgaactga acctgtctac aaaataaatc caagcttggt tgctgatcta    120
tacagtgatt ggatcatgcc attgacaaag gaagttcaag ttgcctatct gttgagaagg    180
ttggattgaa cataacaaaa agtacctttt caattacagt gtttataggg ttatttatct    240
tttctaggaa atgatacttg caatgggtaa tttctcttga atcatgattc atgactataa    300
acttgagctt ttgtaactaa catatgagga agctgatatt gggttcttat ataataatta    360
atggcatctt ttatgttgtt ccaaaaaaaa gacatggact aatccaaaaa aaagcggccg    420
ctct                                                                 424
```

<210> SEQ ID NO 285
<211> LENGTH: 297
<212> TYPE: DNA
<213> ORGANISM: Zea mays

<400> SEQUENCE: 285

```
tgccctcaca agccagaagg ttccatgttt gtcatggtga aactaaattt gtatcttttg     60
gagagcatcc atgatgatat tgattttgt tgcaagctgg caaaagaaga gtccgtgatt     120
ttgtgtccag ggagtgtttt gggaatggaa aactggatcc gtatcacttt cgccattgat    180
tcatcttctc ttcttgatgg tcttgagagg ctgaaatctt tctgccaaag gcataagaag    240
aagaatttgc ttaatggcca ttaactatat acgacttcag agttgttacc cacttcc       297
```

<210> SEQ ID NO 286
<211> LENGTH: 291
<212> TYPE: DNA
<213> ORGANISM: Zea mays

<400> SEQUENCE: 286

```
cacatgccct cacaagccag aaggttccat gtttgtcatg gtgaaactaa atttgtatct     60
tttggagagc atccatgatg atattgattt ttgttgcaag ctggcaaaag aagagtccgt    120
gattttgtgt ccagggagtg ttttgggaat ggaaaactgg atccgtatca ctttcgccat    180
tgattcatct tctcttcttg atggtcttga gaggctgaaa tctttctgcc aaaggcataa    240
gaagaagaat tgcttaatg gccattaact atattcgact caaagttgt t                291
```

<210> SEQ ID NO 287
<211> LENGTH: 265
<212> TYPE: DNA
<213> ORGANISM: Zea mays

<400> SEQUENCE: 287

```
ctcttgccga caagaatact gttgccatgg tcattgtgaa cccaggaaac ccatgtggca     60
atgtgtactc ctatgagcac ctggccaagg tcgctgagac cgcgcgaaag cttggcatat    120
tcgtcatagc agatgaggtt tacgcacact tgacatttgg agagaggaaa tttgtgccga    180
tgggtgtgtt tggggctgtg gctccagtgt taacactggg gtccatatca aagagatgga    240
tggtgcctgg atggcggctt ggatg                                          265
```

<210> SEQ ID NO 288
<211> LENGTH: 296
<212> TYPE: DNA
<213> ORGANISM: Zea mays

<400> SEQUENCE: 288

```
aaaccccaac aatccttgcg gcagtgtcta cacccgtgaa catttagcca aggttgcaga     60
ggtagcaagg aagcttggaa tactaatcat cgctgatgaa gtgtatggaa acctggtgtt    120
tggggacacc ccttacgtcc caatgggtgt ctttggccac attgcccctg tgttgagcat    180
aggatcacta tcgacgagat ggatagtgcc tgggtggcga cttggttggg tagctgtatg    240
tgatcccaac aagattctgc aagacaccaa gatcattgca tcaataacaa acttcc        296
```

<210> SEQ ID NO 289
<211> LENGTH: 232
<212> TYPE: DNA
<213> ORGANISM: Zea mays

<400> SEQUENCE: 289

```
cggctcgagc cttgcggcag tgtctacacc cgtgaacatt tagccaaggt cgcggaggta     60
gcaaggcagc ttggaatact agtcatcgct gatgaagtgt atggaaacct ggtgtttggg    120
gacaccccct tacgtcccaat gggtgtcttt ggccatattg ccctgtgtt gagcttagga    180
tcactatcga agagatggat agtgcctggg tggcgacttg gttgggtagc tg            232
```

<210> SEQ ID NO 290
<211> LENGTH: 253
<212> TYPE: DNA
<213> ORGANISM: Zea mays

<400> SEQUENCE: 290

```
cgacgacatc ttcgtcaccg ccggaggacg acaagccatc gaggtggtgg tctcagtcct      60
cgcgcagccg ggcaccaaca tactgctccc gaggccgggc tatccgaact acgaggcgcg     120
cgcagggctg cacaacctgg aagtccgccg gttcaatctg atccccgaga gagggtggga     180
gattgacatc gacggtctgg agtcgatcgc cgacaagaac accaccgcca tggtcatcat     240 aaacccccaac aac                                                        253

<210> SEQ ID NO 291
<211> LENGTH: 235
<212> TYPE: DNA
<213> ORGANISM: Zea mays

<400> SEQUENCE: 291
cccacgcgtc cgctctggcg gacacctgtc gagcgacctt ccatacaagc tgtcgagcga      60
cgacatcttc gtcaccgccg gaggacgcaa gccatcgagg tggtggtctc agtcctcgcg     120
caccgggcac caacatactg ctcccgaggc cgggctatcc gaactacgag gcgcgcgcag     180
ggctgcacaa cctggaagtt cgccggttca atctgatccc cgagagaggg tggga          235

<210> SEQ ID NO 292
<211> LENGTH: 398
<212> TYPE: DNA
<213> ORGANISM: Zea mays
<220> FEATURE:
<223> OTHER INFORMATION: unsure at all n locations

<400> SEQUENCE: 292
cccacgcgtc cggtggtggt ctcagtcctc gcgcagccgg gcaccaacat actgctcccg      60
aggccgggct atccgaacta cgaggcgcgc gcagggctgc acaacctgga agttcgccgg     120
ttcaatctga tccccgagag agggtgggag attgacatcg acggtctgga gtcgatcgcc     180
gacaagaaca ccaccgccat ggtcatcata aaccccaaca accccttgcgg gagtgtctac     240 acccgtgagc atttggccaa ggtcgcggag gtggcaagga agcttggaat actggtcatc     300
gctgatgagg tgtatggaaa tctggtgttt ggggacaccc ctttcgtccc catggggtgt     360
cttggccaca ttgcccctgg gttgaccata ngatcact                              398

<210> SEQ ID NO 293
<211> LENGTH: 246
<212> TYPE: DNA
<213> ORGANISM: Glycine max

<400> SEQUENCE: 293 cgttttctc accattggtg gcacacaagc catagatata attttacctt ccctagcacg       60
tcctggtgcc aacattctcc ttccaaaacc agggtaccca cattatgaac ttcgtgccac     120
tcgttgtctt cttgaaattc gacactttga tcttttgcct gagagaggat gggaagttga     180
ccttgactct ttggaagctt tggcagatga aacactgtg ccattgttt tcatcagtcc      240 tagtag                                                                246

<210> SEQ ID NO 294
<211> LENGTH: 262
<212> TYPE: DNA
<213> ORGANISM: Glycine max

<400> SEQUENCE: 294
cgaacccttc agtcacacaa gtttcgtggc tatgctccca ctgcaggtct tccacaggcc      60
aggattgcca ttgctgaata cctgtctcgt gaccttcctt accaattatc aaatgaggat     120
```

```
gtttatatca cttgtggatg cacacaagcc attgatgatt cagtggcaat gcttgctcgc    180
cccggtgcaa acatcttgct tccaagacca ggcttcccac tctatgaact tagtgcttca    240
tttagagggg ttgaagtgag gc                                             262
```

<210> SEQ ID NO 295
<211> LENGTH: 264
<212> TYPE: DNA
<213> ORGANISM: Glycine max

<400> SEQUENCE: 295

```
tgcttccaga gaaaggttgg gaggttgatc tagatgctgt tgaagctctt gctgatcaga    60
acacagtggc gttggcgatc ataaaccctg ggaatccttg tgggaatgtg tacagttacc    120
accatttgga gaagattgct gaaactgcaa acgggttgg aacaattgtg atctctgatg    180
aagtttatgg tcaccttgca tttgggagca agccttttgt accgatggga gttttggct    240 ctactgttcc tgttctcact cttg                                           264
```

<210> SEQ ID NO 296
<211> LENGTH: 244
<212> TYPE: DNA
<213> ORGANISM: Glycine max

<400> SEQUENCE: 296

```
tgttcctgtt ctgactcttg gctcattttc taagagatgg atagttcctg gatggaggct    60
tggttggttt gttacaaatg atccatctgg cactttaga aatccaaagg tagatgagcg    120
aattaaaaag tactttgatc ttttgggagg tcctgccacc ttcatccagg cagctctacc    180
tcagataatt gcgcatactg aagaggtttt cttcaagaaa accattgata atttgaggca    240
tgct                                                                 244
```

<210> SEQ ID NO 297
<211> LENGTH: 247
<212> TYPE: DNA
<213> ORGANISM: Glycine max

<400> SEQUENCE: 297

```
cttgcatttg caggcagcct tttgtgccaa tgggagtttt tggctatatt gttcctgttc    60
tgaatctagg ctcatttct aagagatgga tatttcctgg atggaggctt ggttggtttg    120
tgacaaatga tccatctggc acttgtagaa atccaaaggt atatgagcgc tttaaaaagt    180
actttgatct tttgggaggt gcagccacct tcatccaggc agctgtacct cagataattc    240
gcatact                                                              247
```

<210> SEQ ID NO 298
<211> LENGTH: 246
<212> TYPE: DNA
<213> ORGANISM: Glycine max
<220> FEATURE:
<223> OTHER INFORMATION: unsure at all n locations

<400> SEQUENCE: 298

```
ttgaagaggc tgtcgctgat gctcttcaat ctcgcaagtt tcatggctat gctcccactg    60
ctggacttct ccaggctaga attgcaattg ctgaatatta tctcgtgacc ttccttatca    120
attatcacga gatgatgtct tcatcacttg tggatgcaca caagccattg atgtttcggt    180
ggcgatgctt gctcgccctg gtgcaaacat cnttccaagg ccaggcttcc caatctatga    240
```

```
actttg                                                          246

<210> SEQ ID NO 299
<211> LENGTH: 396
<212> TYPE: DNA
<213> ORGANISM: Glycine max

<400> SEQUENCE: 299
atagagagta agcctgagat catggaaaaa gttggtgtgg ctgtaaatag caaaaatcaa    60
gaatccaaag caacttccac cattaccatt aagggtttca tgagccttct aatgaaaagt   120
gtagatgaga atggtgatgg tagcaagaga gttatttctc tgggtatggg tgacccaact   180
ctcaccactt atttttccccat ctcaaatgta gctgaaaaag ctgttgctga agcacttcag   240
tcacacaggt ttcgtggcta tgctcccact gcaggtcttc cacaggccag gattgcaatt   300
gctgaatacc tgtctcgtga ccttccttac caattatcaa gtgatgatgt ttacatcacc   360
tgtggatgca cacaagccat tgatgtttca gtggcg                             396

<210> SEQ ID NO 300
<211> LENGTH: 443
<212> TYPE: DNA
<213> ORGANISM: Glycine max

<400> SEQUENCE: 300
tggggttgtg gctgtgaaca acaacatcaa caactatgaa tccaaggcaa cttccaccgt    60
caccattaag ggcattctca gccttctaat ggaaagcatt gatgatgaga attgtgatgg   120
tggtggaagc aagaagagag ttatttctct tggtatgggt gacccaactc tcaccacatt   180
gttccacaca ccaaaggttg ttgaagaggc tgtcgctgat gctcttcaat ctcgcaagtt   240
tcatggctat gctcccactg ctggacttct ccaggctaga attgcaattg ctgaatatct   300
atctcgtgac ctttcttatc aattatcacg agatgatgtc ttcatcactt gtggatgcac   360
acaagccatt gatgtttcgg tggccatgct tgctcgccct ggtgcaaaca tcttgcttcc   420
aaggccaagc tttccaatct atg                                           443

<210> SEQ ID NO 301
<211> LENGTH: 278
<212> TYPE: DNA
<213> ORGANISM: Zea mays

<400> SEQUENCE: 301
tgtcacgtat catttaaaac taatatataa ctttttaaatt gaatatttat ttgtaatcat    60
ttttaacgat tatttacaag ttttttctaa tatggcatct tggtttatag aagttcttcc   120
aacagctccg atcgaaattt ttgctcttgc tcgagctttt cggaagatt cttttgcaga    180 aaaagttgac cttggcattg gagcctatcg tactgatgaa ggtcaaccat gggtacttcc   240
agttgttcgt gaagccgaaa tcagcattgc caatgata                           278

<210> SEQ ID NO 302
<211> LENGTH: 304
<212> TYPE: DNA
<213> ORGANISM: Zea mays

<400> SEQUENCE: 302
ctctggagct gaggaaggct atctgcaaaa agcttgagga ggagaatggt ctatcatact    60
ccgccgatca ggtgctagta agcaatggag ccaagcagtg cattacacaa gcagtactcg   120
ctgtctgctc acctggcgat gaagtttga tacctgcacc atattgggtc agctacccctg   180
```

```
agatggctag actggctggt gcaacgccag ttattctccc tacaagcata tcagacaatt    240
acctgctaag gccagagtca cttgcctcag tgatcaatga aaattcaagg atcttgattc    300
tctg                                                                 304

<210> SEQ ID NO 303
<211> LENGTH: 128
<212> TYPE: DNA
<213> ORGANISM: Zea mays

<400> SEQUENCE: 303
agaatttctt gcaaggcact atcacgaggt taaactttc ttgctcctat ctgttttgct     60
gcttcctgat tataatgcat gactgctaaa tcatacaaat atattccagc gcactatcta   120
catcccac                                                            128

<210> SEQ ID NO 304
<211> LENGTH: 322
<212> TYPE: DNA
<213> ORGANISM: Zea mays
<220> FEATURE:
<223> OTHER INFORMATION: unsure at all n locations

<400> SEQUENCE: 304
tgnggagatc acccanaagt cttcaccta tctggcttga acgttaggag ctaccgctat     60
tatgatcctg caacatgcag ccttcacttc gaaggactcc tggaagacct cggttctgct   120
ccttcaggtt caattgtact gctgcatgcc tgtgctcaca accctactgg agtagatcct   180
accatcgaac agtgggaaca gattaggcag ctgatgagat canaatcact gcttccgttc   240
tttgacagtg cctatcaagg ctttgcaagt cggagtcttg acnaagatgc tcagtcagtg   300
cgtatgtttt gtgctgatgg tg                                            322

<210> SEQ ID NO 305
<211> LENGTH: 302
<212> TYPE: DNA
<213> ORGANISM: Zea mays

<400> SEQUENCE: 305
tgcgaggccg agcgccggat cgcgggcaac ctcaacatgg agtaccttcc gatgggaggc     60
agcatcaaga tgattgaaga gtcactgaag ctggcgtacg gagaagattc tgacttcatc   120
aaagataaga ggatagcagc ggtgcaggcg ctttcaggca ctggtgcctg ccggctcttt   180
gctgatttcc aaaagcgttt tttgccggat tcgcagatct acataccaac accaacgtgg   240
tccaaccatc acaatatttg gagggatgct caagtgccac agaagacatt cacatactac   300
ca                                                                  302

<210> SEQ ID NO 306
<211> LENGTH: 138
<212> TYPE: DNA
<213> ORGANISM: Zea mays

<400> SEQUENCE: 306
gttcattctt tttgcttcat gcatgtgctc ataatcccac cggtgtagct cctacggagg     60
aaccatggcg cgaaatatcc catcagttca aggtgaacaa acatttacca ttctttgaca   120
tggaatcacc cgggtttg                                                 138

<210> SEQ ID NO 307
```

```
<211> LENGTH: 181
<212> TYPE: DNA
<213> ORGANISM: Zea mays

<400> SEQUENCE: 307
gttcattctt tttgcttcat gcatgtgctc ataatcccac cggtgtagat cctacggagg      60
aacaatggag agaaatatcc catcagttca aggtgaaaaa acatttttcca ttctttgaca    120 tggcatacca agggttttgcc agtggtgatc cagagagagc tgccaaggcc atctgatttt    180
c                                                                     181

<210> SEQ ID NO 308
<211> LENGTH: 184
<212> TYPE: DNA
<213> ORGANISM: Zea mays

<400> SEQUENCE: 308
gttcattctt tttgcttcat gcatgtgctc ataatccca ctgtgaagat cctaataaga      60
cccactggag agaacatata cccatacagt tcaaggtgaa aaaacatttt ccattacttt    120
gacatggcat accaagggtt tgccagtggt gatccagaga gagatgccaa ggcaatccga    180
attt                                                                  184

<210> SEQ ID NO 309
<211> LENGTH: 135
<212> TYPE: DNA
<213> ORGANISM: Zea mays

<400> SEQUENCE: 309
aattcattct ttttgcttca tgcatgtgct cataatccca gcggtgtaga tcctatggac     60
ggactatgga gagaaatgac ccatcagttc aaggtgaaaa acatttttcc attctttgac   120
atggcattca agggt                                                      135

<210> SEQ ID NO 310
<211> LENGTH: 310
<212> TYPE: DNA
<213> ORGANISM: Zea mays

<400> SEQUENCE: 310
cagacatatt tgtctctgat ggtgccaaat gtgacatatc tcgcttgcag gtcctttttg     60
gatctaatgt gacaattgcg gtccaagatc catcataccc tgcatatgtt gattcaagtg    120
ttatcatggg gcaaactgac ttatatcagc aagacgttca gaagtatgga acattgagt    180 acatgagatg cggtccagaa aatggatttt tcctgatctg tcaactgtcc ctaggacaga    240
tattattttc ttttgttcac ccaacaatcc tactggtgct gctgcatctc gggaccaact    300
aaccaaatta                                                            310

<210> SEQ ID NO 311
<211> LENGTH: 296
<212> TYPE: DNA
<213> ORGANISM: Zea mays

<400> SEQUENCE: 311
gctgcggcag gccggcgtgc cggttatcgg tctagccgcg ggggagccag acttcgacac     60
gccgcccgcg atcgcggagg ccgggatggc tgcaattagg aatggttata caagatacac    120
tcctaatgct gggactttgg agctgaggaa ggctatactg tactaaactc aggagggaa    180 cggggtatcc tacctcccag atgaggtgct ggtgagcaat ggagctaagc aatgcatcac    240
```

```
ataagctgtg cttgcagttt gctcacctgg tgatgaggtt ttgattccag ccccat        296
```

<210> SEQ ID NO 312
<211> LENGTH: 119
<212> TYPE: DNA
<213> ORGANISM: Zea mays
<220> FEATURE:
<223> OTHER INFORMATION: unsure at all n locations

<400> SEQUENCE: 312

```
gaccacnagt ggtccaccga ttggactctg gacntgaagg ccatggctgt taggatcatt     60
aacatgaggc aacaactatt tatgcgctga atccagagga ancectggtg attgagcct    119
```

<210> SEQ ID NO 313
<211> LENGTH: 246
<212> TYPE: DNA
<213> ORGANISM: Zea mays

<400> SEQUENCE: 313

```
ggctaagatc aagtgtagta tctggtctta tcaatttaat atctgatatg tggactatgt     60
gttcactttg atattaaatt tattttctgt ggcggagagt ccaccaccgt ggcttgccac    120
tggtccccct tgagcgtcgct cggactgggc cccttgagcg tcgctcggcc gttgcactac   180
tggctgagcc tggcgcaccc caaccaatcc aattcgagat ttttcccca accaatctaa     240 tttgag                                                                246
```

<210> SEQ ID NO 314
<211> LENGTH: 295
<212> TYPE: DNA
<213> ORGANISM: Zea mays

<400> SEQUENCE: 314

```
cacttaagga aaatcttgaa aagctaggtt cacctttgtc atgggatcat atcactaatc     60
agattggaat gttctgctac agtgggatga cacctgaaca agttgaccgt ttaacaaatg    120
aataccacat ttacatgacc cgcaatggga ggataagcat ggctggtgtt acgacaggaa    180
atgttagtta cctagcaaat gcaattcatg aggttaccaa accaaattga gttagggtcc    240
taccttcttt ggtcgatgga agctgatgga atgagactgt gaagcggcgt ttccc          295
```

<210> SEQ ID NO 315
<211> LENGTH: 262
<212> TYPE: DNA
<213> ORGANISM: Zea mays

<400> SEQUENCE: 315

```
atcagattgg aatgttctgc tacagtggga tgacacctga acaagttgac cgtttaacaa     60
atgaatacca catttacatg acccgcaatg gaggataag catggctggt gtaacgacag     120
gaaatgttgg ttacctagca aatgcaattc atgaggttac caaaccaaat tgagttaggg    180
tgctaccttc tttggtcgat ggaagctgat ggaatgagac tgtgaagcgg cgtttccccc    240
ctctgttcct gacagaaata ag                                              262
```

<210> SEQ ID NO 316
<211> LENGTH: 133
<212> TYPE: DNA
<213> ORGANISM: Zea mays

<400> SEQUENCE: 316

```
atcagattgg aatgttctgc tacagtggga tgacacctga acaagttgac cgtttaacaa    60
atgaatacca catttacatg acccgcaatg ggaggataag catggctggt gtaacgacag   120
gaaatgttgg tta                                                      133

<210> SEQ ID NO 317
<211> LENGTH: 372
<212> TYPE: DNA
<213> ORGANISM: Zea mays

<400> SEQUENCE: 317
aacgagcaag ggccgcagcc ggagctccaa tggcctcctt ctcctccctc tctgcctcct    60
cctccacctc cacccgtcc ttcaacctcc ccgcaaaaac ctccgctggc acaggctccc   120
tgtcattcca cagggcgagg gagtcgcaga agtccagggc caggatggtg acggtgcggg   180
cggaggcggt tgacacgacc atcagcccgc gggtgaatgc gctcaggccg tccaagacca   240
tggccatcac cgaccaggcc acggcgctgc gacaggccgg cgtgccagtc atcggactcg   300
ccgctgggga gcccgacttc gacacgccag ccgtgatcgc cgaggctggg ataaatgcca   360
tcagagatgg gg                                                       372

<210> SEQ ID NO 318
<211> LENGTH: 305
<212> TYPE: DNA
<213> ORGANISM: Zea mays

<400> SEQUENCE: 318
cggaccgtgg tcccgtttcg ctctctgccg ccgccaccgc acaagaagct agctcctgcc    60
tgtaccgccc cgtcatggcg atgctatcca gtgcagctcc tccgcggccc ggcgcccgct   120
gctgccgccg cctaggcttc tggcggtgag ggcgatggcg tcgtcgctct tcggccacgt   180
cgagccggcg cccaaggacc ccatcctcgg cgtcaccgag ctttcctcg ccgacccctc    240 gtccgacaaa gtgaacgtcg gcgtcggcgc ctaccgggac gacaacggcc agcccgtcgt   300
gctca                                                               305

<210> SEQ ID NO 319
<211> LENGTH: 294
<212> TYPE: DNA
<213> ORGANISM: Zea mays

<400> SEQUENCE: 319
cggagccgtg ggacaaaagc ccacagcttc ttctccctac tcctccagtc ctccgtcatc    60
cgtttcgctc tctgccgccg ccaccgcaca agaagctagc tcctgcctgt accgcccgt   120 catggcgatg ctatcccgcg cacctcctcc gcggcccggc gcccgctgct gccgccgcct   180
aggcttctgg cggtgagggc gatggcgtcg tcgctcttcg gccacgtcga gccggcgccc   240
aaggacccca tcctcggcgt caccgaggct ttcctcgccg acccctcgtc cgac         294

<210> SEQ ID NO 320
<211> LENGTH: 263
<212> TYPE: DNA
<213> ORGANISM: Zea mays

<400> SEQUENCE: 320
caagaagcta gctcctgcct gtaccgcccc gtcatggcga tgctatcccg cgcgcgctcc    60
tccgctgccc ggcgcccgct gctgccgccg cctaggcttc tggcggtgag ggcgatggcg   120
tcgtcgctct tcggccacgt cgagccggcg gccaaggacc ccatcctcgg cgtcaccgag   180
```

```
gctttcctcg ccgacgcctc gtccgacaaa gtgaacgtcg gcgtcggcgc ctaccgggac    240
gacaacggcc agcccgtcgt gct                                            263

<210> SEQ ID NO 321
<211> LENGTH: 290
<212> TYPE: DNA
<213> ORGANISM: Zea mays

<400> SEQUENCE: 321
gtgacaaaag cccacagctt cttctcccta ctcctccagt cctccgtcat ccgtttcgct    60
ctctgccgcc gccaccgcac aagaagctag ctcctgcctg taccgccccg tcatggcgat   120
gctatcccgc gcagctcctc gcggccccgg cgcccgctgc tgccgccgcc taggcttctg   180
gcggtgaggg cgatggcgtc gtcgctcttc ggccacgtcg agccggcgcc caaggacccc   240
atcctcggcg tcaccgaggc tttcctcgcc gacccctcgt ccgacaaagt                290

<210> SEQ ID NO 322
<211> LENGTH: 319
<212> TYPE: DNA
<213> ORGANISM: Zea mays

<400> SEQUENCE: 322
gaaaattgca gatgtcattc aagagaaaaa gcatatgcca ttctttgatg ttgcatatca    60
aggttttgcc agtagaagcc ttgatgaaga tgcattttct gtcaggcttt ttgttaagcg   120
tggcatggaa gtatttgttg cacaatctta cagcaagaac cttggtctat attctgaaag   180
gattggtgcg ataaatgtcg tgtgctcagc accagaagtt gcagataggg taaagagcca   240
gctgaaacga ttggcacgtc ccatgtactc gaaccccccct attcacggtg ccaagatagt   300
tgccaacgtt gttggtgat                                                  319

<210> SEQ ID NO 323
<211> LENGTH: 295
<212> TYPE: DNA
<213> ORGANISM: Zea mays

<400> SEQUENCE: 323
ggttggtgca ataaatgtcg tgtgctcagc accagaagtt gcagataggg taaagagcca    60
gctgaaacga ttggcacgtc ccatgtactc gaaccccccct attcacggtg ccaagatagt   120
tgccaacgtt gttggtgatc caaccatgtt tggtgaatgg aaacaagaga tggagctaat   180
ggctggacgg atcaagaatg taagacagaa gctctacgac agtttgtctg ccaaggacaa   240
gagcggcaag gactggtctt tcattctgag gcagattggc atgttctcct acacc          295

<210> SEQ ID NO 324
<211> LENGTH: 291
<212> TYPE: DNA
<213> ORGANISM: Zea mays

<400> SEQUENCE: 324
aatcttacag caagaacctt ggtctatatt ctgaaagggt tggtgcgata aatgtcgtgt    60
gctcagcacc agaagttgca gatagggtaa agagccagct gaaacgattg gcacgtccca   120
tgtactcgaa ccccctatt cacggtgcca agatagttgc caacgttgtt ggtgatccaa    180
tcatgtttgg tgaatggaaa caagagatgg agctaatggc tggacggatc aagaatgtaa   240
gacagaagct ctacgacagt ttgtctgcca aggataagag cggcaaggac t              291
```

```
<210> SEQ ID NO 325
<211> LENGTH: 278
<212> TYPE: DNA
<213> ORGANISM: Zea mays

<400> SEQUENCE: 325
cccacgcgtc cgcaactcct gaacagtggg agaaaattgc agatgtcatt caagagaaaa      60
agcatatgcc attctttgat gttgcatatc agggttttgc cagtggaagc cttgatgaag     120
atgcattttc tgtcaggctt tttgttaagc gtggcatgga agtgtttgtt gcacaatctt     180
acagcaagaa ccttggttta tattctgaaa gggttggtgc aataaatgtc gtgtgctcag     240
caccagaagt tgcagatagg gtaaatagcc agctgaaa                            278

<210> SEQ ID NO 326
<211> LENGTH: 318
<212> TYPE: DNA
<213> ORGANISM: Zea mays

<400> SEQUENCE: 326
cccacgcgtc cgctaatggc tggacggatc aagaatgtaa gacagaagct ctacgacagt      60
ttgtctgcca aggataagag cggcaaggac tggtctttca ttctgaggca gattggcatg     120
ttctcctaca ccggcttgaa caaagcacag agtgacaaca tgacggataa atggcatatt     180
tacatgacca aggatgggcg gatctcctta gctgggctgt ccctggctaa gtgtgattat     240
cttgccgacg ccatcatcga ttccttccat aatgtgaact aggctgaggt acgatagttg     300
agggtcaagc tattgatg                                                  318

<210> SEQ ID NO 327
<211> LENGTH: 271
<212> TYPE: DNA
<213> ORGANISM: Zea mays

<400> SEQUENCE: 327 cttttttgtta agcgtggcat ggaagtgttt gttgcacaat cttacagcaa gaaccttggt      60
ctatattctg aaagggttgg tgcgataaat gtcgtgtgct cagcaccaga agttgcagat     120
agggtaaaga gccagctgaa acgattggca cgtcccatgt actcgaaccc ccctattcac     180
ggtgccaaga tagttgccaa cgttgttggt gatccaatca tgtttggtga atggaaacaa     240
gagatggagc taatggctgg acggatcaag a                                   271

<210> SEQ ID NO 328
<211> LENGTH: 251
<212> TYPE: DNA
<213> ORGANISM: Zea mays

<400> SEQUENCE: 328
gccattcttt gatgttgcat atcagggttt tgccagtgga agccttgatg aagatgcatt      60
ttctgtcagg cttttttgtta agcgtggcat ggaagtgttt gttgcacaat cttacagcaa     120
gaatcttggt ttatattctg aaagggttgg tgcaataaat gtcgtgtgct cagcaccaga     180
agttgcagat agggtaaata gccagctgaa acgattggca cgtcccatgt actcgaaccc     240
ccctattcac g                                                         251

<210> SEQ ID NO 329
<211> LENGTH: 263
<212> TYPE: DNA
<213> ORGANISM: Zea mays
```

<400> SEQUENCE: 329

```
gccattcttt gatgttgcat atcagggttt tgccagtgga agccttgatg aagatgcatt    60
ttctgtcagg cttttgtta agcgtggcat ggaagtgttt gttgcacaat cttacagcaa   120
gaaccttggt ttatattctg aaagggtgtg tgcaataaat gtcgtgtgct cagcaccaga   180
agttgcagat agggtaaata gccagctgaa acgattggca cgtcccatgt actcgaaccc   240
ccctattcac ggtgccaaga tag                                          263
```

<210> SEQ ID NO 330
<211> LENGTH: 274
<212> TYPE: DNA
<213> ORGANISM: Zea mays

<400> SEQUENCE: 330

```
tgaatggaaa caagagatgg agctaatggc tggacggatc aagaatgtaa gacagaagct    60
ctacgacagt ttgtctgcca aggacaagag cggcaaggac tggtctttca ttctgaggca   120
gattggcatg ttctcctaca ccggcttgaa caaagcgcag agtgacaaca tgacggataa   180
atggcatatt tacatgacca aggatgggcg gatctcgtta gctgggctgt ccctggctaa   240
gtgtgattat cttgccgacg ccatcatcga ttct                               274
```

<210> SEQ ID NO 331
<211> LENGTH: 252
<212> TYPE: DNA
<213> ORGANISM: Zea mays

<400> SEQUENCE: 331

```
taaagagcca gctgaaacga ttggcacgtc ccatgtactc gaaccccct attcacggtg     60
ccaagatagt tgccaacgtt gttggtgatc caatcatgtt tggtgaatgg aaacaagaga   120
tggagctaat ggctggacgg atcaaggatg taagacagaa gctctacgac agtttgtctg   180
ccaaggataa gagcggcaag gactggtctt tcattctgag gcagattggc atgttctcct   240
acaccggctt ga                                                       252
```

<210> SEQ ID NO 332
<211> LENGTH: 240
<212> TYPE: DNA
<213> ORGANISM: Zea mays

<400> SEQUENCE: 332

```
gcacaatctt acagcaagaa ccttggttta tattctgaaa gggttggtgc aataaatgtc    60
gtgtgctcag caccagaagt tgcagatagg gtaaatagcc agctgaaacg attggcacgt   120
cccatgtact cgaaccccc tattcacggt gccaagatag ttgccaacgt tgttggtgat   180
ccaaccatgt ttggtgaatg gaaacaagag atggagctaa tggctggacg gatcaagaat   240
```

<210> SEQ ID NO 333
<211> LENGTH: 268
<212> TYPE: DNA
<213> ORGANISM: Zea mays

<400> SEQUENCE: 333

```
caagagcggc aaggactggt ctttcattct gaggcagatt ggcatgttct cctacaccgg    60
cttgaacaaa gcgcagagtg acaacatgac ggataaatgg catatttaca tgaccaagga   120
tgggcggatc tcgttagctg ggctgtccct ggctaagtgt gattatcttg ccgacgccat   180
```

```
catcgattcc ttccataatg tgaactaggc tgagatatgg agcaacaacg acggcggaga    240
agctgttttg cgtccacgac acaagctg                                      268

<210> SEQ ID NO 334
<211> LENGTH: 251
<212> TYPE: DNA
<213> ORGANISM: Zea mays

<400> SEQUENCE: 334
tgtttggtga atggaaacaa gagatggagc taatggctgg acggatcaag aatgtaagac    60
agaagctcta cgacagtttg tctgccaagg ataagagcgg caaggactgg tctttcattc   120
tgaggcagat tggcaggtct cctacaacgg cttgaacaaa gcacagagtt accacatgac   180
gggtaaatgg gctaattaac atgaccaaga tgggcggatc tccttagctg ggctgtccct   240
ggctaagtgt g                                                        251

<210> SEQ ID NO 335
<211> LENGTH: 249
<212> TYPE: DNA
<213> ORGANISM: Zea mays

<400> SEQUENCE: 335
gtgattatct tgccgacgcc atcatcgatt ccttccataa tgtgaactag gctgaggtac    60
gatagttgag ggtcaagcta ttgatgttta gttccgtgga cgctaggctg ggattttggg   120
gtccttccag ctatacagct cttccgttgt gctccatctg gtgtaacttg gataaataaa   180
aattttgtcg ctgaactaaa actcgtgtgc ttttttacct gtaactgtaa ggtcagcgcg   240
tggctacag                                                           249

<210> SEQ ID NO 336
<211> LENGTH: 193
<212> TYPE: DNA
<213> ORGANISM: Zea mays

<400> SEQUENCE: 336
gtcgctgaac taaaaatat tttatgatcc aagttcacac agatggagca caacggaaga    60
gctgtatagc tggaaggacc caaaaatccc agcctagcgt ccacggaact aaacatcaat   120
agcttgaccc tcaactatcg tacctcagcc tagttcacat tatggaagga atcgatgatg   180
gcgtcggcaa gat                                                      193

<210> SEQ ID NO 337
<211> LENGTH: 314
<212> TYPE: DNA
<213> ORGANISM: Zea mays

<400> SEQUENCE: 337
cggacgcgtg gcgagacgcg tgggctccct tcttcagtgc agcagcaggc cagcgagacc    60
caccaccctc actcccgcct ccgatccgct gcttactcgc cacccggaga tggccaccgc   120
cgccgccttc tccgtctcct cgccggcggc ctccgccgtc gccgcgcgat ccaaggtgtt   180
tggaggagtt aaccaggcga gaactagaac tggctgccgc gtcggcatca cgcggaagaa   240
ctttggccgt gtcatgatgg cccttgcagt ggatgtttct cgttttgaag gagtgccaat   300
ggctcctcca gacc                                                     314

<210> SEQ ID NO 338
<211> LENGTH: 285
```

```
<212> TYPE: DNA
<213> ORGANISM: Zea mays

<400> SEQUENCE: 338
aagcgacggg cgtcatatcc catcctgatc tctcctccct tcttcagtgc agcagcaggc    60
cagcagcacg ccacccgccc cactcctgcc tccgatccgc tgcttactcg ccacccggag   120
atggccaccg ccgccgcctt ctccgtctcc tcgccggcgg cctccgccgt cgccgcgcga   180
tccaaggtgt ttggaggagg agttaaccag gcgagaacta gaactggctg ccgcgtcggc   240
atcacgcgga agaactttgg ccgtgtcatg atggcccttg cagtg                  285

<210> SEQ ID NO 339
<211> LENGTH: 263
<212> TYPE: DNA
<213> ORGANISM: Zea mays

<400> SEQUENCE: 339
cccacgcgtc cgactagttc tagttctcgc ctggttaact cctccaaaca ccttggatcg    60
cgcggcgacg gcggaggccg ccggcgagga gacggagaag gcggcggcgg tggccatctc   120
cgggtggcga gtaagcagcg gatcggaggc ggtagtgagg cgggtggcgt gccgctggcc   180
tgctgctgca ctgaagaagg gagcgccccc tatatacgga ggggcccgag ctcatcgccg   240
cggcccctcc ctccctgcgc ctg                                          263

<210> SEQ ID NO 340
<211> LENGTH: 116
<212> TYPE: DNA
<213> ORGANISM: Zea mays

<400> SEQUENCE: 340
ctcccgcctc cgatccgctg cttactcgcc acccggagat ggccaccgcc gccgccttct    60
ccgtctcctc gccggcggcc tccgccgtcg ccgcgcgatc caaggtgttt ggagga       116

<210> SEQ ID NO 341
<211> LENGTH: 260
<212> TYPE: DNA
<213> ORGANISM: Zea mays

<400> SEQUENCE: 341
atggagcact actgcttaga agatgctcat attgtcaacc tcttctcgtt ctcaaaggct    60
tatgaaatga tgggtggcg tgtaggatac attgcatttc caaatgaagc tgatggcttc   120
catgatcagc tcctcaaggt gcaagacaac ataccgatct gcgcctccat catcgggcag   180
cgcctggcgc tctactcgct ggaggccggc cccgagtgga tcaaagaacg ggtgaaagac   240
ctggtgaaaa accgggcgct                                              260

<210> SEQ ID NO 342
<211> LENGTH: 274
<212> TYPE: DNA
<213> ORGANISM: Zea mays

<400> SEQUENCE: 342
ctttatgtat gatggaatgg agcactactg cttagaagat gctcatattg tcaacctctt    60
ctcgttctca aaggcttatg gaatgatggg gtggcgtgta ggatacattg catttccaaa   120
tgaagctgat ggcttccatg atcagctcct caaggtgcaa gacaacatac cgatctgcgc   180
ctccatcatc gggcagcgct ggcgctctac tcgctggagg ccggccccga gtggatcaaa   240
```
gaacgggtga agacctggt gaaaaaccgg gcgc 274

<210> SEQ ID NO 343
<211> LENGTH: 320
<212> TYPE: DNA
<213> ORGANISM: Zea mays

<400> SEQUENCE: 343
ctttagggag ctgccaggtg tcaagatatc ggaacctcag ggagccttct atttattcat 60
cgacttcagc tcgtactatg ggtctgaggt ggaaggtttt ggtaccatca aggactctga 120
gtccctctgt ctgttcctgt tggagaaggc acaggttgcg cttgtccctg gggatgcatt 180
tggcgatgac aagggtgttc gcatttcata tgctgcagct atgtcgacac tgcaaactgc 240
aatgggaaag ataaaagaag cgatggctct gctcaggcac cctgttgccg tttaacaaaa 300
ccaacgtatc gctaatcagt 320

<210> SEQ ID NO 344
<211> LENGTH: 295
<212> TYPE: DNA
<213> ORGANISM: Zea mays
<220> FEATURE:
<223> OTHER INFORMATION: unsure at all n locations

<400> SEQUENCE: 344
gttgatcaat aatccgtcac gtgtcaagga gtacctacca atcaccggtc tggctgaatt 60
caataagctg agcgctaagc ttatctttgg cgctgacagc cctgctattc aggagaatag 120
ggttgctacc gtgcagtgcc tatcgggtac tggttcttta gaagtcggag gtgaatttct 180
tgcaaggcac tatcacgagc gcactatcta catcccacaa ccaacctggg ganatcaccc 240
aaagtcttca cctatctggc ttgaacgtag gagctacgct atatgatctg cacat 295

<210> SEQ ID NO 345
<211> LENGTH: 299
<212> TYPE: DNA
<213> ORGANISM: Zea mays

<400> SEQUENCE: 345
gttgatcaat aatccgtcac gtgtcaatga gtatctacca atcaccggtc tggctgaatt 60
caataagctg agcgctaagc ttatctttag cgctgacagc cctactattc aggagaatag 120
ggttgctacc gtgcagtgcc tatcgggtac tggtactttg agagtcggag gtgaatttgc 180
ttgcaaggca ctatcacgag cgcactatct acatcccaca accaacctgg ggaaatcacc 240
caaaagtctt caccctatct ggcttgaacg ttaggagcta ccgctattat gatcctgca 299

<210> SEQ ID NO 346
<211> LENGTH: 267
<212> TYPE: DNA
<213> ORGANISM: Zea mays

<400> SEQUENCE: 346
ctcgagccgc ggtctggctg aattcaataa gctgagcgct aagcttatct ttggcgctga 60
cagccctgct attcaggaga atagggttgc taccgtgcag tgcctatcgg gtactggttc 120
tttaagagtc ggaggtgaat tcttgcaag gcactatcac gagcgcacta tctacatccc 180
acaaccaacc tggggaaatc acccaaaagt cttcacccta tctggcttga acgttaggag 240
ctaccgctat tatgatcctg caacatg 267

```
<210> SEQ ID NO 347
<211> LENGTH: 269
<212> TYPE: DNA
<213> ORGANISM: Zea mays

<400> SEQUENCE: 347
ctcgaatcgt tccccaccat ggcgtcgcag ggatcctccg tcttcgccgc actcgagcag        60
gccccggagg accccatcct cggagtgacc gttgcctaca acaaggatcc cagccccgtg       120
aaggtcaacc tcggggtcgg cgcctaccgg accgaggaag ggaagcccct agtgctgaac       180
gtggtcaggc gcgccgagca aatgttgatc aataatccgt cacgtgtcaa ggagtaccta       240
ccaatcaccg gtctggctga attcaataa                                        269

<210> SEQ ID NO 348
<211> LENGTH: 294
<212> TYPE: DNA
<213> ORGANISM: Zea mays

<400> SEQUENCE: 348
gcagcagaca cctccgccac ctccaccctc gaatcgttcc ccaccatggc gtcgcaggga        60
tcctccgtct tcgccgcact cgagcaggcc ccggaggacc ccatcctcgg agtgaccgtt       120
gcctacaaca aggatcccag ccccgtgaag gtcaacctcg gggtcggcgc ctaccggacc       180
gaggaaggga agcccctagt gctgaacgtg gtcaggcgcg ccgagcaaat gttgatcaat       240
aatccgtcac gtgtcaagga gtacctacca atcaccggtc tggctgaatt cata            294

<210> SEQ ID NO 349
<211> LENGTH: 264
<212> TYPE: DNA
<213> ORGANISM: Zea mays

<400> SEQUENCE: 349
agcagacacc tccgccacct ccaccctcga atcgttcccc accatggcgt cgcagggatc        60
ctccgtcttc gccgcactcg agcaggcccc ggaggacccc atcctcggag tgaccgttgc       120
ctacaacaag gatcccagcc ccgtgaaggt caacctcggg gtcggcgcct accggaccga       180
ggaagggaag cccctagtgc tgaacgtggt caggcgcgcc gagcaaatgt tgatcaataa       240
tccgtcacgt gtcaaggagt acct                                             264

<210> SEQ ID NO 350
<211> LENGTH: 304
<212> TYPE: DNA
<213> ORGANISM: Zea mays

<400> SEQUENCE: 350
cagacacctc cgccacctcc accctcgaat cgttccccac catggcgtcg cagggatcct        60
ccgtcttcgc cgcactcgag caggccccgg agtaccccat cctcggagtg accgttgcct       120
acaacaagga tcccagcccc atgaaggtca acctcggggt tggcgcctac cggaccgagg       180
aagggaagcc cctagtgctg aacgtggtca ggcgcgccga gcaaatgttg atcaataatc       240
cgtcacgtgt caaggagtac ctaccaatca ccggtctggc tgaattcaat aagctgagcg       300
ctaa                                                                    304

<210> SEQ ID NO 351
<211> LENGTH: 284
<212> TYPE: DNA
<213> ORGANISM: Zea mays
```

<400> SEQUENCE: 351

```
gcagcagaca cctctcccac ctccaccctc gaatcgttcc ccaccatggc gtcgcaggga    60
tcctccgtct tcgccgcact cgagcaggcc ccggaggacc ccatcctcgg agtgaccgtt   120
gcctacaaca aggatcccag ccccgtgaag gtcaacctcg ggtcggcgc ctaccggacc    180 gaggaaggga agcccctagt gctgaacgtg tcaggcgcg ccgagcaaat gttgatcaat    240
aatccgtcac gtgtcaagga gtacctacca atcaccggtc tggc                   284
```

<210> SEQ ID NO 352
<211> LENGTH: 291
<212> TYPE: DNA
<213> ORGANISM: Zea mays
<220> FEATURE:
<223> OTHER INFORMATION: unsure at all n locations

<400> SEQUENCE: 352

```
cagacaccac cgccacctcc anctcgaat cgttccccac catggcgtcg cagggatcct    60
ccgtcttcgc cgcactcgag caggccccgg aggacccccat cctcggagtg accgttgcct   120
acaacaagga tccagccccc gtgaaggtca acctcggggt cggcgcctac cggaccgagg   180
aagggaagcc cctagtgctg aacgtagtca ggcgcgccga gcaaatgttg atcaataatc   240
cgtcacgtgt caaggagtac ctaccaatca ccggtctggc tgaattcaat a            291
```

<210> SEQ ID NO 353
<211> LENGTH: 281
<212> TYPE: DNA
<213> ORGANISM: Zea mays

<400> SEQUENCE: 353

```
gcagcagaca cctcgccacc tccaccctcg aatcgttccc caccatggcg tcgcagggat    60
cctccgtctt cgccgcactc gagcaggccc cggaggaccc catcctcgga gtgaccgttg   120
cctacaacaa ggatcccagc cccgtgaagg tcaacctcgg ggtcggcgcc taccggaccg   180
aggaagggaa gccccctagtg ctgaacgtgg tcaggcgcgc cgagcaaatg ttgatcaata   240
atccgtcacg tgtcaaggag tacctaccaa tcaccggtct g                       281
```

<210> SEQ ID NO 354
<211> LENGTH: 247
<212> TYPE: DNA
<213> ORGANISM: Zea mays

<400> SEQUENCE: 354

```
cagcagacac ctccgccacc tccaccctcg aatcgttccc caccatggcg tcgcagggat    60
cctccgtctt cgccgcactc gagcaggccc cggaggaccc catcctcgga gtgaccgttg   120
cctacaacaa ggatcccagc cccgtgaagg tcaacctcgg ggtcggcgcc taccggaccg   180
aggaagggaa gccccctagtg ctgaacgtgg tcaggcgcgc cgagcaaatg ttgatcaata   240
atccgtc                                                             247
```

<210> SEQ ID NO 355
<211> LENGTH: 266
<212> TYPE: DNA
<213> ORGANISM: Zea mays

<400> SEQUENCE: 355

```
gccacctcca tcctcgaatc gttccccacc atggcgtcgc aggatcctc cgtcttcgcc     60 gcactcgagc aggccccgga ggaccccatc ctcggagtga ccgttgccta caacaaggat   120
```

```
cccagccccg tgaaggtcaa cctcggggtc ggcgcctacc ggaccgagga agggaagccc      180
ctagtgctga acgtggtcag gcgcgccgag caaatgttga tcaataatcc gtcacgtgtc      240
aaggagtacc taccaatcac ggtctg                                          266

<210> SEQ ID NO 356
<211> LENGTH: 274
<212> TYPE: DNA
<213> ORGANISM: Zea mays

<400> SEQUENCE: 356
cagcagacac ctccgccacc tccaccctcg aatcgttccc caccatggcg tcgacaggat       60
cctccgtctt cgccgcactc gagcaggccc cggaggaccc catcctcgga gtgaccgttg      120
cctacaacaa ggatcccagc cccgtgaagg tcaacctcgg ggtcggcgcc taccggaccg      180
aggaagggaa gcccctagtg ctgaacgtgg tcaggcgcgc cgagcaaatg ttgatcaata      240
atccgtcacg tgtcaaggag tacctaccaa tcac                                 274

<210> SEQ ID NO 357
<211> LENGTH: 299
<212> TYPE: DNA
<213> ORGANISM: Zea mays

<400> SEQUENCE: 357
gtgcgcgctg cgcaggcgca ggcccccagc gccgaccgca gattaagtac gctagtgggg       60
cacctgctgc cttcctcccc acgaagagca gcagcagaca cctccgccac ctccaccctc      120
gaatcgttcc ccaccatggc gtcgcaggga tcctccgtct tcgccgcact cgagcaggcc      180
ccggaggacc ccatcctcgg agtgaccgtt gcctacaaca acgatcccag ccccgtgaac      240
gtcaacctcg gggtcggcgc ctaccggacc gaggaaggga agcccctagt gctgaacgt       299

<210> SEQ ID NO 358
<211> LENGTH: 251
<212> TYPE: DNA
<213> ORGANISM: Zea mays

<400> SEQUENCE: 358
cagacacctc cgccacctcc accctcgaat cgttccccac catggcgtcg caaggatcct       60
ccgtcttcgc cgcactcgag caggcaccgg aggaccacat cctcggagtg accgttgcct      120
acaacaagga tccagccccc gtgaaggtca acctcggggt cggcgcctac ggaccgagg       180 aagggaagcc cctagtgctg aacgtggtca ggcgcgccga gcaaatgttg atcaataatc      240
cgtcacgtgt c                                                          251

<210> SEQ ID NO 359
<211> LENGTH: 237
<212> TYPE: DNA
<213> ORGANISM: Zea mays

<400> SEQUENCE: 359
ctgacgcgtg gctggacgcg tggggcagca gacacctccg ccacctccac cctcgaatcg       60
taccccacca tggcgtcgca tggatcctcc gtcttcgccg cactcgagca ggccccggag      120
gaccccatcc tcggagtgac cgttgcctac aacaaggatc cagcccccgt gaaggtcaac      180
ctcggggtcg gcgcctaccg gaccgaggaa gggaagcccc tagtgctgaa cgtggtc        237

<210> SEQ ID NO 360
```

<211> LENGTH: 175
<212> TYPE: DNA
<213> ORGANISM: Zea mays

<400> SEQUENCE: 360

```
tgcgcctacc ggaccgacga agggaagccc tagtgctgaa cgtggtcagg cgcgccgagc      60
aaatgttgat caataatccg tcacgtgtca aggagtacct accaatcacc ggtctggctc     120
aattcaataa gctgagcgct aagcttatct ttagcgctga cagccctgct attca          175
```

<210> SEQ ID NO 361
<211> LENGTH: 447
<212> TYPE: DNA
<213> ORGANISM: Zea mays
<220> FEATURE:
<223> OTHER INFORMATION: unsure at all n locations

<400> SEQUENCE: 361

```
agctgcttta gcgtactaac tcgnaatcga ctcgacagca cagacacctc cgccacctcc      60
actctcgaat cgttcccacc atggcgtcgc agcngatcct cgcgtcattc gcacgcagct     120
cgagcgaggc actcgggagg gacncgcatg cctccggacg tnggaccgta tgcactacat     180
gacataagga tcccccagct cccagtgana ngggtcaacc attcggnggt cggcggcctt     240
acgtcggacc gagggaaggg aagctcctag tgctgaacgt ggtcaggcgc gccgagcana     300
tgttgatcaa taatccgtca cgtgtcaagg agtacctaca atcacagtca tgctgaattc     360
ataactgacg ctaacttatc ttgcgtgaca gctgctatca gagataggtc tacgtcatgc     420
tacggtctgt cttagatcga gtgatct                                          447
```

<210> SEQ ID NO 362
<211> LENGTH: 274
<212> TYPE: DNA
<213> ORGANISM: Zea mays

<400> SEQUENCE: 362

```
gacacctccg ccacctccac cctcgaatcg ttccccacca tggcgtcgca gggatcctcc      60
gtcttcgccg cactcgagca ggccccggag gaccccatcc tcggagtgac cgttgcctac     120
aacaaggatc ccagccccgt gaaggtcaac ctcggggtcg cgcgcctaccg gaccgaggaa     180
gggaagcccc tagtgctgaa cgtggtcagg cgcgccgagc aaatgttgat caataatccg     240
tcacgtgtca aggagtacct accaatcacc ggtc                                   274
```

<210> SEQ ID NO 363
<211> LENGTH: 163
<212> TYPE: DNA
<213> ORGANISM: Zea mays
<220> FEATURE:
<223> OTHER INFORMATION: unsure at all n locations

<400> SEQUENCE: 363

```
cagcagcaga cacctccgcc acctccaccc tcgaatcgtt ccccaccatg gcgtgctcgg      60
atcctccgtc ttcgccgcac tcgagcaggc cccggaggac cccatcctcg gtctcancgt     120
tgcctacaac aaggatccca gccccgtgaa ggtcaacctc ggg                        163
```

<210> SEQ ID NO 364
<211> LENGTH: 280
<212> TYPE: DNA
<213> ORGANISM: Zea mays

<400> SEQUENCE: 364

```
tgacactccg ccacctccac cctcgaatcg ttccccacta tggcgtcgca gggatcctcc        60
gtcttcgccg cactcgagca ggccccggag accccatcc tcggagtgac cgttgcctac        120
aacaagggat ccagcccgt gaaagtcaac ctcgggggtc ggcgctaacg gaaccgagga        180 agggaaccc tagtgctgaa cgtgttaagc gcgcgagcaa tgttgatcat aatcgtcagt       240
gtcaggagta ctaccatcac gttctgctga atcatagctg                              280
```

<210> SEQ ID NO 365
<211> LENGTH: 128
<212> TYPE: DNA
<213> ORGANISM: Zea mays
<220> FEATURE:
<223> OTHER INFORMATION: unsure at all n locations

<400> SEQUENCE: 365

```
ctcgaatcgt tcnccaccat ggcgtcgcag ggatcctccg tcttcgccgc actcgagcag        60
gcaccggagg actccatcct cggagtgacc gttgcctaca acaaggatcn cagccccgtg       120
aaggtcaa                                                                 128
```

<210> SEQ ID NO 366
<211> LENGTH: 183
<212> TYPE: DNA
<213> ORGANISM: Zea mays

<400> SEQUENCE: 366

```
gcagacacct ccgccacatc cacactcgaa tcgttcccca ccatggcgtc gcagggatcc        60
tccgtcttcg ccgcactcga gcaggccccg gaggacacca tcctcggagt gaccgttgcc       120
tacaacaagg atcccagccc cgtgaacgtc aacctcgggg tcggcgccta caggaccgag       180
gaa                                                                      183
```

<210> SEQ ID NO 367
<211> LENGTH: 324
<212> TYPE: DNA
<213> ORGANISM: Zea mays

<400> SEQUENCE: 367

```
cccacgcgtc cgggcggaga catgggtagc ttcgctaagc tggcgaggag ggcggtggag        60
acggacgctc cggtcatggt gaagatacaa gaactgctcc gaggggccaa ggatgtgatg       120
tcgcttgcgc agggagttgt ttactggcaa cctcccgagt cagctatgga taagatcgaa       180
aagatcatca gggaaccaat agtcagtaaa tatggttctg atgatgggct tcctgagctt       240
cgagaagcac ttctcgaaaa gctaagcaga gagaacaagc ttaccaaatc atcagtcatg       300
gtcactgctg gtgcaaatca ggct                                               324
```

<210> SEQ ID NO 368
<211> LENGTH: 327
<212> TYPE: DNA
<213> ORGANISM: Zea mays

<400> SEQUENCE: 368

```
gtgccaatgg ctcctccaga cccaattctt ggggtttctg aggcctttaa agcagataaa        60
agcgagctga agctcaatct tggtgttggt gcctatagga cagaagagct gcagccctac       120
gtgctcaatg tagtcaagaa ggctgaaaat cttatgttgg agaaaggaga aaacaaagag       180
tatcttccca ttgaaggttt agccgcgttt aacaaagcaa cagcagagct attgcttgga       240
```

```
gctgataacc ctgttattaa tcaaggactg gttgctacac ttcagtctct ctcgggcact    300
ggatcactgc gtctcgctgc agcattc                                        327
```

<210> SEQ ID NO 369
<211> LENGTH: 318
<212> TYPE: DNA
<213> ORGANISM: Zea mays

<400> SEQUENCE: 369

```
gcgtttaaca aagcaacagc agagctattg cttggagctg ataaccctgt tattaatcaa     60
ggactggttg ctacacttca gtctctctcg ggcactggat cactgcgtct cgctgcagca    120
ttcatacaaa gatactttcc tgaagctaaa gtgctgatat cgtcgcctac ctggggtaac    180
cacaagaata tcttcaatga tgctagggta ccttggtcag agtacaggta ctatgacccc    240
aagactgttg ggttggattt tgagggaatg atagctgata ttgaggctgc tcctgaagga    300
tcttttgttc tgctacat                                                  318
```

<210> SEQ ID NO 370
<211> LENGTH: 319
<212> TYPE: DNA
<213> ORGANISM: Zea mays

<400> SEQUENCE: 370

```
agagctgcag ccctacgtgc tcaatgtagt caagaaggct gaaaatctta tgttggagaa     60
aggagaaaac aaagagtatc ttcccattga aggtttagcc gcgtttaaca aagcaacagc    120
agagctattg cttggagctg ataaccctgt tattaatcaa ggactggttg ctacacttca    180
gtctctctcg ggcactggat cactgcgtct cgctgcagca ttcatacaaa gatactttcc    240
tgaagctaaa gtgctgatat cgtcgcctac ctggggtaac cacaagaata tcttcaatga    300
tgctagggta ccttggtca                                                 319
```

<210> SEQ ID NO 371
<211> LENGTH: 301
<212> TYPE: DNA
<213> ORGANISM: Zea mays

<400> SEQUENCE: 371

```
gaagctaaag tgctgatatc gtcgcctacc tggggtaacc acaagaatat cttcaatgat     60
gctagggtac ttggtcagag tacaggtact atgaccccaa gactgttggg ttggattttg    120
agggaatgat agctgatatt gaggctgctc ctgaaggatc ttttgttctg ctacatggtt    180
gtgctcacaa cccaactgga atagacccaa ctcctgaaca gtgggagaaa attgcagatg    240
tcattccaga gaaaaagcat atgacattct tgatgttgc atatcaaggt tttgccagtg    300
g                                                                    301
```

<210> SEQ ID NO 372
<211> LENGTH: 264
<212> TYPE: DNA
<213> ORGANISM: Zea mays

<400> SEQUENCE: 372

```
ttttgaggga atgatagctg atattgaggc tgctcctgaa ggatcttttg ttctgctaca     60
tggttgtgct cacaacccaa ctggaataga cccaactcct gaacagtggg agaaaattgc    120
agatgtcatt caagagaaaa agcatatgcc attcttgat gttgcatatc aaggttttgc    180
cagtggaagc cttgatgaag atgcattttc tgtcaggctt tttgttaagc gtggcatgga    240
```
agtgtttgtt gcacaatctt acag                                          264

<210> SEQ ID NO 373
<211> LENGTH: 293
<212> TYPE: DNA
<213> ORGANISM: Zea mays

<400> SEQUENCE: 373
attggggttt ctgaggcctt taaagcagat aaaagcgagc tgaagctcaa tcttggtgtt    60
ggtgcctata ggacagaaga gctgcagccc tacgtgctca atgtagtcaa gaaggctgaa   120
aatcttatgt tggagaaagg agaaaacaaa gagtatcttc ccattgaagg tttagccgcg   180
tttaacaaag caacagcaga gctattgctt ggagctgata accctgttat taatcaagga   240
ctggttgcta cacttcagtc tctctcgggc actggatcac tgcgtctcgc tgc          293

<210> SEQ ID NO 374
<211> LENGTH: 285
<212> TYPE: DNA
<213> ORGANISM: Zea mays

<400> SEQUENCE: 374
tggattttga gggaatgata gctgacattg aggctgctcc tgaaggttct tttgttctgc    60
tacatggttg tgctcacaac ccaactggaa tagacccaac tcctgaacag tgggagaaaa   120
ttgcagatgt cattcaagag aaaaagcata tgccattctt tgatgttgca tatcagggtt   180
ttgccagtgg aagccttgat gaagatgcat tttctgtcag cttttttgtt aagcgtggca   240
tggaagtgtt tgttgcacaa tcttacagca agaaccttgg tttat                   285

<210> SEQ ID NO 375
<211> LENGTH: 275
<212> TYPE: DNA
<213> ORGANISM: Zea mays

<400> SEQUENCE: 375
caagaaggct gaaaatctta tgttggagaa aggagaaaac aaagagtatc ttcccattga    60
aggtttagcc gcgtttaaca aagcaacagc agagctattg cttggagctg ataaccctgt   120
tattaatcaa ggactggttg ctacacttca gtctctctcg ggcactggat cactgcgtct   180
cgctgcagca ttcatacaaa gatactttcc tgaagctaaa gtgctgatat cgtcgcctac   240
ctggggtaac cacaagaata tcttcaatga tgcta                              275

<210> SEQ ID NO 376
<211> LENGTH: 268
<212> TYPE: DNA
<213> ORGANISM: Zea mays

<400> SEQUENCE: 376
gataaaagcg cactgaagct caatcttggt gttggtgcct ataggacaga agagctgcag    60
ccatacgtgc tcaatgtagt caagaaggct gaaaatctta tgttggagaa aggagaaaac   120
aaagagtatc ttcccattga aggtttagcc gcgtttaaca aagcaacagc agagctattg   180
cttggagctg ataaccctgt tattaatcaa ggactggttg ctacacttca gtctctctcg   240
ggcactggat cactgcgtct cgctgcag                                      268

<210> SEQ ID NO 377
<211> LENGTH: 261
<212> TYPE: DNA

<213> ORGANISM: Zea mays

<400> SEQUENCE: 377

```
agcagataaa agcgagctga agctcaatct tggtgttggt gcctatagga cagaagagct      60
gcagccatac gtgctcaatg tagtcaagaa ggctgaaaat cttatgttgg agaaggagaa     120
aacaaagagt atcttcccat tgaaggttta gccgcgttta caaagcaac agcagagcta     180
ttgcttggag ctgataaccc tgttattaat caaggactgg ttgctacact tcagtctctc    240
tcgggcactg gatcactgcg t                                              261
```

<210> SEQ ID NO 378
<211> LENGTH: 261
<212> TYPE: DNA
<213> ORGANISM: Zea mays

<400> SEQUENCE: 378

```
tggattttga gggaatgata gctgacattg aggctgctcc tgaaggttct tttgttctgc     60
tacatggttg tgctcacaac ccaactggaa tagacccaac tcctgaacag tgggagaaaa    120
ttgcagatgt cattcaagag aaaaagcata tgccattctt tgatgttgca atcagggtt    180
ttgccagtgg aagccttgat gaagatgcat tttctgtcag gcttttgtt aagcgtggca    240
tggaagtgtt tgttgcacaa t                                              261
```

<210> SEQ ID NO 379
<211> LENGTH: 247
<212> TYPE: DNA
<213> ORGANISM: Zea mays

<400> SEQUENCE: 379

```
gagtgccaat ggctcctcca gacccaattc ttggggtttc tgaggccttt aaagcagata     60
aaagcgagct gaagctcaat cttggtgttg gtgcctatag gacagaagag ctgcagccct    120
acgtgctcaa tgtagtcaag aaggctgaaa atcttatgtt ggagaaagga gaaaacaaag    180
agtatcttcc cattgaaggt ttagccgcgt ttaacaaagc aacagcagag ctattgcttg    240
gagctga                                                              247
```

<210> SEQ ID NO 380
<211> LENGTH: 293
<212> TYPE: DNA
<213> ORGANISM: Zea mays

<400> SEQUENCE: 380

```
caaggctgaa aatcttatgt tggagaaagg agaaaacaaa gagtatcttc ccattgaagg     60
tttagccgcg tttaacaaag caacagcaga gctattgctt ggagctgata accctgttat    120
taatcaagga ctggttgcta cacttcagtc tctctcgggc actggatcac tgcgtctcgc    180
tgcagcattc atacaaagat actttcctga agctaaagtg ctgatatcgt cgcctacctg    240
gggtaaccac aagaatatct tcaatgatgc ttagggacct tggtcagagt aca            293
```

<210> SEQ ID NO 381
<211> LENGTH: 281
<212> TYPE: DNA
<213> ORGANISM: Zea mays

<400> SEQUENCE: 381

```
ctcgagccgt gcagccatac gtgctcaatg tagtcaagaa ggctgaaaat cttaagttgg     60
agaaaggaga aaacaaagag tatcttccca ttgaaggttt agccgcgttt aacaaagcaa    120
```

-continued

```
cagcagagct attgcttgga gctgataacc ctgttattaa tcaaggactg gttgctacac    180
ttcagtctct ctcgggcact ggatcacagc gtctcgctgc agcattcata caaagatact    240
ttcctgaagc taaagtgctg atatcgtcgc ctacctgggg t                        281
```

<210> SEQ ID NO 382
<211> LENGTH: 262
<212> TYPE: DNA
<213> ORGANISM: Zea mays

<400> SEQUENCE: 382

```
gagaaaggag aaaacaaaga gtatcttccc attgaaggtt tagccgcgtt taacaaagca    60
acagcagagc tattgcttgg agctgataac cctgttatta atcaaggact ggttgctaca    120
cttcagtctc tctcgggcac tggatcactg cgtctcgctg cagcattcat acaaagatac    180
tttcctgaag ctaaagtgct gatatcgtcg cctacctggg gtaaccacaa gaatatcttc    240
aatgtgctag ggtacttggt ca                                              262
```

<210> SEQ ID NO 383
<211> LENGTH: 278
<212> TYPE: DNA
<213> ORGANISM: Zea mays

<400> SEQUENCE: 383

```
tggattttga gggaatgata gctgacattg aggctgctcc tgaaggtgct tttgttctgc    60
tacatggttg tgatcacaac ccaactggaa tagacccaac tcctgaacag tgggagaaaa    120
ttgcagatgt cattcaagag aaaaagcata tgccattctt tgatgttgca tatcagggtt    180
aggtcagtgg aagccttgat gaagatgcat tttctgtcag gcttttttgtt agcgtagcat    240 ggaagtgttt gttgcacaat cttacagcaa gaacttgg                             278
```

<210> SEQ ID NO 384
<211> LENGTH: 180
<212> TYPE: DNA
<213> ORGANISM: Zea mays

<400> SEQUENCE: 384

```
cggattttga gggaatgata gctgacattg aggctgctcc tgaaggttct tttgttctgc    60
tacatggttg tgctcacaac ccaactggaa tagacccaac tcctgaacag tgggagaaaa    120
ttgcagatgt cattcaggag aaaaagcata tgccattctt tgatgttgca tatcagggtt    180
```

<210> SEQ ID NO 385
<211> LENGTH: 210
<212> TYPE: DNA
<213> ORGANISM: Zea mays

<400> SEQUENCE: 385

```
catggttgtg ctcacaaccc aactggaata gacccaactc ctgaacatgg agaaaattg     60 cagatgtcat tcaagagaaa aagcatatgc cattcttgga tgttgcatat cagggttttg    120
ccagtggaag ccttgatgaa gatgcatttt ctgtcaggct ttttgttaag cgtggcatgg    180
aagtgtttgt tgcacaatct tacagcaaga                                      210
```

<210> SEQ ID NO 386
<211> LENGTH: 292
<212> TYPE: DNA
<213> ORGANISM: Zea mays

<400> SEQUENCE: 386

```
gtgctcataa tcccaccggt gtagatccta cggaggaaca atggagagaa atatcccatc    60
agttcaaggt gaaaaaacat tttccattct ttgacatggc ataccaaggg tttgccagtg   120
gtgatccaga gagagatgcc aaggcaatcc gaatttttcct tgaagatgga caccaaattg   180
gatgtgctca gtcatacgca aagaacatgg gactttatgg acagagagca ggatgcctga   240
gtattctgtg tgaggatgag atgcaagcag ttgctgtcaa gagccaactg ca            292
```

<210> SEQ ID NO 387
<211> LENGTH: 290
<212> TYPE: DNA
<213> ORGANISM: Zea mays

<400> SEQUENCE: 387

```
ggcataccaa gggtttgcca gtggtgatcc agagagagat gccaaggcaa tccgaatttt    60
ccttgaagat ggacaccaaa ttggatgtgc tcagtcatac gcaaagaaca tgggacttta   120
tggacaaaga gcaggatgcc tgagtatttt gtgtgaggat gagatgcaag cagttgctgt   180
caagagccaa atgcaacaga tcgcaagacc aatgtacagc aacccacctg ttcatggtgc   240
actggttgtc tctataatcc tcagtgatcc agaattgaag agttgtggtt               290
```

<210> SEQ ID NO 388
<211> LENGTH: 281
<212> TYPE: DNA
<213> ORGANISM: Zea mays

<400> SEQUENCE: 388

```
cttcattctt ttagcttcat gtatatagat ctaaatctag aggtgtagat cctacggacg    60
aacaatggag agatatatcc catcagttca aggtgaaaaa acattttcca ttctttgaca   120
tggcatacca agggtttgcc agtggtgatc cagagagaga tgccaaggca atccgaattt   180
tccttgaaga tggacaccaa attggatgtg ctcagtcata cgcaaagaac atgggacttt   240
atggacaaag agcaggatgc ttgagtattt tgtgtgaaga t                        281
```

<210> SEQ ID NO 389
<211> LENGTH: 175
<212> TYPE: DNA
<213> ORGANISM: Zea mays

<400> SEQUENCE: 389

```
gttcattctt tttgcttcat gcatgtgctc ataatcccac cggtgtagat cctacggagg    60
aacaatggag agaaatatcc catcagttca aggtgaaaaa acattttcca ttctttgaca   120
tggcatacca agggtttgcc agtggtgatc cagagagaga tgccaaggca atccg         175
```

<210> SEQ ID NO 390
<211> LENGTH: 136
<212> TYPE: DNA
<213> ORGANISM: Zea mays

<400> SEQUENCE: 390

```
aaaacatttt ccattctttg acatggcata ccaagggttt gccagtggtg atccagagag    60
agatgccaag gcaatccgaa ttttccttga agatggacac caaattggat gtgctcagtc   120
atacgcaaag aacatg                                                   136
```

<210> SEQ ID NO 391
<211> LENGTH: 181

```
<212> TYPE: DNA
<213> ORGANISM: Zea mays

<400> SEQUENCE: 391
gttcattctt tttgcttcat gcatgtgctc ataatcccac cggtgtagat cctacggagg    60
aacaatggag agaaatatcc catcagttca aggtgaaaaa acattttcca ttctttgaca   120
tggcatacca agggtttgcc agtggtgatc cagagagaga tgccaaggca atccgaattt   180
c                                                                  181

<210> SEQ ID NO 392
<211> LENGTH: 177
<212> TYPE: DNA
<213> ORGANISM: Zea mays

<400> SEQUENCE: 392
gttcatactt tttgcttcat gcatgtgctc ataatcccac cggtgtaaaa ctacggagaa    60
caatggagag aaatatcaca tcagttcaag gtgaaaaaac attttccata ctttgacatg   120
gcataccaag ggtttgccag tggtgatcca gagagagatg ccaaggcgat ccgaatt      177

<210> SEQ ID NO 393
<211> LENGTH: 259
<212> TYPE: DNA
<213> ORGANISM: Zea mays

<400> SEQUENCE: 393
gtcaactgtc cctaggacag atattatttt cttttgttca cccaacaatc ctactggtgc    60
tgctgcatct cgggaccaac taaccaaatt agtaaaattt gcaaaggaca acgggtccat   120
catagtctat gattctgctt atgcaatgta catatcagat gacagcccaa agtctatctt   180
tgaaattcct ggagcaaagg aggttgctat tgagacagcc tcattctcga agtacgctgg   240
gttcacaggt gtccgtcta                                               259

<210> SEQ ID NO 394
<211> LENGTH: 343
<212> TYPE: DNA
<213> ORGANISM: Zea mays

<400> SEQUENCE: 394
tgacagccca agtctatctt tgaaattcct ggagcaaagg aggttgctat tgagacagc     60 ctcattctcg aagtacgctg ggttcacagg tgtccgtcta ggttggactg ttgtcgccaa   120
ggagctcctt ttctcggatg gacatccagt tgctaaagat ttcaatcgca tagtttgcac   180
ttgcttcaat gggcatcaaa cattgcgcaa ctggtggttt agcctgcctc tctccagacg   240
gtctaaaggc tatgcaagat gttgttggct tctacaagga gaacactgaa ataatcgttg   300
agacatttac atcactcgga ttcgacgtct atggcgcaaa gac                    343

<210> SEQ ID NO 395
<211> LENGTH: 171
<212> TYPE: DNA
<213> ORGANISM: Zea mays
<220> FEATURE:
<223> OTHER INFORMATION: unsure at all n locations

<400> SEQUENCE: 395
ccaaagtcta tctttgacat tcctggagca aaggaggttg ctattgagac agcctcattc    60
tcgaaatacg ctgggttcac aggtgtccgt ctaggttgga ctgttgtccc caaggagctc   120
```

```
ctttctcgg atggacatcc agttgctana gatttcaatc gcatagtttg c          171
```

<210> SEQ ID NO 396
<211> LENGTH: 256
<212> TYPE: DNA
<213> ORGANISM: Zea mays

<400> SEQUENCE: 396

```
ctgacttata tcagcaagac gttcagaagt atggaaacat tgagtacatg agatgcggtc    60
cagaaaatgg attttttcct gatctgtcaa ctgtccctag acagatatt attttctttt   120 gttcacccaa caatcctact ggtgctgctg catctcggga ccaactaacc aaattagtaa   180
aatttgcaaa ggacaatggg tccatcatag tctgtgattc tgcttatgca atgtacatat   240
agatgacagc ccaaag                                                   256
```

<210> SEQ ID NO 397
<211> LENGTH: 299
<212> TYPE: DNA
<213> ORGANISM: Zea mays
<220> FEATURE:
<223> OTHER INFORMATION: unsure at all n locations

<400> SEQUENCE: 397

```
gctccttcag gttcaattgt actgctgnca tgcctgtgct cacaaccta ctggagtaga     60 tcctaccatc gaacagtggg aacagattag gcagctgatg agatcaaaat cactgcttcc   120
gttctttgac agtgcctatc aaggctttgc aagtggaagt cttgacaaag atgctcagtc   180
agtgcgtatg tttgttgctg atggtggtga acttctcatg gctcagagct acgctaagaa   240
catgggattg tatggagagc gtgttggcgc tttgagcatt gtatgtaaag tgccgatgt    299
```

<210> SEQ ID NO 398
<211> LENGTH: 297
<212> TYPE: DNA
<213> ORGANISM: Zea mays
<220> FEATURE:
<223> OTHER INFORMATION: unsure at all n locations

<400> SEQUENCE: 398

```
aagaacttct catgggctca gagctacgct aagaacatgg gattgtatgg agagcgtgtt    60
ggcgctttga gcattgtatg taaaagtgcc gatgtagctg ttagggttga aagtcaactc   120
aaacttgtca tcaggcctat gtattcaaac cctcctcttc atggtgcctc tatcgttgct   180
accatactca gggacagcga gatgttcaac gaatggactc tggaactgaa ggccatggct   240
gatangatca ttaacatgag gcaacaacta tttaatgcgc tgaaatccag aggaacc     297
```

<210> SEQ ID NO 399
<211> LENGTH: 279
<212> TYPE: DNA
<213> ORGANISM: Zea mays

<400> SEQUENCE: 399

```
gtatgtttgt tgctgatggt ggtgaacttc tcatggctca gagctacgct aagaacatgg    60
gattgtatgg agagcgtgtt ggcgctttga gcattgtatg taaaagtgcc gatgtagctg   120
ttagggttga aagtcaactc aaacttgtca tcaggcctat gtattcaaac cctcctcttc   180
atggtgcctc tatcgttgct accatactca gggacagcga gatgttcaac gaatggactc   240
tggaactgaa ggccatggct gataggatca ttaacatgg                          279
```

<210> SEQ ID NO 400
<211> LENGTH: 269
<212> TYPE: DNA
<213> ORGANISM: Zea mays

<400> SEQUENCE: 400
gctttgcaag tggaagtctt gacaaagatg ctcagtcagt gcgtatgttt gttgctgatg     60
gtggtgaact tctcatggct cagagctacg ctaagaacat gggattgtat ggagagcgtg    120
ttggcgcttt gagcattgta tgtaaaagtg ccgatgtagc tgttagggtt gaaagtcaac    180
tcaaacttgt catcaggcct atgtattcaa accctcctct tcatggtgcc tctatcgttg    240
ctaccatact cagggacagc gagatgttc                                      269

<210> SEQ ID NO 401
<211> LENGTH: 318
<212> TYPE: DNA
<213> ORGANISM: Zea mays
<220> FEATURE:
<223> OTHER INFORMATION: unsure at all n locations

<400> SEQUENCE: 401
gtttgttgct gatggtggtg aacttctcat ggctcagagc tacgctaaga acatgggatt     60
gtatggagag cgtgttggcg ctttgagcat tgtatgtaaa agtgccgatg tagctgttag    120
ggttgaaagt caactcaaac ttgtcatcag gcctatgtat tcaaaccctc tcttcatgg    180 tgcctctatc gttgctacca tactcaggga cagcgagatg ttcaacgaat ggactctgga    240
actgaaggcc atggctgata ggatcataac atgaggcaac aatatttaat gcgctgaaat    300
ccagangaac ccctggtg                                                  318

<210> SEQ ID NO 402
<211> LENGTH: 282
<212> TYPE: DNA
<213> ORGANISM: Zea mays
<220> FEATURE:
<223> OTHER INFORMATION: unsure at all n locations

<400> SEQUENCE: 402
tttgganatc acccaaaagt cttcacccta tctggcttga acgttaggtg ctaccgctat     60
tatgatcctg caacatgcag ccttcacttc gaaggactcc tggaagacct cggttctgct    120
ccttcaggtt caattgtact gctgcatgcc tgtgctcaca accctactgg agtagatcct    180
accatcgaac agtgggaaca gattaggcag ctgatgagat caaaatcact gcttccgttc    240
tttgacagtg cctatcaagg cttttgcaagt ggaagtcttg ac                      282

<210> SEQ ID NO 403
<211> LENGTH: 260
<212> TYPE: DNA
<213> ORGANISM: Zea mays

<400> SEQUENCE: 403
gttgctgatg gtggtgaact tctcatggct cagagctacg ctaagaacat gggattgtat     60
ggagagcgtg ttggcgcttt gagcattgta tgtaaaagtg ccgatgtagc tgttagggtt    120
gaaagtcaac tcaaacttgt catcaggcct atgtattcaa accctcctct tcatggtgcc    180
tctatcgttg ctaccatact cagggacagc gagatgttca acgaatggac tctggaactg    240
aaggccatgg ctgataggat                                                260

<210> SEQ ID NO 404

<211> LENGTH: 302
<212> TYPE: DNA
<213> ORGANISM: Zea mays

<400> SEQUENCE: 404

```
gggttgctac cgtgcagtgc ctatcgggta ctggttcttt aagagtcgga ggtgaatttc    60
ttgcaaggca ctatcacgag cgcactatct acatcccaca accaacctgg ggaaatcacc   120
caaaagtctt caccctatct ggcttgaacg ttaggagatg aacgctatta tgatcctgca   180
acatgcagcc ttcacttcga aggactcctg gaagacctcg ttctgctcc ttcaggttca    240
attgtactgc tgcatgcctg tgctcacaac cctactggag tagatcctac catcgaacag   300
tg                                                                  302
```

<210> SEQ ID NO 405
<211> LENGTH: 280
<212> TYPE: DNA
<213> ORGANISM: Zea mays
<220> FEATURE:
<223> OTHER INFORMATION: unsure at all n locations

<400> SEQUENCE: 405

```
cgaacttctc atggctcaga gctacgctaa gancatggga ttgtatgnng agcgtgttgg    60
cgctttgagc attgtatgtn aaagtgccga tgtagctgtt agggttgana gtcaactcaa   120
acttgtcatc aggcctatgt attcaaaccc tcctcttcat ggtgcctcta tcgttgctac   180
catactcagg acagcgaga tgttcaacga atggactctg gaactgaagg ccatggctga    240
taggntctta acatgaggca caactatttt aatgcgctga                         280
```

<210> SEQ ID NO 406
<211> LENGTH: 264
<212> TYPE: DNA
<213> ORGANISM: Zea mays

<400> SEQUENCE: 406

```
acttctcatg gctcagagct acgctaagaa catgggattg tatggagagc gtgttggcgc    60
tttgagcatt gtatgtaaaa gtgccgatgt agctgttagg gttgaaagtc aactcaaact   120
tgtcatcagg ccatgtattc aaaccctcct cttcatggtg cctctatcgt tgctaccata   180
ctcagggaca gcgagatgtt caacgaatgg actctggaac tgaaggccat ggctgatagg   240
atcattaaca tgaggcaaca actt                                          264
```

<210> SEQ ID NO 407
<211> LENGTH: 252
<212> TYPE: DNA
<213> ORGANISM: Zea mays

<400> SEQUENCE: 407

```
caggacagcg agatgttcaa cgaatggact ctggaactga aggccatggc tgataggatc    60
attaacatga ggcaacaact atttaatgcg ctgaaatcca gaggaacccc tggtgattgg   120
agccatatca ttaagcaaat tgggatgttt actttcactg gctgaatag cgaacaagtc    180
gcattcatga ggcaggaata ccacatttat atgacatctg atgggaggat cagcatggcc   240
ggtttgagca tg                                                       252
```

<210> SEQ ID NO 408
<211> LENGTH: 254
<212> TYPE: DNA
<213> ORGANISM: Zea mays

```
<400> SEQUENCE: 408
taagatgttc aacgaatgga ctctggaact gaaggccatg gctgatagga tcattaacat      60
gaggcaacaa ctatttaatg cgctgaaatc cagaggaacc cctggtgatt ggagccatat     120
cattaagcaa attgggatgt ttactttcac tgggctgaat agcgaacaag tcgcattcat     180
gaggcaggaa taccacattt atatgacatc tgatgggagg atcagcatgg ccggtttgag     240
catgaggact gtgc                                                       254

<210> SEQ ID NO 409
<211> LENGTH: 254
<212> TYPE: DNA
<213> ORGANISM: Zea mays

<400> SEQUENCE: 409
gtaaaagtgc cgatgtagct gttagggttg aaagtcaact caaacttgtc atcaggccta      60
tgtattcaaa ccctcctctt catggtgcct ctatcgttgc taccatactc agggacagcg     120
agatgttcaa cgaatggact ctggaactga aggccatggc tgataggatc attaacatga     180
ggcaacaact atttaatgcg ctgaaatcca gaggaacccc tggtgattgg agccatatca     240
ttaagcaaat tggg                                                       254

<210> SEQ ID NO 410
<211> LENGTH: 255
<212> TYPE: DNA
<213> ORGANISM: Zea mays

<400> SEQUENCE: 410
ctgttagggt tgaaagtcaa ctcaaacttg tcatcaggcc tatgtattca aaccctcctc      60
ttcatggtgc ctctatcgtt gctaccatac tcagggacag cgagatgttc aacgaatgga     120
ctctggaact gaaggccatg gctgatagga tcattaacat gaggcaacaa ctatttaatg     180
cgctgaaatc cagaggaacc cctggtgatt ggagccatat cattaagcaa attgggatgt     240
ttactttcac tgggc                                                      255

<210> SEQ ID NO 411
<211> LENGTH: 235
<212> TYPE: DNA
<213> ORGANISM: Zea mays

<400> SEQUENCE: 411
gattaggcag ctgatgagat caaaatcact gcttccgttc tttgacagtg cctatcaagg      60
ctttgcaagt ggaagtcttg acaaagatgc tcagtcagtg cgtatgtttg ttgctgatgg     120
tggtgaactt ctcatggctc agagctacgc taagaacatg ggattgtatg gagagcgtgt     180
tggcgctttg agcattgtat gtaaaagtgc cgatgtagct gttaggttg aaagt          235

<210> SEQ ID NO 412
<211> LENGTH: 272
<212> TYPE: DNA
<213> ORGANISM: Zea mays
<220> FEATURE:
<223> OTHER INFORMATION: unsure at all n locations

<400> SEQUENCE: 412
acttctcatg gctcagagct acgctaagaa catgggattg tatggagagc gtgttggcgc      60
tttgagcatt gtatgtaaaa gtgccgatnt agctgttagg gttgaaagtc aactcaaact     120
```

```
tgtcancagg cctatgtatt caaaccctcc tcttcatggt gcctctatcg ttgctaccat      180
annncaggac agcgagatgt tcaacgaatg gactctggaa tgaaggccat ggctgatagg      240
atcataacat gaggcaacaa ctattaatgc gc                                    272

<210> SEQ ID NO 413
<211> LENGTH: 243
<212> TYPE: DNA
<213> ORGANISM: Zea mays

<400> SEQUENCE: 413
caggcctatg tattcaaacc ctcctcttca tggtgcctct atcgttgcta ccatactcag       60
ggacagcgag atgttcaacg aatggactct ggaactgaag gccatggctg ataggatcat      120
taacatgagg caacaactat ttaatgcgct gaaatccaga ggaacccctg gtgattggag      180
ccatatcatt aagcaaattg ggatgtttac tttcactggg ctgaatagcg aacaagtcgc      240
att                                                                    243

<210> SEQ ID NO 414
<211> LENGTH: 241
<212> TYPE: DNA
<213> ORGANISM: Zea mays

<400> SEQUENCE: 414
gtcttgacaa agatgctcag tcagtgcgta tgtttgttgc tgatggtggt gaacttctca       60
tggctcagag ctacgctaag aacatgggat tgtatggaga gcgtgttggc gctttgagca      120
ttgtatgtaa aagtgccgat gtagctgtta gggttgaaag tcaactcaaa cttgtcatca      180
ggcctatgta ttcaaaccct cctcttcatg gtgcctctat cgttgctacc atactcaggg      240
a                                                                      241

<210> SEQ ID NO 415
<211> LENGTH: 254
<212> TYPE: DNA
<213> ORGANISM: Zea mays

<400> SEQUENCE: 415
tgagaagttc accaccatca gcaacaaaca tacgcactga ctgagcatct ttgtcaagac       60
ttccacttgc aaagccttga taggcactgt caaagaacgg aagcagtgat tttgatctca      120
tcagctgcct aatctgttcc cactgttcga tggtaggatc tactccagta gggttgtgag      180
cacaggcatg cagcagtaca attgaacctg aaggagcaga accgaggtct tccaggagtc      240
cttcgaagtg aagg                                                        254

<210> SEQ ID NO 416
<211> LENGTH: 221
<212> TYPE: DNA
<213> ORGANISM: Zea mays

<400> SEQUENCE: 416
gattaggcag ctgatgagat caaaatcact gcttccgttc tttgacagtg cctatcaagg       60
ctttgcaagt ggaagtcttg acaaagatgc tcagtcagtg cgtatgtttg ttgctgatgg      120
tggtgaactt ctcatggctc agagctacg taagaacatg ggattgtatg gagagcgtgt      180
tggcgctttg agcattgtat gtaaaagtgc cgatgtagct g                          221

<210> SEQ ID NO 417
<211> LENGTH: 328
```

```
<210> SEQ ID NO 417
<211> LENGTH: 328
<212> TYPE: DNA
<213> ORGANISM: Zea mays

<400> SEQUENCE: 417
ctagttctag atcgccagcc gccgctcggg ccgctcgatc tagaactagc ccacgcgtcc     60
gcggacgcgt ggcacgagcg cactatctac atcccacaac caatcctggg gaaatcaccc    120
aaaagtcttc acactatctg gcttgaacgt taggagctac cgctattatg atcctgcaac    180
atgcagcctt cacttcgaag gactcctgga acacctcggt tctgctcctt caggttcaat    240
tgtactgctg catgcctgtg ctcacaaccc tactggagta gatcctacca tcgaacagtg    300
ggaacagatt aggcagctga tgagatca                                        328

<210> SEQ ID NO 418
<211> LENGTH: 272
<212> TYPE: DNA
<213> ORGANISM: Zea mays

<400> SEQUENCE: 418
atatcattaa gcaaattggg atgtttactt tcactgggct gaatagcgaa caagtcgcat     60
tcatgaggca ggaataccac atttatatga catctgatgg gaggatcagc atggccggtt    120
tgagcatgag gactgtgccc catcttgcag atgccataca cgctgcagtt actcaactga    180
aatgaggata gtatcgcagc tttcgtgaat aaaacctgaa tcacccacaa caatgttcta    240
agtactcagc cagtggtatc tactggttga cc                                   272

<210> SEQ ID NO 419
<211> LENGTH: 249
<212> TYPE: DNA
<213> ORGANISM: Zea mays
<220> FEATURE:
<223> OTHER INFORMATION: unsure at all n locations

<400> SEQUENCE: 419
cggaacgctg gttntaatgc gctgaaatcc agaggaaccc ctggtgattg gagccatatc     60
aanaagcaaa ttgggatgtt tactttcact gggctgaata gcgaacaagt cgcattcatg    120
aggcaggaat accacattta tgacatctct gatgggagga tcagcatggc cggtttgagc    180
atgaggactg tgccccatct tgcagatgcc atacacgctg cagttactca actgaaatga    240
ggatagtat                                                             249

<210> SEQ ID NO 420
<211> LENGTH: 224
<212> TYPE: DNA
<213> ORGANISM: Zea mays

<400> SEQUENCE: 420
gcgagatgtt caacgaatgg actctggaac tgaaggccat ggctgatagg atcattaaca     60
tgaggcaaca actatttaat gcgctgaaat ccagaggaac ccctggtgat tggagccata    120
tcattaagca aattggatgt ttactttcac tgggctgaat agcgaacaag tcgcattcat    180
gaggcaggaa taccacattt atatgacatc tgatgggagg atca                     224

<210> SEQ ID NO 421
<211> LENGTH: 234
<212> TYPE: DNA
<213> ORGANISM: Zea mays

<400> SEQUENCE: 421
```

```
atccagagga accoctggtg attggagcca tatcattaag caaattggga tgtttacttt    60
cactgggctg aatagcgaac aagtcgcatt catgaggcag gaataccaca tttatatgac   120
atctgatggg aggatcagca tggccggttt gagcatgagg actgtgcccc atcttgcaga   180
tgccatacac gctgcagtta ctcaactgac atgaggctag tatcgcagct ttcg         234
```

<210> SEQ ID NO 422
<211> LENGTH: 280
<212> TYPE: DNA
<213> ORGANISM: Zea mays

<400> SEQUENCE: 422

```
gggttgctac cgtgcagtgc ctatcgggta ctggttcttt aagagtcgga ggtgaatttc    60
ttgcaaggca ctatcacgag cgcactatct acatcccaca accaacctgg ggaaatcacc   120
caaaagtctt caccctatct ggcttgaacg ttaggagcta ccgctattat gatcctgcaa   180
catgcagcct tcacttcgaa ggactcctgg aaagactcgg ttctgctact tcaggttcat   240
tgtactgctg catgcctgtg ctcacaacct actggagtag                         280
```

<210> SEQ ID NO 423
<211> LENGTH: 278
<212> TYPE: DNA
<213> ORGANISM: Zea mays

<400> SEQUENCE: 423

```
gtgaaatcca gaggaacccc tggtgattgg agccatatca ttaagcgaat tgggatgttt    60
actttcactg gctgaatag cgaacaagtc gcattcatga ggcaggaata ccacatttat   120
atgacatctg atgggaggat cagcatggcc ggtttgagca tgaggactgt gccccatctt   180
gcagatgcca tacacgctgc agttactcaa ctgaaatgag gatagtatcg cagctttcgt   240
gaataaaacc tgaatcaccc acaacaatgt tctaagta                           278
```

<210> SEQ ID NO 424
<211> LENGTH: 229
<212> TYPE: DNA
<213> ORGANISM: Zea mays
<220> FEATURE:
<223> OTHER INFORMATION: unsure at all n locations

<400> SEQUENCE: 424

```
ggaggtgaat tcttgcaag gcactatcac gagcgcacta tctacatccc acaaccaacc    60
tggggaaatc acccaaaagt cttcaccta tctggcttga acgttaggng ctaccgctat   120
tatgatcctg caacatgcag ccttcacttc gaaggactcc tggaagacct cggttctgct   180
ccttcaggtt caattgtact gctgcatgcc tgtgctcaca ccctactg                229
```

<210> SEQ ID NO 425
<211> LENGTH: 268
<212> TYPE: DNA
<213> ORGANISM: Zea mays

<400> SEQUENCE: 425

```
aagtcgcatt catgaggcag gaataccact ttatatgaca tctgatggga ggatcagcat    60
ggccggtttg agcatgagga ctgtgcccca tcttgcagat gccatacacg ctgcagttac   120
tcaactgaaa tgaggatagt atcgcagctt tcgtgaataa aacctgaatc acccacaaca   180
atgttctaag tactcagcca gtggtattta ctggttgacc tactgtagtt tgcgtcggaa   240
tagatatgtt ttttactct tcgtgggg                                       268
```

<210> SEQ ID NO 426
<211> LENGTH: 279
<212> TYPE: DNA
<213> ORGANISM: Zea mays

<400> SEQUENCE: 426
cccctggtga ttggagccat atcattaagc aaattgggat gtttactttc actgggctga      60
atagcgaaca agtcgcattc atgaggcagg ataccacat ttatatgaca tctgatggga     120
ggatcagcat ggccggtttg agcatgagga ctgtgcccca tcttgcagat gccatacacg    180
ctgcagttac tcaactgaaa tgaggatagt atcgcagctt tcgtgaataa aacctgaatc    240
acccacaaca atgttctaag tactcagcca gtggtattt                            279

<210> SEQ ID NO 427
<211> LENGTH: 209
<212> TYPE: DNA
<213> ORGANISM: Zea mays

<400> SEQUENCE: 427
gtcttgacaa agatgctcag tcagtgcgta tgtttgttgc tgatggtggt gaacttctca     60
tggctcagag ctacgctaag aacatgggat tgtatggaga gcgtgttggc gctttgagca    120
ttgtatgtaa aatgccgatg tagctgttag ggttgaaagt caactcaaac ttgtcatcag    180
gcctatgtat tcaaaccctc ctcttcatg                                       209

<210> SEQ ID NO 428
<211> LENGTH: 270
<212> TYPE: DNA
<213> ORGANISM: Zea mays

<400> SEQUENCE: 428
agcaaattgg gatgtttact ttcactgggc tgaatagcga acaagtcgca ttcatgaggc     60
aggaatacca catttatatg acatctgatg ggaggatcag catggccggt ttgagcatga    120
ggactgtgcc ccatcttgca gatgccatac acgctgcagt tactcaactg aaatgaggat    180
agtatcgcag ctttcgtgaa taaaacctga atcacccaca acaatgttct aagtactcag    240
ccagtggtat tactggttga cctactgtag                                      270

<210> SEQ ID NO 429
<211> LENGTH: 187
<212> TYPE: DNA
<213> ORGANISM: Zea mays

<400> SEQUENCE: 429
ctgaaatcca gaggaacccc tggtgattgg agccatatca ttaagcaaat tgggatgttt     60
actttcactg ggctgaatag cgaacaagtc gcattcaatg aggcaggaat aaccacattt    120
atatgacatc tgatgggagg atcagcatgg ccggtttgag catgaggact gtgccccatc    180
ttcaaga                                                               187

<210> SEQ ID NO 430
<211> LENGTH: 214
<212> TYPE: DNA
<213> ORGANISM: Zea mays

<400> SEQUENCE: 430
ttgggatgtt tactttcact gggctgaata gcgaacaagt cgcattcatg aggcaggaat     60

```
accacattta tatgacatct gatgggagga tcagcatggc cggtttgagc atgaggactg    120
tgccccatct tgcagatgcc atacacgctg cagttactca actgacatga ggctagtatc    180
gcagctttcg tgaataaaac ctgaatcacc caca                                214
```

<210> SEQ ID NO 431
<211> LENGTH: 188
<212> TYPE: DNA
<213> ORGANISM: Zea mays

<400> SEQUENCE: 431

```
tgtagctgtt aggattgaaa gtcaactcaa acttgtcatc aggcctatgt attcaaaccc     60
acctcatcat ggtgcctcta tcgtagctac catactcagc gacagcgaga tgttcaacga    120
atggacactg gaacagaagg ccatggctga taggatcatt aacatgaggc aacaactatt    180
taatgcgc                                                             188
```

<210> SEQ ID NO 432
<211> LENGTH: 256
<212> TYPE: DNA
<213> ORGANISM: Zea mays

<400> SEQUENCE: 432

```
ctgaaatcca gaggaacccc ggtgattgga gccatatcat taagcaaatt gggatgttta     60
ctttcactgg gctgaatagc gaacaagtcg cattcatgag gcaggaatac cacatttata    120
tgacatctga tggaggatc agcatggccg gtttgagcat gaggactgtg ccccatcttg    180
cagatgccat acacgtcgca gttactcaac tgaaatgagg atagtatcgc agctttcgtg    240
aataaacctg aatcac                                                    256
```

<210> SEQ ID NO 433
<211> LENGTH: 263
<212> TYPE: DNA
<213> ORGANISM: Zea mays

<400> SEQUENCE: 433

```
tgagccatat cattaagcaa attgggatgt ttactttcac tgggctgaat agcgaacaag     60
tcgcattcat gaggcaggaa taccacattt atatgacatc tgatgggagg atcagcatgg    120
ccggtttgag catgaggact gtgacccatc ttgcagatgc catacacgct gcagttactc    180
aactgaaatg aggatagtat cgcagctttc gtgaataaaa cctgaatcac ccacaacaat    240
gttctaagta ctcagccagt ggt                                            263
```

<210> SEQ ID NO 434
<211> LENGTH: 241
<212> TYPE: DNA
<213> ORGANISM: Zea mays

<400> SEQUENCE: 434

```
atgacatctg atgggaggat cagcatggcc ggtttgagca tgaggactgt gccccatctt     60
gcagatgcca tacacgctgc agttactcaa ctgaaatgag gatagtatcg cagctttcgt    120
gaataaaacc tgaatcaccc acaacaatgt tctaagtact caaccagtgg tatttactgg    180
ttgacctact gtagtttgcg tcggaataga tatgtttttt tactcttcgt ggggcagttt    240
t                                                                    241
```

<210> SEQ ID NO 435
<211> LENGTH: 162

```
<212> TYPE: DNA
<213> ORGANISM: Zea mays

<400> SEQUENCE: 435
gtcaactcaa acttgtcatc aggcctatgt attcaaaccc tcctcttcat ggtgcctcta      60
tcgttgctac catactcagg gacagcgaga tgttcaacga atggactctg gaactgaagg     120
ccatggctga taggatcatt aacatgaggc aacaactatt ta                       162

<210> SEQ ID NO 436
<211> LENGTH: 151
<212> TYPE: DNA
<213> ORGANISM: Zea mays

<400> SEQUENCE: 436
ctcgagcgcg ctgaaatcca gaggaacccc tggtgattgg agccatatca ttaagcatat      60
tgggatgttt actttcactg ggctgaatag cgaacaagtc gcattcatga ggcaggaata    120
ccacatttat atgacatctg atgggaggat c                                   151

<210> SEQ ID NO 437
<211> LENGTH: 276
<212> TYPE: DNA
<213> ORGANISM: Zea mays

<400> SEQUENCE: 437
tgccggtttg agcatgagga ctgtgcccca tcttgcagat gccatacacg ctgcagttac      60
tcaactgaaa tgaggatagt atcgcagctt tcgtgaataa aacctgaatc acccacaaca    120
atgttctaag tactcagcca gtggtattta ctggttgacc tactgtagtt tgcgtcggaa    180
tagatatgtt tttttactct tcgtggggca gttttgtact ggtggattca taaggactct    240
gattatggtg cgttcggaac ttataataat aagcac                              276

<210> SEQ ID NO 438
<211> LENGTH: 112
<212> TYPE: DNA
<213> ORGANISM: Zea mays

<400> SEQUENCE: 438
ctgagatcaa aatcactgct tccgttcttt gacagtgcct atcaaggctt tgcaagtgga      60
agtcttgaca aagatgctca gtcagtgcgt atgtttgttg ctgatggtgg tg            112

<210> SEQ ID NO 439
<211> LENGTH: 164
<212> TYPE: DNA
<213> ORGANISM: Zea mays

<400> SEQUENCE: 439
acccacaaca atgttctaag tactcagcca gtggtattta ctggttgacc tactgtagtt      60
tgcgtcggaa tagatatgtt tttttactct tcgtggggca gttttgtact ggtggattca    120
taaggactct gattatggtg cgttcggaac ttataataat aagc                     164

<210> SEQ ID NO 440
<211> LENGTH: 173
<212> TYPE: DNA
<213> ORGANISM: Zea mays

<400> SEQUENCE: 440
caatgttcta agtactcagc cagtggtatt tactggttga cctactgtag tttgcgtcgg      60
```

```
aatagatatg tttttttact cttcgtgggg cagttttgta ctggtggatt cataaggact    120
ctgattatgg tgcgttcgga acttataata ataagcacat gaaattttgc ttc           173
```

<210> SEQ ID NO 441
<211> LENGTH: 173
<212> TYPE: DNA
<213> ORGANISM: Zea mays

<400> SEQUENCE: 441

```
caatgttcta agtactcagc cagtggtatt tactggttga cctactgtag tttgcgtcgg     60
aatagatatg tttttttact cttcgtgggg cagttttgta ctggtggatt cataaggcct    120
ctgattatgg tgcgttcgga acttataata ataagcacat gaaattttgc ttc           173
```

<210> SEQ ID NO 442
<211> LENGTH: 429
<212> TYPE: DNA
<213> ORGANISM: Zea mays

<400> SEQUENCE: 442

```
atccgaattt tccttgaaga tggacaccaa attggatgtg ctcagtcata cccaaagaac     60
atgggacttt atggacaaag agcaggatgc ctgagtattt tgtgtgagga tgagatgcaa    120
gcagttgctg tcaagagcca actgcaacag atcgcaagac caatgtacag caacccacct    180
gttcatggtg cactggttgt tctataatc ctcagtgatc cagaattgaa gagtttgtgg     240
ttaaaagaag tcaagggtat ggctgatcgt atcattggaa tgcggaaggc acttaaggaa    300
aatcttgaaa agctaggttc acctttgtca tgggatcata tcactaatca gattggaatg    360
ttctgctaca gtgggatgac acctgaacaa gttgaccgtt aacaaatga ataccacatt     420 tacatgacc                                                             429
```

<210> SEQ ID NO 443
<211> LENGTH: 325
<212> TYPE: DNA
<213> ORGANISM: Zea mays

<400> SEQUENCE: 443

```
tcgcaaactc ttcaattctg gatcactgaa gagctggagg cacttaagga aaatctggaa     60
gagctaggtt cacctttgtc atgtgatcat atcactaatc agattggaat gttctgctac    120
agtgggatga cacctgaaca agtttaccgt ttaacaaatg aataccagag ttacattacc    180
cgtaatggga ggataagctt tgctggtgtt acgacaggat atgttgacta cctttcatat    240
gcaattcatg aggttaccaa accaaattga gttagggtcc taccttcttt ggtcgatgga    300
agctgatgga atgagactgt taagc                                          325
```

<210> SEQ ID NO 444
<211> LENGTH: 279
<212> TYPE: DNA
<213> ORGANISM: Zea mays

<400> SEQUENCE: 444

```
cgaagagcca actgcaacag atcgcatgac caatgtacag caacccacct ggtcagtgtg     60
cactggttgt ttgtataatc ctcagtgatc cagaattgaa gagtttgtgg ttaaaagaag    120
tcaagggtat ggctgatcgt atcattggaa tgcgtaattc acttaaggat aaatcttaat    180
agctaggttc acctttgtta tggtatcata tatttaatta ttattgtatt gttctttttt    240
tgttttattt attttttttt tttttttttt tttttttt                            279
```

<210> SEQ ID NO 445
<211> LENGTH: 355
<212> TYPE: DNA
<213> ORGANISM: Zea mays
<220> FEATURE:
<223> OTHER INFORMATION: unsure at all n locations

<400> SEQUENCE: 445
gccagctgaa acgattggca cgtcccatgt nttcgaaccc ccctattcac ggtgccaaga      60
nggttggnaa cnttggtggt gatgcaacca ntgtttggtn aaatggaaac angagttggg     120
tctaatngct tgancgantc naagatngta ananaaaann ttaaaaacag gttntttttc     180
aaaggncaaa aaccgcaaga actgggnttt tatttnnagg ggntattgna atgttttttt     240
anacggnttt aaaaaaannc antgggnaac attgcggntn anntggatnt tatttgacaa     300
angnngggggg gatttgnaaa natggggtnt cctgggttaa cggggatatt tttgc         355

<210> SEQ ID NO 446
<211> LENGTH: 442
<212> TYPE: DNA
<213> ORGANISM: Zea mays

<400> SEQUENCE: 446
cggacgcgtg ggatgagatg caagcagttg ctgtcaagag ccaactgcaa cagatcgcaa      60
gaccaatgta cagcaaccca cctgttcatg gtgcactggt tgtttctata atcctcagtg     120
atccagaatt gaagagtttg tggttaaaag aagtcaaggg tatggctgat cgtatcattg     180
gaatgcggaa ggcacttaag gaaaatcttg aaaagctagg ttcacctttg tcatgggatc     240
atatcactaa tcagattgga atgttctgct acagtgggat gacacctgaa caagttgacc     300
gtttaacaaa tgaataccac atttacatga cccgcaatgg gtggataagc atggctggtg     360
ttacgacagg aaatgttggt tacctagcaa attcttttca tgaggttacc aaactcaatt     420
tagttatggt cctaccttct tt                                              442

<210> SEQ ID NO 447
<211> LENGTH: 471
<212> TYPE: DNA
<213> ORGANISM: Zea mays
<220> FEATURE:
<223> OTHER INFORMATION: unsure at all n locations

<400> SEQUENCE: 447
gctagcagcc gcctcctcgt caggccnttt ttncttcacc ctcgccaaac ccgcctcctn      60
nggtccgaac tccgtctgct tcatctgagc gtccgggagg acaaaacacg cggcgaggac     120
caggatggcg attgtgcggg aggaggcaag tggacacgtc catcagccca agggtgagcg     180
cgctgcggcc gtccaaaacc atggccatca ccgatnaggc catggcgctg cggcaggccg     240
gcgtgccggt tatcggtcta gccgcgggggg agccagactt ncgacacgcn ccccgtgatc     300
gnggangccc ggattgatgc aattaggaat ggttatacaa agatacactt ntaatgctgg     360
gacttttgaa ctgangaaang ggtatttnta ctaaaacttn angaggagaa cggggggnttc     420
taacttccaa atnaaggtct tngtaacaan ggaactaaaa antnnnntan a               471

<210> SEQ ID NO 448
<211> LENGTH: 433
<212> TYPE: DNA
<213> ORGANISM: Zea mays

-continued

```
<400> SEQUENCE: 448
caaaagccca cagcttcttc tccctactcc tccagtcctc cgtcatccgt ttcggtcgct      60
gccgccgcca ccgcacaaga agctagctcc tgcctgtacc gccccgtcat ggcgatgcta     120
tcccgcgcag cctcctccgc ggcccggcgc ccgctgctgc cgccgcctag gcttctggcg     180
gtgagggcga tggcgtcgtc gctcttcggc cacgtcgagc cggcgcccaa ggaccccatc     240
ctcggcgtca ccgaggcttt cctcgccgac ccctcgtccg acaaagtgaa cgtcggcgtc     300
ggcgcctacc gggacgacaa cggccagccc gtcgtgctca gctgcgtgcg cgaggccgag     360
cgccggatcg cgggcaacct caacatggag taccttccga tgggaggcag cgtcaagatg     420
attgaagagt cac                                                        433

<210> SEQ ID NO 449
<211> LENGTH: 237
<212> TYPE: DNA
<213> ORGANISM: Zea mays

<400> SEQUENCE: 449
cggacacgtg ggtctgccgc cgccaccgca caagaagcta gctcctgcct gtaccacccc      60
ggcatggcga tgctatcccg cgcagcctcc tccgcggccc ggcgcccgct gctgccgccg     120
cctaggcttc tggcggtgag ggcgatggcg tcgtcgctct tcggcacgt cgagccggcg      180 cccaaggacc ccatcctcgg cgtcaccgag gctttcctcg ccgacccctc gtccgac       237

<210> SEQ ID NO 450
<211> LENGTH: 371
<212> TYPE: DNA
<213> ORGANISM: Zea mays

<400> SEQUENCE: 450
ccattctttg atgttgcata tcaaggtttt gccagtggaa gccttgatga agatgcattt      60
tctgtcaggc ttttttgttaa gcgtggcatg gaagtgtttg ttgcacaatc ttacagcaag     120
aaccttggtc tatattctga aagggttggt gcgataaatg tcgtgtgctc agcaccagaa     180
gttgcagata gggtaaagag ccagctgaaa cgattggcac gtcccatgta ctcgaacccc     240
cctattcacg gtgccaagat agttgccaac gttgttggtg atccaatcat gtttggtgaa     300
tggaaacaag agatggagct aatggctgga cggatcaaga atgtaagaca gaagctctac     360
gacagtttgt c                                                          371

<210> SEQ ID NO 451
<211> LENGTH: 433
<212> TYPE: DNA
<213> ORGANISM: Zea mays

<400> SEQUENCE: 451
acggccaggt gaaacgattg gcacgtacca tgtattcgat accccgctat tcacggtgcc      60
aagatggttg gcgaacgttg ttggtgatgc aaccatgttt ggtgaatgga acaagagat     120 ggagctaatg gctggactga tcaagaatgt aagacaaaag ctctacgaca gtttgtctgc     180
caaggacaag agcggcaagg actggtcttt cattctgagg cagattggca tgttctccta     240
caccggcttg aacaaagcgc agagtgacaa catgacggat aaatggcata tttacatgac     300
caaggatggg cggatctcgt tagctgggct gtccctggct aagtgtgatt atcttgccga     360
cgccatcatc gattccttcc ataatgtgaa ctatgctgaa gtactatagt tgagggtcaa     420
gctattgatg ttt                                                        433
```

<210> SEQ ID NO 452
<211> LENGTH: 362
<212> TYPE: DNA
<213> ORGANISM: Zea mays

<400> SEQUENCE: 452

```
acccacgcgt ccgggaaaca agagatggag ctaatggctg gacggatcaa gaatgtaaga        60
cagaagctct acgacagttt gtctgccaag gacaagagcg gcaaggactg gtctttcatt       120
ctgaggcaga ttggcatgtt ctcctacacc ggcttgaaca agcgcagag tgacaacatg        180
acggataaat ggcatattta catgaccaag gatgggcgga tctcgttagc tgggctgtcc       240
ctggctaagt gtgattatct tgccgacgcc atcatcgatt ccttccataa tgtgaactag       300
gctgaggtac gatagttgag ggtcaagcta ttgatgttta gttccgtgga cgctaggctg       360
gg                                                                      362
```

<210> SEQ ID NO 453
<211> LENGTH: 493
<212> TYPE: DNA
<213> ORGANISM: Zea mays
<220> FEATURE:
<223> OTHER INFORMATION: unsure at all n locations

<400> SEQUENCE: 453

```
gtncgcagtt taggaacgtt agcctgtcag tacgcgtcga aattccaagg tcccaccaag        60
ccttcgtagg aaccaaaaaa tggaccaaat ggctggacgg ttaaaaatg taagacagaa        120
cctctacaac agtttgtctg ccaaggacaa aaccggcaag gactggtctt tcattctgag       180
gcagattggc atgttctcct acaccggctt gaacaaagcg cagagtgaca acatgacgga       240
taaatggcat atttacatga ccaaggatgg gcggatctcg ttagctgggc tgtccctggc       300
taagtgtgat tatcttgccg acgccatcat cgattccttc cataatgtga actaagctga       360
ggtacgatag ttgagggtca agctattgat gtttagttcc gtggacgcta ggctgggatt       420
tttgggtcct tccagctata cagctcttcc cgttgtgctc aatctggtgt aacttggata       480
aataaaattt tgt                                                          493
```

<210> SEQ ID NO 454
<211> LENGTH: 336
<212> TYPE: DNA
<213> ORGANISM: Zea mays

<400> SEQUENCE: 454

```
cccgcctccg atccgctgct tactcgccac ccggagatgg ccaccgccgc cgccttctcc        60
gtctcctcgc cggcggcctc cgccgtcgcc gcgcgatcca aggtgtttgg aggagttaag       120
caggcgagaa ctagaactgg ctgccgcatc tgcatcacgc ggaagaactt tggccgtgtc       180
atgatggccc ttgcagtgga tgtttctcgt tttgaaggac tgccaatggc tcctccagac       240
ccaattcttg gggtttctga ggcctttaaa gcagagtaga gcgagctgac gctcaatctt       300
ggtgttggtg cctataggac agaggagctg cagcca                                 336
```

<210> SEQ ID NO 455
<211> LENGTH: 422
<212> TYPE: DNA
<213> ORGANISM: Zea mays

<400> SEQUENCE: 455

```
cgaaaagcta agcagagaga acaagcttac caaatcatca gtcatggtca ctgctggtgc      60
aaatcaggct tttgtgaact tggtcctcac tctttgtgat gctggtgatt ccgttgtcat     120
gtttgcaccg tattatttca atgcctacat gtcattccag atgacaggtg ttactgacat     180
attagttggt ggctgcgatc ccaagacact tcatcctgat gttgattggt tggagaaggt     240
tctgaaagaa aatgagccta tccctaaact tgtcactgtt gtgaatccgg ggaaccctg      300 tggagctttt atttcaaggc ctatgcttga gagaatttca gatctgtgca aaaatgctgg     360
tgcatggctt gtggttgaca atacctatga gtactttatg tatgatggaa tggagcacta     420
ct                                                                    422
```

<210> SEQ ID NO 456
<211> LENGTH: 389
<212> TYPE: DNA
<213> ORGANISM: Zea mays
<220> FEATURE:
<223> OTHER INFORMATION: unsure at all n locations

<400> SEQUENCE: 456

```
agacacctcc gccacctcca ccctcgaatc gttccccacc atggcgtcgc agggatcctc      60
cgtcttcgcc gcactcgagc aggccccgga ggaccccatc ctcggagtga ccgttgccta     120
caacaaggat cccagccccg tgaaggtcaa cctcggggtc ggcgcctacc ggaccgagga     180
agggaagccc ctagtgctga acgtggtcag gcgcgccgag caaatgttga tcaataatcc     240
gtcacgtgtc aaggagtacc taccaatcac cggtctggct gaattcaata agctgagcgc     300
taagcttatc tttggcgctg acagccctgc tattcaggag aatanggttg ctaccgtgca     360
gtgcctatcg ggtactggtt ctttaagag                                       389
```

<210> SEQ ID NO 457
<211> LENGTH: 382
<212> TYPE: DNA
<213> ORGANISM: Zea mays
<220> FEATURE:
<223> OTHER INFORMATION: unsure at all n locations

<400> SEQUENCE: 457

```
gcagcagaca cctccgccac ctccaccctc gaatcgttcc ccaccatggc gtcgcaggga      60
tcctccgtct tcgccgcact cgagcaggcc ccggaggacc ccatcctcgg agtgaccgtt     120
gcctacaaca aggatcccag ccccgtgaag gtcaacctcg gggtcggcgc ctaccggacc     180
gaggaaggga agcccctagt gctgaacgtg gtcaggcgcg ccgagcaaat gttgatcaat     240
aatccgtcac gtgtcaagga gtacctacca atcaccggtc tggctgaatt caataagctg     300
agcgctaagc ttatctttgg cgctgacagc cctgctattc aggagaatan ggttgctacc     360
gtgcagtgcc tatcgggtac tg                                              382
```

<210> SEQ ID NO 458
<211> LENGTH: 337
<212> TYPE: DNA
<213> ORGANISM: Zea mays

<400> SEQUENCE: 458

```
ctcgaatcga tccccaccat ggcgtcgcag ggatcctccg tcttcgccgc actcgagcag      60
gccccggagg accccatcct cggagtgacc gttgcctaca acaaggatcc cagccccgtg     120
aaggtcaacc tcggggtcgg cgcctaccgg accgaggaag gaagcccct agtgctgaac     180 gtggtcaggc gcgccgagca aatgttgatc aataatccgt cacgtgtcaa ggagtaccta     240
```

```
ccaatcaccg gtctggctga attcaataag ctgagcgcta agcttatctt tggcgctgac    300
agccctgcta ttcaggagaa tagggttgct accgtgc                             337

<210> SEQ ID NO 459
<211> LENGTH: 429
<212> TYPE: DNA
<213> ORGANISM: Zea mays

<400> SEQUENCE: 459
gtccgacgtc ccaccggccc ccgctctcgt tttcccccgc cggaacaagc acgctcaagc     60
gctgcgcaac ggattggccc tgctaacgtt cgccccgggc aagggcaagg ccccaacgcc    120
caacgcaagg taagttagcc aattgggcaa ctggcggctt tctccccaag aaaaacaaca    180
agcaaaaact tcggcaacct caaccctcga atcgttcccc accatggcgt cgcagggatc    240
ctccgtcttc gccgcactcg agcaggcccc ggaggacccc atcctcggag tgaccgttgc    300
ctacaacaag gatcccagcc ccgtgaaggt caacctcggg gtcggcgcct accggaccga    360
ggaagggaag cccctagtgc tgaacgtggt caggcgcgcc gagcaaatgt tgatcaataa    420
tccgtcacg                                                            429

<210> SEQ ID NO 460
<211> LENGTH: 411
<212> TYPE: DNA
<213> ORGANISM: Zea mays

<400> SEQUENCE: 460
acgcccacct ggagagctac tcgcgcgtgc tcgagagcct ggcgtacagc gtcatgtccc     60
gcatcgagga cgtgctgagc gcggacgcgg cggcgcagaa cctgacggcg agcgaggcgg    120
cgcggcgagc gctggagtcg acgtcggcgg agctgcccgc ggcgcggaag ctggacgcca    180
aggaggagct ggagaagctg aacgaggccc ggcgtcgat dacgctgttc gacttcatgg    240
gctggcactt cgaccaggac gagctgatga agcgcaggga ggacggcaca ctggacgcgg    300
acggggaggc catgctcctc aagaaggcgc ctagcatggc ccccaagaag ttctcctacg    360
tcgacagcct ctcctccggc ggcatgagga gcccctccgc gcgccactga t             411

<210> SEQ ID NO 461
<211> LENGTH: 417
<212> TYPE: DNA
<213> ORGANISM: Zea mays

<400> SEQUENCE: 461
ccacgcgtcc gcgggtacgc cctcctggag agctactcgc gcgtgctgga gagcctggcg     60
tacagcgtca tgtcccgcat cgaggacgtg ctgagcgcgg acgcggcggc acagaacctg    120
acggcgaccg aggcggcgcg gcgggtgctg gagtcggcgg acctgctcgc gccgcggaag    180
ctggacgcca aggaggagct ggagaagctg aacgaggccc ggcgtcgat dacgctcttc    240 gacttcatgg gctggcactt cgaccaggac gagctgatga agcgcaggga ggacggcacg    300
ctggacgccg acgcgaggc catgctcctc aagaaggcgc ccagcgtggc gcccaagaag    360
ttctcctacg tcgacagcct ctcctccggc ggcatgagga gccccctctgc gcgccac      417

<210> SEQ ID NO 462
<211> LENGTH: 411
<212> TYPE: DNA
<213> ORGANISM: Zea mays
```

<400> SEQUENCE: 462

```
aacaaagcaa cagcagagct attgcttgga gctgataacc ctgttattaa tcaaggactg      60
gttgctgcac ttcagtctct ctcgggcact ggatcactgc gtctcgctgc agcattcata     120
caaagatact ttcctgaagc taaagtgctg atatcgtcgc ctacctgggg taaccacaag     180
aatatcttca atgatgctag ggtaccttgg tcagagtacc ggtattatga ccccaagact     240
gttgggttgg attttgaggg aatgatagct gacattgaag ctgctcctga aggttctttt     300
gttctgctac atggttgtgc tcacaaccca actggaatag acccaactcc tgaacagtgg     360
gagaaaattg cagatgtcat tcaagagaaa agcatatgc cattctttga t              411
```

<210> SEQ ID NO 463
<211> LENGTH: 441
<212> TYPE: DNA
<213> ORGANISM: Zea mays
<220> FEATURE:
<223> OTHER INFORMATION: unsure at all n locations

<400> SEQUENCE: 463

```
tgagggtgga gagtgatttg aannttccca gtctcncagt cgcnatatct ctggaattac      60
cttatcgacc caggcgtcct aacaaagcaa catcagagct attgcttggt tctgattacc     120
ctgttattaa tcaaggactg tgtgctgcac tacagtctct ctgggcact ggatcactgc      180 gtctcgctgc agcattcata caaagatact ttcctgaagc taaagtgctg atatcgtctc     240
ctacctgggg taaccacaag aatatcttca atgatgctag ggtaccttgg tcagagtacc     300
ggtattatga ccccaagact gttgggttgg attttgaggg aatgatagct gacattgagg     360
ctgctcctga acgttctttt gttcttctac atggtttgtt ctcacaaccc aactggaata     420
gacccaactc cttaacattt t                                                441
```

<210> SEQ ID NO 464
<211> LENGTH: 318
<212> TYPE: DNA
<213> ORGANISM: Zea mays

<400> SEQUENCE: 464

```
gttggtgcct ataggacaga agagctgcag ccatacgtgc tcaatgtagt caagaaggct      60
gaaaatctta tgttggagaa aggagaaaac aaagagtatc ttcccattga aggtttagcc     120
gcgtttaaca agcaacagc agagctattg cttggagctg ataaccctgt tattaatcaa      180
ggactggttg ctacacttca gtctctctcg ggcactggat cactgcgtct cgctgcagca     240
ttcatacaaa gatactttcc tgaaactaaa gtgctgatat cgtcgcctac ctggggtaac     300
cacaagaata tcttcaat                                                    318
```

<210> SEQ ID NO 465
<211> LENGTH: 427
<212> TYPE: DNA
<213> ORGANISM: Zea mays

<400> SEQUENCE: 465

```
cggacgcgtg ggcaagaatg ctccagatgg ttcattcttt ttgcttcatg catgtgctca      60
taatcccacc ggtgtagatc ctacggagga acaatggaga gaaatatccc atcagttcaa     120
ggtgaaaaaa cattttccat tctttgacat ggcataccaa gggtttgcca gtggtgatcc     180
agagagagat gccaaggcaa tccgaatttt ccttgaagat ggacaccaaa ttggatgtgc     240
tcagtcatac gcaaagaaca tgggactttta tggacaaaga gcaggatgcc tgagtatttt     300
```

```
gtgtgaggat gagatgcaag cagttgctgt caagagccaa ctgcaacaga tcgcaagacc    360
aatgtacagc aacccacctg ttcatggtgc actggttgtt tctataatcc tcagtgatcc    420
agaattg                                                              427

<210> SEQ ID NO 466
<211> LENGTH: 434
<212> TYPE: DNA
<213> ORGANISM: Zea mays

<400> SEQUENCE: 466
ggcaaactga cttatatcag caagacgttc agaagtatgg aaacattgag tacatgagat     60
gcggtccaga aaatggattt tttcctgatc tgtcaactgt ccctaggaca gatattattt    120
tcttttgttc acccaacaat cctactggtg ctgctgcatc tcgggaccaa ctaaccaaat    180
tagtaaaatt tgcaaaggac aacaggtcca tcatagtcta tgattctgct tatgcaatgt    240
acatatcaga tgacagccca agtctatctt tgaaattcc tggagcaaag gaggttgcta    300
ttgagacagc ctcattctcg aaatacgctg gttcacagg tgtccgtcta ggttggactg     360
ttgtccccaa ggagctcctt ttctcggatg acatccagt tgctaaagat ttcaatcgca    420
tagtttgcac ttgc                                                      434

<210> SEQ ID NO 467
<211> LENGTH: 497
<212> TYPE: DNA
<213> ORGANISM: Zea mays
<220> FEATURE:
<223> OTHER INFORMATION: unsure at all n locations

<400> SEQUENCE: 467 gggggggntaa aggggganntt tattggaacc ccaattcccg ggtaccggta ttatgatcct    60
gcaacatgca gccttcactt cgaaggactc ctggaagacc tcggttctgc tccttnaggt   120
tcaatngtac tgctgcatgc ctgtgctcac aaccctactg gagtagatcc taccatcgaa   180
cagtgggaac agattaggca gctgatgaga tcaaaatcac tgcttccgtt ctttgacagt   240
gcctatcaag gctttgcaag tggaagtctt gacaaagatg ctcagtcagt gcgtatgttt   300
gttgctgatg gtggtgaact tctcatggct cagagctacg ctaagaacat gggattgtat   360
ggagagcgtg ttggcgcttt gagcattgna tgtaaaagtg ccgatgtagc tgttagggtt   420
gaaagtcaac tcaaacttgn catcaggcct atgtattcaa accttctct tcatggngcc   480 tctatcgntg ctaccat                                                   497

<210> SEQ ID NO 468
<211> LENGTH: 386
<212> TYPE: DNA
<213> ORGANISM: Zea mays

<400> SEQUENCE: 468
ttatcatggc tcagagctac gctaagaaca tgggattgta tggagagcgt gttggcgctt     60
tgagcattgt atgtaaaagt gccgatgtag ctgttagggt tgaaagtcaa ctcaaacttg   120
tcatcaggcc tatgtattca aaccctcctc ttcatggtgc ctctatcgtt gctaccatac   180
tcagggacag cgagatgttc aacgaatgga ctctggaact gaaggccatg gctgatagga   240
tcattaacat gaggcaacaa ctatttaatg cgctgaaatc cagaggaacc cctggtgatt   300
ggagccatat cattaagcaa attgggatgt ttactttcac tggggcctga atagcgaaac   360
```

| | |
|---|---|
| aaagtcgccc cattcatgag gcagga | 386 |

<210> SEQ ID NO 469
<211> LENGTH: 405
<212> TYPE: DNA
<213> ORGANISM: Zea mays
<220> FEATURE:
<223> OTHER INFORMATION: unsure at all n locations
<400> SEQUENCE: 469

| | |
|---|---|
| actcccaata gtgagtcgta ttacagagct acgctaagaa catgggattg tatggagagc | 60 |
| gtgttggcgc tttgagcatt gtatgtaaaa gtgccgatgt agctgttagg gttgaaagtc | 120 |
| aactcaaact tgtcatcagg cctatgtatt caaaccctcc tcttcatggt gcctctatcg | 180 |
| ttgctaccat actcagggac agcgagatgt tcaacgaatg gactctggaa ctgaaggcca | 240 |
| tggctgatag gatcattaac atgangcaac aactatttaa tgcgctgaaa tccangagga | 300 |
| acccctggtg attggagcca tatcattaaa gcaaattggg atgtttacnt tccctggggn | 360 |
| cngaaataan cgaagcnngg tcggccnntt cangagggna gggag | 405 |

<210> SEQ ID NO 470
<211> LENGTH: 396
<212> TYPE: DNA
<213> ORGANISM: Zea mays
<400> SEQUENCE: 470

| | |
|---|---|
| cccacgcgtc cgcccacgcg tccggcgtgt tggcgcttcg agcattgtat gtaaaagtgg | 60 |
| cgatgtagct gggagggttg aaagtcaact caaacttgtc atcaggccta tgtattcaaa | 120 |
| ccctcctata catggtgcct ctatcggtgc taccatactc agggacagcc agatgttcaa | 180 |
| cgaatggact ctggaactga agccattgc tgataagatc attcacatga ggcatcaact | 240 |
| atttaatgcc cctaaatcca atgaacccc tggagattgg agccatatca ttgagcacat | 300 |
| tcggatgtac actgtgactg agctgaataa cgaacaagtc gcattcatga ggcaggaata | 360 |
| cctcatttac atgacatctg atgatatgaa catcat | 396 |

<210> SEQ ID NO 471
<211> LENGTH: 416
<212> TYPE: DNA
<213> ORGANISM: Zea mays
<400> SEQUENCE: 471

| | |
|---|---|
| agttgctacc atactcaggg acagcgagat gttcaacgaa tggactctgg aactgaaggc | 60 |
| catggttgaa aggttaatat acataaggca acaccaatta atgccccgga atccaaaaga | 120 |
| aaccctggtg aatggagcca tatcaataag caaattggga tgtttacttt cactgggctg | 180 |
| aatagcgaac aagtcgcatt cacgaggcac gaataccaca tttatatgac atctgatggg | 240 |
| aagatcagca tggccggttt gagcatgagg actgtgcccc atcttgcaca tgccatacac | 300 |
| gctgcagtta ctcaactgaa atgaggatag tatcgcagct ttcgtgaata aaacctgaat | 360 |
| catccacaac aatgttctaa gtactcatcc actggtattt actggttgac ctactg | 416 |

<210> SEQ ID NO 472
<211> LENGTH: 404
<212> TYPE: DNA
<213> ORGANISM: Zea mays
<220> FEATURE:
<223> OTHER INFORMATION: unsure at all n locations
<400> SEQUENCE: 472

```
ccctatagtg agtcgtatta aagagctacg ctaagaacat gggattgtat ggagagcgtg      60
ttggcgcttt gagcattgta ngtaanagtg ccgatgtagc ngtnagggnt gaaagtcanc     120
tcaancttgt catcaggcnn atgtattcaa accctcctct tcatggtgcc tctancgttg    180
ctaccatnct cagggacagc gagatgttca ncgaatggac tctgaactg aaggccatgg     240 ctgataggat cattaacang aggcaacaac tatttaatgc gctgaaatcc agaggaaccc    300
ctggtgantg gagccatntc ngttaagnca aattgggatg tntactttca nnggggcct    360 naagtaagcg aaacagnntn cgnccttttcc cggnggggcgg ggag                    404

<210> SEQ ID NO 473
<211> LENGTH: 294
<212> TYPE: DNA
<213> ORGANISM: Zea mays

<400> SEQUENCE: 473
atacacgctg cagttactca actgaaatga ggatagtatc gcagctttcg tgaataaaac     60
ctgaatcacc cacaagaatg ttctaagtac tcagccagtg gtatttactg gttgacctac    120
tgtagtttgc gtcggaatag atatgttttt ttactcttcg tggggcagtt ttgtactggt    180
ggattcataa ggactctgat tatggtgcgt tcggaactta taataataag cacatgaaat    240
tttgcttcaa aaaaaaacta tatcaccctc aatactacaa caacagtcag ccac          294

<210> SEQ ID NO 474
<211> LENGTH: 259
<212> TYPE: DNA
<213> ORGANISM: Zea mays

<400> SEQUENCE: 474
actgaaatga ggatagtatc gcagctttcg tgattaaaac ctgaatcacc cacagcggtg     60
ttctaagtac tcagccagtg gtatttactg gttgacctac tgtagtttgc gtcggaatag    120
atttgttttt ttactcttcg tggggcagtt ttgtactggt ggattcataa ggactctgat    180
tatggtgcgt tcggaactta taataataag cacatgaaat tttgcttcaa aaaaatacta    240
ccattcaaac agataaaaa                                                 259

<210> SEQ ID NO 475
<211> LENGTH: 262
<212> TYPE: DNA
<213> ORGANISM: Glycine max
<220> FEATURE:
<223> OTHER INFORMATION: unsure at all n locations

<400> SEQUENCE: 475
ccaaagaggt tgccatcgag acttcatcat ttagcaagta tgctgggttc actggagtcc     60
gattgggttg gactgtggtt ccaaagcagt tgctgttttc tgatggattt cctgttgcca    120
aggacttcaa ccgtattgta tgcacttgtt tcaatggtgc atcaaatatt tcccaggcag    180
gtggtctggc ttgcctttca ccagacggtc ttaaggctat gcgagatgtt attggattct    240
acaaaganaa taccgacatt at                                             262

<210> SEQ ID NO 476
<211> LENGTH: 262
<212> TYPE: DNA
<213> ORGANISM: Glycine max

<400> SEQUENCE: 476
```

```
ctcgagccgc tgtcataccc acttcccctt caagagcaca cgcccagatc agcgttaaca    60
acgtcttaca actgcgaaac aaaaccaatc tgaaatgtcc gaccaacaag agatttacgc   120
tgcgttcccc aacgtccctc aggctcctcc tgattccatc ttccaattga ccgctcgtta   180
cgtcgccgac aagcatccga acaagatcaa cctgggtgtc ggggcataca ggacggacga   240
tgggaaacct tgggtcttgc cc                                            262
```

<210> SEQ ID NO 477
<211> LENGTH: 271
<212> TYPE: DNA
<213> ORGANISM: Glycine max

<400> SEQUENCE: 477

```
gtcgactata aaggataca gtgggtatgg agctgaacaa ggtgaaaagc cattaagaag    60
ggcacttgct tcaacatttt acagcgatct tggcatagaa gaggatgata tatttgtctc   120
agatggagca aagtgtgata tatccgtctc cagattgtct ttgggtcaaa tgtaaaaatg   180
gctgtgcaat acccttcata tccggcctat gtagactcta gtgtaattat gggccagact   240
ggcctcttcc agaagaatgt tgagaagttt g                                  271
```

<210> SEQ ID NO 478
<211> LENGTH: 256
<212> TYPE: DNA
<213> ORGANISM: Glycine max

<400> SEQUENCE: 478

```
gttttgtgcc agagtataaa gcaagtagct gcactaaaaa gccaactgca gctgatgtcc    60
catgcaatgt atagcagcat ccttttcag ggtatttcac tagttactat gatattaagc   120
gagccagata cagaagcact tggagaaaaa gagataaagg tcatggctaa acggattcaa   180
actatgcgaa ctaccttgcg gcattgtctt gagaacttgc attcatcttt caattgggag   240
cacataactg atcagg                                                   256
```

<210> SEQ ID NO 479
<211> LENGTH: 286
<212> TYPE: DNA
<213> ORGANISM: Glycine max

<400> SEQUENCE: 479

```
ctgaaatcca gaggaacccc tggtgattgg agccatatca ttaagcaaat tgggatgttt    60
actttcactg ggctgaatag cgaacaagtc gcattcatga ggcaggaata ccacatttat   120
atgacatctg atgggaggat cagcatggcc ggtttgagca tgaggactgt gccccatctt   180
gcagatgcca tacacgctgc agttactcaa ctgaaatgag gatagtatcg cagctttcgt   240
gaataaaacc tgaatcaccc acaacaatgt tctaagtact cagcca                  286
```

<210> SEQ ID NO 480
<211> LENGTH: 256
<212> TYPE: DNA
<213> ORGANISM: Glycine max

<400> SEQUENCE: 480

```
tcttccaggt aaaaatcat ttcccattct ttgacatggc ttatcaagga ttttcaagtg    60
gggatcttga caaggatgca atagcacttc gaattttcct tgaagatggg catttgattg   120
gttgtgctca atcttttgca aagaacatgg gattatcaga acataaagct ggttgtctta   180
ggtaagaata gtcctatatc ctagtgagta gagattcaga ggcagagcat attctatgac   240
```
acgtataata gaagtt 256

<210> SEQ ID NO 481
<211> LENGTH: 232
<212> TYPE: DNA
<213> ORGANISM: Glycine max

<400> SEQUENCE: 481 cttttatga tgttctgttc tgcattattt tcaggtcacg caacaaggaa tatattccgt 60
tcgttgggct tgctgatttt aataaattga gtgctaagct tattttcgg gctgacagcc 120 ctgctattca agacaacagg gttaccactg ttcaatgctt gtctggaact ggttctttaa 180
gagttggggg tgaattttg gctaaacact atcaccaacg gactatatac tt 232

<210> SEQ ID NO 482
<211> LENGTH: 209
<212> TYPE: DNA
<213> ORGANISM: Glycine max
<220> FEATURE:
<223> OTHER INFORMATION: unsure at all n locations

<400> SEQUENCE: 482
gccgaaaggn ttggngcaat caatgtggtt tcatcatcgc ccgaatctgc agcaagggta 60
nanagtcagt tgtaaggatt gcccgaccan gtactctaat ctncagtaca cgnggtagat 120
agtngcgtgt gttggaanca gtccttatga tgaagngaat gcatgtggtg gagntaagnt 180
tagcacgtat agtattattc aagacanag 209

<210> SEQ ID NO 483
<211> LENGTH: 236
<212> TYPE: DNA
<213> ORGANISM: Glycine max

<400> SEQUENCE: 483
ttccagagcc ccttctaaag aggatttcag atctctgcaa gaatgctggc tcttggcttg 60
ttgttgataa tacatacgag tatttatgt atgatggcct gaaacactct tgtgttgagg 120
gaaatcatat tgttaatgtt ttctcattct caaaagcata tggaatgatg ggatggcggg 180
ttggatatat agcgtacccc tctgaagtaa aagacttcgc tgaacaactt ctcaaa 236

<210> SEQ ID NO 484
<211> LENGTH: 247
<212> TYPE: DNA
<213> ORGANISM: Glycine max

<400> SEQUENCE: 484 ggaactttg tgtgctgttc tacttctgtt acatctcgtg aatcgtttgc aacttcttca 60
ccgttttctg tatgcagatg gcttcttcgt ttctatccgc agcttcgcac gctgtctcac 120
cctcttgttc tctgtccacc acgcacaacg ggaagcacat gcttggaggc aacactttga 180
gatttcacaa aggacccaat tccttctcta gttcaaggtc tagaggtcgg atctctatgg 240
ctgttgc 247

<210> SEQ ID NO 485
<211> LENGTH: 153
<212> TYPE: DNA
<213> ORGANISM: Glycine max

<400> SEQUENCE: 485

```
ccacagagga cccaattcct tctctagttc aaggtctacc ggctggatct ctatggctgt      60
tgcagttaac gtttctcggt ttgaaggcat acctctggcg cctcctgatc caattctagg     120
agtttctgag gcatttaagg tggacaatag tga                                  153

<210> SEQ ID NO 486
<211> LENGTH: 271
<212> TYPE: DNA
<213> ORGANISM: Glycine max

<400> SEQUENCE: 486
agagcagttg aaaaggattg cccgaccaat gtactctaat ccaccggtac acggggctag      60
gatagttgcc gatgttgttg gaaacccagt tctctttaat gaatggaaag cagagatgga     120
aatgatggct ggaaggataa agaatgttag acagcagcta tatgatagta ttacttcgaa     180
agacaaaagt ggaaaggatt ggtcattcgt acttaagcag ataggcatgt tctcattcac     240
tggcttgaac aagaaccaga gtgacaacat g                                    271

<210> SEQ ID NO 487
<211> LENGTH: 247
<212> TYPE: DNA
<213> ORGANISM: Glycine max

<400> SEQUENCE: 487
aacggagcca acagagtat tgctcaggca gtgcttgcag tttcctcccc tggagatgag       60
gttattattc cagctccatt ctgggttagt tacccagaaa tggcaaggtt ggctgatgca     120
acacctgtga ttcttccaac cttaatatct gataatttcc ttttggatcc caaactcctc     180
gaatccaaaa ttactgaaag atcaagactg cttattcttt gttctccatc taacccaacg     240
ggatctg                                                               247

<210> SEQ ID NO 488
<211> LENGTH: 261
<212> TYPE: DNA
<213> ORGANISM: Glycine max

<400> SEQUENCE: 488
cggagcaaac agagtattgc tcaggcagtg cttgcagttt cctcccctgg agatgaggtt      60
attattccag ctccattctg ggttagttac ccagaaatgg caaggttggc tgatgcaaca     120
cctgtgattc ttccaacctt aatatctgat aatttccttt tggatcccaa actcctcgaa     180
tccaaaatta ctgaaagatc aagactgctt attctttgag ctccatctaa cccaacggga     240
tctgtctacc caaagaatt a                                                261

<210> SEQ ID NO 489
<211> LENGTH: 273
<212> TYPE: DNA
<213> ORGANISM: Glycine max

<400> SEQUENCE: 489
gggattagtt atactcctga ccaagttgtg gttagtatcg gagccaaaca gagcattgct      60
caggcagtgc ttgcagtttg ctcccccgga gatgaggtta ttattccagc tccattctgg     120
gttagttacc cagaaatggc aaggttggc gatgcgacac ctgtgattct tccaacctta     180
atatctgata atttcctttt ggatcccaaa ctccttgaat ccaaaattac tgaaagatcg     240
agactgctca ttctttgttc accatctaac cca                                  273
```

<210> SEQ ID NO 490
<211> LENGTH: 273
<212> TYPE: DNA
<213> ORGANISM: Glycine max
<220> FEATURE:
<223> OTHER INFORMATION: unsure at all n locations

<400> SEQUENCE: 490
cggggctagg atagtngccg atgttgttgg aaacccagtt ctctttaatg aatggaaagc    60
agagatggaa atgatggctg aaggataaaa gaatgttaga cagcagctat atgatagtat   120
tacttcaaaa gacaaaagtg gaaggattg gtcattcata cttaagcaga taggcatgtt   180
ctcattcact ggcttgaaca agaaccagag tgacaacatg acaaacaagt ggcacgtata   240
catgacaaag gatggaagga tttccctggc agg                                273

<210> SEQ ID NO 491
<211> LENGTH: 258
<212> TYPE: DNA
<213> ORGANISM: Glycine max

<400> SEQUENCE: 491
aaagaatgtt agacagcagc tatatgatag tattacttca aaagacaaaa gtggaaagga    60
ttggtcattc atacttaagc agataggcat gttctcattc acgggcttga acacgaacca   120
gagtgacaac atgacaaaca gtggcacgt atacatgaca aaggatggaa ggatttccct   180
ggcaggattg tcattggcta atgtgaata ccttgcagat gctattattg actcatatca   240
taatgtcagc tgaaactc                                                 258

<210> SEQ ID NO 492
<211> LENGTH: 249
<212> TYPE: DNA
<213> ORGANISM: Glycine max

<400> SEQUENCE: 492
tgccgatgtt gttggaaacc cagttctctt taatgaatgg aaagcagaga tggaaatgat    60
ggctggaagg ataaagaatg ttagacagca gctatatgat agtattactt caaaagacaa   120
aagtggaaag gattggtcat tcatacttaa gcagataggc atgttctcat tcactggctt   180
gaacaagaac cagagtgaca acacgacaaa caagtggcac gtatacatga caaaggatgg   240
aaggatttc                                                           249

<210> SEQ ID NO 493
<211> LENGTH: 268
<212> TYPE: DNA
<213> ORGANISM: Glycine max

<400> SEQUENCE: 493
gttcgcactc tgtctttccc ctgtttccgc gtcactgagt catcgcgatt cgcaactcgc    60
tcaccggcca attcctccgc cgcagctccg tcgccggagc aaggctcatg tcttcttcgt   120
cctcatggtt ccggagcatc gagcccgctc ccaaggatcc tatcctcgga gtcactgaag   180
ctttcctcgc cgatcagagt ccaaacaaag tcaacgtcgg agtgggtgcg tatcgcgatg   240
accacggaaa acctgtggtt ttggaatg                                      268

<210> SEQ ID NO 494
<211> LENGTH: 268
<212> TYPE: DNA
<213> ORGANISM: Glycine max

<400> SEQUENCE: 494

```
ctctctccct ctctgttcgc actctgtctt tccctgttt ccgcgtcact gagtcatggc      60
gattcgcaac tcgctcaccg gccaattcct ccgccgcagc tccgtcgccg gagcaaggct     120
catgtcttct tcgtcctcat ggttccggag catcgagccc gctcccaagg atcctatcct    180
cggagtcact gaagctttcc tcgccgatca gagtccaaac aaagtcaacg tcggagtggg    240
tgcgtatcgc gatgaccacg gcaaacct                                      268
```

<210> SEQ ID NO 495
<211> LENGTH: 241
<212> TYPE: DNA
<213> ORGANISM: Glycine max

<400> SEQUENCE: 495

```
cctctctgtt cgcactctgt ctttcccctg tttccgcgtc actgagtcat tgcgattcgc     60
aactcgctca ccggccaatt cctccgccgc agctccgtcg ccggagcaag gctcatgtct    120
tcttcgtcct catggttccg gagcatcgag cccgttccca aggatcctat cctcggagtc    180
actgaagctt tcctcgccga tcagagtcca aacaaagtca acgtcggagt gggtgcgtat    240
c                                                                    241
```

<210> SEQ ID NO 496
<211> LENGTH: 170
<212> TYPE: DNA
<213> ORGANISM: Glycine max

<400> SEQUENCE: 496

```
ctctctccct ctctgttcgc actctgtctt tccctgttt ccgcgtcact gagtcatcgc      60
gattcgcaac tcgctcaccg gccaattcct ccgccgcagc tccgtcgccg gagcaaggct    120
catgtcttct tcgtcctcat ggttccggag catcgagccc gctcccaagg                170
```

<210> SEQ ID NO 497
<211> LENGTH: 284
<212> TYPE: DNA
<213> ORGANISM: Glycine max
<220> FEATURE:
<223> OTHER INFORMATION: unsure at all n locations

<400> SEQUENCE: 497

```
ggagatgggt tcgtccgtga agctttcagg agggccttgg aaactgagat gcccgttatg     60
gttcagatgc aggaattgca acgaggagct aagaatgcct tgtctttggc ccaggggtg    120
gtttactggc agcctcccaa gcaagcgttg gaaaaagtga agaacttgt atctgagcct    180
ttaattagtc gttatggtaa cgatgaaggt attcctgaac tcagagcagc attagtcaaa    240
aagttgcgng atgaaaataa tttgcacaaa tcttcagtat ggtt                    284
```

<210> SEQ ID NO 498
<211> LENGTH: 276
<212> TYPE: DNA
<213> ORGANISM: Glycine max

<400> SEQUENCE: 498

```
caacatttta ctgggtatat aagtggagag tgtaactgaa attatgtgga ggtgcatcaa     60
tggaagaatt gccagaagat ttttatccac ttcttctgcc agtgcccgtg gttggtggga    120
ccatgtaagg ccagcaccga aggacccat tgttcgtgtg aacgaggcat ttctagctga    180
ccctttttccc cataagatca atcttggaat aggtacttat aagggtgatg atggcaaagc    240
```

```
tttcattcct caaagcgttc gtgaggcaga aacaaa                              276
```

<210> SEQ ID NO 499
<211> LENGTH: 290
<212> TYPE: DNA
<213> ORGANISM: Glycine max
<220> FEATURE:
<223> OTHER INFORMATION: unsure at all n locations

<400> SEQUENCE: 499

```
attaagcaac attttactgn tgtatataag tggagagtgt aactgaaatt atgtggaggt   60
gcatcaatgg aagaattgcc agaagatttt tatccacttc ttctgccagt gcccgtggtt  120
ggtgggacca tgtaaggcca gcaccgaagg accccattgt tcgtgtgaac gaggcatttc  180
tagctgaccc ttttccccat aagagcaatc ttggaatagg tacttataag ggtgatgatg  240
gcaaagcttt cattcctcaa agcgttcgtg aggcagaaac aaagattcag             290
```

<210> SEQ ID NO 500
<211> LENGTH: 273
<212> TYPE: DNA
<213> ORGANISM: Glycine max

<400> SEQUENCE: 500

```
caacatttta ctgggtatat aagtggagag tgtaactgaa attatgtgga ggtgcatcaa   60
tggaagaatt gccagaagat ttttatccac ttcttctgcc agtgcccgtg gttggtggga  120
ccatgtaagg ccagcaccga aggaccccat tgttcgtgtg aacgaggcat ttctagctga  180
ccctttttccc cataagatca atcttggaat aggtacttat aagggtgatg atggcaaagc  240
tttcattcct caaagcgttc gtgaggcaga aac                                273
```

<210> SEQ ID NO 501
<211> LENGTH: 263
<212> TYPE: DNA
<213> ORGANISM: Glycine max

<400> SEQUENCE: 501

```
aagcaacatt ttactgggta tataagtgga gagtgtaact gaaattatgt ggaggtgcat   60
caatggaaga attgccagaa gattttttatc cacttcttct gccagtgccc gtggttggtg  120
gaccatgta aggccagcac cgaaggaccc cattgttcgt gtgaacgagg catttctagc   180
tgaccctttt ccccataaga tcaatcttgg aataggtact tataagggtg atgatggcaa  240
agctttcatt cctcaaagcg ttc                                           263
```

<210> SEQ ID NO 502
<211> LENGTH: 246
<212> TYPE: DNA
<213> ORGANISM: Glycine max

<400> SEQUENCE: 502

```
gaattaagca acattttact gggtatataa gtggagagtg taactgaaat tatgtggagg   60
tgcatcaatg aagaattgc cagaagatttt ttatccactt cttctgccag tgcccgtggt  120
tggtgggacc atgtaaggcc agcaccgaag gaccccattg ttcgtgtgaa cgaggcattt  180
ctagctgacc cttttcccca taagatcaat cttggaatag gtacttataa gggtgatgat  240
ggcaaa                                                              246
```

<210> SEQ ID NO 503

```
<211> LENGTH: 261
<212> TYPE: DNA
<213> ORGANISM: Glycine max
<220> FEATURE:
<223> OTHER INFORMATION: unsure at all n locations

<400> SEQUENCE: 503 taacattta ctgggtatat aagtggagag tgtaactgaa attatgtgga tgtgcatcaa      60
tggaagaatt gccagaagat ttttatccac ttcttctgcc agtgcccgtg gttggtggga    120
ccatgtaagg ccagcaccga aggacccat tgttcgtgtg aacgaggcat ttctagctga     180
ccctttccc cataagatca atcttggnaa aggtacttat aagggtgatg atggcaaagc     240
tttcattcct caaagcgttc g                                              261

<210> SEQ ID NO 504
<211> LENGTH: 236
<212> TYPE: DNA
<213> ORGANISM: Glycine max

<400> SEQUENCE: 504
aagcaacatt ttactgggta tataagtgga gagtgtaacc gaaattatgt ggaggtgcat     60
caatggaaga attgccagaa gatttttatc cacttcttct gccagtgccc gtggttggtg   120
ggaccatgta aggccagcac cgaaggaccc cattgttcgt gtgaacgagg catttctagc   180
tgacccttt ccccataaga tcaatcttgg aataggtact tataagggtg atgatg        236

<210> SEQ ID NO 505
<211> LENGTH: 380
<212> TYPE: DNA
<213> ORGANISM: Glycine max

<400> SEQUENCE: 505
ctggttcttt aagagttggg ggtgaatttt tggctaaaca ctatcaccaa cggactatat     60
acttgccaac accaacttgg ggcaatcacc cgaagttttc aacttagcag gcttgtctgt   120
caaaacatac cgctactatg ctccagcaac acgaggactt gactttcaag gacttctgga   180
agaccttggt tctgctccat ctggatctat tgttttgcta catgcatgcg cacataaccc   240
cactggtgtg gatccaaccc ttgagcaatg ggagcagatt aggcagctaa taagatcaaa   300
agctttgtta cctttctttg acagtgctta tcagggtttt gctagtggaa gtctagatgc   360
agatgcccaa cctgttcgtt                                                380

<210> SEQ ID NO 506
<211> LENGTH: 329
<212> TYPE: DNA
<213> ORGANISM: Glycine max
<220> FEATURE:
<223> OTHER INFORMATION: unsure at all n locations

<400> SEQUENCE: 506
gcggactata tacttgccaa caccaacttg gggcaatcac ccgaagtttt caacttagca     60
ggcttgtctg tcaaaacata ccgtactatg ctccagcaac acgaggactt gactttcaag   120
gacttctgga agaccttggt tctgctccat ctggatctat tgttttgcta catgcatgcg   180
cacataaccc cactggtgtg gatccaaccc ttgagcaatg ggagcagatt aggcagctaa   240
taagatcaaa agctttgtta ctttctttga cagtgcttat cagggtttgc tatggnatct   300
agattgcaga tgccaactgt cgttgttgt                                      329
```

<210> SEQ ID NO 507
<211> LENGTH: 261
<212> TYPE: DNA
<213> ORGANISM: Glycine max
<220> FEATURE:
<223> OTHER INFORMATION: unsure at all n locations

<400> SEQUENCE: 507
attgttttgc tacatgcatg cgcacataac nacactggtg tggatccaac ccttgagcaa    60
tgggagcaga ttaggcagct aataagatca aaagctttgt tacctttctt tgacagtgct   120
tatcagggtt ttgctagtgg aagtctagat gcagatgccc aacctgttcg tttgtttgtt   180
gctgatggag gcgaattgct ggtagcacaa agctatgcaa agaatctggg tctttatggg   240
gaacgtgttg gcgccttaag c                                             261

<210> SEQ ID NO 508
<211> LENGTH: 264
<212> TYPE: DNA
<213> ORGANISM: Glycine max

<400> SEQUENCE: 508
ttcaatgctt gtctggaact ggttctttaa gagttggggg tgaattttg gctaaacact     60
atcaccaacg gactatatac ttgccaacac caactggggg caatcacccg aaggttttca   120
acttagcagg cttgtctgtc aaaacatacc gctactatgc tccagcaaca cgaggacttg   180
actttcaagg acttctggaa gaccttggtt ctgctccatc tggatctatt gttttgctac   240
atgcatgcgc acataacccc actg                                          264

<210> SEQ ID NO 509
<211> LENGTH: 264
<212> TYPE: DNA
<213> ORGANISM: Glycine max
<220> FEATURE:
<223> OTHER INFORMATION: unsure at all n locations

<400> SEQUENCE: 509
gggaagacct tggttctgct ccatctggat ctattgtttt gctacatgca tgcgcacata    60
accccactgg tgtggatcca acccttgagc aatgggagca gattaggcag ctaatancga   120
tcaaaagctt tgttaccttt ctttgacagt gcttatcagg gttttgctag tggaagtcta   180
gatgcagatg cccaacctgt tcgtttgttt gttgctgatg gaggcgaatt gctggtagca   240
caaagctatg caaagaatct gggt                                          264

<210> SEQ ID NO 510
<211> LENGTH: 287
<212> TYPE: DNA
<213> ORGANISM: Glycine max
<220> FEATURE:
<223> OTHER INFORMATION: unsure at all n locations

<400> SEQUENCE: 510
gcggactata tacttgccaa caccaacttg gggcaatcac ccgangtttt caacttagca    60
ggcttgtctg tacaaaacat accgctacta tgctccagca acacgaggac ttgactttca   120
aggacttctg gaagaccttg gttctgctcc atctggatct atgttttgct acatgcatgc   180
gcacataacc ccactggtgt ggatccaacc cttgagcaat gggagcagat tangcagcta   240
ataagatcaa agctttgtt actttctttg acagngctta tcagggt                  287

<210> SEQ ID NO 511

```
<211> LENGTH: 117
<212> TYPE: DNA
<213> ORGANISM: Glycine max

<400> SEQUENCE: 511
caggtattgc tacatgcatg cgcacataac cccactggtg tggatccaac ccttgagcaa    60
tgggagcaga ttaggctgct aatatgatca aaagctttgt tatcttacta cgacagt      117

<210> SEQ ID NO 512
<211> LENGTH: 273
<212> TYPE: DNA
<213> ORGANISM: Glycine max

<400> SEQUENCE: 512
aacaatccta ctggtgctgc ggcaacaagg gaacaactga cccaactcgt tcagtttgct    60
aaggacaatg gttctatagt aatccatgat tcagcttatg caatgtatat ttctggtgac   120
aaccctcgct ctattttga aatcctggag ccaaagaggt tgccatcgag acttcatcat   180
ttagcaagta tgctgggttc actggagtcc gattgggttg gactgtggtt ccaaagcagt   240
tgctgttttc tgatggattt cctgttgcca agg                                273

<210> SEQ ID NO 513
<211> LENGTH: 237
<212> TYPE: DNA
<213> ORGANISM: Glycine max

<400> SEQUENCE: 513
aacaatccta ctggtgctgc ggcaacaagg gaacaactga ccccactcgt tcagtttgct    60
acggacactg gttctatagt aatccatgat tcagcttatg caatgtatat ttctggtgac   120
aaccctcgct ctattttga aattcctgga gccacagagg ttgccatcga gacttcatca   180
tttagcaagt atgctgggtt cactggagtc cgattgggtt ggactgtggt tccaaag     237

<210> SEQ ID NO 514
<211> LENGTH: 276
<212> TYPE: DNA
<213> ORGANISM: Glycine max

<400> SEQUENCE: 514
ggggaacgtg ttggcgcctt aagcattgtc tgcaagtcag ctgatgttgc aagcagggtt    60
gagagccagc tgaagctagt gattaggccc atgtactcaa gtcctcccat tcatggtgca   120
tccattgtgg ctgccattct caaggaccgg aatttgttca atgactggac tattgagttg   180
aaggcaatgg ctgatccatc atcagtatgc gccaagaact tttcgatgct ttatgttcca   240
gaggcacacc tggcgattgg agtcacatta tcaaac                             276

<210> SEQ ID NO 515
<211> LENGTH: 271
<212> TYPE: DNA
<213> ORGANISM: Glycine max

<400> SEQUENCE: 515
gcttatcagg gttttgctag tggaagtcta gatgcagatg cccaacctgt tcgtttgttt    60
gttgctgatg gaggcgaatt gctggtagca caaagctatg caaagaatct gggtctttat   120
ggggaacgtg ttggcgcctt aagcattgtc tgcaagtcag ctgatgttgc aagcagggtt   180
gagagccagc tgaagctagt gattaggccc atgtactcaa gtcctcccat tcatggtgca   240
tccattgtgg ctgccattct caaggaccgg a                                  271
```

<210> SEQ ID NO 516
<211> LENGTH: 283
<212> TYPE: DNA
<213> ORGANISM: Glycine max

<400> SEQUENCE: 516

```
tgcttatcag ggttttgcta gcggaagtct agatgcagat gcccagcctg ttcgtttgtt      60
tgttgctgat gggggtgaat tgctggtggc acaaagctat gcaagaatc tgggtcttta      120
tggggaacgt gttggcgcct taagcattgt ctgaagtcag ctgatgttgc aagcagggtc      180
gagagccagc tgaaactagt gattaggccc atgtactcaa gtcctcctat tcatggtgca      240
tccattgtgg ctgccattct caaggaccgg gatttgttca atg                        283
```

<210> SEQ ID NO 517
<211> LENGTH: 227
<212> TYPE: DNA
<213> ORGANISM: Glycine max
<220> FEATURE:
<223> OTHER INFORMATION: unsure at all n locations

<400> SEQUENCE: 517

```
aaagaatctg ggtctttatg gggaacgngt tggcgcctta agccttgtct gnccgtcagc      60
tgatgttgca agcagggttg agagccagct gaagctagtg attaggccca tgtactcaag      120
tcctcccatt catggtgcat ccattgtggc tgccattctc aaggaccgga atttgttcaa      180
tgactggact attgagttga aggcaatggc tgatcgcatc atcagtt                    227
```

<210> SEQ ID NO 518
<211> LENGTH: 259
<212> TYPE: DNA
<213> ORGANISM: Glycine max
<220> FEATURE:
<223> OTHER INFORMATION: unsure at all n locations

<400> SEQUENCE: 518

```
aagctttgnt acctttcttt gacagtgcnn atcagggntn tgctagngga agtctagatt      60
gcngatggcc caacctgttc gtttgtntgt tgntgatgna ggcgaattgc tggtagcaca      120
aagctatgcn aagaatctgg gtcttnatgg ggaacgtgtt ggcgccttaa gcanngtctg      180
caagtcanct gatgttgcaa gcagggttga gagccagctg aagctagtga taggcccatg      240
tactcaagtc ctcccattt                                                   259
```

<210> SEQ ID NO 519
<211> LENGTH: 280
<212> TYPE: DNA
<213> ORGANISM: Glycine max

<400> SEQUENCE: 519

```
aacagattgg aatgtttact ttcactggat tgaatgcgga caagtttcc ttcatgacta       60
aagagttcca tatatacatg acatctgatg ggaggattag catggctggt ctgagttcca     120
aaactgtccc acttctggcg gatgcgatac atgcagctgt aacccgagtt gtctaaaaca     180
tgttgacaac agttttcaac atgctcccta gtccctatag gagaacttcc attattttg      240
tttaataatt gtcaacatca acaatgaaac cttttatttg                           280
```

<210> SEQ ID NO 520
<211> LENGTH: 250
<212> TYPE: DNA

<213> ORGANISM: Glycine max

<400> SEQUENCE: 520

| acattatcaa acagattgga atgtttactt tcactggatt gaatgcggaa caagtttcct | 60 |
| tcatgactaa agagttccat atatacatga catctgatgg gaggattagc atggctggtc | 120 |
| tgagttccaa aactgtccca cttctggcgg atgcgataca tgcagctgta acccgagttg | 180 |
| tctaaaacat gttgacaaca gttttcaaca tgctccctag tccctatagg agaacttcca | 240 |
| ttattttttgt | 250 |

<210> SEQ ID NO 521
<211> LENGTH: 285
<212> TYPE: DNA
<213> ORGANISM: Glycine max

<400> SEQUENCE: 521

| tacggctgcg aggacgacag aaggggataa tacatacgag tattttatgt atgatggcct | 60 |
| gaaacactct tgtgttgagg gaaatcatat tgttaatgtt tcctcattct caaaagcatt | 120 |
| tggatagatg ggatggcggg ttggatatat agcatatccc tctgaagtaa aagactttgc | 180 |
| tgaacatctt ctcaaagttc aagacaacat tcccatctgt gcttcaatat tatcacagta | 240 |
| tcttgccctg tattcattgg aagtggggcc tcaatgggtt gtaga | 285 |

<210> SEQ ID NO 522
<211> LENGTH: 249
<212> TYPE: DNA
<213> ORGANISM: Glycine max

<400> SEQUENCE: 522

| gggaaatcat attgttaatg ttttctcatt ctcaaaagca tttggaatga tgggatggcg | 60 |
| ggttggatat atagcatatc cctctgaagt aaaagacttt gctgaacaac ttctcaaagt | 120 |
| tcaagacaac attcccatct gtgcttcaat attatcacag tatcttgccc tgtattcatt | 180 |
| ggaagtgggg cctcaatggg ttgtagatca ggtaaaaact cttgaaaaga acagagaaat | 240 |
| tgttttaga | 249 |

<210> SEQ ID NO 523
<211> LENGTH: 264
<212> TYPE: DNA
<213> ORGANISM: Glycine max

<400> SEQUENCE: 523

| gttgcgtgat gaaaataatt tgcacaaatc ttcagtaatg gttacatcag gtgccaatca | 60 |
| ggcatttgtg aatctagttc ttactctctg tgatccgggt gattctgtgg ttatgtttgc | 120 |
| tccttactac ttcaatgcgt acatgtcctt ccagatgact ggcattacca atattctagt | 180 |
| tggtcctggt agctcagaca cactccatcc tgatgcaggg ggttcacata ttggttaaat | 240 |
| gttggatgga ttgggtctgt atac | 264 |

<210> SEQ ID NO 524
<211> LENGTH: 296
<212> TYPE: DNA
<213> ORGANISM: Glycine max

<400> SEQUENCE: 524

| cctggattta caacagtaac aagctttgga gccggtttat ttctgataaa tattctttcc | 60 |
| aaccaatctg catcaggatg gagtgtgtct gagctaccag gaccaactag aatattggta | 120 |

```
atgccagtca tctggaagga catgtacgca ttgaagtagt aaggagcaaa cataaccaca    180
gaatcacccg atcacagag agtaagaact agattcacaa atgcctgatt ggcacctgat     240
gtaaccatta ctgaagattt gtgcaaatta ttttcatcac gcaactttt gactaa          296

<210> SEQ ID NO 525
<211> LENGTH: 284
<212> TYPE: DNA
<213> ORGANISM: Glycine max

<400> SEQUENCE: 525
gtggaagcct tgatgaagat gcagcttctg tgagactgtt tgtggcacgt gggcatcgag     60
gttcttgtag ctcaatctta cagtaaaaat ctcggtctct atgctgaaag gattggagca    120
atcaatgtga tttcatcgtc accagaatct gcagcaaggg taaagagcca actgaaaagg    180
attgcccgac caatgtactc taatccaccg gtacacgggg ctaggatagt tgccgatgtt    240
gttggaaacc cagttctctt taatgaatgg aaagcagaga tgga                    284

<210> SEQ ID NO 526
<211> LENGTH: 253
<212> TYPE: DNA
<213> ORGANISM: Glycine max

<400> SEQUENCE: 526
gaaaagaacc acattccctt ttttgatgtt gcttaccagg ggtttgctag tggaagcctt     60
gatgaagatg cagcttctgt gagactgttt gtggcacgtg gcatcgaggt tcttgtagct    120
caatcttaca gtaaaaatct cggtctctat gctgaaagga ttggagcaat caatgtgatt    180
tcatcgtcac cagaatctgc agcaagggta aagagccaac tgaaaaggat tgcccgacca    240
atgaactcta atc                                                      253

<210> SEQ ID NO 527
<211> LENGTH: 262
<212> TYPE: DNA
<213> ORGANISM: Glycine max
<220> FEATURE:
<223> OTHER INFORMATION: unsure at all n locations

<400> SEQUENCE: 527
gcttcttcgt ttctatccgc agcttcgcac gctgtctcac cctcttgttc tctgtccacc     60
acgcacaagg ganagcccat gcttggaggc aacactttga gatttcacaa aggacccaat    120
tccttctcta gttcaaggtc tagaggtcgg atctctatgg ctgttgcagt taatgtatct    180
cggtttgaag gcatacctat ggctcctcct gatccaattc tcggagtttc cgaggcgttt    240
aaggcagaca atagtgatgt ca                                            262

<210> SEQ ID NO 528
<211> LENGTH: 277
<212> TYPE: DNA
<213> ORGANISM: Glycine max

<400> SEQUENCE: 528
ctacaacaca cttttgtaag tgattcgttc gcagaaacat ggcatcttcg ttgctatccg     60
cagcttcgca cgctgtctca ccctcttgtt ctctgtccac cacgcacaag ggatagccca    120
tccttggagg caacactttg agatttcaca aggacccaa ttccttctct agttcaaggt    180
ctataggtcg gatctctatg gctgttgcag ttaatgtatc tcggtttgaa ggcatacccta   240
```

-continued

```
tggctcctcc tgatccaatt ctcggatttt ccgaggt                                  277
```

<210> SEQ ID NO 529
<211> LENGTH: 266
<212> TYPE: DNA
<213> ORGANISM: Glycine max

<400> SEQUENCE: 529

```
cgcacttcgc acgctgtctc accctcttgc tctctgtcca ccacgcacaa gggacatcca    60
ttcttggagg caacactttg agatttcaca aaggacccaa ttccttctct agttcaaggt   120
ctagaggtcg gatctctatg gctgttgcag ttaatgtatc tcggtttgaa ggcataccta   180
tggctcctcc tgatccaatt ctcggagttt ccgaggcgtt taaggcagac aatagtgatg   240
tcaagctcaa tcttggagtt ggggca                                        266
```

<210> SEQ ID NO 530
<211> LENGTH: 257
<212> TYPE: DNA
<213> ORGANISM: Glycine max

<400> SEQUENCE: 530

```
gtttccttca tcttcttctt cttcttctat ctctctacaa cacactttt taagtgattc     60
gttcgcagaa acatggcttc ttcgtttcta tccgcagctt cgcacgctgt ctcaccctct   120
tgttctctgt ccaccacgca aagggaaag cccatgcttg gaggcaacac tttgagattt    180
cacaaaggac ccaattcctt ctctagttca aggtctagag gtcggatctc tatggctgtt   240
gcagttaatg tatctcg                                                  257
```

<210> SEQ ID NO 531
<211> LENGTH: 271
<212> TYPE: DNA
<213> ORGANISM: Glycine max

<400> SEQUENCE: 531

```
gagatttcac aaaggaccca attccttctc tagttcaagg tctagaggtc ggatctctat    60
ggctgttgca gttaatgtat ctcggtttga aggcatacct atggctcctc ctgatccaat   120
tctcggagtt ccgaggcgt ttaaggcaga caatagtgat gtcaagctca atcttggagt    180
tggggcatac agaacagaag aactacagcc atatgtgctt atgttgttaa gaaggtcttt   240
gttccgtatt ttatgtgtct tctgtgattt g                                  271
```

<210> SEQ ID NO 532
<211> LENGTH: 244
<212> TYPE: DNA
<213> ORGANISM: Glycine max
<220> FEATURE:
<223> OTHER INFORMATION: unsure at all n locations

<400> SEQUENCE: 532

```
ctacaacaca ctttttaag tgattcgttc gcagaaacat ggcttcttcg nttctatccg      60
cagcttcgca cgctgtctca nctcttgttc tctgtccanc acgcacaagg gagagcccat   120
gcttggaggc aacactttga gatttcacaa aggacccaat tcctctctag ttcaaggtct   180
agaggtcgga tctctatggc tgttgcagtt aatgtatctc ggtttgaagg catacctatg   240
gcnc                                                                244
```

<210> SEQ ID NO 533
<211> LENGTH: 272

```
<212> TYPE: DNA
<213> ORGANISM: Glycine max

<400> SEQUENCE: 533 cactgttttcc ttcatcttct tcttcttctt ctatctctct acaacacact tttttaagtg    60
attcgttcgc agaaacatgg cttcttcgtt tctatccgca gcttcgcacg ctgtctcacc   120
ctcttgttct ctgtccacca cgacaaggga aagcccatgc ttggaggcaa cactttgaga   180
tttcacaaag gacccaattc cttctctagt tcaaggtcta gaggtcggat ctctatggct   240
gttgcagtta atgtatctcg gtttgaaggc at                                  272

<210> SEQ ID NO 534
<211> LENGTH: 288
<212> TYPE: DNA
<213> ORGANISM: Glycine max
<220> FEATURE:
<223> OTHER INFORMATION: unsure at all n locations

<400> SEQUENCE: 534
tgccgaattc cgctcgagct cgagccggtt tccntcatct tcttcttctt cttctatctc    60
tctacaacac acttttttaa cacattcgtt cgcagaaaca tggcttcttc gtttctatcc   120
gcagcttcgc acgctgtctc accctcttgt tctctgtcca ccacgcacaa gggacagccc   180
atgcttggag gcaacacttt gagatttcac aaaggaccca attccttctc tagttcaagg   240
tctagaggtc ggatctctat ggctgttgca gttaatgtat ctcggttt                 288

<210> SEQ ID NO 535
<211> LENGTH: 254
<212> TYPE: DNA
<213> ORGANISM: Glycine max

<400> SEQUENCE: 535
attttctatt gcagatggct tcgtcggttc tctccgcagc ttcgcactct gtctcaccct    60
catgttctct gtccaccacg cacaagggaa agcccatgat tagagacaac actttgggat   120
tccacagagg acccaattcc ttctctagtt caaggtctag aggtcggatc tctatggctg   180
ttgcagttaa cgtttctcgg tttgaaggca tacctatggc gcctcctgat ccaattctag   240
gagtttctga ggca                                                      254

<210> SEQ ID NO 536
<211> LENGTH: 272
<212> TYPE: DNA
<213> ORGANISM: Glycine max
<220> FEATURE:
<223> OTHER INFORMATION: unsure at all n locations

<400> SEQUENCE: 536
tgttctgttc tgtnctgnna catctcgtna atcgnttana anttcttaac cgtnttctgt    60
tgcagctggg cttctncgtt tatntaccgc agcttngcac gctgtntcac nctcttgttc   120
tctgtnnacc angcacaagg gaaagcacat gcttggaggc aacactttga gatttcacaa   180
aggncccaat tccttctcta gttcaaggtc tagaggtcgg atctctatgg ctgttgcagt   240
taatgtatct cggtttgaag gcatacctat ng                                  272

<210> SEQ ID NO 537
<211> LENGTH: 275
<212> TYPE: DNA
<213> ORGANISM: Glycine max
```

<400> SEQUENCE: 537

```
cctcgagccg attcggctcg aggttacatc tcgtgaattg ttacaatctg ttaaccattt      60
tccattgcag atggcttcgt cacttctctc cgcagcttcg cactctgtct caccctcatg     120
ttctctgtcc accacgcaca gggaaagccc atgattagag acaacacttt gggtttccac     180
agaggaccca attccttctc tagttcaagg tctagaggtc ggatctctat ggctgttgca     240
gttaacgttt ctcggtttga aggcatacct atggc                                275
```

<210> SEQ ID NO 538
<211> LENGTH: 277
<212> TYPE: DNA
<213> ORGANISM: Glycine max
<220> FEATURE:
<223> OTHER INFORMATION: unsure at all n locations

<400> SEQUENCE: 538

```
agaaacatgg cttcgtcggt tctctccgca gcttcgcacn cctgtctcac cctcatgttc      60
nctgtncacc acgcacaagg gnaagcccat gantagagac aanactttgg gattccacag     120
aggacccaat tccttctcna gttcaaggtn tagaggtcgg ntctctatgg ctgttgcagt     180
taacgnttct cgggttngag gcatacctat gggcgcctcc tgatccaaat tcttagggag     240
tttctgaggn atntaaggtg gaccaatagt ggtgtnc                              277
```

<210> SEQ ID NO 539
<211> LENGTH: 254
<212> TYPE: DNA
<213> ORGANISM: Glycine max

<400> SEQUENCE: 539

```
agattaatca atcatagata gatccattat tcatagttaa acataataac tgttgtgtta      60
catctcgtga attgttacaa ctgcttaacc attttctatt gcagatggct tcgtcggttc     120
tctccgcagc ttcgcactct gtctcaccct catgttctct gtccaccacg cacaagggaa     180
agcccatgat tagagacaac actttgggat tccacagagg acccaatttc ttctctagtt     240
caaggtctag aggt                                                       254
```

<210> SEQ ID NO 540
<211> LENGTH: 267
<212> TYPE: DNA
<213> ORGANISM: Glycine max

<400> SEQUENCE: 540

```
atcgtattct ctacgctatt cctattaaat gaatcatagt catagataga tccattattc      60
atagtttaaa ttaggaacct tttgtgttct gttctgttct gttacatctc gtgaatcgtt     120
tacaacttct taaccgtttt ctgttgcaga tggcttcttc gtttctatcc gcagcttcgc     180
acgctgtctc accctcttgt tctctgtcca ccacgcacaa gggaaagccc atgcttggag     240
gcaacacttt gagatttcac aaaggac                                         267
```

<210> SEQ ID NO 541
<211> LENGTH: 259
<212> TYPE: DNA
<213> ORGANISM: Glycine max

<400> SEQUENCE: 541

```
cgctattcct attaaatgaa tcatagtcat agatagatcc attattcata gtttaaatta      60
ggaacctttt gtgctctgtt ctgttctgtt acatctcgtg aatcgtttac aacttcttaa     120
```

```
ccgttttctg ttgcagatgg cttcttcgtt tctatccgca gcttcgcacg ctgtctcacc      180
ctcttgttct ctgtccacca cgcacaaggg aaagcccatg cttggaggca cactttgag      240 atttcacaaa ggacccaat                                                   259
```

<210> SEQ ID NO 542
<211> LENGTH: 259
<212> TYPE: DNA
<213> ORGANISM: Glycine max

<400> SEQUENCE: 542

```
tacgctattc cgattaatca atcatagata gatccattat tcatagttaa acataataac      60
tgttgtgtta catctcgtga attgttacaa ctgcttaacc attttctatt gcagatggct      120
tcgtcggttc tctccgcagc ttcgcactct gtctcaccct catgttctct gtccaccacg      180 cacagggac agcccatgat tagagacaac actttggatt ccacagagga cccaattcaa       240
tctctagttc aaggtctag                                                   259
```

<210> SEQ ID NO 543
<211> LENGTH: 270
<212> TYPE: DNA
<213> ORGANISM: Glycine max

<400> SEQUENCE: 543

```
ttcgtattct ctacgctatt ccgattaatc aatcatagat agatccatta ttcatagtta      60
aacataataa ctgttgtgtt acatctcgtg aattgttaca actgcttaac cattttctat      120
tgcagatggc ttcgtcggtt ctctccgcag cttcgcactc tgtctcaccc tcatgttctc      180
tgtcaaccac gcacaaggga gagcccatga ttagagacaa cactttggga ttccacagag      240
gacacaattc cttctctagt tcaaggtcta                                       270
```

<210> SEQ ID NO 544
<211> LENGTH: 266
<212> TYPE: DNA
<213> ORGANISM: Glycine max

<400> SEQUENCE: 544

```
gcatacctat ggcgcctcct gatccaattc taggagtttc tgaggcattt aaggtggaca      60
atagtgatgt caagctcaat cttggagttg gggcatacag aacagaagaa ctacagccat      120
atgtgcttaa tgttgttaag aaggcagaga atcttatgct ggagagaggg gataacaaag      180
agtatctccc aattgagggt tcggctgcat ttaataaggc aactgcagag ttgttacttg      240
gagcagacaa cccagcaatc aaacag                                           266
```

<210> SEQ ID NO 545
<211> LENGTH: 169
<212> TYPE: DNA
<213> ORGANISM: Glycine max
<220> FEATURE:
<223> OTHER INFORMATION: unsure at all n locations

<400> SEQUENCE: 545

```
cttgggagtt gggcataca gaacagaaga actacagcca tatgtncttaa atgttgttaa      60 gaaggcagag aatcttatgc tggagagagg ggataacaaa gagtatctcc caattgaggg      120
tttggcagca tttaataagg caactgcaga gttgttactc ggagcagac                  169
```

<210> SEQ ID NO 546

<211> LENGTH: 272
<212> TYPE: DNA
<213> ORGANISM: Glycine max

<400> SEQUENCE: 546

```
ctatcctcgg ggtaactgtc gcttataaca aagatccaag tccagttaag ctcaacttgg      60
gagttggtgc ttaccgaact gaggaaggaa aacctcttgt tttgaatgta gtgaggcgag     120
ttgaacagca actcataaat gacgtgtcac gcaacaagga atatattccg atcgttgggc     180
ttgctgattt aataaattg agtgctaagc ttattttgg ggctgacagc cctgctattc       240
aagacaacag ggttaccact gttcaatgct tg                                    272
```

<210> SEQ ID NO 547
<211> LENGTH: 270
<212> TYPE: DNA
<213> ORGANISM: Glycine max

<400> SEQUENCE: 547

```
cttccgcaaa tggcttctca cgacagcatc tccgcttctc caaactccgc ttctgattcc      60
gtcttcaatc acctcgttcg tgctcccgaa gatcctatcc tcggggtaac tgtcgcttat    120
aacaaagatc caagtccagt taagctcaac ttgggagttg gtgcttaccg aactgaggaa    180
ggaaaacctc ttgttttgaa tgtagtgagg cgagttgaac agcaactcat aaatgacgtg    240
tcacgcaaca aggaatatat tccgatcgtt                                       270
```

<210> SEQ ID NO 548
<211> LENGTH: 281
<212> TYPE: DNA
<213> ORGANISM: Glycine max

<400> SEQUENCE: 548

```
tgcaaatggc ttctcacgac agcatctccg cttctccaac ctccgcttct gattccgtct      60
tcaatcacct cgttcgtgct cccgaagatc ctatcctcgg ggtaactgtc gcttataaca    120
aagatccaag tccagttaag ctcaacttgg gagttggtgc ttaccgaact gaggaaggaa    180
aacctcttgt tttgaatgta gtgaggcgag ttgaacagca actcataaat gacgtgtcac    240
gcaacaagga atatattccg atcgttgggc ttgcggattt a                         281
```

<210> SEQ ID NO 549
<211> LENGTH: 257
<212> TYPE: DNA
<213> ORGANISM: Glycine max

<400> SEQUENCE: 549

```
cgcttctgat tccgtcttca atcacctcgt tcgtgctccc gaagatccta tcctcggggt      60
aactgtcgct tataacaaag atccaagtcc agttaagctc aacttgggag ttggtgctta    120
ccgaactgag gaaggaaaac tcttgttttt gaatgtagtg aggcgagttg aacagcaact    180
cataaatgac gtgtcacgca acaaggaata tattccgatc gttgggcttg ctgattttaa    240
taaattgagt gctaagc                                                    257
```

<210> SEQ ID NO 550
<211> LENGTH: 282
<212> TYPE: DNA
<213> ORGANISM: Glycine max

<400> SEQUENCE: 550

```
caacactctc tccagacact tccttcatca aatggcttct cacgacggca tctccgctgc      60
```

-continued

```
ttcttcagat tccgtcttca atcacctcgt tcgtgctccc gaagatccta tcctcggggt      120
aactgttgct tataacaaag atccaagtcc agttaagctc aacttgggag ttggtgctta      180
ccgaactgag gaaggaaaac ctcttgtttt gaatgtagtg aggcgagttg agcagcaact      240
cataaatgac gtgtcacgca acaaggaata tattccgatt gt                        282
```

<210> SEQ ID NO 551
<211> LENGTH: 250
<212> TYPE: DNA
<213> ORGANISM: Glycine max

<400> SEQUENCE: 551

```
cttccgcaaa tggcttctca cgacagcatc tccgcttctc caacctccgc ttctgattcc      60
gtcttcaatc acctcgttcg tgctcccgaa gatcctatcc tcggggtaac tgtcgcttat      120
aacaaagatc caagtccagt taagctcaac ttgggagttg gtgcttaccg aactgaggaa      180
ggaaaacctc ttgttttgaa tgtagtgagg cgagttgaac agcaactcat aaatgacgtg      240
tcacgcaaca                                                            250
```

<210> SEQ ID NO 552
<211> LENGTH: 273
<212> TYPE: DNA
<213> ORGANISM: Glycine max

<400> SEQUENCE: 552

```
ctcgctagac acttccttcc gcaaatggct tctcacgaca gcatctccgc ttctccaacc      60
tccgcttctt attccttctt caatcacctc gttcgtgctc ccgaagatcc tatcctcggg      120
gtaactgtcg cttataacaa agatccaagt ccagttaagc tcaacttggg agttggtgct      180
taccgaactg aggaaggaaa acctcttgtt ttgaatgtag tgaggcgagt tgaacagcaa      240
ctcataaatg acgtgtcacg caacaaggaa tat                                  273
```

<210> SEQ ID NO 553
<211> LENGTH: 262
<212> TYPE: DNA
<213> ORGANISM: Glycine max
<220> FEATURE:
<223> OTHER INFORMATION: unsure at all n locations

<400> SEQUENCE: 553

```
ctgtgatcgc agactcaaca ctctcgctag acanttcctt ccgcaaatgg cttctcacga      60
cagcatctcc gcttctccaa cctccgcttc tgattccgtc ttcaatcacc tcgttcgtnc      120
tcccgaagat cctatcctcg ggtaactnt ngcttataac aaagatccaa gtccagttaa      180
gctcaacttg ggagttggtg cttaccgaac tgaggaagga aaacctcttg ttttgaatgt      240
agtgaggcga gtgaacagca at                                              262
```

<210> SEQ ID NO 554
<211> LENGTH: 239
<212> TYPE: DNA
<213> ORGANISM: Glycine max
<220> FEATURE:
<223> OTHER INFORMATION: unsure at all n locations

<400> SEQUENCE: 554

```
agttaagctc aacttgggag ttggtgctta ccgaactgag gaaggaaaac ctcttgtttt      60
gaatgtagtg angcgagttg aacagcaact cataaatgac gtgtcacgca acaaggaata    120
```

```
tattccgatc gttgggcttg ctgattttaa taaattgagt gctaagctta tttttggggc    180
tgacagccct gctattcaag acaacagggt taccactgtt caatgcttgt ctggaactg    239
```

<210> SEQ ID NO 555
<211> LENGTH: 253
<212> TYPE: DNA
<213> ORGANISM: Glycine max

<400> SEQUENCE: 555

```
atggcttctc acgacggcat ctccgctgct tcttcagatt ccgtcttcaa tcacctcgtt    60
cgtgctcccg aagatcctat cctcggggta actgttgctt ataacaaaga tccaagtcca   120
gttaagctca acttgggagt tggtgcttac cgaactgagg aaggaaaacc tcttgttttg   180
aatgtagtga ggcgagttga gcagcaactc ataaatgacg tgtcacgcaa caaggaatat   240
attccgattg ttg                                                      253
```

<210> SEQ ID NO 556
<211> LENGTH: 252
<212> TYPE: DNA
<213> ORGANISM: Glycine max

<400> SEQUENCE: 556

```
tctaattcgt ggagggaata cttttccatt acgcacgcac tttaattaca gacgagaaaa    60
ttataattaa tagtaataca gacagcagca tgcgcccacc ggttattctc aaaactacca   120
cctctctttt ggattcttct tcttcttcac caccctgtga tcgcagactc aacactctcg   180
ctagacactt ccttccgcaa atggcttctc acgacagcat ctccgcttct ccaacctccg   240
cttctgattc cg                                                       252
```

<210> SEQ ID NO 557
<211> LENGTH: 249
<212> TYPE: DNA
<213> ORGANISM: Glycine max

<400> SEQUENCE: 557

```
caaatggctt ctcacgacgg catctccgct gcttcttcag attccgtctt caatcacctc    60
gttcgtgctc ccgaagatcc tatcctcggg gtaactgttg cttataacaa agatccaagt   120
ccagttaagc tcaacttggg agttggtgct taccgaactg aggaaggaaa acctcttgtt   180
ttgaatgtag tgaggcgagt tgagcagcaa ctcataaatg acgtgtcacg caacaaggaa   240
tatattccg                                                           249
```

<210> SEQ ID NO 558
<211> LENGTH: 250
<212> TYPE: DNA
<213> ORGANISM: Glycine max

<400> SEQUENCE: 558

```
atggcttctc acgacggcat ctccgctgct tcttcagatt ccgtcttcaa tcacctcgtt    60
cgtgctcccg aagatcctat cctcggggta actgttgctt ataacacaga tccaagtcca   120
gttaagctca acttgggagt tggtgcttac cgaactgagg aaggaaaacc tcttgttttg   180
aatgtagtga ggcgagttga gcagcaactc ataaatgacg tgtcacgcaa caaggaatat   240
attccgattg                                                          250
```

<210> SEQ ID NO 559
<211> LENGTH: 261

```
<212> TYPE: DNA
<213> ORGANISM: Glycine max

<400> SEQUENCE: 559
gttcatcgca gactcaacac tctctccaga cacttccttc atcaaatggc ttctcacgac    60
ggcatctccg ctgcttcttc agattccgtc ttcaatcacc tcgttcgtgc tcccgaagat   120
cctatcctcg gggtactgtt gcttataaca aagatccaag tccagttaag ctcaacttgg   180
gagttggtgc ttaccgaact gaggaaggaa aacctcttgt tttgaatgta gtgaggcgag   240
ttgagcagca actcataaat g                                             261

<210> SEQ ID NO 560
<211> LENGTH: 248
<212> TYPE: DNA
<213> ORGANISM: Glycine max
<220> FEATURE:
<223> OTHER INFORMATION: unsure at all n locations

<400> SEQUENCE: 560
accaccctgt gatngcagac tcaacactct cgctagacac ttccttccgc aaatngcttc    60
tcangacagc atctccgctt ctncaacctc cgcntctgat tccgtcttca atcacctcgt   120
nngnnctcnc naaatccta tnctcggggt aactnnagct tataacaaag atccaagtnc   180
agttaagctc aacttgggag ttggtgctta ccgaactgag gaaggaaaac ctcttgtttt   240
gaatgtag                                                            248

<210> SEQ ID NO 561
<211> LENGTH: 235
<212> TYPE: DNA
<213> ORGANISM: Glycine max

<400> SEQUENCE: 561
gctcaacttg ggagttggtg cttaccgaac tgaggaagga aaacctcttg ttttgaatgt    60
agtgaggcga gttgaacagc aactcataaa tgacgtgtca cgcaacaagg aatatattcc   120
gatcgttggg cttgctgatt ttaataaatt gagtgctaag cttattttg gggctgacag   180 ccctgctatt caagacaaca gggttaccac tgttcaatgc ttgtctggaa ctggt         235

<210> SEQ ID NO 562
<211> LENGTH: 260
<212> TYPE: DNA
<213> ORGANISM: Glycine max
<220> FEATURE:
<223> OTHER INFORMATION: unsure at all n locations

<400> SEQUENCE: 562
gttcatcgca gactcaacac tctctccaga cacttccttc atcaaatggc ttctncacga    60
cggcatctcc gctgcttctt cagattccgt cttcaatcac ctcgttcgtg ctcccgaaga   120
tcctatcctc ggggtaactg ttgcttataa caaagatcca agtccagtta agctcaactt   180
gggagttggt gcttaccgaa ctgaggaagg aaaacctctt gttttgaatg tagtgaggcg   240
agttgagcag caactcataa                                               260

<210> SEQ ID NO 563
<211> LENGTH: 248
<212> TYPE: DNA
<213> ORGANISM: Glycine max

<400> SEQUENCE: 563
```

```
cagacacttc cttcatcaaa tggcttctca cgacggcatc tccgctgctt cttcagattc    60
cgtcttcaat cacctcgttc gtgctcccga agatcctatc ctcggggtaa ctgttgctta   120
taacaaagat ccaagtccag ttaagctcaa cttgggagtt ggtgcttacc gaactgagga   180
aggaaaacct cttgttttga atgtagtgag gcgagttgag cagcaactca taaatgacgt   240
gtcacgca                                                            248
```

<210> SEQ ID NO 564
<211> LENGTH: 266
<212> TYPE: DNA
<213> ORGANISM: Glycine max

<400> SEQUENCE: 564

```
ctttggattc ttattgttca tcgcagactc aacactctct ccagacactt ccttcatcaa    60
atggcttctc acgacggcat ctccgctgct tcttcagatt ccgtcttcaa tcacctcgtt   120
cgtgctcccg aagatcctat cctcggggta actgttgctt ataacaaaga tccaagtcct   180
gttaagctca acttgggagt tggtgcttac cgaactgagg aaggaaaacc tcttgttttg   240
aatgtagtga ggcgagttga gcagca                                        266
```

<210> SEQ ID NO 565
<211> LENGTH: 254
<212> TYPE: DNA
<213> ORGANISM: Glycine max

<400> SEQUENCE: 565

```
gttcatcgca gactcaacac tctctccaga cacttccttc atcaaatggc ttctcacgac    60
ggcatctccg ctgcttcttc agattccgtc ttcaatcacc tcgttcgtgc tcccgaagat   120
cctatcctcg gggtaactgt tgcttataac aaagatccaa gtccagttaa gctcaactgg   180
gagttggtgc ttaccgaact gaggaaggaa aacctcttgt tttgaatgta gtgaagcgag   240
ttgagcagca actc                                                     254
```

<210> SEQ ID NO 566
<211> LENGTH: 230
<212> TYPE: DNA
<213> ORGANISM: Glycine max

<400> SEQUENCE: 566

```
cacttccttc cgcaaatggc ttctcacgac agcatctccg cttctccaac ctccgcttct    60
gattccgtct tcaatcacct cgttagttct cccgaagatc ctatcctcgg ggtaactgtc   120
gcttataaca aagatccaag tccagttaag ctcaacttgg gagttggtgc ttaccgaact   180
gaggtaggaa aacctcttgt tttgaatgta gtgaggcgag ttgaacagca                230
```

<210> SEQ ID NO 567
<211> LENGTH: 249
<212> TYPE: DNA
<213> ORGANISM: Glycine max

<400> SEQUENCE: 567

```
ttaaaaatga ataagaaaa actcaacttt gtaattcgtg gagggaatac ttttccatta    60
cgcacgcact ttaattacag acgagaaaat tataattaat agtaatacag acagcagcat   120
gcgcccaccg gttattctca aaactaccac ctctcttttg gattcttctt cttcttcacc   180
accctgtgat cgcagactca acactctcgc tagacacttc cttccgcaaa tggcttctca   240
cgacagcat                                                           249
```

<210> SEQ ID NO 568
<211> LENGTH: 266
<212> TYPE: DNA
<213> ORGANISM: Glycine max

<400> SEQUENCE: 568

```
cctcgagccg cttccgcaaa tcgcttctca cgacagcatc tccgcttctc caacctccgc      60
ttcaccttcc gtcttcaatc acctcgttcg tgctcccgaa gatcctatcc tcggggtaac     120
tgtcgcttat aacaaagatc caagtccagt taagctcaac ttgggagttg gtgcttaccg     180
aactgaggaa ggaaaacctc ttgttttgaa tgtagtgagg cgagttgaac agcaactcat     240
aaatgacgtg tcacgcaaca aggatt                                          266
```

<210> SEQ ID NO 569
<211> LENGTH: 269
<212> TYPE: DNA
<213> ORGANISM: Glycine max

<400> SEQUENCE: 569

```
ctcttattgt tcatcgcaga ctcaacactc tctccagaca cttccttcat caaatggctt      60
ctcacgacgg catctccgct gcttcttcag attccgtctt caatcacctc gttcgtgctc     120
ccgaagatcc tatcctcggg gtaactgttg cttataacaa agatccaagt ccagttaagc     180
tcaacttggg agttggtgct taccgaactg aggaaggaaa acctcttgtt ttgaatgtag     240
tgaggcgagt tgagcagcaa ctcataaat                                       269
```

<210> SEQ ID NO 570
<211> LENGTH: 251
<212> TYPE: DNA
<213> ORGANISM: Glycine max

<400> SEQUENCE: 570

```
atcgcagact caacactctc tccagacact tccttcatta caatggcttc tcacgacggc      60
atctccgctg cttcttcaga ttccgttttc aatcacctcg ttcgtgctcc cgaagatcct     120
atcctcgggg taactgttgc ttataacaaa gatccaagtc cagttaagct caacttggga     180
gttggtgctt accgaactga ggaaggaaaa cctcttgttt tgaatgtagt gaggcgagtt     240
gagcagcaac t                                                          251
```

<210> SEQ ID NO 571
<211> LENGTH: 264
<212> TYPE: DNA
<213> ORGANISM: Glycine max
<220> FEATURE:
<223> OTHER INFORMATION: unsure at all n locations

<400> SEQUENCE: 571

```
ccttcatcaa atggcttctc acgacggcat ctccgctgct tcttcagatt ccgtcttcaa      60
tccacctcgt tcgtgctccc gaagatccta tcctcggggt aactgttgct tataacaaag     120
atccaagtcc agttaanctc aacttgggan ttggtgttac cgaactgagg aagggaaaac     180
ctcttgtttt gaatgtagtg aggcgagttg agcagcaact cataaatgan gtgtcncgca     240
acaagnattt nccncgtggg gggg                                            264
```

<210> SEQ ID NO 572
<211> LENGTH: 260
<212> TYPE: DNA

<213> ORGANISM: Glycine max

<400> SEQUENCE: 572

```
tccatgcgcc caccggttat tctcaaaact accacctctc ttttggattc ttcttcttct     60
tcaccaccct gtgatcgcag actcaacact ctcgctagac acttccttcc gcaaatcgct    120
tctcacgaca gcatctccgc ttctccaacc tccgcttctg attccgtctt caatcacctc    180
gttcgtcctc ccgaagatcc tatcctcggg gtaactatcg cttataacaa agatccaagt    240
ccagttaagc tcaacttggg                                                260
```

<210> SEQ ID NO 573
<211> LENGTH: 251
<212> TYPE: DNA
<213> ORGANISM: Glycine max

<400> SEQUENCE: 573

```
tacggctgcg agaaggacag aagggtacgg ctgcgagaag acgacagaag ggggcagact     60
caacactctc tccagacact tccttcatca aatggcttct cacgacggca tctccgctgc    120
ttcttcagat tccgtcttca atcacctcgt tcgtgctccc gaagatccta tcctcggggt    180
aactgttgct tataacaaag atccaagtcc agttaagctc aacttgggag ttggtgctta    240
ccgaactgag g                                                         251
```

<210> SEQ ID NO 574
<211> LENGTH: 185
<212> TYPE: DNA
<213> ORGANISM: Glycine max

<400> SEQUENCE: 574

```
ctcggggtaa ctgtcgctta taacaaagat ccaagtccag ttaagctcaa ctcgggagtt     60
ggtgcttacc gaactgagga cagaaaacct cttgttttga atgtagtacg cgagttgaac    120
agcaactcat aaatgacgtg tcacgcaaca aggaatatat tccgatcgtt gggcttgctg    180
atttt                                                                185
```

<210> SEQ ID NO 575
<211> LENGTH: 249
<212> TYPE: DNA
<213> ORGANISM: Glycine max

<400> SEQUENCE: 575

```
gaaagatcaa gactgcttat tctttgttct tcatctaacc caacgggatc tgtctacccc     60
aaagaattac ttgaagagat agcccgaatt gttgcaaagc accccaggct tctggttctc    120
tctgatgaaa tttacgaaca cataatttat gcaccagcaa ctcacacgag ctttgcatct    180
ttaccaggaa tgtgggacag aactcttact gtgaatggat tttctaaggc ctttgcaatg    240
actggttgg                                                            249
```

<210> SEQ ID NO 576
<211> LENGTH: 276
<212> TYPE: DNA
<213> ORGANISM: Glycine max

<400> SEQUENCE: 576

```
gatagcccga attgttgcaa agcaccccag gcttctggtt ctctctgatg aaatttacga     60
acacataatt tatgcaccag caactcacac gagctttgca tctttaccag gaatgtggga    120
cagaactctt actgtgaatg gatttctaa ggcctttgca atgactggtt ggcggctggg    180
```

```
atatattgct ggtccaaaac attttgttgc agcatgtgga aagatccaaa gtcagtttac    240
ttcaggggcc agtagtatag ctcagaaagc tgcagt                              276

<210> SEQ ID NO 577
<211> LENGTH: 264
<212> TYPE: DNA
<213> ORGANISM: Glycine max
<220> FEATURE:
<223> OTHER INFORMATION: unsure at all n locations

<400> SEQUENCE: 577
gcaaagcacc ccaggntcnt ggttntctcc gatgaaattt atgaacacat aatttatgca    60
ccagcaactg cacacaagtt ttgcatcttt accaggantg tgggacagaa ctcttactgt   120
gaatggattt tccaaggcct tgcaatgan tggttggcgg cttggatata ttgctggtcc    180 aaaacactt gttgcagcat gtggaaagat ccaaagtcag ttcacttcag ggccagtag    240 tatagctcag aaagctgcag ttgc                                          264

<210> SEQ ID NO 578
<211> LENGTH: 286
<212> TYPE: DNA
<213> ORGANISM: Glycine max

<400> SEQUENCE: 578
caagagatag cccaaattgt agcaaagcac cccaggcttc tggttctctc tgatgaaaat    60
tatgaacaca taatttatgc accggcaact catacaagct tgcatcgtt accgggaatg   120 tgggacagaa ctctaattgt gaatggactt tccaagacat tgcaatgac tggttggcgg    180 cttgggtata ttgctggtcc aaaacatttt gttgctgcat gtgaaaagat tcaaagccag   240
tttacttcag ggcaagtag tatatctcag aaagctgggg ttgctg                   286

<210> SEQ ID NO 579
<211> LENGTH: 233
<212> TYPE: DNA
<213> ORGANISM: Glycine max

<400> SEQUENCE: 579
gatagcccga attgttgcaa agcacccag gcttctggtt ctctctgatg aaatttacga    60
acacataatt tatgcaccag caactcacac gagctttgca tctttaccag gaatgtggga   120
cagaactctt actgtgaatg gattttctaa ggcctttgca atgactggtt ggcggcttgg    180
atatattgct ggtccaaaac attttgttgc agcatgtgga aagatccaaa gtc          233

<210> SEQ ID NO 580
<211> LENGTH: 284
<212> TYPE: DNA
<213> ORGANISM: Glycine max

<400> SEQUENCE: 580
ggattttcta aggcctttgc aatgactggt tggcggcttg gatatattgc tggtccaaaa    60
cattttgttg cagcatgtgg aaagatccaa agtcagtttta cttcaggggc cagtagtata   120
gctcagaaag ctgcagttgc tgcattagga ctaggccatg ctggtgggga ggcagtttct   180
accatggtga aagcatttag ggagcgaagg gatttcttag tacaaagttt tagagaaata   240
gatggcatca agatatctga accccaggga gcattttatc tatt                   284

<210> SEQ ID NO 581
```

<211> LENGTH: 247
<212> TYPE: DNA
<213> ORGANISM: Glycine max

<400> SEQUENCE: 581

```
gctccagcta ctcatacaag ttttgcatct ttacctggaa tgtgggaccg aactctaact      60
gtgaatggat tttccaagac atttgcaatg actggttggc ggcttgggta cattgctggt     120
acaaaacatt tgttgcagc atgcggaaag attcaaagtc agttcacttc aggtgcaagt      180
agtatatctc agaaagctgg agttgctgca ttaggactag ctatgctgg tggggaagct     240
gtttcaa                                                               247
```

<210> SEQ ID NO 582
<211> LENGTH: 260
<212> TYPE: DNA
<213> ORGANISM: Glycine max
<220> FEATURE:
<223> OTHER INFORMATION: unsure at all n locations

<400> SEQUENCE: 582

```
ctgaacttgg agagccatgg gtactaccat gcgttcggaa aactgagctg ttgatggcgc      60
agaatgattc gcttaatcac gagtacctcc ccgtgttggg gttcgaacca tttngtaaag     120
ctgctgtcac tcttttgctc ggtgacgtcg agacttccac acnactagcc gacgcnaggg     180
ctttnggagt gcaaacactg ngtggtatgg agcatangng ttacagntga atnccgagaa     240
aattcncata nannanattt                                                 260
```

<210> SEQ ID NO 583
<211> LENGTH: 305
<212> TYPE: DNA
<213> ORGANISM: Glycine max

<400> SEQUENCE: 583

```
cgatgctaac tcttcaagct tcgtctcgta aagaaaatgc gaaggctcaa tagagagaac      60
tcaattgaat catcaaatga ggacagtgat ttcgcgcttg atccattcca cgccttacat     120
tttcaggctc aatgccacgg cagcatccat cacccatact tatatgtgac cctttctat      180
cttactaaat acccaattcc ttctctaatt cacagtctac aggtctgatc tctatggctg     240
ttgcaattaa tgtatctcgg tttgaaagca tacctattgc tcctcctgat ccaattttta     300
gagtt                                                                 305
```

<210> SEQ ID NO 584
<211> LENGTH: 247
<212> TYPE: DNA
<213> ORGANISM: Glycine max

<400> SEQUENCE: 584

```
cccacgcgtc cgtacggctg caagaagacg acagaagggg agtaatacag acagcaacat      60
gcgcccagcg gttattctca aaactaccat ctctcttttg gaggcgtcgt cgtcctcaac     120
accctgtgat ggcagactca acactctcgc tagacacgtc cttccacaaa tggcttctca     180
tgacatgatc tgagaatctt caacctacgc atctgaatcc gtcatcaatc atctcgttcg     240
tactccc                                                               247
```

<210> SEQ ID NO 585
<211> LENGTH: 385
<212> TYPE: DNA
<213> ORGANISM: Glycine max

```
<220> FEATURE:
<223> OTHER INFORMATION: unsure at all n locations

<400> SEQUENCE: 585
attaatagta atacaaacag cagcatgcgc ccacccgtta ttctcaaaac taccaccgtg      60
tttgtggaat ctttcttctc gtcaccaccc tgtgatcgca gactcaacac tctcgctaga    120
cacttccttt cgcaaatggc ttctcacgac agcatctccg cttctacaac ctccgcttct    180
gattccgtct tcaatcacct cgttcgtgct cccgaagatc ctatcctcgg ggtaactgtc    240
gcttataaca aagatccaag tccagttaag ctcaacttgg gagttggtgc ttaccgaact    300
gaggaaggaa aacctcttgt ttttgatgta gtgaggcgag ttgaacagnc actcataaat    360
gacgtgtcac gcaacaagga atata                                          385

<210> SEQ ID NO 586
<211> LENGTH: 455
<212> TYPE: DNA
<213> ORGANISM: Glycine max
<220> FEATURE:
<223> OTHER INFORMATION: unsure at all n locations

<400> SEQUENCE: 586
ctctccctct ctgttcgcac tctgtctttc ccctgtttcc gcgtcactga gtcatggcga     60
ttcgcaactc gctcaccggc caattcctcc gccgcagctc cgtcgccgga gcaaggctca    120
tgtcttcttc gtcctcatgg ttccggagca tcgagcccgc tcccaaggat cctatcctcg    180
gagtcactga agctttcctc gccgatcaga gtccaaacaa agtcaacgtc ggagtgggtg    240
cgtatcgcga tgaccacgga aaacctgtgg ttttggaatg tgttagagaa gcagagagga    300
gggttgccgg aagtcaattc atggagtatc ttcccatggg tggaagcata aaatgatag     360
aagaatcgct gaagctggca tttggagaca actctgagtt catcaaggat aaaagaatag    420
ctgcagtgca tgctntatct gngactggtg catgt                                455

<210> SEQ ID NO 587
<211> LENGTH: 360
<212> TYPE: DNA
<213> ORGANISM: Glycine max

<400> SEQUENCE: 587
gcgagcggcc gccctttttt tttttttttt tttttttttt tttttttttt ggggaaacgg     60
aataaaaatg ttataatgct aaatctctgg atggagcccg gtaggcagaa aagtttcctt    120
taaaaatctc acatcaaata aaaggtttca ttgttgatgt tgacaattat aaacaaaaa     180
taatggaagt tctcctatag ggactaggga gcatgttgaa aactgttgtc aacatgtttt    240
agacaactcg ggttacagct gcatgtatcg cattcgccag aagtgggaca gttttggaac    300
tcagaccagc catgctaatc ctcccatcaa atgtcatgta tatatggaac tctttaatca    360

<210> SEQ ID NO 588
<211> LENGTH: 366
<212> TYPE: DNA
<213> ORGANISM: Glycine max

<400> SEQUENCE: 588
ctgcattgca tgtatctgca tcgagaatga tgttctggtt gtcactgatc aagtctatga     60
caagtgggct ttgatatgg agcacatatc gatggcttat ttgcctgtaa tgttcgaaag     120
gacagtgaca ttgaactcct tggggaagac attctcctta acacgatgga agattggttg    180
```

-continued

```
ggccatagca cccgcacact tatcatgggg agtgctacag gcacacgctt tgctgacttt    240
cgcaactgcc cattcttttc agagtgctgc tgcagcatct atgagagcac cagactctta    300
ctatgtagag ctgaagaggg attatatggc atatagagct attttgattg aaggattgaa    360
ggctgt                                                                366

<210> SEQ ID NO 589
<211> LENGTH: 413
<212> TYPE: DNA
<213> ORGANISM: Glycine max

<400> SEQUENCE: 589
cttttgtgtt ctgttctgtt ctgttacatc tcgtgaatcg tttacaactt cttaaccgtt    60
ttctgttgca gatggcttct tcgtttctat ccgcagcttc gcacgctgtc tcaccctctt    120
gttctctgtc caccacgcac aagggaaagc ccatgcttgg aggcaacact ttgagatttc    180
acaaaggacc caattccttc tctagttcaa ggtctagagg tcggatctct atggctgttg    240
cagttaatgt atctcggttt gaaggcatac ctatggctcc tcctgatcca attctcggag    300
tttccgaggc gtttaaggca gacaatagtg atgtcaagct caatcttgga gttggggcat    360
acagaacaga agaactacag ccatatgtgc ttaatgttgt taagaaggca gag           413

<210> SEQ ID NO 590
<211> LENGTH: 401
<212> TYPE: DNA
<213> ORGANISM: Glycine max

<400> SEQUENCE: 590
cttttgtgta tcgttctgtt ctgttacatc tcgtgaatcg gttacaactt cttaaccgtt    60
ttctgttgca gatggcttct tcgtttctat ccgcagcttc gcacgctgtc tcaccctctt    120
gttctctgtc caccacgcac aagggaaagc ccatgcttgg aggcaacact ttgagatttc    180
acaaaggacc caattccttc tctagttcaa ggtctagagg tcggatctct atggctgttg    240
cagttaatgt atctcggttt gaaggcatac ctatggctcc tcctgatcca attctcggag    300
tttccgaggc gtttaaggca gacaatagtg atgtcaagct caatcttgga gttggggcat    360
acagaacaga agaactacag ccatatgtgc ttaatgttgt t                        401

<210> SEQ ID NO 591
<211> LENGTH: 331
<212> TYPE: DNA
<213> ORGANISM: Glycine max

<400> SEQUENCE: 591
gatcagttct gttctgttac atctcgtgaa tgatttacaa ctaattaacc ggtgtctgtt    60
gcagatggct tcttcgtttc tatccgcagc ttcgcacgct gtctcaccct cttgatctct    120
gtccaccacg cacaagggaa agcccatgct tggaggcaac actttgagat tcacaaagg    180 acccaattcc ttctctagtt caaggtctag aggtcggatc tctatggctg ttgcagataa    240
tgtatctcgg tttgaaggca tacctatggc tcctcctgat ccaattctcg gagttttcga    300
agcgtttaag catacaatat tgatgtcaag c                                  331

<210> SEQ ID NO 592
<211> LENGTH: 349
<212> TYPE: DNA
<213> ORGANISM: Glycine max

<400> SEQUENCE: 592
```

```
acggacgcga aagacgaca gaagggact actacttgat cacatcgtat tctctatgct    60
attccgatta atcaatcata gatagatcca ttattcatag ttaaacataa taactgttgt   120
gttacatctc gtgaattgtt acaactgctt aaccattttc tattgcagat ggcttcgtcg   180
gttctctccg cagcttcaca ctctgtctca tcctcatgtt ctctgtccac cacgcacaag   240
ggaaagccca tgattagaga caacactttg ggattccaca gaggacccaa ttccttctct   300
agttcaaggt ctaaaggtcg gatctctatg gctgttgcag ttaacgttt              349
```

<210> SEQ ID NO 593
<211> LENGTH: 440
<212> TYPE: DNA
<213> ORGANISM: Glycine max
<220> FEATURE:
<223> OTHER INFORMATION: unsure at all n locations

<400> SEQUENCE: 593

```
cggacgcgtg ggttccgcaa atggcttctc acgacagcat ctccgcttct ccaacctccg    60
gttctgattc cgtgttcaat caccctcgtc gtgctcccga agatcctatc ctcggggtaa   120
ctgtcgctta taacaaagat ccaagtccag ttaagctcaa cttgggagtt ggtgcttacc   180
gaactgagga aggaaaacct cttgttttga atgtagtgag gcgagttgaa cagcaactca   240
taaatgacgt gtcacgcaac atggaatata ttccgatcgt tgggcttgct gattttaata   300
aattgagtgc taagcttatt tttggggctg acagccctgc tattcaagac aacagggtta   360
ccactgttca atgctngtct ggaactggtt ctttaagagt tgggggtgaa attttggcta   420
aacactatca ccaacggact                                              440
```

<210> SEQ ID NO 594
<211> LENGTH: 410
<212> TYPE: DNA
<213> ORGANISM: Glycine max

<400> SEQUENCE: 594

```
cttccttccg caaatggctt ctcacgacag catctccgct tctccaacct ccgcttctga    60
ttccgtcttc aatcaccctcg ttcgtgctcc cgaagatcct atcctcgggg taactgtcgc   120
ttagaagaaa gatccaagtc cagttaagct caacttggga gttggtgctt accgaactga   180
ggaaggaaaa cctcttgttt tgaatgtagt gaggcgagtt gaacagcaac tcataaatga   240
cgtgtcacgc aacaaggaat atattccgat cgttgggctt gctgatttta ataaattgag   300
tgctaagctt attttggggg ctgacagccc tgctattcaa gacaacaggg ttaccactgt   360
tcaatgcttg tctggaactg gttctttaac actttgcggt gaattttggg              410
```

<210> SEQ ID NO 595
<211> LENGTH: 389
<212> TYPE: DNA
<213> ORGANISM: Glycine max
<220> FEATURE:
<223> OTHER INFORMATION: unsure at all n locations

<400> SEQUENCE: 595

```
gtaattcgtg gagggaatac ttttccatta cgcacgcact ttaattacag acgagacaat    60
tataattaat agtaatacag acagcagcat gcgcccaccg gttattctca aaactacgac   120
ctctcttttg gattcttctt cttcttcacc ccctgtgat cgcagactca acactctcgc    180
tagacacttc cttccgcata tggcttctca cgacagcatc tccgcatcgc caaactccgc   240
```

| | |
|---|---|
| ttctggatcc gtcttcaagc acctcgtacg tgctcccgaa gatcctatcc tcggggtaac | 300 |
| tgtcgcttac aacaaagatc cangtccagt taagctcaac ttgggagttg gtgcataccg | 360 |
| aactgaggaa tgaaaacctc ttgttttga | 389 |

<210> SEQ ID NO 596
<211> LENGTH: 427
<212> TYPE: DNA
<213> ORGANISM: Glycine max
<220> FEATURE:
<223> OTHER INFORMATION: unsure at all n locations

<400> SEQUENCE: 596

| | |
|---|---|
| cccacgcgtc cgcccacgcg tccgcttttc tattctatta attacaggga ccatcaaaac | 60 |
| caaaaagcc aattaatagt tattcttttg gattcttatt gttcatcgca gactcaacac | 120 |
| tctctccaga cacttccttc atcaaatggc ttctcacgac ggcatctccg ctgcttcttc | 180 |
| agattccgtc ttcaatcacc tcgttcgtgc tcccgaagat cctatcctcg ggtaactgt | 240 |
| tgcttataac aaagatccaa gtccagttaa gctcaacttg ggagttggtg cttaccgaac | 300 |
| tgaggaagga aaacctcttg ttttgaatgt agtgaggcga gttgagcagc aactcataaa | 360 |
| tgacgtgtca cgcaacangg aatatattcc gattgttggg ctagctgatt ttaataaatt | 420 |
| gagtgct | 427 |

<210> SEQ ID NO 597
<211> LENGTH: 405
<212> TYPE: DNA
<213> ORGANISM: Glycine max

<400> SEQUENCE: 597

| | |
|---|---|
| taaattatgt gttcataaat tatgcaccag caactcacac aagttttgca tctttaccag | 60 |
| gaatgtggga cagaactctt actgtgaatg gattttccaa ggcctttgca atgactggtt | 120 |
| ggcggcttgg atatattgct ggtccaaaac attttgttgc agcatgtgga aagatccaaa | 180 |
| gtcagttcac ttcaggggcc agtagtatag ctcagaaagc tgcagttgct gcattaggac | 240 |
| taggccatgc tggtggggag gcagtttcta ccatggtgaa agcatttagg gagcgaaggg | 300 |
| atttcttggt aaaaagtttt agagaaatag atggtgtcaa gatatctgaa ccccagggag | 360 |
| cattttatct attccttgat ttcagcttct attatggaag agaag | 405 |

<210> SEQ ID NO 598
<211> LENGTH: 251
<212> TYPE: DNA
<213> ORGANISM: Zea mays

<400> SEQUENCE: 598

| | |
|---|---|
| ctcaactcca tggtgctcgc caacaactcg gagaacgtgc tgctcccgct caacgagccg | 60 |
| gtgctagtaa ccaagcgccg cagccagata caaacgttcc tggaccacca cggcggcccc | 120 |
| ggcgtgcagc acatggcgct ggccagcgac gacgtgctaa ggacgctgag ggagtgcacg | 180 |
| ctagctcggc catgggcggc ttcgagttca atggcgcctc caacatcgga ttattgacgg | 240 |
| cgtgtagcgg c | 251 |

<210> SEQ ID NO 599
<211> LENGTH: 115
<212> TYPE: DNA
<213> ORGANISM: Zea mays

<400> SEQUENCE: 599
agcgctggcc agcgacgacg tgctcaggac gctgagggag atgcaggcgc gctcggccat    60
gggcggcttc gagttcatgg cgcctcccac atccgactac tacgacggcg tgagg        115

<210> SEQ ID NO 600
<211> LENGTH: 368
<212> TYPE: DNA
<213> ORGANISM: Zea mays

<400> SEQUENCE: 600
aagtcacccc agccgcaaac tgcagctctg caagctacag aggccaccac gagtccacga    60
cgccacgccc tccgagagaa agagaaagag aaaaccaaag cacgataatg cccccgaccc   120
ccacagccgc cgcagccggc gccgccgtgg cggcggcatc agcagcggag caggcggcgt   180
tccgcctcgt gggccaccgc aacttcgtcc gcttcaaccc gcgctccgac cgcttccaca   240
cgctcgcgtt ccaccacgtg gagctctggt gcgccgacgc ggcctccgcc gcgggccgct   300
tctccttcgg cctgggcgcg ccgctcgccg cgcgctccga cctctccacg ggcaactccg   360
cgcacgcg                                                            368

<210> SEQ ID NO 601
<211> LENGTH: 259
<212> TYPE: DNA
<213> ORGANISM: Glycine max
<220> FEATURE:
<223> OTHER INFORMATION: unsure at all n locations

<400> SEQUENCE: 601
accgtgccgc tgatgtgttg accgttgacc agattaagca gtgtgaggag cttgggattc    60
ttgttgacag anatgatcag ggcactctgc ttcagatttt caccaagcct gttggggaca   120
ggccantcga tattcataga gataattcag aggatcgggt gcatggtgga ngatgangaa   180
gggaaggtgt acatccangg tncatgtggg ggttttggga aaggcanttt tctgagcttt   240
caaatccatt gaagatatg                                                259

<210> SEQ ID NO 602
<211> LENGTH: 269
<212> TYPE: DNA
<213> ORGANISM: Glycine max

<400> SEQUENCE: 602
gctgcctcct ccgcctccat tcccagtttc gacgccgcca cctgccttgc cttcgctgcc    60
aaacacggct tcggcgtccg cgccatcgcc ttggaagtcg ccgacgcgga agccgctttc   120
agcgccagcg tcgcgaaagg agccgagccg gcgtcgccgc cggttctcgt cgacgatcgc   180
accggcttcg cggaggtgcg cctctacggc gacgtggtgc tccgctacgt cagctacaag   240
gacgccgcgc catagcccca cacgcagat                                     269

<210> SEQ ID NO 603
<211> LENGTH: 268
<212> TYPE: DNA
<213> ORGANISM: Glycine max

<400> SEQUENCE: 603
cttgggattc ttgttgacag agatgatcag ggcactctgc ttcagatttt caccaagcct    60
gttggggaca ggccaacgat attcatagag ataattcaga ggatcgggtg catggtggag   120
gatgaggaag ggaaggtgta ccagaagggt gcatgtgggg gttttgggaa aggcaatttt   180

```
tctgagcttt tcaaatccat tgaagaatat gagaagactt tggaagctaa agaaccgcg     240 taagcacatt ggaagaacac aaatactc                                       268

<210> SEQ ID NO 604
<211> LENGTH: 257
<212> TYPE: DNA
<213> ORGANISM: Glycine max

<400> SEQUENCE: 604
gttgacagag atgatcaggg cactctgctt cagattttca ccaagcctgt tggggacagg     60
ccaacgatat tcatagagat aattcagagg atcgggtgca tggtggagga tgaggaaggg    120
aaggtgtacc agaagggtgc atgtgggggt tttgggaaag gcaattttc tgagcttttc    180 aaatccattg aagaatatga aagactttg gaagctaaaa gaaccgcgta agcacattgg    240
aagaacacaa atactcc                                                   257

<210> SEQ ID NO 605
<211> LENGTH: 265
<212> TYPE: DNA
<213> ORGANISM: Glycine max

<400> SEQUENCE: 605
taagcagtgt gaggagcttg ggattcttgt tgacagagat gatcagggca ctctgcttca     60
gattttcacc aagcctgttg gggacagggc aacgatattc atacagataa ttcagaggat    120
ccggtgcatg gtggaggatg acgaacggaa cgtgtagcag aacggtgcat gtgggggttt    180 tgggaaggc aattttctg agcttttcaa atccattgga gaatatgaga cactttggt     240 agctaaaaga accgcgtaag cacat                                          265

<210> SEQ ID NO 606
<211> LENGTH: 473
<212> TYPE: DNA
<213> ORGANISM: Glycine max

<400> SEQUENCE: 606
accggcttcg cggaggtgcg cctctacggc gacgtggtgc tccgctacgt cagctacaag     60
gacgccgcgc cgcatgcgcc acacgcagat ccgtcgcggt ggttcctgcc gggattcgag    120
gccgcggcgt cgtcgtcttc gtttccggag ctggactacg gatccggcg ctggaccac     180 gccgtcggga acgttccgga gctggcgccg gcggtgaggt acctgaaaagg cttcagcgga    240 ttccacgagt tcgcggagtt caccgtggag gacgtgggaa cgagcgagag cgggttgaac    300
tcggtggttc tggcgaacaa ctcggagacg gtgttgctgc cgctgaacga gccggtttac    360
ggaacgaaga ggaagagcca gattgagacg tatttggaac acagcgaatg tgctggtgtg    420
cagcaccttg cgcttgttac tcacgacatc ttcaccacac tgagagagat gag          473

<210> SEQ ID NO 607
<211> LENGTH: 441
<212> TYPE: DNA
<213> ORGANISM: Glycine max
<220> FEATURE:
<223> OTHER INFORMATION: unsure at all n locations

<400> SEQUENCE: 607
gccaataccc atgtgcaacg aaattcaagc ccaagcccaa gcccaagccc agcccaacc     60 tgggttgaag ctcgtcggtt gcaagaactt cgtccgaacc aatcctaagt cggaccgctt    120
tcaagtcaac cgcttccacc acatcgagtt ctggtgcacc gatgccacca acgcctctcg    180
```

```
ccgattctct tggggacttg gaatgcctat tgtggcaaaa tctgatctct ccaccggaaa    240
ccaaatccac gcctcctacc tcctccgctc cggcgacctc tccttcctct ctccgctcc    300 ttactctccc tctctctccg ccggctcctc cgctgcctcc tccgcctcca ttcccagttt    360
cgacgccgnc acctgccttg ccttcgctgc caaacacggc ttcggcgtcc gcgccatcgc    420
cttggaagtc gccgacgcgg a                                              441
```

<210> SEQ ID NO 608
<211> LENGTH: 304
<212> TYPE: DNA
<213> ORGANISM: Zea mays
<220> FEATURE:
<223> OTHER INFORMATION: unsure at all n locations
<400> SEQUENCE: 608

```
gacntggctg tccggcgccc attttcagct ccctgatctt ggcccaattg gtgagcatgg    60
nntggcttcg ccgagggatt tcctttcccc gacagcatgg tttgagcagg agcaccaccc    120
tggatacaca atagtgcaca agtatggtgg cgagctgttc agcgccacgc aggatttctc    180
tccattcaac gtggtcgcgt ggcatgggaa ttatgtccct tacaagtatg atctgagtaa    240
gttctgtcca ttcaacaccg tcctcttgga tatggcgacc gtcagtgaac acagttctaa    300
ctgc                                                                 304
```

<210> SEQ ID NO 609
<211> LENGTH: 266
<212> TYPE: DNA
<213> ORGANISM: Zea mays
<400> SEQUENCE: 609

```
gcgagatcgt cgtgatccct caaggtctcc gatttgctgt cgacttgccg gatggcccct    60
cgcgtggcta tgtctctgag atcttcggcg cccattttca gctccctgat cttggcccaa    120
ttggtgccaa tggcttggct tcgccgaggg atttcctttc ccgacagca tggtttgagc     180 aggagcacca ccctggatac acaatagtgc acaagtatgg tggcgagctg ttcagcgcca    240
cgcaggattt ctctccattc aacgtg                                         266
```

<210> SEQ ID NO 610
<211> LENGTH: 282
<212> TYPE: DNA
<213> ORGANISM: Zea mays
<400> SEQUENCE: 610

```
gtcccttaca agtatgatct gagtaagttc tgtccattca acaccgtcct cttggatcat    60
ggcgacccgt cagtgaacac agttctaact gcgccaactg ataagcctgg cgtcgcgttg    120
cttgattttg taatattccc acccagatgg ctggttgctg agaatacatt ccgcccaccc    180
tactaccacc gcaactgcat gagcgaattc atgggcctca tctatgggat gtacgaggct    240
aaggccgatg gttttcttcc tggtggcgcc agcttcacag ct                       282
```

<210> SEQ ID NO 611
<211> LENGTH: 272
<212> TYPE: DNA
<213> ORGANISM: Zea mays
<400> SEQUENCE: 611

```
ctacaccgtc tgcggcgccg gcagctcatg cctccgacac ggatacgcca tccacatgta    60
```

-continued

| | |
|---|---|
| tgctgctaac aagcccatgg atggatgctc cttgtgcaat gcggacggtg acttcctcat | 120 |
| tgttccccag caaggaaggt tattatcaca accgagtgcg aaggctgct ggtttcaccc | 180 |
| ggcgagatcg tcgtgatccc tcaaggtctc cgatttgctg tcgacttgcc ggatggcccc | 240 |
| tcgcgtggct atgtctctga gatcttcggc gc | 272 |

```
<210> SEQ ID NO 612
<211> LENGTH: 253
<212> TYPE: DNA
<213> ORGANISM: Zea mays

<400> SEQUENCE: 612
```

| | |
|---|---|
| ctacaccgtc tgcggcgccg gcagctcatg cctccgacac ggatacgcca tccacatgta | 60 |
| tgctgctaac aagcccatgg atggatgctc cttgtgcaat gcggacggtg acttcctcat | 120 |
| tgttccccag caaggaaggt ttttatcaca accgagtgcg aaggctgct ggtttcatcc | 180 |
| ggcgagatcg tcgtgatccc tcaaggtctc cgatttgctg tcgacttgcc ggatggcccc | 240 |
| tcgcgtggct atg | 253 |

```
<210> SEQ ID NO 613
<211> LENGTH: 295
<212> TYPE: DNA
<213> ORGANISM: Zea mays

<400> SEQUENCE: 613
```

| | |
|---|---|
| ctcgacaagc aatggccatg gaggaggagc agacaccacc cgagctgcgc tacctctcgg | 60 |
| gcctgggcaa caccttcacg tcggaggcgg tgccggggtc gctccccgtg gggcagaaca | 120 |
| acccgctagt gtgcccgctg ggactctacg ccgagcagct ctccggcacc tccttcacca | 180 |
| ccccgcgcgc ccggaacctg cgcacgtggc tgtaccggat caagccgtcg gtgacccacg | 240 |
| aacccttcta tccgcggaac cccaccaacg agcgcctcgt cggcgagttc gaccg | 295 |

```
<210> SEQ ID NO 614
<211> LENGTH: 293
<212> TYPE: DNA
<213> ORGANISM: Zea mays

<400> SEQUENCE: 614
```

| | |
|---|---|
| ccgttgccgg cttgccccgt ccgtgcgtcc atctgtttcc accttggatc ctcgacaagc | 60 |
| aatggccatg gaggaggagc agacaccacc cgagctgcgc tacctctcgg gcctggggca | 120 |
| acaccttcac gtcggacgcg gtgccggggt cgctccccga ggggcagaac aacccgctag | 180 |
| tgtgcccgct gggactctac gccgagcagc tctccggcac ctccttcacc acaccgcgcg | 240 |
| cccggaacct gcgcacgtgg ctgtaccgga tcaagccgtc ggtgacccac gaa | 293 |

```
<210> SEQ ID NO 615
<211> LENGTH: 449
<212> TYPE: DNA
<213> ORGANISM: Zea mays

<400> SEQUENCE: 615
```

| | |
|---|---|
| cggacgcgtg ggattgtttt gtcacaccga gaacccatac ttacctaaac tgtgtgtgtg | 60 |
| tgtgcaggtg ccaatggctt ggcttcgccg agggatttcc tttccccgac agcatggttt | 120 |
| gagcaggagc accaccctgg atacacaata gtgcacaagt atggtggcga gctgttcagc | 180 |
| gccacgcagg atttctctcc attcaacgtg gtcgcgtggc atgggaatta tgtcccttac | 240 |
| aaggtgtgtt gtatgccatt gtacacctgt ctgccattga gatgtgtgtc gctgttcact | 300 |

```
ccacccccctt ctctttcagt atgatctgag taagttctgt ccattcaaca ccgtcctctt      360
ggatcatggc gacccgtcag tgaacacagt tctaactgcg ccaactgata agcctggcgt      420
cgcgttgctt gattttgtaa tattcccac                                        449

<210> SEQ ID NO 616
<211> LENGTH: 212
<212> TYPE: DNA
<213> ORGANISM: Glycine max

<400> SEQUENCE: 616
atgaggccaa ggctgatgga tttcttcccg gtggtgcaag tctccataat tgtatgactc       60
cccatggtcc tgatacaaag tcatatgagg ctaccattgc acgaggaaat gatggaggac      120
cttgtaagat cacggacaca atggctttta tgtttgaatc gagtttgata ccccgtatca      180
gtcaatgggc cctggaatca ccgttcttgg at                                    212

<210> SEQ ID NO 617
<211> LENGTH: 269
<212> TYPE: DNA
<213> ORGANISM: Glycine max

<400> SEQUENCE: 617
cgacggtggc gagttcgtgt acctttccgg gttcggcaac cacttctcct ccgaggccct       60
cgccggagct ctgccggtgg cgcagaacag cccctcgtc tgcccgtacg gcctctacgc      120
cgagcaaatc tctggcacct ccttcacctc ccctcgcaac cgcaacctct tcagttggtt      180
ttatcggatc aagccatcgg tgactcacga accgttcaag cctagggtac tggtaatgg       240 cagaattttg agtgagttta acaactcca                                        269

<210> SEQ ID NO 618
<211> LENGTH: 269
<212> TYPE: DNA
<213> ORGANISM: Glycine max

<400> SEQUENCE: 618 cttttgtgttc actctttctc tttttttggtg ttagttcggt gaatcatgga gaacccaatc     60
gacggtggcg agttcgtgta cctttccggg ttcggcaacc acttctcctc cgaggccctc     120
gccggagctc tgccggtggc gcagaacagc cccctcgtct gcccgtacgg cctctacgcc     180
gagcaaatct ctggcacctc cttcacctcc cctcgcaacc gcaacctctt cagttggttt     240
tatcggatca agccatcggt gactcacga                                        269

<210> SEQ ID NO 619
<211> LENGTH: 285
<212> TYPE: DNA
<213> ORGANISM: Glycine max

<400> SEQUENCE: 619
attcggctcg agacaaatac taccatttcg gtgaatcatg gcgaacccaa tcgacggtgg       60
cgagttcgag tgcctttccg ggttcggcaa ccacttctcc tccgaggccc tcgccggagc     120
tctgccggcg gcgcagaaca gccccctcgt ctgcccgtac ggactatacg ccgagcaaat     180
ctccggcacc tccttcactt ctcctcgcaa ccgcaacctc ttcagttggt tttatcggat     240
caaaccatca gtgactcacg aaccgttcaa gccaagagta ccggg                      285

<210> SEQ ID NO 620
```

```
<211> LENGTH: 255
<212> TYPE: DNA
<213> ORGANISM: Glycine max
<220> FEATURE:
<223> OTHER INFORMATION: unsure at all n locations

<400> SEQUENCE: 620
gngatttaag aagttcaatt ctttactcaa actttgtgtt cactctttct cttttttggt      60
gttagttcgg tgaatcatgg agaacccaat cgacggtggc gagttcgtgt acctttccgg     120
gttcggcaac cacttctctc cgaggccctc gccggagctc tgccggtggc gcagaacagc     180
cccctcgtct gcccgtacgg cctctacgcc gagcaaatct ctggcacctc cttcacctcc     240
cctcgcaacc gcaac                                                      255

<210> SEQ ID NO 621
<211> LENGTH: 257
<212> TYPE: DNA
<213> ORGANISM: Glycine max

<400> SEQUENCE: 621
aattatgttc catatatgta tgatttaaac aaattctgcc cttataatac agttctgttt      60
gatcatagtg atccatcaat caatactgtg ttgacagcac caactgataa acctggagtg     120
gcattgcttg atttgtcat tttcccaccc agatggctgg ttgctgagca tacttttccgg     180 cctccatatt atcatcgcaa ttgcatgagt gaatttatgg gcctcattca tggtggttat     240
gaggccaagg ctgatgg                                                    257

<210> SEQ ID NO 622
<211> LENGTH: 225
<212> TYPE: DNA
<213> ORGANISM: Zea mays

<400> SEQUENCE: 622
cgagcccatc gccgtcctcg ccggggacgc gctgctctcg ctctccttcc accacatggc      60
cagcgtcggg tcctaccctc cggacgtgga ccccggagaag caccccgccc gcgtcgtccg     120
agccattggg gagctcgcgc gctgcatcgg atccgaggga ctcgtcgccg gccaggttgt     180
cgatctcgag atgacgggca catcagagac ggtgcccctc gaacg                     225

<210> SEQ ID NO 623
<211> LENGTH: 337
<212> TYPE: DNA
<213> ORGANISM: Zea mays

<400> SEQUENCE: 623
gtgccggcag cgactattcc tgatgccacg acgacaagcg tcactgagcg gacttcggtt      60
tcatctcttt tagaggttgt atcggaggac ttgctcagcc ttaacaacaa tctcaaatcg     120
cttgttggtg cagaaaatcc agttttagtt tctgcagctg aacaaattttt tggtgctggt     180 ggaaaaagat taaggccagc attggttttc ctggtgtcta gagcaactgc tgaattagct     240
ggtttgtcgg agttaactgc agaacatcga cgcttggcag agattatcga gatgattcac     300
actgcgagtt aatacatga tgatgtcata gatgata                               337

<210> SEQ ID NO 624
<211> LENGTH: 350
<212> TYPE: DNA
<213> ORGANISM: Zea mays

<400> SEQUENCE: 624
```

```
caagaccgcc gcattgctcg aggcctcggt tgtgattggg gcgatcatcg gaggcggcgc    60
tgacgagcag atcgagaggg tgtggaagta cgcgaggtcg atcgggctgc tgttccaggt   120
ggtcgacgac atactcgatg tcaccaagtc gtcagaggag ctcggcaaga cagcggggaa   180
ggacctggca agcgacaaaa cgacgtaccc taagctgctg gggctagaaa agtcgcggga   240
gttcgcggag gagttgctct ctgatgccgt atagcagctt gcttgcttcg acaaggagaa   300
ggcagcgcct ctgttgcatc tggccaacta tatcgtccat atgcacaact              350
```

<210> SEQ ID NO 625
<211> LENGTH: 245
<212> TYPE: DNA
<213> ORGANISM: Glycine max

<400> SEQUENCE: 625

```
ttgaagggtt attcagaaga ccccatttcc cctgctaggc tttttgaagt ggttgccgat    60
gatctgctaa ctctcaataa aaatcttcag tcgattgtag agcagaaaaa tccagttttg   120
atgtctgcag ctgagcagat ttttagtgct ggtggaaaga ggatgagacc agctttggtg   180
ttcttggtgt caagggcgac tgcagagtta cttggcttga aggaacttac tgcaaagcat   240
cgacg                                                              245
```

<210> SEQ ID NO 626
<211> LENGTH: 273
<212> TYPE: DNA
<213> ORGANISM: Glycine max

<400> SEQUENCE: 626

```
gctcgagcac ttgtcccgcc acaagccctt ctgtaccaat cgatcttgct aactccccaa    60
tcgcgcaaac cacgcgtgac gccgatacgc cctccgtgga caccgccacg tgctcaaacg   120
cgaaggcgag aactgccacg tcctcgtcct agaccttgtg gttggtcggc tttccgtggt   180
agaggtcgtc gttgtccata tagggcaggt tgtcgtggat gagcgccatg gtgccgttga   240
cgagctcgca tgtggtgatg cagagcacgg ggc                                273
```

<210> SEQ ID NO 627
<211> LENGTH: 270
<212> TYPE: DNA
<213> ORGANISM: Glycine max

<400> SEQUENCE: 627

```
cagagaaatt tatttgagtg gttccccggt gagaaacag ggtatccaat gttttcactt    60
ttaattttgc ctataagcaa tgtaattggt taatgcaaac aagggagccg cctttggagg   120
atcgaagcca gacaattgtt ccttggcatc ctttaacaat tcttgagcaa attcctttga   180
cttatctatc cccaatagct tgggataagt aaccttatca gccaccaaat ccttccccgc   240
cgtcttcccc aattcctccg acgacttcgt                                   270
```

NUCLEIC ACID MOLECULES ASSOCIATED WITH THE TOCOPHEROL PATHWAY

CROSS REFERENCE TO RELATED APPLICATIONS

This application is a continuation under 35 U.S.C. § 120 of U.S. application Ser. No. 09/267,199 filed Mar. 12, 1999, now abandoned herein incorporated by reference in its entirety. U.S. application Ser. No. 09/267,199 is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/267,199 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/267,199 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Serial. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/267,199 is also a continuation-in-part of U.S. application Ser. No. 09/252,974, filed Feb. 19, 1999 (abandoned), which claims the benefit of U.S. Provisional Appln. Ser. No. 60/076,709, filed Mar. 4, 1998; and to U.S. Provisional Appln. Ser. No. 60/084,684, filed May 8, 1998. U.S. application Ser. No. 09/267,199 is also a continuation-in-part of U.S. application Ser. No. 09/262,979, filed Mar. 4, 1999 (abandoned), which claims the benefit of U.S. Provisional Appln. Ser. No. 60/076,912, filed Mar. 6, 1998. U.S. application Ser. No. 09/267,199 is also a continuation-in-part of U.S. application Ser. No. 09/233,218, filed Jan. 20, 1999, now abandoned which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S.

Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Serial. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/267,199 is also a continuation-in-part of U.S. application Ser. No. 09/237,183, filed Jan. 26, 1999 which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/237,183 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/237,183 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Ser. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/237,183 is also a continuation-in-part of U.S. application Ser. No. 09/233,218, filed Jan. 20, 1999, now abandoned which is a continuation-in-part of U.S. application Ser. No. 09/198,779, filed Nov. 24, 1998 (abandoned), which claims the benefit of U.S. Provisional Appln. Ser. No. 60/067,000, filed Nov. 24, 1997; and to U.S. Provisional Appln. Ser. No. 60/066,873, filed Nov. 25, 1997; and to U.S. Provisional Appln. Ser. No. 60/069,472, filed Dec. 9, 1997; and to U.S. Provisional Appln. Ser. No. 60/074,201, filed Feb. 10, 1998; and to U.S. Provisional Appln. Ser. No. 60/074,280, filed Feb. 10, 1998; and to U.S. Provisional Appln. Ser. No. 60/074,281, filed Feb. 10, 1998; and to U.S. Provisional Appln. Ser. No. 60/074,282, filed Feb. 10, 1998; and to U.S. Provisional Appln. Ser. No. 60/074,565, filed Feb. 12, 1998; and to U.S. Provisional Appln. Ser. No. 60/074,566, filed Feb. 12, 1998; and to U.S. Provisional Appln. Ser. No. 60/074,567, filed Feb. 12, 1998; and to U.S. Provisional Appln. Ser. No. 60/074,789, filed Feb. 19, 1998; and to U.S. Provisional Appln. Ser. No. 60/075,459, filed Feb. 19, 1998; and to U.S. Provisional Appln. Ser. No. 60/075,460, filed Feb. 19, 1998; and to U.S. Provisional Appln. Ser. No. 60/075,461, filed Feb. 19, 1998; and to U.S. Provisional Appln. Ser. No. 60/075,462, filed Feb. 19, 1998; and to U.S. Provisional Appln. Ser. No. 60/075,463, filed Feb. 19, 1998; and to U.S. Provisional Appln. Ser. No. 60/075,464, filed Feb. 19, 1998; and to U.S. Provisional Appln. Ser. No. 60/077,229, filed Mar. 9, 1998; and to U.S. Provisional Appln. Ser. No. 60/077,230, filed Mar. 9, 1998; and to U.S. Provisional Appln. Ser. No. 60/077,231, filed Mar. 9, 1998; and to U.S. Provisional Appln. Ser. No. 60/078,031, filed Mar. 16, 1998; and to U.S. Provisional Appln. Ser. No. 60/078,368, filed Mar. 18, 1998; and to U.S. Provisional Appln. Ser. No. 60/080,844, filed Apr. 7, 1998; and to U.S. Provisional Appln. Ser. No. 60/083,067, filed Apr. 27, 1998; and to U.S. Provisional Appln. Ser. No. 60/083,386, filed Apr. 29, 1998; and to U.S. Provisional Appln. Ser. No. 60/083,387, filed Apr. 29, 1998; and to U.S. Provisional Appln. Ser. No. 60/083,388, filed Apr. 29, 1998; and to U.S. Provisional Appln. Ser. No. 60/083,389, filed Apr. 29, 1998; and to U.S. Provisional Appln. Ser. No. 60/084,684, filed May 8, 1998; and to U.S. Provisional Appln. Ser. No. 60/085,222, filed May 13, 1998; and to U.S. Provisional Appln. Ser. No. 60/085,223, filed May 13, 1998; and to U.S. Provisional Appln. Ser. No. 60/085,224, filed May 13, 1998; and to U.S. Provisional Appln. Ser. No. 60/085,245, filed May 13, 1998; and to U.S. Provisional Appln. Ser. No. 60/086,183, filed May 21, 1998; and to U.S. Provisional Appln. Ser. No. 60/086,184, filed May 21, 1998; and to U.S. Provisional Appln. Ser. No. 60/086,185, filed May 21, 1998; and to U.S. Provisional Appln. Ser. No. 60/086,186, filed May 21, 1998; and to U.S. Provisional Appln. Ser. No. 60/086,187, filed May 21, 1998; and to U.S. Provisional Appln. Ser. No. 60/086,188, filed May 21, 1998; and to U.S. Provisional Appln. Ser. No. 60/086,339, filed May 21, 1998; and to U.S. Provisional Appln. Ser. No. 60/089,524, filed Jun. 16, 1998; and to U.S. Provisional Appln. Ser. No. 60/089,810, filed Jun. 18, 1998; and to U.S. Provisional Appln. Ser. No. 60/089,814, filed Jun. 18, 1998; and to U.S. Provisional Appln. Ser. No. 60/091,247, filed Jun. 30, 1998; and to U.S. Provisional Appln. Ser. No. 60/092,036, filed Jul. 8, 1998; and to U.S. Provisional Appln. Ser. No. 60/099,667, filed Sep. 9, 1998; and to U.S. Provisional Appln. Ser. No. 60/099,668, filed Sep. 9, 1998; and to U.S. Provisional Appln. Ser. No. 60/099,670, filed Sep. 9, 1998; and to U.S. Provisional Appln. Ser. No. 60/099,697, filed Sep. 9, 1998; and to U.S. Provisional Appln. Ser. No. 60/100,672, filed Sep. 16, 1998; and to U.S. Provisional Appln. Ser. No. 60/100,673, filed Sep. 16, 1998; and to U.S. Provisional Appln. Ser. No. 60/100,674, filed Sep. 16, 1998; and to U.S. Provisional Appln. Ser. No. 60/101,130, filed Sep. 21, 1998; and to U.S. Provisional Appln. Ser. No. 60/101,132, filed Sep. 21, 1998; and to U.S. Provisional Appln. Ser. No. 60/108,996, filed Nov. 18, 1998; and to U.S. Provisional Appln. Ser. No. 60/109,018, filed Nov. 18, 1998. U.S. application Ser. No. 09/233,218 is also a continuation-in-part of U.S. application Ser. No. 09/227,586, filed Jan. 8, 1999 (abandoned), which claims the benefit of U.S. Provisional Appln. Ser. No. 60/071,064, filed Jan. 9, 1998; and to U.S. Provisional Appln. Ser. No. 60/090,170, filed Jun. 22, 1998; and to U.S. Provisional Appln. Ser. No. 60/092,036, filed Jul. 8, 1998. U.S. application Ser. No. 09/233,218 is also a continuation-in-part of U.S. application Ser. No. 09/229,413, filed Jan. 12, 1999 (abandoned), which claims the benefit of U.S. Appln. Ser. No. 60/071,479, filed Jan. 13, 1998; and to U.S. Provisional Appln. Ser. No. 60/085,533, filed May 15, 1998; and to U.S. Provisional Appln. Ser. No. 60/089,806, filed Jun. 18, 1998; and to U.S. Provisional Appln. Ser. No. 60/089,807, filed Jun. 18, 1998; and to U.S. Provisional Appln. Ser. No. 60/089,808, filed Jun. 18, 1998; and to U.S. Provisional Appln. Ser. No. 60/089,811, filed Jun. 18, 1998; and to U.S. Provisional Appln. Ser. No. 60/089,812, filed Jun. 18, 1998; and to U.S. Provisional Appln. Ser. No. 60/089,813, filed Jun. 18, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/099,697, filed Sep. 9, 1998; and to U.S. Provisional Appln. Ser. No. 60/100,963, filed Sep. 17, 1998; and to U.S. Provisional Appln. Ser. No. 60/101,343, filed Sep. 22, 1998; and to U.S. Provisional Appln. Serial. No. 60/101,344, filed Sep. 22, 1998; and to U.S. Provisional Appln. Ser. No. 60/101,347, filed Sep. 22, 1998; and to U.S. Provisional Appln. Ser. No. 60/101,508, filed Sep. 22, 1998; and to U.S. Provisional Appln. Ser. No. 60/101,707, filed Sep. 25, 1998; and to U.S. Provisional Appln. Ser. No. 60/104,124, filed Oct. 13, 1998; and to U.S. Provisional Appln. Ser. No. 60/104,126, filed Oct. 13, 1998; and to U.S. Provisional Appln. Ser. No. 60/104,127, filed Oct. 13, 1998; and to U.S. Provisional Appln. Ser. No. 60/104,128, filed Oct. 13, 1998; and to U.S. Provisional Appln. Ser. No. 60/111,981, filed Dec. 11, 1998. U.S. application Ser. No. 09/233,218 also claims the benefit of U.S. Provisional Appln. Ser. No. 60/072,027, filed Jan. 21, 1998; and to U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/237,183 also claims the benefit of U.S. Provisional Appln. Ser. No. 60/072,888, filed Jan. 27, 1998; and to U.S. Provisional Appln. Ser. No. 60/076,709, filed Mar. 4, 1998; and to U.S. Provisional Appln. Ser. No. 60/076,912, filed Mar. 6, 1998; and to U.S. Provisional Appln. Ser. No. 60/078,031, filed Mar. 16, 1998;

and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. U.S. application Ser. No. 09/267,199 also claims the benefit of U.S. Provisional Appln. Ser. No. 60/078,031, filed Mar. 16, 1998; and to U.S. Provisional Appln. Ser. No. 60/083,390, filed Apr. 29, 1998; and to U.S. Provisional Appln. Ser. No. 60/084,684, filed May 8, 1998; and to U.S. Provisional Appln. Ser. No. 60/085,057, filed May 8, 1998; and to U.S. Provisional Appln. Ser. No. 60/085,429, filed May 8, 1998; and to U.S. Provisional Appln. Ser. No. 60/085,245, filed May 13, 1998; and to U.S. Provisional Appln. Ser. No. 60/085,533, filed May 15, 1998; and to U.S. Provisional Appln. Ser. No. 60/085,940, filed May 19, 1998; and to U.S. Provisional Appln. Ser. No. 60/086,339, filed May 21, 1998; and to U.S. Provisional Appln. Ser. No. 60/086,594, filed May 22, 1998; and to U.S. Provisional Appln. Ser. No. 60/086,608, filed May 22, 1998; and to U.S. Provisional Appln. Ser. No. 60/087,422, filed Jun. 1, 1998; and to U.S. Provisional Appln. Ser. No. 60/087,631, filed Jun. 2, 1998; and to U.S. Provisional Appln. Ser. No. 60/087,762, filed Jun. 2, 1998; and to U.S. Provisional Appln. Ser. No. 60/087,972 filed Jun. 4, 1998; and to U.S. Provisional Appln. Ser. No. 60/087,973 filed Jun. 4, 1998; and to U.S. Provisional Appln. Ser. No. 60/088,441, filed Jun. 8, 1998; and to U.S. Provisional Appln. Ser. No. 60/089,627, filed Jun. 16, 1998; and to U.S. Provisional Appln. Ser. No. 60/089,789, filed Jun. 18, 1998; and to U.S. Provisional Appln. Ser. No. 60/090,170, filed Jun. 22, 1998; and to U.S. Provisional Appln. Ser. No. 60/090,856, filed Jun. 26, 1998; and to U.S. Provisional Appln. Ser. No. 60/090,928, filed Jun. 26, 1998; and to U.S. Provisional Appln. Ser. No. 60/091,035, filed Jun. 29, 1998; and to U.S. Provisional Appln. Ser. No. 60/091,247, filed Jun. 30, 1998; and to U.S. Provisional Appln. Ser. No. 60/091,405, filed Jun. 30, 1998; and to U.S. Provisional Appln. Ser. No. 60/092,036, filed Jul. 8, 1998; and to U.S. Provisional Appln. Ser. No. 60/100,963, filed Sep. 17, 1998; and to U.S. Provisional Appln. Ser. No. 60/110,108, filed Nov. 25, 1998; and to U.S. Provisional Appln. Ser. No. 60/110,109, filed Nov. 25, 1998; and to U.S. Provisional Appln. Ser. No. 60/111,033, filed Dec. 4, 1998; and to U.S. Provisional Appln. Ser. No. 60/111,742, filed Dec. 10, 1998. All of the above-listed applications are herein incorporated by reference in their entirety.

INCORPORATION OF SEQUENCE LISTING

This application contains a sequence listing, which is contained on three identical CD-ROMs: two copies of the sequence listing (Copy 1 and Copy 2) and a sequence listing Computer Readable Form (CRF), all of which are herein incorporated by reference. All three CD-ROMs each contain one file called "15092C seq list.txt" which is 311,296 bytes in size (measured in Windows XP) and which was created on Jan. 11, 2006.

FIELD OF THE INVENTION

The present invention is in the field of plant biochemistry. More specifically the invention relates to nucleic acid sequences from plant cells, in particular, nucleic acid sequences from maize and soybean plants associated with the tocopherol synthesis pathway in plants. The invention encompasses nucleic acid molecules that encode proteins and fragments of proteins. In addition, the invention also encompasses proteins and fragments of proteins so encoded and antibodies capable of binding these proteins or fragments. The invention also relates to methods of using the nucleic acid molecules, proteins and fragments of proteins and antibodies, for example for genome mapping, gene identification and analysis, plant breeding, preparation of constructs for use in plant gene expression and transgenic plants.

BACKGROUND OF THE INVENTION

I. Tocopherol Synthesis Pathway

The chloroplast of higher plants exhibit interconnected biochemical pathways that lead to secondary metabolites, including tocopherols, that not only perform functions in plants but can also be important for mammalian nutrition. In plastids, tocopherols account up to 40% of the total quinone pool. The biosynthetic pathway of $\alpha$-tocopherol in higher plants involves condensation of homogentisic acid and phytylpyrophosphate to form 2-methyl-6 phytylbenzoquinol (Fiedler et al., *Planta* 155: 511-515 (1982); Soll et al., *Arch. Biochem. Biophys.* 204: 544-550 (1980); Marshall et al., *Phytochem.* 24: 1705-1711 (1985), all of which are herein incorporated by reference in their entirety). The plant tocopherol biosynthetic pathway can be divided into four parts: synthesis of homogentisic acid, which contributes to the aromatic ring of tocopherol; synthesis of phytylpyrophosphate, which contributes to the side chain of tocopherol; cyclization which plays a role in chirality and chromanol substructure of the vitamin E family; and S-adenosyl methionine dependent methylation of an aromatic ring, which effects the compositional quality of the vitamin E family.

Homogentisate is an aromatic precursor in the biosynthesis of tocopherols in chloroplasts and is formed from the aromatic shikimate metabolite, p-hydroxyphenylpyruvate. The aromatic amino acids phenylalanine, tyrosine, and tryptophan are formed by a reaction sequence that initiates from the two carbohydrate precursors, D-erythrose 4-phosphate and phosphoenolpyruvate, via shikimate, and forms prearomatic and aromatic compounds (Bentley, *Critical Rev. Biochem. Mol. Biol.* 25: 307-384 (1990), the entirety of which is herein incorporated by reference). Approximately 20% of the total carbon fixed by green plants is routed through the shikimate pathway with end products being aromatic amino acids and other aromatic secondary metabolites such as flavonoids, vitamins, lignins, alkaloids, and phenolics (Herrmann, *Plant Physiol.* 107: 7-12 (1995), Kishore and Shah, *Ann. Rev. Biochem.* 57:67-663 (1988), both of which are herein incorporated by reference in their entirety). Various aspects of the shikimate pathway have been reviewed (Bentley, *Critical Rev. Biochem. Mol. Biol.* 25: 307-384 (1990); Herrmann, *Plant Physiol.* 107: 7-12 (1995); Kishore and Shah, *Ann. Rev. Biochem.* 57:67-663 (1988)).

The first reported committed reaction in the shikimate pathway is catalyzed by the enzyme 3-deoxyarabino-heptulosonate 7-phosphate synthase (also known as 3-deoxy-D-arabino-heptulosonate 7-phosphate synthase, deoxyarabino-heptulosonate-P-synthase, and DAHP synthase (EC. 4.1.2.15)), which has been reported to control carbon flow into the shikimate pathway. The plastid localized DAHP synthase catalyzes the formation of 3-deoxy-D-arabino-heptulosonate 7-phosphate by condensing D-erythrose 4-phosphate with phosphoenolpyruvate. DAHP synthase has been isolated from plant sources including carrot and potato. DAHP synthase has substrate specificity for D-erythrose 4-phosphate and phosphoenolpyruvate, is a dimer of subunits having a molecular weight of 53 KD and is activated by $Mn^{2+}$ (Herrmann, *Plant Physiol.* 107: 7-12 (1995)). Aromatic amino acids are not reported to act as feedback regulators. Purified DAHP synthase is activated by tryptophan and, to a lesser extent, by tyrosine in a hysteric fashion (Suzich et al., *Plant Physiol.* 79: 765-770 (1985), the entirety of which is herein incorporated by reference).

The next reported enzyme in the shikimate pathway is 3-dehydroquinate synthase (EC 4.6.1.3), which catalyzes the formation of dehydroquinate, the first carbocyclic metabolite in the biosynthesis of aromatic amino acids, from the substrates D-erythrose 4-phosphate and phosphoenolpyruvate. The enzyme reaction involves a NAD (nicotinamide adenine dinucleotide) cofactor dependent oxidation-reduction, β-elimination, and an intramolecular aldol condensation. 3-dehydroquinate synthase has been purified from *Phaseolus mungo* seedlings and pea seedlings, has a native molecular weight of 66 KD and is a dimer (Yamamoto, *Phytochem.* 19: 779-802 (1980); Pompliano et al., *J. Am. Chem. Soc.* 111: 1866-1871-1871 (1989), both of which are herein incorporated by reference in their entirety).

3-dehydroquinate dehydratase (EC 4.2.1.10) catalyzes the stereospecific syn-dehydration of dehydroquinate to dehydroshikimate and has been reported to be responsible for initiating the process of aromatization by introducing the first of three double bonds of the aromatic ring system. 3-dehydroquinate dehydratase has been cloned from *E. coli* (Duncan et al., *Biochem. J.* 238:475-483 (1986), the entirety of which is herein incorporated by reference).

Shikimate dehydrogenase (EC 1.1.1.25) catalyzes the NADPH (reduced nicotinamide adenine dinucleotide phosphate)-dependent conversion of dehydroshikimate to shikimate. Bifunctional 3-dehydroquinate dehydratase-shikimate dehydrogenase has been reported in spinach, pea seedling, and Maize (Bentley, *Critical Rev. Biochem. Mol. Biol.* 25: 307-384 (1990), Kishore and Shah, *Ann. Rev. Biochem.* 57:67-663 (1988)). *E. coli* shikimate dehydrogenase has been reported to be a monomeric, monofunctional protein with a molecular weight of 32,000 daltons (Chaudhuri and Coggins, *Biochem. J.* 226:217-223 (1985), the entirety of which is herein incorporated by reference).

Shikimate kinase (EC 2.7.1.71) catalyzes the phosphorylation of shikimate to shikimate-3-phosphate. Shikimate kinase exists as isoforms in *E. coli* and *S. typhimurium*. Plant shikimate kinase has been partially purified from mung bean and sorghum (Bentley, *Critical Rev. Biochem. Mol. Biol.* 25: 307-384 (1990); Kishore and Shah, *Ann. Rev. Biochem.* 57:67-663 (1988)). Certain plant species accumulate shikimate and shikimate kinase may play a role in regulating flux in the tocopherol synthesis pathway.

5-Enolpyruvyl-shikimate-3-phosphate synthase (also known as enolpyruvyl-shikimate-P-synthase, and EPSPS (EC 2.5.1.19)) catalyzes the reversible transfer of the carboxyvinyl moiety of phosphoenolpyruvate to shikimate-3-phosphate, yielding 5-enolpyruvyl-shikimate-3-phosphate. 5-Enolpyruvyl-shikimate-3-phosphate synthase is a target of the broad spectrum, nonselective, postemergence herbicide, glyphosate. Chemical modification studies indicate that lysine, arginine, and histidine residues are essential for activity of the enzyme (Kishore and Shah, *Ann. Rev. Biochem.* 57:67-663 (1988)). 5-Enolpyruvyl-shikimate-3-phosphate synthase has been isolated and characterized from microbial and plant sources including tomato, petunia, *Arabidopsis*, and *Brassica* (Kishore and Shah, *Ann. Rev. Biochem,* 57:67-663 (1988)).

Chorismate synthase (EC 4.6.1.4) catalyzes the conversion of 5-enolpyruvyl-shikimate-3-phosphate to chorismic acid and introduces a second double bond in an aromatic ring and a trans-1,4-elimination of inorganic phosphorous. Chorismate is the last reported common intermediate in the biosynthesis of aromatic compounds via the shikimate pathway. The enzyme reaction involves no change in the oxidation state of the substrate. Chorismate synthase from various sources requires a reduced flavin cofactor, FMNH2 (reduced flavin mononucleotide) or FADH2 (reduced flavin adenine dinucleotide), for catalytic activity (Bentley, *Critical Rev. Biochem. Mol. Biol.* 25: 307-384 (1990); Kishore and Shah, *Ann. Rev. Biochem.* 57:67-663 (1988)).

The next reported enzyme in the tocopherol biosynthetic pathway is chorismate mutase (EC 5.4.99.5), which catalyzes the conversion of chorismic acid to prephenic acid. Chorismic acid is a substrate for a number of enzymes involved in the biosynthesis of aromatic compounds. Plant chorismate mutase exists in two isoforms, chorismate mutase-1 and chorismate mutase-2, that differ in feedback regulation by aromatic amino acids (Singh et al., *Arch. Biochem. Biophys.* 243: 374-384 (1985); Goers et al., *Planta* 162: 109-124 (1984), both of which are herein incorporated by reference in their entirety). It has been reported that chloroplastic chorismate mutase-1 may play a role in biosynthesis of aromatic amino acids as this enzyme is activated by tyrosine and phyenlalanine. Cytosolic isozyme chorismate mutase-2 is not regulated by aromatic amino acids and may play a role in providing the aromatic nucleus for synthesis of aromatic secondary metabolites including tocopherol (d'Amato et al., *Planta,* 162: 104-108 (1984), the entirety of which is herein incorporated by reference).

The metabolic pathways branch after prephenic acid and lead not only to phenylalanine and tyrosine, but also to a number of secondary metabolites. Tyrosine is synthesized from prephenate via either 4-hydroxyphenylpyruvate or arogenate. Both routes have been reported in plants (Bentley, *Critical Rev. Biochem. Mol. Biol.* 25: 307-384 (1990)).

The formation of 4-hydroxyphenylpyruvate from prephenate is catalyzed by prephenate dehydrogenase (EC 1.3.1.12 for NAD specific prephenate dehydrogenase and EC 1.3.1.13 for NADP specific prephenate dehydrogenase). 4-Hydroxyphenylpyruvate associated with tocopherol biosynthesis may also come from tyrosine pool by the action of tyrosine transaminase (EC 2.6.1.5) or L-amino acid oxidase (EC 1.4.3.2). Tyrosine transaminase catalyzes the pyridoxal-phosphate dependent conversion of L-tyrosine to 4-hydroxyphenylpyruvate. This reversible enzyme reaction transfers the amino group of tyrosine to 2-oxoglutarate to form 4-hydroxyphenylpyruvate and glutamate. L-amino acid oxidase (EC 1.4.3.2) catalyzes the conversion of tyrosine to 4-hydroxyphenylpyruvate by acting on the amino group of tyrosine with oxygen acting as an acceptor. L-amino acid oxidase is not specific to tyrosine. In *E. coli*, aromatic amino acid amino transferase (also referred to as aromatic-amino-acid transaminase (EC 2.6.1.57)) converts 4-hydroxyphenylpyruvate to tyrosine and plays a role in phenylalanine and tyrosine biosynthesis (Oue et al., *J. Biochem. (Tokyo)* 121: 161-171 (1997); Soto-Urzua et al., *Can. J. Microbiol.* 42: 294-298 (1996); Hayashi et al., *Biochemistry* 32: 12229-12239 (1993), all of which are herein incorporated by reference in their entirety).

Aspartic acid amino transferase or transaminase A (EC 2.6.1.1) exhibits a broad substrate specificity and may utilize phenylpyruvate or p-hydroxyphenylpyruvate to form phenylalanine and tyrosine, respectively. Transaminase A has been characterized in *Aradidopsis* (Wilkie et al., *Biochem J.* 319: 969-976 (1996); Wilkie et al., *Plant Mol. Biol.* 27: 1227-1233 (1995), both of which are herein incorporated by reference in their entirety), rice (Song et al., *DNA Res.* 3: 303-310 (1996), herein incorporated by reference in its entirety), *Panicum miliaceum* L (Taniguchi et al., *Arch. Biochem. Biophys.* 318: 295-306 (1995), herein incorporated by reference in its entirety), *Lupinus angustifolius* (Winefield et al., *Plant Physiol.* 104: 417-423 (1994), herein incorporated by reference in its entirety), and soybean (Wadsworth et al., *Plant Mol. Biol.* 21: 993-1009 (1993), herein incorporated by reference in its entirety).

A precursor molecule, homogentisic acid, is produced in the chloroplast from the shikimate pathway intermediate p-hydroxyphenylpyruvate. p-Hydroxyphenylpyruvate dioxygenase (also known as 4-hydroxyphenylpyruvate dioxygenase (EC 1.13.11.27)) catalyzes the formation of homogentisate from hydroxyphenylpyruvate through an oxidative decarboxylation of the 2-oxoacid side chain accompanied by hydroxylation of the aromatic ring and a 1,2 migration of the carboxymethyl group. Norris et al. reported functional identification of a pdsI gene that encodes p-Hydroxyphenylpyruvate dioxygenase (Norris et al., *Plant Cell* 7: 2139-2149 (1995), the entirety of which is herein incorporated by reference). p-Hydroxyphenylpyruvate dioxygenase has been cloned from *Arabidopsis* and carrot (GENBANK accession numbers U89267, AF000228, and U87257; Garcia et al., *Biochem. J.* 325: 761-769 (1997), herein incorporated by reference in its entirety). Fiedler et al. reported the localization and presence of this enzyme in both isolated spinach chloroplast and the peroxisome (Fiedler et al., *Planta*, 155: 511-515 (1982)). Garcia et al. reported the purification of the cytosolic form of hydroxyphenylpyruvate dioxygenase from cultured carrot protoplast (Garcia et al., *Biochem. J.* 325: 761-769 (1997), the entirety of which is herein incorporated by reference). It has been reported that the chloroplastic isoform may be involved in the biosynthesis of prenylquinones, and that the peroxisomal and cytosolic isoform may be involved in the degradation of tyrosine.

The carbon flow to the pool of phytol, i.e., the isoprene-derived side chain of tocopherol, occurs via the mevalonate pathway or non-mevalonate pathway. Geranylgeranyl-pyrophosphate synthase (GGPP synthase (EC 2.5.1.29)) catalyzes the formation of geranylgeranylpyrophosphate by prenyl-transferring an isoprene moiety from isopentenylpyrophosphate to farnesylpyrophosphate. A gene encoding geranylgeranyl-pyrophosphate synthase has been isolated from *Arabidopsis* and *Cantharanthus roseus* (Zhu et al., *Plant Cell Physiol.* 38: 357-361 (1997), Bantignies et al., *Plant Physiol.* 110: 336-336 (1995), both of which are herein incorporated by reference in their entirety). Geranylgeranylpyrophosphate synthesized by GGPP synthase is used in the carotenoid and tocopherol biosynthesis pathways.

The NADPH-dependent hydrogenation of geranylgeranylpyrophosphate is catalyzed by geranylgeranylpyrophosphate hydrogenase (also called geranylgeranylpyrophosphate reductase) to form phytylpyrophosphate (Soll et al., *Plant Physiol.* 71: 849-854 (1983), the entirety of which is herein incorporated by reference). Geranylgeranylpyrophosphate hydrogenase appears to be localized to two sites: the chloroplast envelope and the thylakoids. The chloroplast envelope form is reported to be responsible for the hydrogenation of geranylgeranylpyrophosphate to a phytyl moiety. The thylakoids form is reported to be responsible for the stepwise reduction of chlorophyll esterified with geranylgeraniol to chlorophyll esterified with phytol. The chloroplast envelope form of geranylgeranylpyrophosphate may play a role in tocopherol and phylloquinone synthesis. A chlP gene cloned from *Synechocystis* has been functionally assigned by complementation in *Rhodobactor sphaeroids* to catalyze the stepwise hydrogenation of geranylgeraniol to phytol (Addlesse et al., *FEBS Lett.* 389: 126-130 (1996), the entirety of which is herein incorporated by reference).

Homogentisate:phytyl transferase (also referred to as phytyl/prenyltransferase) catalyzes the decarboxylation followed by condensation of homogentisic acid with a phytol moiety from phytylpyrophosphate to form 2-methyl-6 phytylbenzoquinol. Prenyltransferase activity has been reported in spinach chloroplasts and such activity is located in chloroplast envelope membranes (Fiedler et al., *Planta* 155: 511-515 (1982)). A reported prenyltransferase gene, termed pdsII, specific to tocopherol biosynthesis has been identified in *Arabidopsis* (Norris et al., *Plant Cell* 7: 2139-2149 (1995)).

Tocopherol cyclase catalyzes the cyclization of 2,3-dimethyl-6-phytylbenzoquinol to form γ-tocopherol and plays a role in the biosynthesis of enantioselective chromanol substructure of the vitamin E subfamily (Stocker et al., *Bioorg. Medic. Chem.* 4: 1129-1134 (1996), the entirety of which is herein incorporated by reference). The preferred substrate specificity of tocopherol cyclase may be either 2,3-dimethyl-6-phytylbenzoquinol or 2-methyl-5-phytylbenzoquinol or both. The substrate, 2-methyl-6 phytylbenzoquinol, is formed by prenyltransferase and requires methylation by an S-adenosylmethionine-dependent methyltransferase before cyclization. Tocopherol cyclase has been purified from green algae chlorella protothecoids, *Dunaliella salina* and from wheat leafs (U.S. Pat. No. 5,432,069, the entirety of which is herein incorporated by reference.

Synthesis of γ-tocopherol from 2-methyl-6 phytylbenzoquinol occurs by two pathways with either δ-tocopherol or 2,3 dimethyl-5-phytylbenzoquinol acting as an intermediate. α-Tocopherol is then synthesized from γ-tocopherol in a final methylation step with S-adenosylmethionine. These steps of α-tocopherol biosynthesis are located in the chloroplast membrane in higher plants. Formation of α-tocopherol from other tocopherols is catalyzed by S-adenosyl methionine (SAM)-dependent γ-tocopherol methyltransferase (EC 2.1.1.95). This enzyme has been partially purified from *Cap-* sicum and *Euglena gracilis* (Shigeoka et al., *Biochim. Biophys. Acta* 1128: 220-226 (1992), d'Harlingue and Camara, *J. Biol. Chem.* 260: 15200-15203 (1985), both of which are herein incorporated by reference in their entirety).

Tocotrienols are similar to tocopherols in molecular structure except that there are three double bonds in the isoprenoid side chain. Although tocotrienols have not been reported in soybean, they are found within in the plant kingdom. The tocotrienol biosynthetic pathway is similar to that of tocopherol up to the formation of homogentisic. It has been reported that homgentisate:phytyl transferase is able to transfer geranylgeranyl-pyrophosphate ("GGPP") to homogentisic acid. A side chain of GGPP may be desaturated by the addition of phytylpyrophosphate to homogentisate. Stocker et al. report that a reduction of the side chain's double bond occurs at an earlier stage of the biosynthesis. Phytylpyrophosphate or GGPP are condensed with homogentisic acid ("HGA") to yield different hydroquinone precursors which are cyclyzed by the same enzyme (Stocker et al., *Bioorg. Medicinal Chem.* 4:1129-1134 (1996), the entirety of which is herein incorporated by reference).

The primary oxidation product of tocopherol is tocopheryl quinone, which can be conjugated to yield glucuronate after prior reduction to the hydroquinone. In animals, glucuronate can be excreted into bile or further catabolized to tocopheronic acid in the kidney and processed for urinary excretion (Traber and Sies, *Ann. Rev. Nutr.* 16:321-347 (1996), the entirety of which is herein incorporated by reference).

In *Aspergillus nidulans*, the aromatic amino acid catabolic pathway involves formation of homogentisic acid followed by aromatic ring cleavage by an homogentisic acid dioxygenase (EC 1.13.11.5) to yield, after an isomerization step, fumarylacetoacetate (Fernandez-Canon et al., *Anal. Biochem.* 245: 218-22 (1997); Hudecova et al., *Int. J. Biochem. Cell Biol.* 27: 1357-1363 (1995); Fernandez-Canon et al., *J. Biol. Chem.* 270: 21199-21205 (1995), all of which are herein incorporated by reference in their entirety). Fumarylacetoacetate, is then split by fumarylacetoacetate (Fernandez-Canon and Penalva, *J. Biol. Chem.* 270:21199-21205 (1995), the entirety of which is herein incorporated by reference). Homogentisic acid dioxygenase uses a tocopherol biosynthetic metabolite homogentisic acid for hydrolysis.

Tocopherol levels are reported to vary in different plants, tissues, and developmental stages. The production of homogentisic acid by p-hydroxyphenylpyruvate dioxygenase may be a regulatory point for bulk flow through the pathway due to the irreversible nature of the enzyme reaction and due to the fact that homogentisic acid production is the first committed step in tocopherol biosynthesis (Norris et al., *Plant Cell* 7: 2139-2149 (1995)). Another regulatory step in tocopherol biosynthesis may be associated with the availability of phytylpyrophosphate pool. Feeding studies in Safflower callus culture showed 1.8-fold and 18-fold increase in tocopherol synthesis by feeding homogentisate and phytol, respectively (Fury et al., *Phytochem.* 26: 2741-2747 (1987), the entirety of which is herein incorporated by reference). In meadow rescue leaf, vitamin E increases in the initial phase of senescence when phytol is cleaved off from the chlorophylls and when a free phytol pool is available (Peskier et al., *J. Plant Physiol.* 135: 428-432 (1989), the entirety of which is herein incorporated by reference).

II. Expressed Sequence Tag Nucleic Acid Molecules

Expressed sequence tags, or ESTs are randomly sequenced members of a cDNA library (or complementary DNA)(McCombie et al., *Nature Genetics* 1:124-130 (1992); Kurata et al., *Nature Genetics* 8: 365-372 (1994); Okubo, et al. *Nature Genetics* 2: 173-179 (1992), all of which references are incorporated herein in their entirety). The randomly selected clones comprise insets that can represent a copy of up to the full length of a mRNA transcript.

Using conventional methodologies, cDNA libraries can be constructed from the mRNA (messenger RNA) of a given tissue or organism using poly dT primers and reverse transcriptase (Efstratiadis et al. *Cell* 7:279-288 (1976), the entirety of which is herein incorporated by reference; Higuchi et al., *Proc. Natl. Acad. Sci.* (*U.S.A.*) 73:3146-3150 (1976), the entirety of which is herein incorporated by reference; Maniatis et al., *Cell* 8:163-182 (1976) the entirety of which is herein incorporated by reference; Land et al., *Nucleic Acids Res.* 9:2251-2266 (1981), the entirety of which is herein incorporated by reference; Okayama et al., *Mol. Cell. Biol.* 2:161-170 (1982), the entirety of which is herein incorporated by reference; Gubler et al., *Gene* 25:263-269 (1983), the entirety of which is herein incorporated by reference).

Several methods may be employed to obtain full-length cDNA constructs. For example, terminal transferase can be used to add homopolymeric tails of dC residues to the free 3' hydroxyl groups (Land et al., *Nucleic Acids Res.* 9:2251-2266 (1981), the entirety of which is herein incorporated by reference). This tail can then be hybridized by a poly dG oligo which can act as a primer for the synthesis of full length second strand cDNA. Okayama and Berg, *Mol. Cell. Biol.* 2: 161-170 (1982), the entirety of which is herein incorporated by reference, report a method for obtaining full length cDNA constructs. This method has been simplified by using synthetic primer-adapters that have both homopolymeric tails for priming the synthesis of the first and second strands and restriction sites for cloning into plasmids (Coleclough et al., *Gene* 34:305-314 (1985), the entirety of which is herein incorporated by reference) and bacteriophage vectors (Krawinkel et al., *Nucleic Acids Res.* 14:1913 (1986), the entirety of which is herein incorporated by reference; Han et al., *Nucleic Acids Res.* 15:6304 (1987), the entirety of which is herein incorporated by reference).

These strategies have been coupled with additional strategies for isolating rare mRNA populations. For example, a typical mammalian cell contains between 10,000 and 30,000 different mRNA sequences (Davidson, *Gene Activity in Early Development*, 2nd ed., Academic Press, New York (1976). The number of clones required to achieve a given probability that a low-abundance mRNA will be present in a cDNA library is $N=(\ln(1-P))/(\ln(1-1/n))$ where N is the number of clones required, P is the probability desired, and 1/n is the fractional proportion of the total mRNA that is represented by a single rare mRNA (Sambrook et al., *Molecular Cloning: A Laboratory Manual*, 2nd ed., Cold Spring Harbor Laboratory Press (1989), the entirety of which is herein incorporated by reference).

A method to enrich preparations of mRNA for sequences of interest is to fractionate by size. One such method is to fractionate by electrophoresis through an agarose gel (Pennica et al., *Nature* 301:214-221 (1983), the entirety of which is herein incorporated by reference). Another such method employs sucrose gradient centrifugation in the presence of an agent, such as methylmercuric hydroxide, that denatures secondary structure in RNA (Schweinfest et al., *Proc. Natl. Acad. Sci.* (*U.S.A.*) 79:4997-5000 (1982), the entirety of which is herein incorporated by reference).

A frequently adopted method is to construct equalized or normalized cDNA libraries (Ko, *Nucleic Acids Res.* 18:5705-5711 (1990), the entirety of which is herein incorporated by reference; Patanjali, S. R. et al., *Proc. Natl. Acad. Sci.* (*U.S.A.*) 88:1943-1947 (1991), the entirety of which is herein incorporated by reference). Typically, the cDNA population is normalized by subtractive hybridization (Schmid et al., *J. Neurochem.* 48:307-312 (1987) the entirety of which is herein incorporated by reference; Fargnoli et al., *Anal. Biochem.* 187:364-373 (1990) the entirety of which is herein incorporated by reference; Travis et al., *Proc. Natl. Acad. Sci (U.S.A.)* 85:1696-1700 (1988) the entirety of which is herein incorporated by reference; Kato, *Eur. J. Neurosci.* 2:704-711 (1990); and Schweinfest et al., *Genet. Anal. Tech. Appl.* 7:64-70 (1990), the entirety of which is herein incorporated by reference). Subtraction represents another method for reducing the population of certain sequences in the cDNA library (Swaroop et al., *Nucleic Acids Res.* 19:1954 (1991), the entirety of which is herein incorporated by reference).

ESTs can be sequenced by a number of methods. Two basic methods may be used for DNA sequencing, the chain termination method of Sanger et al., *Proc. Natl. Acad. Sci. (U.S.A.)* 74: 5463-5467 (1977), the entirety of which is herein incorporated by reference, and the chemical degradation method of Maxam and Gilbert, *Proc. Nat. Acad. Sci. (U.S.A.)* 74: 560-564 (1977), the entirety of which is herein incorporated by reference. Automation and advances in technology such as the replacement of radioisotopes with fluorescence-based sequencing have reduced the effort required to sequence DNA (Craxton, *Methods* 2: 20-26 (1991), the entirety of which is herein incorporated by reference; Ju et al., *Proc. Natl. Acad. Sci. (U.S.A.)* 92: 4347-4351 (1995), the entirety of which is herein incorporated by reference; Tabor and Richardson, *Proc. Natl. Acad. Sci. (U.S.A.)* 92: 6339-6343 (1995), the entirety of which is herein incorporated by reference). Automated sequencers are available from, for example, Pharmacia Biotech, Inc., Piscataway, N.J. (Pharmacia ALF), LI-COR, Inc., Lincoln, Nebr. (LI-COR 4,000) and Millipore, Bedford, Mass. (Millipore BaseStation).

In addition, advances in capillary gel electrophoresis have also reduced the effort required to sequence DNA and such advances provide a rapid high resolution approach for sequencing DNA samples (Swerdlow and Gesteland, *Nucleic Acids Res.* 18:1415-1419 (1990); Smith, *Nature* 349:812-813 (1991); Luckey et al., *Methods Enzymol.* 218:154-172 (1993); Lu et al., *J. Chromatog. A.* 680:497-501 (1994); Carson et al., *Anal. Chem.* 65:3219-3226 (1993); Huang et al., *Anal. Chem* 64:2149-2154 (1992); Kheterpal et al., *Electrophoresis* 17:1852-1859 (1996); Quesada and Zhang, *Electrophoresis* 17:1841-1851 (1996); Baba, *Yakugaku Zasshi* 117: 265-281 (1997), all of which are herein incorporated by reference in their entirety).

ESTs longer than 150 nucleotides have been found to be useful for similarity searches and mapping (Adams et al., *Science* 252:1651-1656 (1991), herein incorporated by reference). ESTs, which can represent copies of up to the full length transcript, may be partially or completely sequenced. Between 150-450 nucleotides of sequence information is usually generated as this is length of sequence information that is routinely and reliably produced using single run sequence data. Typically, only single run sequence data is obtained from the cDNA library (Adams et al., *Science* 252: 1651-1656 (1991). Automated single run sequencing typically results in an approximately 2-3% error or base ambiguity rate (Boguski et al., *Nature Genetics* 4:332-333 (1993), the entirety of which is herein incorporated by reference).

EST databases have been constructed or partially constructed from, for example, *C. elegans* (McCombrie et al., *Nature Genetics* 1:124-131 (1992)), human liver cell line HepG2 (Okubo et al., *Nature Genetics* 2:173-179 (1992)), human brain RNA (Adams et al., *Science* 252:1651-1656 (1991)); Adams et al., *Nature* 355:632-635 (1992)), *Arabidopsis*, (Newman et al., *Plant Physiol.* 106:1241-1255 (1994)); and rice (Kurata et al., *Nature Genetics* 8:365-372 (1994)).

III. Sequence Comparisons

A characteristic feature of a protein or DNA sequence is that it can be compared with other known protein or DNA sequences. Sequence comparisons can be undertaken by determining the similarity of the test or query sequence with sequences in publicly available or proprietary databases ("similarity analysis") or by searching for certain motifs ("intrinsic sequence analysis")(e.g. cis elements) (Coulson, *Trends in Biotechnology* 12: 76-80 (1994), the entirety of which is herein incorporated by reference); Birren et al., *Genome Analysis* 1: Cold Spring Harbor Laboratory Press, Cold Spring Harbor, N.Y. 543-559 (1997), the entirety of which is herein incorporated by reference).

Similarity analysis includes database search and alignment. Examples of public databases include the DNA Database of Japan (DDBJ)(available on the Worldwide Web at ddbj.nig.ac.jp/); Genebank (available on the Worldwide Web at ncbi.nlm.nih.gov/Web/Search/Index.html); and the European Molecular Biology Laboratory Nucleic Acid Sequence Database (EMBL) (available on the Worldwide Web at ebi-.ac.uk/ebi_docs/embl_db/embl-db.html). A number of different search algorithms have been developed, one example of which are the suite of programs referred to as BLAST programs. There are five implementations of BLAST, three designed for nucleotide sequences queries (BLASTN, BLASTX, and TBLASTX) and two designed for protein sequence queries (BLASTP and TBLASTN) (Coulson, *Trends in Biotechnology* 12: 76-80 (1994); Birren et al., *Genome Analysis* 1: Cold Spring Harbor Laboratory Press, Cold Spring Harbor, N.Y. 543-559 (1997)).

BLASTN takes a nucleotide sequence (the query sequence) and its reverse complement and searches them against a nucleotide sequence database. BLASTN was designed for speed, not maximum sensitivity, and may not find distantly related coding sequences. BLASTX takes a nucleotide sequence, translates it in three forward reading frames and three reverse complement reading frames, and then compares the six translations against a protein sequence database. BLASTX is useful for sensitive analysis of preliminary (single-pass) sequence data and is tolerant of sequencing errors (Gish and States, *Nature Genetics* 3: 266-272 (1993), the entirety of which is herein incorporated by reference). BLASTN and BLASTX may be used in concert for analyzing EST data (Coulson, *Trends in Biotechnology* 12: 76-80 (1994); Birren et al., *Genome Analysis* 1: 543-559 (1997)).

Given a coding nucleotide sequence and the protein it encodes, it is often preferable to use the protein as the query sequence to search a database because of the greatly increased sensitivity to detect more subtle relationships. This is due to the larger alphabet of proteins (20 amino acids) compared with the alphabet of nucleic acid sequences (4 bases), where it is far easier to obtain a match by chance. In addition, with nucleotide alignments, only a match (positive score) or a mismatch (negative score) is obtained, but with proteins, the presence of conservative amino acid substitutions can be taken into account. Here, a mismatch may yield a positive score if the non-identical residue has physical/chemical properties similar to the one it replaced. Various scoring matrices are used to supply the substitution scores of all possible amino acid pairs. A general purpose scoring system is the BLOSUM62 matrix (Henikoff and Henikoff, *Proteins* 17: 49-61 (1993), the entirety of which is herein incorporated by reference), which is currently the default choice for BLAST programs. BLOSUM62 is tailored for alignments of moderately diverged sequences and thus may not yield the best results under all conditions. Altschul, *J. Mol. Biol.* 36: 290-300 (1993), the entirety of which is herein incorporated by reference, describes a combination of three matrices to cover all contingencies. This may improve sensitivity, but at the expense of slower searches. In practice, a single BLOSUM62 matrix is often used but others (PAM40 and PAM250) may be attempted when additional analysis is necessary. Low PAM matrices are directed at detecting very strong but localized sequence similarities, whereas high PAM matrices are directed at detecting long but weak alignments between very distantly related sequences.

Homologues in other organisms are available that can be used for comparative sequence analysis. Multiple alignments are performed to study similarities and differences in a group of related sequences. CLUSTAL W is a multiple sequence alignment package that performs progressive multiple sequence alignments based on the method of Feng and Doolittle, *J. Mol. Evol.* 25: 351-360 (1987), the entirety of which is herein incorporated by reference. Each pair of sequences is aligned and the distance between each pair is calculated; from this distance matrix, a guide tree is calculated, and all of the sequences are progressively aligned based on this tree. A feature of the program is its sensitivity to the effect of gaps on the alignment; gap penalties are varied to encourage the insertion of gaps in probable loop regions instead of in the middle of structured regions. Users can specify gap penalties, choose between a number of scoring matrices, or supply their own scoring matrix for both pairwise alignments and multiple alignments. CLUSTAL W for UNIX and VMS systems is available at: ftp.ebi.ac.uk. Another program is MACAW (Schuler et al., *Proteins Struct. Func. Genet.* 9:180-190 (1991), the entirety of which is herein incorporated by reference, for which both Macintosh and Microsoft Windows versions are available. MACAW uses a graphical interface, provides a choice of several alignment algorithms, and is available by anonymous ftp at: ncbi.nlm.nih.gov (directory/pub/macaw).

Sequence motifs are derived from multiple alignments and can be used to examine individual sequences or an entire database for subtle patterns. With motifs, it is sometimes possible to detect distant relationships that may not be demonstrable based on comparisons of primary sequences alone. Currently, the largest collection of sequence motifs in the world is PROSITE (Bairoch and Bucher, *Nucleic Acid Research* 22: 3583-3589 (1994), the entirety of which is herein incorporated by reference). PROSITE may be accessed via either the ExPASy server on the World Wide Web or anonymous ftp site. Many commercial sequence analysis packages also provide search programs that use PROSITE data.

A resource for searching protein motifs is the BLOCKS E-mail server developed by S. Henikoff, *Trends Biochem Sci.* 18:267-268 (1993), the entirety of which is herein incorporated by reference; Henikoff and Henikoff, *Nucleic Acid Research* 19:6565-6572 (1991), the entirety of which is herein incorporated by reference; Henikoff and Henikoff, *Proteins,* 17: 49-61 (1993). BLOCKS searches a protein or nucleotide sequence against a database of protein motifs or "blocks." Blocks are defined as short, ungapped multiple alignments that represent highly conserved protein patterns. The blocks themselves are derived from entries in PROSITE as well as other sources. Either a protein query or a nucleotide query can be submitted to the BLOCKS server; if a nucleotide sequence is submitted, the sequence is translated in all six reading frames and motifs are sought for these conceptual translations. Once the search is completed, the server will return a ranked list of significant matches, along with an alignment of the query sequence to the matched BLOCKS entries.

Conserved protein domains can be represented by two-dimensional matrices, which measure either the frequency or probability of the occurrences of each amino acid residue and deletions or insertions in each position of the domain. This type of model, when used to search against protein databases, is sensitive and usually yields more accurate results than simple motif searches. Two popular implementations of this approach are profile searches (such as GCG program ProfileSearch) and Hidden Markov Models (HMMs) (Krough. et al., *J. Mol. Biol.* 235:1501-1531, (1994); Eddy, *Current Opinion in Structural Biology,* 6:361-365, (1996), both of which are herein incorporated by reference in their entirety). In both cases, a large number of common protein domains have been converted into profiles, as present in the PROSITE library, or HHM models, as in the Pfam protein domain library (Sonnhammer et al., *Proteins* 28:405-420 (1997), the entirety of which is herein incorporated by reference). Pfam contains more than 500 HMM models for enzymes, transcription factors, signal transduction molecules, and structural proteins. Protein databases can be queried with these profiles or HMM models, which will identify proteins containing the domain of interest. For example, HMMSW or HMMFS, two programs in a public domain package called HMMER (Sonnhammer et al., *Proteins* 28:405-420, (1997)) can be used.

PROSITE and BLOCKS represent collected families of protein motifs. Thus, searching these databases entails submitting a single sequence to determine whether or not that sequence is similar to the members of an established family. Programs working in the opposite direction compare a collection of sequences with individual entries in the protein databases. An example of such a program is the Motif Search Tool, or MoST (Tatusov et al. *Proc. Natl. Acad. Sci.* 91: 12091-12095 (1994), the entirety of which is herein incorporated by reference). On the basis of an aligned set of input sequences, a weight matrix is calculated by using one of four methods (selected by the user). A weight matrix is simply a representation, position by position of how likely a particular amino acid will appear. The calculated weight matrix is then used to search the databases. To increase sensitivity, newly found sequences are added to the original data set, the weight matrix is recalculated, and the search is performed again. This procedure continues until no new sequences are found.

SUMMARY OF THE INVENTION

The present invention provides a substantially purified nucleic acid molecule that encodes a maize or soybean tocopherol synthesis pathway enzyme or fragment thereof, wherein the maize or soybean tocopherol synthesis pathway enzyme is selected from the group consisting of: (a) deoxyarabino-heptulosonate-P-synthase; (b) putative deoxyarabino-heptulosonate-P-synthase; (c) dehydroquinate synthase; (d) dehydroquinate dehydratase; (e) putative dehydroquinate dehydratase; (f) shikimate dehydrogenase; (g) shikimate kinase; (h) enolpyruvylshikimate-P-synthase; (i) chorismate synthase; (j) chorismate mutase; (k) tyrosine transaminase; (l) putative tyrosine transaminase; (m) transaminase A; (n) putative Transaminase A; (o) 4-hydroxyphenylpyruvate dioxygenase; (p) homogentisic acid dioxygenase; and (q) geranylgeranylpyrophosphate synthase.

The present invention also provides a substantially purified nucleic acid molecule that encodes a plant tocopherol synthesis pathway enzyme or fragment thereof, wherein the nucleic acid molecule is selected from the group consisting of a nucleic acid molecule that encodes a maize or soybean deoxyarabiono-heptulosonate-P-synthase enzyme or fragment thereof; a nucleic acid molecule that encodes a maize or soybean putative deoxyarabiono-heptulosonate-P-synthase enzyme or fragment thereof; a nucleic acid molecule that encodes a maize or soybean dehydroquinate synthase enzyme or fragment thereof; a nucleic acid molecule that encodes a maize or soybean dehydroquinate dehydratase enzyme or fragment thereof; a nucleic acid molecule that encodes a maize or soybean putative dehydroquinate dehydratase enzyme or fragment thereof; a nucleic acid molecule that encodes a maize or soybean shikimate dehydrogenase enzyme or fragment thereof; a nucleic acid molecule that encodes a maize or soybean shikimate kinase enzyme or fragment thereof; a nucleic acid molecule that encodes a maize or soybean enolpyruvylshikimate-P-synthase enzyme or fragment thereof; a nucleic acid molecule that encodes a maize or soybean chorismate synthase enzyme or fragment thereof; a nucleic acid molecule that encodes a maize or soybean chorismate mutase enzyme or fragment thereof; a nucleic acid molecule that encodes a maize or soybean tyrosine transaminase enzyme or fragment thereof; a nucleic acid molecule that encodes a maize or soybean putative Tyrosine transaminase enzyme or fragment thereof; a nucleic acid molecule that encodes a maize or soybean transaminase A enzyme or fragment thereof; a nucleic acid molecule that encodes a maize or soybean putative transaminase A enzyme or fragment thereof; a nucleic acid molecule that encodes a maize or soybean 4-hydroxyphenylpyruvate dioxygenase enzyme or fragment thereof; a nucleic acid molecule that encodes a maize or soybean homogentisic acid dioxygenase enzyme or fragment thereof; and a nucleic acid molecule that encodes a maize or soybean geranylgeranylpyrophosphate synthase enzyme or fragment thereof.

The present invention also provides a substantially purified maize or soybean tocopherol synthesis pathway enzyme or fragment thereof, wherein the maize or soybean tocopherol synthesis pathway enzyme is selected from the group consisting of (a) deoxyarabiono-heptulosonate-P-synthase or fragment thereof; (b) putative deoxyarabiono-heptulosonate-P-synthase or fragment thereof; (c) dehydroquinate synthase or fragment thereof; (d) dehydroquinate dehydratase or fragment thereof; (e) putative dehydroquinate dehydratase or fragment thereof; (f) shikimate dehydrogenase or fragment thereof; (g) shikimate kinase or fragment thereof; (h) enolpyruvylshikimate-P-synthase or fragment thereof; (i) chorismate synthase or fragment thereof; (j) chorismate mutase or fragment thereof; (k) tyrosine transaminase or fragment thereof; (l) putative tyrosine transaminase or fragment thereof; (m) transaminase A or fragment thereof; (n) putative Transaminase A or fragment thereof; (o) 4-hydroxyphenylpyruvate dioxygenase or fragment thereof; (p) homogentisic acid dioxygenase or fragment thereof; and (q) geranylgeranylpyrophosphate synthase or fragment thereof.

The present invention also provides a substantially purified maize or soybean tocopherol synthesis pathway enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 1 through SEQ ID NO: 627.

The present invention also provides a substantially purified maize or soybean deoxyarabiono-heptulosonate-P-synthase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 1 through SEQ ID NO: 97 and SEQ ID NO: 100 through SEQ ID NO: 146.

The present invention also provides a substantially purified maize or soybean deoxyarabiono-heptulosonate-P-synthase enzyme or fragment thereof encoded by a nucleic acid sequence selected from the group consisting of SEQ ID NO: 1 through SEQ ID NO: 97 and SEQ ID NO: 100 through SEQ ID NO: 146.

The present invention also provides a substantially purified maize or soybean putative deoxyarabiono-heptulosonate-P-synthase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 98 through SEQ ID NO: 99 and SEQ ID NO: 147 through SEQ ID NO: 152.

The present invention also provides a substantially purified maize or soybean putative deoxyarabiono-heptulosonate-P-synthase enzyme or fragment thereof encoded by a nucleic acid sequence selected from the group consisting of SEQ ID NO: 98 through SEQ ID NO: 99 and SEQ ID NO: 147 through SEQ ID NO: 152.

The present invention also provides a substantially purified maize dehydroquinate synthase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 153 through SEQ ID NO: 157.

The present invention also provides a substantially purified maize dehydroquinate synthase enzyme or fragment thereof encoded by a nucleic acid sequence selected from the group consisting of SEQ ID NO: 153 through SEQ ID NO: 157.

The present invention also provides a substantially purified soybean dehydroquinate dehydratase enzyme or fragment thereof enzyme or fragment thereof encoded by a first nucleic acid molecule which specifically hybridizes to a second nucleic acid molecule, the second nucleic acid molecule having a nucleic acid sequence of a complement of SEQ ID NO: 160.

The present invention also provides a substantially purified soybean dehydroquinate dehydratase enzyme or fragment thereof encoded by a nucleic acid sequence of SEQ ID NO: 160.

The present invention also provides a substantially purified maize putative dehydroquinate dehydratase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 158 through SEQ ID NO: 159.

The present invention also provides a substantially purified maize putative dehydroquinate dehydratase enzyme or fragment thereof encoded by a nucleic acid sequence selected from the group consisting of SEQ ID NO: 158 through SEQ ID NO: 159.

The present invention also provides a substantially purified maize or soybean shikimate dehydrogenase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 158 through SEQ ID NO: 159 and SEQ ID NO: 160.

The present invention also provides a substantially purified maize or soybean shikimate dehydrogenase enzyme or fragment thereof encoded by a nucleic acid sequence selected from the group consisting of SEQ ID NO: 158 through SEQ ID NO: 159 and SEQ ID NO: 160.

The present invention also provides a substantially purified maize or soybean shikimate kinase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 161 through SEQ ID NO: 179 and SEQ ID NO: 180 through SEQ ID NO: 183.

The present invention also provides a substantially purified maize or soybean shikimate kinase enzyme or fragment thereof encoded by a nucleic acid sequence selected from the group consisting of SEQ ID NO: 161 through SEQ ID NO: 179 and SEQ ID NO: 180 through SEQ ID NO: 183.

The present invention also provides a substantially purified maize enolpyruvylshikimate-P-synthase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 184 through SEQ ID NO: 198.

The present invention also provides a substantially purified maize enolpyruvylshikimate-P-synthase enzyme or fragment thereof encoded by a nucleic acid sequence selected from the group consisting of SEQ ID NO: 184 through SEQ ID NO: 198.

The present invention also provides a substantially purified maize or soybean chorismate synthase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 199 through SEQ ID NO: 231 and SEQ ID NO: 232 through SEQ ID NO: 255.

The present invention also provides a substantially purified maize or soybean chorismate synthase enzyme or fragment thereof encoded by a nucleic acid sequence selected from the group consisting of SEQ ID NO: 199 through SEQ ID NO: 231 and SEQ ID NO: 232 through SEQ ID NO: 255.

The present invention also provides a substantially purified maize or soybean chorismate mutase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 256 through SEQ ID NO: 277 and SEQ ID NO: 278 through SEQ ID NO: 284.

The present invention also provides a substantially purified maize or soybean chorismate mutase enzyme or fragment thereof encoded by a nucleic acid sequence selected from the group consisting of SEQ ID NO: 256 through SEQ ID NO: 277 and SEQ ID NO: 278 through SEQ ID NO: 284.

The present invention also provides a substantially purified maize tyrosine transaminase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 285 through SEQ ID NO: 286.

The present invention also provides a substantially purified maize tyrosine transaminase enzyme or fragment thereof encoded by a nucleic acid sequence selected from the group consisting of SEQ ID NO: 285 through SEQ ID NO: 286.

The present invention also provides a substantially purified maize or soybean putative tyrosine transaminase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 287 through SEQ ID NO: 292 and SEQ ID NO: 293 through SEQ ID NO: 300.

The present invention also provides a substantially purified maize or soybean putative tyrosine transaminase enzyme or fragment thereof encoded by a nucleic acid sequence selected from the group consisting of SEQ ID NO: 287 through SEQ ID NO: 292 and SEQ ID NO: 293 through SEQ ID NO: 300.

The present invention also provides a substantially purified maize or soybean transaminase A enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 301 through SEQ ID NO: 474 and SEQ ID NO: 475 through SEQ ID NO: 581.

The present invention also provides a substantially purified maize or soybean transaminase A enzyme or fragment thereof encoded by a nucleic acid sequence selected from the group consisting of SEQ ID NO: 301 through SEQ ID NO: 474 and SEQ ID NO: 475 through SEQ ID NO: 581.

The present invention also provides a substantially purified soybean putative transaminase A enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 582 through SEQ ID NO: 597.

The present invention also provides a substantially purified soybean putative transaminase A enzyme or fragment thereof encoded by a nucleic acid sequence selected from the group consisting of SEQ ID NO: 582 through SEQ ID NO: 597.

The present invention also provides a substantially purified maize or soybean 4-hydroxyphenylpyruvate dioxygenase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 598 through SEQ ID NO: 600 and SEQ ID NO: 601 through SEQ ID NO: 607.

The present invention also provides a substantially purified maize or soybean 4-hydroxyphenylpyruvate dioxygenase enzyme or fragment thereof encoded by a nucleic acid sequence selected from the group consisting of SEQ ID NO: 598 through SEQ ID NO: 600 and SEQ ID NO: 601 through SEQ ID NO: 607.

The present invention also provides a substantially purified maize or soybean homogentisic acid dioxygenase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 608 through SEQ ID NO: 615 and SEQ ID NO: 616 through SEQ ID NO: 621.

The present invention also provides a substantially purified maize or soybean homogentisic acid dioxygenase enzyme or fragment thereof encoded by a nucleic acid sequence selected from the group consisting of SEQ ID NO: 608 through SEQ ID NO: 615 and SEQ ID NO: 616 through SEQ ID NO: 621.

The present invention also provides a substantially purified maize or soybean geranylgeranylpyrophosphate synthase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 622 through SEQ ID NO: 624 and SEQ ID NO: 625 through SEQ ID NO: 627.

The present invention also provides a substantially purified maize or soybean geranylgeranylpyrophosphate synthase enzyme or fragment thereof encoded by a nucleic acid sequence selected from the group consisting of SEQ ID NO: 622 through SEQ ID NO: 624 and SEQ ID NO: 625 through SEQ ID NO: 627.

The present invention also provides a purified antibody or fragment thereof which is capable of specifically binding to a maize or soybean tocopherol synthesis pathway enzyme or fragment thereof, wherein the maize or soybean tocopherol synthesis pathway enzyme or fragment thereof is encoded by a nucleic acid molecule comprising a nucleic acid sequence selected from the group consisting of SEQ ID NO: 1 through SEQ ID NO: 627.

The present invention also provides a substantially purified antibody or fragment thereof, the antibody or fragment thereof capable of specifically binding to a substantially purified maize or soybean deoxyarabiono-heptulosonate-P-synthase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 1 through SEQ ID NO: 97 and SEQ ID NO: 100 through SEQ ID NO: 146.

The present invention also provides a substantially purified antibody or fragment thereof, the antibody or fragment thereof capable of specifically binding to a maize or soybean putative deoxyarabiono-heptulosonate-P-synthase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 98 through SEQ ID NO: 99 and SEQ ID NO: 147 through SEQ ID NO: 152.

The present invention also provides a substantially purified antibody or fragment thereof, the antibody or fragment thereof capable of specifically binding to a maize dehydroquinate synthase enzyme or fragment thereof encoded by a first nucleic acid molecule which specifically hybridizes to a second nucleic acid molecule, the second nucleic acid molecule having a nucleic acid sequence consisting of a complement of SEQ ID NO: 153 through SEQ ID NO: 157.

The present invention also provides a substantially purified antibody or fragment thereof, the antibody or fragment thereof capable of specifically binding to a soybean dehydroquinate dehydratase enzyme or fragment thereof enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 160.

The present invention also provides a substantially purified antibody or fragment thereof, the antibody or fragment thereof capable of specifically binding to a maize putative dehydroquinate dehydratase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 158 through SEQ ID NO: 159.

The present invention also provides a substantially purified antibody or fragment thereof, the antibody or fragment thereof capable of specifically binding to a maize or soybean shikimate dehydrogenase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 158 through SEQ ID NO: 159 and SEQ ID NO: 160.

The present invention also provides a substantially purified antibody or fragment thereof, the antibody or fragment thereof capable of specifically binding to a maize or soybean shikimate kinase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 161 through SEQ ID NO: 179 and SEQ ID NO: 180 through SEQ ID NO: 183.

The present invention also provides a substantially purified antibody or fragment thereof, the antibody or fragment thereof capable of specifically binding to a maize enolpyruvylshikimate-P-synthase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 184 through SEQ ID NO: 198.

The present invention also provides a substantially purified antibody or fragment thereof, the antibody or fragment thereof capable of specifically binding to a maize or soybean chorismate synthase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 199 through SEQ ID NO: 231 and SEQ ID NO: 232 through SEQ ID NO: 255.

The present invention also provides a substantially purified antibody or fragment thereof, the antibody or fragment thereof capable of specifically binding to a maize or soybean chorismate mutase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 256 through SEQ ID NO: 277 and SEQ ID NO: 278 through SEQ ID NO: 284.

The present invention also provides a substantially purified antibody or fragment thereof, the antibody or fragment thereof capable of specifically binding to a maize tyrosine transaminase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 285 through SEQ ID NO: 286.

The present invention also provides a substantially purified antibody or fragment thereof, the antibody or fragment thereof capable of specifically binding to a maize or soybean putative tyrosine transaminase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 287 through SEQ ID NO: 292 and SEQ ID NO: 293 through SEQ ID NO: 300.

The present invention also provides a substantially purified antibody or fragment thereof, the antibody or fragment thereof capable of specifically binding to a maize or soybean transaminase A enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 301 through SEQ ID NO: 474 and SEQ ID NO: 475 through SEQ BD NO: 581.

The present invention also provides a substantially purified antibody or fragment thereof, the antibody or fragment thereof capable of specifically binding to a soybean putative transaminase A enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 582 through SEQ ID NO: 597.

The present invention also provides a substantially purified antibody or fragment thereof, the antibody or fragment thereof capable of specifically binding to a maize or soybean 4-hydroxyphenylpyruvate dioxygenase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 598 through SEQ ID NO: 600 and SEQ ID NO: 601 through SEQ ID NO: 607.

The present invention also provides a substantially purified antibody or fragment thereof, the antibody or fragment thereof capable of specifically binding to a maize or soybean homogentisic acid dioxygenase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 608 through SEQ ID NO: 615 and SEQ ID NO: 616 through SEQ ID NO: 621.

The present invention also provides a substantially purified antibody or fragment thereof, the antibody or fragment thereof capable of specifically binding to a maize or soybean geranylgeranylpyrophosphate synthase enzyme or fragment thereof encoded by a first nucleic acid molecule which specifically hybridizes to a second nucleic acid molecule, the second nucleic acid molecule having a nucleic acid sequence selected from the group consisting of a complement of SEQ ID NO: 622 through SEQ ID NO: 624 and SEQ ID NO: 625 through SEQ ID NO: 627.

The present invention also provides a transformed plant having a nucleic acid molecule which comprises: (A) an exogenous promoter region which functions in a plant cell to cause the production of a mRNA molecule; (B) a structural nucleic acid molecule comprising a nucleic acid sequence selected from the group consisting of (a) a nucleic acid sequence which encodes for a deoxyarabiono-heptulosonate-P-synthase enzyme or fragment thereof; (b) a nucleic acid sequence which encodes for a putative deoxyarabiono-heptulosonate-P-synthase enzyme or fragment thereof; (c) a nucleic acid sequence which encodes for a dehydroquinate synthase enzyme or fragment thereof; (d) a nucleic acid sequence which encodes for a dehydroquinate dehydratase enzyme or fragment thereof; (e) a nucleic acid sequence which encodes for a putative dehydroquinate dehydratase enzyme or fragment thereof; (f) a nucleic acid sequence which encodes for a shikimate dehydrogenase enzyme or fragment thereof; (g) a nucleic acid sequence which encodes for a shikimate kinase enzyme or fragment thereof; (h) a nucleic acid sequence which encodes for an enolpyruvylshikimate-P-synthase enzyme or fragment thereof; (i) a nucleic acid sequence which encodes for a chorismate synthase enzyme or fragment thereof; (j) a nucleic acid sequence which encodes for a chorismate mutase enzyme or fragment thereof; (k) a nucleic acid sequence which encodes for a tyrosine transaminase enzyme or fragment thereof; (l) a nucleic acid sequence which encodes for a putative Tyrosine transaminase enzyme or fragment thereof; (m) a nucleic acid sequence which encodes for a transaminase A enzyme or fragment thereof; (n) a nucleic acid sequence which encodes for a putative transaminase A enzyme or fragment thereof; (o) a nucleic acid sequence which encodes for a 4-hydroxyphenylpyruvate dioxygenase enzyme or fragment thereof; (p) a nucleic acid sequence which encodes for a homogentisic acid dioxygenase enzyme or fragment thereof; (q) a nucleic acid sequence which encodes for a geranylgeranylpyrophosphate synthase enzyme or fragment thereof; and (r) a nucleic acid sequence which is complementary to any of the nucleic acid sequences of (a) through (q); and (C) a 3' non-translated sequence that functions in the plant cell to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of a mRNA molecule; which is linked to (B) a structural nucleic acid molecule, wherein the structural nucleic acid molecule encodes a plant tocopherol synthesis pathway enzyme or fragment thereof, the structural nucleic acid molecule comprising a nucleic acid sequence selected from the group consisting of SEQ ID NO: 1 through SEQ ID NO: 627 or fragment thereof; which is linked to (C) a 3' non-translated sequence that functions in the plant cell to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of a mRNA molecule; which is linked to (B) a structural nucleic acid molecule, wherein the structural nucleic acid molecule is selected from the group consisting of a nucleic acid molecule that encodes for a deoxyarabiono-heptulosonate-P-synthase enzyme or fragment thereof; a nucleic acid molecule that encodes for a putative deoxyarabiono-heptulosonate-P-synthase enzyme or fragment thereof; a nucleic acid molecule that encodes for a dehydroquinate synthase enzyme or fragment thereof; a nucleic acid molecule that encodes for a dehydroquinate dehydratase enzyme or fragment thereof; a nucleic acid molecule that encodes for a putative dehydroquinate dehydratase enzyme or fragment thereof; a nucleic acid molecule that encodes for a shikimate dehydrogenase enzyme or fragment thereof; a nucleic acid molecule that encodes for a shikimate kinase enzyme or fragment thereof; a nucleic acid molecule that encodes for an enolpyruvylshikimate-P-synthase enzyme or fragment thereof; a nucleic acid molecule that encodes for a chorismate synthase enzyme or fragment thereof; a nucleic acid molecule that encodes for a chorismate mutase enzyme or fragment thereof; a nucleic acid molecule that encodes for a tyrosine transaminase enzyme or fragment thereof; a nucleic acid molecule that encodes for a putative Tyrosine transaminase enzyme or fragment thereof; a nucleic acid molecule that encodes for a transaminase A enzyme or fragment thereof; a nucleic acid molecule that encodes for a putative transaminase A enzyme or fragment thereof; a nucleic acid molecule that encodes for a 4-hydroxyphenylpyruvate dioxygenase enzyme or fragment thereof; a nucleic acid molecule that encodes for a homogentisic acid dioxygenase enzyme or fragment thereof; a nucleic acid molecule that encodes for a geranylgeranylpyrophosphate synthase enzyme or fragment thereof; which is linked to (C) a 3' non-translated sequence that functions in the plant cell to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of a mRNA molecule; which is linked to (B) a transcribed nucleic acid molecule with a transcribed strand and a non-transcribed strand, wherein the transcribed strand is complementary to a nucleic acid molecule comprising a nucleic acid sequence selected from the group consisting of SEQ ID NO: 1 through SEQ ID NO: 627 or fragment thereof; which is linked to (C) a 3' non-translated sequence that functions in plant cells to cause termination of transcription and addition of polyadenylated ribonucleotides to a 3' end of the mRNA molecule.

The present invention also provides a transformed plant having a nucleic acid molecule which comprises: (A) an exogenous promoter region which functions in a plant cell to cause the production of a mRNA molecule; which is linked to: (B) a transcribed nucleic acid molecule with a transcribed strand and a non-transcribed strand, wherein a transcribed mRNA of the transcribed strand is complementary to an endogenous mRNA molecule having a nucleic acid sequence selected from the group consisting of an endogenous mRNA molecule that encodes a maize or soybean deoxyarabiono-heptulosonate-P-synthase enzyme or fragment thereof; an endogenous mRNA molecule that encodes a maize or soybean putative deoxyarabiono-heptulosonate-P-synthase enzyme or fragment thereof; an endogenous mRNA molecule that encodes a maize dehydroquinate synthase enzyme or fragment thereof; an endogenous mRNA molecule that encodes a soybean dehydroquinate dehydratase enzyme or fragment thereof; an endogenous mRNA molecule that encodes a maize putative dehydroquinate dehydratase enzyme or fragment thereof; an endogenous mRNA molecule that encodes a maize or soybean shikimate dehydrogenase enzyme or fragment thereof; an endogenous mRNA molecule that encodes a maize or soybean shikimate kinase enzyme or fragment thereof; an endogenous mRNA molecule that encodes a maize enolpyruvylshikimate-P-synthase enzyme or fragment thereof; an endogenous mRNA molecule that encodes a maize or soybean chorismate synthase enzyme or fragment thereof; an endogenous mRNA molecule that encodes a maize or soybean chorismate mutase enzyme or fragment thereof; an endogenous mRNA molecule that encodes a maize tyrosine transaminase enzyme or fragment thereof; an endogenous mRNA molecule that encodes a maize or soybean putative tyrosine transaminase enzyme or fragment thereof; an endogenous mRNA molecule that encodes a maize or soybean transaminase A enzyme or fragment thereof; an endogenous mRNA molecule that encodes a soybean putative transaminase A enzyme or fragment thereof; an endogenous mRNA molecule that encodes a maize or soybean 4-hydroxyphenylpyruvate dioxygenase enzyme or fragment thereof; an endogenous mRNA molecule that encodes a maize or soybean homogentisic acid dioxygenase enzyme or fragment thereof; an endogenous mRNA molecule that encodes a maize or soybean geranylgeranylpyrophosphate synthase enzyme or fragment thereof; which is linked to (C) a 3' non-translated sequence that functions in the plant cell to cause termination of transcription and addition of polyadenylated ribonucleotides to a 3' end of the mRNA molecule.

The present invention also provides a method for determining a level or pattern of a plant tocopherol synthesis pathway enzyme in a plant cell or plant tissue comprising: (A) incubating, under conditions permitting nucleic acid hybridization, a marker nucleic acid molecule, the marker nucleic acid molecule having a nucleic acid sequence selected from the group consisting of SEQ ID NO: 1 through SEQ ID NO: 627 or complements thereof or fragment of either, with a complementary nucleic acid molecule obtained from the plant cell or plant tissue, wherein nucleic acid hybridization between the marker nucleic acid molecule and the complementary nucleic acid molecule obtained from the plant cell or plant tissue permits the detection of the plant tocopherol synthesis pathway enzyme; (B) permitting hybridization between the marker nucleic acid molecule and the complementary nucleic acid molecule obtained from the plant cell or plant tissue; and (C) detecting the level or pattern of the complementary nucleic acid, wherein the detection of the complementary nucleic acid is predictive of the level or pattern of the plant tocopherol synthesis pathway enzyme.

The present invention also provides a method for determining a level or pattern of a plant tocopherol synthesis pathway enzyme in a plant cell or plant tissue comprising: (A) incubating, under conditions permitting nucleic acid hybridization, a marker nucleic acid molecule, the marker nucleic acid molecule comprising a nucleic acid molecule that encodes a maize or soybean deoxyarabiono-heptulosonate-P-synthase enzyme or complement thereof or fragment of either; a nucleic acid molecule that encodes a maize or soybean putative deoxyarabiono-heptulosonate-P-synthase enzyme or complement thereof or fragment of either; a nucleic acid molecule that encodes a maize dehydroquinate synthase enzyme or complement thereof or fragment of either; a nucleic acid molecule that encodes a soybean dehydroquinate dehydratase enzyme or complement thereof or fragment of either; a nucleic acid molecule that encodes a maize putative dehydroquinate dehydratase enzyme or complement thereof or fragment of either; a nucleic acid molecule that encodes a maize or soybean shikimate dehydrogenase enzyme or complement thereof or fragment of either; a nucleic acid molecule that encodes a maize or soybean shikimate kinase enzyme or complement thereof or fragment of either; a nucleic acid molecule that encodes a maize enolpyruvylshikimate-P-synthase enzyme or complement thereof or fragment of either; a nucleic acid molecule that encodes a maize or soybean chorismate synthase enzyme or complement thereof or fragment of either; a nucleic acid molecule that encodes a maize or soybean chorismate mutase enzyme or complement thereof or fragment of either; a nucleic acid molecule that encodes a maize tyrosine transaminase enzyme or complement thereof or fragment of either; a nucleic acid molecule that encodes a maize or soybean putative tyrosine transaminase enzyme or complement thereof or fragment of either; a nucleic acid molecule that encodes a maize or soybean transaminase A enzyme or complement thereof or fragment of either; a nucleic acid molecule that encodes a soybean putative transaminase A enzyme or complement thereof or fragment of either; a nucleic acid molecule that encodes a maize or soybean 4-hydroxyphenylpyruvate dioxygenase enzyme or complement thereof or fragment of either; a nucleic acid molecule that encodes a maize or soybean homogentisic acid dioxygenase enzyme or complement thereof or fragment of either; a nucleic acid molecule that encodes a maize or soybean geranylgeranylpyrophosphate synthase enzyme or complement thereof or fragment of either, with a complementary nucleic acid molecule obtained from the plant cell or plant tissue, wherein nucleic acid hybridization between the marker nucleic acid molecule and the complementary nucleic acid molecule obtained from the plant cell or plant tissue permits the detection of the plant tocopherol synthesis pathway enzyme; (B) permitting hybridization between the marker nucleic acid molecule and the complementary nucleic acid molecule obtained from the plant cell or plant tissue; and (C) detecting the level or pattern of the complementary nucleic acid, wherein the detection of the complementary nucleic acid is predictive of the level or pattern of the plant tocopherol synthesis pathway enzyme.

The present invention also provides a method for determining a level or pattern of a plant tocopherol synthesis pathway enzyme in a plant cell or plant tissue under evaluation which comprises assaying the concentration of a molecule, whose concentration is dependent upon the expression of a gene, the gene specifically hybridizes to a nucleic acid molecule having a nucleic acid sequence selected from the group consisting of SEQ ID NO: 1 through SEQ ID NO: 627 or complements thereof, in comparison to the concentration of that molecule present in a reference plant cell or a reference plant tissue with a known level or pattern of the plant tocopherol synthesis pathway enzyme, wherein the assayed concentration of the molecule is compared to the assayed concentration of the molecule in the reference plant cell or reference plant tissue with the known level or pattern of the plant tocopherol synthesis pathway enzyme.

The present invention also provides a method for determining a level or pattern of a plant tocopherol synthesis pathway enzyme in a plant cell or plant tissue under evaluation which comprises assaying the concentration of a molecule, whose concentration is dependent upon the expression of a gene, the gene specifically hybridizes to a nucleic acid molecule selected from the group consisting of a nucleic acid molecule that encodes a maize or soybean deoxyarabiono-heptulosonate-P-synthase enzyme; a nucleic acid molecule that encodes a maize or soybean putative deoxyarabiono-heptulosonate-P-synthase enzyme or complement thereof; a nucleic acid molecule that encodes a maize dehydroquinate synthase enzyme or complement thereof; a nucleic acid molecule that encodes a soybean dehydroquinate dehydratase enzyme or complement thereof; a nucleic acid molecule that encodes a maize putative dehydroquinate dehydratase enzyme or complement thereof; a nucleic acid molecule that encodes a maize or soybean shikimate dehydrogenase enzyme or complement thereof; a nucleic acid molecule that encodes a maize or soybean shikimate kinase enzyme or complement thereof; a nucleic acid molecule that encodes a maize enolpyruvylshikimate-P-synthase enzyme or complement thereof; a nucleic acid molecule that encodes a maize or soybean chorismate synthase enzyme or complement thereof; a nucleic acid molecule that encodes a maize or soybean chorismate mutase enzyme or complement thereof; a nucleic acid molecule that encodes a maize tyrosine transaminase enzyme or complement thereof; a nucleic acid molecule that encodes a maize or soybean putative tyrosine transaminase enzyme or complement thereof; a nucleic acid molecule that encodes a maize or soybean transaminase A enzyme or complement thereof; a nucleic acid molecule that encodes a soybean putative transaminase A enzyme or complement thereof; a nucleic acid molecule that encodes a maize or soybean 4-hydroxyphenylpyruvate dioxygenase enzyme or complement thereof; a nucleic acid molecule that encodes a maize or soybean homogentisic acid dioxygenase enzyme or complement thereof; a nucleic acid molecule that encodes a maize or soybean geranylgeranylpyrophosphate synthase enzyme or complement thereof, in comparison to the concentration of that molecule present in a reference plant cell or a reference plant tissue with a known level or pattern of the plant tocopherol synthesis pathway enzyme, wherein the assayed concentration of the molecule is compared to the assayed concentration of the molecule in the reference plant cell or the reference plant tissue with the known level or pattern of the plant tocopherol synthesis pathway enzyme.

The present invention provides a method of determining a mutation in a plant whose presence is predictive of a mutation affecting a level or pattern of a protein comprising the steps: (A) incubating, under conditions permitting nucleic acid hybridization, a marker nucleic acid, the marker nucleic acid selected from the group of marker nucleic acid molecules which specifically hybridize to a nucleic acid molecule having a nucleic acid sequence selected from the group of SEQ ID NO: 1 through SEQ ID NO: 627 or complements thereof or fragment of either and a complementary nucleic acid molecule obtained from the plant, wherein nucleic acid hybridization between the marker nucleic acid molecule and the complementary nucleic acid molecule obtained from the plant permits the detection of a polymorphism whose presence is predictive of a mutation affecting the level or pattern of the protein in the plant; (B) permitting hybridization between the marker nucleic acid molecule and the complementary nucleic acid molecule obtained from the plant; and (C) detecting the presence of the polymorphism, wherein the detection of the polymorphism is predictive of the mutation.

The present invention also provides a method for determining a mutation in a plant whose presence is predictive of a mutation affecting the level or pattern of a plant tocopherol synthesis pathway enzyme comprising the steps: (A) incubating, under conditions permitting nucleic acid hybridization, a marker nucleic acid molecule, the marker nucleic acid molecule comprising a nucleic acid molecule that is linked to a gene, the gene specifically hybridizes to a nucleic acid molecule having a nucleic acid sequence selected from the group consisting of SEQ ID NO: 1 through SEQ ID NO: 627 or complements thereof and a complementary nucleic acid molecule obtained from the plant, wherein nucleic acid hybridization between the marker nucleic acid molecule and the complementary nucleic acid molecule obtained from the plant permits the detection of a polymorphism whose presence is predictive of a mutation affecting the level or pattern of the plant tocopherol synthesis pathway enzyme in the plant; (B) permitting hybridization between the marker nucleic acid molecule and the complementary nucleic acid molecule obtained from the plant; and (C) detecting the presence of the polymorphism, wherein the detection of the polymorphism is predictive of the mutation.

The present invention also provides a method for determining a mutation in a plant whose presence is predictive of a mutation affecting the level or pattern of a plant tocopherol synthesis pathway enzyme comprising the steps: (A) incubating, under conditions permitting nucleic acid hybridization, a marker nucleic acid molecule, the marker nucleic acid molecule comprising a nucleic acid molecule that is linked to a gene, the gene specifically hybridizes to a nucleic acid molecule selected from the group consisting of a nucleic acid molecule that encodes a maize or soybean deoxyarabiono-heptulosonate-P-synthase enzyme or complement thereof; a nucleic acid molecule that encodes a maize or soybean putative deoxyarabiono-heptulosonate-P-synthase enzyme or complement thereof; a nucleic acid molecule that encodes a maize dehydroquinate synthase enzyme or complement thereof; a nucleic acid molecule that encodes a soybean dehydroquinate dehydratase enzyme or complement thereof; a nucleic acid molecule that encodes a maize putative dehydroquinate dehydratase enzyme or complement thereof; a nucleic acid molecule that encodes a maize or soybean shikimate dehydrogenase enzyme or complement thereof; a nucleic acid molecule that encodes a maize or soybean shikimate kinase enzyme or complement thereof; a nucleic acid molecule that encodes a maize enolpyruvylshikimate-P-synthase enzyme or complement thereof; a nucleic acid molecule that encodes a maize or soybean chorismate synthase enzyme or complement thereof; a nucleic acid molecule that encodes a maize or soybean chorismate mutase enzyme or complement thereof; a nucleic acid molecule that encodes a maize tyrosine transaminase enzyme or complement thereof; a nucleic acid molecule that encodes a maize or soybean putative tyrosine transaminase enzyme or complement thereof; a nucleic acid molecule that encodes a maize or soybean transaminase A enzyme or complement thereof; a nucleic acid molecule that encodes a soybean putative transaminase A enzyme or complement thereof; a nucleic acid molecule that encodes a maize or soybean 4-hydroxyphenylpyruvate dioxygenase enzyme or complement thereof; a nucleic acid molecule that encodes a maize or soybean homogentisic acid dioxygenase enzyme or complement thereof; a nucleic acid molecule that encodes a maize or soybean geranylgeranylpyrophosphate synthase enzyme or complement thereof, and a complementary nucleic acid molecule obtained from the plant, wherein nucleic acid hybridization between the marker nucleic acid molecule and the complementary nucleic acid molecule obtained from the plant permits the detection of a polymorphism whose presence is predictive of a mutation affecting the level or pattern of the plant tocopherol synthesis pathway enzyme in the plant; (B) permitting hybridization between the marker nucleic acid molecule and the complementary nucleic acid molecule obtained from the plant; and (C) detecting the presence of the polymorphism, wherein the detection of the polymorphism is predictive of the mutation.

The present invention also provides a method of producing a plant containing an overexpressed protein comprising: (A) transforming the plant with a functional nucleic acid molecule, wherein the functional nucleic acid molecule comprises a promoter region, wherein the promoter region is linked to a structural region, wherein the structural region has a nucleic acid sequence selected from group consisting of SEQ ID NO: 1 through SEQ ID NO: 627; wherein the structural region is linked to a 3' non-translated sequence that functions in the plant to cause termination of transcription and addition of polyadenylated ribonucleotides to a 3' end of a mRNA molecule; and wherein the functional nucleic acid molecule results in overexpression of the protein; and (B) growing the transformed plant.

The present invention also provides a method of producing a plant containing an overexpressed plant tocopherol synthesis pathway enzyme comprising: (A) transforming the plant with a functional nucleic acid molecule, wherein the functional nucleic acid molecule comprises a promoter region, wherein the promoter region is linked to a structural region, wherein the structural region comprises a nucleic acid molecule having a nucleic acid sequence selected from the group consisting of SEQ ID NO: 1 through SEQ ID NO: 627 or fragment thereof; wherein the structural region is linked to a 3' non-translated sequence that functions in the plant to cause termination of transcription and addition of polyadenylated ribonucleotides to a 3' end of a mRNA molecule; and wherein the functional nucleic acid molecule results in overexpression of the plant tocopherol synthesis pathway enzyme; and (B) growing the transformed plant.

The present invention also provides a method of producing a plant containing an overexpressed plant tocopherol synthesis pathway enzyme comprising: (A) transforming the plant with a functional nucleic acid molecule, wherein the functional nucleic acid molecule comprises a promoter region, wherein the promoter region is linked to a structural region, wherein the structural region comprises a nucleic acid molecule selected from the group consisting of a nucleic acid molecule that encodes a maize or soybean deoxyarabiono-heptulosonate-P-synthase enzyme or fragment thereof; a nucleic acid molecule that encodes a maize or soybean putative deoxyarabiono-heptulosonate-P-synthase enzyme or fragment thereof; a nucleic acid molecule that encodes a maize dehydroquinate synthase enzyme or fragment thereof; a nucleic acid molecule that encodes a soybean dehydroquinate dehydratase enzyme or fragment thereof; a nucleic acid molecule that encodes a maize putative dehydroquinate dehydratase enzyme or fragment thereof; a nucleic acid molecule that encodes a maize or soybean shikimate dehydrogenase enzyme or fragment thereof; a nucleic acid molecule that encodes a maize or soybean shikimate kinase enzyme or fragment thereof; a nucleic acid molecule that encodes a maize enolpyruvylshikimate-P-synthase enzyme or fragment thereof; a nucleic acid molecule that encodes a maize or soybean chorismate synthase enzyme or fragment thereof; a nucleic acid molecule that encodes a maize or soybean chorismate mutase enzyme or fragment thereof; a nucleic acid molecule that encodes a maize tyrosine transaminase enzyme or fragment thereof; a nucleic acid molecule that encodes a maize or soybean putative tyrosine transaminase enzyme or fragment thereof; a nucleic acid molecule that encodes a maize or soybean transaminase A enzyme or fragment thereof; a nucleic acid molecule that encodes a soybean putative transaminase A enzyme or fragment thereof; a nucleic acid molecule that encodes a maize or soybean 4-hydroxyphenylpyruvate dioxygenase enzyme or fragment thereof; a nucleic acid molecule that encodes a maize or soybean homogentisic acid dioxygenase enzyme or fragment thereof; a nucleic acid molecule that encodes a maize or soybean geranylgeranylpyrophosphate synthase enzyme or fragment thereof; wherein the structural region is linked to a 3' non-translated sequence that functions in the plant to cause termination of transcription and addition of polyadenylated ribonucleotides to a 3' end of a mRNA molecule; and wherein the functional nucleic acid molecule results in overexpression of the plant tocopherol synthesis pathway enzyme; and (B) growing the transformed plant.

The present invention also provides a method of producing a plant containing reduced levels of a plant tocopherol synthesis pathway enzyme comprising: (A) transforming the plant with a functional nucleic acid molecule, wherein the functional nucleic acid molecule comprises a promoter region, wherein the promoter region is linked to a structural region, wherein the structural region comprises a nucleic acid molecule having a nucleic acid sequence selected from the group consisting of SEQ ID NO: 1 through SEQ ID NO: 627; wherein the structural region is linked to a 3' non-translated sequence that functions in the plant to cause termination of transcription and addition of polyadenylated ribonucleotides to a 3' end of a mRNA molecule; and wherein the functional nucleic acid molecule results in co-suppression of the plant tocopherol synthesis pathway enzyme; and (B) growing the transformed plant.

The present invention also provides a method of producing a plant containing reduced levels of a plant tocopherol synthesis pathway enzyme comprising: (A) transforming the plant with a functional nucleic acid molecule, wherein the functional nucleic acid molecule comprises a promoter region, wherein the promoter region is linked to a structural region, wherein the structural region comprises a nucleic acid molecule having a nucleic acid sequence selected from the group consisting of a nucleic acid molecule that encodes a maize or soybean deoxyarabiono-heptulosonate-P-synthase enzyme or fragment thereof; a nucleic acid molecule that encodes a maize or soybean putative deoxyarabiono-heptulosonate-P-synthase enzyme or fragment thereof; a nucleic acid molecule that encodes a maize dehydroquinate synthase enzyme or fragment thereof; a nucleic acid molecule that encodes a soybean dehydroquinate dehydratase enzyme or fragment thereof; a nucleic acid molecule that encodes a maize putative dehydroquinate dehydratase enzyme or fragment thereof; a nucleic acid molecule that encodes a maize or soybean shikimate dehydrogenase enzyme or fragment thereof; a nucleic acid molecule that encodes a maize or soybean shikimate kinase enzyme or fragment thereof; a nucleic acid molecule that encodes a maize enolpyruvylshikimate-P-synthase enzyme or fragment thereof; a nucleic acid molecule that encodes a maize or soybean chorismate synthase enzyme or fragment thereof; a nucleic acid molecule that encodes a maize or soybean chorismate mutase enzyme or fragment thereof; a nucleic acid molecule that encodes a maize tyrosine transaminase enzyme or fragment thereof; a nucleic acid molecule that encodes a maize or soybean putative tyrosine transaminase enzyme or fragment thereof; a nucleic acid molecule that encodes a maize or soybean transaminase A enzyme or fragment thereof; a nucleic acid molecule that encodes a soybean putative transaminase A enzyme or fragment thereof; a nucleic acid molecule that encodes a maize or soybean 4-hydroxyphenylpyruvate dioxygenase enzyme or fragment thereof; a nucleic acid molecule that encodes a maize or soybean homogentisic acid dioxygenase enzyme or fragment thereof; a nucleic acid molecule that encodes a maize or soybean geranylgeranylpyrophosphate synthase enzyme or fragment thereof, wherein the structural region is linked to a 3' non-translated sequence that functions in the plant to cause termination of transcription and addition of polyadenylated ribonucleotides to a 3' end of a mRNA molecule; and wherein the functional nucleic acid molecule results in co-suppression of the plant tocopherol synthesis pathway enzyme; and (B) growing the transformed plant.

The present invention also provides a method for reducing expression of a plant tocopherol synthesis pathway enzyme in a plant comprising: (A) transforming the plant with a nucleic acid molecule, the nucleic acid molecule having an exogenous promoter region which functions in a plant cell to cause the production of a mRNA molecule, wherein the exogenous promoter region is linked to a transcribed nucleic acid molecule having a transcribed strand and a non-transcribed strand, wherein the transcribed strand is complementary to a nucleic acid molecule having a nucleic acid sequence selected from the group consisting of SEQ ID NO: 1 through SEQ ID NO: 627 or complements thereof or fragments of either and the transcribed strand is complementary to an endogenous mRNA molecule; and wherein the transcribed nucleic acid molecule is linked to a 3' non-translated sequence that functions in the plant cell to cause termination of transcription and addition of polyadenylated ribonucleotides to a 3' end of a mRNA molecule; and (B) growing the transformed plant.

The present invention also provides a method for reducing expression of a plant tocopherol synthesis pathway enzyme in a plant comprising: (A) transforming the plant with a nucleic acid molecule, the nucleic acid molecule having an exogenous promoter region which functions in a plant cell to cause the production of a mRNA molecule, wherein the exogenous promoter region is linked to a transcribed nucleic acid molecule having a transcribed strand and a non-transcribed strand, wherein a transcribed mRNA of the transcribed strand is complementary to a nucleic acid molecule selected from the group consisting of an endogenous mRNA molecule that encodes a maize or soybean deoxyarabiono-heptulosonate-P-synthase enzyme or fragment thereof; an endogenous mRNA molecule that encodes a maize or soybean putative deoxyarabiono-heptulosonate-P-synthase enzyme or fragment thereof; an endogenous mRNA molecule that encodes a maize dehydroquinate synthase enzyme or fragment thereof; an endogenous mRNA molecule that encodes a soybean dehydroquinate dehydratase enzyme or fragment thereof; an endogenous mRNA molecule that encodes a maize putative dehydroquinate dehydratase enzyme or fragment thereof; an endogenous mRNA molecule that encodes a maize or soybean shikimate dehydrogenase enzyme or fragment thereof; an endogenous mRNA molecule that encodes a maize or soybean shikimate kinase enzyme or fragment thereof; an endogenous mRNA molecule that encodes a maize enolpyruvylshikimate-P-synthase enzyme or fragment thereof; an endogenous mRNA molecule that encodes a maize or soybean chorismate synthase enzyme or fragment thereof; an endogenous mRNA molecule that encodes a maize or soybean chorismate mutase enzyme or fragment thereof; an endogenous mRNA molecule that encodes a maize tyrosine transaminase enzyme or fragment thereof; an endogenous mRNA molecule that encodes a maize or soybean putative tyrosine transaminase enzyme or fragment thereof; an endogenous mRNA molecule that encodes a maize or soybean transaminase A enzyme or fragment thereof; an endogenous mRNA molecule that encodes a soybean putative transaminase A enzyme or fragment thereof; an endogenous mRNA molecule that encodes a maize or soybean 4-hydroxyphenylpyruvate dioxygenase enzyme or fragment thereof; an endogenous mRNA molecule that encodes a maize or soybean homogentisic acid dioxygenase enzyme or fragment thereof; and an endogenous mRNA molecule that encodes a maize or soybean geranylgeranylpyrophosphate synthase enzyme or fragment thereof; and wherein the transcribed nucleic acid molecule is linked to a 3' non-translated sequence that functions in the plant cell to cause termination of transcription and addition of polyadenylated ribonucleotides to a 3' end of a mRNA molecule; and (B) growing the transformed plant.

The present invention also provides a method of determining an association between a polymorphism and a plant trait comprising: (A) hybridizing a nucleic acid molecule specific for the polymorphism to genetic material of a plant, wherein the nucleic acid molecule has a nucleic acid sequence selected from the group consisting of SEQ ID NO: 1 through SEQ ID NO: 627 or complements thereof or fragment of either; and (B) calculating the degree of association between the polymorphism and the plant trait.

The present invention also provides a method of determining an association between a polymorphism and a plant trait comprising: (A) hybridizing a nucleic acid molecule specific for the polymorphism to genetic material of a plant, wherein the nucleic acid molecule is selected from the group consisting of a nucleic acid molecule that encodes a maize or soybean deoxyarabiono-heptulosonate-P-synthase enzyme or complement thereof or fragment of either; a nucleic acid molecule that encodes a maize or soybean putative deoxyarabiono-heptulosonate-P-synthase enzyme or complement thereof or fragment of either; a nucleic acid molecule that encodes a maize dehydroquinate synthase enzyme or complement thereof or fragment of either; a nucleic acid molecule that encodes a soybean dehydroquinate dehydratase enzyme or complement thereof or fragment of either; a nucleic acid molecule that encodes a maize putative dehydroquinate dehydratase enzyme or complement thereof or fragment of either; a nucleic acid molecule that encodes a maize or soybean shikimate dehydrogenase enzyme or complement thereof or fragment of either; a nucleic acid molecule that encodes a maize or soybean shikimate kinase enzyme or complement thereof or fragment of either; a nucleic acid molecule that encodes a maize enolpyruvylshikimate-P-synthase enzyme or complement thereof or fragment of either; a nucleic acid molecule that encodes a maize or soybean chorismate synthase enzyme or complement thereof or fragment of either; a nucleic acid molecule that encodes a maize or soybean chorismate mutase enzyme or complement thereof or fragment of either; a nucleic acid molecule that encodes a maize tyrosine transaminase enzyme or complement thereof or fragment of either; a nucleic acid molecule that encodes a maize or soybean putative tyrosine transaminase enzyme or complement thereof or fragment of either; a nucleic acid molecule that encodes a maize or soybean transaminase A enzyme or complement thereof or fragment of either; a nucleic acid molecule that encodes a soybean putative transaminase A enzyme or complement thereof or fragment of either; a nucleic acid molecule that encodes a maize or soybean 4-hydroxyphenylpyruvate dioxygenase enzyme or complement thereof or fragment of either; a nucleic acid molecule that encodes a maize or soybean homogentisic acid dioxygenase enzyme or complement thereof or fragment of either; and a nucleic acid molecule that encodes a maize or soybean geranylgeranylpyrophosphate synthase enzyme or complement thereof or fragment of either; and (B) calculating the degree of association between the polymorphism and the plant trait.

The present invention also provides a method of isolating a nucleic acid that encodes a plant tocopherol synthesis pathway enzyme or fragment thereof comprising: (A) incubating under conditions permitting nucleic acid hybridization, a first nucleic acid molecule comprising a nucleic acid sequence selected from the group consisting of SEQ ID NO: 1 through SEQ ID NO: 627 or complements thereof or fragment of either with a complementary second nucleic acid molecule obtained from a plant cell or plant tissue; (B) permitting hybridization between the first nucleic acid molecule and the second nucleic acid molecule obtained from the plant cell or plant tissue; and (C) isolating the second nucleic acid molecule.

The present invention also provides a method of isolating a nucleic acid molecule that encodes a plant tocopherol synthesis pathway enzyme or fragment thereof comprising: (A) incubating under conditions permitting nucleic acid hybridization, a first nucleic acid molecule selected from the group consisting of a nucleic acid molecule that encodes a maize or soybean copalyl diphosphate synthase enzyme or complement thereof or fragment of either, a nucleic acid molecule that encodes a maize or soybean deoxyarabiono-heptulosonate-P-synthase enzyme or complement thereof or fragment of either; a nucleic acid molecule that encodes a maize or soybean putative deoxyarabiono-heptulosonate-P-synthase enzyme or complement thereof or fragment of either; a nucleic acid molecule that encodes a maize dehydroquinate synthase enzyme or complement thereof or fragment of either; a nucleic acid molecule that encodes a soybean dehydroquinate dehydratase enzyme or complement thereof or fragment of either; a nucleic acid molecule that encodes a maize putative dehydroquinate dehydratase enzyme or complement thereof or fragment of either; a nucleic acid molecule that encodes a maize or soybean shikimate dehydrogenase enzyme or complement thereof or fragment of either; a nucleic acid molecule that encodes a maize or soybean shikimate kinase enzyme or complement thereof or fragment of either; a nucleic acid molecule that encodes a maize enolpyruvylshikimate-P-synthase enzyme or complement thereof or fragment of either; a nucleic acid molecule that encodes a maize or soybean chorismate synthase enzyme or complement thereof or fragment of either; a nucleic acid molecule that encodes a maize or soybean chorismate mutase enzyme or complement thereof or fragment of either; a nucleic acid molecule that encodes a maize tyrosine transaminase enzyme or complement thereof or fragment of either; a nucleic acid molecule that encodes a maize or soybean putative tyrosine transaminase enzyme or complement thereof or fragment of either; a nucleic acid molecule that encodes a maize or soybean transaminase A enzyme or complement thereof or fragment of either; a nucleic acid molecule that encodes a soybean putative transaminase A enzyme or complement thereof or fragment of either; a nucleic acid molecule that encodes a maize or soybean 4-hydroxyphenylpyruvate dioxygenase enzyme or complement thereof or fragment of either; a nucleic acid molecule that encodes a maize or soybean homogentisic acid dioxygenase enzyme or complement thereof or fragment of either; and a nucleic acid molecule that encodes a maize or soybean geranylgeranylpyrophosphate synthase enzyme or complement thereof or fragment of either, with a complementary second nucleic acid molecule obtained from a plant cell or plant tissue; (B) permitting hybridization between the plant tocopherol synthesis pathway enzyme nucleic acid molecule and the complementary nucleic acid molecule obtained from the plant cell or plant tissue; and (C) isolating the second nucleic acid molecule.

DETAILED DESCRIPTION OF THE INVENTION

Definitions and Agents of the Present Invention

Definitions:

As used herein, a tocopherol synthesis pathway enzyme is any enzyme that is associated with the synthesis or degradation of tocopherol.

As used herein, a tocopherol synthesis enzyme is any enzyme that is associated with the synthesis of tocopherol.

As used herein, a tocopherol degradation enzyme is any enzyme that is associated with the degradation of tocopherol.

As used herein, deoxyarabinoheptulosonate phosphate synthase (DAHP synthase) is any enzyme that catalyzes the formation of deoxyarabinoheptulosonate phosphate from erythrose phosphate.

As used herein, dehydroquinate synthase is any enzyme that catalyzes the formation of dehydroquinate from erythrose phosphate via an NAD-dependent reaction.

As used herein, dehydroquinate dehydratase is any enzyme that catalyzes the stereospecific syn-dehydration of dehydroquinate to dehydroshikimate.

As used herein, shikimate dehydrogenase is any enzyme that catalyzes the NADPH-dependent conversion of dehydroshikimate to shikimate.

As used herein, shikimate kinase is any enzyme that catalyzes the phosphorylation of skikimate to shikimate-3-phosphate.

As used herein, enolpyruvylshikimatephosphate synthase (EPSPS) is any enzyme that catalyzes the reversible transfer of the carboxyvinyl moiety of phosphoenolpyruvate to shikimatephosphate, yielding enolpyruvylshikimate phosphate.

As used herein, chorismate synthase is any enzyme that catalyzes the conversion of enolpyruvylshikimate phosphate to chorismic acid with the introduction of a double bond of the aromatic ring in a trans-1,4-elimination of inorganic phosphorous.

As used herein, chorismate mutase is any enzyme that catalyzes the reaction that converts chorismic acid to prephenic acid.

As used herein, prephenate dehydrogenase is any enzyme that catalyzes the formation of 4-hydroxyphenylpyruvate from prephenate via an NAD-dependent or an NADP-dependent reaction.

As used herein, tyrosine transaminase is any enzyme that catalyzes the pyridoxal-phosphate dependent conversion of L-tyrosine to 4-hydroxyphenylpyruvate.

As used herein, L-amino-acid oxidase is any enzyme that catalyzes the reaction to convert tyrosine to 4-hydroxyphenylpyruvate.

As used herein, aromatic amino acid amino transferase is any enzyme that catalyzes the reaction that converts 4-hydroxyphenylpyruvate to tyrosine.

As used herein, an aspartic acid amino transferase or transaminase A is any enzyme that catalyzes the formation of phenylalanine and tyrosine using phenylpyruvate or p-hydroxy phenylpyruvate, respectively.

As used herein, hydroxyphenylpyruvate dioxygenase is any enzyme that catalyzes the formation of homogentisate from phydroxyphenylpyruvate.

As used herein, geranylgeranyl-pyrophosphate synthase is any enzyme that catalyzes the formation of geranylgeranylpyrophosphate by prenyltransferring isoprene moiety from isopentenylpyrophosphate to farnesylpyrophosphate.

As used herein, geranylgeranylpyrophosphate (GGPP) hydrogenase is any enzyme that catalyzes the reaction to convert geranylgeranylpyrophosphate to phytylpyrophosphate via an NADPH-dependent reaction.

As used herein, homogentisate:phytyl transferase is any enzyme that catalyzes the reaction to convert homogentisic acid to 2-methyl-6-phytylbenzoquinol.

As used herein, tocopherol cyclase is any enzyme that catalyzes the cyclization of 2,3-dimethyl-6-phytylbenzoquinol to form γ-tocopherol.

As used herein, tocopherol methyltransferase is any enzyme that catalyzes the reaction that forms α-tocopherol from other tocopherols via an S-adenosyl methionine (SAM)-dependent reaction.

As used herein, homogentisic acid dioxygenase is any enzyme that catalyzes the reaction to convert homogentisic acid to fumarylacetoacetate.

Agents (a) Nucleic Acid Molecules

Agents of the present invention include plant nucleic acid molecules and more preferably include maize and soybean nucleic acid molecules and more preferably include nucleic acid molecules of the maize genotypes B73 (Illinois Foundation Seeds, Champaign, Ill. U.S.A.), B73xMo17 (Illinois Foundation Seeds, Champaign, Ill. U.S.A.), DK604 (Dekalb Genetics, Dekalb, Ill. U.S.A.), H99 (Illinois Foundation Seeds, Champaign, Ill. U.S.A.), RX601 (Asgrow Seed Company, Des Moines, Iowa), Mo17 (Illinois Foundation Seeds, Champaign, Ill. U.S.A.), and soybean types Asgrow 3244 (Asgrow Seed Company, Des Moines, Iowa), C1944 (United States Department of Agriculture (USDA) Soybean Germplasm Collection, Urbana, Ill. U.S.A.), Cristalina (USDA Soybean Germplasm Collection, Urbana, Ill. U.S.A.), FT108 (Monsoy, Brazil), Hartwig (USDA Soybean Germplasm Collection, Urbana, Ill. U.S.A.), BW211S Null (Tohoku University, Morioka, Japan), P1507354 (USDA Soybean Germplasm Collection, Urbana, Ill. U.S.A.), Asgrow A4922 (Asgrow Seed Company, Des Moines, Iowa U.S.A.), PI227687 (USDA Soybean Germplasm Collection, Urbana, Ill. U.S.A.), PI229358 (USDA Soybean Germplasm Collection, Urbana, Ill. U.S.A.) and Asgrow A3237 (Asgrow Seed Company, Des Moines, Iowa U.S.A.).

A subset of the nucleic acid molecules of the present invention includes nucleic acid molecules that are marker molecules. Another subset of the nucleic acid molecules of the present invention include nucleic acid molecules that encode a protein or fragment thereof. Another subset of the nucleic acid molecules of the present invention are EST molecules.

Fragment nucleic acid molecules may encode significant portion(s) of, or indeed most of, these nucleic acid molecules. Alternatively, the fragments may comprise smaller oligonucleotides (having from about 15 to about 250 nucleotide residues and more preferably, about 15 to about 30 nucleotide residues).

As used herein, an agent, be it a naturally occurring molecule or otherwise may be "substantially purified," if desired, such that one or more molecules that is or may be present in a naturally occurring preparation containing that molecule will have been removed or will be present at a lower concentration than that at which it would normally be found.

The agents of the present invention will preferably be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic and thus involve the capacity of the agent to mediate a chemical reaction or response.

The agents of the present invention may also be recombinant. As used herein, the term recombinant means any agent (e.g. DNA, peptide etc.), that is, or results, however indirect, from human manipulation of a nucleic acid molecule.

It is understood that the agents of the present invention may be labeled with reagents that facilitate detection of the agent (e.g. fluorescent labels, Prober et al., Science 238:336-340 (1987); Albarella et al., EP 144914; chemical labels, Sheldon et al., U.S. Pat. No. 4,582,789; Albarella et al., U.S. Pat. No. 4,563,417; modified bases, Miyoshi et al., EP 119448, all of which are hereby incorporated by reference in their entirety).

It is further understood, that the present invention provides recombinant bacterial, mammalian, microbial, insect, fungal and plant cells and viral constructs comprising the agents of the present invention. (See, for example, Uses of the Agents of the Invention, Section (a) Plant Constructs and Plant Transformants; Section (b) Fungal Constructs and Fungal Transformants; Section (c) Mammalian Constructs and Transformed Mammalian Cells; Section (d) Insect Constructs and Transformed Insect Cells; and Section (e) Bacterial Constructs and Transformed Bacterial Cells)

Nucleic acid molecules or fragments thereof of the present invention are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al.,

*Molecular Cloning*, A Laboratory Manual, 2nd Ed., Cold Spring Harbor Press, Cold Spring Harbor, N.Y. (1989) and by Haymes et al., *Nucleic Acid Hybridization, A Practical Approach*, IRL Press, Washington, D.C. (1985), the entirety of which is herein incorporated by reference. Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2× SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

In a preferred embodiment, a nucleic acid of the present invention will specifically hybridize to one or more of the nucleic acid molecules set forth in SEQ ID NO: 1 through SEQ ID NO: 627 or complements thereof under moderately stringent conditions, for example at about 2.0×SSC and about 65° C.

In a particularly preferred embodiment, a nucleic acid of the present invention will include those nucleic acid molecules that specifically hybridize to one or more of the nucleic acid molecules set forth in SEQ ID NO: 1 through SEQ ID NO: 627 or complements thereof under high stringency conditions such as 0.2×SSC and about 65° C.

In one aspect of the present invention, the nucleic acid molecules of the present invention have one or more of the nucleic acid sequences set forth in SEQ ID NO: 1 through SEQ ID NO: 627 or complements thereof. In another aspect of the present invention, one or more of the nucleic acid molecules of the present invention share between 100% and 90% sequence identity with one or more of the nucleic acid sequences set forth in SEQ ID NO: 1 through SEQ ID NO: 627 or complements thereof. In a further aspect of the present invention, one or more of the nucleic acid molecules of the present invention share between 100% and 95% sequence identity with one or more of the nucleic acid sequences set forth in SEQ ID NO: 1 through SEQ ID NO: 627 or complements thereof. In a more preferred aspect of the present invention, one or more of the nucleic acid molecules of the present invention share between 100% and 98% sequence identity with one or more of the nucleic acid sequences set forth in SEQ ID NO: 1 through SEQ ID NO: 627 or complements thereof. In an even more preferred aspect of the present invention, one or more of the nucleic acid molecules of the present invention share between 100% and 99% sequence identity with one or more of the sequences set forth in SEQ ID NO: 1 through SEQ ID NO: 627 or complements thereof.

In a further more preferred aspect of the present invention, one or more of the nucleic acid molecules of the present invention exhibit 100% sequence identity with a nucleic acid molecule present within MONN01, SATMON001, SATMON003 through SATMON014, SATMON016, SATMON017, SATMON019 through SATMON031, SATMON033, SATMON034, SATMON-001, SATMONN01, SATMONN04 through SATMONN06, CMz029 through CMz031, CMz033 through CMz037, CMz039 through CMz042, CMz044 through CMz045, CMz047 through CMz050, SOYMON001 through SOYMON038, Soy51 through Soy56, Soy58 through Soy62, Soy65 through Soy71, Soy 73 and Soy76 through Soy77 (Monsanto Company, St. Louis, Mo. U.S.A.).

(i) Nucleic Acid Molecules Encoding Proteins or Fragments Thereof

Nucleic acid molecules of the present invention can comprise sequences that encode a tocopherol synthesis pathway enzyme or fragment thereof. Such tocopherol synthesis pathway enzymes or fragments thereof include homologues of known tocopherol synthesis pathway enzymes in other organisms.

In a preferred embodiment of the present invention, a maize or soybean tocopherol synthesis pathway enzyme or fragment thereof of the present invention is a homologue of another plant tocopherol synthesis pathway enzyme. In another preferred embodiment of the present invention, a maize or soybean tocopherol synthesis pathway enzyme or fragment thereof of the present invention is a homologue of a fungal tocopherol synthesis pathway enzyme. In another preferred embodiment of the present invention, a maize or soybean tocopherol synthesis pathway enzyme or fragment thereof of the present invention is a homologue of a bacterial tocopherol synthesis pathway enzyme. In another preferred embodiment of the present invention, a soybean tocopherol synthesis pathway enzyme or fragment thereof of the present invention is a homologue of a maize tocopherol synthesis pathway enzyme. In another preferred embodiment of the present invention, a maize tocopherol synthesis pathway enzyme homologue or fragment thereof of the present invention is a homologue of a soybean tocopherol synthesis pathway enzyme. In another preferred embodiment of the present invention, a maize or soybean tocopherol synthesis pathway enzyme homologue or fragment thereof of the present invention is a homologue of an *Arabidopsis thaliana* tocopherol synthesis pathway enzyme.

In a preferred embodiment of the present invention, the nucleic molecule of the present invention encodes a maize or soybean tocopherol synthesis pathway enzyme or fragment thereof where a maize or soybean tocopherol synthesis pathway enzyme exhibits a BLAST probability score of greater than 1E-12, preferably a BLAST probability score of between about 1E-30 and about 1E-12, even more preferably a BLAST probability score of greater than 1E-30 with its homologue.

In another preferred embodiment of the present invention, the nucleic acid molecule encoding a maize or soybean tocopherol synthesis pathway enzyme or fragment thereof exhibits a % identity with its homologue of between about 25% and about 40%, more preferably of between about 40 and about 70%, even more preferably of between about 70% and about 90% and even more preferably between about 90% and 99%. In another preferred embodiment of the present invention, a maize or soybean tocopherol synthesis pathway enzyme or fragments thereof exhibits a % identity with its homologue of 100%.

In a preferred embodiment of the present invention, the nucleic molecule of the present invention encodes a maize or soybean tocopherol synthesis pathway enzyme or fragment thereof where a maize or soybean tocopherol synthesis pathway enzyme exhibits a BLAST score of greater than 120, preferably a BLAST score of between about 1450 and about 120, even more preferably a BLAST score of greater than 1450 with its homologue.

Nucleic acid molecules of the present invention also include non-maize, non-soybean homologues. Preferred non-maize, non-soybean homologues are selected from the group consisting of alfalfa, *Arabidopsis*, barley, *Brassica*, broccoli, cabbage, citrus, cotton, garlic, oat, oilseed rape, onion, canola, flax, an ornamental plant, pea, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, oil palm and *Phaseolus*.

In a preferred embodiment, nucleic acid molecules having SEQ ID NO: 1 through SEQ ID NO: 627 or complements and fragments of either can be utilized to obtain such homologues.

The degeneracy of the genetic code, which allows different nucleic acid sequences to code for the same protein or peptide, is known in the literature. (U.S. Pat. No. 4,757,006, the entirety of which is herein incorporated by reference).

In an aspect of the present invention, one or more of the nucleic acid molecules of the present invention differ in nucleic acid sequence from those encoding a maize or soybean tocopherol synthesis pathway enzyme or fragment thereof in SEQ ID NO: 1 through SEQ ID NO: 627 due to the degeneracy in the genetic code in that they encode the same tocopherol synthesis pathway enzyme but differ in nucleic acid sequence.

In another further aspect of the present invention, one or more of the nucleic acid molecules of the present invention differ in nucleic acid sequence from those encoding a maize or soybean tocopherol synthesis pathway enzyme or fragment thereof in SEQ ID NO: 1 through SEQ ID NO: 627 due to fact that the different nucleic acid sequence encodes a tocopherol synthesis pathway enzyme having one or more conservative amino acid residue. Examples of conservative substitutions are set forth in Table 1. It is understood that codons capable of coding for such conservative substitutions are known in the art.

TABLE 1

| Original Residue | Conservative Substitutions |
| --- | --- |
| Ala | Ser |
| Arg | Lys |
| Asn | Gln; His |
| Asp | Glu |
| Cys | Ser; Ala |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

In a further aspect of the present invention, one or more of the nucleic acid molecules of the present invention differ in nucleic acid sequence from those encoding a maize or soybean tocopherol synthesis pathway enzyme or fragment thereof set forth in SEQ ID NO: 1 through SEQ ID NO: 627 or fragment thereof due to the fact that one or more codons encoding an amino acid has been substituted for a codon that encodes a nonessential substitution of the amino acid originally encoded.

Agents of the present invention include nucleic acid molecules that encode a maize or soybean tocopherol synthesis pathway enzyme or fragment thereof and particularly substantially purified nucleic acid molecules selected from the group consisting of a nucleic acid molecule that encodes a maize or soybean deoxyarabiono-heptulosonate-P-synthase enzyme or fragment thereof; a nucleic acid molecule that encodes a maize or soybean putative deoxyarabiono-heptulosonate-P-synthase enzyme or fragment thereof; a nucleic acid molecule that encodes a maize dehydroquinate synthase enzyme or fragment thereof; a nucleic acid molecule that encodes a soybean dehydroquinate dehydratase enzyme or fragment thereof; a nucleic acid molecule that encodes a maize putative dehydroquinate dehydratase enzyme or fragment thereof; a nucleic acid molecule that encodes a maize or soybean shikimate dehydrogenase enzyme or fragment thereof; a nucleic acid molecule that encodes a maize or soybean shikimate kinase enzyme or fragment thereof; a nucleic acid molecule that encodes a maize enolpyruvylshikimate-P-synthase enzyme or fragment thereof; a nucleic acid molecule that encodes a maize or soybean chorismate synthase enzyme or fragment thereof; a nucleic acid molecule that encodes a maize or soybean chorismate mutase enzyme or fragment thereof; a nucleic acid molecule that encodes a maize tyrosine transaminase enzyme or fragment thereof; a nucleic acid molecule that encodes a maize or soybean putative tyrosine transaminase enzyme or fragment thereof; a nucleic acid molecule that encodes a maize or soybean transaminase A enzyme or fragment thereof; a nucleic acid molecule that encodes a soybean putative transaminase A enzyme or fragment thereof; a nucleic acid molecule that encodes a maize or soybean 4-hydroxyphenylpyruvate dioxygenase enzyme or fragment thereof; a nucleic acid molecule that encodes a maize or soybean homogentisic acid dioxygenase enzyme or fragment thereof; a nucleic acid molecule that encodes a maize or soybean geranylgeranylpyrophosphate synthase enzyme or fragment thereof.

Non-limiting examples of such nucleic acid molecules of the present invention are nucleic acid molecules comprising: SEQ ID NO: 1 through SEQ ID NO: 627 or fragment thereof that encode for a plant tocopherol synthesis pathway enzyme or fragment thereof, SEQ ID NO: 1 through SEQ ID NO: 97 and SEQ ID NO: 100 through SEQ ID NO: 146 or fragment thereof that encodes for a maize or soybean deoxyarabiono-heptulosonate-P-synthase enzyme or fragment thereof; SEQ ID NO: 98 through SEQ ID NO: 99 and SEQ ID NO: 147 through SEQ ID NO: 152 or fragment thereof that encodes for a maize or soybean putative deoxyarabiono-heptulosonate-P-synthase enzyme or fragment thereof; SEQ ID NO: 153 through SEQ ID NO: 157 or fragment thereof that encodes for a maize dehydroquinate synthase enzyme or fragment thereof; SEQ ID NO: 160 or fragment thereof that encodes for a soybean dehydroquinate dehydratase enzyme or fragment thereof; SEQ ID NO: 158 through SEQ ID NO: 159 or fragment thereof that encodes for a maize putative dehydroquinate dehydratase enzyme or fragment thereof; SEQ ID NO: 158 through SEQ ID NO: 159 and SEQ ID NO: 160 or fragment thereof that encodes for a maize or soybean shikimate dehydrogenase enzyme or fragment thereof; SEQ ID NO: 161 through SEQ ID NO: 179 and SEQ ID NO: 180 through SEQ ID NO: 183 or fragment thereof that encodes for a maize or soybean shikimate kinase enzyme or fragment thereof; SEQ ID NO: 184 through SEQ ID NO: 198 or fragment thereof that encodes for a maize enolpyruvylshikimate-P-synthase enzyme or fragment thereof; SEQ ID NO: 199 through SEQ ID NO: 231 and SEQ ID NO: 232 through SEQ ID NO: 255 or fragment thereof that encodes for a maize or soybean chorismate synthase enzyme or fragment thereof; SEQ ID NO: 256 through SEQ ID NO: 277 and SEQ ID NO: 278 through SEQ ID NO: 284 or fragment thereof that encodes for a maize or soybean chorismate mutase enzyme or fragment thereof; SEQ ID NO: 285 through SEQ ID NO: 286 or fragment thereof that encodes for a maize tyrosine transaminase enzyme or fragment thereof; SEQ ID NO: 287 through SEQ ID NO: 292 and SEQ ID NO: 293 through SEQ ID NO: 300 or fragment thereof that encodes for a maize or soybean putative tyrosine transaminase enzyme or fragment thereof; SEQ ID NO: 301 through SEQ ID NO: 474 and SEQ ID NO: 475 through SEQ ID NO: 581 or fragment thereof that encodes for a maize or soybean transaminase A enzyme or fragment thereof; SEQ ID NO: 582 through SEQ ID NO: 597 or fragment thereof that encodes for a soybean putative transaminase A enzyme or fragment thereof; SEQ ID NO: 598 through SEQ ID NO: 600 and SEQ ID NO: 601 through SEQ ID NO: 607 or fragment thereof that encodes for a maize or soybean 4-hydroxyphenylpyruvate dioxygenase enzyme or fragment thereof; SEQ ID NO: 608 through SEQ ID NO: 615 and SEQ ID NO: 616 through SEQ ID NO: 621 or fragment thereof that encodes for a maize or soybean homogentisic acid dioxygenase enzyme or fragment thereof; SEQ ID NO: 622 through SEQ ID NO: 624 and SEQ ID NO: 625 through SEQ ID NO: 627 or fragment thereof that encodes for a maize or soybean geranylgeranylpyrophosphate synthase enzyme or fragment thereof.

A nucleic acid molecule of the present invention can also encode an homologue of a maize or soybean deoxyarabiono-heptulosonate-P-synthase enzyme or fragment thereof; a maize or soybean putative deoxyarabiono-heptulosonate-P-synthase enzyme or fragment thereof; a maize dehydroquinate synthase enzyme or fragment thereof; a soybean dehydroquinate dehydratase enzyme or fragment thereof; a maize putative dehydroquinate dehydratase enzyme or fragment thereof; a maize or soybean shikimate dehydrogenase enzyme or fragment thereof; a maize or soybean shikimate kinase enzyme or fragment thereof; a maize enolpyruvylshikimate-P-synthase enzyme or fragment thereof; a maize or soybean chorismate synthase enzyme or fragment thereof; a maize or soybean chorismate mutase enzyme or fragment thereof; a maize tyrosine transaminase enzyme or fragment thereof; a maize or soybean putative tyrosine transaminase enzyme or fragment thereof; a maize or soybean transaminase A enzyme or fragment thereof; a soybean putative transaminase A enzyme or fragment thereof; a maize or soybean 4-hydroxyphenylpyruvate dioxygenase enzyme or fragment thereof; a maize or soybean homogentisic acid dioxygenase enzyme or fragment thereof; and a maize or soybean geranylgeranylpyrophosphate synthase enzyme or fragment thereof. As used herein a homologue protein molecule or fragment thereof is a counterpart protein molecule or fragment thereof in a second species (e.g., maize copalyl diphosphate synthase is a homologue of *Arabidopsis* copalyl diphosphate synthase).

(ii) Nucleic Acid Molecule Markers and Probes

One aspect of the present invention concerns markers that include nucleic acid molecules SEQ ID NO: 1 through SEQ ID NO: 627 or complements thereof or fragments of either that can act as markers or other nucleic acid molecules of the present invention that can act as markers. Genetic markers of the present invention include "dominant" or "codominant" markers "Codominant markers" reveal the presence of two or more alleles (two per diploid individual) at a locus. "Dominant markers" reveal the presence of only a single allele per locus. The presence of the dominant marker phenotype (e.g., a band of DNA) is an indication that one allele is present in either the homozygous or heterozygous condition. The absence of the dominant marker phenotype (e.g. absence of a DNA band) is merely evidence that "some other" undefined allele is present. In the case of populations where individuals are predominantly homozygous and loci are predominately dimorphic, dominant and codominant markers can be equally valuable. As populations become more heterozygous and multi-allelic, codominant markers often become more informative of the genotype than dominant markers. Marker molecules can be, for example, capable of detecting polymorphisms such as single nucleotide polymorphisms (SNPs).

SNPs are single base changes in genomic DNA sequence. They occur at greater frequency and are spaced with a greater uniformly throughout a genome than other reported forms of polymorphism. The greater frequency and uniformity of SNPs means that there is greater probability that such a polymorphism will be found near or in a genetic locus of interest than would be the case for other polymorphisms. SNPs are located in protein-coding regions and noncoding regions of a genome. Some of these SNPs may result in defective or variant protein expression (e.g., as a results of mutations or defective splicing). Analysis (genotyping) of characterized SNPs can require only a plus/minus assay rather than a lengthy measurement, permitting easier automation.

SNPs can be characterized using any of a variety of methods. Such methods include the direct or indirect sequencing of the site, the use of restriction enzymes (Botstein et al., *Am. J. Hum. Genet.* 32:314-331 (1980), the entirety of which is herein incorporated reference; Konieczny and Ausubel, *Plant J.* 4:403-410 (1993), the entirety of which is herein incorporated by reference), enzymatic and chemical mismatch assays (Myers et al., *Nature* 313:495-498 (1985), the entirety of which is herein incorporated by reference), allele-specific PCR (Newton et al., *Nucl. Acids Res.* 17:2503-2516 (1989), the entirety of which is herein incorporated by reference; Wu et al., *Proc. Natl. Acad. Sci. (U.S.A.)* 86:2757-2760 (1989), the entirety of which is herein incorporated by reference), ligase chain reaction (Barany, *Proc. Natl. Acad. Sci. (U.S.A.)* 88:189-193 (1991), the entirety of which is herein incorporated by reference), single-strand conformation polymorphism analysis (Labrune et al., *Am. J. Hum. Genet.* 48: 1115-1120 (1991), the entirety of which is herein incorporated by reference), primer-directed nucleotide incorporation assays (Kuppuswami et al., *Proc. Natl. Acad. Sci. USA* 88:1143-1147 (1991), the entirety of which is herein incorporated by reference), dideoxy fingerprinting (Sarkar et al., *Genomics* 13:441-443 (1992), the entirety of which is herein incorporated by reference), solid-phase ELISA-based oligonucleotide ligation assays (Nikiforov et al., *Nucl. Acids Res.* 22:4167-4175 (1994), the entirety of which is herein incorporated by reference), oligonucleotide fluorescence-quenching assays (Livak et al., *PCR Methods Appl.* 4:357-362 (1995), the entirety of which is herein incorporated by reference), 5'-nuclease allele-specific hybridization TaqMan assay (Livak et al., *Nature Genet.* 9:341-342 (1995), the entirety of which is herein incorporated by reference), template-directed dye-terminator incorporation (TDI) assay (Chen and Kwok, *Nucl. Acids Res.* 25:347-353 (1997), the entirety of which is herein incorporated by reference), allele-specific molecular beacon assay (Tyagi et al., *Nature Biotech.* 16: 49-53 (1998), the entirety of which is herein incorporated by reference), PinPoint assay (Haff and Smirnov, *Genome Res.* 7: 378-388 (1997), the entirety of which is herein incorporated by reference) and dCAPS analysis (Neff et al., *Plant J.* 14:387-392 (1998), the entirety of which is herein incorporated by reference).

Additional markers, such as AFLP markers, RFLP markers and RAPD markers, can be utilized (Walton, Seed World 22-29 (July, 1993), the entirety of which is herein incorporated by reference; Burow and Blake, *Molecular Dissection of Complex Traits,* 13-29, Paterson (ed.), CRC Press, New York (1988), the entirety of which is herein incorporated by reference). DNA markers can be developed from nucleic acid molecules using restriction endonucleases, the PCR and/or DNA sequence information. RFLP markers result from single base changes or insertions/deletions. These codominant markers are highly abundant in plant genomes, have a medium level of polymorphism and are developed by a combination of restriction endonuclease digestion and Southern blotting hybridization. CAPS are similarly developed from restriction nuclease digestion but only of specific PCR products. These markers are also codominant, have a medium level of polymorphism and are highly abundant in the genome. The CAPS result from single base changes and insertions/deletions.

Another marker type, RAPDs, are developed from DNA amplification with random primers and result from single base changes and insertions/deletions in plant genomes. They are dominant markers with a medium level of polymorphisms and are highly abundant. AFLP markers require using the PCR on a subset of restriction fragments from extended adapter primers. These markers are both dominant and codominant are highly abundant in genomes and exhibit a medium level of polymorphism.

SSRs require DNA sequence information. These codominant markers result from repeat length changes, are highly polymorphic and do not exhibit as high a degree of abundance in the genome as CAPS, AFLPs and RAPDs SNPs also require DNA sequence information. These codominant markers result from single base substitutions. They are highly abundant and exhibit a medium of polymorphism (Rafalski et al., In: *Nonmammalian Genomic Analysis,* Birren and Lai (ed.), Academic Press, San Diego, Calif., pp. 75-134 (1996), the entirety of which is herein incorporated by reference). It is understood that a nucleic acid molecule of the present invention may be used as a marker.

A PCR probe is a nucleic acid molecule capable of initiating a polymerase activity while in a double-stranded structure to with another nucleic acid. Various methods for determining the structure of PCR probes and PCR techniques exist in the art. Computer generated searches using programs such as Primer3 (available on the Worldwide Web at genome.wi.mit.edu/cgi-bin/primer/primer3.cgi), STSPipeline (available on the Worldwide Web at genome.wi.mit.edu/cgi-bin/www-STS_Pipeline), or GeneUp (Pesole et al., *BioTechniques* 25:112-123 (1998) the entirety of which is herein incorporated by reference), for example, can be used to identify potential PCR primers.

It is understood that a fragment of one or more of the nucleic acid molecules of the present invention may be a probe and specifically a PCR probe.

(b) Protein and Peptide Molecules

A class of agents comprises one or more of the protein or fragments thereof or peptide molecules encoded by SEQ ID NO: 1 through SEQ ID NO: 627 or one or more of the protein or fragment thereof and peptide molecules encoded by other nucleic acid agents of the present invention. As used herein, the term "protein molecule" or "peptide molecule" includes any molecule that comprises five or more amino acids. It is well known in the art that proteins may undergo modification, including post-translational modifications, such as, but not limited to, disulfide bond formation, glycosylation, phosphorylation, or oligomerization. Thus, as used herein, the term "protein molecule" or "peptide molecule" includes any protein molecule that is modified by any biological or non-biological process. The terms "amino acid" and "amino acids" refer to all naturally occurring L-amino acids. This definition is meant to include norleucine, ornithine, homocysteine and homoserine.

Non-limiting examples of the protein or fragment thereof of the present invention include a maize or soybean tocopherol synthesis pathway enzyme or fragment thereof, a maize or soybean deoxyarabiono-heptulosonate-P-synthase enzyme or fragment thereof, a maize or soybean putative deoxyarabiono-heptulosonate-P-synthase enzyme or fragment thereof; a maize dehydroquinate synthase enzyme or fragment thereof; a soybean dehydroquinate dehydratase enzyme or fragment thereof; a maize putative dehydroquinate dehydratase enzyme or fragment thereof; a maize or soybean shikimate dehydrogenase enzyme or fragment thereof; a maize or soybean shikimate kinase enzyme or fragment thereof; a maize enolpyruvylshikimate-P-synthase enzyme or fragment thereof; a maize or soybean chorismate synthase enzyme or fragment thereof; a maize or soybean chorismate mutase enzyme or fragment thereof; a maize tyrosine transaminase enzyme or fragment thereof; a maize or soybean putative tyrosine transaminase enzyme or fragment thereof; a maize or soybean transaminase A enzyme or fragment thereof; a soybean putative transaminase A enzyme or fragment thereof; a maize or soybean 4-hydroxyphenylpyruvate dioxygenase enzyme or fragment thereof; a maize or soybean homogentisic acid dioxygenase enzyme or fragment thereof; and a maize or soybean geranylgeranylpyrophosphate synthase enzyme or fragment thereof.

Non-limiting examples of the protein or fragment molecules of the present invention are a tocopherol synthesis pathway enzyme or fragment thereof encoded by: SEQ ID NO: 1 through SEQ ID NO: 627 or fragment thereof that encode for a tocopherol synthesis pathway enzyme or fragment thereof, SEQ ID NO: 1 through SEQ ID NO: 97 and SEQ ID NO: 100 through SEQ ID NO: 146 or fragment thereof that encodes for a maize or soybean deoxyarabiono-heptulosonate-P-synthase enzyme or fragment thereof; SEQ ID NO: 98 through SEQ ID NO: 99 and SEQ ID NO: 147 through SEQ ID NO: 152 or fragment thereof that encodes for a maize or soybean putative deoxyarabiono-heptulosonate-P-synthase enzyme or fragment thereof; SEQ ID NO: 153 through SEQ ID NO: 157 or fragment thereof that encodes for a maize dehydroquinate synthase enzyme or fragment thereof; SEQ ID NO: 160 or fragment thereof that encodes for a soybean dehydroquinate dehydratase enzyme or fragment thereof; SEQ ID NO: 158 through SEQ ID NO: 159 or fragment thereof that encodes for a maize putative dehydroquinate dehydratase enzyme or fragment thereof; SEQ ID NO: 158 through SEQ ID NO: 159 and SEQ ID NO: 160 or fragment thereof that encodes for a maize or soybean shikimate dehydrogenase enzyme or fragment thereof; SEQ ID NO: 161 through SEQ ID NO: 179 and SEQ ID NO: 180 through SEQ ID NO: 183 or fragment thereof that encodes for a maize or soybean shikimate kinase enzyme or fragment thereof; SEQ ID NO: 184 through SEQ ID NO: 198 or fragment thereof that encodes for a maize enolpyruvylshikimate-P-synthase enzyme or fragment thereof; SEQ ID NO: 199 through SEQ ID NO: 231 and SEQ ID NO: 232 through SEQ ID NO: 255 or fragment thereof that encodes for a maize or soybean chorismate synthase enzyme or fragment thereof; SEQ ID NO: 256 through SEQ ID NO: 277 and SEQ ID NO: 278 through SEQ ID NO: 284 or fragment thereof that encodes for a maize or soybean chorismate mutase enzyme or fragment thereof; SEQ ID NO: 285 through SEQ ID NO: 286 or fragment thereof that encodes for a maize tyrosine transaminase enzyme or fragment thereof; SEQ ID NO: 287 through SEQ ID NO: 292 and SEQ ID NO: 293 through SEQ ID NO: 300 or fragment thereof that encodes for a maize or soybean putative tyrosine transaminase enzyme or fragment thereof; SEQ ID NO: 301 through SEQ ID NO: 474 and SEQ ID NO: 475 through SEQ ID NO: 581 or fragment thereof that encodes for a maize or soybean transaminase A enzyme or fragment thereof; SEQ ID NO: 582 through SEQ ID NO: 597 or fragment thereof that encodes for a soybean putative transaminase A enzyme or fragment thereof; SEQ ID NO: 598 through SEQ ID NO: 600 and SEQ ID NO: 601 through SEQ ID NO: 607 or fragment thereof that encodes for a maize or soybean 4-hydroxyphenylpyruvate dioxygenase enzyme or fragment thereof; SEQ ID NO: 608 through SEQ ID NO: 615 and SEQ ID NO: 616 through SEQ ID NO: 621 or fragment thereof that encodes for a maize or soybean homogentisic acid dioxygenase enzyme or fragment thereof; SEQ ID NO: 622 through SEQ ID NO: 624 and SEQ ID NO: 625 through SEQ ID NO: 627 or fragment thereof that encodes for a maize or soybean geranylgeranylpyrophosphate synthase enzyme or fragment thereof.

One or more of the protein or fragment of peptide molecules may be produced via chemical synthesis, or more preferably, by expressing in a suitable bacterial or eucaryotic host. Suitable methods for expression are described by Sambrook et al., (In: *Molecular Cloning, A Laboratory Manual, 2nd Edition, Cold Spring Harbor Press*, Cold Spring Harbor, N.Y. (1989)), or similar texts. For example, the protein may be expressed in, for example, Uses of the Agents of the Invention, Section (a) Plant Constructs and Plant Transformants; Section (b) Fungal Constructs and Fungal Transformants; Section (c) Mammalian Constructs and Transformed Mammalian Cells; Section (d) Insect Constructs and Transformed Insect Cells; and Section (e) Bacterial Constructs and Transformed Bacterial Cells.

A "protein fragment" is a peptide or polypeptide molecule whose amino acid sequence comprises a subset of the amino acid sequence of that protein. A protein or fragment thereof that comprises one or more additional peptide regions not derived from that protein is a "fusion" protein. Such molecules may be derivatized to contain carbohydrate or other moieties (such as keyhole limpet hemocyanin, etc.). Fusion protein or peptide molecules of the present invention are preferably produced via recombinant means.

Another class of agents comprise protein or peptide molecules or fragments or fusions thereof encoded by SEQ ID NO: 1 through SEQ ID NO: 627 or complements thereof in which conservative, non-essential or non-relevant amino acid residues have been added, replaced or deleted. Computerized means for designing modifications in protein structure are known in the art (Dahiyat and Mayo, *Science* 278:82-87 (1997), the entirety of which is herein incorporated by reference).

The protein molecules of the present invention include plant homologue proteins. An example of such a homologue is a homologue protein of a non-maize or non-soybean plant species, that include but not limited to alfalfa, *Arabidopsis*, barley, *Brassica*, broccoli, cabbage, citrus, cotton, garlic, oat, oilseed rape, onion, canola, flax, an ornamental plant, pea, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, oil palm, *Phaseolus* etc. Particularly preferred non-maize or non-soybean for use for the isolation of homologs would include, *Arabidopsis*, barley, cotton, oat, oilseed rape, rice, canola, ornamentals, sugarcane, sugarbeet, tomato, potato, wheat and turf grasses. Such a homologue can be obtained by any of a variety of methods. Most preferably, as indicated above, one or more of the disclosed sequences (SEQ ID NO: 1 through SEQ ID NO: 627 or complements thereof) will be used to define a pair of primers that may be used to isolate the homologue-encoding nucleic acid molecules from any desired species. Such molecules can be expressed to yield homologues by recombinant means.

(c) Antibodies

One aspect of the present invention concerns antibodies, single-chain antigen binding molecules, or other proteins that specifically bind to one or more of the protein or peptide molecules of the present invention and their homologues, fusions or fragments. Such antibodies may be used to quantitatively or qualitatively detect the protein or peptide molecules of the present invention. As used herein, an antibody or peptide is said to "specifically bind" to a protein or peptide molecule of the present invention if such binding is not competitively inhibited by the presence of non-related molecules.

Nucleic acid molecules that encode all or part of the protein of the present invention can be expressed, via recombinant means, to yield protein or peptides that can in turn be used to elicit antibodies that are capable of binding the expressed protein or peptide. Such antibodies may be used in immunoassays for that protein. Such protein-encoding molecules, or their fragments may be a "fusion" molecule (i.e., a part of a larger nucleic acid molecule) such that, upon expression, a fusion protein is produced. It is understood that any of the nucleic acid molecules of the present invention may be expressed, via recombinant means, to yield proteins or peptides encoded by these nucleic acid molecules.

The antibodies that specifically bind proteins and protein fragments of the present invention may be polyclonal or monoclonal and may comprise intact immunoglobulins, or antigen binding portions of immunoglobulins fragments (such as (F(ab'), F(ab')$_2$), or single-chain immunoglobulins producible, for example, via recombinant means. It is understood that practitioners are familiar with the standard resource materials which describe specific conditions and procedures for the construction, manipulation and isolation of antibodies (see, for example, Harlow and Lane, In: *Antibodies: A Laboratory Manual*, Cold Spring Harbor Press, Cold Spring Harbor, N.Y. (1988), the entirety of which is herein incorporated by reference).

Murine monoclonal antibodies are particularly preferred. BALB/c mice are preferred for this purpose, however, equivalent strains may also be used. The animals are preferably immunized with approximately 25 μg of purified protein (or fragment thereof) that has been emulsified in a suitable adjuvant (such as TiterMax adjuvant (Vaxcel, Norcross, Ga.)). Immunization is preferably conducted at two intramuscular sites, one intraperitoneal site and one subcutaneous site at the base of the tail. An additional i.v. injection of approximately 25 μg of antigen is preferably given in normal saline three weeks later. After approximately 11 days following the second injection, the mice may be bled and the blood screened for the presence of anti-protein or peptide antibodies. Preferably, a direct binding Enzyme-Linked Immunoassay (ELISA) is employed for this purpose.

More preferably, the mouse having the highest antibody titer is given a third i.v. injection of approximately 25 μg of the same protein or fragment. The splenic leukocytes from this animal may be recovered 3 days later and then permitted to fuse, most preferably, using polyethylene glycol, with cells of a suitable myeloma cell line (such as, for example, the P3X63Ag8.653 myeloma cell line). Hybridoma cells are selected by culturing the cells under "HAT" (hypoxanthineaminopterin-thymine) selection for about one week. The resulting clones may then be screened for their capacity to produce monoclonal antibodies ("mAbs"), preferably by direct ELISA.

In one embodiment, anti-protein or peptide monoclonal antibodies are isolated using a fusion of a protein or peptide of the present invention, or conjugate of a protein or peptide of the present invention, as immunogens. Thus, for example, a group of mice can be immunized using a fusion protein emulsified in Freund's complete adjuvant (e.g. approximately 50 µg of antigen per immunization). At three week intervals, an identical amount of antigen is emulsified in Freund's incomplete adjuvant and used to immunize the animals. Ten days following the third immunization, serum samples are taken and evaluated for the presence of antibody. If antibody titers are too low, a fourth booster can be employed. Polysera capable of binding the protein or peptide can also be obtained using this method.

In a preferred procedure for obtaining monoclonal antibodies, the spleens of the above-described immunized mice are removed, disrupted and immune splenocytes are isolated over a ficoll gradient. The isolated splenocytes are fused, using polyethylene glycol with BALB/c-derived HGPRT (hypoxanthine guanine. phosphoribosyl transferase) deficient P3x63xAg8.653 plasmacytoma cells. The fused cells are plated into 96 well microtiter plates and screened for hybridoma fusion cells by their capacity to grow in culture medium supplemented with hypothanthine, aminopterin and thymidine for approximately 2-3 weeks.

Hybridoma cells that arise from such incubation are preferably screened for their capacity to produce an immunoglobulin that binds to a protein of interest. An indirect ELISA may be used for this purpose. In brief, the supernatants of hybridomas are incubated in microtiter wells that contain immobilized protein. After washing, the titer of bound immunoglobulin can be determined using, for example, a goat anti-mouse antibody conjugated to horseradish peroxidase. After additional washing, the amount of immobilized enzyme is determined (for example through the use of a chromogenic substrate). Such screening is performed as quickly as possible after the identification of the hybridoma in order to ensure that a desired clone is not overgrown by non-secreting neighbor cells. Desirably, the fusion plates are screened several times since the rates of hybridoma growth vary. In a preferred sub-embodiment, a different antigenic form may be used to screen the hybridoma. Thus, for example, the splenocytes may be immunized with one immunogen, but the resulting hybridomas can be screened using a different immunogen. It is understood that any of the protein or peptide molecules of the present invention may be used to raise antibodies.

As discussed below, such antibody molecules or their fragments may be used for diagnostic purposes. Where the antibodies are intended for diagnostic purposes, it may be desirable to derivatize them, for example with a ligand group (such as biotin) or a detectable marker group (such as a fluorescent group, a radioisotope or an enzyme).

The ability to produce antibodies that bind the protein or peptide molecules of the present invention permits the identification of mimetic compounds of those molecules. A "mimetic compound" is a compound that is not that compound, or a fragment of that compound, but which nonetheless exhibits an ability to specifically bind to antibodies directed against that compound.

It is understood that any of the agents of the present invention can be substantially purified and/or be biologically active and/or recombinant.

Uses of the Agents of the Invention

Nucleic acid molecules and fragments thereof of the present invention may be employed to obtain other nucleic acid molecules from the same species (e.g., ESTs or fragment thereof from maize may be utilized to obtain other nucleic acid molecules from maize). Such nucleic acid molecules include the nucleic acid molecules that encode the complete coding sequence of a protein and promoters and flanking sequences of such molecules. In addition, such nucleic acid molecules include nucleic acid molecules that encode for other isozymes or gene family members. Such molecules can be readily obtained by using the above-described nucleic acid molecules or fragments thereof to screen cDNA or genomic libraries obtained from maize or soybean. Methods for forming such libraries are well known in the art.

Nucleic acid molecules and fragments thereof of the present invention may also be employed to obtain nucleic acid homologues. Such homologues include the nucleic acid molecule of other plants or other organisms (e.g., alfalfa, *Arabidopsis*, barley, *Brassica*, broccoli, cabbage, citrus, cotton, garlic, oat, oilseed rape, onion, canola, flax, an ornamental plant, pea, peanut, pepper, potato, rice, rye, sorghum, strawberry, sugarcane, sugarbeet, tomato, wheat, poplar, pine, fir, eucalyptus, apple, lettuce, lentils, grape, banana, tea, turf grasses, sunflower, oil palm, *Phaseolus*, etc.) including the nucleic acid molecules that encode, in whole or in part, protein homologues of other plant species or other organisms, sequences of genetic elements such as promoters and transcriptional regulatory elements. Such molecules can be readily obtained by using the above-described nucleic acid molecules or fragments thereof to screen cDNA or genomic libraries obtained from such plant species. Methods for forming such libraries are well known in the art. Such homologue molecules may differ in their nucleotide sequences from those found in one or more of SEQ ID NO: 1 through SEQ ID NO: 627 or complements thereof because complete complementarity is not needed for stable hybridization. The nucleic acid molecules of the present invention therefore also include molecules that, although capable of specifically hybridizing with the nucleic acid molecules may lack "complete complementarity."

Any of a variety of methods may be used to obtain one or more of the above-described nucleic acid molecules (Zamechik et al., *Proc. Natl. Acad. Sci.* (*U.S.A.*) 83:4143-4146 (1986), the entirety of which is herein incorporated by reference; Goodchild et al., *Proc. Natl. Acad. Sci.* (*U.S.A.*) 85:5507-5511 (1988), the entirety of which is herein incorporated by reference; Wickstrom et al., *Proc. Natl. Acad. Sci.* (*U.S.A.*) 85:1028-1032 (1988), the entirety of which is herein incorporated by reference; Holt et al., *Molec. Cell. Biol.* 8:963-973 (1988), the entirety of which is herein incorporated by reference; Gerwirtz et al., *Science* 242:1303-1306 (1988), the entirety of which is herein incorporated by reference; Anfossi et al., *Proc. Natl. Acad. Sci.* (*U.S.A.*) 86:3379-3383 (1989), the entirety of which is herein incorporated by reference; Becker et al., *EMBO J.* 8:3685-3691 (1989); the entirety of which is herein incorporated by reference). Automated nucleic acid synthesizers may be employed for this purpose. In lieu of such synthesis, the disclosed nucleic acid molecules may be used to define a pair of primers that can be used with the polymerase chain reaction (Mullis et al., *Cold Spring Harbor Symp. Quant. Biol.* 51:263-273 (1986); Erlich et al., European Patent 50,424; European Patent 84,796; European Patent 258,017; European Patent 237,362; Mullis, European Patent 201,184; Mullis et al., U.S. Pat. No. 4,683,202; Erlich, U.S. Pat. No. 4,582,788; and Saiki et al., U.S. Pat. No. 4,683, 194, all of which are herein incorporated by reference in their entirety) to amplify and obtain any desired nucleic acid molecule or fragment.

Promoter sequence(s) and other genetic elements, including but not limited to transcriptional regulatory flanking sequences, associated with one or more of the disclosed nucleic acid sequences can also be obtained using the disclosed nucleic acid sequence provided herein. In one embodiment, such sequences are obtained by incubating EST nucleic acid molecules or preferably fragments thereof with members of genomic libraries (e.g. maize and soybean) and recovering clones that hybridize to the EST nucleic acid molecule or fragment thereof. In a second embodiment, methods of "chromosome walking," or inverse PCR may be used to obtain such sequences (Frohman et al., *Proc. Natl. Acad. Sci.* (*U.S.A.*) 85:8998-9002 (1988); Ohara et al., *Proc. Natl. Acad. Sci.* (*U.S.A.*) 86:5673-5677 (1989); Pang et al., *Biotechniques* 22:1046-1048 (1977); Huang et al., *Methods Mol. Biol.* 69:89-96 (1997); Huang et al., *Method Mol. Biol.* 67:287-294 (1997); Benkel et al., *Genet. Anal.* 13:123-127 (1996); Hartl et al., *Methods Mol. Biol.* 58:293-301 (1996), all of which are herein incorporated by reference in their entirety).

The nucleic acid molecules of the present invention may be used to isolate promoters of cell enhanced, cell specific, tissue enhanced, tissue specific, developmentally or environmentally regulated expression profiles. Isolation and functional analysis of the 5' flanking promoter sequences of these genes from genomic libraries, for example, using genomic screening methods and PCR techniques would result in the isolation of useful promoters and transcriptional regulatory elements. These methods are known to those of skill in the art and have been described (See, for example, Birren et al., *Genome Analysis: Analyzing DNA*, 1, (1997), Cold Spring Harbor Laboratory Press, Cold Spring Harbor, N.Y., the entirety of which is herein incorporated by reference). Promoters obtained utilizing the nucleic acid molecules of the present invention could also be modified to affect their control characteristics. Examples of such modifications would include but are not limited to enhanced sequences as reported in Uses of the Agents of the Invention, Section (a) Plant Constructs and Plant Transformants. Such genetic elements could be used to enhance gene expression of new and existing traits for crop improvements.

In one sub-aspect, such an analysis is conducted by determining the presence and/or identity of polymorphism(s) by one or more of the nucleic acid molecules of the present invention and more preferably one or more of the EST nucleic acid molecule or fragment thereof which are associated with a phenotype, or a predisposition to that phenotype.

Any of a variety of molecules can be used to identify such polymorphism(s). In one embodiment, one or more of the EST nucleic acid molecules (or a sub-fragment thereof) may be employed as a marker nucleic acid molecule to identify such polymorphism(s). Alternatively, such polymorphisms can be detected through the use of a marker nucleic acid molecule or a marker protein that is genetically linked to (i.e., a polynucleotide that co-segregates with) such polymorphism(s).

In an alternative embodiment, such polymorphisms can be detected through the use of a marker nucleic acid molecule that is physically linked to such polymorphism(s). For this purpose, marker nucleic acid molecules comprising a nucleotide sequence of a polynucleotide located within 1 mb of the polymorphism(s) and more preferably within 100 kb of the polymorphism(s) and most preferably within 10 kb of the polymorphism(s) can be employed.

The genomes of animals and plants naturally undergo spontaneous mutation in the course of their continuing evolution (Gusella, *Ann. Rev. Biochem.* 55:831-854 (1986)). A "polymorphism" is a variation or difference in the sequence of the gene or its flanking regions that arises in some of the members of a species. The variant sequence and the "original" sequence co-exist in the species' population. In some instances, such co-existence is in stable or quasi-stable equilibrium.

A polymorphism is thus said to be "allelic," in that, due to the existence of the polymorphism, some members of a species may have the original sequence (i.e., the original "allele") whereas other members may have the variant sequence (i.e., the variant "allele"). In the simplest case, only one variant sequence may exist and the polymorphism is thus said to be di-allelic. In other cases, the species' population may contain multiple alleles and the polymorphism is termed tri-allelic, etc. A single gene may have multiple different unrelated polymorphisms. For example, it may have a di-allelic polymorphism at one site and a multi-allelic polymorphism at another site.

The variation that defines the polymorphism may range from a single nucleotide variation to the insertion or deletion of extended regions within a gene. In some cases, the DNA sequence variations are in regions of the genome that are characterized by short tandem repeats (STRs) that include tandem di- or tri-nucleotide repeated motifs of nucleotides. Polymorphisms characterized by such tandem repeats are referred to as "variable number tandem repeat" ("VNTR") polymorphisms. VNTRs have been used in identity analysis (Weber, U.S. Pat. No. 5,075,217; Armour et al., *FEBS Lett.* 307:113-115 (1992); Jones et al., *Eur. J. Haematol.* 39:144-147 (1987); Horn et al., PCT Patent Application WO91/14003; Jeffreys, European Patent Application 370,719; Jeffreys, U.S. Pat. No. 5,175,082; Jeffreys et al., *Amer. J. Hum. Genet.* 39:11-24 (1986); Jeffreys et al., *Nature* 316:76-79 (1985); Gray et al., *Proc. R. Acad. Soc. Lond.* 243:241-253 (1991); Moore et al., *Genomics* 10:654-660 (1991); Jeffreys et al., *Anim. Genet.* 18:1-15 (1987); Hillel et al., *Anim. Genet.* 20:145-155 (1989); Hillel et al., *Genet.* 124:783-789 (1990), all of which are herein incorporated by reference in their entirety).

The detection of polymorphic sites in a sample of DNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis or other means.

The most preferred method of achieving such amplification employs the polymerase chain reaction ("PCR") (Mullis et al., *Cold Spring Harbor Symp. Quant. Biol.* 51:263-273 (1986); Erlich et al., European Patent Appln. 50,424; European Patent Appln. 84,796; European Patent Application 258,017; European Patent Appln. 237,362; Mullis, European Patent Appln. 201,184; Mullis et al., U.S. Pat. No. 4,683,202; Erlich, U.S. Pat. No. 4,582,788; and Saiki et al., U.S. Pat. No. 4,683,194), using primer pairs that are capable of hybridizing to the proximal sequences that define a polymorphism in its double-stranded form.

In lieu of PCR, alternative methods, such as the "Ligase Chain Reaction" ("LCR") may be used (Barany, *Proc. Natl. Acad. Sci.* (*U.S.A.*) 88:189-193 (1991), the entirety of which is herein incorporated by reference). LCR uses two pairs of oligonucleotide probes to exponentially amplify a specific target. The sequences of each pair of oligonucleotides is selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

LCR can be performed with oligonucleotides having the proximal and distal sequences of the same strand of a polymorphic site. In one embodiment, either oligonucleotide will be designed to include the actual polymorphic site of the polymorphism. In such an embodiment, the reaction conditions are selected such that the oligonucleotides can be ligated together only if the target molecule either contains or lacks the specific nucleotide that is complementary to the polymorphic site present on the oligonucleotide. Alternatively, the oligonucleotides may be selected such that they do not include the polymorphic site (see, Segev, PCT Application WO 90/01069, the entirety of which is herein incorporated by reference).

The "Oligonucleotide Ligation Assay" ("OLA") may alternatively be employed (Landegren et al., *Science* 241:1077-1080 (1988), the entirety of which is herein incorporated by reference). The OLA protocol uses two oligonucleotides which are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Nickerson et al., have described a nucleic acid detection assay that combines attributes of PCR and OLA (Nickerson et al., *Proc. Natl. Acad. Sci. (U.S.A.)* 87:8923-8927 (1990), the entirety of which is herein incorporated by reference). In this method, PCR is used to achieve the exponential amplification of target DNA, which is then detected using OLA. In addition to requiring multiple and separate, processing steps, one problem associated with such combinations is that they inherit all of the problems associated with PCR and OLA.

Schemes based on ligation of two (or more) oligonucleotides in the presence of nucleic acid having the sequence of the resulting "di-oligonucleotide", thereby amplifying the di-oligonucleotide, are also known (Wu et al., *Genomics* 4:560-569 (1989), the entirety of which is herein incorporated by reference) and may be readily adapted to the purposes of the present invention.

Other known nucleic acid amplification procedures, such as allele-specific oligomers, branched DNA technology, transcription-based amplification systems, or isothermal amplification methods may also be used to amplify and analyze such polymorphisms (Malek et al., U.S. Pat. No. 5,130,238; Davey et al., European Patent Application 329,822; Schuster et al., U.S. Pat. No. 5,169,766; Miller et al., PCT Patent Application WO 89/06700; Kwoh et al., *Proc. Natl. Acad. Sci. (U.S.A.)* 86:1173-1177 (1989); Gingeras et al., PCT Patent Application WO 88/10315; Walker et al., *Proc. Natl. Acad. Sci. (U.S.A.)* 89:392-396 (1992), all of which are herein incorporated by reference in their entirety).

The identification of a polymorphism can be determined in a variety of ways. By correlating the presence or absence of it in a plant with the presence or absence of a phenotype, it is possible to predict the phenotype of that plant. If a polymorphism creates or destroys a restriction endonuclease cleavage site, or if it results in the loss or insertion of DNA (e.g., a VNTR polymorphism), it will alter the size or profile of the DNA fragments that are generated by digestion with that restriction endonuclease. As such, individuals that possess a variant sequence can be distinguished from those having the original sequence by restriction fragment analysis. Polymorphisms that can be identified in this manner are termed "restriction fragment length polymorphisms" ("RFLPs"). RFLPs have been widely used in human and plant genetic analyses (Glassberg, UK Patent Application 2135774; Skolnick et al., *Cytogen. Cell Genet.* 32:58-67 (1982); Botstein et al., *Ann. J. Hum. Genet.* 32:314-331 (1980); Fischer et al., (PCT Application WO90/13668); Uhlen, PCT Application WO90/11369).

Polymorphisms can also be identified by Single Strand Conformation Polymorphism (SSCP) analysis. SSCP is a method capable of identifying most sequence variations in a single strand of DNA, typically between 150 and 250 nucleotides in length (Elles, *Methods in Molecular Medicine: Molecular Diagnosis of Genetic Diseases*, Humana Press (1996), the entirety of which is herein incorporated by reference); Orita et al., *Genomics* 5:874-879 (1989), the entirety of which is herein incorporated by reference). Under denaturing conditions a single strand of DNA will adopt a conformation that is uniquely dependent on its sequence conformation. This conformation usually will be different, even if only a single base is changed. Most conformations have been reported to alter the physical configuration or size sufficiently to be detectable by electrophoresis. A number of protocols have been described for SSCP including, but not limited to, Lee et al., *Anal. Biochem.* 205:289-293 (1992), the entirety of which is herein incorporated by reference; Suzuki et al., *Anal. Biochem.* 192:82-84 (1991), the entirety of which is herein incorporated by reference; Lo et al., *Nucleic Acids Research* 20:1005-1009 (1992), the entirety of which is herein incorporated by reference; Sarkar et al., *Genomics* 13:441-443 (1992), the entirety of which is herein incorporated by reference. It is understood that one or more of the nucleic acids of the present invention, may be utilized as markers or probes to detect polymorphisms by SSCP analysis.

Polymorphisms may also be found using a DNA fingerprinting technique called amplified fragment length polymorphism (AFLP), which is based on the selective PCR amplification of restriction fragments from a total digest of genomic DNA to profile that DNA (Vos et al., *Nucleic Acids Res.* 23:4407-4414 (1995), the entirety of which is herein incorporated by reference). This method allows for the specific co-amplification of high numbers of restriction fragments, which can be visualized by PCR without knowledge of the nucleic acid sequence.

AFLP employs basically three steps. Initially, a sample of genomic DNA is cut with restriction enzymes and oligonucleotide adapters are ligated to the restriction fragments of the DNA. The restriction fragments are then amplified using PCR by using the adapter and restriction sequence as target sites for primer annealing. The selective amplification is achieved by the use of primers that extend into the restriction fragments, amplifying only those fragments in which the primer extensions match the nucleotide flanking the restriction sites. These amplified fragments are then visualized on a denaturing polyacrylamide gel.

AFLP analysis has been performed on *Salix* (Beismann et al., *Mol. Ecol.* 6:989-993 (1997), the entirety of which is herein incorporated by reference), *Acinetobacter* (Janssen et al., *Int. J. Syst. Bacteriol.* 47:1179-1187 (1997), the entirety of which is herein incorporated by reference), *Aeromonas popoffi* (Huys et al., *Int. J. Syst. Bacteriol.* 47:1165-1171 (1997), the entirety of which is herein incorporated by reference), rice (McCouch et al., *Plant Mol. Biol.* 35:89-99 (1997), the entirety of which is herein incorporated by reference; Nandi et al., *Mol. Gen. Genet.* 255:1-8 (1997), the entirety of which is herein incorporated by reference; Cho et al., *Genome* 39:373-378 (1996), the entirety of which is herein incorporated by reference), barley (*Hordeum vulgare*)(Simons et al.,

*Genomics* 44:61-70 (1997), the entirety of which is herein incorporated by reference; Waugh et al., *Mol. Gen. Genet.* 255:311-321 (1997), the entirety of which is herein incorporated by reference; Qi et al., *Mol. Gen. Genet.* 254:330-336 (1997), the entirety of which is herein incorporated by reference; Becker et al., *Mol. Gen. Genet.* 249:65-73 (1995), the entirety of which is herein incorporated by reference), potato (Van der Voort et al., *Mol. Gen. Genet.* 255:438-447 (1997), the entirety of which is herein incorporated by reference; Meksem et al., *Mol. Gen. Genet.* 249:74-81 (1995), the entirety of which is herein incorporated by reference), *Phytophthora infestans* (Van der Lee et al., *Fungal Genet. Biol.* 21:278-291 (1997), the entirety of which is herein incorporated by reference), *Bacillus anthracis* (Keim et al., *J. Bacteriol.* 179:818-824 (1997), the entirety of which is herein incorporated by reference), *Astragalus cremnophylax* (Travis et al., *Mol. Ecol.* 5:735-745 (1996), the entirety of which is herein incorporated by reference), *Arabidopsis* (Cnops et al., *Mol. Gen. Genet.* 253:32-41 (1996), the entirety of which is herein incorporated by reference), *Escherichia coli* (Lin et al., *Nucleic Acids Res.* 24:3649-3650 (1996), the entirety of which is herein incorporated by reference), *Aeromonas* (Huys et al., *Int. J. Syst. Bacteriol.* 46:572-580 (1996), the entirety of which is herein incorporated by reference), nematode (Folkertsma et al., *Mol. Plant. Microbe Interact.* 9:47-54 (1996), the entirety of which is herein incorporated by reference), tomato (Thomas et al., *Plant J.* 8:785-794 (1995), the entirety of which is herein incorporated by reference) and human (Latorra et al., *PCR Methods Appl.* 3:351-358 (1994), the entirety of which is herein incorporated by reference). AFLP analysis has also been used for fingerprinting mRNA (Money et al., *Nucleic Acids Res.* 24:2616-2617 (1996), the entirety of which is herein incorporated by reference; Bachem et al., *Plant J.* 9:745-753 (1996), the entirety of which is herein incorporated by reference). It is understood that one or more of the nucleic acids of the present invention, may be utilized as markers or probes to detect polymorphisms by AFLP analysis or for fingerprinting RNA.

Polymorphisms may also be found using random amplified polymorphic DNA (RAPD) (Williams et al., *Nucl. Acids Res.* 18:6531-6535 (1990), the entirety of which is herein incorporated by reference) and cleaveable amplified polymorphic sequences (CAPS) (Lyamichev et al., *Science* 260:778-783 (1993), the entirety of which is herein incorporated by reference). It is understood that one or more of the nucleic acid molecules of the present invention, may be utilized as markers or probes to detect polymorphisms by RAPD or CAPS analysis.

Through genetic mapping, a fine scale linkage map can be developed using DNA markers and, then, a genomic DNA library of large-sized fragments can be screened with molecular markers linked to the desired trait. Molecular markers are advantageous for agronomic traits that are otherwise difficult to tag, such as resistance to pathogens, insects and nematodes, tolerance to abiotic stress, quality parameters and quantitative traits such as high yield potential.

The essential requirements for marker-assisted selection in a plant breeding program are: (1) the marker(s) should co-segregate or be closely linked with the desired trait; (2) an efficient means of screening large populations for the molecular marker(s) should be available; and (3) the screening technique should have high reproducibility across laboratories and preferably be economical to use and be user-friendly.

The genetic linkage of marker molecules can be established by a gene mapping model such as, without limitation, the flanking marker model reported by Lander and Botstein, *Genetics* 121:185-199 (1989) and the interval mapping, based on maximum likelihood methods described by Lander and Botstein, *Genetics* 121:185-199 (1989) and implemented in the software package MAPMAKER/QTL (Lincoln and Lander, Mapping Genes Controlling Quantitative Traits Using MAPMAKER/QTL, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y., the manual of which is herein incorporated by reference in its entirety). Use of Qgene software is a particularly preferred approach.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL).

The LOD score essentially indicates how much more likely the data are to have arisen assuming the presence of a QTL than in its absence. The LOD threshold value for avoiding a false positive with a given confidence, say 95%, depends on the number of markers and the length of the genome. Graphs indicating LOD thresholds are set forth in Lander and Botstein, *Genetics* 121:185-199 (1989) the entirety of which is herein incorporated by reference and further described by Arús and Moreno-González, *Plant Breeding*, Hayward et al., (eds.) Chapman & Hall, London, pp. 314-331 (1993), the entirety of which is herein incorporated by reference.

Additional models can be used. Many modifications and alternative approaches to interval mapping have been reported, including the use non-parametric methods (Kruglyak and Lander, *Genetics* 139:1421-1428 (1995), the entirety of which is herein incorporated by reference). Multiple regression methods or models can be also be used, in which the trait is regressed on a large number of markers (Jansen, *Biometrics in Plant Breeding*, van Oijen and Jansen (eds.), Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994), both of which is herein incorporated by reference in their entirety). Procedures combining interval mapping with regression analysis, whereby the phenotype is regressed onto a single putative QTL at a given marker interval and at the same time onto a number of markers that serve as 'cofactors,' have been reported by Jansen and Stam, *Genetics* 136:1447-1455 (1994), the entirety of which is herein incorporated by reference and Zeng, *Genetics* 136:1457-1468 (1994) the entirety of which is herein incorporated by reference. Generally, the use of cofactors reduces the bias and sampling error of the estimated QTL positions (Utz and Melchinger, *Biometrics in Plant Breeding*, van Oijen and Jansen (eds.) Proceedings of the Ninth Meeting of the Eucarpia Section Biometrics in Plant Breeding, The Netherlands, pp. 195-204 (1994), the entirety of which is herein incorporated by reference, thereby improving the precision and efficiency of QTL mapping (Zeng, *Genetics* 136:1457-1468 (1994)). These models can be extended to multi-environment experiments to analyze genotype-environment interactions (Jansen et al., *Theo. Appl. Genet.* 91:33-37 (1995), the entirety of which is herein incorporated by reference).

Selection of an appropriate mapping populations is important to map construction. The choice of appropriate mapping population depends on the type of marker systems employed (Tanksley et al., *Molecular mapping plant chromosomes. Chromosome structure and function: Impact of new concepts*, Gustafson and Appels (eds.), Plenum Press, New York, pp 157-173 (1988), the entirety of which is herein incorporated by reference). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted×adapted).

An $F_2$ population is the first generation of selfing after the hybrid seed is produced. Usually a single $F_1$ plant is selfed to generate a population segregating for all the genes in Mendelian (1:2:1) fashion. Maximum genetic information is obtained from a completely classified $F_2$ population using a codominant marker system (Mather, *Measurement of Linkage in Heredity*, Methuen and Co., (1938), the entirety of which is herein incorporated by reference). In the case of dominant markers, progeny tests (e.g. $F_3$, $BCF_2$) are required to identify the heterozygotes, thus making it equivalent to a completely classified $F_2$ population. However, this procedure is often prohibitive because of the cost and time involved in progeny testing. Progeny testing of $F_2$ individuals is often used in map construction where phenotypes do not consistently reflect genotype (e.g. disease resistance) or where trait expression is controlled by a QTL. Segregation data from progeny test populations (e.g. $F_3$ or $BCF_2$) can be used in map construction. Marker-assisted selection can then be applied to cross progeny based on marker-trait map associations ($F_2$, $F_3$), where linkage groups have not been completely disassociated by recombination events (i.e., maximum disequillibrium).

Recombinant inbred lines (RIL) (genetically related lines; usually >$F_5$, developed from continuously selfing $F_2$ lines towards homozygosity) can be used as a mapping population. Information obtained from dominant markers can be maximized by using RIL because all loci are homozygous or nearly so. Under conditions of tight linkage (i.e., about <10% recombination), dominant and co-dominant markers evaluated in RIL populations provide more information per individual than either marker type in backcross populations (Reiter et al., *Proc. Natl. Acad. Sci. (U.S.A.)* 89:1477-1481 (1992), the entirety of which is herein incorporated by reference). However, as the distance between markers becomes larger (i.e., loci become more independent), the information in RIL populations decreases dramatically when compared to codominant markers.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., *Proc. Natl. Acad. Sci. (U.S.A.)* 89:1477-1481 (1992)). Information obtained from backcross populations using either codominant or dominant markers is less than that obtained from $F_2$ populations because one, rather than two, recombinant gametes are sampled per plant. Backcross populations, however, are more informative (at low marker saturation) when compared to RILs as the distance between linked loci increases in RIL populations (i.e. about 15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the polymorphic loci are expected to map to a selected region.

Bulk segregant analysis (BSA) is a method developed for the rapid identification of linkage between markers and traits of interest (Michelmore et al., *Proc. Natl. Acad. Sci. (U.S.A.)* 88:9828-9832 (1991), the entirety of which is herein incorporated by reference). In BSA, two bulked DNA samples are drawn from a segregating population originating from a single cross. These bulks contain individuals that are identical for a particular trait (resistant or susceptible to particular disease) or genomic region but arbitrary at unlinked regions (i.e. heterozygous). Regions unlinked to the target region will not differ between the bulked samples of many individuals in BSA.

It is understood that one or more of the nucleic acid molecules of the present invention may be used as molecular markers. It is also understood that one or more of the protein molecules of the present invention may be used as molecular markers.

In accordance with this aspect of the present invention, a sample nucleic acid is obtained from plants cells or tissues. Any source of nucleic acid may be used. Preferably, the nucleic acid is genomic DNA. The nucleic acid is subjected to restriction endonuclease digestion. For example, one or more nucleic acid molecule or fragment thereof of the present invention can be used as a probe in accordance with the above-described polymorphic methods. The polymorphism obtained in this approach can then be cloned to identify the mutation at the coding region which alters the protein's structure or regulatory region of the gene which affects its expression level.

In an aspect of the present invention, one or more of the nucleic molecules of the present invention are used to determine the level (i.e., the concentration of mRNA in a sample, etc.) in a plant (preferably maize or soybean) or pattern (i.e., the kinetics of expression, rate of decomposition, stability profile, etc.) of the expression of a protein encoded in part or whole by one or more of the nucleic acid molecule of the present invention (collectively, the "Expression Response" of a cell or tissue). As used herein, the Expression Response manifested by a cell or tissue is said to be "altered" if it differs from the Expression Response of cells or tissues of plants not exhibiting the phenotype. To determine whether an Expression Response is altered, the Expression Response manifested by the cell or tissue of the plant exhibiting the phenotype is compared with that of a similar cell or tissue sample of a plant not exhibiting the phenotype. As will be appreciated, it is not necessary to re-determine the Expression Response of the cell or tissue sample of plants not exhibiting the phenotype each time such a comparison is made; rather, the Expression Response of a particular plant may be compared with previously obtained values of normal plants. As used herein, the phenotype of the organism is any of one or more characteristics of an organism (e.g. disease resistance, pest tolerance, environmental tolerance such as tolerance to abiotic stress, male sterility, quality improvement or yield etc.). A change in genotype or phenotype may be transient or permanent. Also as used herein, a tissue sample is any sample that comprises more than one cell. In a preferred aspect, a tissue sample comprises cells that share a common characteristic (e.g. derived from root, seed, flower, leaf, stem or pollen etc.).

In one aspect of the present invention, an evaluation can be conducted to determine whether a particular mRNA molecule is present. One or more of the nucleic acid molecules of the present invention, preferably one or more of the EST nucleic acid molecules or fragments thereof of the present invention are utilized to detect the presence or quantity of the mRNA species. Such molecules are then incubated with cell or tissue extracts of a plant under conditions sufficient to permit nucleic acid hybridization. The detection of double-stranded probe-mRNA hybrid molecules is indicative of the presence of the mRNA; the amount of such hybrid formed is proportional to the amount of mRNA. Thus, such probes may be used to ascertain the level and extent of the mRNA production in a plant's cells or tissues. Such nucleic acid hybridization may be conducted under quantitative conditions (thereby providing a numerical value of the amount of the mRNA present). Alternatively, the assay may be conducted as a qualitative assay that indicates either that the mRNA is present, or that its level exceeds a user set, predefined value.

A principle of in situ hybridization is that a labeled, single-stranded nucleic acid probe will hybridize to a complementary strand of cellular DNA or RNA and, under the appropriate conditions, these molecules will form a stable hybrid. When nucleic acid hybridization is combined with histological techniques, specific DNA or RNA sequences can be identified within a single cell. An advantage of in situ hybridization over more conventional techniques for the detection of nucleic acids is that it allows an investigator to determine the precise spatial population (Angerer et al., *Dev. Biol.* 101:477-484 (1984), the entirety of which is herein incorporated by reference; Angerer et al., *Dev. Biol.* 112:157-166 (1985), the entirety of which is herein incorporated by reference; Dixon et al., *EMBO J.* 10:1317-1324 (1991), the entirety of which is herein incorporated by reference). In situ hybridization may be used to measure the steady-state level of RNA accumulation. It is a sensitive technique and RNA sequences present in as few as 5-10 copies per cell can be detected (Hardin et al., *J. Mol. Biol.* 202:417-431 (1989), the entirety of which is herein incorporated by reference). A number of protocols have been devised for in situ hybridization, each with tissue preparation, hybridization and washing conditions (Meyerowitz, *Plant Mol. Biol. Rep.* 5:242-250 (1987), the entirety of which is herein incorporated by reference; Cox and Goldberg, In: *Plant Molecular Biology: A Practical Approach*, Shaw (ed.), pp 1-35, IRL Press, Oxford (1988), the entirety of which is herein incorporated by reference; Raikhel et al., *In situ RNA hybridization in plant tissues*, In: *Plant Molecular Biology Manual*, vol. B9: 1-32, Kluwer Academic Publisher, Dordrecht, Belgium (1989), the entirety of which is herein incorporated by reference).

In situ hybridization also allows for the localization of proteins within a tissue or cell (Wilkinson, In Situ Hybridization, Oxford University Press, Oxford (1992), the entirety of which is herein incorporated by reference; Langdale, *In Situ Hybridization* In: *The Maize Handbook*, Freeling and Walbot (eds.), pp 165-179, Springer-Verlag, New York (1994), the entirety of which is herein incorporated by reference). It is understood that one or more of the molecules of the present invention, preferably one or more of the EST nucleic acid molecules or fragments thereof of the present invention or one or more of the antibodies of the present invention may be utilized to detect the level or pattern of a tocopherol synthesis pathway enzyme or mRNA thereof by in situ hybridization.

Fluorescent in situ hybridization allows the localization of a particular DNA sequence along a chromosome which is useful, among other uses, for gene mapping, following chromosomes in hybrid lines or detecting chromosomes with translocations, transversions or deletions. In situ hybridization has been used to identify chromosomes in several plant species (Griffor et al., *Plant Mol. Biol.* 17:101-109 (1991), the entirety of which is herein incorporated by reference; Gustafson et al., *Proc. Natl. Acad. Sci. (U.S.A.)* 87:1899-1902 (1990), herein incorporated by reference; Mukai and Gill, *Genome* 34:448-452 (1991), the entirety of which is herein incorporated by reference; Schwarzacher and Heslop-Harrison, *Genome* 34:317-323 (1991); Wang et al., *Jpn. J. Genet.* 66:313-316 (1991), the entirety of which is herein incorporated by reference; Parra and Windle, *Nature Genetics* 5:17-21 (1993), the entirety of which is herein incorporated by reference). It is understood that the nucleic acid molecules of the present invention may be used as probes or markers to localize sequences along a chromosome.

Another method to localize the expression of a molecule is tissue printing. Tissue printing provides a way to screen, at the same time on the same membrane many tissue sections from different plants or different developmental stages. Tissue-printing procedures utilize films designed to immobilize proteins and nucleic acids. In essence, a freshly cut section of a tissue is pressed gently onto nitrocellulose paper, nylon membrane or polyvinylidene difluoride membrane. Such membranes are commercially available (e.g. Millipore, Bedford, Mass. U.S.A.). The contents of the cut cell transfer onto the membrane and the contents and are immobilized to the membrane. The immobilized contents form a latent print that can be visualized with appropriate probes. When a plant tissue print is made on nitrocellulose paper, the cell walls leave a physical print that makes the anatomy visible without further treatment (Varner and Taylor, *Plant Physiol.* 91:31-33 (1989), the entirety of which is herein incorporated by reference).

Tissue printing on substrate films is described by Daoust, *Exp. Cell Res.* 12:203-211 (1957), the entirety of which is herein incorporated by reference, who detected amylase, protease, ribonuclease and deoxyribonuclease in animal tissues using starch, gelatin and agar films. These techniques can be applied to plant tissues (Yomo and Taylor, *Planta* 112:35-43 (1973); the entirety of which is herein incorporated by reference; Harris and Chrispeels, *Plant Physiol.* 56:292-299 (1975), the entirety of which is herein incorporated by reference). Advances in membrane technology have increased the range of applications of Daoust's tissue-printing techniques allowing (Cassab and Varner, *J. Cell. Biol.* 105:2581-2588 (1987), the entirety of which is herein incorporated by reference) the histochemical localization of various plant enzymes and deoxyribonuclease on nitrocellulose paper and nylon (Spruce et al., *Phytochemistry* 26:2901-2903 (1987), the entirety of which is herein incorporated by reference; Barres et al., *Neuron* 5:527-544 (1990), the entirety of which is herein incorporated by reference; Reid and Pont-Lezica, *Tissue Printing: Tools for the Study of Anatomy, Histochemistry and Gene Expression*, Academic Press, New York, N.Y. (1992), the entirety of which is herein incorporated by reference; Reid et al., *Plant Physiol.* 93:160-165 (1990), the entirety of which is herein incorporated by reference; Ye et al., *Plant J.* 1:175-183 (1991), the entirety of which is herein incorporated by reference).

It is understood that one or more of the molecules of the present invention, preferably one or more of the EST nucleic acid molecules or fragments thereof of the present invention or one or more of the antibodies of the present invention may be utilized to detect the presence or quantity of a tocopherol synthesis pathway enzyme or mRNA thereof by tissue printing.

Further it is also understood that any of the nucleic acid molecules of the present invention may be used as marker nucleic acids and or probes in connection with methods that require probes or marker nucleic acids. As used herein, a probe is an agent that is utilized to determine an attribute or feature (e.g. presence or absence, location, correlation, etc.) of a molecule, cell, tissue or plant. As used herein, a marker nucleic acid is a nucleic acid molecule that is utilized to determine an attribute or feature (e.g., presence or absence, location, correlation, etc.) or a molecule, cell, tissue or plant.

A microarray-based method for high-throughput monitoring of plant gene expression may be utilized to measure gene-specific hybridization targets. This 'chip'-based approach involves using microarrays of nucleic acid molecules as gene-specific hybridization targets to quantitatively measure expression of the corresponding plant genes (Schena et al., *Science* 270:467-470 (1995), the entirety of which is herein incorporated by reference; Shalon, Ph.D. Thesis, Stanford University (1996), the entirety of which is herein incorporated by reference). Every nucleotide in a large sequence can be queried at the same time. Hybridization can be used to efficiently analyze nucleotide sequences.

Several microarray methods have been described. One method compares the sequences to be analyzed by hybridization to a set of oligonucleotides representing all possible subsequences (Bains and Smith, *J. Theor. Biol.* 135:303-307 (1989), the entirety of which is herein incorporated by reference). A second method hybridizes the sample to an array of oligonucleotide or cDNA molecules. An array consisting of oligonucleotides complementary to subsequences of a target sequence can be used to determine the identity of a target sequence, measure its amount and detect differences between the target and a reference sequence. Nucleic acid molecule microarrays may also be screened with protein molecules or fragments thereof to determine nucleic acid molecules that specifically bind protein molecules or fragments thereof.

The microarray approach may be used with polypeptide targets (U.S. Pat. No. 5,445,934; U.S. Pat. No. 5,143,854; U.S. Pat. No. 5,079,600; U.S. Pat. No. 4,923,901, all of which are herein incorporated by reference in their entirety). Essentially, polypeptides are synthesized on a substrate (microarray) and these polypeptides can be screened with either protein molecules or fragments thereof or nucleic acid molecules in order to screen for either protein molecules or fragments thereof or nucleic acid molecules that specifically bind the target polypeptides. (Fodor et al., *Science* 251:767-773 (1991), the entirety of which is herein incorporated by reference). It is understood that one or more of the nucleic acid molecules or protein or fragments thereof of the present invention may be utilized in a microarray based method.

In a preferred embodiment of the present invention microarrays may be prepared that comprise nucleic acid molecules where such nucleic acid molecules encode at least one, preferably at least two, more preferably at least three tocopherol synthesis pathway enzymes, more preferably at least four tocopherol synthesis pathway enzymes, more preferably at least five tocopherol synthesis pathway enzymes, more preferably at least six tocopherol synthesis pathway enzymes, more preferably at least seven tocopherol synthesis pathway enzymes, more preferably at least eight tocopherol synthesis pathway enzymes, more preferably at least nine tocopherol synthesis pathway enzymes, more preferably at least ten tocopherol synthesis pathway enzymes, more preferably at least eleven tocopherol synthesis pathway enzymes, more preferably at least twelve tocopherol synthesis pathway enzymes, more preferably at least thirteen tocopherol synthesis pathway enzymes, more preferably at least fourteen tocopherol synthesis pathway enzymes, more preferably at least fifteen tocopherol synthesis pathway enzymes, more preferably at least sixteen tocopherol synthesis pathway enzymes, and even more preferably at least seventeen tocopherol synthesis pathway enzymes. In a preferred embodiment the nucleic acid molecules are selected from the group consisting of a nucleic acid molecule that encodes a maize or soybean deoxyarabiono-heptulosonate-P-synthase enzyme or fragment thereof; a nucleic acid molecule that encodes a maize or soybean putative deoxyarabiono-heptulosonate-P-synthase enzyme or fragment thereof; a nucleic acid molecule that encodes a maize dehydroquinate synthase enzyme or fragment thereof; a nucleic acid molecule that encodes a soybean dehydroquinate dehydratase enzyme or fragment thereof; a nucleic acid molecule that encodes a maize putative dehydroquinate dehydratase enzyme or fragment thereof; a nucleic acid molecule that encodes a maize or soybean shikimate dehydrogenase enzyme or fragment thereof; a nucleic acid molecule that encodes a maize or soybean shikimate kinase enzyme or fragment thereof; a nucleic acid molecule that encodes a maize enolpyruvylshikimate-P-synthase enzyme or fragment thereof; a nucleic acid molecule that encodes a maize or soybean chorismate synthase enzyme or fragment thereof; a nucleic acid molecule that encodes a maize or soybean chorismate mutase enzyme or fragment thereof; a nucleic acid molecule that encodes a maize tyrosine transaminase enzyme or fragment thereof; a nucleic acid molecule that encodes a maize or soybean putative tyrosine transaminase enzyme or fragment thereof; a nucleic acid molecule that encodes a maize or soybean transaminase A enzyme or fragment thereof; a nucleic acid molecule that encodes a soybean putative transaminase A enzyme or fragment thereof; a nucleic acid molecule that encodes a maize or soybean 4-hydroxyphenylpyruvate dioxygenase enzyme or fragment thereof; a nucleic acid molecule that encodes a maize or soybean homogentisic acid dioxygenase enzyme or fragment thereof; and a nucleic acid molecule that encodes a maize or soybean geranylgeranylpyrophosphate synthase enzyme or fragment thereof.

Site directed mutagenesis may be utilized to modify nucleic acid sequences, particularly as it is a technique that allows one or more of the amino acids encoded by a nucleic acid molecule to be altered (e.g. a threonine to be replaced by a methionine). Three basic methods for site directed mutagenesis are often employed. These are cassette mutagenesis (Wells et al., *Gene* 34:315-323 (1985), the entirety of which is herein incorporated by reference), primer extension (Gilliam et al., *Gene* 12:129-137 (1980), the entirety of which is herein incorporated by reference; Zoller and Smith, *Methods Enzymol.* 100:468-500 (1983), the entirety of which is herein incorporated by reference; Dalbadie-McFarland et al., *Proc. Natl. Acad. Sci. (U.S.A.)* 79:6409-6413 (1982), the entirety of which is herein incorporated by reference) and methods based upon PCR (Scharf et al., *Science* 233:1076-1078 (1986), the entirety of which is herein incorporated by reference; Higuchi et al., *Nucleic Acids Res.* 16:7351-7367 (1988), the entirety of which is herein incorporated by reference). Site directed mutagenesis approaches are also described in European Patent 0 385 962, the entirety of which is herein incorporated by reference; European Patent 0 359 472, the entirety of which is herein incorporated by reference; and PCT Patent Application WO 93/07278, the entirety of which is herein incorporated by reference.

Site directed mutagenesis strategies have been applied to plants for both in vitro as well as in vivo site directed mutagenesis (Lanz et al., *J. Biol. Chem.* 266:9971-9976 (1991), the entirety of which is herein incorporated by reference; Kovgan and Zhdanov, *Biotekhnologiya* 5:148-154; No. 207160n, Chemical Abstracts 110:225 (1989), the entirety of which is herein incorporated by reference; Ge et al., *Proc.*

Natl. Acad. Sci. (U.S.A.) 86:4037-4041 (1989), the entirety of which is herein incorporated by reference; Zhu et al., *J. Biol. Chem.* 271:18494-18498 (1996), the entirety of which is herein incorporated by reference; Chu et al., *Biochemistry* 33:6150-6157 (1994), the entirety of which is herein incorporated by reference; Small et al., *EMBO J.* 11: 1291-1296 (1992), the entirety of which is herein incorporated by reference; Cho et al., *Mol. Biotechnol.* 8:13-16 (1997), the entirety of which is herein incorporated by reference; Kita et al., *J. Biol. Chem.* 271:26529-26535 (1996), the entirety of which is herein incorporated by reference, Jin et al., *Mol. Microbiol.* 7:555-562 (1993), the entirety of which is herein incorporated by reference; Hatfield and Vierstra, *J. Biol. Chem.* 267:14799-14803 (1992), the entirety of which is herein incorporated by reference; Zhao et al., *Biochemistry* 31:5093-5099 (1992), the entirety of which is herein incorporated by reference).

Any of the nucleic acid molecules of the present invention may either be modified by site directed mutagenesis or used as, for example, nucleic acid molecules that are used to target other nucleic acid molecules for modification. It is understood that mutants with more than one altered nucleotide can be constructed using techniques that practitioners are familiar with such as isolating restriction fragments and ligating such fragments into an expression vector (see, for example, Sambrook et al., *Molecular Cloning: A Laboratory Manual*, Cold Spring Harbor Press (1989)).

Sequence-specific DNA-binding proteins play a role in the regulation of transcription. The isolation of recombinant cDNAs encoding these proteins facilitates the biochemical analysis of their structural and functional properties. Genes encoding such DNA-binding proteins have been isolated using classical genetics (Vollbrecht et al., *Nature* 350: 241-243 (1991), the entirety of which is herein incorporated by reference) and molecular biochemical approaches, including the screening of recombinant cDNA libraries with antibodies (Landschulz et al., *Genes Dev.* 2:786-800 (1988), the entirety of which is herein incorporated by reference) or DNA probes (Bodner et al., *Cell* 55:505-518 (1988), the entirety of which is herein incorporated by reference). In addition, an in situ screening procedure has been used and has facilitated the isolation of sequence-specific DNA-binding proteins from various plant species (Gilmartin et al., *Plant Cell* 4:839-849 (1992), the entirety of which is herein incorporated by reference; Schindler et al., *EMBO J.* 11:1261-1273 (1992), the entirety of which is herein incorporated by reference). An in situ screening protocol does not require the purification of the protein of interest (Vinson et al., *Genes Dev.* 2:801-806 (1988), the entirety of which is herein incorporated by reference; Singh et al., *Cell* 52:415-423 (1988), the entirety of which is herein incorporated by reference).

Two steps may be employed to characterize DNA-protein interactions. The first is to identify promoter fragments that interact with DNA-binding proteins, to titrate binding activity, to determine the specificity of binding and to determine whether a given DNA-binding activity can interact with related DNA sequences (Sambrook et al., *Molecular Cloning: A Laboratory Manual*, 2$^{nd}$ edition, Cold Spring Harbor Laboratory Press, Cold Spring Harbor, N.Y. (1989)). Electrophoretic mobility-shift assay is a widely used assay. The assay provides a rapid and sensitive method for detecting DNA-binding proteins based on the observation that the mobility of a DNA fragment through a nondenaturing, low-ionic strength polyacrylamide gel is retarded upon association with a DNA-binding protein (Fried and Crother, *Nucleic Acids Res.* 9:6505-6525 (1981), the entirety of which is herein incorporated by reference). When one or more specific binding activities have been identified, the exact sequence of the DNA bound by the protein may be determined. Several procedures for characterizing protein/DNA-binding sites are used, including methylation and ethylation interference assays (Maxam and Gilbert, *Methods Enzymol.* 65:499-560 (1980), the entirety of which is herein incorporated by reference; Wissman and Hillen, *Methods Enzymol.* 208:365-379 (1991), the entirety of which is herein incorporated by reference), footprinting techniques employing DNase I (Galas and Schmitz, *Nucleic Acids Res.* 5:3157-3170 (1978), the entirety of which is herein incorporated by reference), 1,10-phenanthroline-copper ion methods (Sigman et al., *Methods Enzymol.* 208:414-433 (1991), the entirety of which is herein incorporated by reference) and hydroxyl radicals methods (Dixon et al., *Methods Enzymol.* 208:414-433 (1991), the entirety of which is herein incorporated by reference). It is understood that one or more of the nucleic acid molecules of the present invention may be utilized to identify a protein or fragment thereof that specifically binds to a nucleic acid molecule of the present invention. It is also understood that one or more of the protein molecules or fragments thereof of the present invention may be utilized to identify a nucleic acid molecule that specifically binds to it.

A two-hybrid system is based on the fact that many cellular functions are carried out by proteins, such as transcription factors, that interact (physically) with one another. Two-hybrid systems have been used to probe the function of new proteins (Chien et al., *Proc. Natl. Acad. Sci. (U.S.A.)* 88:9578-9582 (1991) the entirety of which is herein incorporated by reference; Durfee et al., *Genes Dev.* 7:555-569 (1993) the entirety of which is herein incorporated by reference; Choi et al., *Cell* 78:499-512 (1994), the entirety of which is herein incorporated by reference; Kranz et al., *Genes Dev.* 8:313-327 (1994), the entirety of which is herein incorporated by reference).

Interaction mating techniques have facilitated a number of two-hybrid studies of protein-protein interaction. Interaction mating has been used to examine interactions between small sets of tens of proteins (Finley and Brent, *Proc. Natl. Acad. Sci. (U.S.A.)* 91:12098-12984 (1994), the entirety of which is herein incorporated by reference), larger sets of hundreds of proteins (Bendixen et al., *Nucl. Acids Res.* 22:1778-1779 (1994), the entirety of which is herein incorporated by reference) and to comprehensively map proteins encoded by a small genome (Bartel et al., *Nature Genetics* 12:72-77 (1996), the entirety of which is herein incorporated by reference). This technique utilizes proteins fused to the DNA-binding domain and proteins fused to the activation domain. They are expressed in two different haploid yeast strains of opposite mating type and the strains are mated to determine if the two proteins interact. Mating occurs when haploid yeast strains come into contact and result in the fusion of the two haploids into a diploid yeast strain. An interaction can be determined by the activation of a two-hybrid reporter gene in the diploid strain. An advantage of this technique is that it reduces the number of yeast transformations needed to test individual interactions. It is understood that the protein-protein interactions of protein or fragments thereof of the present invention may be investigated using the two-hybrid system and that any of the nucleic acid molecules of the present invention that encode such proteins or fragments thereof may be used to transform yeast in the two-hybrid system.

(a) Plant Constructs and Plant Transformants

One or more of the nucleic acid molecules of the present invention may be used in plant transformation or transfection. Exogenous genetic material may be transferred into a plant cell and the plant cell regenerated into a whole, fertile or sterile plant. Exogenous genetic material is any genetic material, whether naturally occurring or otherwise, from any source that is capable of being inserted into any organism. Such genetic material may be transferred into either monocotyledons and dicotyledons including, but not limited to maize (pp 63-69), soybean (pp 50-60), *Arabidopsis* (p 45), phaseolus (pp 47-49), peanut (pp 49-50), alfalfa (p 60), wheat (pp 69-71), rice (pp 72-79), oat (pp 80-81), sorghum (p 83), rye (p 84), tritordeum (p 84), millet (p85), fescue (p 85), perennial ryegrass (p 86), sugarcane (p87), cranberry (p110), papaya (pp 101-102), banana (p 103), banana (p 103), muskmelon (p 104), apple (p 104), cucumber (p 105), dendrobium (p 109), gladiolus (p 110), chrysanthemum (p 110), liliacea (p 111), cotton (pp113-114), eucalyptus (p 115), sunflower (p 118), canola (p 118), turfgrass (p121), sugarbeet (p 122), coffee (p 122) and dioscorea (p 122) (Christou, In: *Particle Bombardment for Genetic Engineering of Plants*, Biotechnology Intelligence Unit. Academic Press, San Diego, Calif. (1996), the entirety of which is herein incorporated by reference).

Transfer of a nucleic acid that encodes for a protein can result in overexpression of that protein in a transformed cell or transgenic plant. One or more of the proteins or fragments thereof encoded by nucleic acid molecules of the present invention may be overexpressed in a transformed cell or transformed plant. Particularly, any of the tocopherol synthesis pathway enzymes or fragments thereof may be overexpressed in a transformed cell or transgenic plant. Such overexpression may be the result of transient or stable transfer of the exogenous genetic material.

Exogenous genetic material may be transferred into a plant cell and the plant cell by the use of a DNA vector or construct designed for such a purpose. Design of such a vector is generally within the skill of the art (See, *Plant Molecular Biology: A Laboratory Manual*, Clark (ed.), Springier, New York (1997), the entirety of which is herein incorporated by reference).

A construct or vector may include a plant promoter to express the protein or protein fragment of choice. A number of promoters which are active in plant cells have been described in the literature. These include the nopaline synthase (NOS) promoter (Ebert et al., *Proc. Natl. Acad. Sci.* (*U.S.A.*) 84:5745-5749 (1987), the entirety of which is herein incorporated by reference), the octopine synthase (OCS) promoter (which are carried on tumor-inducing plasmids of *Agrobacterium tumefaciens*), the caulimovirus promoters such as the cauliflower mosaic virus (CaMV) 19S promoter (Lawton et al., *Plant Mol. Biol.* 9:315-324 (1987), the entirety of which is herein incorporated by reference) and the CAMV 35S promoter (Odell et al., *Nature* 313:810-812 (1985), the entirety of which is herein incorporated by reference), the figwort mosaic virus 35S-promoter, the light-inducible promoter from the small subunit of ribulose-1,5-bis-phosphate carboxylase (ssRUBISCO), the Adh promoter (Walker et al., *Proc. Natl. Acad. Sci.* (*U.S.A.*) 84:6624-6628 (1987), the entirety of which is herein incorporated by reference), the sucrose synthase promoter (Yang et al., *Proc. Natl. Acad. Sci.* (*U.S.A.*) 87:4144-4148 (1990), the entirety of which is herein incorporated by reference), the R gene complex promoter (Chandler et al., *The Plant Cell* 1:1175-1183 (1989), the entirety of which is herein incorporated by reference) and the chlorophyll a/b binding protein gene promoter, etc. These promoters have been used to create DNA constructs which have been expressed in plants; see, e.g., PCT publication WO 84/02913, herein incorporated by reference in its entirety.

Promoters which are known or are found to cause transcription of DNA in plant cells can be used in the present invention. Such promoters may be obtained from a variety of sources such as plants and plant viruses. It is preferred that the particular promoter selected should be capable of causing sufficient expression to result in the production of an effective amount of the tocopherol synthesis pathway enzyme to cause the desired phenotype. In addition to promoters that are known to cause transcription of DNA in plant cells, other promoters may be identified for use in the current invention by screening a plant cDNA library for genes which are selectively or preferably expressed in the target tissues or cells.

For the purpose of expression in source tissues of the plant, such as the leaf, seed, root or stem, it is preferred that the promoters utilized in the present invention have relatively high expression in these specific tissues. For this purpose, one may choose from a number of promoters for genes with tissue- or cell-specific or -enhanced expression. Examples of such promoters reported in the literature include the chloroplast glutamine synthetase GS2 promoter from pea (Edwards et al., *Proc. Natl. Acad. Sci.* (*U.S.A.*) 87:3459-3463 (1990), herein incorporated by reference in its entirety), the chloroplast fructose-1,6-biphosphatase (FBPase) promoter from wheat (Lloyd et al., *Mol. Gen. Genet.* 225:209-216 (1991), herein incorporated by reference in its entirety), the nuclear photosynthetic ST-LS1 promoter from potato (Stockhaus et al., *EMBO J.* 8:2445-2451 (1989), herein incorporated by reference in its entirety), the serine/threonine kinase (PAL) promoter and the glucoamylase (CHS) promoter from *Arabidopsis thaliana*. Also reported to be active in photosynthetically active tissues are the ribulose-1,5-bisphosphate carboxylase (RbcS) promoter from eastern larch (*Larix laricina*), the promoter for the cab gene, cab6, from pine (Yamamoto et al., *Plant Cell Physiol.* 35:773-778 (1994), herein incorporated by reference in its entirety), the promoter for the Cab-1 gene from wheat (Fejes et al., *Plant Mol. Biol.* 15:921-932 (1990), herein incorporated by reference in its entirety), the promoter for the CAB-1 gene from spinach (Lubberstedt et al., *Plant Physiol.* 104:997-1006 (1994), herein incorporated by reference in its entirety), the promoter for the cab1R gene from rice (Luan et al., *Plant Cell.* 4:971-981 (1992), the entirety of which is herein incorporated by reference), the pyruvate, orthophosphate dikinase (PPDK) promoter from maize (Matsuoka et al., *Proc. Natl. Acad. Sci.* (*U.S.A.*) 90: 9586-9590 (1993), herein incorporated by reference in its entirety), the promoter for the tobacco Lhcb1*2 gene (Cerdan et al., *Plant Mol. Biol.* 33:245-255 (1997), herein incorporated by reference in its entirety), the *Arabidopsis thaliana* SUC2 sucrose-H+ symporter promoter (Truernit et al., *Planta.* 196:564-570 (1995), herein incorporated by reference in its entirety) and the promoter for the thylakoid membrane proteins from spinach (psaD, psaF, psaE, PC, FNR, atpC, atpD, cab, rbcS). Other promoters for the chlorophyll a/b-binding proteins may also be utilized in the present invention, such as the promoters for LhcB gene and PsbP gene from white mustard (*Sinapis alba*; Kretsch et al., *Plant Mol. Biol.* 28:219-229 (1995), the entirety of which is herein incorporated by reference).

For the purpose of expression in sink tissues of the plant, such as the tuber of the potato plant, the fruit of tomato, or the seed of maize, wheat, rice and barley, it is preferred that the promoters utilized in the present invention have relatively high expression in these specific tissues. A number of promoters for genes with tuber-specific or -enhanced expression are known, including the class I patatin promoter (Bevan et al., *EMBO J.* 8:1899-1906 (1986); Jefferson et al., *Plant Mol. Biol.* 14:995-1006 (1990), both of which are herein incorporated by reference in its entirety), the promoter for the potato tuber ADPGPP genes, both the large and small subunits, the sucrose synthase promoter (Salanoubat and Belliard, *Gene.*

60:47-56 (1987), Salanoubat and Belliard, *Gene.* 84:181-185 (1989), both of which are incorporated by reference in their entirety), the promoter for the major tuber proteins including the 22 kd protein complexes and proteinase inhibitors (Hannapel, *Plant Physiol.* 101:703-704 (1993), herein incorporated by reference in its entirety), the promoter for the granule bound starch synthase gene (GBSS) (Visser et al., *Plant Mol. Biol.* 17:691-699 (1991), herein incorporated by reference in its entirety) and other class I and II patatins promoters (Koster-Topfer et al., *Mol Gen Genet.* 219:390-396 (1989); Mignery et al., *Gene.* 62:27-44 (1988), both of which are herein incorporated by reference in their entirety).

Other promoters can also be used to express a tocopherol synthesis pathway enzyme or fragment thereof in specific tissues, such as seeds or fruits. The promoter for β-conglycinin (Chen et al., *Dev. Genet.* 10: 112-122 (1989), herein incorporated by reference in its entirety) or other seed-specific promoters such as the napin and phaseolin promoters, can be used. The zeins are a group of storage proteins found in maize endosperm. Genomic clones for zein genes have been isolated (Pedersen et al., *Cell* 29:1015-1026 (1982), herein incorporated by reference in its entirety) and the promoters from these clones, including the 15 kD, 16 kD, 19 kD, 22 kD, 27 kD and γ genes, could also be used. Other promoters known to function, for example, in maize include the promoters for the following genes: waxy, Brittle, Shrunken 2, Branching enzymes I and II, starch synthases, debranching enzymes, oleosins, glutelins and sucrose synthases. A particularly preferred promoter for maize endosperm expression is the promoter for the glutelin gene from rice, more particularly the Osgt-1 promoter (Zheng et al., *Mol. Cell. Biol.* 13:5829-5842 (1993), herein incorporated by reference in its entirety). Examples of promoters suitable for expression in wheat include those promoters for the ADPglucose pyrosynthase (ADPGPP) subunits, the granule bound and other starch synthase, the branching and debranching enzymes, the embryogenesis-abundant proteins, the gliadins and the glutenins. Examples of such promoters in rice include those promoters for the ADPGPP subunits, the granule bound and other starch synthase, the branching enzymes, the debranching enzymes, sucrose synthases and the glutelins. A particularly preferred promoter is the promoter for rice glutelin, Osgt-1. Examples of such promoters for barley include those for the ADPGPP subunits, the granule bound and other starch synthase, the branching enzymes, the debranching enzymes, sucrose synthases, the hordeins, the embryo globulins and the aleurone specific proteins.

Root specific promoters may also be used. An example of such a promoter is the promoter for the acid chitinase gene (Samac et al., *Plant Mol. Biol.* 25:587-596 (1994), the entirety of which is herein incorporated by reference). Expression in root tissue could also be accomplished by utilizing the root specific subdomains of the CaMV35S promoter that have been identified (Lam et al., *Proc. Natl. Acad. Sci. (U.S.A.)* 86:7890-7894 (1989), herein incorporated by reference in its entirety). Other root cell specific promoters include those reported by Conkling et al. (Conkling et al., *Plant Physiol.* 93:1203-1211 (1990), the entirety of which is herein incorporated by reference).

Additional promoters that may be utilized are described, for example, in U.S. Pat. Nos. 5,378,619; 5,391,725; 5,428,147; 5,447,858; 5,608,144; 5,608,144; 5,614,399; 5,633,441; 5,633,435; and 4,633,436, all of which are herein incorporated in their entirety. In addition, a tissue specific enhancer may be used (Fromm et al., *The Plant Cell* 1:977-984 (1989), the entirety of which is herein incorporated by reference).

Constructs or vectors may also include with the coding region of interest a nucleic acid sequence that acts, in whole or in part, to terminate transcription of that region. For example, such sequences have been isolated including the Tr7 3' sequence and the NOS 3' sequence (Ingelbrecht et al., *The Plant Cell* 1:671-680 (1989), the entirety of which is herein incorporated by reference; Bevan et al., *Nucleic Acids Res.* 11:369-385 (1983), the entirety of which is herein incorporated by reference), or the like.

A vector or construct may also include regulatory elements. Examples of such include the Adh intron 1 (Callis et al., *Genes and Develop.* 1:1183-1200 (1987), the entirety of which is herein incorporated by reference), the sucrose synthase intron (Vasil et al., Plant Physiol. 91:1575-1579 (1989), the entirety of which is herein incorporated by reference) and the TMV omega element (Gallie et al., *The Plant Cell* 1:301-311 (1989), the entirety of which is herein incorporated by reference). These and other regulatory elements may be included when appropriate.

A vector or construct may also include a selectable marker. Selectable markers may also be used to select for plants or plant cells that contain the exogenous genetic material. Examples of such include, but are not limited to, a neo gene (Potrykus et al., *Mol. Gen. Genet.* 199:183-188 (1985), the entirety of which is herein incorporated by reference) which codes for kanamycin resistance and can be selected for using kanamycin, G418, etc.; a bar gene which codes for bialaphos resistance; a mutant EPSP synthase gene (Hinchee et al., *Bio/Technology* 6:915-922 (1988), the entirety of which is herein incorporated by reference) which encodes glyphosate resistance; a nitrilase gene which confers resistance to bromoxynil (Stalker et al., *J. Biol. Chem.* 263:6310-6314 (1988), the entirety of which is herein incorporated by reference); a mutant acetolactate synthase gene (ALS) which confers imidazolinone or sulphonylurea resistance (European Patent Application 154,204 (Sep. 11, 1985), the entirety of which is herein incorporated by reference); and a methotrexate resistant DHFR gene (Thillet et al., *J. Biol. Chem.* 263:12500-12508 (1988), the entirety of which is herein incorporated by reference).

A vector or construct may also include a transit peptide. Incorporation of a suitable chloroplast transit peptide may also be employed (European Patent Application Publication Number 0218571, the entirety of which is herein incorporated by reference). Translational enhancers may also be incorporated as part of the vector DNA. DNA constructs could contain one or more 5' non-translated leader sequences which may serve to enhance expression of the gene products from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence. For a review of optimizing expression of transgenes, see Koziel et al., *Plant Mol. Biol.* 32:393-405 (1996), the entirety of which is herein incorporated by reference.

A vector or construct may also include a screenable marker. Screenable markers may be used to monitor expression. Exemplary screenable markers include a β-glucuronidase or uidA gene (GUS) which encodes an enzyme for which various chromogenic substrates are known (Jefferson, *Plant Mol. Biol, Rep.* 5:387-405 (1987), the entirety of which is herein incorporated by reference; Jefferson et al., *EMBO J.* 6:3901-3907 (1987), the entirety of which is herein incorporated by reference); an R-locus gene, which encodes a product that regulates the production of anthocyanin pigments (red color) in plant tissues (Dellaporta et al., Stadler Symposium 11:263-282 (1988), the entirety of which is herein incorporated by reference); a β-lactamase gene (Sutcliffe et al., *Proc. Natl. Acad. Sci. (U.S.A.)* 75:3737-3741 (1978), the entirety of which is herein incorporated by reference), a gene which encodes an enzyme for which various chromogenic substrates are known (e.g., PADAC, a chromogenic cephalosporin); a luciferase gene (Ow et al., *Science* 234:856-859 (1986), the entirety of which is herein incorporated by reference); a xylE gene (Zukowsky et al., *Proc. Natl. Acad. Sci. (U.S.A.)* 80:1101-1105 (1983), the entirety of which is herein incorporated by reference) which encodes a catechol diozygenase that can convert chromogenic catechols; an α-amylase gene (Ikatu et al., *Bio/Technol.* 8:241-242 (1990), the entirety of which is herein incorporated by reference); a tyrosinase gene (Katz et al., *J. Gen. Microbiol.* 129:2703-2714 (1983), the entirety of which is herein incorporated by reference) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

There are many methods for introducing transforming nucleic acid molecules into plant cells. Suitable methods are believed to include virtually any method by which nucleic acid molecules may be introduced into a cell, such as by *Agrobacterium* infection or direct delivery of nucleic acid molecules such as, for example, by PEG-mediated transformation, by electroporation or by acceleration of DNA coated particles, etc (Potrykus, *Ann. Rev. Plant Physiol. Plant Mol. Biol.* 42:205-225 (1991), the entirety of which is herein incorporated by reference; Vasil, *Plant Mol. Biol.* 25:925-937 (1994), the entirety of which is herein incorporated by reference). For example, electroporation has been used to transform maize protoplasts (Fromm et al., *Nature* 312:791-793 (1986), the entirety of which is herein incorporated by reference).

Other vector systems suitable for introducing transforming DNA into a host plant cell include but are not limited to binary artificial chromosome (BIBAC) vectors (Hamilton et al., *Gene* 200:107-116 (1997), the entirety of which is herein incorporated by reference); and transfection with RNA viral vectors (Della-Cioppa et al., *Ann. N.Y. Acad. Sci.* (1996), 792 (Engineering Plants for Commercial Products and Applications), 57-61, the entirety of which is herein incorporated by reference). Additional vector systems also include plant selectable YAC vectors such as those described in Mullen et al., *Molecular Breeding* 4:449-457 (1988), the entirety of which is herein incorporated by reference).

Technology for introduction of DNA into cells is well known to those of skill in the art. Four general methods for delivering a gene into cells have been described: (1) chemical methods (Graham and van der Eb, *Virology* 54:536-539 (1973), the entirety of which is herein incorporated by reference); (2) physical methods such as microinjection (Capecchi, *Cell* 22:479-488 (1980), the entirety of which is herein incorporated by reference), electroporation (Wong and Neumann, *Biochem. Biophys. Res. Commun.* 107:584-587 (1982); Fromm et al., *Proc. Natl. Acad. Sci. (U.S.A.)* 82:5824-5828 (1985); U.S. Pat. No. 5,384,253, all of which are herein incorporated in their entirety); and the gene gun (Johnston and Tang, *Methods Cell Biol.* 43:353-365 (1994), the entirety of which is herein incorporated by reference); (3) viral vectors (Clapp, *Clin. Perinatol.* 20:155-168 (1993); Lu et al., *J. Exp. Med.* 178:2089-2096 (1993); Eglitis and Anderson, *Biotechniques* 6:608-614 (1988), all of which are herein incorporated in their entirety); and (4) receptor-mediated mechanisms (Curiel et al., *Hum. Gen. Ther.* 3:147-154 (1992), Wagner et al., *Proc. Natl. Acad. Sci. (U.S.A.)* 89:6099-6103 (1992), both of which are incorporated by reference in their entirety).

Acceleration methods that may be used include, for example, microprojectile bombardment and the like. One example of a method for delivering transforming nucleic acid molecules to plant cells is microprojectile bombardment. This method has been reviewed by Yang and Christou (eds.), *Particle Bombardment Technology for Gene Transfer*, Oxford Press, Oxford, England (1994), the entirety of which is herein incorporated by reference). Non-biological particles (microprojectiles) that may be coated with nucleic acids and delivered into cells by a propelling force. Exemplary particles include those comprised of tungsten, gold, platinum and the like.

A particular advantage of microprojectile bombardment, in addition to it being an effective means of reproducibly transforming monocots, is that neither the isolation of protoplasts (Cristou et al., *Plant Physiol.* 87:671-674 (1988), the entirety of which is herein incorporated by reference) nor the susceptibility of *Agrobacterium* infection are required. An illustrative embodiment of a method for delivering DNA into maize cells by acceleration is a biolistics α-particle delivery system, which can be used to propel particles coated with DNA through a screen, such as a stainless steel or Nytex screen, onto a filter surface covered with corn cells cultured in suspension. Gordon-Kamm et al., describes the basic procedure for coating tungsten particles with DNA (Gordon-Kamm et al., *Plant Cell* 2:603-618 (1990), the entirety of which is herein incorporated by reference). The screen disperses the tungsten nucleic acid particles so that they are not delivered to the recipient cells in large aggregates. A particle delivery system suitable for use with the present invention is the helium acceleration PDS-1000/He gun is available from Bio-Rad Laboratories (Bio-Rad, Hercules, Calif.) (Sanford et al., *Technique* 3:3-16 (1991), the entirety of which is herein incorporated by reference).

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from one to ten and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Methods disclosed for plastid transformation in higher plants include the particle gun delivery of DNA containing a selectable marker and targeting of the DNA to the plastid genome through homologous recombination (Svab et al., *Proc. Natl. Acad. Sci. (U.S.A.)* 87:8526-8530 (1990); Svab and Maliga, *Proc. Natl. Acad. Sci. (U.S.A.)* 90:913-917 (1993); Staub and Maliga, *EMBO J.* 12:601-606 (1993); U.S. Pat. Nos. 5,451,513 and 5,545,818, all of which are herein incorporated by reference in their entirety).

Accordingly, it is contemplated that one may wish to adjust various aspects of the bombardment parameters in small scale studies to fully optimize the conditions. One may particularly wish to adjust physical parameters such as gap distance, flight distance, tissue distance and helium pressure. One may also minimize the trauma reduction factors by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example the methods described by Fraley et al., *Bio/Technology* 3:629-635 (1985) and Rogers et al., *Methods Enzymol.* 153:253-277 (1987), both of which are herein incorporated by reference in their entirety. Further, the integration of the Ti-DNA is a relatively precise process resulting in few rearrangements. The region of DNA to be transferred is defined by the border sequences and intervening DNA is usually inserted into the plant genome as described (Spielmann et al., *Mol. Gen. Genet.* 205:34 (1986), the entirety of which is herein incorporated by reference).

Modern *Agrobacterium* transformation vectors are capable of replication in *E. coli* as well as *Agrobacterium*, allowing for convenient manipulations as described (Klee et al., In: *Plant DNA Infectious Agents*, Hohn and Schell (eds.), Springer-Verlag, New York, pp. 179-203 (1985), the entirety of which is herein incorporated by reference. Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes (Rogers et al., *Methods Enzymol.* 153:253-277 (1987)). In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

A transgenic plant formed using *Agrobacterium* transformation methods typically contains a single gene on one chromosome. Such transgenic plants can be referred to as being heterozygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for the gene of interest.

It is also to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and outcrossing with a non-transgenic plant are also contemplated, as is vegetative propagation.

Transformation of plant protoplasts can be achieved using methods based on calcium phosphate precipitation, polyethylene glycol treatment, electroporation and combinations of these treatments (See, for example, Potrykus et al., *Mol. Gen. Genet.* 205:193-200 (1986); Lorz et al., *Mol. Gen. Genet.* 199:178 (1985); Fromm et al., *Nature* 319:791 (1986); Uchimiya et al., *Mol. Gen. Genet.* 204:204 (1986); Marcotte et al., *Nature* 335:454-457 (1988), all of which are herein incorporated by reference in their entirety).

Application of these systems to different plant strains depends upon the ability to regenerate that particular plant strain from protoplasts. Illustrative methods for the regeneration of cereals from protoplasts are described (Fujimura et al., *Plant Tissue Culture Letters* 2:74 (1985); Toriyama et al., *Theor Appl. Genet.* 205:34 (1986); Yamada et al., *Plant Cell Rep.* 4:85 (1986); Abdullah et al., *Biotechnolog* 4:1087 (1986), all of which are herein incorporated by reference in their entirety).

To transform plant strains that cannot be successfully regenerated from protoplasts, other ways to introduce DNA into intact cells or tissues can be utilized. For example, regeneration of cereals from immature embryos or explants can be effected as described (Vasil, *Biotechnology* 6:397 (1988), the entirety of which is herein incorporated by reference). In addition, "particle gun" or high-velocity microprojectile technology can be utilized (Vasil et al., *Bio/Technology* 10:667 (1992), the entirety of which is herein incorporated by reference).

Using the latter technology, DNA is carried through the cell wall and into the cytoplasm on the surface of small metal particles as described (Klein et al., *Nature* 328:70 (1987); Klein et al., *Proc. Natl. Acad. Sci. (U.S.A.)* 85:8502-8505 (1988); McCabe et al., *Bio/Technology* 6:923 (1988), all of which are herein incorporated by reference in their entirety). The metal particles penetrate through several layers of cells and thus allow the transformation of cells within tissue explants.

Other methods of cell transformation can also be used and include but are not limited to introduction of DNA into plants by direct DNA transfer into pollen (Zhou et al., *Methods Enzymol.* 101:433 (1983); Hess et al., *Intern Rev. Cytol.* 107:367 (1987); Luo et al., *Plant Mol. Biol. Reporter* 6:165 (1988), all of which are herein incorporated by reference in their entirety), by direct injection of DNA into reproductive organs of a plant (Pena et al., *Nature* 325:274 (1987), the entirety of which is herein incorporated by reference), or by direct injection of DNA into the cells of immature embryos followed by the rehydration of desiccated embryos (Neuhaus et al., *Theor. Appl. Genet.* 75:30 (1987), the entirety of which is herein incorporated by reference).

The regeneration, development and cultivation of plants from single plant protoplast transformants or from various transformed explants is well known in the art (Weissbach and Weissbach, In: *Methods for Plant Molecular Biology*, Academic Press, San Diego, Calif., (1988), the entirety of which is herein incorporated by reference). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated.

Methods for transforming dicots, primarily by use of *Agrobacterium tumefaciens* and obtaining transgenic plants have been published for cotton (U.S. Pat. Nos. 5,004,863; 5,159,135; 5,518,908, all of which are herein incorporated by reference in their entirety); soybean (U.S. Pat. Nos. 5,569,834; 5,416,011; McCabe et. al., *Biotechnology* 6:923 (1988); Christou et al., *Plant Physiol.* 87:671-674 (1988); all of which are herein incorporated by reference in their entirety); *Brassica* (U.S. Pat. No. 5,463,174, the entirety of which is herein incorporated by reference); peanut (Cheng et al., *Plant Cell Rep.* 15:653-657 (1996), McKently et al., *Plant Cell Rep.* 14:699-703 (1995), all of which are herein incorporated by reference in their entirety); papaya; and pea (Grant et al., *Plant Cell Rep.* 15:254-258 (1995), the entirety of which is herein incorporated by reference).

Transformation of monocotyledons using electroporation, particle bombardment and *Agrobacterium* have also been reported. Transformation and plant regeneration have been achieved in asparagus (Bytebier et al., *Proc. Natl. Acad. Sci. (U.S.A.)* 84:5354 (1987), the entirety of which is herein incorporated by reference); barley (Wan and Lemaux, *Plant Physiol* 104:37 (1994), the entirety of which is herein incorporated by reference); maize (Rhodes et al., *Science* 240:204 (1988); Gordon-Kamm et al., *Plant Cell* 2:603-618 (1990); Fromm et al., *Bio/Technology* 8:833 (1990); Koziel et al., *Bio/Technology* 11:194 (1993); Armstrong et al., *Crop Science* 35:550-557 (1995); all of which are herein incorporated by reference in their entirety); oat (Somers et al., *Bio/Technology* 10:1589 (1992), the entirety of which is herein incorporated by reference); orchard grass (Horn et al., *Plant Cell Rep.* 7:469 (1988), the entirety of which is herein incorporated by reference); rice (Toriyama et al., *Theor Appl. Genet.* 205:34 (1986); Part et al., *Plant Mol. Biol.* 32:1135-1148 (1996); Abedinia et al., *Aust. J. Plant Physiol.* 24:133-141 (1997); Zhang and Wu, *Theor. Appl. Genet.* 76:835 (1988); Zhang et al., *Plant Cell Rep.* 7:379 (1988); Battraw and Hall, *Plant Sci.* 86:191-202 (1992); Christou et al., *Bio/Technology* 9:957 (1991), all of which are herein incorporated by reference in their entirety); rye (De la Pena et al., *Nature* 325:274 (1987), the entirety of which is herein incorporated by reference); sugarcane (Bower and Birch, *Plant J.* 2:409 (1992), the entirety of which is herein incorporated by reference); tall fescue (Wang et al., *Bio/Technology* 10:691 (1992), the entirety of which is herein incorporated by reference) and wheat (Vasil et al., *Bio/Technology* 10:667 (1992), the entirety of which is herein incorporated by reference; U.S. Pat. No. 5,631,152, the entirety of which is herein incorporated by reference.)

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454-457 (1988), the entirety of which is herein incorporated by reference; Marcotte et al., *Plant Cell* 1:523-532 (1989), the entirety of which is herein incorporated by reference; McCarty et al., *Cell* 66:895-905 (1991), the entirety of which is herein incorporated by reference; Hattori et al., *Genes Dev.* 6:609-618 (1992), the entirety of which is herein incorporated by reference; Goff et al., *EMBO J.* 9:2517-2522 (1990), the entirety of which is herein incorporated by reference). Transient expression systems may be used to functionally dissect gene constructs (see generally, Mailga et al., *Methods in Plant Molecular Biology*, Cold Spring Harbor Press (1995)).

Any of the nucleic acid molecules of the present invention may be introduced into a plant cell in a permanent or transient manner in combination with other genetic elements such as vectors, promoters, enhancers etc. Further, any of the nucleic acid molecules of the present invention may be introduced into a plant cell in a manner that allows for overexpression of the protein or fragment thereof encoded by the nucleic acid molecule.

Cosuppression is the reduction in expression levels, usually at the level of RNA, of a particular endogenous gene or gene family by the expression of a homologous sense construct that is capable of transcribing mRNA of the same strandedness as the transcript of the endogenous gene (Napoli et al., *Plant Cell* 2:279-289 (1990), the entirety of which is herein incorporated by reference; van der Krol et al., *Plant Cell* 2:291-299 (1990), the entirety of which is herein incorporated by reference). Cosuppression may result from stable transformation with a single copy nucleic acid molecule that is homologous to a nucleic acid sequence found with the cell (Prolls and Meyer, *Plant J.* 2:465-475 (1992), the entirety of which is herein incorporated by reference) or with multiple copies of a nucleic acid molecule that is homologous to a nucleic acid sequence found with the cell (Mittlesten et al., *Mol. Gen. Genet.* 244:325-330 (1994), the entirety of which is herein incorporated by reference). Genes, even though different, linked to homologous promoters may result in the cosuppression of the linked genes (Vaucheret, *C.R. Acad. Sci. III* 1316:1471-1483 (1993), the entirety of which is herein incorporated by reference).

This technique has, for example, been applied to generate white flowers from red petunia and tomatoes that do not ripen on the vine. Up to 50% of petunia transformants that contained a sense copy of the glucoamylase (CHS) gene produced white flowers or floral sectors; this was as a result of the post-transcriptional loss of mRNA encoding CHS (Flavell, *Proc. Natl. Acad. Sci.* (*U.S.A.*) 91:3490-3496 (1994), the entirety of which is herein incorporated by reference); van Blokland et al., *Plant J.* 6:861-877 (1994), the entirety of which is herein incorporated by reference). Cosuppression may require the coordinate transcription of the transgene and the endogenous gene and can be reset by a developmental control mechanism (Jorgensen, *Trends Biotechnol.* 8:340-344 (1990), the entirety of which is herein incorporated by reference; Meins and Kunz, In: *Gene Inactivation and Homologous Recombination in Plants*, Paszkowski (ed.), pp. 335-348, Kluwer Academic, Netherlands (1994), the entirety of which is herein incorporated by reference).

It is understood that one or more of the nucleic acids of the present invention may be introduced into a plant cell and transcribed using an appropriate promoter with such transcription resulting in the cosuppression of an endogenous tocopherol synthesis pathway enzyme.

Antisense approaches are a way of preventing or reducing gene function by targeting the genetic material (Mol et al., *FEBS Lett.* 268:427-430 (1990), the entirety of which is herein incorporated by reference). The objective of the antisense approach is to use a sequence complementary to the target gene to block its expression and create a mutant cell line or organism in which the level of a single chosen protein is selectively reduced or abolished. Antisense techniques have several advantages over other 'reverse genetic' approaches. The site of inactivation and its developmental effect can be manipulated by the choice of promoter for antisense genes or by the timing of external application or microinjection. Antisense can manipulate its specificity by selecting either unique regions of the target gene or regions where it shares homology to other related genes (Hiatt et al., In: *Genetic Engineering*, Setlow (ed.), Vol. 11, New York: Plenum 49-63 (1989), the entirety of which is herein incorporated by reference).

The principle of regulation by antisense RNA is that RNA that is complementary to the target mRNA is introduced into cells, resulting in specific RNA:RNA duplexes being formed by base pairing between the antisense substrate and the target mRNA (Green et al., *Annu. Rev. Biochem.* 55:569-597 (1986), the entirety of which is herein incorporated by reference). Under one embodiment, the process involves the introduction and expression of an antisense gene sequence. Such a sequence is one in which part or all of the normal gene sequences are placed under a promoter in inverted orientation so that the 'wrong' or complementary strand is transcribed into a noncoding antisense RNA that hybridizes with the target mRNA and interferes with its expression (Takayama and Inouye, *Crit. Rev. Biochem. Mol. Biol.* 25:155-184 (1990), the entirety of which is herein incorporated by reference). An antisense vector is constructed by standard procedures and introduced into cells by transformation, transfection, electroporation, microinjection, infection, etc. The type of transformation and choice of vector will determine whether expression is transient or stable. The promoter used for the antisense gene may influence the level, timing, tissue, specificity, or inducibility of the antisense inhibition.

It is understood that the activity of a tocopherol synthesis pathway enzyme in a plant cell may be reduced or depressed by growing a transformed plant cell containing a nucleic acid molecule whose non-transcribed strand encodes a tocopherol synthesis pathway enzyme or fragment thereof.

Antibodies have been expressed in plants (Hiatt et al., *Nature* 342:76-78 (1989), the entirety of which is herein incorporated by reference; Conrad and Fielder, *Plant Mol. Biol.* 26:1023-1030 (1994), the entirety of which is herein incorporated by reference). Cytoplamsic expression of a scFv (single-chain Fv antibodies) has been reported to delay infection by artichoke mottled crinkle virus. Transgenic plants that express antibodies directed against endogenous proteins may exhibit a physiological effect (Philips et al., *EMBO J.* 16:4489-4496 (1997), the entirety of which is herein incorporated by reference; Marion-Poll, *Trends in Plant Science* 2:447-448 (1997), the entirety of which is herein incorporated by reference). For example, expressed anti-abscisic antibodies have been reported to result in a general perturbation of seed development (Philips et al., *EMBO J.* 16: 4489-4496 (1997)).

Antibodies that are catalytic may also be expressed in plants (abzymes). The principle behind abzymes is that since antibodies may be raised against many molecules, this recognition ability can be directed toward generating antibodies that bind transition states to force a chemical reaction forward (Persidas, *Nature Biotechnology* 15:1313-1315 (1997), the entirety of which is herein incorporated by reference; Baca et al., *Ann. Rev. Biophys. Biomol. Struct.* 26:461-493 (1997), the entirety of which is herein incorporated by reference). The catalytic abilities of abzymes may be enhanced by site directed mutagenesis. Examples of abzymes are, for example, set forth in U.S. Pat. Nos. 5,658,753; 5,632,990; 5,631,137; 5,602,015; 5,559,538; 5,576,174; 5,500,358; 5,318,897; 5,298,409; 5,258,289 and 5,194,585, all of which are herein incorporated in their entirety.

It is understood that any of the antibodies of the present invention may be expressed in plants and that such expression can result in a physiological effect. It is also understood that any of the expressed antibodies may be catalytic.

(b) Fungal Constructs and Fungal Transformants

The present invention also relates to a fungal recombinant vector comprising exogenous genetic material. The present invention also relates to a fungal cell comprising a fungal recombinant vector. The present invention also relates to methods for obtaining a recombinant fungal host cell comprising introducing into a fungal host cell exogenous genetic material.

Exogenous genetic material may be transferred into a fungal cell. In a preferred embodiment the exogenous genetic material includes a nucleic acid molecule of the present invention having a sequence selected from the group consisting of SEQ ID NO: 1 through SEQ ID NO: 627 or complements thereof or fragments of either or other nucleic acid molecule of the present invention. The fungal recombinant vector may be any vector which can be conveniently subjected to recombinant DNA procedures. The choice of a vector will typically depend on the compatibility of the vector with the fungal host cell into which the vector is to be introduced. The vector may be a linear or a closed circular plasmid. The vector system may be a single vector or plasmid or two or more vectors or plasmids which together contain the total DNA to be introduced into the genome of the fungal host.

The fungal vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the fungal cell, is integrated into the genome and replicated together with the chromosome(s) into which it has been integrated. For integration, the vector may rely on the nucleic acid sequence of the vector for stable integration of the vector into the genome by homologous or nonhomologous recombination. Alternatively, the vector may contain additional nucleic acid sequences for directing integration by homologous recombination into the genome of the fungal host. The additional nucleic acid sequences enable the vector to be integrated into the host cell genome at a precise location(s) in the chromosome(s). To increase the likelihood of integration at a precise location, there should be preferably two nucleic acid sequences which individually contain a sufficient number of nucleic acids, preferably 400 bp to 1500 bp, more preferably 800 bp to 1000 bp, which are highly homologous with the corresponding target sequence to enhance the probability of homologous recombination. These nucleic acid sequences may be any sequence that is homologous with a target sequence in the genome of the fungal host cell and, furthermore, may be non-encoding or encoding sequences.

For autonomous replication, the vector may further comprise an origin of replication enabling the vector to replicate autonomously in the host cell in question. Examples of origin of replications for use in a yeast host cell are the 2 micron origin of replication and the combination of CEN3 and ARS 1. Any origin of replication may be used which is compatible with the fungal host cell of choice.

The fungal vectors of the present invention preferably contain one or more selectable markers which permit easy selection of transformed cells. A selectable marker is a gene the product of which provides, for example biocide or viral resistance, resistance to heavy metals, prototrophy to auxotrophs and the like. The selectable marker may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase) and sC (sulfate adenyltransferase) and trpC (anthranilate synthase). Preferred for use in an *Aspergillus* cell are the amdS and pyrG markers of *Aspergillus nidulans* or *Aspergillus oryzae* and the bar marker of *Streptomyces hygroscopicus*. Furthermore, selection may be accomplished by co-transformation, e.g., as described in WO 91/17243, the entirety of which is herein incorporated by reference. A nucleic acid sequence of the present invention may be operably linked to a suitable promoter sequence. The promoter sequence is a nucleic acid sequence which is recognized by the fungal host cell for expression of the nucleic acid sequence. The promoter sequence contains transcription and translation control sequences which mediate the expression of the protein or fragment thereof.

A promoter may be any nucleic acid sequence which shows transcriptional activity in the fungal host cell of choice and may be obtained from genes encoding polypeptides either homologous or heterologous to the host cell. Examples of suitable promoters for directing the transcription of a nucleic acid construct of the invention in a filamentous fungal host are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase and hybrids thereof. In a yeast host, a useful promoter is the *Saccharomyces cerevisiae* enolase (eno-1) promoter. Particularly preferred promoters are the TAKA amylase, NA2-tpi (a hybrid of the promoters from the genes encoding *Aspergillus niger* neutral alpha-amylase and *Aspergillus oryzae* triose phosphate isomerase) and glaA promoters.

A protein or fragment thereof encoding nucleic acid molecule of the present invention may also be operably linked to a terminator sequence at its 3' terminus. The terminator sequence may be native to the nucleic acid sequence encoding the protein or fragment thereof or may be obtained from foreign sources. Any terminator which is functional in the fungal host cell of choice may be used in the present invention, but particularly preferred terminators are obtained from the genes encoding *Aspergillus oryzae* TAKA amylase, *Aspergillus niger* glucoamylase, *Aspergillus nidulans* anthranilate synthase, *Aspergillus niger* alpha-glucosidase and *Saccharomyces cerevisiae* enolase.

A protein or fragment thereof encoding nucleic acid molecule of the present invention may also be operably linked to a suitable leader sequence. A leader sequence is a nontranslated region of a mRNA which is important for translation by the fungal host. The leader sequence is operably linked to the 5' terminus of the nucleic acid sequence encoding the protein or fragment thereof. The leader sequence may be native to the nucleic acid sequence encoding the protein or fragment thereof or may be obtained from foreign sources. Any leader sequence which is functional in the fungal host cell of choice may be used in the present invention, but particularly preferred leaders are obtained from the genes encoding *Aspergillus oryzae* TAKA amylase and *Aspergillus oryzae* triose phosphate isomerase.

A polyadenylation sequence may also be operably linked to the 3' terminus of the nucleic acid sequence of the present invention. The polyadenylation sequence is a sequence which when transcribed is recognized by the fungal host to add polyadenosine residues to transcribed mRNA. The polyadenylation sequence may be native to the nucleic acid sequence encoding the protein or fragment thereof or may be obtained from foreign sources. Any polyadenylation sequence which is functional in the fungal host of choice may be used in the present invention, but particularly preferred polyadenylation sequences are obtained from the genes encoding *Aspergillus oryzae* TAKA amylase, *Aspergillus niger* glucoamylase, *Aspergillus nidulans* anthranilate synthase and *Aspergillus niger* alpha-glucosidase.

To avoid the necessity of disrupting the cell to obtain the protein or fragment thereof and to minimize the amount of possible degradation of the expressed protein or fragment thereof within the cell, it is preferred that expression of the protein or fragment thereof gives rise to a product secreted outside the cell. To this end, a protein or fragment thereof of the present invention may be linked to a signal peptide linked to the amino terminus of the protein or fragment thereof. A signal peptide is an amino acid sequence which permits the secretion of the protein or fragment thereof from the fungal host into the culture medium. The signal peptide may be native to the protein or fragment thereof of the invention or may be obtained from foreign sources. The 5' end of the coding sequence of the nucleic acid sequence of the present invention may inherently contain a signal peptide coding region naturally linked in translation reading frame with the segment of the coding region which encodes the secreted protein or fragment thereof. Alternatively, the 5' end of the coding sequence may contain a signal peptide coding region which is foreign to that portion of the coding sequence which encodes the secreted protein or fragment thereof. The foreign signal peptide may be required where the coding sequence does not normally contain a signal peptide coding region. Alternatively, the foreign signal peptide may simply replace the natural signal peptide to obtain enhanced secretion of the desired protein or fragment thereof. The foreign signal peptide coding region may be obtained from a glucoamylase or an amylase gene from an *Aspergillus* species, a lipase or proteinase gene from *Rhizomucor miehei*, the gene for the alpha-factor from *Saccharomyces cerevisiae*, or the calf preprochymosin gene. An effective signal peptide for fungal host cells is the *Aspergillus oryzae* TAKA amylase signal, *Aspergillus niger* neutral amylase signal, the *Rhizomucor miehei* aspartic proteinase signal, the *Humicola lanuginosus* cellulase signal, or the *Rhizomucor miehei* lipase signal. However, any signal peptide capable of permitting secretion of the protein or fragment thereof in a fungal host of choice may be used in the present invention.

A protein or fragment thereof encoding nucleic acid molecule of the present invention may also be linked to a propeptide coding region. A propeptide is an amino acid sequence found at the amino terminus of aproprotein or proenzyme. Cleavage of the propeptide from the proprotein yields a mature biochemically active protein. The resulting polypeptide is known as a propolypeptide or proenzyme (or a zymogen in some cases). Propolypeptides are generally inactive and can be converted to mature active polypeptides by catalytic or autocatalytic cleavage of the propeptide from the propolypeptide or proenzyme. The propeptide coding region may be native to the protein or fragment thereof or may be obtained from foreign sources. The foreign propeptide coding region may be obtained from the *Saccharomyces cerevisiae* alpha-factor gene or *Myceliophthora thermophila* laccase gene (WO 95/33836, the entirety of which is herein incorporated by reference).

The procedures used to ligate the elements described above to construct the recombinant expression vector of the present invention are well known to one skilled in the art (see, for example, Sambrook et al., *Molecular Cloning, A Laboratory Manual*, 2nd ed., Cold Spring Harbor, N.Y., (1989)).

The present invention also relates to recombinant fungal host cells produced by the methods of the present invention which are advantageously used with the recombinant vector of the present invention. The cell is preferably transformed with a vector comprising a nucleic acid sequence of the invention followed by integration of the vector into the host chromosome. The choice of fungal host cells will to a large extent depend upon the gene encoding the protein or fragment thereof and its source. The fungal host cell may, for example, be a yeast cell or a filamentous fungal cell.

"Yeast" as used herein includes *Ascosporogenous* yeast (*Endomycetales*), *Basidiosporogenous* yeast and yeast belonging to the *Fungi Imperfecti* (*Blastomycetes*). The *Ascosporogenous* yeasts are divided into the families Spermophthoraceae and Saccharomycetaceae. The latter is comprised of four subfamilies, Schizosaccharomycoideae (for example, genus *Schizosaccharomyces*), Nadsonioideae, Lipomycoideae and Saccharomycoideae (for example, genera *Pichia*, *Kluyveromyces* and *Saccharomyces*). The *Basidiosporogenous* yeasts include the genera *Leucosporidim*, *Rhodosporidium*, *Sporidiobolus*, *Filobasidium* and *Filobasidiella*. Yeast belonging to the *Fungi Imperfecti* are divided into two families, Sporobolomycetaceae (for example, genera *Sorobolomyces* and *Bullera*) and Cryptococcaceae (for example, genus *Candida*). Since the classification of yeast may change in the future, for the purposes of this invention, yeast shall be defined as described in Biology and Activities of Yeast (Skinner et al., *Soc. App. Bacteriol. Symposium Series* No. 9, (1980), the entirety of which is herein incorporated by reference). The biology of yeast and manipulation of yeast genetics are well known in the art (see, for example, *Biochemistry and Genetics of Yeast*, Bacil et al. (ed.), 2nd edition, 1987; The Yeasts, Rose and Harrison (eds.), 2nd ed., (1987); and *The Molecular Biology of the Yeast Saccharomyces*, Strathern et al. (eds.), (1981), all of which are herein incorporated by reference in their entirety).

"Fungi" as used herein includes the phyla *Ascomycota*, *Basidiomycota*, *Chytridiomycota* and *Zygomycota* (as defined by Hawksworth et al., In: Ainsworth and Bisby's *Dictionary of The Fungi*, 8th edition, 1995, CAB International, University Press, Cambridge, UK; the entirety of which is herein incorporated by reference) as well as the *Oomycota* (as cited in Hawksworth et al., In: Ainsworth and Bisby's *Dictionary of The Fungi*, 8th edition, 1995, CAB International, University Press, Cambridge, UK) and all mitosporic fungi (Hawksworth et al., In: Ainsworth and Bisby's *Dictionary of The Fungi*, 8th edition, 1995, CAB International, University Press, Cambridge, UK). Representative groups of *Ascomycota* include, for example, *Neurospora*, *Eupenicillium* (=*Penicillium*), *Emericella* (=*Aspergillus*), *Eurotiun* (=*Aspergillus*) and the true yeasts listed above. Examples of *Basidiomycota* include mushrooms, rusts and smuts. Representative groups of *Chytridiomycota* include, for example, *Allomyces*, *Blastocladiella*, *Coelomomyces* and aquatic fungi. Representative groups of *Oomycota* include, for example, *Saprolegniomycetous* aquatic fungi (water molds) such as *Achlya*. Examples of mitosporic fungi include *Aspergillus*, *Penicilliun*, *Candida* and *Alternaria*. Representative groups of *Zygomycota* include, for example, *Rhizopus* and *Mucor*.

"Filamentous fungi" include all filamentous forms of the subdivision *Eumycota* and *Oomycota* (as defined by Hawksworth et al., In: Ainsworth and Bisby's *Dictionary of The Fungi*, 8th edition, 1995, CAB International, University Press, Cambridge, UK). The filamentous fungi are characterized by a vegetative mycelium composed of chitin, cellulose, glucan, chitosan, mannan and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In one embodiment, the fungal host cell is a yeast cell. In a preferred embodiment, the yeast host cell is a cell of the species of *Candida*, *Kluyveromyces*, *Saccharomyces*, *Schizosaccharomyces*, *Pichia* and *Yarrowia*. In a preferred embodiment, the yeast host cell is a *Saccharomyces cerevisiae* cell, a *Saccharomyces carlsbergensis*, *Saccharomyces diastaticus* cell, a *Saccharomyces douglasii* cell, a *Saccharomyces kluyveri* cell, a *Saccharomyces norbensis* cell, or a *Saccharomyces oviformis* cell. In another preferred embodiment, the yeast host cell is a *Kluyveromyces lactis* cell. In another preferred embodiment, the yeast host cell is a *Yarrowia lipolytica* cell.

In another embodiment, the fungal host cell is a filamentous fungal cell. In a preferred embodiment, the filamentous fungal host cell is a cell of the species of, but not limited to, *Acremonium*, *Aspergillus*, *Fusarium*, *Humicola*, *Myceliophthora*, *Mucor*, *Neurospora*, *Penicillium*, *Thielavia*, *Tolypocladium* and *Trichoderma*. In a preferred embodiment, the filamentous fungal host cell is an *Aspergillus* cell. In another preferred embodiment, the filamentous fungal host cell is an *Acremonium* cell. In another preferred embodiment, the filamentous fungal host cell is a *Fusarium* cell. In another preferred embodiment, the filamentous fungal host cell is a *Humicola* cell. In another preferred embodiment, the filamentous fungal host cell is a *Myceliophthora* cell. In another even preferred embodiment, the filamentous fungal host cell is a *Mucor* cell. In another preferred embodiment, the filamentous fungal host cell is a *Neurospora* cell. In another preferred embodiment, the filamentous fungal host cell is a *Penicillium* cell. In another preferred embodiment, the filamentous fungal host cell is a *Thielavia* cell. In another preferred embodiment, the filamentous fungal host cell is a *Tolypocladiun* cell. In another preferred embodiment, the filamentous fungal host cell is a *Trichoderma* cell. In a preferred embodiment, the filamentous fungal host cell is an *Aspergillus oryzae* cell, an *Aspergillus niger* cell, an *Aspergillus foetidus* cell, or an *Aspergillus japonicus* cell. In another preferred embodiment, the filamentous fungal host cell is a *Fusarium oxysporum* cell or a *Fusarium graminearum* cell. In another preferred embodiment, the filamentous fungal host cell is a *Humicola insolens* cell or a *Humicola lanuginosus* cell. In another preferred embodiment, the filamentous fungal host cell is a *Myceliophthora thermophila* cell. In a most preferred embodiment, the filamentous fungal host cell is a *Mucor miehei* cell. In a most preferred embodiment, the filamentous fungal host cell is a *Neurospora crassa* cell. In a most preferred embodiment, the filamentous fungal host cell is a *Penicillium purpurogenum* cell. In another most preferred embodiment, the filamentous fungal host cell is a *Thielavia terrestris* cell. In another most preferred embodiment, the *Trichoderma* cell is a *Trichoderma reesei* cell, a *Trichoderma viride* cell, a *Trichoderma longibrachiatum* cell, a *Trichoderma harzianum* cell, or a *Trichoderma koningii* cell. In a preferred embodiment, the fungal host cell is selected from an *A. nidulans* cell, an *A. niger* cell, an *A. oryzae* cell and an *A. sojae* cell. In a further preferred embodiment, the fungal host cell is an *A. nidulans* cell.

The recombinant fungal host cells of the present invention may further comprise one or more sequences which encode one or more factors that are advantageous in the expression of the protein or fragment thereof, for example, an activator (e.g., a trans-acting factor), a chaperone and a processing protease. The nucleic acids encoding one or more of these factors are preferably not operably linked to the nucleic acid encoding the protein or fragment thereof. An activator is a protein which activates transcription of a nucleic acid sequence encoding a polypeptide (Kudla et al., *EMBO* 9:1355-1364(1990); Jarai and Buxton, *Current Genetics* 26:2238-244(1994); Verdier, *Yeast* 6:271-297(1990), all of which are herein incorporated by reference in their entirety). The nucleic acid sequence encoding an activator may be obtained from the genes encoding *Saccharomyces cerevisiae* heme activator protein 1 (hap1), *Saccharomyces cerevisiae* galactose metabolizing protein 4 (gal4) and *Aspergillus nidulans* ammonia regulation protein (areA). For further examples, see Verdier, *Yeast* 6:271-297 (1990); MacKenzie et al., *Journal of Gen. Microbiol.* 139:2295-2307 (1993), both of which are herein incorporated by reference in their entirety). A chaperone is a protein which assists another protein in folding properly (Hartl et al., *TIBS* 19:20-25 (1994); Bergeron et al., *TIBS* 19:124-128 (1994); Demolder et al., *J. Biotechnology* 32:179-189 (1994); Craig, *Science* 260:1902-1903(1993); Gething and Sambrook, *Nature* 355:33-45 (1992); Puig and Gilbert, *J. Biol. Chem.* 269:7764-7771 (1994); Wang and Tsou, *FASEB Journal* 7:1515-11157 (1993); Robinson et al., *Bio/Technology* 1:381-384 (1994), all of which are herein incorporated by reference in their entirety). The nucleic acid sequence encoding a chaperone may be obtained from the genes encoding *Aspergillus oryzae* protein disulphide isomerase, *Saccharomyces cerevisiae* calnexin, *Saccharomyces cerevisiae* BiP/GRP78 and *Saccharomyces cerevisiae* Hsp70. For further examples, see Gething and Sambrook, *Nature* 355:33-45 (1992); Hartl et al., *TIBS* 19:20-25 (1994). A processing protease is a protease that cleaves a propeptide to generate a mature biochemically active polypeptide (Enderlin and Ogrydziak, *Yeast* 10:67-79 (1994); Fuller et al., *Proc. Natl. Acad. Sci.* (*U.S.A.*) 86:1434-1438 (1989); Julius et al., *Cell* 37:1075-1089 (1984); Julius et al., *Cell* 32:839-852 (1983), all of which are incorporated by reference in their entirety). The nucleic acid sequence encoding a processing protease may be obtained from the genes encoding *Aspergillus niger* Kex2, *Saccharomyces cerevisiae* dipeptidylaminopeptidase, *Saccharomyces cerevisiae* Kex2 and *Yarrowia lipolytica* dibasic processing endoprotease (xpr6). Any factor that is functional in the fungal host cell of choice may be used in the present invention.

Fungal cells may be transformed by a process involving protoplast formation, transformation of the protoplasts and regeneration of the cell wall in a manner known per se. Suitable procedures for transformation of *Aspergillus* host cells are described in EP 238 023 and Yelton et al., *Proc. Natl. Acad. Sci.* (*U.S.A.*) 81:1470-1474 (1984), both of which are herein incorporated by reference in their entirety. A suitable method of transforming *Fusarium* species is described by Malardier et al., *Gene* 78:147-156 (1989), the entirety of which is herein incorporated by reference. Yeast may be transformed using the procedures described by Becker and Guarente, In: Abelson and Simon, (eds.), *Guide to Yeast Genetics and Molecular Biology, Methods Enzymol.* Volume 194, pp 182-187, Academic Press, Inc., New York; Ito et al., *J. Bacteriology* 153:163 (1983); Hinnen et al., *Proc. Natl. Acad. Sci.* (*U.S.A.*) 75:1920 (1978), all of which are herein incorporated by reference in their entirety.

The present invention also relates to methods of producing the protein or fragment thereof comprising culturing the recombinant fungal host cells under conditions conducive for expression of the protein or fragment thereof. The fungal cells of the present invention are cultivated in a nutrient medium suitable for production of the protein or fragment thereof using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the protein or fragment thereof to be expressed and/or isolated. The cultivation takes place in a suitable nutrient medium comprising carbon and nitrogen sources and inorganic salts, using procedures known in the art (see, e.g., Bennett and LaSure (eds.), More Gene Manipulations in Fungi, Academic Press, CA, (1991), the entirety of which is herein incorporated by reference). Suitable media are available from commercial suppliers or may be prepared according to published compositions (e.g., in catalogues of the American Type Culture Collection, Manassas, Va.). If the protein or fragment thereof is secreted into the nutrient medium, a protein or fragment thereof can be recovered directly from the medium. If the protein or fragment thereof is not secreted, it is recovered from cell lysates.

The expressed protein or fragment thereof may be detected using methods known in the art that are specific for the particular protein or fragment. These detection methods may include the use of specific antibodies, formation of an enzyme product, or disappearance of an enzyme substrate. For example, if the protein or fragment thereof has enzymatic activity, an enzyme assay may be used. Alternatively, if polyclonal or monoclonal antibodies specific to the protein or fragment thereof are available, immunoassays may be employed using the antibodies to the protein or fragment thereof. The techniques of enzyme assay and immunoassay are well known to those skilled in the art.

The resulting protein or fragment thereof may be recovered by methods known in the arts. For example, the protein or fragment thereof may be recovered from the nutrient medium by conventional procedures including, but not limited to, centrifugation, filtration, extraction, spray-drying, evaporation, or precipitation. The recovered protein or fragment thereof may then be further purified by a variety of chromatographic procedures, e.g., ion exchange chromatography, gel filtration chromatography, affinity chromatography, or the like.

(c) Mammalian Constructs and Transformed Mammalian Cells

The present invention also relates to methods for obtaining a recombinant mammalian host cell, comprising introducing into a mammalian host cell exogenous genetic material. The present invention also relates to a mammalian cell comprising a mammalian recombinant vector. The present invention also relates to methods for obtaining a recombinant mammalian host cell, comprising introducing into a mammalian cell exogenous genetic material. In a preferred embodiment the exogenous genetic material includes a nucleic acid molecule of the present invention having a sequence selected from the group consisting of SEQ ID NO: 1 through SEQ ID NO: 627 or complements thereof or fragments of either or other nucleic acid molecule of the present invention.

Mammalian cell lines available as hosts for expression are known in the art and include many immortalized cell lines available from the American Type Culture Collection (ATCC, Manassas, Va.), such as HeLa cells, Chinese hamster ovary (CHO) cells, baby hamster kidney (BHK) cells and a number of other cell lines. Suitable promoters for mammalian cells are also known in the art and include viral promoters such as that from Simian Virus 40 (SV40) (Fiers et al., *Nature* 273: 113 (1978), the entirety of which is herein incorporated by reference), Rous sarcoma virus (RSV), adenovirus (ADV) and bovine papilloma virus (BPV). Mammalian cells may also require terminator sequences and poly-A addition sequences. Enhancer sequences which increase expression may also be included and sequences which promote amplification of the gene may also be desirable (for example methotrexate resistance genes).

Vectors suitable for replication in mammalian cells may include viral replicons, or sequences which insure integration of the appropriate sequences encoding HCV epitopes into the host genome. For example, another vector used to express foreign DNA is vaccinia virus. In this case, for example, a nucleic acid molecule encoding a protein or fragment thereof is inserted into the vaccinia genome. Techniques for the insertion of foreign DNA into the vaccinia virus genome are known in the art and may utilize, for example, homologous recombination. Such heterologous DNA is generally inserted into a gene which is non-essential to the virus, for example, the thymidine kinase gene (tk), which also provides a selectable marker. Plasmid vectors that greatly facilitate the construction of recombinant viruses have been described (see, for example, Mackett et al, *J. Virol.* 49:857 (1984); Chakrabarti et al., *Mol. Cell. Biol.* 5:3403 (1985); Moss, In: *Gene Transfer Vectors For Mammalian Cells* (Miller and Calos, eds., Cold Spring Harbor Laboratory, N.Y., p. 10, (1987); all of which are herein incorporated by reference in their entirety). Expression of the HCV polypeptide then occurs in cells or animals which are infected with the live recombinant vaccinia virus.

The sequence to be integrated into the mammalian sequence may be introduced into the primary host by any convenient means, which includes calcium precipitated DNA, spheroplast fusion, transformation, electroporation, biolistics, lipofection, microinjection, or other convenient means. Where an amplifiable gene is being employed, the amplifiable gene may serve as the selection marker for selecting hosts into which the amplifiable gene has been introduced. Alternatively, one may include with the amplifiable gene another marker, such as a drug resistance marker, e.g. neomycin resistance (G418 in mammalian cells), hygromycin in resistance etc., or an auxotrophy marker (HIS3, TRP1, LEU2, URA3, ADE2, LYS2, etc.) for use in yeast cells.

Depending upon the nature of the modification and associated targeting construct, various techniques may be employed for identifying targeted integration. Conveniently, the DNA may be digested with one or more restriction enzymes and the fragments probed with an appropriate DNA fragment which will identify the properly sized restriction fragment associated with integration.

One may use different promoter sequences, enhancer sequences, or other sequence which will allow for enhanced levels of expression in the expression host. Thus, one may combine an enhancer from one source, a promoter region from another source, a 5'-noncoding region upstream from the initiation methionine from the same or different source as the other sequences and the like. One may provide for an intron in the non-coding region with appropriate splice sites or for an alternative 3'-untranslated sequence or polyadenylation site. Depending upon the particular purpose of the modification, any of these sequences may be introduced, as desired.

Where selection is intended, the sequence to be integrated will have with it a marker gene, which allows for selection. The marker gene may conveniently be downstream from the target gene and may include resistance to a cytotoxic agent, e.g. antibiotics, heavy metals, or the like, resistance or susceptibility to HAT, gancyclovir, etc., complementation to an auxotrophic host, particularly by using an auxotrophic yeast as the host for the subject manipulations, or the like. The marker gene may also be on a separate DNA molecule, particularly with primary mammalian cells. Alternatively, one may screen the various transformants, due to the high efficiency of recombination in yeast, by using hybridization analysis, PCR, sequencing, or the like.

For homologous recombination, constructs can be prepared where the amplifiable gene will be flanked, normally on both sides with DNA homologous with the DNA of the target region. Depending upon the nature of the integrating DNA and the purpose of the integration, the homologous DNA will generally be within 100 kb, usually 50 kb, preferably about 25 kb, of the transcribed region of the target gene, more preferably within 2 kb of the target gene. Where modeling of the gene is intended, homology will usually be present proximal to the site of the mutation. The homologous DNA may include the 5'-upstream region outside of the transcriptional regulatory region or comprising any enhancer sequences, transcriptional initiation sequences, adjacent sequences, or the like. The homologous region may include a portion of the coding region, where the coding region may be comprised only of an open reading frame or combination of exons and introns. The homologous region may comprise all or a portion of an intron, where all or a portion of one or more exons may also be present. Alternatively, the homologous region may comprise the 3'-region, so as to comprise all or a portion of the transcriptional termination region, or the region 3' of this region. The homologous regions may extend over all or a portion of the target gene or be outside the target gene comprising all or a portion of the transcriptional regulatory regions and/or the structural gene.

The integrating constructs may be prepared in accordance with conventional ways, where sequences may be synthesized, isolated from natural sources, manipulated, cloned, ligated, subjected to in vitro mutagenesis, primer repair, or the like. At various stages, the joined sequences may be cloned and analyzed by restriction analysis, sequencing, or the like. Usually during the preparation of a construct where various fragments are joined, the fragments, intermediate constructs and constructs will be carried on a cloning vector comprising a replication system functional in a prokaryotic host, e.g., *E. coli* and a marker for selection, e.g., biocide resistance, complementation to an auxotrophic host, etc. Other functional sequences may also be present, such as polylinkers, for ease of introduction and excision of the construct or portions thereof, or the like. A large number of cloning vectors are available such as pBR322, the pUC series, etc. These constructs may then be used for integration into the primary mammalian host.

In the case of the primary mammalian host, a replicating vector may be used. Usually, such vector will have a viral replication system, such as SV40, bovine papilloma virus, adenovirus, or the like. The linear DNA sequence vector may also have a selectable marker for identifying transfected cells. Selectable markers include the neo gene, allowing for selection with G418, the herpes tk gene for selection with HAT medium, the gpt gene with mycophenolic acid, complementation of an auxotrophic host, etc.

The vector may or may not be capable of stable maintenance in the host. Where the vector is capable of stable maintenance, the cells will be screened for homologous integration of the vector into the genome of the host, where various techniques for curing the cells may be employed. Where the vector is not capable of stable maintenance, for example, where a temperature sensitive replication system is employed, one may change the temperature from the permissive temperature to the non-permissive temperature, so that the cells may be cured of the vector. In this case, only those cells having integration of the construct comprising the amplifiable gene and, when present, the selectable marker, will be able to survive selection.

Where a selectable marker is present, one may select for the presence of the targeting construct by means of the selectable marker. Where the selectable marker is not present, one may select for the presence of the construct by the amplifiable gene. For the neo gene or the herpes tk gene, one could employ a medium for growth of the transformants of about 0.1-1 mg/ml of G418 or may use HAT medium, respectively. Where DHFR is the amplifiable gene, the selective medium may include from about 0.01-0.5 µM of methotrexate or be deficient in glycine-hypoxanthine-thymidine and have dialysed serum (GHT media).

The DNA can be introduced into the expression host by a variety of techniques that include calcium phosphate/DNA co-precipitates, microinjection of DNA into the nucleus, electroporation, yeast protoplast fusion with intact cells, transfection, polycations, e.g., polybrene, polyornithine, etc., or the like. The DNA may be single or double stranded DNA, linear or circular. The various techniques for transforming mammalian cells are well known (see Keown et al., *Methods Enzymol.* (1989); Keown et al., *Methods Enzymol.* 185:527-537 (1990); Mansour et al., *Nature* 336:348-352, (1988); all of which are herein incorporated by reference in their entirety).

(d) Insect Constructs and Transformed Insect Cells

The present invention also relates to an insect recombinant vectors comprising exogenous genetic material. The present invention also relates to an insect cell comprising an insect recombinant vector. The present invention also relates to methods for obtaining a recombinant insect host cell, comprising introducing into an insect cell exogenous genetic material. In a preferred embodiment the exogenous genetic material includes a nucleic acid molecule of the present invention having a sequence selected from the group consisting of SEQ ID NO: 1 through SEQ ID NO: 627 or complements thereof or fragments of either or other nucleic acid molecule of the present invention.

The insect recombinant vector may be any vector which can be conveniently subjected to recombinant DNA procedures and can bring about the expression of the nucleic acid sequence. The choice of a vector will typically depend on the compatibility of the vector with the insect host cell into which the vector is to be introduced. The vector may be a linear or a closed circular plasmid. The vector system may be a single vector or plasmid or two or more vectors or plasmids which together contain the total DNA to be introduced into the genome of the insect host. In addition, the insect vector may be an expression vector. Nucleic acid molecules can be suitably inserted into a replication vector for expression in the insect cell under a suitable promoter for insect cells. Many vectors are available for this purpose and selection of the appropriate vector will depend mainly on the size of the nucleic acid molecule to be inserted into the vector and the particular host cell to be transformed with the vector. Each vector contains various components depending on its function (amplification of DNA or expression of DNA) and the particular host cell with which it is compatible. The vector components for insect cell transformation generally include, but are not limited to, one or more of the following: a signal sequence, origin of replication, one or more marker genes and an inducible promoter.

The insect vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the insect cell, is integrated into the genome and replicated together with the chromosome(s) into which it has been integrated. For integration, the vector may rely on the nucleic acid sequence of the vector for stable integration of the vector into the genome by homologous or nonhomologous recombination. Alternatively, the vector may contain additional nucleic acid sequences for directing integration by homologous recombination into the genome of the insect host. The additional nucleic acid sequences enable the vector to be integrated into the host cell genome at a precise location(s) in the chromosome(s). To increase the likelihood of integration at a precise location, there should be preferably two nucleic acid sequences which individually contain a sufficient number of nucleic acids, preferably 400 bp to 1500 bp, more preferably 800 bp to 1000 bp, which are highly homologous with the corresponding target sequence to enhance the probability of homologous recombination. These nucleic acid sequences may be any sequence that is homologous with a target sequence in the genome of the insect host cell and, furthermore, may be non-encoding or encoding sequences.

Baculovirus expression vectors (BEVs) have become important tools for the expression of foreign genes, both for basic research and for the production of proteins with direct clinical applications in human and veterinary medicine (Doerfler, *Curr. Top. Microbiol. Immunol.* 131:51-68 (1968); Luckow and Summers, *Bio/Technology* 6:47-55 (1988a); Miller, *Annual Review of Microbiol.* 42:177-199 (1988);

Summers, *Curr. Comm. Molecular Biology*, Cold Spring Harbor Press, Cold Spring Harbor, N.Y. (1988); all of which are herein incorporated by reference in their entirety). BEVs are recombinant insect viruses in which the coding sequence for a chosen foreign gene has been inserted behind a baculovirus promoter in place of the viral gene, e.g., polyhedrin (Smith and Summers, U.S. Pat. No. 4,745,051, the entirety of which is incorporated herein by reference).

The use of baculovirus vectors relies upon the host cells being derived from *Lepidopteran* insects such as *Spodoptera frugiperda* or *Trichoplusia ni*. The preferred *Spodoptera frugiperda* cell line is the cell line Sf9. The *Spodoptera frugiperda* Sf9 cell line was obtained from American Type Culture Collection (Manassas, Va.) and is assigned accession number ATCC CRL 1711 (Summers and Smith, *A Manual of Methods for Baculovirus Vectors and Insect Cell Culture Procedures*, Texas Ag. Exper. Station Bulletin No. 1555 (1988), the entirety of which is herein incorporated by reference). Other insect cell systems, such as the silkworm *B. mori* may also be used.

The proteins expressed by the BEVs are, therefore, synthesized, modified and transported in host cells derived from *Lepidopteran* insects. Most of the genes that have been inserted and produced in the baculovirus expression vector system have been derived from vertebrate species. Other baculovirus genes in addition to the polyhedrin promoter may be employed to advantage in a baculovirus expression system. These include immediate-early (alpha), delayed-early (β), late (γ), or very late (delta), according to the phase of the viral infection during which they are expressed. The expression of these genes occurs sequentially, probably as the result of a "cascade" mechanism of transcriptional regulation. (Guarino and Summers, *J. Virol.* 57:563-571 (1986); Guarino and Summers, *J. Virol.* 61:2091-2099 (1987); Guarino and Summers, *Virol.* 162:444-451 (1988); all of which are herein incorporated by reference in their entirety).

Insect recombinant vectors are useful as intermediates for the infection or transformation of insect cell systems. For example, an insect recombinant vector containing a nucleic acid molecule encoding a baculovirus transcriptional promoter followed downstream by an insect signal DNA sequence is capable of directing the secretion of the desired biologically active protein from the insect cell. The vector may utilize a baculovirus transcriptional promoter region derived from any of the over 500 baculoviruses generally infecting insects, such as for example the Orders *Lepidoptera, Diptera, Orthoptera, Coleoptera* and *Hymenoptera*, including for example but not limited to the viral DNAs of *Autographa californica* MNPV, *Bombyx mori* NPV, *Trichoplusia ni* MNPV, *Rachiplusia ou* MNPV or *Galleria mellonella* MNPV, wherein said baculovirus transcriptional promoter is a baculovirus immediate-early gene IE1 or IEN promoter; an immediate-early gene in combination with a baculovirus delayed-early gene promoter region selected from the group consisting of 39K and a HindIII-k fragment delayed-early gene; or a baculovirus late gene promoter. The immediate-early or delayed-early promoters can be enhanced with transcriptional enhancer elements. The insect signal DNA sequence may code for a signal peptide of a *Lepidopteran* adipokinetic hormone precursor or a signal peptide of the *Manduca sexta* adipokinetic hormone precursor (Summers, U.S. Pat. No. 5,155,037; the entirety of which is herein incorporated by reference). Other insect signal DNA sequences include a signal peptide of the *Orthoptera Schistocerca gregaria* locust adipokinetic hormone precursor and the *Drosophila melanogaster* cuticle genes CP1, CP2, CP3 or CP4 or for an insect signal peptide having substantially a similar chemical composition and function (Summers, U.S. Pat. No. 5,155,037).

Insect cells are distinctly different from animal cells. Insects have a unique life cycle and have distinct cellular properties such as the lack of intracellular plasminogen activators in which are present in vertebrate cells. Another difference is the high expression levels of protein products ranging from 1 to greater than 500 mg/liter and the ease at which cDNA can be cloned into cells (Frasier, *In Vitro Cell. Dev. Biol.* 25:225 (1989); Summers and Smith, In: *A Manual of Methods for Baculovirus Vectors and Insect Cell Culture Procedures*, Texas Ag. Exper. Station Bulletin No. 1555 (1988), both of which are incorporated by reference in their entirety).

Recombinant protein expression in insect cells is achieved by viral infection or stable transformation. For viral infection, the desired gene is cloned into baculovirus at the site of the wild-type polyhedron gene (Webb and Summers, *Technique* 2:173 (1990); Bishop and Posse, *Adv. Gene Technol.* 1:55 (1990); both of which are incorporated by reference in their entirety). The polyhedron gene is a component of a protein coat in occlusions which encapsulate virus particles. Deletion or insertion in the polyhedron gene results the failure to form occlusion bodies. Occlusion negative viruses are morphologically different from occlusion positive viruses and enable one skilled in the art to identify and purify recombinant viruses.

The vectors of present invention preferably contain one or more selectable markers which permit easy selection of transformed cells. A selectable marker is a gene the product of which provides, for example biocide or viral resistance, resistance to heavy metals, prototrophy to auxotrophs and the like. Selection may be accomplished by co-transformation, e.g., as described in WO 91/17243, a nucleic acid sequence of the present invention may be operably linked to a suitable promoter sequence. The promoter sequence is a nucleic acid sequence which is recognized by the insect host cell for expression of the nucleic acid sequence. The promoter sequence contains transcription and translation control sequences which mediate the expression of the protein or fragment thereof. The promoter may be any nucleic acid sequence which shows transcriptional activity in the insect host cell of choice and may be obtained from genes encoding polypeptides either homologous or heterologous to the host cell.

For example, a nucleic acid molecule encoding a protein or fragment thereof may also be operably linked to a suitable leader sequence. A leader sequence is a nontranslated region of a mRNA which is important for translation by the fungal host. The leader sequence is operably linked to the 5' terminus of the nucleic acid sequence encoding the protein or fragment thereof. The leader sequence may be native to the nucleic acid sequence encoding the protein or fragment thereof or may be obtained from foreign sources. Any leader sequence which is functional in the insect host cell of choice may be used in the present invention.

A polyadenylation sequence may also be operably linked to the 3' terminus of the nucleic acid sequence of the present invention. The polyadenylation sequence is a sequence which when transcribed is recognized by the insect host to add polyadenosine residues to transcribed mRNA. The polyadenylation sequence may be native to the nucleic acid sequence encoding the protein or fragment thereof or may be obtained from foreign sources. Any polyadenylation sequence which is functional in the fungal host of choice may be used in the present invention.

To avoid the necessity of disrupting the cell to obtain the protein or fragment thereof and to minimize the amount of possible degradation of the expressed polypeptide within the cell, it is preferred that expression of the polypeptide gene gives rise to a product secreted outside the cell. To this end, the protein or fragment thereof of the present invention may be linked to a signal peptide linked to the amino terminus of the protein or fragment thereof. A signal peptide is an amino acid sequence which permits the secretion of the protein or fragment thereof from the insect host into the culture medium. The signal peptide may be native to the protein or fragment thereof of the invention or may be obtained from foreign sources. The 5' end of the coding sequence of the nucleic acid sequence of the present invention may inherently contain a signal peptide coding region naturally linked in translation reading frame with the segment of the coding region which encodes the secreted protein or fragment thereof.

At present, a mode of achieving secretion of a foreign gene product in insect cells is by way of the foreign gene's native signal peptide. Because the foreign genes are usually from non-insect organisms, their signal sequences may be poorly recognized by insect cells and hence, levels of expression may be suboptimal. However, the efficiency of expression of foreign gene products seems to depend primarily on the characteristics of the foreign protein. On average, nuclear localized or non-structural proteins are most highly expressed, secreted proteins are intermediate and integral membrane proteins are the least expressed. One factor generally affecting the efficiency of the production of foreign gene products in a heterologous host system is the presence of native signal sequences (also termed presequences, targeting signals, or leader sequences) associated with the foreign gene. The signal sequence is generally coded by a DNA sequence immediately following (5' to 3') the translation start site of the desired foreign gene.

The expression dependence on the type of signal sequence associated with a gene product can be represented by the following example: If a foreign gene is inserted at a site downstream from the translational start site of the baculovirus polyhedrin gene so as to produce a fusion protein (containing the N-terminus of the polyhedrin structural gene), the fused gene is highly expressed. But less expression is achieved when a foreign gene is inserted in a baculovirus expression vector immediately following the transcriptional start site and totally replacing the polyhedrin structural gene.

Insertions into the region −50 to −1 significantly alter (reduce) steady state transcription which, in turn, reduces translation of the foreign gene product. Use of the pVL941 vector optimizes transcription of foreign genes to the level of the polyhedrin gene transcription. Even though the transcription of a foreign gene may be optimal, optimal translation may vary because of several factors involving processing: signal peptide recognition, mRNA and ribosome binding, glycosylation, disulfide bond formation, sugar processing, oligomerization, for example.

The properties of the insect signal peptide are expected to be more optimal for the efficiency of the translation process in insect cells than those from vertebrate proteins. This phenomenon can generally be explained by the fact that proteins secreted from cells are synthesized as precursor molecules containing hydrophobic N-terminal signal peptides. The signal peptides direct transport of the select protein to its target membrane and are then cleaved by a peptidase on the membrane, such as the endoplasmic reticulum, when the protein passes through it.

Another exemplary insect signal sequence is the sequence encoding for *Drosophila* cuticle proteins such as CP1, CP2, CP3 or CP4 (Summers, U.S. Pat. No. 5,278,050; the entirety of which is herein incorporated by reference). Most of a 9 kb region of the *Drosophila* genome containing genes for the cuticle proteins has been sequenced. Four of the five cuticle genes contains a signal peptide coding sequence interrupted by a short intervening sequence (about 60 base pairs) at a conserved site. Conserved sequences occur in the 5' mRNA untranslated region, in the adjacent 35 base pairs of upstream flanking sequence and at −200 base pairs from the mRNA start position in each of the cuticle genes.

Standard methods of insect cell culture, cotransfection and preparation of plasmids are set forth in Summers and Smith (Summers and Smith, *A Manual of Methods for Baculovirus Vectors and Insect Cell Culture Procedures*, Texas Agricultural Experiment Station Bulletin No. 1555, Texas A&M University (1987)). Procedures for the cultivation of viruses and cells are described in Volkman and Summers, *J. Virol* 19:820-832 (1975) and Volkman et al., *J. Virol* 19:820-832 (1976); both of which are herein incorporated by reference in their entirety.

(e) Bacterial Constructs and Transformed Bacterial Cells

The present invention also relates to a bacterial recombinant vector comprising exogenous genetic material. The present invention also relates to a bacteria cell comprising a bacterial recombinant vector. The present invention also relates to methods for obtaining a recombinant bacteria host cell, comprising introducing into a bacterial host cell exogenous genetic material. In a preferred embodiment the exogenous genetic material includes a nucleic acid molecule of the present invention having a sequence selected from the group consisting of SEQ ID NO: 1 through SEQ ID NO: 627 or complements thereof or fragments of either or other nucleic acid molecule of the present invention.

The bacterial recombinant vector may be any vector which can be conveniently subjected to recombinant DNA procedures. The choice of a vector will typically depend on the compatibility of the vector with the bacterial host cell into which the vector is to be introduced. The vector may be a linear or a closed circular plasmid. The vector system may be a single vector or plasmid or two or more vectors or plasmids which together contain the total DNA to be introduced into the genome of the bacterial host. In addition, the bacterial vector may be an expression vector. Nucleic acid molecules encoding protein homologues or fragments thereof can, for example, be suitably inserted into a replicable vector for expression in the bacterium under the control of a suitable promoter for bacteria. Many vectors are available for this purpose and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: a signal sequence, an origin of replication, one or more marker genes and an inducible promoter.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene* 2:95 (1977); the entirety of which is herein incorporated by reference). pBR322 contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes.

Nucleic acid molecules encoding protein or fragments thereof may be expressed not only directly, but also as a fusion with another polypeptide, preferably a signal sequence or other polypeptide having a specific cleavage site at the N-terminus of the mature polypeptide. In general, the signal sequence may be a component of the vector, or it may be a part of the polypeptide DNA that is inserted into the vector. The heterologous signal sequence selected should be one that is recognized and processed (i.e., cleaved by a signal peptidase) by the host cell. For bacterial host cells that do not recognize and process the native polypeptide signal sequence, the signal sequence is substituted by a bacterial signal sequence selected, for example, from the group consisting of the alkaline phosphatase, penicillinase, lpp, or heat-stable enterotoxin II leaders.

Both expression and cloning vectors contain a nucleic acid sequence that enables the vector to replicate in one or more selected host cells. Generally, in cloning vectors this sequence is one that enables the vector to replicate independently of the host chromosomal DNA and includes origins of replication or autonomously replicating sequences. Such sequences are well known for a variety of bacteria. The origin of replication from the plasmid pBR322 is suitable for most Gram-negative bacteria.

Expression and cloning vectors also generally contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous protein homologue or fragment thereof produce a protein conferring drug resistance and thus survive the selection regimen.

The expression vector for producing a protein or fragment thereof can also contains an inducible promoter that is recognized by the host bacterial organism and is operably linked to the nucleic acid encoding, for example, the nucleic acid molecule encoding the protein homologue or fragment thereof of interest. Inducible promoters suitable for use with bacterial hosts include the β-lactamase and lactose promoter systems (Chang et al., *Nature* 275:615 (1978); Goeddel et al., *Nature* 281:544 (1979); both of which are herein incorporated by reference in their entirety), the arabinose promoter system (Guzman et al., *J. Bacteriol.* 174:7716-7728 (1992); the entirety of which is herein incorporated by reference), alkaline phosphatase, a tryptophan (trp) promoter system (Goeddel, *Nucleic Acids Res.* 8:4057 (1980); EP 36,776; both of which are herein incorporated by reference in their entirety) and hybrid promoters such as the tac promoter (deBoer et al., *Proc. Natl. Acad. Sci.* (*U.S.A.*) 80:21-25 (1983); the entirety of which is herein incorporated by reference). However, other known bacterial inducible promoters are suitable (Siebenlist et al., *Cell* 20:269 (1980); the entirety of which is herein incorporated by reference).

Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA.

Construction of suitable vectors containing one or more of the above-listed components employs standard ligation techniques. Isolated plasmids or DNA fragments are cleaved, tailored and re-ligated in the form desired to generate the plasmids required. Examples of available bacterial expression vectors include, but are not limited to, the multifunctional *E. coli* cloning and expression vectors such as Bluescript™ (Stratagene, La Jolla, Calif.), in which, for example, encoding an *A. nidulans* protein homologue or fragment thereof homologue, may be ligated into the vector in frame with sequences for the amino-terminal Met and the subsequent 7 residues of β-galactosidase so that a hybrid protein is produced; pIN vectors (Van Heeke and Schuster, *J. Biol. Chem.* 264:5503-5509 (1989), the entirety of which is herein incorporated by reference); and the like. pGEX vectors (Promega, Madison Wis. U.S.A.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

Suitable host bacteria for a bacterial vector include archaebacteria and eubacteria, especially eubacteria and most preferably Enterobacteriaceae. Examples of useful bacteria include *Escherichia, Enterobacter, Azotobacter, Erwinia, Bacillus, Pseudomonas, Klebsiella, Proteus, Salmonella, Serratia, Shigella, Rhizobia, Vitreoscilla* and *Paracoccus*. Suitable *E. coli* hosts include *E. coli* W3110 (American Type Culture Collection (ATCC) 27,325, Manassas, Va. U.S.A.), *E. coli* 294 (ATCC 31,446), *E. coli* B and *E. coli* X1776 (ATCC 31,537). These examples are illustrative rather than limiting. Mutant cells of any of the above-mentioned bacteria may also be employed. It is, of course, necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon. *E. coli* strain W3110 is a preferred host or parent host because it is a common host strain for recombinant DNA product fermentations. Preferably, the host cell should secrete minimal amounts of proteolytic enzymes.

Host cells are transfected and preferably transformed with the above-described vectors and cultured in conventional nutrient media modified as appropriate for inducing promoters, selecting transformants, or amplifying the genes encoding the desired sequences.

Numerous methods of transfection are known to the ordinarily skilled artisan, for example, calcium phosphate and electroporation. Depending on the host cell used, transformation is done using standard techniques appropriate to such cells. The calcium treatment employing calcium chloride, as described in section 1.82 of Sambrook et al., *Molecular Cloning: A Laboratory Manual*, New York: Cold Spring Harbor Laboratory Press, (1989), is generally used for bacterial cells that contain substantial cell-wall barriers. Another method for transformation employs polyethylene glycol/DMSO, as described in Chung and Miller (Chung and Miller, *Nucleic Acids Res.* 16:3580 (1988); the entirety of which is herein incorporated by reference). Yet another method is the use of the technique termed electroporation.

Bacterial cells used to produce the polypeptide of interest for purposes of this invention are cultured in suitable media in which the promoters for the nucleic acid encoding the heterologous polypeptide can be artificially induced as described generally, e.g., in Sambrook et al., *Molecular Cloning: A Laboratory Manual*, New York: Cold Spring Harbor Laboratory Press, (1989). Examples of suitable media are given in U.S. Pat. Nos. 5,304,472 and 5,342,763; both of which are incorporated by reference in their entirety.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., *Molecular Cloning: A Laboratory Manual*, Cold Spring Harbor Press (1989); Mailga et al., *Methods in Plant Molecular Biology*, Cold Spring Harbor Press (1995), the entirety of which is herein incorporated by reference; Birren et al., *Genome Analysis: Analyzing DNA,* 1, Cold Spring Harbor, N.Y., the entirety of which is herein incorporated by reference).

(f) Computer Readable Media

The nucleotide sequence provided in SEQ ID NO: 1 through SEQ ID NO: 627 or fragment thereof, or complement thereof, or a nucleotide sequence at least 90% identical, preferably 95%, identical even more preferably 99% or 100% identical to the sequence provided in SEQ ID NO: 1 through SEQ ID NO: 627 or fragment thereof, or complement thereof, can be "provided" in a variety of mediums to facilitate use. Such a medium can also provide a subset thereof in a form that allows a skilled artisan to examine the sequences.

A preferred subset of nucleotide sequences are those nucleic acid sequences that encode a first nucleic acid molecule selected from the group consisting of a nucleic acid molecule that encodes a maize or soybean copalyl diphosphate synthase enzyme or complement thereof or fragment of either, a nucleic acid molecule that encodes a maize or soybean deoxyarabiono-heptulosonate-P-synthase enzyme or complement thereof or fragment of either; a nucleic acid molecule that encodes a maize or soybean putative deoxyarabiono-heptulosonate-P-synthase enzyme or complement thereof or fragment of either; a nucleic acid molecule that encodes a maize dehydroquinate synthase enzyme or complement thereof or fragment of either; a nucleic acid molecule that encodes a soybean dehydroquinate dehydratase enzyme or complement thereof or fragment of either; a nucleic acid molecule that encodes a maize putative dehydroquinate dehydratase enzyme or complement thereof or fragment of either; a nucleic acid molecule that encodes a maize or soybean shikimate dehydrogenase enzyme or complement thereof or fragment of either; a nucleic acid molecule that encodes a maize or soybean shikimate kinase enzyme or complement thereof or fragment of either; a nucleic acid molecule that encodes a maize enolpyruvylshikimate-P-synthase enzyme or complement thereof or fragment of either; a nucleic acid molecule that encodes a maize or soybean chorismate synthase enzyme or complement thereof or fragment of either; a nucleic acid molecule that encodes a maize or soybean chorismate mutase enzyme or complement thereof or fragment of either; a nucleic acid molecule that encodes a maize tyrosine transaminase enzyme or complement thereof or fragment of either; a nucleic acid molecule that encodes a maize or soybean putative tyrosine transaminase enzyme or complement thereof or fragment of either; a nucleic acid molecule that encodes a maize or soybean transaminase A enzyme or complement thereof or fragment of either; a nucleic acid molecule that encodes a soybean putative transaminase A enzyme or complement thereof or fragment of either; a nucleic acid molecule that encodes a maize or soybean 4-hydroxyphenylpyruvate dioxygenase enzyme or complement thereof or fragment of either; a nucleic acid molecule that encodes a maize or soybean homogentisic acid dioxygenase enzyme or complement thereof or fragment of either; and a nucleic acid molecule that encodes a maize or soybean geranylgeranylpyrophosphate synthase enzyme or complement thereof or fragment of either.

A further preferred subset of nucleic acid sequences is where the subset of sequences which encode two proteins or fragments thereof, more preferably three proteins or fragments thereof, more preferable four proteins or fragments thereof, more preferably four proteins or fragments thereof, more preferably five proteins or fragments thereof, more preferably six proteins or fragments thereof, more preferably seven proteins or fragments thereof, more preferably eight proteins or fragments thereof, more preferably nine proteins or fragments thereof, more preferably ten proteins or fragments thereof, more preferably eleven proteins or fragments thereof, more preferably twelve proteins or fragments thereof, more preferably thirteen proteins or fragments thereof, more preferably fourteen proteins or fragments thereof, more preferably fifteen proteins or fragments thereof, more preferably sixteen proteins or fragments thereof, and even more preferably seventeen proteins or fragments thereof. These nucleic acid sequences are selected from the group that encodes a maize or soybean copalyl diphosphate synthase enzyme or complement thereof or fragment of either, a nucleic acid molecule that encodes a maize or soybean deoxyarabiono-heptulosonate-P-synthase enzyme or complement thereof or fragment of either; a nucleic acid molecule that encodes a maize or soybean putative deoxyarabiono-heptulosonate-P-synthase enzyme or complement thereof or fragment of either; a nucleic acid molecule that encodes a maize dehydroquinate synthase enzyme or complement thereof or fragment of either; a nucleic acid molecule that encodes a soybean dehydroquinate dehydratase enzyme or complement thereof or fragment of either; a nucleic acid molecule that encodes a maize putative dehydroquinate dehydratase enzyme or complement thereof or fragment of either; a nucleic acid molecule that encodes a maize or soybean shikimate dehydrogenase enzyme or complement thereof or fragment of either; a nucleic acid molecule that encodes a maize or soybean shikimate kinase enzyme or complement thereof or fragment of either; a nucleic acid molecule that encodes a maize enolpyruvylshikimate-P-synthase enzyme or complement thereof or fragment of either; a nucleic acid molecule that encodes a maize or soybean chorismate synthase enzyme or complement thereof or fragment of either; a nucleic acid molecule that encodes a maize or soybean chorismate mutase enzyme or complement thereof or fragment of either; a nucleic acid molecule that encodes a maize tyrosine transaminase enzyme or complement thereof or fragment of either; a nucleic acid molecule that encodes a maize or soybean putative tyrosine transaminase enzyme or complement thereof or fragment of either; a nucleic acid molecule that encodes a maize or soybean transaminase A enzyme or complement thereof or fragment of either; a nucleic acid molecule that encodes a soybean putative transaminase A enzyme or complement thereof or fragment of either; a nucleic acid molecule that encodes a maize or soybean 4-hydroxyphenylpyruvate dioxygenase enzyme or complement thereof or fragment of either; a nucleic acid molecule that encodes a maize or soybean homogentisic acid dioxygenase enzyme or complement thereof or fragment of either; and a nucleic acid molecule that encodes a maize or soybean geranylgeranylpyrophosphate synthase enzyme or complement thereof or fragment of either.

In one application of this embodiment, a nucleotide sequence of the present invention can be recorded on computer readable media. As used herein, "computer readable media" refers to any medium that can be read and accessed directly by a computer. Such media include, but are not limited to: magnetic storage media, such as floppy discs, hard disc, storage medium and magnetic tape: optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention.

As used herein, "recorded" refers to a process for storing information on computer readable medium. A skilled artisan can readily adopt any of the presently known methods for recording information on computer readable medium to generate media comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of data processor structuring formats (e.g. text file or database) in order to obtain computer readable medium having recorded thereon the nucleotide sequence information of the present invention.

By providing one or more of nucleotide sequences of the present invention, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., *J. Mol. Biol.* 215:403-410 (1990), the entirety of which is herein incorporated by reference) and BLAZE (Brutlag et al., *Comp. Chem.* 17:203-207 (1993), the entirety of which is herein incorporated by reference) search algorithms on a Sybase system can be used to identify open reading frames (ORFs) within the genome that contain homology to ORFs or proteins from other organisms. Such ORFs are protein-encoding fragments within the sequences of the present invention and are useful in producing commercially important proteins such as enzymes used in amino acid biosynthesis, metabolism, transcription, translation, RNA processing, nucleic acid and a protein degradation, protein modification and DNA replication, restriction, modification, recombination and repair.

The present invention further provides systems, particularly computer-based systems, which contain the sequence information described herein. Such systems are designed to identify commercially important fragments of the nucleic acid molecule of the present invention. As used herein, "a computer-based system" refers to the hardware means, software means and data storage means used to analyze the nucleotide sequence information of the present invention. The minimum hardware means of the computer-based systems of the present invention comprises a central processing unit (CPU), input means, output means and data storage means. A skilled artisan can readily appreciate that any one of the currently available computer-based system are suitable for use in the present invention.

As indicated above, the computer-based systems of the present invention comprise a data storage means having stored therein a nucleotide sequence of the present invention and the necessary hardware means and software means for supporting and implementing a search means. As used herein, "data storage means" refers to memory that can store nucleotide sequence information of the present invention, or a memory access means which can access manufactures having recorded thereon the nucleotide sequence information of the present invention. As used herein, "search means" refers to one or more programs which are implemented on the computer-based system to compare a target sequence or target structural motif with the sequence information stored within the data storage means. Search means are used to identify fragments or regions of the sequence of the present invention that match a particular target sequence or target motif. A variety of known algorithms are disclosed publicly and a variety of commercially available software for conducting search means are available can be used in the computer-based systems of the present invention. Examples of such software include, but are not limited to, MacPattern (EMBL), BLASTIN and BLASTIX (NCBIA). One of the available algorithms or implementing software packages for conducting homology searches can be adapted for use in the present computer-based systems.

The most preferred sequence length of a target sequence is from about 10 to 100 amino acids or from about 30 to 300 nucleotide residues. However, it is well recognized that during searches for commercially important fragments of the nucleic acid molecules of the present invention, such as sequence fragments involved in gene expression and protein processing, may be of shorter length.

As used herein, "a target structural motif," or "target motif," refers to any rationally selected sequence or combination of sequences in which the sequences the sequence(s) are chosen based on a three-dimensional configuration which is formed upon the folding of the target motif. There are a variety of target motifs known in the art. Protein target motifs include, but are not limited to, enzymatic active sites and signal sequences. Nucleic acid target motifs include, but are not limited to, promoter sequences, cis elements, hairpin structures and inducible expression elements (protein binding sequences).

Thus, the present invention further provides an input means for receiving a target sequence, a data storage means for storing the target sequences of the present invention sequence identified using a search means as described above and an output means for outputting the identified homologous sequences. A variety of structural formats for the input and output means can be used to input and output information in the computer-based systems of the present invention. A preferred format for an output means ranks fragments of the sequence of the present invention by varying degrees of homology to the target sequence or target motif. Such presentation provides a skilled artisan with a ranking of sequences which contain various amounts of the target sequence or target motif and identifies the degree of homology contained in the identified fragment.

A variety of comparing means can be used to compare a target sequence or target motif with the data storage means to identify sequence fragments sequence of the present invention. For example, implementing software which implement the BLAST and BLAZE algorithms (Altschul et al., *J. Mol. Biol.* 215:403-410 (1990)) can be used to identify open frames within the nucleic acid molecules of the present invention. A skilled artisan can readily recognize that any one of the publicly available homology search programs can be used as the search means for the computer-based systems of the present invention.

Having now generally described the invention, the same will be more readily understood through reference to the following examples which are provided by way of illustration and are not intended to be limiting of the present invention, unless specified.

EXAMPLE 1

The MONN01 cDNA library is a normalized library generated from maize (DK604, Dekalb Genetics, Dekalb, Ill. U.S.A.) total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The older, more juvenile leaves, which are in a basal position, as well as the younger, more adult leaves, which are more apical are cut at the base of the leaves. The leaves are then pooled and immediately transferred to liquid nitrogen containers in which the pooled leaves are crushed. The harvested tissue is then stored at −80° C. until RNA preparation. The RNA is purified from the stored tissue and the cDNA library is constructed as described in Example 2.

The SATMON001 cDNA library is generated from maize (B73, Illinois Foundation Seeds, Champaign, Ill. U.S.A.) immature tassels at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue from the maize plant is collected at the V6 stage. At that stage the tassel is an immature tassel of about 2-3 cm in length. The tassels are removed and frozen in liquid nitrogen. The harvested tissue is then stored at −80° C. until RNA preparation. The RNA is purified from the stored tissue and the cDNA library is constructed as described in Example 2.

The SATMON003 library is generated from maize (B73xMo17, Illinois Foundation Seeds, Champaign, Ill. U.S.A.) roots at the V6 developmental stage. Seeds are planted at a depth of approximately 3 cm in coil into 2-3 inch peat pots containing Metro 200 growing medium. After 2-3 weeks growth, the seedlings are transplanted into 10 inch pots containing the Metro 200 growing medium. Plants are watered daily before transplantation and approximately 3 times a week after transplantation. Peters 15-16-17 fertilizer is applied approximately three times per week after transplanting at a concentration of 150 ppm N. Two to three times during the life time of the plant from transplanting to flowering a total of approximately 900 mg Fe is added to each pot. Maize plants are grown in the green house in approximately 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6 leaf development stage. The root system is cut from maize plant and washed with water to free it from the soil. The tissue is then immediately frozen in liquid nitrogen. The harvested tissue is then stored at −80° C. until RNA preparation. The RNA is purified from the stored tissue and the cDNA library is constructed as described in Example 2.

The SATMON004 cDNA library is generated from maize (B73xMo17, Illinois Foundation Seeds, Champaign, Ill. U.S.A.) total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The older, more juvenile leaves, which are in a basal position, as well as the younger, more adult leaves, which are more apical are cut at the base of the leaves. The leaves are then pooled and immediately transferred to liquid nitrogen containers in which the pooled leaves are crushed. The harvested tissue is then stored at −80° C. until RNA preparation. The RNA is purified from the stored tissue and the cDNA library is constructed as described in Example 2.

The SATMON005 cDNA library is generated from maize (B73xMo17, Illinois Foundation Seeds, Champaign Ill., U.S.A.) root tissue at the V6 development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The root system is cut from the mature maize plant and washed with water to free it from the soil. The tissue is immediately frozen in liquid nitrogen and the harvested tissue is then stored at −80° C. until RNA preparation. The RNA is purified from the stored tissue and the cDNA library is constructed as described in Example 2.

The SATMON006 cDNA library is generated from maize (B73xMo17, Illinois Foundation Seeds, Champaign Ill., U.S.A.) total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The older more juvenile leaves, which are in a basal position, as well as the younger more adult leaves, which are more apical are cut at the base of the leaves. The leaves are then pooled and immediately transferred to liquid nitrogen containers in which the pooled leaves are crushed. The harvested tissue is then stored at −80° C. until RNA preparation. The RNA is purified from the stored tissue and the cDNA library is constructed as described in Example 2.

The SATMON007 cDNA library is generated from the primary root tissue of 5 day old maize (DK604, Dekalb Genetics, Dekalb, Ill. U.S.A.) seedlings. Seeds are planted on a moist filter paper on a covered tray that is kept in the dark until germination (one day). After germination, the trays, along with the moist paper, are moved to a greenhouse where the maize plants are grown in the greenhouse in 15 hr day/9 hr night cycles for approximately 5 days. The daytime temperature is approximately 80° F. and the nighttime temperature is approximately 70° F. Supplemental lighting is provided by 1000 W sodium vapor lamps. The primary root tissue is collected when the seedlings are 5 days old. At this stage, the primary root (radicle) is pushed through the coleorhiza which itself is pushed through the seed coat. The primary root, which is about 2-3 cm long, is cut and immediately frozen in liquid nitrogen and then stored at −80° C. until RNA preparation. The RNA is purified from the stored tissue and the cDNA library is constructed as described in Example 2.

The SATMON008 cDNA library is generated from the primary shoot (coleoptile 2-3 cm) of maize (DK604, Dekalb Genetics, Dekalb, Ill. U.S.A.) seedlings which are approximately 5 days old. Seeds are planted on a moist filter paper on a covered tray that is kept in the dark until germination (one day). Then the trays containing the seeds are moved to a greenhouse at 15 hr daytime/9 hr nighttime cycles and grown until they are 5 days post germination. The daytime temperature is approximately 80° F. and the nighttime temperature is approximately 70° F. Tissue is collected when the seedlings are 5 days old. At this stage, the primary shoot (coleoptile) is pushed through the seed coat and is about 2-3 cm long. The coleoptile is dissected away from the rest of the seedling, immediately frozen in liquid nitrogen and then stored at −80° C. until RNA preparation. The RNA is purified from the stored tissue and the cDNA library is constructed as described in Example 2.

The SATMON009 cDNA library is generated from maize (DK604, Dekalb Genetics, Dekalb, Ill. U.S.A.) leaves at the 8 leaf stage (V8 plant development stage). Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is 80° F. and the nighttime temperature is 70° F. Supplemental lighting is provided by 1000 W sodium vapor lamps. Tissue is collected when the maize plant is at the 8-leaf development stage. The older more juvenile leaves, which are in a basal position, as well as the younger more adult leaves, which are more apical, are cut at the base of the leaves. The leaves are then pooled and then immediately transferred to liquid nitrogen containers in which the pooled leaves are crushed. The harvested tissue is then stored at −80° C. until RNA preparation. The RNA is purified from the stored tissue and the cDNA library is constructed as described in Example 2.

The SATMON010 cDNA library is generated from maize (DK604, Dekalb Genetics, Dekalb, Ill. U.S.A.) root tissue at the V8 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is 80° F. and the nighttime temperature is 70° F. Supplemental lighting is provided by 1000 W sodium vapor lamps. Tissue is collected when the maize plant is at the V8 development stage. The root system is cut from this mature maize plant and washed with water to free it from the soil. The tissue is immediately frozen in liquid nitrogen. The harvested tissue is then stored at −80° C. until RNA preparation. The RNA is purified from the stored tissue and the cDNA library is constructed as described in Example 2.

The SATMON011 cDNA library is generated from undeveloped maize (DK604, Dekalb Genetics, Dekalb, Ill. U.S.A.) leaf at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The second youngest leaf which is at the base of the apical leaf of V6 stage maize plant is cut at the base and immediately transferred to liquid nitrogen containers in which the leaf is crushed. The harvested tissue is then stored at −80° C. until RNA preparation. The RNA is purified from the stored tissue and the cDNA library is constructed as described in Example 2.

The SATMON012 cDNA library is generated from 2 day post germination maize (DK604, Dekalb Genetics, Dekalb, Ill. U.S.A.) seedlings. Seeds are planted on a moist filter paper on a covered tray that is kept in the dark until germination (one day). Then the trays containing the seeds are moved to the greenhouse and grown at 15 hr daytime/9 hr nighttime cycles until 2 days post germination. The daytime temperature is approximately 80° F. and the nighttime temperature is approximately 70° F. Tissue is collected when the seedlings are 2 days old. At the two day stage, the coleorhiza is pushed through the seed coat and the primary root (the radicle) is pierced the coleorhiza but is barely visible. Also, at this two day stage, the coleoptile is just emerging from the seed coat. The 2 days post germination seedlings are then immersed in liquid nitrogen and crushed. The harvested tissue is stored at −80° C. until preparation of total RNA. The RNA is purified from the stored tissue and the cDNA library is constructed as described in Example 2.

The SATMON013 cDNA library is generated from apical maize (DK604, Dekalb Genetics, Dekalb, Ill. U.S.A.) meristem founder at the V4 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Prior to tissue collection, the plant is at the 4 leaf stage. The lead at the apex of the V4 stage maize plant is referred to as the meristem founder. This apical meristem founder is cut, immediately frozen in liquid nitrogen and crushed. The harvested tissue is then stored at −80° C. until RNA preparation. The RNA is purified from the stored tissue and the cDNA library is constructed as described in Example 2.

The SATMON014 cDNA library is generated from maize (DK604, Dekalb Genetics, Dekalb, Ill. U.S.A.) endosperm fourteen days after pollination. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. After the V10 stage, the maize plant ear shoots are ready for fertilization. At this stage, the ear shoots are enclosed in a paper bag before silk emergence to withhold the pollen. The ear shoots are pollinated and 14 days after pollination, the ears are pulled out and then the kernels are plucked out of the ears. Each kernel is then dissected into the embryo and the endosperm and the aleurone layer is removed. After dissection, the endosperms are immediately frozen in liquid nitrogen and then stored at −80° C. until RNA preparation. The RNA is purified from the stored tissue and the cDNA library is constructed as described in Example 2.

The SATMON016 library is a maize (DK604, Dekalb Genetics, Dekalb, Ill. U.S.A.) sheath library collected at the V8 developmental stage. Seeds are planted in a depth of approximately 3 cm in solid into 2-3 inch pots containing Metro growing medium. After 2-3 weeks growth, they are transplanted into 10" pots containing the same. Plants are watered daily before transplantation and approximately the times a week after transplantation. Peters 15-16-17 fertilizer is applied approximately three times per week after transplanting, at a strength of 150 ppm N. Two to three times during the life time of the plant from transplanting to flowering, a total of approximately 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. When the maize plants are at the V8 stage the $5^{th}$ and $6^{th}$ leaves from the bottom exhibit fully developed leaf blades. At the base of these leaves, the ligule is differentiated and the leaf blade is joined to the sheath. The sheath is dissected away from the base of the leaf then the sheath is frozen in liquid nitrogen and crushed. The tissue is then stored at −80° C. until RNA preparation. The RNA is purified from the stored tissue and the cDNA library is constructed as described in Example 2.

The SATMON017 cDNA library is generated from maize (DK604, Dekalb Genetics, Dekalb, Ill. U.S.A.) embryo seventeen days after pollination. Seeds are planted at a depth of approximately 3 cm into 2-3 inch peat pots containing Metro 200 growing medium. After 2-3 weeks growth the seeds are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. After the V10 stage, the ear shoots of maize plant, which are ready for fertilization, are enclosed in a paper bag before silk emergence to withhold the pollen. The ear shoots are fertilized and 21 days after pollination, the ears are pulled out and the kernels are plucked out of the ears. Each kernel is then dissected into the embryo and the endosperm and the aleurone layer is removed. After dissection, the embryos are immediately frozen in liquid nitrogen and then stored at −80° C. until RNA preparation. The RNA is purified from the stored tissue and the cDNA library is constructed as described in Example 2.

The SATMON019 (Lib3054) cDNA library is generated from maize (DK604, Dekalb Genetics, Dekalb, Ill. U.S.A.) culm (stem) at the V8 developmental stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. When the maize plant is at the V8 stage, the 5th and 6th leaves from the bottom have fully developed leaf blades. The region between the nodes of the 5th and the sixth leaves from the bottom is the region of the stem that is collected. The leaves are pulled out and the sheath is also torn away from the stem. This stem tissue is completely free of any leaf and sheath tissue. The stem tissue is then frozen in liquid nitrogen and stored at −80° C. until RNA preparation. The RNA is purified from the stored tissue and the cDNA library is constructed as described in Example 2.

The SATMON020 cDNA library is from a maize (DK604, Dekalb Genetics, Dekalb, Ill. U.S.A.) Hill Type II-Initiated Callus. Petri plates containing approximately 25 ml of Type II initiation media are prepared. This medium contains N6 salts and vitamins, 3% sucrose, 2.3 g/liter proline 0.1 g/liter enzymatic casein hydrolysate, 2 mg/liter 2,4-dichloro phenoxyacetic acid (2,4, D), 15.3 mg/liter $AgNO_3$ and 0.8% bacto agar and is adjusted to pH 6.0 before autoclaving. At 9-11 days after pollination, an ear with immature embryos measuring approximately 1-2 mm in length is chosen. The husks and silks are removed and then the ear is broken into halves and placed in an autoclaved solution of Clorox/TWEEN 20 sterilizing solution. Then the ear is rinsed with deionized water. Then each embryo is extracted from the kernel. Intact embryos are placed in contact with the medium, scutellar side up). Multiple embryos are plated on each plate and the plates are incubated in the dark at 25° C. Type II calluses are friable, can be subcultured with a spatula, frequently regenerate via somatic embryogenesis and are relatively undifferentiated. As seen in the microscope, the Tape II calluses show color ranging from translucent to light yellow and heterogeneity on with respect to embryoid structure as well as stage of embryoid development. Once Type II callus are formed, the calluses is transferred to type II callus maintenance medium without $AgNO_3$. Every 7-10 days, the callus is subcultured. About 4 weeks after embryo isolation the callus is removed from the plates and then frozen in liquid nitrogen. The harvested tissue is stored at −80° C. until RNA preparation. The RNA is purified from the stored tissue and the cDNA library is constructed as described in Example 2.

The SATMON021 cDNA library is generated from the immature maize (DK604, Dekalb Genetics, Dekalb Ill., U.S.A.) tassel at the V8 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. As the maize plant enters the V8 stage, tassels which are 15-20 cm in length are collected and frozen in liquid nitrogen. The harvested tissue is stored at −80° C. until RNA preparation. The RNA is purified from the stored tissue and the cDNA library is constructed as described in Example 2.

The SATMON022 cDNA library is generated from maize (DK604, Dekalb Genetics, Dekalb, Ill. U.S.A.) ear (growing silks) at the V8 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the plant is in the V8 stage. At this stage, some immature ear shoots are visible. The immature ear shoots (approximately 1 cm in length) are pulled out, frozen in liquid nitrogen and then stored at −80° C. until RNA preparation. The RNA is purified from the stored tissue and the cDNA library is constructed as described in Example 2.

The SATMON23 cDNA library is generated from maize (DK604, Dekalb Genetics, Dekalb, Ill. U.S.A.) ear (growing silk) at the V8 development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. When the tissue is harvested at the V8 stage, the length of the ear that is harvested is about 10-15 cm and the silks are just exposed (approximately 1 inch). The ear along with the silks is frozen in liquid nitrogen and then the tissue is stored at −80° C. until RNA preparation. The RNA is purified from the stored tissue and the cDNA library is constructed as described in Example 2.

The SATMON024 cDNA library is generated from the immature maize (DK604, Dekalb Genetics, Dekalb, Ill. U.S.A.) tassel at the V9 development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. As a maize plant enters the V9 stage, the tassel is rapidly developing and a 37 cm tassel along with the glume, anthers and pollen is collected and frozen in liquid nitrogen. The harvested tissue is stored at −80° C. until RNA preparation. The RNA is purified from the stored tissue and the cDNA library is constructed as described in Example 2.

The SATMON025 cDNA library is from maize (DK604, Dekalb Genetics, Dekalb, Ill. U.S.A.) Hill Type II-Regenerated Callus. Type II callus is grown in initiation media as described for SATMON020 and then the embryoids on the surface of the Type II callus are allowed to mature and germinate. The 1-2 gm fresh weight of the soft friable type callus containing numerous embryoids are transferred to 100×15 mm petri plates containing 25 ml of regeneration media. Regeneration media consists of Murashige and Skoog (MS) basal salts, modified White's vitamins (0.2 g/liter glycine and 0.5 g/liter myo-inositoland 0.8% bacto agar (6SMS0D)). The plates are then placed in the dark after covering with parafilm. After 1 week, the plates are moved to a lighted growth chamber with 16 hr light and 8 hr dark photoperiod. Three weeks after plating the Type II callus to 6SMS0D, the callus exhibit shoot formation. The callus and the shoots are transferred to fresh 6SMS0D plates for another 2 weeks. The callus and the shoots are then transferred to petri plates with reduced sucrose (3SMS0D). Upon distinct formation of a root and shoot, the newly developed green plants are then removed out with a spatula and frozen in liquid nitrogen containers. The harvested tissue is then stored at −80° C. until RNA preparation. The RNA is purified from the stored tissue and the cDNA library is constructed as described in Example 2.

The SATMON026 cDNA library is generated from maize (DK604, Dekalb Genetics, Dekalb, Ill. U.S.A.) juvenile/adult shift leaves at the V8 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plants are at the 8-leaf development stage. Leaves are founded sequentially around the meristem over weeks of time and the older, more juvenile leaves arise earlier and in a more basal position than the younger, more adult leaves, which are in a more apical position. In a V8 plant, some leaves which are in the middle portion of the plant exhibit characteristics of both juvenile as well as adult leaves. They exhibit a yellowing color but also exhibit, in part, a green color. These leaves are termed juvenile/adult shift leaves. The juvenile/adult shift leaves (the 4th, 5th leaves from the bottom) are cut at the base, pooled and transferred to liquid nitrogen in which they are then crushed. The harvested tissue is then stored at −80° C. until RNA preparation. The RNA is purified from the stored tissue and the cDNA library is constructed as described in Example 2.

The SATMON027 cDNA library is generated from 6 day maize (DK604, Dekalb Genetics, Dekalb, Ill. U.S.A.) leaves. Seeds are planted at a depth of approximately 3 cm into 2-3 inch peat pots containing Metro 200 growing medium. After 2-3 weeks growth they are transplanted into 10 inch pots containing the Metro 200 growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Prior to tissue collection, when the plant is at the 8-leaf stage, water is held back for six days. The older, more juvenile leaves, which are in a basal position, as well as the younger, more adult leaves, which are more apical, are all cut at the base of the leaves. All the leaves exhibit significant wilting. The leaves are then pooled and immediately transferred to liquid nitrogen containers in which the pooled leaves are then crushed. The harvested tissue is then stored at −80° C. until RNA preparation. The RNA is purified from the stored tissue and the cDNA library is constructed as described in Example 2.

The SATMON028 cDNA library is generated from maize (DK604, Dekalb Genetics, Dekalb, Ill. U.S.A.) roots at the V8 developmental stage that are subject to six days water stress. Seeds are planted at a depth of approximately 3 cm into 2-3 inch peat pots containing Metro 200 growing medium. After 2-3 weeks growth they are transplanted into 10 inch pots containing the Metro 200 growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Prior to tissue collection, when the plant is at the 8-leaf stage, water is held back for six days. The root system is cut, shaken and washed to remove soil. Root tissue is then pooled and immediately transferred to liquid nitrogen containers in which the pooled leaves are then crushed. The harvested tissue is then stored at −80° C. until RNA preparation. The RNA is purified from the stored tissue and the cDNA library is constructed as described in Example 2.

The SATMON029 cDNA library is generated from maize (DK604, Dekalb Genetics, Dekalb, Ill. U.S.A.) seedlings at the etiolated stage. Seeds are planted on a moist filter paper on a covered tray that is kept in the dark for 4 days at approximately 70° F. Tissue is collected when the seedlings are 4 days old. By 4 days, the primary root has penetrated the coleorhiza and is about 4-5 cm and the secondary lateral roots have also made their appearance. The coleoptile has also pushed through the seed coat and is about 4-5 cm long. The seedlings are frozen in liquid nitrogen and crushed. The RNA is purified from the stored tissue and the cDNA library is constructed as described in Example 2.

The SATMON030 cDNA library is generated from maize (DK604, Dekalb Genetics, Dekalb, Ill. U.S.A.) root tissue at the V4 plant development stage. Seeds are planted at a depth of approximately 3 cm into 2-3 inch peat pots containing Metro 200 growing medium. After 2-3 weeks growth, they are transplanted into 10 inch pots containing the same. Plants are watered daily before transplantation and approximately 3 times a week after transplantation. Peters 15-16-17 fertilizer is applied approximately three times per week after transplanting, at a strength of 150 ppm N. Two to three times during the life time of the plant, from transplanting to flowering, a total of approximately 900 mg Fe is added to each pot. Maize plants are grown in the green house in 15 hr day/9 hr night cycles. The daytime temperature is approximately 80°

F. and the nighttime temperature is approximately 70° F. Supplemental lighting is provided by 1000 sodium vapor lamps. Tissue is collected when the maize plant is at the 4 leaf development stage. The root system is cut from the mature maize plant and washed with water to free it from the soil. The tissue is then immediately frozen in liquid nitrogen. The harvested tissue is then stored at −80° C. until RNA preparation. The RNA is purified from the stored tissue and the cDNA library is constructed as described in Example 2.

The SATMON031 cDNA library is generated from the maize (DK604, Dekalb Genetics, Dekalb, Ill. U.S.A.) leaf tissue at the V4 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is 80° F. and the nighttime temperature is 70° F. Supplemental lighting is provided by 1000 W sodium vapor lamps. Tissue is collected when the maize plant is at the 4-leaf development stage. The third leaf from the bottom is cut at the base and immediately frozen in liquid nitrogen and crushed. The tissue is immediately frozen in liquid nitrogen. The harvested tissue is then stored at −80° C. until RNA preparation. The RNA is purified from the stored tissue and the cDNA library is constructed as described in Example 2.

The SATMON033 cDNA library is generated from maize (DK604, Dekalb Genetics, Dekalb, Ill. U.S.A.) embryo tissue 13 days after pollination. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. After the V10 stage, the ear shoots of the maize plant, which are ready for fertilization, are enclosed in a paper bag before silk emergent to withhold the pollen. The ear shoots are pollinated and 13 days after pollination, the ears are pulled out and then the kernels are plucked out of the ears. Each kernel is then dissected into the embryo and the endosperm and the aleurone layer is removed. After dissection, the embryos are immediately frozen in liquid nitrogen and then stored at −80° C. until RNA preparation. The RNA is purified from the stored tissue and the cDNA library is constructed as described in Example 2.

The SATMON034 cDNA library is generated from cold stressed maize (DK604, Dekalb Genetics, Dekalb, Ill. U.S.A.) seedlings. Seeds are planted on a moist filter paper on a covered tray that is kept on at 10° C. for 7 days. After 7 days, the temperature is shifted to 15° C. for one day until germination of the seed. Tissue is collected once the seedlings are 1 day old. At this point, the coleorhiza has just pushed out of the seed coat and the primary root is just making its appearance. The coleoptile has not yet pushed completely through the seed coat and is also just making its appearance. These 1 day old cold stressed seedlings are frozen in liquid nitrogen and crushed. The harvested tissue is then stored at −80° C. until RNA preparation. The RNA is purified from the stored tissue and the cDNA library is constructed as described in Example 2.

The SATMON~001 (Lib36, Lib83, Lib84) cDNA library is generated from maize leaves at the V8 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue from the maize plant is collected at the V8 stage. The older more juvenile leaves in a basal position was well as the younger more adult leaves which are more apical are all cut at the base, pooled and frozen in liquid nitrogen. The harvested tissue is then stored at −80° C. until RNA preparation. The RNA is purified from the stored tissue and the cDNA library is constructed as described in Example 2.

The SATMONN01 cDNA library is generated from maize (B73, Illinois Foundation Seeds, Champaign, Ill. U.S.A.) normalized immature tassels at the V6 plant development stage normalized tissue. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in a greenhouse in 15 hr day/9 hr night cycles. The daytime temperature is approximately 80° F. and the nighttime temperature is approximately 70° F. Supplemental lighting is provided by 1000 W sodium vapor lamps. Tissue from the maize plant is collected at the V6 stage. At that stage the tassel is an immature tassel of about 2-3 cm in length. The tassels are removed and frozen in liquid nitrogen. The harvested tissue is then stored at −80° C. until RNA preparation. The RNA is purified from the stored tissue and the normalized cDNA library is constructed as described in Example 2.

The SATMONN04 cDNA library is generated from maize (B73xMo17, Illinois Foundation Seeds, Champaign, Ill. U.S.A.) normalized total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The older, more juvenile leaves, which are in a basal position, as well as the younger, more adult leaves, which are more apical are cut at the base of the leaves. The leaves are then pooled and immediately transferred to liquid nitrogen containers in which the pooled leaves are crushed. The harvested tissue is then stored at −80° C. until RNA preparation. The RNA is purified from the stored tissue and the normalized cDNA library is constructed as described in Example 2.

The SATMONN05 cDNA library is generated from maize (B73xMo17, Illinois Foundation Seeds, Champaign Ill., U.S.A.) normalized root tissue at the V6 development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The root system is cut from the mature maize plant and washed with water to free it from the soil. The tissue is immediately frozen in liquid nitrogen and the harvested tissue is then stored at −80° C. until RNA preparation. The RNA is purified from the stored tissue and the normalized cDNA library is constructed as described in Example 2.

The SATMONN06 cDNA library is generated from maize (B73xMo17, Illinois Foundation Seeds, Champaign Ill., U.S.A.) normalized total leaf tissue at the V6 plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 6-leaf development stage. The older more juvenile leaves, which are in a basal position, as well as the younger more adult leaves, which are more apical are cut at the base of the leaves. The leaves are then pooled and immediately transferred to liquid nitrogen containers in which the pooled leaves are crushed. The harvested tissue is then stored at −80° C. until RNA preparation. The RNA is purified from the stored tissue and the normalized cDNA library is constructed as described in Example 2.

The CMZ029 (SATMON036) cDNA library is generated from maize (DK604, Dekalb Genetics, Dekalb, Ill. U.S.A.) endosperm 22 days after pollination. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the green house in 15 hr day/9 hr night cycles. The daytime temperature is approximately 80° F. and the nighttime temperature is approximately 70° F. Supplemental lighting is provided by 1000 W sodium vapor lamps. After the V10 stage, the ear shoots of the maize plant, which are ready for fertilization, are enclosed in a paper bag before silk emergent to withhold the pollen. The ear shoots are pollinated and 22 days after pollination, the ears are pulled out and then the kernels are plucked out of the ears. Each kernel is then dissected into the embryo and the endosperm and the alurone layer is removed. After dissection, the endosperms are immediately frozen in liquid nitrogen and then stored at −80° C. until RNA preparation. The RNA is purified from the stored tissue and the cDNA library is constructed as described in Example 2.

The CMz030 (Lib143) cDNA library is generated from maize seedling tissue two days post germination. Seeds are planted on a moist filter paper on a covered try that is keep in the dark until germination. The trays are then moved to the bench top at 15 hr daytime/9 hr nighttime cycles for 2 days post-germination. The day time temperature is 80° F. and the nighttime temperature is 70° F. Tissue is collected when the seedlings are 2 days old. At this stage, the colehrhiza has pushed through the seed coat and the primary root (the radicle) is just piercing the colehrhiza and is barely visible. The seedlings are placed at 42° C. for 1 hour. Following the heat shock treatment, the seedlings are immersed in liquid nitrogen and crushed. The harvested tissue is stored at −80° until RNA preparation. The RNA is purified from the stored tissue and the cDNA library is constructed as described in Example 2.

The CMz031 (Lib148) cDNA library is generated from maize pollen tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants. The ear shoots, which are ready for fertilization, are enclosed in a paper bag to withhold pollen. Twenty-one days after pollination, prior to removing the ears, the paper bag is shaken to collect the mature pollen. The mature pollen is immediately frozen in liquid nitrogen containers and the pollen is crushed. The harvested tissue is then stored at −80° C. until RNA preparation. The RNA is purified from the stored tissue and the cDNA library is constructed as described in Example 2.

The CMz033 (Lib189) cDNA library is generated from maize pooled leaf tissue. Samples are harvested from open pollinated plants. Tissue is collected from maize leaves at the anthesis stage. The leaves are collect from 10-12 plants and frozen in liquid nitrogen. The harvested tissue is then stored at −80° C. until RNA preparation. The RNA is purified from the stored tissue and the cDNA library is constructed as described in Example 2.

The CMz034 (Lib3060) cDNA library is generated from maize mature tissue at 40 days post pollination plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from leaves located two leaves below the ear leaf. This sample represents those genes expressed during onset and early stages of leaf senescence. The leaves are pooled and immediately transferred to liquid nitrogen. The harvested tissue is then stored at −80° C. until RNA preparation. The RNA is purified from the stored tissue and the cDNA library is constructed as described in Example 2.

The CMz035 (Lib3061) cDNA library is generated from maize endosperm tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants. The ear shoots, which are ready for fertilization, are enclosed in a paper bag prior to silk emergence to withhold pollen. Thirty-two days after pollination, the ears are pulled out and the kernels are removed from the cob. Each kernel is dissected into the embryo and the endosperm and the aleurone layer is removed. After dissection, the endosperms are immediately transferred to liquid nitrogen. The harvested tissue is then stored at 80° C. until RNA preparation. The RNA is purified from the stored tissue and the cDNA library is constructed as described in Example 2.

The CMz036 (Lib3062) cDNA library is generated from maize husk tissue at the 8 week old plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from 8 week old plants. The husk is separated from the ear and immediately transferred to liquid nitrogen containers. The harvested tissue is then stored at −80° C. until RNA preparation. The RNA is purified from the stored tissue and the cDNA library is constructed as described in Example 2.

The CMz037 (Lib3059) cDNA library is generated from maize pooled kernal at 12-15 days after pollination plant development stage. Sample were collected from field grown material. Whole kernals from hand pollinated (control pollination) are harvested as whole ears and immediately frozen on dry ice. Kernels from 10-12 ears were pooled and ground together in liquid nitrogen. The harvested tissue is then stored at −80° C. until RNA preparation. The RNA is purified from the stored tissue and the cDNA library is constructed as described in Example 2.

The CMz039 (Lib3066) cDNA library is generated from maize immature anther tissue at the 7 week old immature tassel stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 7 week old immature tassel stage. At this stage, prior to anthesis, the immature anthers are green and enclosed in the staminate spikelet. The developing anthers are dissected away from the 7 week old immature tassel and immediately frozen in liquid nitrogen. The harvested tissue is then stored at −80° C. until RNA preparation. The RNA is purified from the stored tissue and the cDNA library is constructed as described in Example 2.

The CMz040 (Lib3067) cDNA library is generated from maize kernel tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants. The ear shoots, which are ready for fertilization, are enclosed in a paper bag before silk emergence to withhold pollen. Five to eight days after controlled pollination. The ears are pulled and the kernels removed. The kernels are immediately frozen in liquid nitrogen. This sample represents genes expressed in early kernel development, during periods of cell division, amyloplast biogenesis and early carbon flow across the material to filial tissue. The harvested kernels tissue is then stored at −80° C. until RNA preparation. The RNA is purified from the stored tissue and the cDNA library is constructed as described in Example 2.

The CMz041 (Lib3068) cDNA library is generated from maize pollen germinating silk tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants when the ear shoots are ready for fertilization at the silk emergence stage. The emerging silks are pollinated with an excess of pollen under controlled pollination conditions in the green house. Eighteen hours after pollination the silks are removed from the ears and immediately frozen in liquid nitrogen. This sample represents genes expressed in both pollen and silk tissue early in pollination. The harvested tissue is then stored at −80° C. until RNA preparation. The RNA is purified from the stored tissue and the cDNA library is constructed as described in Example 2.

The CMz042 (Lib3069) cDNA library is generated from maize ear tissue excessively pollinated at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ stage plants and the ear shoots which are ready for fertilization are at the silk emergence stage. The immature ears are pollinated with an excess of pollen under controlled pollination conditions. Eighteen hours post-pollination, the ears are removed and immediately transferred to liquid nitrogen containers. The harvested tissue is then stored at −80° C. until RNA preparation. The RNA is purified from the stored tissue and the cDNA library is constructed as described in Example 2.

The CMz044 (Lib3075) cDNA library is generated from maize microspore tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from immature anthers from 7 week old tassels. The immature anthers are first dissected from the 7 week old tassel with a scalpel on a glass slide covered with water. The microspores (immature pollen) are released into the water and are recovered by centrifugation. The microspore suspension is immediately frozen in liquid nitrogen. The harvested tissue is then stored at −80° C. until RNA preparation. The RNA is purified from the stored tissue and the cDNA library is constructed as described in Example 2.

The CMz045 (Lib3076) cDNA library is generated from maize immature ear megaspore tissue. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from immature ear (megaspore) obtained from 7 week old plants. The immature ears are harvested from the 7 week old plants and are approximately 2.5 to 3 cm in length. The kernels are removed from the cob immediately frozen in liquid nitrogen. The harvested tissue is then stored at −80° C. until RNA preparation. The RNA is purified from the stored tissue and the cDNA library is constructed as described in Example 2.

The CMz047 (Lib3078) cDNA library is generated from maize $CO_2$ treated high-exposure shoot tissue at the V10+ plant development stage. RX601 maize seeds are sterilized for i minute with a 10% clorox solution. The seeds are rolled in germination paper, and germinated in 0.5 mM calcium sulfate solution for two days ate 30° C. The seedlings are planted at a depth of approximately 3 cm into 2-3 inch peat pots containing Metro 200 growing medium at a rate of 2-3 seedlings per pot. Twenty pots are placed into a high $CO_2$ environment (approximately 1000 ppm $CO_2$). Twenty plants were grown under ambient greenhouse $CO_2$ (approximately 450 ppm $CO_2$). Plants are watered daily before transplantation and three times a week after transplantation. Peters 20-20-20 fertilizer is also lightly applied. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. At ten days post planting, the shoots from both atmosphere are frozen in liquid nitrogen and lightly ground. The roots are washed in deionized water to remove the support media and the tissue is immediately transferred to liquid nitrogen containers. The harvested tissue is then stored at −80° C. until RNA preparation. The RNA is purified from the stored tissue and the cDNA library is constructed as described in Example 2.

The CMz048 (Lib3079) cDNA library is generated from maize basal endosperm transfer layer tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected from V10+ maize plants. The ear shoots, which are ready for fertilization, are enclosed in a paper bag prior to silk emergence, to withhold the pollen. Kernels are harvested at 12 days post-pollination and placed on wet ice for dissection. The kernels are cross sectioned laterally, dissecting just above the pedicel region, including 1-2 mm of the lower endosperm and the basal endosperm transfer region. The pedicel and lower endosperm region containing the basal endosperm transfer layer is pooled and immediately frozen in liquid nitrogen. The harvested tissue is then stored at −80° C. until RNA preparation. The RNA is purified from the stored tissue and the cDNA library is constructed as described in Example 2.

The CMz049(Lib3088) cDNA library is generated from maize immature anther tissue at the 7 week old immature tassel stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is at the 7 week old immature tassel stage. At this stage, prior to anthesis, the immature anthers are green and enclosed in the staminate spikelet. The developing anthers are dissected away from the 7 week old immature tassel and immediately transferred to liquid nitrogen container. The harvested tissue is then stored at −80° C. until RNA preparation. The RNA is purified from the stored tissue and the cDNA library is constructed as described in Example 2.

The CMz050 (Lib3114) cDNA library is generated from maize silk tissue at the V10+ plant development stage. Seeds are planted at a depth of approximately 3 cm into 2-3 inch peat pots containing Metro 200 growing medium. After 2-3 weeks growth they are transplanted into 10 inch pots containing the same growing medium. Plants are watered daily before transplantation and three times a week after transplantation. Peters 15-16-17 fertilizer is applied three times per week after transplanting at a strength of 150 ppm N. Two to three times during the lifetime of the plant, from transplanting to flowering, a total of 900 mg Fe is added to each pot. Maize plants are grown in the greenhouse in 15 hr day/9 hr night cycles. The daytime temperature is approximately 80° F. and the nighttime temperature is approximately 70° F. Supplemental lighting is provided by 1000 W sodium vapor lamps. Tissue is collected when the maize plant is beyond the 10-leaf development stage and the ear shoots are approximately 15-20 cm in length. The ears are pulled and silks are separated from the ears and immediately transferred to liquid nitrogen containers. The harvested tissue is then stored at −80° C. until RNA preparation. The RNA is purified from the stored tissue and the cDNA library is constructed as described in Example 2.

The SOYMON001 cDNA library is generated from soybean cultivar Asgrow 3244 (Asgrow Seed Company, Des Moines, Iowa U.S.A.) total leaf tissue at the V4 plant development stage. Leaf tissue from 38, field grown V4 stage plants is harvested from the 4 node. Leaf tissue is removed from the plants and immediately frozen in dry-ice. The harvested tissue is then stored at −80° C. until RNA preparation. The RNA is purified from the stored tissue and the cDNA library is constructed as described in Example 2.

The SOYMON002 cDNA library is generated from soybean cultivar Asgrow 3244 (Asgrow Seed Company, Des Moines, Iowa U.S.A.) root tissue at the V4 plant development stage. Root tissue from 76, field grown V4 stage plants is harvested. The root systems is cut from the soybean plant and washed with water to free it from the soil and immediately frozen in dry-ice. The harvested tissue is then stored at −80° C. until RNA preparation. The RNA is purified from the stored tissue and the cDNA library is constructed as described in Example 2.

The SOYMON003 cDNA library is generated from soybean cultivar Asgrow 3244 (Asgrow Seed Company, Des Moines, Iowa U.S.A.) seedling hypocotyl axis tissue harvested 2 day post-imbibition. Seeds are planted at a depth of approximately 2 cm into 2-3 inch peat pots containing Metromix 350 medium. Trays are placed in an environmental chamber and grown at 12 hr daytime/12 hr nighttime cycles. The daytime temperature is approximately 29° C. and the nighttime temperature approximately 24° C. Soil is checked and watered daily to maintain even moisture conditions. Tissue is collected 2 days after the start of imbibition. The 2 days after imbibition samples are separated into 3 collections after removal of any adhering seed coat. At the 2 day stage, the hypocotyl axis is emerging from the soil. A few seedlings have cracked the soil surface and exhibited slight greening of the exposed cotyledons. The seedlings are washed in water to remove soil, hypocotyl axis harvested and immediately frozen in liquid nitrogen. The harvested tissue is then stored at −80° C. until RNA preparation. The RNA is purified from the stored tissue and the cDNA library is constructed as described in Example 2.

The SOYMON004 cDNA library is generated from soybean cultivar Asgrow 3244 (Asgrow Seed Company, Des Moines, Iowa U.S.A.) seedling cotyledon tissue harvested 2 day post-imbibition. Seeds are planted at a depth of approximately 2 cm into 2-3 inch peat pots containing Metromix 350 medium. Trays are placed in an environmental chamber and grown at 12 hr daytime/12 hr nighttime cycles. The daytime temperature is approximately 29° C. and the nighttime temperature approximately 24° C. Soil is checked and watered daily to maintain even moisture conditions. Tissue is collected 2 days after the start of imbibition. The 2 days after imbibition samples are separated into 3 collections after removal of any adhering seed coat. At the 2 day stage, the hypocotyl axis is emerging from the soil. A few seedlings have cracked the soil surface and exhibited slight greening of the exposed cotyledons. The seedlings are washed in water to remove soil, hypocotyl axis harvested and immediately frozen in liquid nitrogen. The harvested tissue is then stored at −80° C. until RNA preparation. The RNA is purified from the stored tissue and the cDNA library is constructed as described in Example 2.

The SOYMON005 cDNA library is generated from soybean cultivar Asgrow 3244 (Asgrow Seed Company, Des Moines, Iowa U.S.A.) seedling hypocotyl axis tissue harvested 6 hour post-imbibition. Seeds are planted at a depth of approximately 2 cm into 2-3 inch peat pots containing Metromix 350 medium. Trays are placed in an environmental chamber and grown at 12 hr daytime/12 hr nighttime cycles. The daytime temperature is approximately 29° C. and the nighttime temperature approximately 24° C. Soil is checked and watered daily to maintain even moisture conditions. Tissue is collected 6 hours after the start of imbibition. The 6 hours after imbibition samples are separated into 3 collections after removal of any adhering seed coat. The 6 hours after imbibition sample is collected over the course of approximately 2 hours starting at 6 hours post imbibition. At the 6 hours after imbibition stage, not all cotyledons have become fully hydrated and germination, or radicle protrusion, has not occurred. The seedlings are washed in water to remove soil, hypocotyl axis harvested and immediately frozen in liquid nitrogen. The harvested tissue is then stored at −80° C. until RNA preparation. The RNA is purified from the stored tissue and the cDNA library is constructed as described in Example 2.

The SOYMON006 cDNA library is generated from soybean cultivar Asgrow 3244 (Asgrow Seed Company, Des Moines, Iowa U.S.A.) seedling cotyledons tissue harvest 6 hour post-imbibition. Seeds are planted at a depth of approximately 2 cm into 2-3 inch peat pots containing Metromix 350 medium. Trays are placed in an environmental chamber and grown at 12 hr daytime/12 hr nightime cycles. The daytime temperature is approximately 29° C. and the nighttime temperature approximately 24° C. Soil is checked and watered daily to maintain even moisture conditions. Tissue is collected 6 hours after imbibition. The 6 hours after imbibition samples are separated into 3 collections after removal of any adhering seed coat. The 6 hours after imbibition sample is collected over the course of approximately 2 hours starting at 6 hours post-imbibition. At the 6 hours after imbibition, not all cotyledons have become fully hydrated and germination or radicle protrusion, have not occurred. The seedlings are washed in water to remove soil, cotyledon harvested and immediately frozen in liquid nitrogen. The harvested tissue is then stored at −80° C. until RNA preparation. The RNA is purified from the stored tissue and the cDNA library is constructed as described in Example 2.

The SOYMON007 cDNA library is generated from soybean cultivar Asgrow 3244 (Asgrow Seed Company, Des Moines, Iowa U.S.A.) seed tissue harvested 25 and 35 days post-flowering. Seed pods from field grown plants are harvested 25 and 35 days after flowering and the seeds extracted from the pods. Approximately 4.4 g and 19.3 g of seeds are harvested from the respective seed pods and immediately frozen in dry ice. The harvested tissue is then stored at −80° C. until RNA preparation. The RNA is purified from the stored tissue and the cDNA library is constructed as described in Example 2.

The SOYMON008 cDNA library is generated from soybean cultivar Asgrow 3244 (Asgrow Seed Company, Des Moines, Iowa U.S.A.) leaf tissue harvested from 25 and 35 days post-flowering plants. Total leaf tissue is harvested from field grown plants. Approximately 19 g and 29 g of leaves are harvested from the fourth node of the plant 25 and 35 days post-flowering and immediately frozen in dry ice. The harvested tissue is then stored at −80° C. until RNA preparation. The RNA is purified from the stored tissue and the cDNA library is constructed as described in Example 2.

The SOYMON009 cDNA library is generated from soybean cultivar C1944 (USDA Soybean Germplasm Collection, Urbana, Ill. U.S.A.) pod and seed tissue harvested 15 days post-flowering. Pods from field grown plants are harvested 15 days post-flowering. Approximately 3 g of pod tissue is harvested and immediately frozen in dry-ice. The harvested tissue is then stored at −80° C. until RNA preparation. The RNA is purified from the stored tissue and the cDNA library is constructed as described in Example 2.

The SOYMON011 cDNA library is generated from soybean cultivar C1944 (USDA Soybean Germplasm Collection, Urbana, Ill. U.S.A.) seed tissue harvested 40 days post-flowering. Pods from field grown plants are harvested 40 days post-flowering. Pods and seeds are separated, approximately 19 g of seed tissue is harvested and immediately frozen in dry-ice. The harvested tissue is then stored at −80° C. until RNA preparation. The RNA is purified from the stored tissue and the cDNA library is constructed as described in Example 2.

The SOYMON011 cDNA library is generated from soybean cultivars Cristalina (USDA Soybean Germplasm Collection, Urbana, Ill. U.S.A.) and FT108 (Monsoy, Brazil) (tropical germ plasma) leaf tissue. Leaves are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 30 g of leaves are harvested from the $4^{th}$ node of each of the Cristalina and FT108 cultivars and immediately frozen in dry ice. The harvested tissue is then stored at −80° C. until RNA preparation. The RNA is purified from the stored tissue and the cDNA library is constructed as described in Example 2.

The SOYMON012 cDNA library is generated from soybean cultivar Asgrow 3244 (Asgrow Seed Company, Des Moines, Iowa U.S.A.) leaf tissue. Leaves from field grown plants are harvested from the fourth node 15 days post-flowering. Approximately 12 g of leaves are harvested and immediately frozen in dry ice. The harvested tissue is then stored at −80° C. until RNA preparation. The RNA is purified from the stored tissue and the cDNA library is constructed as described in Example 2.

The SOYMON013 cDNA library is generated from soybean cultivar Asgrow 3244 (Asgrow Seed Company, Des Moines, Iowa U.S.A.) root and nodule tissue. Approximately, 28 g of root tissue from field grown plants is harvested 15 days post-flowering. The root system is cut from the soybean plant, washed with water to free it from the soil and immediately frozen in dry-ice. The harvested tissue is then stored at −80° C. until RNA preparation. The RNA is purified from the stored tissue and the cDNA library is constructed as described in Example 2.

The SOYMON014 cDNA library is generated from soybean cultivar Asgrow 3244 (Asgrow Seed Company, Des Moines, Iowa U.S.A.) seed tissue harvested 25 and 35 days after flowering. Seed pods from field grown plants are harvested 15 days after flowering and the seeds extracted from the pods. Approximately 5 g of seeds are harvested from the respective seed pods and immediately frozen in dry ice. The harvested tissue is then stored at −80° C. until RNA preparation. The RNA is purified from the stored tissue and the cDNA library is constructed as described in Example 2.

The SOYMON015 cDNA is generated from soybean cultivar Asgrow 3244 (Asgrow Seed Company, Des Moines, Iowa U.S.A.) seed tissue harvested 45 and 55 days post-flowering. Seed pods from field grown plants are harvested 45 and 55 days after flowering and the seeds extracted from the pods. Approximately 19 g and 31 g of seeds are harvested from the respective seed pods and immediately frozen in dry ice. The harvested tissue is then stored at −80° C. until RNA preparation. The RNA is purified from the stored tissue and the cDNA library is constructed as described in Example 2.

The SOYMON016 cDNA library is generated from soybean cultivar Asgrow 3244 (Asgrow Seed Company, Des Moines, Iowa U.S.A.) root tissue. Approximately, 61 g and 38 g of root tissue from field grown plants is harvested 25 and 35 days post-flowering is harvested. The root system is cut from the soybean plant and washed with water to free it from the soil. The tissue is placed in 14 ml polystyrene tubes and immediately frozen in dry-ice. The harvested tissue is then stored at −80° C. until RNA preparation. The RNA is purified from the stored tissue and the cDNA library is constructed as described in Example 2.

The SOYMON017 cDNA library is generated from soybean cultivar Asgrow 3244 (Asgrow Seed Company, Des Moines, Iowa U.S.A.) root tissue. Approximately 28 g of root tissue from field grown plants is harvested 45 and 55 days post-flowering. The root system is cut from the soybean plant, washed with water to free it from the soil and immediately frozen in dry-ice. The harvested tissue is then stored at −80° C. until RNA preparation. The RNA is purified from the stored tissue and the cDNA library is constructed as described in Example 2.

The SOYMON018 cDNA is generated from soybean cultivar Asgrow 3244 (Asgrow Seed Company, Des Moines, Iowa U.S.A.) leaf tissue harvested 45 and 55 days post-flowering. Leaves from field grown plants are harvested 45 and 55 days after flowering from the fourth node. Approximately 27 g and 33 g of seeds are harvested from the respective seed pods and immediately frozen in dry ice. The harvested tissue is then stored at −80° C. until RNA preparation. The RNA is purified from the stored tissue and the cDNA library is constructed as described in Example 2.

The SOYMON019 cDNA library is generated from soybean cultivars Cristalina (USDA Soybean Germplasm Collection, Urbana, Ill. U.S.A.) and FT108 (Monsoy, Brazil) (tropical germ plasma) root tissue. Roots are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 50 g and 56 g of roots are harvested from each of the Cristalina and FT108 cultivars and immediately frozen in dry ice. The harvested tissue is then stored at −80° C. until RNA preparation. The RNA is purified from the stored tissue and the cDNA library is constructed as described in Example 2.

The SOYMON020 cDNA is generated from soybean cultivar Asgrow 3244 (Asgrow Seed Company, Des Moines, Iowa U.S.A.) seed tissue harvested 65 and 75 days post-flowering. Seed pods from field grown plants are harvested 45 and 55 days after flowering and the seeds extracted from the pods. Approximately 14 g and 31 g of seeds are harvested from the respective seed pods and immediately frozen in dry ice. The harvested tissue is then stored at −80° C. until RNA preparation. The RNA is purified from the stored tissue and the cDNA library is constructed as described in Example 2.

The SOYMON021 cDNA library is generated from Soybean Cyst Nematode-resistant soybean cultivar Hartwig (USDA Soybean Germplasm Collection, Urbana, Ill. U.S.A.) root tissue. Plants are grown in tissue culture at room temperature. At approximately 6 weeks post-germination, the plants are exposed to sterilized Soybean Cyst Nematode eggs. Infection is then allowed to progress for 10 days. After the 10 day infection process, the tissue is harvested. Agar from the culture medium and nematodes are removed and the root tissue is immediately frozen in dry ice. The harvested tissue is then stored at −80° C. until RNA preparation. The RNA is purified from the stored tissue and the cDNA library is constructed as described in Example 2.

The SOYMON022 (Lib3030) cDNA library is generated from soybean cultivar Asgrow 3244 (Asgrow Seed Company, Des Moines, Iowa U.S.A.) partially opened flower tissue. Partially to fully opened flower tissue is harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. A total of 3 g of flower tissue is harvested and immediately frozen in dry ice. The harvested tissue is then stored at −80° C. until RNA preparation. The RNA is purified from the stored tissue and the cDNA library is constructed as described in Example 2.

The SOYMON023 cDNA library is generated from soybean genotype BW211S Null (Tohoku University, Morioka, Japan) seed tissue harvested 15 and 40 days post-flowering. Seed pods from field grown plants are harvested 15 and 40 days post-flowering and the seeds extracted from the pods. Approximately 0.7 g and 14.2 g of seeds are harvested from the respective seed pods and immediately frozen in dry ice. The harvested tissue is then stored at −80° C. until RNA preparation. The RNA is purified from the stored tissue and the cDNA library is constructed as described in Example 2.

The SOYMON024 cDNA library is generated from soybean cultivar Asgrow 3244 (Asgrow Seed Company, Des Moines, Iowa U.S.A.) internode-2 tissue harvested 18 days post-imbibition. Seeds are planted at a depth of approximately 2 cm into 2-3 inch peat pots containing Metromix 350 medium. The plants are grown in a greenhouse for 18 days after the start of imbibition at ambient temperature. Soil is checked and watered daily to maintain even moisture conditions. Stem tissue is harvested 18 days after the start of imbibition. The samples are divided into hypocotyl and internodes 1 through 5. The fifth internode contains some leaf bud material. Approximately 3 g of each sample is harvested and immediately frozen in dry ice. The harvested tissue is then stored at −80° C. until RNA preparation. The RNA is purified from the stored tissue and the cDNA library is constructed as described in Example 2.

The SOYMON025 cDNA library is generated from soybean cultivar Asgrow 3244 (Asgrow Seed Company, Des Moines, Iowa U.S.A.) leaf tissue harvested 65 days post-flowering. Leaves are harvested from the fourth node of field grown plants 65 days post-flowering. Approximately 18.4 g of leaf tissue is harvested and immediately frozen in dry ice. The harvested tissue is then stored at −80° C. until RNA preparation. The RNA is purified from the stored tissue and the cDNA library is constructed as described in Example 2.

SOYMON026 cDNA library is generated from soybean cultivar Asgrow 3244 (Asgrow Seed Company, Des Moines, Iowa U.S.A.) root tissue harvested 65 and 75 days post-flowering. Approximately 27 g and 40 g of root tissue from field grown plants is harvested 65 and 75 days post-flowering. The root system is cut from the soybean plant, washed with water to free it from the soil and immediately frozen in dry-ice. The harvested tissue is then stored at −80° C. until RNA preparation. The RNA is purified from the stored tissue and the cDNA library is constructed as described in Example 2.

The SOYMON027 cDNA library is generated from soybean cultivar Asgrow 3244 (Asgrow Seed Company, Des Moines, Iowa U.S.A.) seed tissue harvested 25 days post-flowering. Seed pods from field grown plants are harvested 25 days post-flowering and the seeds extracted from the pods. Approximately 17 g of seeds are harvested from the seed pods and immediately frozen in dry ice. The harvested tissue is then stored at −80° C. until RNA preparation. The RNA is purified from the stored tissue and the cDNA library is constructed as described in Example 2.

The SOYMON028 cDNA library is generated from soybean cultivar Asgrow 3244 (Asgrow Seed Company, Des Moines, Iowa U.S.A.) drought-stressed root tissue. The plants are grown in an environmental chamber under 12 hr daytime/12 hr nighttime cycles. The daytime temperature is approximately 29° C. and the nighttime temperature 24° C. Soil is checked and watered daily to maintain even moisture conditions. At the R3 stage of development, water is withheld from half of the plant collection (drought stressed population). After 3 days, half of the plants from the drought stressed condition and half of the plants from the control population are harvested. After another 3 days (6 days post drought induction) the remaining plants are harvested. A total of 27 g and 40 g of root tissue is harvested and immediately frozen in dry ice. The harvested tissue is then stored at −80° C. until RNA preparation. The RNA is purified from the stored tissue and the cDNA library is constructed as described in Example 2.

The SOYMON029 cDNA library is generated from Soybean Cyst Nematode-resistant soybean cultivar PI07354 (USDA Soybean Germplasm Collection, Urbana, Ill. U.S.A.) root tissue. Late fall to early winter greenhouse grown plants are exposed to Soybean Cyst Nematode eggs. At 10 days post-infection, the plants are uprooted, rinsed briefly and the roots frozen in liquid nitrogen. Approximately 20 grams of root tissue is harvested from the infected plants. The harvested tissue is then stored at −80° C. until RNA preparation. The RNA is purified from the stored tissue and the cDNA library is constructed as described in Example 2.

The SOYMON030 cDNA library is generated from soybean cultivar Asgrow 3244 (Asgrow Seed Company, Des Moines, Iowa U.S.A.) flower bud tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature approximately 24° C. Soil is checked and watered daily to maintain even moisture conditions. Flower buds are removed from the plant at the pedicel. A total of 100 mg of flower buds are harvested and immediately frozen in liquid nitrogen. The harvested tissue is then stored at −80° C. until RNA preparation. The RNA is purified from the stored tissue and the cDNA library is constructed as described in Example 2.

The SOYMON031 cDNA library is generated from soybean cultivar Asgrow 3244 (Asgrow Seed Company, Des Moines, Iowa U.S.A.) carpel and stamen tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature approximately 24° C. Soil is checked and watered daily to maintain even moisture conditions. Flower buds are removed from the plant at the pedicel. Flowers are dissected to separate petals, sepals and reproductive structures (carpels and stamens). A total of 300 mg of carpel and stamen tissue are harvested and immediately frozen in liquid nitrogen. The harvested tissue is then stored at −80° C. until RNA preparation. The RNA is purified from the stored tissue and the cDNA library is constructed as described in Example 2.

The SOYMON032 cDNA library is prepared from the Asgrow cultivar A4922 (Asgrow Seed Company, Des Moines, Iowa U.S.A.) rehydrated dry soybean seed meristem tissue. Surface sterilized seeds are germinated in liquid media for 24 hours. The seed axis is then excised from the barely germinating seed, placed on tissue culture media and incubated overnight at 20° C. in the dark. The supportive tissue is removed from the explant prior to harvest. Approximately 570 mg of tissue is harvested and frozen in liquid nitrogen. The harvested tissue is then stored at −80° C. until RNA preparation. The RNA is purified from the stored tissue and the cDNA library is constructed as described in Example 2.

The SOYMON033 cDNA library is generated from soybean cultivar Asgrow 3244 (Asgrow Seed Company, Des Moines, Iowa U.S.A.) heat-shocked seedling tissue without cotyledons. Seeds are imbibed and germinated in vermiculite for 2 days under constant illumination. After 48 hours, the seedlings are transferred to an incubator set at 40° C. under constant illumination. After 30, 60 and 180 minutes seedlings are harvested and dissected. A portion of the seedling consisting of the root, hypocotyl and apical hook is frozen in liquid nitrogen and stored at −80° C. The seedlings after 2 days of imbibition are beginning to emerge from the vermiculite surface. The apical hooks are dark green in appearance. Total RNA and poly A$^+$ RNA is prepared from equal amounts of pooled tissue. The RNA is purified from the stored tissue and the cDNA library is constructed as described in Example 2.

The SOYMON034 cDNA library is generated from soybean cultivar Asgrow 3244 (Asgrow Seed Company, Des Moines, Iowa U.S.A.) cold-shocked seedling tissue without cotyledons. Seeds are imbibed and germinated in vermiculite for 2 days under constant illumination. After 48 hours, the seedlings are transferred to a cold room set at 5° C. under constant illumination. After 30, 60 and 180 minutes seedlings are harvested and dissected. The seedlings after 2 days of imbibition are beginning to emerge from the vermiculite surface. The apical hooks are dark green in appearance. A portion of the seedling consisting of the root, hypocotyl and apical hook is frozen in liquid nitrogen and stored at −80° C. The RNA is purified from the stored tissue and the cDNA library is constructed as described in Example 2.

The SOYMON035 cDNA library is generated from soybean cultivar Asgrow 3244 (Asgrow Seed Company, Des Moines, Iowa U.S.A.) seed coat tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. Seeds are harvested from mid to nearly full maturation (seed coats are not yellowing). The entire embryo proper is removed from the seed coat sample and the seed coat tissue are harvested and immediately frozen in liquid nitrogen. The harvested tissue is then stored at −80° C. until RNA preparation. The RNA is purified from the stored tissue and the cDNA library is constructed as described in Example 2.

The SOYMON036 cDNA library is generated from soybean cultivars PI171451, P1227687 and PI229358 (USDA Soybean Germplasm Collection, Urbana, Ill. U.S.A.) insect challenged leaves. Plants from each of the three cultivars are grown in screenhouse conditions. The screenhouse is divided in half and one half of the screenhouse is infested with soybean looper and the other half infested with velvetbean caterpillar. A single leaf is taken from each of the representative plants at 3 different time points, 11 days after infestation, 2 weeks after infestation and 5 weeks after infestation and immediately frozen in liquid nitrogen. The harvested tissue is then stored at −80° C. until RNA preparation. Total RNA and poly A+ RNA is isolated from pooled tissue consisting of equal quantities of all 18 samples (3 genotypes×3 sample times×2 insect genotypes). The RNA is purified from the stored tissue and the cDNA library is constructed as described in Example 2.

The SOYMON037 cDNA library is generated from soybean cultivar A3244 (Asgrow Seed Company, Des Moines, Iowa U.S.A.) etiolated axis and radical tissue. Seeds are planted in moist vermiculite, wrapped and kept at room temperature in complete darkness until harvest. Etiolated axis and hypocotyl tissue is harvested at 2, 3 and 4 days post-planting. A total of 1 gram of each tissue type is harvested at 2, 3 and 4 days after planting and immediately frozen in liquid nitrogen. The harvested tissue is then stored at −80° C. until RNA preparation. The RNA is purified from the stored tissue and the cDNA library is constructed as described in Example 2.

The SOYMON038 cDNA library is generated from soybean variety Asgrow A3237 (Asgrow Seed Company, Des Moines, Iowa U.S.A.) rehydrated dry seeds. Explants are prepared for transformation after germination of surface-sterilized seeds on solid tissue media. After 6 days, at 28° C. and 18 hours of light per day, the germinated seeds are cold shocked at 4° C. for 24 hours. Meristemic tissue and part of the hypocotyl is remove and cotyledon excised. The prepared explant is then wounded for *Agrobacterium* infection. The 2 grams of harvested tissue is frozen in liquid nitrogen and stored at −80° C. until RNA preparation. The RNA is purified from the stored tissue and the cDNA library is constructed as described in Example 2.

The Soy51 (LIB3027) normalized seed pool cDNA library is prepared from equal amounts tissue harvested from SOYMON007, SOYMON015 and SOYMON020 prepared tissue. Single stranded and double stranded DNA representing approximately $1\times10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single stranded molecules remaining after hybrid capture are converted to double stranded form and represent the primary normalized library.

The Soy52 (LIB3028) cDNA library is generated from normalized flower DNA. Single stranded DNA representing approximately $1\times10^6$ colony forming units of SOYMON022 harvested tissue is used as the starting material for normalization. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single stranded molecules remaining after hybrid capture are converted to double stranded form and represent the primary normalized library.

The Soy53 (LIB3039) cDNA library is generated from soybean cultivar Asgrow 3244 (Asgrow Seed Company, Des Moines, Iowa U.S.A.) seedling shoot apical meristem tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. Apical tissue is harvested from seedling shoot meristem tissue, 7-8 days after the start of imbibition. The apex of each seedling is dissected to include the fifth node to the apical meristem. The fifth node corresponds to the third trifoliate leaf in the very early stages of development. Stipules completely envelop the leaf primordia at this time. A total of 200 mg of apical tissue is harvested and immediately frozen in liquid nitrogen. The harvested tissue is then stored at −80° C. until RNA preparation. The RNA is purified from the stored tissue and the cDNA library is constructed as described in Example 2.

The Soy54 (LIB3040) cDNA library is generated from soybean cultivar Asgrow 3244 (Asgrow Seed Company, Des Moines, Iowa U.S.A.) heart to torpedo stage embryo tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. Seeds are collected and embryos removed from surrounding endosperm and maternal tissues. Embryos from globular to young torpedo stages (by corresponding analogy to *Arabidopsis*) are collected with a bias towards the middle of this spectrum. Embryos which are beginning to show asymmetric development of cotyledons are considered the upper developmental boundary for the collection and are excluded. A total of 12 mg embryo tissue is frozen in liquid nitrogen. The harvested tissue is stored at −80° C. until RNA preparation. The RNA is purified from the stored tissue and the cDNA library is constructed as described in Example 2.

Soy55 (LIB3049) cDNA library is generated from soybean cultivar Asgrow 3244 (Asgrow Seed Company, Des Moines, Iowa U.S.A.) young seed tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. Seeds are collected from very young pods (5 to 15 days after flowering). A total of 100 mg of seeds are harvested and frozen in liquid nitrogen. The harvested tissue is stored at −80° C. until RNA preparation. The RNA is purified from the stored tissue and the cDNA library is constructed as described in Example 2.

Soy56 (LIB3029) non-normalized seed pool cDNA library is prepared from equal amounts tissue harvested from SOYMON007, SOYMON015 and SOYMON020 prepared tissue. Single stranded and double stranded DNA representing approximately $1\times10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single stranded molecules remaining after hybrid capture are not converted to double stranded form and represent a non-normalized seed pool for comparison to Soy51 cDNA libraries.

The Soy58 (LIB3050) cDNA library is generated from soybean cultivar Asgrow 3244 (Asgrow Seed Company, Des Moines, Iowa U.S.A.) drought stressed root tissue subtracted from control root tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. At the R3 stage of the plant drought is induced by withholding water. After 3 and 6 days root tissue from both drought stressed and control (watered regularly) plants are collected and frozen in dry-ice. The harvested tissue is stored at −80° C. until RNA preparation. The RNA is prepared from the stored tissue and the subtracted cDNA library is constructed as described in Example 2.

The Soy59 (LIB3051) cDNA library is generated from soybean cultivar Asgrow 3244 (Asgrow Seed Company, Des Moines, Iowa U.S.A.) endosperm tissue. Seeds are germinated on paper towels under laboratory ambient light conditions. At 8, 10 and 14 hours after imbibition, the seed coats are harvested. The endosperm consists of a very thin layer of tissue affixed to the inside of the seed coat. The seed coat and endosperm are frozen immediately after harvest in liquid nitrogen. The harvested tissue is stored at −80° C. until RNA preparation. The RNA is prepared from the stored tissue and the cDNA library is constructed as described in Example 2.

The Soy60 (LIB3072) cDNA library is generated from soybean cultivar Asgrow 3244 (Asgrow Seed Company, Des Moines, Iowa U.S.A.) drought stressed seed plus pod subtracted from control seed plus pod tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 26° C. and the nighttime temperature 21° C. and 70% relative humidity. Soil is checked and watered daily to maintain even moisture conditions. At the R3 stage of the plant drought is induced by withholding water. After 3 and 6 days seeds and pods from both drought stressed and control (watered regularly) plants are collected from the fifth and sixth node and frozen in dry-ice. The harvested tissue is stored at −80° C. until RNA preparation. The RNA is prepared from the stored tissue and the subtracted cDNA library is constructed as described in Example 2.

The Soy61 (LIB3073) cDNA library is generated from soybean cultivar Asgrow 3244 (Asgrow Seed Company, Des Moines, Iowa U.S.A.) jasmonic acid treated seedling subtracted from control tissue. Seeds are planted at a depth of approximately 2 cm into 2-3 inch peat pots containing Metromix 350 medium and the plants are grown in a greenhouse. The daytime temperature is approximately 29.4° C. and the nighttime temperature 20° C. Soil is checked and watered daily to maintain even moisture conditions. At 9 days post planting, the plantlets are sprayed with either control buffer of 0.1% Tween-20 or jasmonic acid (Sigma J-2500, Sigma, St. Louis, Mo. U.S.A.) at 1 mg/ml in 0.1% Tween-20. Plants are sprayed until runoff and the soil and the stem is socked with the spraying solution. At 18 hours post application of jasmonic acid, the soybean plantlets appear growth retarded. After 18 hours, 24 hours and 48 hours post treatment, the cotyledons are removed and the remaining leaf and stem tissue above the soil is harvested and frozen in liquid nitrogen. The harvested tissue is stored at −80° C. until RNA preparation. To make RNA, the three sample timepoints were combined and ground. The RNA is prepared from the stored tissue and the subtracted cDNA library is constructed as described in Example 2. For this library's construction, the eighth fraction of the cDNA size fractionation step was used for ligation.

The Soy62 (LIB3074) cDNA library is generated from soybean cultivar Asgrow 3244 (Asgrow Seed Company, Des Moines, Iowa U.S.A.) jasmonic acid treated seedling subtracted from control tissue. Seeds are planted at a depth of approximately 2 cm into 2-3 inch peat pots containing Metromix 350 medium and the plants are grown in a greenhouse. The daytime temperature is approximately 29.4° C. and the nighttime temperature 20° C. Soil is checked and watered daily to maintain even moisture conditions. At 9 days post planting, the plantlets are sprayed with either control buffer of 0.1% Tween-20 or jasmonic acid (Sigma J-2500, Sigma, St. Louis, Mo. U.S.A.) at 1 mg/ml in 0.1% Tween-20. Plants are sprayed until runoff and the soil and the stem is socked with the spraying solution. At 18 hours post application of jasmonic acid, the soybean plantlets appear growth retarded. After 18 hours, 24 hours and 48 hours post treatment, the cotyledons are removed and the remaining leaf and stem tissue above the soil is harvested and frozen in liquid nitrogen. The harvested tissue is stored at −80° C. until RNA preparation. To make RNA, the three sample timepoints were combined and ground. The RNA is prepared from the stored tissue and the subtracted cDNA library is constructed as described in Example 2. For this library's construction, the ninth fraction of the cDNA size fractionation step was used for ligation.

The Soy65 (LIB3107) 07cDNA library is generated from soybean cultivar Asgrow 3244 (Asgrow Seed Company, Des Moines, Iowa U.S.A.) drought-stressed abscission zone tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature 24° C. Soil is checked and watered daily to maintain even moisture conditions. Plants are irrigated with 15-16-17 Peter's Mix. At the R3 stage of development, drought is imposed by withholding water. At 3, 4, 5 and 6 days, tissue is harvested and wilting is not obvious until the fourth day. Abscission layers from reproductive organs are harvested by cutting less than one millimeter proximal and distal to the layer and immediately frozen in liquid nitrogen. The harvested tissue is stored at −80° C. until RNA preparation. The RNA is prepared from the stored tissue and the cDNA library is constructed as described in Example 2.

The Soy66 (LIB3109) cDNA library is generated from soybean cultivar Asgrow 3244 (Asgrow Seed Company, Des Moines, Iowa U.S.A.) non-drought stressed abscission zone tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 29° C. and the nighttime temperature approximately 24° C. Soil is checked and watered daily to maintain even moisture conditions. Plants are irrigated with 15-16-17 Peter's Mix. At 3, 4, 5 and 6 days, control abscission layer tissue is harvested. Abscission layers from reproductive organs are harvested by cutting less than one millimeter proximal and distal to the layer and immediately frozen in liquid nitrogen. The harvested tissue is stored at −80° C. until RNA preparation. The RNA is prepared from the stored tissue and the cDNA library is constructed as described in Example 2.

Soy67 (LIB3065) normalized seed pool cDNA library is prepared from equal amounts tissue harvested from SOYMON007, SOYMON015 and SOYMON020 prepared tissue. Single stranded and double stranded DNA representing approximately $1 \times 10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. Captured hybrids are eluted with water.

Soy68 (LIB3052) normalized seed pool cDNA library is prepared from equal amounts tissue harvested from SOYMON007, SOYMON015 and SOYMON020 prepared tissue. Single stranded and double stranded DNA representing approximately $1 \times 10^6$ colony forming units are isolated using standard protocols. RNA, complementary to the single stranded DNA, is synthesized using the double stranded DNA as a template. Biotinylated dATP is incorporated into the RNA during the synthesis reaction. The single stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. Captured hybrids are eluted with water.

Soy69 (LIB3053) normalized cDNA library is generated from soybean cultivars Cristalina (USDA Soybean Germplasm Collection, Urbana, Ill. U.S.A.) and FT108 (Monsoy, Brazil) (tropical germ plasma) normalized leaf tissue. Leaves are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 30 g of leaves are harvested from the $4^{th}$ node of each of the Cristalina and FT108 cultivars and immediately frozen in dry ice. The harvested tissue is then stored at −80° C. until RNA preparation. The RNA is prepared from the stored tissue and the normalized cDNA library is constructed as described in Example 2.

Soy70 (LIB3055) cDNA library is generated from soybean cultivars Cristalina (USDA Soybean Germplasm Collection, Urbana, Ill. U.S.A.) and FT108 (Monsoy, Brazil) (tropical germ plasma) leaf tissue. Leaves are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 30 g of leaves are harvested from the $4^{th}$ node of each of the Cristalina and FT108 cultivars and immediately frozen in dry ice. The harvested tissue is then stored at −80° C. until RNA preparation. The RNA is prepared from the stored tissue and the cDNA library is constructed as described in Example 2.

Soy71 (LIB3056) cDNA library is generated from soybean cultivars Cristalina and FT108 (tropical germ plasma) root tissue. Roots are harvested from plants grown in an environmental chamber under 12 hr daytime/12 hr nighttime cycles. The daytime temperature is approximately 29° C. and the nighttime temperature approximately 24° C. Soil is checked and watered daily to maintain even moisture conditions. Approximately 50 g and 56 g of roots are harvested from each of the Cristalina and FT108 cultivars and immediately frozen in dry ice. The harvested tissue is then stored at −80° C. until RNA preparation. The RNA is prepared from the stored tissue and the cDNA library is constructed as described in Example 2.

Soy73 (LIB3093) cDNA library is generated from soybean cultivar Asgrow 3244 (Asgrow Seed Company, Des Moines, Iowa U.S.A.) drought stressed leaf subtracted from control tissue. Seeds are planted at a depth of approximately 2 cm into 2-3 inch peat pots containing Metromix 350 medium and the plants are grown in an environmental chamber under 12 hr daytime/12 hr nighttime cycles. The daytime temperature is approximately 26° C. and the nighttime temperature 21° C. and 70% relative humidity. Soil is checked and watered daily to maintain even moisture conditions. At the R3 stage of the plant drought is induced by withholding water. After 3 and 6 days seeds and pods from both drought stressed and control (watered regularly) plants are collected from the fifth and sixth node and frozen in dry-ice. The harvested tissue is stored at −80° C. until RNA preparation. The RNA is prepared from the stored tissue and the subtraction cDNA library is constructed as described in Example 2.

The Soy76 (Lib3106) cDNA library is generated from soybean cultivar Asgrow 3244 (Asgrow Seed Company, Des Moines, Iowa U.S.A.) jasmonic acid and arachidonic treated seedling subtracted from control tissue. Seeds are planted at a depth of approximately 2 cm into 2-3 inch peat pots containing Metromix 350 medium and the plants are grown in a greenhouse. The daytime temperature is approximately 29.4° C. and the nighttime temperature 20° C. Soil is checked and watered daily to maintain even moisture conditions. At 9 days post planting, the plantlets are sprayed with either control buffer of 0.1% Tween-20 or jasmonic acid (Sigma J-2500, Sigma, St. Louis, Mo. U.S.A.) at 1 mg/ml in 0.1% Tween-20. Plants are sprayed until runoff and the soil and the stem is socked with the spraying solution. At 18 hours post application of jasmonic acid, the soybean plantlets appear growth retarded. Arachidonic treated seedlings are sprayed with 1 m/ml arachidonic acid in 0.1% Tween-20. After 18 hours, 24 hours and 48 hours post treatment, the cotyledons are removed and the remaining leaf and stem tissue above the soil is harvested and frozen in liquid nitrogen. The harvested tissue is stored at −80° C. until RNA preparation. To make RNA, the three sample timepoints were combined and ground. The RNA from the arachidonic treated seedlings is isolated separately. The RNA is prepared from the stored tissue and the subtraction cDNA library is constructed as described in Example 2. For this subtraction library, fraction 10 of the size fractionated cDNA is ligated into the pSPORT vector (Invitrogen, Carlsbad Calif. U.S.A.) in order to capture some of the smaller transcripts characteristic of antifungal proteins.

Soy77 (LIB3108) cDNA library is generated from soybean cultivar Asgrow 3244 (Asgrow Seed Company, Des Moines, Iowa U.S.A.) jasmonic acid control tissue. Seeds are planted at a depth of approximately 2 cm into 2-3 inch peat pots containing Metromix 350 medium and the plants are grown in a greenhouse. The daytime temperature is approximately 29.4° C. and the nighttime temperature 20° C. Soil is checked and watered daily to maintain even moisture conditions. At 9 days post planting, the plantlets are sprayed with either control buffer of 0.1% Tween-20 or jasmonic acid (Sigma J-2500, Sigma, St. Louis, Mo. U.S.A.) at 1 mg/ml in 0.1% Tween-20. Plants are sprayed until runoff and the soil and the stem is socked with the spraying solution. At 18 hours post application of jasmonic acid, the soybean plantlets appear growth retarded. Arachidonic treated seedlings are sprayed with 1 m/ml arachidonic acid in 0.1% Tween-20. After 18 hours, 24 hours and 48 hours post treatment, the cotyledons are removed and the remaining leaf and stem tissue above the soil is harvested and frozen in liquid nitrogen. The harvested tissue is stored at −80° C. until RNA preparation. To make RNA, the three sample timepoints were combined and ground. The RNA from the arachidonic treated seedlings is isolated separately. The RNA is prepared from the stored tissue and the subtraction cDNA library is constructed as described in Example 2. For this subtraction cDNA library, fraction 10 of the size fractionated cDNA is ligated into the pSPORT vector in order to capture some of the smaller transcripts characteristic of antifungal proteins.

EXAMPLE 2

The stored RNA is purified using Trizol reagent from Life Technologies (Gibco BRL, Life Technologies, Gaithersburg, Md. U.S.A.), essentially as recommended by the manufacturer. Poly A+ RNA (mRNA) is purified using magnetic oligo dT beads essentially as recommended by the manufacturer (Dynabeads, Dynal Corporation, Lake Success, N.Y. U.S.A.).

Construction of plant cDNA libraries is well-known in the art and a number of cloning strategies exist. A number of cDNA library construction kits are commercially available. The Superscript™ Plasmid System for cDNA synthesis and Plasmid Cloning (Gibco BRL, Life Technologies, Gaithersburg, Md. U.S.A.) is used, following the conditions suggested by the manufacturer.

Normalized libraries are made using essentially the Soares procedure (Soares et al., *Proc. Natl. Acad. Sci.* (*U.S.A.*) 91:9228-9232 (1994), the entirety of which is herein incorporated by reference). This approach is designed to reduce the initial 10,000-fold variation in individual cDNA frequencies to achieve abundances within one order of magnitude while maintaining the overall sequence complexity of the library. In the normalization process, the prevalence of high-abundance cDNA clones decreases dramatically, clones with mid-level abundance are relatively unaffected and clones for rare transcripts are effectively increased in abundance.

Normalized libraries are prepared from single-stranded and double-stranded DNA. Single-stranded and double-stranded DNA representing approximately $1 \times 10^6$ colony forming units are isolated using standard protocols. RNA, complementary to the single-stranded DNA, is synthesized using the double stranded DNA as a template. Biotinylated dATP is incorporated into the RNA during the synthesis reaction. The single-stranded DNA is mixed with the biotinylated RNA in a 1:10 molar ratio) and allowed to hybridize. DNA-RNA hybrids are captured on Dynabeads M280 streptavidin (Dynabeads, Dynal Corporation, Lake Success, N.Y. U.S.A.). The dynabeads with captured hybrids are collected with a magnet. The non-hybridized single-stranded molecules remaining after hybrid capture are converted to double stranded form and represent the primary normalized library.

For subtraction, target cDNA is made from the drought stressed tissue total RNA using the SMART cDNA synthesis system from Clonetech (Clonetech Laboratories, Palo Alto, Calif. U.S.A.). Driver first strand cDNA is covalently linked to Dynabeads following a protocol similar to that described in the Dynal literature (Dynabeads, Dynal Corporation, Lake Success, N.Y. U.S.A.). The target cDNA is then heat denatured and the second strand trapped using Dynabeads oligo-dT. The target second strand cDNA is then hybridized to the driver cDNA in 400 μl 2×SSPE for two rounds of hybridization at 65° C. and 20 hours. After each hybridization, the hybridization solution is removed from the system and the hybridized target cDNA removed from the driver by heat denaturation in water. After hybridization, the remaining cDNA is trapped with Dynabeads oligo-dT. The trapped cDNA is then amplified as in previous PCR based libraries and the resulting cDNA ligated into the pSPORT vector (Invitrogen, Carlsbad Calif. U.S.A.).

EXAMPLE 3

The cDNA libraries are plated on LB agar containing the appropriate antibiotics for selection and incubated at 37° for a sufficient time to allow the growth of individual colonies. Single colonies are individually placed in each well of a 96-well microtiter plates containing LB liquid including the selective antibiotics. The plates are incubated overnight at approximately 37° C. with gentle shaking to promote growth of the cultures. The plasmid DNA is isolated from each clone using Qiaprep plasmid isolation kits, using the conditions recommended by the manufacturer (Qiagen Inc., Santa Clara, Calif. U.S.A.).

Template plasmid DNA clones are used for subsequent sequencing. For sequencing, the ABI PRISM dRhodamine Terminator Cycle Sequencing Ready Reaction Kit with AmpliTaq® DNA Polymerase, FS, is used (PE Applied Biosystems, Foster City, Calif. U.S.A.).

EXAMPLE 4

Nucleic acid sequences that encode for the following tocopherol synthesis pathway enzymes: deoxyarabiono-heptulosonate-P-synthase; putative deoxyarabiono-heptulosonate-P-synthase; dehydroquinate synthase; dehydroquinate dehydratase; putative dehydroquinate dehydratase; shikimate dehydrogenase; shikimate kinase; enolpyruvylshikimate-P-synthase; chorismate synthase; chorismate mutase; tyrosine transaminase; putative tyrosine transaminase; transaminase A; putative transaminase A; 4-hydroxyphenylpyruvate dioxygenase; homogentisic acid dioxygenase; and geranylgeranylpyrophosphate synthase are identified from the Monsanto EST PhytoSeq database using TBLASTN (default values)(TBLASTN compares a protein query against the six reading frames of a nucleic acid sequence). Matches found with BLAST P values equal or less than 0.001 (probability) or BLAST Score of equal or greater than 90 are classified as hits. If the program used to determine the hit is HMMSW then the score refers to HMMSW score.

In addition, the GenBank database is searched with BLASTN and BLASTX (default values) using ESTs as queries. EST that pass the hit probability threshold of $10e^{-8}$ for the following enzymes are combined with the hits generated by using TBLASTN (described above) and classified by enzyme (see Table A below).

A cluster refers to a set of overlapping clones in the PhytoSeq database. Such an overlapping relationship among clones is designated as a "cluster" when BLAST scores from pairwise sequence comparisons of the member clones meets a predetermined minimum value or product score of 50 or more (Product Score=(BLAST SCORE×Percentage Identity)/(5×minimum [length (Seq1), length (Seq2)])).

Since clusters are formed on the basis of single-linkage relationships, it is possible for two non-overlapping clones to be members of the same cluster if, for instance, they both overlap a third clone with at least the predetermined minimum BLAST score (stringency). A cluster ID is arbitrarily assigned to all of those clones which belong to the same cluster at a given stringency and a particular clone will belong to only one cluster at a given stringency. If a cluster contains only a single clone (a "singleton"), then the cluster ID number will be negative, with an absolute value equal to the clone ID number of its single member. Clones grouped in a cluster in most cases represent a contiguous sequence.

TABLE A*

| Seq No. | Cluster ID | CloneID | Library | NCBI gi | Method | Score | P-value | % Ident |
|---|---|---|---|---|---|---|---|---|
| | | | deoxyarabiono-heptulosonate-P-synthase-maize | | | | | |
| 1 | -700223776 | 700223776H1 | SATMON011 | g2398680 | BLASTN | 388 | 1e-51 | 77 |
| 2 | -700260027 | 700260027H1 | SATMON017 | g169475 | BLASTX | 112 | 1e-10 | 75 |
| 3 | -700356188 | 700356188H1 | SATMON024 | g2398679 | BLASTX | 93 | 1e-13 | 78 |
| 4 | -700430072 | 700430072H1 | SATMONN01 | g2398679 | BLASTX | 180 | 1e-17 | 85 |
| 5 | 1228 | 700623827H1 | SATMON034 | g416252 | BLASTN | 1030 | 1e-105 | 87 |
| 6 | 1228 | 700452503H1 | SATMON028 | g416252 | BLASTN | 1141 | 1e-88 | 87 |
| 7 | 1228 | 700551557H1 | SATMON022 | g416252 | BLASTN | 547 | 1e-83 | 88 |
| 8 | 1228 | 700571345H1 | SATMON030 | g416252 | BLASTN | 712 | 1e-83 | 83 |
| 9 | 1228 | 700452527H1 | SATMON028 | g416252 | BLASTN | 908 | 1e-83 | 88 |
| 10 | 1228 | 700050505H1 | SATMON003 | g416252 | BLASTN | 1080 | 1e-83 | 90 |
| 11 | 1228 | 700551749H1 | SATMON022 | g416252 | BLASTN | 1029 | 1e-79 | 90 |
| 12 | 1228 | 700569172H1 | SATMON030 | g416252 | BLASTN | 993 | 1e-76 | 84 |
| 13 | 1228 | 700613721H1 | SATMON033 | g416252 | BLASTN | 491 | 1e-75 | 85 |
| 14 | 1228 | 700160395H1 | SATMON012 | g416252 | BLASTN | 969 | 1e-74 | 91 |
| 15 | 1228 | 701163236H1 | SATMONN04 | g416252 | BLASTN | 721 | 1e-73 | 84 |
| 16 | 1228 | 700267876H1 | SATMON017 | g416252 | BLASTN | 555 | 1e-65 | 86 |
| 17 | 1228 | 700096649H1 | SATMON008 | g169474 | BLASTN | 889 | 1e-65 | 79 |
| 18 | 1228 | 700346229H1 | SATMON021 | g166687 | BLASTN | 880 | 1e-64 | 78 |
| 19 | 1228 | 700259208H1 | SATMON017 | g169474 | BLASTN | 754 | 1e-63 | 76 |
| 20 | 1228 | 700454345H1 | SATMON029 | g416252 | BLASTN | 828 | 1e-62 | 86 |
| 21 | 1228 | 700151789H1 | SATMON007 | g416252 | BLASTN | 830 | 1e-62 | 87 |
| 22 | 1228 | 700803047H1 | SATMON036 | g169474 | BLASTN | 658 | 1e-61 | 77 |
| 23 | 1228 | 700049005H1 | SATMON003 | g416252 | BLASTN | 818 | 1e-61 | 89 |
| 24 | 1228 | 700617057H1 | SATMON033 | g170224 | BLASTN | 737 | 1e-60 | 79 |
| 25 | 1228 | 700204532H1 | SATMON003 | g2398680 | BLASTN | 486 | 1e-58 | 75 |
| 26 | 1228 | 700195344H1 | SATMON014 | g416252 | BLASTN | 774 | 1e-58 | 90 |
| 27 | 1228 | 700041845H1 | SATMON004 | g170224 | BLASTN | 806 | 1e-58 | 78 |
| 28 | 1228 | 700452030H1 | SATMON028 | g416252 | BLASTN | 574 | 1e-57 | 87 |
| 29 | 1228 | 700093451H1 | SATMON008 | g169474 | BLASTN | 511 | 1e-56 | 74 |
| 30 | 1228 | 700048096H1 | SATMON003 | g169474 | BLASTN | 774 | 1e-55 | 75 |
| 31 | 1228 | 700424054H1 | SATMONN01 | g170224 | BLASTN | 444 | 1e-54 | 81 |
| 32 | 1228 | 700448927H1 | SATMON028 | g416252 | BLASTN | 736 | 1e-54 | 83 |
| 33 | 1228 | 700579786H1 | SATMON031 | g169474 | BLASTN | 737 | 1e-52 | 74 |
| 34 | 1228 | 700168659H1 | SATMON013 | g169474 | BLASTN | 727 | 1e-51 | 79 |
| 35 | 1228 | 700150987H1 | SATMON007 | g166687 | BLASTN | 711 | 1e-50 | 81 |
| 36 | 1228 | 700022040H1 | SATMON001 | g294284 | BLASTN | 713 | 1e-50 | 80 |
| 37 | 1228 | 700449746H2 | SATMON028 | g416252 | BLASTN | 680 | 1e-49 | 90 |
| 38 | 1228 | 700165534H1 | SATMON013 | g169474 | BLASTN | 696 | 1e-49 | 76 |
| 39 | 1228 | 700257864H1 | SATMON017 | g169474 | BLASTN | 693 | 1e-48 | 78 |
| 40 | 1228 | 700452534H1 | SATMON028 | g416252 | BLASTN | 636 | 1e-45 | 85 |
| 41 | 1228 | 700042596H1 | SATMON004 | g416252 | BLASTN | 640 | 1e-45 | 84 |
| 42 | 1228 | 700151812H1 | SATMON007 | g416252 | BLASTN | 643 | 1e-45 | 89 |
| 43 | 1228 | 700421687H1 | SATMONN01 | g170224 | BLASTN | 646 | 1e-45 | 76 |
| 44 | 1228 | 700053344H1 | SATMON003 | g170224 | BLASTN | 657 | 1e-45 | 80 |
| 45 | 1228 | 701178585H1 | SATMONN05 | g166687 | BLASTN | 427 | 1e-44 | 80 |
| 46 | 1228 | 700239365H1 | SATMON010 | g170224 | BLASTN | 628 | 1e-43 | 80 |
| 47 | 1228 | 700153542H1 | SATMON007 | g169474 | BLASTN | 617 | 1e-42 | 76 |
| 48 | 1228 | 700380557H1 | SATMON021 | g416252 | BLASTN | 500 | 1e-41 | 90 |
| 49 | 1228 | 700570454H1 | SATMON030 | g170224 | BLASTN | 614 | 1e-41 | 79 |
| 50 | 1228 | 700264817H1 | SATMON017 | g169474 | BLASTN | 410 | 1e-39 | 75 |
| 51 | 1228 | 700153524H1 | SATMON007 | g169474 | BLASTN | 361 | 1e-37 | 77 |
| 52 | 1228 | 700618945H1 | SATMON034 | g416252 | BLASTN | 458 | 1e-36 | 79 |
| 53 | 1228 | 700193060H1 | SATMON014 | g1245452 | BLASTN | 547 | 1e-36 | 74 |
| 54 | 1228 | 700047557H1 | SATMON003 | g416252 | BLASTN | 511 | 1e-34 | 83 |
| 55 | 1228 | 700341009H1 | SATMON020 | g169474 | BLASTN | 324 | 1e-30 | 66 |
| 56 | 1228 | 700048589H1 | SATMON003 | g166689 | BLASTN | 409 | 1e-30 | 77 |
| 57 | 1228 | 700334956H1 | SATMON019 | g2398681 | BLASTN | 183 | 1e-26 | 85 |
| 58 | 1228 | 700027629H1 | SATMONN03 | g169475 | BLASTX | 189 | 1e-19 | 87 |
| 59 | 29578 | 700219020H1 | SATMON011 | g2398678 | BLASTN | 694 | 1e-49 | 72 |
| 60 | 3007 | 700153267H1 | SATMON007 | g2398678 | BLASTN | 587 | 1e-40 | 71 |
| 61 | 3007 | 700352639H1 | SATMON024 | g2398678 | BLASTN | 506 | 1e-33 | 70 |
| 62 | 3007 | 700259481H1 | SATMON017 | g2398678 | BLASTN | 268 | 1e-13 | 66 |
| 63 | 31415 | 700219261H1 | SATMON011 | g166689 | BLASTN | 501 | 1e-32 | 77 |
| 64 | 32242 | 700090119H1 | SATMON011 | g2398680 | BLASTN | 803 | 1e-58 | 76 |
| 65 | 3227 | 700268010H1 | SATMON017 | g2398680 | BLASTN | 773 | 1e-55 | 73 |
| 66 | 3227 | 700450763H1 | SATMON028 | g166689 | BLASTN | 713 | 1e-50 | 73 |
| 67 | 3227 | 700241730H1 | SATMON010 | g2398680 | BLASTN | 686 | 1e-48 | 73 |
| 68 | 3227 | 700071633H1 | SATMON007 | g166689 | BLASTN | 628 | 1e-43 | 71 |
| 69 | 3227 | 700267002H1 | SATMON017 | g169474 | BLASTN | 446 | 1e-26 | 74 |
| 70 | 3227 | 700452543H1 | SATMON028 | g2546987 | BLASTN | 281 | 1e-25 | 75 |
| 71 | 5023 | 700378721H1 | SATMON020 | g2546988 | BLASTX | 183 | 1e-18 | 94 |
| 72 | -L1487205 | LIB148-064-Q1-E1-F6 | LIB148 | g2398679 | BLASTX | 296 | 1e-53 | 59 |
| 73 | -L30622733 | LIB3062-014-Q1-K1-D2 | LIB3062 | g2546987 | BLASTN | 484 | 1e-31 | 68 |
| 74 | -L30622734 | LIB3062-014-Q1-K1-D6 | LIB3062 | g416252 | BLASTN | 479 | 1e-29 | 68 |

TABLE A*-continued

| Seq No. | Cluster ID | CloneID | Library | NCBI gi | Method | Score | P-value | % Ident |
|---|---|---|---|---|---|---|---|---|
| 75 | -L30661773 | LIB3066-011-Q1-K1-D6 | LIB3066 | g170224 | BLASTN | 747 | 1e-52 | 70 |
| 76 | -L30664853 | LIB3066-031-Q1-K1-F6 | LIB3066 | g169474 | BLASTN | 1139 | 1e-86 | 72 |
| 77 | -L30685059 | LIB3068-008-Q1-K1-A11 | LIB3068 | g166687 | BLASTN | 450 | 1e-26 | 64 |
| 78 | -L30691358 | LIB3069-002-Q1-K1-D6 | LIB3069 | g2398680 | BLASTN | 466 | 1e-28 | 60 |
| 79 | 1228 | LIB3062-032-Q1-K1-F11 | LIB3062 | g416252 | BLASTN | 1508 | 1e-119 | 88 |
| 80 | 1228 | LIB143-004-Q1-E1-H9 | LIB143 | g169474 | BLASTN | 1221 | 1e-92 | 78 |
| 81 | 1228 | LIB3069-027-Q1-K1-E11 | LIB3069 | g169474 | BLASTN | 746 | 1e-91 | 77 |
| 82 | 1228 | LIB143-045-Q1-E1-F10 | LIB143 | g170224 | BLASTN | 1056 | 1e-79 | 77 |
| 83 | 1228 | LIB3069-001-Q1-K1-E2 | LIB3069 | g416252 | BLASTN | 598 | 1e-78 | 87 |
| 84 | 1228 | LIB3068-006-Q1-K1-F10 | LIB3068 | g169474 | BLASTN | 1048 | 1e-78 | 74 |
| 85 | 1228 | LIB3062-008-Q1-K1-A5 | LIB3062 | g169474 | BLASTN | 806 | 1e-75 | 79 |
| 86 | 1228 | LIB148-045-Q1-E1-G7 | LIB148 | g2398678 | BLASTN | 735 | 1e-60 | 72 |
| 87 | 1228 | LIB3068-034-Q1-K1-E6 | LIB3068 | g170224 | BLASTN | 819 | 1e-59 | 78 |
| 88 | 1228 | LIB3061-040-Q1-K1-B8 | LIB3061 | g170224 | BLASTN | 771 | 1e-54 | 80 |
| 89 | 1228 | LIB143-024-Q1-E1-B4 | LIB143 | g169474 | BLASTN | 736 | 1e-50 | 73 |
| 90 | 1228 | LIB3068-032-Q1-K1-D10 | LIB3068 | g169474 | BLASTN | 598 | 1e-39 | 72 |
| 91 | 24030 | LIB3066-047-Q1-K1-A9 | LIB3066 | g170225 | BLASTN | 121 | 1e-30 | 57 |
| 92 | 29578 | LIB3066-011-Q1-K1-D4 | LIB3066 | g2546987 | BLASTN | 1212 | 1e-92 | 75 |
| 93 | 29578 | LIB148-058-Q1-E1-F2 | LIB148 | g169474 | BLASTN | 680 | 1e-47 | 72 |
| 94 | 31415 | LIB148-009-Q1-E1-E8 | LIB148 | g2398680 | BLASTN | 492 | 1e-29 | 74 |
| 95 | 32242 | LIB148-018-Q1-E1-B2 | LIB148 | g2398680 | BLASTN | 1280 | 1e-97 | 76 |
| 96 | 32242 | LIB3067-058-Q1-K1-C8 | LIB3067 | g2398680 | BLASTN | 1079 | 1e-81 | 76 |
| 97 | 5023 | LIB3079-006-Q1-K1-D10 | LIB3079 | g2398681 | BLASTX | 143 | 1e-28 | 88 |
| | | putative deoxyarabiono-heptulosonate-P-synthase-maize | | | | | | |
| 98 | -701178041 | 701178041H1 | SATMONN05 | g1742787 | BLASTX | 121 | 1e-9 | 49 |
| 99 | 13211 | 700267210H1 | SATMON017 | g1742787 | BLASTX | 72 | 1e-9 | 59 |
| | | deoxyarabiono-heptulosonate-P-synthase-soybean | | | | | | |
| 100 | -700750583 | 700750583H1 | SOYMON014 | g169475 | BLASTX | 149 | 1e-13 | 78 |
| 101 | -700756739 | 700756739H1 | SOYMON014 | g410315 | BLASTX | 170 | 1e-21 | 55 |
| 102 | -700897290 | 700897290H1 | SOYMON027 | g1245452 | BLASTN | 1047 | 1e-78 | 93 |
| 103 | -700953858 | 700953858H1 | SOYMON022 | g2398678 | BLASTN | 673 | 1e-47 | 74 |
| 104 | -700958333 | 700958333H1 | SOYMON022 | g2398678 | BLASTN | 531 | 1e-35 | 77 |
| 105 | -701212422 | 701212422H1 | SOYMON035 | g410487 | BLASTN | 527 | 1e-35 | 77 |
| 106 | 11948 | 701214211H1 | SOYMON035 | g2398678 | BLASTN | 860 | 1e-62 | 79 |
| 107 | 11948 | 700941217H1 | SOYMON024 | g2398678 | BLASTN | 843 | 1e-61 | 79 |
| 108 | 11948 | 700749762H1 | SOYMON013 | g2398678 | BLASTN | 659 | 1e-58 | 79 |
| 109 | 11948 | 701015341H1 | SOYMON019 | g169474 | BLASTN | 758 | 1e-54 | 78 |
| 110 | 11948 | 700787714H2 | SOYMON011 | g169474 | BLASTN | 613 | 1e-42 | 80 |
| 111 | 11948 | 700963862H1 | SOYMON022 | g2398678 | BLASTN | 581 | 1e-39 | 78 |
| 112 | 11948 | 701144405H1 | SOYMON031 | g2546987 | BLASTN | 266 | 1e-27 | 71 |
| 113 | 11948 | 700897376H1 | SOYMON027 | g2398679 | BLASTX | 136 | 1e-21 | 85 |
| 114 | 12144 | 700564714H1 | SOYMON002 | g170225 | BLASTX | 78 | 1e-14 | 54 |
| 115 | 12144 | 701036988H1 | SOYMON029 | g170225 | BLASTX | 64 | 1e-10 | 55 |
| 116 | 12144 | 701142430H1 | SOYMON038 | g170225 | BLASTX | 66 | 1e-10 | 52 |
| 117 | 18499 | 700746365H1 | SOYMON013 | g1245452 | BLASTN | 726 | 1e-62 | 85 |
| 118 | 18499 | 700565543H1 | SOYMON002 | g1245452 | BLASTN | 700 | 1e-49 | 88 |
| 119 | 19009 | 700953162H1 | SOYMON022 | g166689 | BLASTN | 679 | 1e-47 | 74 |
| 120 | 19009 | 700681944H1 | SOYMON008 | g2398680 | BLASTN | 613 | 1e-42 | 77 |
| 121 | 19576 | 701097076H1 | SOYMON028 | g1245452 | BLASTN | 1156 | 1e-87 | 92 |
| 122 | 19576 | 700669658H1 | SOYMON006 | g1245452 | BLASTN | 895 | 1e-65 | 90 |
| 123 | 19576 | 700656892H1 | SOYMON004 | g410487 | BLASTN | 410 | 1e-48 | 79 |
| 124 | 5102 | 700901033H1 | SOYMON027 | g2398678 | BLASTN | 894 | 1e-65 | 82 |
| 125 | 5102 | 700901290H1 | SOYMON027 | g2398678 | BLASTN | 837 | 1e-60 | 82 |
| 126 | 5102 | 701051386H1 | SOYMON032 | g170224 | BLASTN | 819 | 1e-59 | 81 |
| 127 | 5102 | 700755856H1 | SOYMON014 | g170224 | BLASTN | 782 | 1e-56 | 82 |
| 128 | 5102 | 701145291H1 | SOYMON031 | g170224 | BLASTN | 487 | 1e-48 | 80 |
| 129 | 5234 | 700565904H1 | SOYMON002 | g2398678 | BLASTN | 584 | 1e-77 | 84 |
| 130 | 5234 | 701138971H1 | SOYMON038 | g2398678 | BLASTN | 946 | 1e-70 | 84 |
| 131 | 5234 | 700725760H1 | SOYMON009 | g2398678 | BLASTN | 908 | 1e-66 | 82 |
| 132 | 5234 | 701097139H1 | SOYMON028 | g2398678 | BLASTN | 772 | 1e-55 | 79 |
| 133 | 5234 | 700952432H1 | SOYMON022 | g2398680 | BLASTN | 689 | 1e-48 | 81 |
| 134 | 5234 | 700996417H1 | SOYMON018 | g410487 | BLASTN | 468 | 1e-40 | 81 |
| 135 | 5699 | 701040351H1 | SOYMON029 | g166690 | BLASTX | 203 | 1e-21 | 69 |
| 136 | 5699 | 700847113H1 | SOYMON021 | g2398679 | BLASTX | 147 | 1e-13 | 72 |
| 137 | 5699 | 700967767H1 | SOYMON033 | g166690 | BLASTX | 149 | 1e-13 | 63 |
| 138 | 5699 | 700841638H1 | SOYMON020 | g166690 | BLASTX | 141 | 1e-12 | 62 |
| 139 | 5699 | 700891749H1 | SOYMON024 | g410486 | BLASTX | 127 | 1e-10 | 76 |
| 140 | 5699 | 700990984H1 | SOYMON011 | g2398679 | BLASTX | 127 | 1e-10 | 67 |
| 141 | 5699 | 700740310H1 | SOYMON012 | g410486 | BLASTX | 127 | 1e-10 | 76 |
| 142 | 5699 | 700834916H1 | SOYMON019 | g294285 | BLASTX | 117 | 1e-9 | 77 |
| 143 | 6819 | 700652910H1 | SOYMON003 | g1245452 | BLASTN | 1408 | 1e-109 | 89 |
| 144 | 6819 | 700761928H1 | SOYMON015 | g1245452 | BLASTN | 924 | 1e-68 | 89 |
| 145 | 6935 | 700987126H1 | SOYMON009 | g2398678 | BLASTN | 667 | 1e-46 | 72 |
| 146 | 6935 | 700734128H1 | SOYMON010 | g169474 | BLASTN | 533 | 1e-35 | 72 |

TABLE A*-continued

| Seq No. | Cluster ID | CloneID | Library | NCBI gi | Method | Score | P-value | % Ident |
|---|---|---|---|---|---|---|---|---|
| | | | putative deoxyarabiono-heptulosonate-P-synthase-soybean | | | | | |
| 147 | -700891658 | 700891658H1 | SOYMON024 | g1742787 | BLASTX | 119 | 1e−9 | 40 |
| 148 | -701148391 | 701148391H1 | SOYMON031 | g1742787 | BLASTX | 109 | 1e−9 | 43 |
| 149 | 4075 | 700992239H1 | SOYMON011 | g1742787 | BLASTX | 66 | 1e−9 | 40 |
| 150 | 4075 | 700686128H1 | SOYMON008 | g1742787 | BLASTX | 62 | 1e−8 | 39 |
| 151 | 19576 | LIB3029-012-Q1-B1-B5 | LIB3029 | g2546987 | BLASTN | 1280 | 1e−97 | 80 |
| 152 | 5699 | LIB3052-011-Q1-N1-E8 | LIB3052 | g166690 | BLASTX | 187 | 1e−39 | 56 |
| | | | dehydroquinate synthase-maize | | | | | |
| 153 | -700257536 | 700257536H1 | SATMON017 | g309862 | BLASTX | 102 | 1e−21 | 69 |
| 154 | 28069 | 700203301H1 | SATMON003 | g1789791 | BLASTX | 140 | 1e−16 | 50 |
| 155 | 7410 | 700225526H1 | SATMON011 | g1619336 | BLASTX | 149 | 1e−21 | 56 |
| 156 | 7410 | 700347409H1 | SATMON023 | g40968 | BLASTX | 83 | 1e−16 | 55 |
| 157 | 28069 | LIB189-001-Q1-E1-D4 | LIB189 | g1789791 | BLASTX | 281 | 1e−48 | 57 |
| | | | putative dehydroquinate dehydratase-maize | | | | | |
| 158 | -700237972 | 700237972H1 | SATMON010 | g535771 | BLASTX | 136 | 1e−18 | 69 |
| 159 | 11022 | 700155850H1 | SATMON007 | g535771 | BLASTX | 247 | 1e−27 | 65 |
| | | | dehydroquinate dehydratase-soybean | | | | | |
| 160 | 4639 | 700834936H1 | SOYMON019 | g535771 | BLASTX | 150 | 1e−20 | 55 |
| | | | Shikimate dehydrogenase-maize | | | | | |
| 158 | -700237972 | 700237972H1 | SATMON010 | g535771 | BLASTX | 136 | 1e−18 | 69 |
| 159 | 11022 | 700155850H1 | SATMON007 | g535771 | BLASTX | 247 | 1e−27 | 65 |
| | | | Shikimate dehydrogenase-soybean | | | | | |
| 160 | 4639 | 700834936H1 | SOYMON019 | g535771 | BLASTX | 150 | 1e−20 | 55 |
| | | | Shikimate kinase-maize | | | | | |
| 161 | -700050913 | 700050913H1 | SATMON003 | g19348 | BLASTN | 403 | 1e−28 | 69 |
| 162 | -700104390 | 700104390H1 | SATMON010 | g19348 | BLASTN | 446 | 1e−26 | 64 |
| 163 | -700452495 | 700452495H1 | SATMON028 | g19348 | BLASTX | 81 | 1e−13 | 57 |
| 164 | -700619865 | 700619865H1 | SATMON034 | g19349 | BLASTX | 142 | 1e−12 | 65 |
| 165 | 15996 | 700030278H1 | SATMON003 | g19349 | BLASTX | 219 | 1e−33 | 66 |
| 166 | 15996 | 700257047H1 | SATMON017 | g19348 | BLASTN | 399 | 1e−32 | 66 |
| 167 | 15996 | 700237902H1 | SATMON010 | g19348 | BLASTN | 472 | 1e−28 | 64 |
| 168 | 15996 | 700155641H1 | SATMON007 | g19348 | BLASTN | 438 | 1e−27 | 66 |
| 169 | 15996 | 700224589H1 | SATMON011 | g19348 | BLASTN | 447 | 1e−27 | 64 |
| 170 | 18563 | 700205659H1 | SATMON003 | g19348 | BLASTN | 443 | 1e−39 | 67 |
| 171 | 18563 | 700243143H1 | SATMON010 | g19349 | BLASTX | 274 | 1e−31 | 64 |
| 172 | 18563 | 700264692H1 | SATMON017 | g19348 | BLASTN | 501 | 1e−31 | 63 |
| 173 | 18563 | 700106054H1 | SATMON010 | g19348 | BLASTN | 280 | 1e−27 | 63 |
| 174 | 18563 | 700026972H1 | SATMON003 | g19349 | BLASTX | 159 | 1e−26 | 66 |
| 175 | 18563 | 700160974H1 | SATMON012 | g19349 | BLASTX | 167 | 1e−17 | 57 |
| 176 | 6303 | 700088964H1 | SATMON011 | g19348 | BLASTN | 470 | 1e−28 | 62 |
| 177 | 6303 | 700572756H1 | SATMON030 | g19349 | BLASTX | 113 | 1e−18 | 60 |
| 178 | 15635 | LIB36-001-Q1-E1-F1 | LIB36 | g19349 | BLASTX | 149 | 1e−28 | 31 |
| 179 | 18563 | LIB3066-029-Q1-K1-G8 | LIB3066 | g19348 | BLASTN | 870 | 1e−63 | 67 |
| | | | Shikimate kinase-soybean | | | | | |
| 180 | -700568344 | 700568344H1 | SOYMON002 | g19349 | BLASTX | 126 | 1e−15 | 42 |
| 181 | -700792015 | 700792015H1 | SOYMON011 | g19348 | BLASTN | 652 | 1e−45 | 72 |
| 182 | 18190 | 700977239H1 | SOYMON009 | g19349 | BLASTX | 97 | 1e−10 | 41 |
| 183 | 18190 | LIB3055-003-Q1-N1-D12 | LIB3055 | g19349 | BLASTX | 139 | 1e−28 | 36 |
| | | | Enolpyruvylshikimate-P-synthase-soybean | | | | | |
| 184 | -700831419 | 700831419H1 | SOYMON019 | g169190 | BLASTN | 453 | 1e−50 | 80 |
| 185 | -700845353 | 700845353H1 | SOYMON021 | g170373 | BLASTN | 629 | 1e−43 | 76 |
| 186 | -700891187 | 700891187H1 | SOYMON024 | g170373 | BLASTN | 620 | 1e−42 | 74 |
| 187 | -700976722 | 700976722H1 | SOYMON009 | g170373 | BLASTN | 774 | 1e−55 | 75 |
| 188 | -700997285 | 700997285H1 | SOYMON018 | g170374 | BLASTN | 124 | 1e−11 | 86 |
| 189 | -701048471 | 701048471H1 | SOYMON032 | g170228 | BLASTN | 886 | 1e−64 | 82 |
| 190 | -701206839 | 701206839H1 | SOYMON035 | g17815 | BLASTX | 154 | 1e−14 | 88 |
| 191 | 17068 | 700942983H1 | SOYMON024 | g169190 | BLASTN | 571 | 1e−58 | 82 |
| 192 | 17068 | 701006194H1 | SOYMON019 | g169190 | BLASTN | 349 | 1e−53 | 79 |
| 193 | 18050 | 700906275H1 | SOYMON022 | g169190 | BLASTN | 868 | 1e−63 | 81 |
| 194 | 18050 | 701134508H1 | SOYMON038 | g169190 | BLASTN | 457 | 1e−60 | 80 |
| 195 | 3411 | 700556807H1 | SOYMON001 | g169190 | BLASTN | 568 | 1e−77 | 83 |
| 196 | 3411 | 700565035H1 | SOYMON002 | g169190 | BLASTN | 913 | 1e−67 | 79 |
| 197 | 3411 | 701008536H1 | SOYMON019 | g169190 | BLASTN | 622 | 1e−56 | 80 |
| 198 | 3411 | 701107917H1 | SOYMON036 | g170228 | BLASTN | 498 | 1e−32 | 84 |
| | | | Chorismate synthase-maize | | | | | |
| 199 | -700104711 | 700104711H1 | SATMON010 | g976374 | BLASTN | 490 | 1e−30 | 70 |

TABLE A*-continued

| Seq No. | Cluster ID | CloneID | Library | NCBI gi | Method | Score | P-value | % Ident |
|---|---|---|---|---|---|---|---|---|
| 200 | 10770 | 700092595H1 | SATMON008 | g410484 | BLASTX | 207 | 1e-21 | 70 |
| 201 | 10770 | 700088420H1 | SATMON011 | g410484 | BLASTX | 191 | 1e-19 | 68 |
| 202 | 10770 | 700333085H1 | SATMON019 | g410484 | BLASTX | 104 | 1e-13 | 67 |
| 203 | 2026 | 700282007H1 | SATMON022 | g410481 | BLASTN | 884 | 1e-64 | 77 |
| 204 | 2026 | 700077339H1 | SATMON007 | g410481 | BLASTN | 612 | 1e-59 | 75 |
| 205 | 2026 | 700571731H1 | SATMON030 | g410481 | BLASTN | 670 | 1e-54 | 77 |
| 206 | 2026 | 700348949H1 | SATMON023 | g410481 | BLASTN | 463 | 1e-53 | 77 |
| 207 | 2026 | 700090790H1 | SATMON011 | g18255 | BLASTN | 694 | 1e-49 | 71 |
| 208 | 2026 | 700236685H1 | SATMON010 | g18255 | BLASTN | 704 | 1e-49 | 77 |
| 209 | 2026 | 700166396H1 | SATMON013 | g410481 | BLASTN | 674 | 1e-47 | 76 |
| 210 | 2026 | 700466807H1 | SATMON025 | g18255 | BLASTN | 452 | 1e-43 | 71 |
| 211 | 2026 | 700335877H1 | SATMON019 | g410481 | BLASTN | 532 | 1e-35 | 74 |
| 212 | 4211 | 700259039H1 | SATMON017 | g18256 | BLASTX | 167 | 1e-18 | 60 |
| 213 | 4211 | 700457104H1 | SATMON029 | g410484 | BLASTX | 186 | 1e-18 | 75 |
| 214 | 4211 | 700153433H1 | SATMON007 | g410482 | BLASTX | 114 | 1e-14 | 68 |
| 215 | 4211 | 700073550H1 | SATMON007 | g18256 | BLASTX | 147 | 1e-13 | 61 |
| 216 | 4211 | 700224255H1 | SATMON011 | g18255 | BLASTX | 290 | 1e-13 | 67 |
| 217 | 4211 | 700440561H1 | SATMON026 | g410482 | BLASTX | 115 | 1e-8 | 66 |
| 218 | 9237 | 700105367H1 | SATMON010 | g410483 | BLASTX | 773 | 1e-55 | 73 |
| 219 | 9237 | 700337228H1 | SATMON020 | g18255 | BLASTN | 776 | 1e-55 | 73 |
| 220 | 9237 | 700159709H1 | SATMON012 | g18255 | BLASTN | 742 | 1e-53 | 76 |
| 221 | 9237 | 700242181H1 | SATMON010 | g410483 | BLASTX | 588 | 1e-40 | 71 |
| 222 | 9237 | 700168082H1 | SATMON013 | g18255 | BLASTN | 521 | 1e-34 | 73 |
| 223 | 9237 | 700169319H1 | SATMON013 | g18255 | BLASTN | 465 | 1e-29 | 78 |
| 224 | 9237 | 700172250H1 | SATMON013 | g18255 | BLASTN | 308 | 1e-15 | 71 |
| 225 | 9237 | 700584289H1 | SATMON031 | g410484 | BLASTX | 93 | 1e-8 | 69 |
| 226 | -L1434254 | LIB143-041-Q1-E1-F6 | LIB143 | g18255 | BLASTN | 541 | 1e-34 | 68 |
| 227 | -L30781785 | LIB3078-015-Q1-K1-E5 | LIB3078 | g410481 | BLASTN | 766 | 1e-55 | 67 |
| 228 | 2026 | LIB3066-009-Q1-K1-C12 | LIB3066 | g410481 | BLASTN | 1124 | 1e-84 | 75 |
| 229 | 2026 | LIB3078-012-Q1-K1-C8 | LIB3078 | g410481 | BLASTN | 992 | 1e-73 | 78 |
| 230 | 2026 | LIB84-014-Q1-E1-D4 | LIB84 | g410481 | BLASTN | 517 | 1e-32 | 77 |
| 231 | 9237 | LIB3067-014-Q1-K1-C5 | LIB3067 | g410484 | BLASTX | 219 | 1e-39 | 74 |
| | | | Chorismate synthase-soybean | | | | | |
| 232 | -700829731 | 700829731H1 | SOYMON019 | g410482 | BLASTX | 163 | 1e-15 | 81 |
| 233 | -700867002 | 700867002H1 | SOYMON016 | g18255 | BLASTN | 871 | 1e-63 | 82 |
| 234 | -700941055 | 700941055H1 | SOYMON024 | g18257 | BLASTN | 621 | 1e-42 | 73 |
| 235 | -700993596 | 700993596H1 | SOYMON011 | g410482 | BLASTX | 648 | 1e-56 | 80 |
| 236 | -701107074 | 701107074H1 | SOYMON036 | g410482 | BLASTX | 119 | 1e-9 | 77 |
| 237 | -701215158 | 701215158H1 | SOYMON035 | g18255 | BLASTN | 404 | 1e-33 | 82 |
| 238 | 11113 | 700792218H1 | SOYMON011 | g18257 | BLASTN | 549 | 1e-36 | 71 |
| 239 | 11113 | 701037327H1 | SOYMON029 | g18257 | BLASTN | 535 | 1e-35 | 70 |
| 240 | 20587 | 701042739H1 | SOYMON029 | g18257 | BLASTN | 537 | 1e-35 | 70 |
| 241 | 20587 | 700565645H1 | SOYMON002 | g18257 | BLASTN | 427 | 1e-31 | 73 |
| 242 | 24472 | 701053135H1 | SOYMON032 | g18255 | BLASTN | 927 | 1e-68 | 78 |
| 243 | 24472 | 700875233H1 | SOYMON018 | g410481 | BLASTN | 843 | 1e-61 | 81 |
| 244 | 6572 | 700652322H1 | SOYMON003 | g18255 | BLASTN | 722 | 1e-65 | 82 |
| 245 | 6572 | 701107063H1 | SOYMON036 | g18255 | BLASTN | 451 | 1e-58 | 81 |
| 246 | 6572 | 701139518H1 | SOYMON038 | g18255 | BLASTN | 682 | 1e-48 | 80 |
| 247 | 6572 | 700653111H1 | SOYMON003 | g410481 | BLASTN | 585 | 1e-39 | 81 |
| 248 | 6572 | 701008289H1 | SOYMON019 | g410481 | BLASTN | 545 | 1e-36 | 76 |
| 249 | 6572 | 701124777H1 | SOYMON037 | g18255 | BLASTN | 446 | 1e-27 | 80 |
| 250 | 6572 | 700556802H1 | SOYMON001 | g410482 | BLASTX | 161 | 1e-19 | 80 |
| 251 | 6572 | 700834126H1 | SOYMON019 | g410482 | BLASTX | 131 | 1e-16 | 77 |
| 252 | 6572 | 700645571H1 | SOYMON009 | g410482 | BLASTX | 172 | 1e-16 | 87 |
| 253 | 6572 | 700834378H1 | SOYMON019 | g18255 | BLASTN | 154 | 1e-15 | 77 |
| 254 | 6572 | 700990811H1 | SOYMON011 | g410484 | BLASTX | 107 | 1e-9 | 69 |
| 255 | 6572 | LIB3030-002-Q1-B1-F12 | LIB3030 | g18255 | BLASTN | 854 | 1e-62 | 77 |
| | | | Chorismate mutase-maize | | | | | |
| 256 | -700050713 | 700050713H1 | SATMON003 | g429153 | BLASTX | 159 | 1e-23 | 81 |
| 257 | -700239884 | 700239884H1 | SATMON010 | g429153 | BLASTX | 146 | 1e-13 | 40 |
| 258 | -700573382 | 700573382H1 | SATMON030 | g429152 | BLASTX | 349 | 1e-18 | 72 |
| 259 | 25556 | 700343477H1 | SATMON021 | g2352928 | BLASTN | 502 | 1e-35 | 70 |
| 260 | 25556 | 700194568H1 | SATMON014 | g429153 | BLASTX | 209 | 1e-21 | 65 |
| 261 | 25556 | 700196845H1 | SATMON014 | g429153 | BLASTX | 97 | 1e-10 | 46 |
| 262 | 32994 | 700089092H1 | SATMON011 | g429153 | BLASTX | 110 | 1e-15 | 48 |
| 263 | 32994 | 700203014H1 | SATMON003 | g429153 | BLASTX | 117 | 1e-9 | 43 |
| 264 | 3773 | 700048888H1 | SATMON003 | g429153 | BLASTX | 91 | 1e-24 | 72 |
| 265 | 3773 | 700090144H1 | SATMON011 | g429153 | BLASTX | 182 | 1e-18 | 55 |
| 266 | 3773 | 700221335H1 | SATMON011 | g429153 | BLASTX | 109 | 1e-10 | 49 |
| 267 | 8783 | 700574324H2 | SATMON030 | g429152 | BLASTN | 290 | 1e-13 | 73 |
| 268 | 8783 | 700164106H1 | SATMON013 | g429153 | BLASTX | 87 | 1e-9 | 58 |
| 269 | 25556 | LIB3062-059-Q1-K1-H12 | LIB3062 | g2352928 | BLASTN | 502 | 1e-33 | 70 |
| 270 | 25556 | LIB3062-023-Q1-K1-F12 | LIB3062 | g2352928 | BLASTN | 493 | 1e-32 | 70 |
| 271 | 25556 | LIB3059-001-Q1-K2-E4 | LIB3059 | g2352928 | BLASTN | 443 | 1e-28 | 68 |

TABLE A*-continued

| Seq No. | Cluster ID | CloneID | Library | NCBI gi | Method | Score | P-value | % Ident |
|---|---|---|---|---|---|---|---|---|
| 272 | 25556 | LIB3069-042-Q1-K1-E10 | LIB3069 | g429152 | BLASTN | 260 | 1e−10 | 71 |
| 273 | 32994 | LIB189-013-Q1-E1-G8 | LIB189 | g429153 | BLASTX | 150 | 1e−36 | 45 |
| 274 | 3773 | LIB3062-011-Q1-K1-E11 | LIB3062 | g429152 | BLASTX | 621 | 1e−41 | 73 |
| 275 | 3773 | LIB3061-006-Q1-K1-B5 | LIB3061 | g429152 | BLASTN | 408 | 1e−40 | 72 |
| 276 | 3773 | LIB3061-035-Q1-K1-B12 | LIB3061 | g429152 | BLASTN | 319 | 1e−15 | 77 |
| 277 | 8783 | LIB3059-017-Q1-K1-C2 | LIB3059 | g429152 | BLASTN | 357 | 1e−18 | 66 |
| | | | Chorismate mutase-soybean | | | | | |
| 278 | -700649675 | 700649675H1 | SOYMON003 | g429153 | BLASTX | 207 | 1e−21 | 62 |
| 279 | 24797 | 701123012H1 | SOYMON037 | g3021541 | BLASTN | 525 | 1e−37 | 75 |
| 280 | 24797 | 701149634H1 | SOYMON031 | g3021541 | BLASTN | 520 | 1e−36 | 75 |
| 281 | 7212 | 700646325H1 | SOYMON013 | g429153 | BLASTX | 116 | 1e−8 | 65 |
| 282 | -GM22414 | LIB3030-009-Q1-B1-B5 | LIB3030 | g429153 | BLASTX | 134 | 1e−39 | 59 |
| 283 | -GM29291 | LIB3050-017-Q1-E1-E9 | LIB3050 | g2352930 | BLASTN | 473 | 1e−30 | 66 |
| 284 | -GM30547 | LIB3050-004-Q1-E1-G9 | LIB3050 | g429153 | BLASTX | 153 | 1e−29 | 64 |
| | | | tyrosine transaminase-maize | | | | | |
| 285 | 16305 | 700337451H1 | SATMON020 | g408894 | BLASTX | 134 | 1e−11 | 33 |
| 286 | 16305 | 700340103H1 | SATMON020 | g408894 | BLASTX | 93 | 1e−10 | 39 |
| | | | putative tyrosine transaminase-maize | | | | | |
| 287 | 14653 | 700220061H1 | SATMON011 | g2842484 | BLASTX | 349 | 1e−41 | 70 |
| 288 | 22902 | 700106817H1 | SATMON010 | g2842484 | BLASTX | 331 | 1e−38 | 58 |
| 289 | 22902 | 701181789H1 | SATMONN06 | g2842484 | BLASTX | 278 | 1e−31 | 62 |
| 290 | 6658 | 700442825H1 | SATMON026 | g2842484 | BLASTX | 209 | 1e−26 | 62 |
| 291 | 6658 | 700152030H1 | SATMON007 | g2842484 | BLASTX | 128 | 1e−18 | 53 |
| 292 | 6658 | LIB3066-020-Q1-K1-F1 | LIB3066 | g2842484 | BLASTX | 348 | 1e−64 | 57 |
| | | | putative tyrosine transaminase-soybean | | | | | |
| 293 | -700848909 | 700848909H1 | SOYMON021 | g2842484 | BLASTX | 281 | 1e−31 | 62 |
| 294 | -700900410 | 700900410H1 | SOYMON027 | g2842484 | BLASTX | 119 | 1e−11 | 42 |
| 295 | 17700 | 700905146H1 | SOYMON022 | g2842484 | BLASTX | 315 | 1e−36 | 67 |
| 296 | 2201 | 700730931H1 | SOYMON009 | g2842484 | BLASTX | 174 | 1e−17 | 43 |
| 297 | 2201 | 700752627H1 | SOYMON014 | g2842484 | BLASTX | 102 | 1e−12 | 41 |
| 298 | 94 | 700658292H1 | SOYMON004 | g2842484 | BLASTX | 100 | 1e−18 | 53 |
| 299 | 6064 | LIB3056-002-Q1-B1-A8 | LIB3056 | g2842484 | BLASTX | 124 | 1e−25 | 34 |
| 300 | 94 | LIB3051-101-Q1-K1-H3 | LIB3051 | g2842484 | BLASTX | 205 | 1e−37 | 44 |
| | | | Transaminase A-maize | | | | | |
| 301 | -700028003 | 700028003H1 | SATMON003 | g63066 | BLASTX | 125 | 1e−10 | 79 |
| 302 | -700072842 | 700072842H1 | SATMON007 | g1001121 | BLASTX | 259 | 1e−28 | 50 |
| 303 | -700194011 | 700194011H1 | SATMON014 | g435456 | BLASTX | 324 | 1e−18 | 73 |
| 304 | -700196486 | 700196486H1 | SATMON014 | g20599 | BLASTX | 68 | 1e−10 | 74 |
| 305 | -700331820 | 700331820H1 | SATMON019 | g20600 | BLASTN | 1192 | 1e−90 | 90 |
| 306 | -700454550 | 700454550H1 | SATMON029 | g435458 | BLASTN | 198 | 1e−20 | 82 |
| 307 | -700454567 | 700454567H1 | SATMON029 | g435458 | BLASTN | 333 | 1e−24 | 82 |
| 308 | -700454642 | 700454642H1 | SATMON029 | g435458 | BLASTN | 269 | 1e−23 | 89 |
| 309 | -700454849 | 700454849H1 | SATMON029 | g435458 | BLASTN | 318 | 1e−26 | 87 |
| 310 | -700468560 | 700468560H1 | SATMON025 | g3328816 | BLASTX | 139 | 1e−19 | 58 |
| 311 | -700476413 | 700476413H1 | SATMON025 | g2984217 | BLASTX | 156 | 1e−22 | 52 |
| 312 | -700615109 | 700615109H1 | SATMON033 | g20598 | BLASTN | 256 | 1e−17 | 81 |
| 313 | -701161385 | 701161385H1 | SATMONN04 | g435458 | BLASTN | 523 | 1e−45 | 80 |
| 314 | 10165 | 700341126H1 | SATMON020 | g20596 | BLASTN | 743 | 1e−71 | 91 |
| 315 | 10165 | 700160220H1 | SATMON012 | g20596 | BLASTN | 769 | 1e−55 | 92 |
| 316 | 10165 | 700158802H1 | SATMON012 | g20596 | BLASTN | 617 | 1e−42 | 94 |
| 317 | 10192 | 700204319H1 | SATMON003 | g2984217 | BLASTX | 148 | 1e−13 | 55 |
| 318 | 10329 | 700095671H1 | SATMON008 | g20600 | BLASTN | 816 | 1e−59 | 87 |
| 319 | 10329 | 700214146H1 | SATMON016 | g20596 | BLASTN | 610 | 1e−42 | 88 |
| 320 | 10329 | 700041823H1 | SATMON004 | g20596 | BLASTN | 615 | 1e−42 | 78 |
| 321 | 10329 | 700094321H1 | SATMON008 | g20596 | BLASTN | 559 | 1e−40 | 88 |
| 322 | 1148 | 700089060H1 | SATMON011 | g633094 | BLASTN | 1397 | 1e−107 | 92 |
| 323 | 1148 | 700044414H1 | SATMON004 | g633094 | BLASTN | 1272 | 1e−97 | 92 |
| 324 | 1148 | 700101429H1 | SATMON009 | g633094 | BLASTN | 1221 | 1e−92 | 91 |
| 325 | 1148 | 700221366H1 | SATMON011 | g633094 | BLASTN | 1205 | 1e−91 | 94 |
| 326 | 1148 | 700101604H1 | SATMON009 | g633094 | BLASTN | 1167 | 1e−88 | 89 |
| 327 | 1148 | 700041864H1 | SATMON004 | g633094 | BLASTN | 1159 | 1e−87 | 91 |
| 328 | 1148 | 700157048H1 | SATMON012 | g633094 | BLASTN | 1121 | 1e−84 | 93 |
| 329 | 1148 | 700581463H1 | SATMON031 | g633094 | BLASTN | 1124 | 1e−84 | 90 |
| 330 | 1148 | 700579938H1 | SATMON031 | g633094 | BLASTN | 661 | 1e−83 | 91 |
| 331 | 1148 | 700432477H1 | SATMONN01 | g633094 | BLASTN | 1050 | 1e−78 | 90 |
| 332 | 1148 | 700154706H1 | SATMON007 | g633094 | BLASTN | 997 | 1e−74 | 90 |
| 333 | 1148 | 700043761H1 | SATMON004 | g633094 | BLASTN | 905 | 1e−66 | 92 |
| 334 | 1148 | 700423679H1 | SATMONN01 | g633094 | BLASTN | 555 | 1e−54 | 81 |
| 335 | 1148 | 700424076H1 | SATMONN01 | g633094 | BLASTN | 228 | 1e−19 | 87 |
| 336 | 1148 | 701166426H1 | SATMONN04 | g633094 | BLASTN | 221 | 1e−16 | 79 |
| 337 | 16872 | 700211160H1 | SATMON016 | g633094 | BLASTN | 482 | 1e−56 | 88 |

TABLE A*-continued

| Seq No. | Cluster ID | CloneID | Library | NCBI gi | Method | Score | P-value | % Ident |
|---|---|---|---|---|---|---|---|---|
| 338 | 16872 | 700043705H1 | SATMON004 | g633094 | BLASTN | 293 | 1e−42 | 85 |
| 339 | 16872 | 700208983H1 | SATMON016 | g633094 | BLASTN | 250 | 1e−15 | 84 |
| 340 | 16872 | 700101375H1 | SATMON009 | g633094 | BLASTN | 154 | 1e−11 | 87 |
| 341 | 17829 | 700194282H1 | SATMON014 | g1001309 | BLASTX | 107 | 1e−11 | 53 |
| 342 | 17829 | 700581970H1 | SATMON031 | g1001309 | BLASTX | 107 | 1e−11 | 53 |
| 343 | 18047 | 700206971H1 | SATMON003 | g1103380 | BLASTX | 107 | 1e−12 | 53 |
| 344 | 19241 | 700472363H1 | SATMON025 | g20598 | BLASTN | 1010 | 1e−81 | 89 |
| 345 | 19241 | 700472263H1 | SATMON025 | g20598 | BLASTN | 916 | 1e−78 | 89 |
| 346 | 19241 | 700806145H1 | SATMON036 | g20598 | BLASTN | 947 | 1e−74 | 92 |
| 347 | 319 | 700076939H1 | SATMON007 | g20598 | BLASTN | 1102 | 1e−83 | 89 |
| 348 | 319 | 700349974H1 | SATMON023 | g20598 | BLASTN | 1018 | 1e−80 | 84 |
| 349 | 319 | 700235923H1 | SATMON010 | g20598 | BLASTN | 1017 | 1e−79 | 88 |
| 350 | 319 | 700206180H1 | SATMON003 | g20598 | BLASTN | 838 | 1e−78 | 86 |
| 351 | 319 | 700476547H1 | SATMON025 | g20598 | BLASTN | 794 | 1e−76 | 88 |
| 352 | 319 | 700258893H1 | SATMON017 | g20598 | BLASTN | 897 | 1e−73 | 89 |
| 353 | 319 | 700612236H1 | SATMON022 | g20598 | BLASTN | 820 | 1e−72 | 86 |
| 354 | 319 | 700806537H1 | SATMON036 | g20598 | BLASTN | 949 | 1e−70 | 87 |
| 355 | 319 | 700450338H1 | SATMON028 | g20598 | BLASTN | 912 | 1e−67 | 85 |
| 356 | 319 | 700806243H1 | SATMON036 | g20598 | BLASTN | 782 | 1e−66 | 87 |
| 357 | 319 | 700263732H1 | SATMON017 | g435456 | BLASTN | 662 | 1e−61 | 86 |
| 358 | 319 | 700806094H1 | SATMON036 | g20598 | BLASTN | 375 | 1e−59 | 91 |
| 359 | 319 | 700152610H1 | SATMON007 | g20598 | BLASTN | 806 | 1e−58 | 85 |
| 360 | 319 | 700614581H1 | SATMON033 | g20598 | BLASTN | 729 | 1e−51 | 89 |
| 361 | 319 | 700349161H1 | SATMON023 | g20598 | BLASTN | 270 | 1e−30 | 87 |
| 362 | 319 | 700805964H1 | SATMON036 | g20598 | BLASTN | 463 | 1e−29 | 79 |
| 363 | 319 | 700450544H1 | SATMON028 | g20598 | BLASTN | 280 | 1e−27 | 86 |
| 364 | 319 | 700618252H1 | SATMON033 | g20598 | BLASTN | 407 | 1e−26 | 86 |
| 365 | 319 | 700615189H1 | SATMON033 | g20598 | BLASTN | 309 | 1e−25 | 87 |
| 366 | 319 | 700264196H1 | SATMON017 | g20598 | BLASTN | 412 | 1e−25 | 84 |
| 367 | 4431 | 700211615H1 | SATMON016 | g1001309 | BLASTX | 96 | 1e−9 | 32 |
| 368 | 541 | 700073508H1 | SATMON007 | g633094 | BLASTN | 1388 | 1e−106 | 91 |
| 369 | 541 | 700098793H1 | SATMON009 | g633094 | BLASTN | 1329 | 1e−101 | 90 |
| 370 | 541 | 700101956H1 | SATMON009 | g633094 | BLASTN | 1307 | 1e−100 | 89 |
| 371 | 541 | 700100132H1 | SATMON009 | g633094 | BLASTN | 1314 | 1e−100 | 93 |
| 372 | 541 | 700799335H1 | SATMON036 | g633094 | BLASTN | 1216 | 1e−92 | 95 |
| 373 | 541 | 700446909H1 | SATMON027 | g633094 | BLASTN | 1154 | 1e−87 | 91 |
| 374 | 541 | 700444305H1 | SATMON027 | g633094 | BLASTN | 988 | 1e−86 | 97 |
| 375 | 541 | 700222187H1 | SATMON011 | g633094 | BLASTN | 1116 | 1e−84 | 89 |
| 376 | 541 | 700093340H1 | SATMON008 | g633094 | BLASTN | 1121 | 1e−84 | 90 |
| 377 | 541 | 700576310H1 | SATMON030 | g633094 | BLASTN | 1107 | 1e−83 | 91 |
| 378 | 541 | 700443474H1 | SATMON027 | g633094 | BLASTN | 584 | 1e−82 | 93 |
| 379 | 541 | 700440955H1 | SATMON026 | g633094 | BLASTN | 803 | 1e−82 | 92 |
| 380 | 541 | 700446111H1 | SATMON027 | g633094 | BLASTN | 939 | 1e−81 | 87 |
| 381 | 541 | 700259835H1 | SATMON017 | g633094 | BLASTN | 1073 | 1e−80 | 87 |
| 382 | 541 | 700551206H1 | SATMON022 | g633094 | BLASTN | 968 | 1e−76 | 89 |
| 383 | 541 | 700445905H1 | SATMON027 | g633094 | BLASTN | 464 | 1e−75 | 89 |
| 384 | 541 | 700446192H1 | SATMON027 | g633094 | BLASTN | 774 | 1e−55 | 92 |
| 385 | 541 | 700614693H1 | SATMON033 | g633094 | BLASTN | 600 | 1e−54 | 80 |
| 386 | 7402 | 700439746H1 | SATMON026 | g20596 | BLASTN | 1353 | 1e−103 | 97 |
| 387 | 7402 | 700621225H1 | SATMON034 | g20596 | BLASTN | 709 | 1e−72 | 97 |
| 388 | 7402 | 700456918H1 | SATMON029 | g20596 | BLASTN | 968 | 1e−71 | 95 |
| 389 | 7402 | 700453876H1 | SATMON029 | g20600 | BLASTN | 761 | 1e−54 | 96 |
| 390 | 7402 | 700623616H1 | SATMON034 | g20596 | BLASTN | 432 | 1e−39 | 96 |
| 391 | 7402 | 700454592H1 | SATMON029 | g20600 | BLASTN | 380 | 1e−30 | 81 |
| 392 | 7402 | 700454593H1 | SATMON029 | g20600 | BLASTN | 310 | 1e−28 | 96 |
| 393 | 7482 | 700197666H1 | SATMON014 | g2621088 | BLASTX | 145 | 1e−24 | 55 |
| 394 | 7482 | 700615228H1 | SATMON033 | g3328816 | BLASTX | 201 | 1e−20 | 61 |
| 395 | 7482 | 700030129H1 | SATMON003 | g3328816 | BLASTX | 178 | 1e−17 | 56 |
| 396 | 7482 | 700579227H1 | SATMON031 | g2621088 | BLASTX | 132 | 1e−15 | 44 |
| 397 | 786 | 700476002H1 | SATMON025 | g20598 | BLASTN | 1119 | 1e−90 | 92 |
| 398 | 786 | 700461103H1 | SATMON033 | g20598 | BLASTN | 1196 | 1e−90 | 91 |
| 399 | 786 | 700240702H1 | SATMON010 | g20598 | BLASTN | 1174 | 1e−89 | 91 |
| 400 | 786 | 700470851H1 | SATMON025 | g20598 | BLASTN | 1138 | 1e−86 | 91 |
| 401 | 786 | 700262654H1 | SATMON017 | g20598 | BLASTN | 1138 | 1e−86 | 91 |
| 402 | 786 | 700452647H1 | SATMON028 | g20598 | BLASTN | 1115 | 1e−84 | 88 |
| 403 | 786 | 700194349H1 | SATMON014 | g20598 | BLASTN | 1115 | 1e−84 | 92 |
| 404 | 786 | 700472225H1 | SATMON025 | g20598 | BLASTN | 645 | 1e−82 | 86 |
| 405 | 786 | 700461203H1 | SATMON033 | g20598 | BLASTN | 1019 | 1e−82 | 90 |
| 406 | 786 | 700581588H1 | SATMON031 | g20598 | BLASTN | 561 | 1e−79 | 90 |
| 407 | 786 | 700194330H1 | SATMON014 | g20598 | BLASTN | 1043 | 1e−78 | 90 |
| 408 | 786 | 700194016H1 | SATMON014 | g20598 | BLASTN | 1044 | 1e−78 | 90 |
| 409 | 786 | 700157347H1 | SATMON012 | g20598 | BLASTN | 1049 | 1e−78 | 90 |
| 410 | 786 | 700195805H1 | SATMON014 | g20598 | BLASTN | 1049 | 1e−78 | 90 |
| 411 | 786 | 700160255H1 | SATMON012 | g20598 | BLASTN | 1040 | 1e−77 | 93 |
| 412 | 786 | 700582138H1 | SATMON031 | g20598 | BLASTN | 885 | 1e−75 | 88 |
| 413 | 786 | 700197148H1 | SATMON014 | g20598 | BLASTN | 1007 | 1e−75 | 90 |

TABLE A*-continued

| Seq No. | Cluster ID | CloneID | Library | NCBI gi | Method | Score | P-value | % Ident |
|---|---|---|---|---|---|---|---|---|
| 414 | 786 | 700159366H1 | SATMON012 | g20598 | BLASTN | 1016 | 1e−75 | 91 |
| 415 | 786 | 701184326H1 | SATMONN06 | g20598 | BLASTN | 815 | 1e−72 | 89 |
| 416 | 786 | 700159491H1 | SATMON012 | g20598 | BLASTN | 979 | 1e−72 | 93 |
| 417 | 786 | 700104663H1 | SATMON010 | g20598 | BLASTN | 966 | 1e−71 | 86 |
| 418 | 786 | 700195003H1 | SATMON014 | g20598 | BLASTN | 779 | 1e−69 | 86 |
| 419 | 786 | 700218254H1 | SATMON016 | g20598 | BLASTN | 942 | 1e−69 | 89 |
| 420 | 786 | 700802451H1 | SATMON036 | g20598 | BLASTN | 581 | 1e−68 | 90 |
| 421 | 786 | 700157772H1 | SATMON012 | g20598 | BLASTN | 887 | 1e−65 | 90 |
| 422 | 786 | 700473425H1 | SATMON025 | g20598 | BLASTN | 466 | 1e−64 | 85 |
| 423 | 786 | 700800486H1 | SATMON036 | g20598 | BLASTN | 868 | 1e−63 | 91 |
| 424 | 786 | 700185039H1 | SATMON014 | g20598 | BLASTN | 859 | 1e−62 | 86 |
| 425 | 786 | 700800057H1 | SATMON036 | g20598 | BLASTN | 567 | 1e−59 | 85 |
| 426 | 786 | 700451832H1 | SATMON028 | g20598 | BLASTN | 501 | 1e−58 | 88 |
| 427 | 786 | 700799994H1 | SATMON036 | g20598 | BLASTN | 570 | 1e−55 | 91 |
| 428 | 786 | 700801486H1 | SATMON036 | g20598 | BLASTN | 750 | 1e−53 | 91 |
| 429 | 786 | 700802086H1 | SATMON036 | g20598 | BLASTN | 459 | 1e−51 | 89 |
| 430 | 786 | 700477105H1 | SATMON025 | g20598 | BLASTN | 708 | 1e−50 | 90 |
| 431 | 786 | 700260426H1 | SATMON017 | g20598 | BLASTN | 702 | 1e−49 | 84 |
| 432 | 786 | 700799811H1 | SATMON036 | g20598 | BLASTN | 409 | 1e−48 | 84 |
| 433 | 786 | 700427005H1 | SATMONN01 | g20598 | BLASTN | 691 | 1e−48 | 89 |
| 434 | 786 | 700803487H1 | SATMON036 | g20598 | BLASTN | 423 | 1e−46 | 83 |
| 435 | 786 | 700262695H1 | SATMON017 | g20598 | BLASTN | 367 | 1e−43 | 89 |
| 436 | 786 | 700471602H1 | SATMON025 | g20598 | BLASTN | 601 | 1e−41 | 90 |
| 437 | 786 | 701185813H2 | SATMONN06 | g20598 | BLASTN | 320 | 1e−39 | 83 |
| 438 | 786 | 700196744H1 | SATMON014 | g20598 | BLASTN | 490 | 1e−32 | 92 |
| 439 | 786 | 701184204H1 | SATMONN06 | g20598 | BLASTN | 247 | 1e−10 | 78 |
| 440 | 786 | 700622453H1 | SATMON034 | g20598 | BLASTN | 230 | 1e−8 | 79 |
| 441 | 786 | 700618768H1 | SATMON034 | g20598 | BLASTN | 230 | 1e−8 | 79 |
| 442 | -L30591931 | LIB3059-009-Q1-K1-C12 | LIB3059 | g20596 | BLASTN | 1989 | 1e−157 | 95 |
| 443 | -L30593805 | LIB3059-022-Q1-K1-H6 | LIB3059 | g20596 | BLASTN | 377 | 1e−56 | 79 |
| 444 | -L30596704 | LIB3059-055-Q1-K1-E5 | LIB3059 | g20596 | BLASTN | 733 | 1e−52 | 89 |
| 445 | -L30624957 | LIB3062-040-Q1-K1-H1 | LIB3062 | g633095 | BLASTX | 112 | 1e−27 | 56 |
| 446 | -L30671766 | LIB3067-014-Q1-K1-B8 | LIB3067 | g20596 | BLASTN | 1132 | 1e−122 | 86 |
| 447 | -L30693715 | LIB3069-012-Q1-K1-F3 | LIB3069 | g142538 | BLASTX | 98 | 1e−24 | 47 |
| 448 | 10329 | LIB3079-007-Q1-K1-B3 | LIB3079 | g20596 | BLASTN | 1201 | 1e−97 | 87 |
| 449 | 10329 | LIB143-052-Q1-E1-E4 | LIB143 | g20596 | BLASTN | 751 | 1e−53 | 86 |
| 450 | 1148 | LIB3078-040-Q1-K1-H1 | LIB3078 | g633094 | BLASTN | 1675 | 1e−130 | 87 |
| 451 | 1148 | LIB3062-040-Q1-K1-H3 | LIB3062 | g633094 | BLASTN | 1310 | 1e−100 | 88 |
| 452 | 1148 | LIB143-054-Q1-E1-F1 | LIB143 | g633094 | BLASTN | 1234 | 1e−94 | 88 |
| 453 | 1148 | LIB83-001-Q1-E1-A10 | LIB83 | g633094 | BLASTN | 1030 | 1e−77 | 81 |
| 454 | 16872 | LIB36-018-Q1-E1-D12 | LIB36 | g633094 | BLASTN | 542 | 1e−69 | 85 |
| 455 | 25099 | LIB3059-012-Q1-K1-G3 | LIB3059 | g1001309 | BLASTX | 130 | 1e−36 | 38 |
| 456 | 319 | LIB143-022-Q1-E1-G3 | LIB143 | g20598 | BLASTN | 1698 | 1e−135 | 89 |
| 457 | 319 | LIB143-048-Q1-E1-G12 | LIB143 | g20598 | BLASTN | 1562 | 1e−126 | 87 |
| 458 | 319 | LIB143-001-Q1-E1-H6 | LIB143 | g20598 | BLASTN | 1462 | 1e−113 | 90 |
| 459 | 319 | LIB143-002-Q1-E1-H2 | LIB143 | g20598 | BLASTN | 484 | 1e−66 | 88 |
| 460 | 32047 | LIB148-034-Q1-E1-F3 | LIB148 | g435456 | BLASTN | 262 | 1e−12 | 68 |
| 461 | 32047 | LIB148-032-Q1-E1-H8 | LIB148 | g435456 | BLASTN | 255 | 1e−11 | 71 |
| 462 | 541 | LIB3062-033-Q1-K1-G2 | LIB3062 | g633094 | BLASTN | 1706 | 1e−133 | 90 |
| 463 | 541 | LIB3062-033-Q1-K1-G3 | LIB3062 | g633094 | BLASTN | 1123 | 1e−94 | 84 |
| 464 | 541 | LIB3060-005-Q1-K1-C1 | LIB3060 | g633094 | BLASTN | 1061 | 1e−90 | 84 |
| 465 | 7402 | LIB3059-004-Q1-K1-F4 | LIB3059 | g20596 | BLASTN | 1461 | 1e−142 | 92 |
| 466 | 7482 | LIB3059-049-Q1-K1-E5 | LIB3059 | g2621088 | BLASTX | 138 | 1e−48 | 51 |
| 467 | 786 | LIB3061-042-Q1-K1-E8 | LIB3061 | g20598 | BLASTN | 1811 | 1e−142 | 88 |
| 468 | 786 | LIB143-040-Q1-E1-D11 | LIB143 | g20598 | BLASTN | 1462 | 1e−113 | 92 |
| 469 | 786 | LIB143-030-Q1-E1-D9 | LIB143 | g20598 | BLASTN | 1141 | 1e−101 | 90 |
| 470 | 786 | LIB3068-035-Q1-K1-A4 | LIB3068 | g20598 | BLASTN | 533 | 1e−99 | 78 |
| 471 | 786 | LIB143-017-Q1-E1-C8 | LIB143 | g20598 | BLASTN | 678 | 1e−92 | 82 |
| 472 | 786 | LIB143-030-Q1-E1-D11 | LIB143 | g20598 | BLASTN | 1165 | 1e−88 | 86 |
| 473 | 786 | LIB3061-048-Q1-K1-D7 | LIB3061 | g20598 | BLASTN | 299 | 1e−15 | 78 |
| 474 | 786 | LIB3059-056-Q1-K1-B1 | LIB3059 | g20598 | BLASTN | 283 | 1e−12 | 74 |
| | | | Transaminase A-soybean | | | | | |
| 475 | -700668054 | 700668054H1 | SOYMON006 | g3328816 | BLASTX | 172 | 1e−16 | 53 |
| 476 | -700685655 | 700685655H1 | SOYMON008 | g387106 | BLASTX | 165 | 1e−15 | 62 |
| 477 | -700729138 | 700729138H1 | SOYMON009 | g2621088 | BLASTX | 136 | 1e−17 | 47 |
| 478 | -700734818 | 700734818H1 | SOYMON010 | g3201622 | BLASTX | 234 | 1e−25 | 54 |
| 479 | -700787411 | 700787411H2 | SOYMON011 | g20598 | BLASTN | 908 | 1e−66 | 90 |
| 480 | -700868646 | 700868646H1 | SOYMON016 | g435458 | BLASTN | 513 | 1e−33 | 75 |
| 481 | -700874369 | 700874369H1 | SOYMON018 | g2654093 | BLASTN | 808 | 1e−63 | 90 |
| 482 | -700974412 | 700974412H1 | SOYMON005 | g169914 | BLASTN | 249 | 1e−11 | 83 |
| 483 | -701009475 | 701009475H1 | SOYMON019 | g1001309 | BLASTX | 111 | 1e−15 | 49 |
| 484 | -701050301 | 701050301H1 | SOYMON032 | g169914 | BLASTN | 263 | 1e−11 | 75 |
| 485 | -701061267 | 701061267H1 | SOYMON033 | g169914 | BLASTN | 235 | 1e−35 | 88 |
| 486 | -701129551 | 701129551H1 | SOYMON037 | g169914 | BLASTN | 1232 | 1e−93 | 93 |
| 487 | 13413 | 700904367H1 | SOYMON022 | g1001121 | BLASTX | 231 | 1e−24 | 52 |

TABLE A*-continued

| Seq No. | Cluster ID | CloneID | Library | NCBI gi | Method | Score | P-value | % Ident |
|---|---|---|---|---|---|---|---|---|
| 488 | 13413 | 700895714H1 | SOYMON027 | g2266762 | BLASTX | 175 | 1e−22 | 49 |
| 489 | 13413 | 700727795H1 | SOYMON009 | g1001121 | BLASTX | 190 | 1e−19 | 48 |
| 490 | 13503 | 700974712H1 | SOYMON005 | g169914 | BLASTN | 1358 | 1e−104 | 99 |
| 491 | 13503 | 700895483H1 | SOYMON027 | g169914 | BLASTN | 1236 | 1e−94 | 97 |
| 492 | 13503 | 700846207H1 | SOYMON021 | g169914 | BLASTN | 1136 | 1e−85 | 94 |
| 493 | 14358 | 700909477H1 | SOYMON022 | g710595 | BLASTN | 1309 | 1e−100 | 98 |
| 494 | 14358 | 700732673H1 | SOYMON010 | g710595 | BLASTN | 1296 | 1e−99 | 98 |
| 495 | 14358 | 700890192H1 | SOYMON024 | g710595 | BLASTN | 913 | 1e−83 | 98 |
| 496 | 14358 | 700727008H1 | SOYMON009 | g710595 | BLASTN | 553 | 1e−55 | 99 |
| 497 | 15432 | 700567458H1 | SOYMON002 | g1001309 | BLASTX | 115 | 1e−8 | 31 |
| 498 | 15529 | 701045375H1 | SOYMON032 | g3201622 | BLASTX | 189 | 1e−19 | 55 |
| 499 | 15529 | 700567374H1 | SOYMON002 | g3201622 | BLASTX | 186 | 1e−18 | 55 |
| 500 | 15529 | 701102885H1 | SOYMON028 | g3201622 | BLASTX | 172 | 1e−16 | 56 |
| 501 | 15529 | 701213187H1 | SOYMON035 | g3201622 | BLASTX | 174 | 1e−16 | 55 |
| 502 | 15529 | 701055675H1 | SOYMON032 | g3201622 | BLASTX | 166 | 1e−15 | 60 |
| 503 | 15529 | 701052631H1 | SOYMON032 | g3201622 | BLASTX | 159 | 1e−14 | 53 |
| 504 | 15529 | 701213639H1 | SOYMON035 | g3201622 | BLASTX | 110 | 1e−13 | 59 |
| 505 | 1566 | 700651242H1 | SOYMON003 | g2654093 | BLASTN | 1433 | 1e−146 | 98 |
| 506 | 1566 | 700661083H1 | SOYMON005 | g2654093 | BLASTN | 898 | 1e−102 | 95 |
| 507 | 1566 | 700668434H1 | SOYMON006 | g2654093 | BLASTN | 1289 | 1e−98 | 99 |
| 508 | 1566 | 700677640H1 | SOYMON007 | g2654093 | BLASTN | 758 | 1e−97 | 99 |
| 509 | 1566 | 700655909H1 | SOYMON004 | g2654093 | BLASTN | 730 | 1e−95 | 100 |
| 510 | 1566 | 700660728H1 | SOYMON005 | g2654093 | BLASTN | 634 | 1e−81 | 90 |
| 511 | 1566 | 700807523H1 | SOYMON016 | g2654093 | BLASTN | 478 | 1e−31 | 87 |
| 512 | 16634 | 700660070H1 | SOYMON004 | g2621088 | BLASTX | 111 | 1e−20 | 54 |
| 513 | 16634 | 700746670H1 | SOYMON013 | g2621088 | BLASTX | 118 | 1e−18 | 53 |
| 514 | 1703 | 700749933H1 | SOYMON013 | g2654093 | BLASTN | 1385 | 1e−106 | 100 |
| 515 | 1703 | 700793749H1 | SOYMON017 | g2654093 | BLASTN | 1370 | 1e−105 | 100 |
| 516 | 1703 | 701127031H1 | SOYMON037 | g2654093 | BLASTN | 716 | 1e−94 | 96 |
| 517 | 1703 | 700997259H1 | SOYMON018 | g2654093 | BLASTN | 1089 | 1e−81 | 97 |
| 518 | 1703 | 700670783H1 | SOYMON006 | g2654093 | BLASTN | 767 | 1e−79 | 93 |
| 519 | 25132 | 700678487H1 | SOYMON007 | g2654093 | BLASTN | 1175 | 1e−104 | 98 |
| 520 | 25132 | 701049020H1 | SOYMON032 | g2654093 | BLASTN | 1260 | 1e−96 | 100 |
| 521 | 25542 | 701151325H1 | SOYMON031 | g1001309 | BLASTX | 96 | 1e−15 | 51 |
| 522 | 25542 | 700964436H1 | SOYMON022 | g1001309 | BLASTX | 107 | 1e−13 | 51 |
| 523 | 26671 | 701106241H1 | SOYMON036 | g1001309 | BLASTX | 121 | 1e−9 | 39 |
| 524 | 26671 | 701149504H1 | SOYMON031 | g1001309 | BLASTX | 122 | 1e−9 | 36 |
| 525 | 27066 | 700605347H2 | SOYMON004 | g169914 | BLASTN | 1147 | 1e−104 | 99 |
| 526 | 27066 | 701053078H1 | SOYMON032 | g169914 | BLASTN | 833 | 1e−87 | 96 |
| 527 | 6297 | 700971234H1 | SOYMON005 | g169914 | BLASTN | 1303 | 1e−99 | 99 |
| 528 | 6297 | 701205146H1 | SOYMON035 | g169914 | BLASTN | 1269 | 1e−96 | 94 |
| 529 | 6297 | 701137753H1 | SOYMON038 | g169914 | BLASTN | 335 | 1e−85 | 93 |
| 530 | 6297 | 700741154H1 | SOYMON012 | g169914 | BLASTN | 1135 | 1e−85 | 100 |
| 531 | 6297 | 700954813H1 | SOYMON022 | g169914 | BLASTN | 1095 | 1e−84 | 100 |
| 532 | 6297 | 701000832H1 | SOYMON018 | g169914 | BLASTN | 410 | 1e−83 | 95 |
| 533 | 6297 | 701039262H1 | SOYMON029 | g169914 | BLASTN | 650 | 1e−82 | 97 |
| 534 | 6297 | 701108365H1 | SOYMON036 | g169914 | BLASTN | 1032 | 1e−80 | 97 |
| 535 | 6297 | 700953963H1 | SOYMON022 | g169914 | BLASTN | 1058 | 1e−79 | 92 |
| 536 | 6297 | 700971364H1 | SOYMON005 | g169914 | BLASTN | 865 | 1e−63 | 95 |
| 537 | 6297 | 701002832H1 | SOYMON019 | g169914 | BLASTN | 599 | 1e−62 | 90 |
| 538 | 6297 | 700650013H1 | SOYMON003 | g169914 | BLASTN | 686 | 1e−61 | 88 |
| 539 | 6297 | 701139166H1 | SOYMON038 | g169914 | BLASTN | 632 | 1e−43 | 83 |
| 540 | 6297 | 701055975H1 | SOYMON032 | g169914 | BLASTN | 611 | 1e−42 | 99 |
| 541 | 6297 | 701131513H1 | SOYMON038 | g169914 | BLASTN | 600 | 1e−41 | 96 |
| 542 | 6297 | 701065138H1 | SOYMON034 | g169914 | BLASTN | 432 | 1e−38 | 89 |
| 543 | 6297 | 701010254H2 | SOYMON019 | g169914 | BLASTN | 427 | 1e−36 | 88 |
| 544 | 7549 | 700666429H1 | SOYMON005 | g169914 | BLASTN | 1249 | 1e−95 | 96 |
| 545 | 7549 | 701001911H1 | SOYMON018 | g169914 | BLASTN | 819 | 1e−59 | 98 |
| 546 | 7585 | 701127651H1 | SOYMON037 | g2654093 | BLASTN | 1360 | 1e−104 | 100 |
| 547 | 7585 | 700668614H1 | SOYMON006 | g2654093 | BLASTN | 1341 | 1e−102 | 99 |
| 548 | 7585 | 701054030H1 | SOYMON032 | g2654093 | BLASTN | 1341 | 1e−102 | 99 |
| 549 | 7585 | 700890128H1 | SOYMON024 | g2654093 | BLASTN | 1285 | 1e−98 | 100 |
| 550 | 7585 | 701056607H1 | SOYMON032 | g2654093 | BLASTN | 1069 | 1e−96 | 96 |
| 551 | 7585 | 700973306H1 | SOYMON005 | g2654093 | BLASTN | 1250 | 1e−95 | 100 |
| 552 | 7585 | 700845404H1 | SOYMON021 | g2654093 | BLASTN | 890 | 1e−94 | 96 |
| 553 | 7585 | 700650253H1 | SOYMON003 | g2654093 | BLASTN | 1232 | 1e−93 | 98 |
| 554 | 7585 | 700672829H1 | SOYMON006 | g2654093 | BLASTN | 1188 | 1e−90 | 99 |
| 555 | 7585 | 700664509H1 | SOYMON005 | g2654093 | BLASTN | 1074 | 1e−87 | 97 |
| 556 | 7585 | 701056892H1 | SOYMON032 | g2654093 | BLASTN | 1158 | 1e−87 | 93 |
| 557 | 7585 | 700605686H2 | SOYMON005 | g2654093 | BLASTN | 1048 | 1e−86 | 97 |
| 558 | 7585 | 700894006H1 | SOYMON024 | g2654093 | BLASTN | 1052 | 1e−85 | 96 |
| 559 | 7585 | 700955412H1 | SOYMON022 | g2654093 | BLASTN | 625 | 1e−84 | 95 |
| 560 | 7585 | 700560909H1 | SOYMON001 | g2654093 | BLASTN | 1119 | 1e−84 | 93 |
| 561 | 7585 | 700895972H1 | SOYMON027 | g2654093 | BLASTN | 1105 | 1e−83 | 100 |
| 562 | 7585 | 700663309H1 | SOYMON005 | g2654093 | BLASTN | 888 | 1e−82 | 95 |
| 563 | 7585 | 700787774H2 | SOYMON011 | g2654093 | BLASTN | 943 | 1e−82 | 96 |

TABLE A*-continued

| Seq No. | Cluster ID | CloneID | Library | NCBI gi | Method | Score | P-value | % Ident |
|---|---|---|---|---|---|---|---|---|
| 564 | 7585 | 701069589H1 | SOYMON034 | g2654093 | BLASTN | 539 | 1e−81 | 93 |
| 565 | 7585 | 700663096H1 | SOYMON005 | g2654093 | BLASTN | 498 | 1e−80 | 95 |
| 566 | 7585 | 700836390H1 | SOYMON020 | g2654093 | BLASTN | 898 | 1e−80 | 95 |
| 567 | 7585 | 700967858H1 | SOYMON033 | g2654093 | BLASTN | 978 | 1e−80 | 92 |
| 568 | 7585 | 701101575H1 | SOYMON028 | g2654093 | BLASTN | 1032 | 1e−80 | 97 |
| 569 | 7585 | 700750565H1 | SOYMON014 | g2654093 | BLASTN | 812 | 1e−79 | 95 |
| 570 | 7585 | 701064276H1 | SOYMON034 | g2654093 | BLASTN | 820 | 1e−75 | 90 |
| 571 | 7585 | 700995223H1 | SOYMON011 | g2654093 | BLASTN | 765 | 1e−68 | 89 |
| 572 | 7585 | 700756072H1 | SOYMON014 | g2654093 | BLASTN | 899 | 1e−66 | 93 |
| 573 | 7585 | 701147945H1 | SOYMON031 | g2654093 | BLASTN | 648 | 1e−64 | 95 |
| 574 | 7585 | 700888603H1 | SOYMON024 | g2654093 | BLASTN | 865 | 1e−63 | 96 |
| 575 | 9138 | 700830720H1 | SOYMON019 | g3257794 | BLASTX | 186 | 1e−27 | 58 |
| 576 | 9138 | 700562918H1 | SOYMON002 | g152149 | BLASTX | 195 | 1e−26 | 61 |
| 577 | 9138 | 700654444H1 | SOYMON004 | g152149 | BLASTX | 191 | 1e−24 | 60 |
| 578 | 9138 | 701100721H1 | SOYMON028 | g3257794 | BLASTX | 206 | 1e−23 | 56 |
| 579 | 9138 | 700958391H1 | SOYMON022 | g3257794 | BLASTX | 217 | 1e−23 | 60 |
| 580 | 9138 | 701037102H1 | SOYMON029 | g152149 | BLASTX | 123 | 1e−16 | 53 |
| 581 | 9138 | 701119543H1 | SOYMON037 | g3257794 | BLASTX | 152 | 1e−13 | 58 |
| colspan | | | putative Transaminase A-soybean | | | | | |
| 582 | -700999272 | 700999272H1 | SOYMON018 | g1326254 | BLASTX | 153 | 1e−15 | 57 |
| 583 | -GM17331 | LIB3055-010-Q1-N1-G4 | LIB3055 | g169914 | BLASTN | 456 | 1e−27 | 85 |
| 584 | -GM25144 | LIB3040-027-Q1-E1-F2 | LIB3040 | g2654093 | BLASTN | 526 | 1e−65 | 85 |
| 585 | -GM41298 | LIB3051-109-Q1-K1-F6 | LIB3051 | g2654093 | BLASTN | 207 | 1e−29 | 83 |
| 586 | 14358 | LIB3051-106-Q1-K1-G8 | LIB3051 | g710595 | BLASTN | 2246 | 1e−178 | 99 |
| 587 | 25132 | LIB3051-063-Q1-K1-D12 | LIB3051 | g2654093 | BLASTN | 1347 | 1e−103 | 96 |
| 588 | 32509 | LIB3056-012-Q1-N1-C3 | LIB3056 | g2648397 | BLASTX | 152 | 1e−29 | 43 |
| 589 | 6297 | LIB3055-010-Q1-N1-G6 | LIB3055 | g169914 | BLASTN | 1721 | 1e−134 | 99 |
| 590 | 6297 | LIB3055-010-Q1-N1-G7 | LIB3055 | g169914 | BLASTN | 1246 | 1e−123 | 97 |
| 591 | 6297 | LIB3055-010-Q1-N1-G8 | LIB3055 | g169914 | BLASTN | 1120 | 1e−84 | 93 |
| 592 | 6297 | LIB3049-021-Q1-E1-C8 | LIB3049 | g169914 | BLASTN | 864 | 1e−63 | 91 |
| 593 | 7585 | LIB3051-105-Q1-K1-F8 | LIB3051 | g2654093 | BLASTN | 2108 | 1e−167 | 99 |
| 594 | 7585 | LIB3028-010-Q1-B1-C7 | LIB3028 | g2654093 | BLASTN | 1973 | 1e−158 | 97 |
| 595 | 7585 | LIB3030-001-Q1-B1-B7 | LIB3030 | g2654093 | BLASTN | 1117 | 1e−138 | 95 |
| 596 | 7585 | LIB3051-040-Q1-K1-D4 | LIB3051 | g2654093 | BLASTN | 1166 | 1e−116 | 94 |
| 597 | 9138 | LIB3065-001-Q1-N1-G1 | LIB3065 | g152149 | BLASTX | 168 | 1e−38 | 52 |

4-hydroxyphenylpyruvate dioxygenase-maize

| 598 | -700428184 | 700428184H1 | SATMONN01 | g2695709 | BLASTN | 773 | 1e−55 | 83 |
|---|---|---|---|---|---|---|---|---|
| 599 | -700578555 | 700578555H1 | SATMON031 | g2695710 | BLASTX | 144 | 1e−12 | 71 |
| 600 | 31568 | LIB143-034-Q1-E1-C6 | LIB143 | g2695709 | BLASTN | 650 | 1e−47 | 74 |

4-hydroxyphenylpyruvate dioxygenase-soybean

| 601 | -700655923 | 700655923H1 | SOYMON004 | g2145038 | BLASTN | 352 | 1e−45 | 77 |
|---|---|---|---|---|---|---|---|---|
| 602 | 11733 | 700833534H1 | SOYMON019 | g2145039 | BLASTX | 124 | 1e−17 | 60 |
| 603 | 13818 | 700961605H1 | SOYMON022 | g2145038 | BLASTN | 785 | 1e−56 | 82 |
| 604 | 13818 | 700906510H1 | SOYMON022 | g2145038 | BLASTN | 744 | 1e−53 | 82 |
| 605 | -GM31671 | LIB3051-002-Q1-E1-A1 | LIB3051 | g2145038 | BLASTN | 668 | 1e−44 | 74 |
| 606 | -GM37087 | LIB3051-068-Q1-K1-H8 | LIB3051 | g2695709 | BLASTN | 593 | 1e−50 | 76 |
| 607 | 11733 | LIB3051-067-Q1-K1-E3 | LIB3051 | g2145038 | BLASTN | 726 | 1e−49 | 74 | homogentisic acid dioxygenase-maize

| 608 | -700215110 | 700215110H1 | SATMON016 | g2832726 | BLASTX | 157 | 1e−26 | 50 |
|---|---|---|---|---|---|---|---|---|
| 609 | -701185447 | 701185447H1 | SATMONN06 | g2832726 | BLASTX | 216 | 1e−28 | 51 |
| 610 | 12601 | 700578778H1 | SATMON031 | g2832726 | BLASTX | 307 | 1e−35 | 67 |
| 611 | 1732 | 700469334H1 | SATMON025 | g2832726 | BLASTX | 146 | 1e−23 | 52 |
| 612 | 1732 | 700469267H1 | SATMON025 | g2832726 | BLASTX | 122 | 1e−19 | 53 |
| 613 | 8522 | 700466728H1 | SATMON025 | g2832726 | BLASTX | 189 | 1e−19 | 53 |
| 614 | 8522 | 700257246H1 | SATMON017 | g2832726 | BLASTX | 182 | 1e−18 | 53 |
| 615 | -L30683918 | LIB3068-049-Q1-K1-D6 | LIB3068 | g1561616 | BLASTX | 158 | 1e−43 | 69 | homogentasic acid dioxygenase-soybean

| 616 | -700854493 | 700854493H1 | SOYMON023 | g1561616 | BLASTX | 113 | 1e−14 | 63 |
|---|---|---|---|---|---|---|---|---|
| 617 | 24903 | 701206316H1 | SOYMON035 | g2832726 | BLASTX | 211 | 1e−22 | 54 |
| 618 | 24903 | 701204527H2 | SOYMON035 | g2832726 | BLASTX | 205 | 1e−21 | 54 |
| 619 | 24903 | 701106917H1 | SOYMON036 | g2832726 | BLASTX | 197 | 1e−20 | 54 |
| 620 | 24903 | 701204272H2 | SOYMON035 | g1561616 | BLASTX | 80 | 1e−10 | 67 |
| 621 | 26239 | 701208301H1 | SOYMON035 | g2832726 | BLASTX | 316 | 1e−36 | 69 | geranylgeranylpyrophosphate synthase-maize

| 622 | -700165387 | 700165387H1 | SATMON013 | g1419758 | BLASTX | 119 | 1e−17 | 67 |
|---|---|---|---|---|---|---|---|---|
| 623 | -700622762 | 700622762H1 | SATMON034 | g1722699 | BLASTX | 115 | 1e−10 | 65 |
| 624 | -L30782383 | LIB3078-012-Q1-K1-D3 | LIB3078 | g1063276 | BLASTX | 149 | 1e−46 | 55 | geranylgeranylpyrophosphate synthase-soybean

| 625 | -700741352 | 700741352H1 | SOYMON012 | g1722699 | BLASTX | 154 | 1e−15 | 59 |

TABLE A*-continued

| Seq No. | Cluster ID | CloneID | Library | NCBI gi | Method | Score | P-value | % Ident |
|---|---|---|---|---|---|---|---|---|
| 626 | -701098728 | 701098728H2 | SOYMON028 | g643094 | BLASTX | 142 | 1e-26 | 69 |
| 627 | -701210428 | 701210428H1 | SOYMON035 | g558924 | BLASTN | 639 | 1e-44 | 78 |

*Table Headings

Cluster ID
A cluster ID is arbitrarily assigned to all of those clones which belong to the same cluster at a given stringency and a particular clone will belong to only one cluster at a given stringency. If a cluster contains only a single clone (a "singleton"), then the cluster ID number will be negative, with an absolute value equal to the clone ID number of its single member. The cluster ID entries in the table refer to the cluster with which the particular clone in each row is associated.

Clone ID
The clone ID number refers to the particular clone in the PhytoSeq database. Each clone ID entry in the table refers to the clone whose sequence is used for (1) the sequence comparison whose scores are presented and/or (2) assignment to the particular cluster which is presented. Note that a clone may be included in this table even if its sequence comparison scores fail to meet the minimum standards for similarity. In such a case, the clone is included due solely to its association with a particular cluster for which sequences of one or more other member clones possess the required level of similarity.

Library
The library ID refers to the particular cDNA library from which a given clone is obtained. Each cDNA library is associated with the particular tissue(s), line(s) and developmental stage(s) from which it is isolated.

NCBI gi
Each sequence in the GENBANK public database is arbitrarily assigned a unique NCBI gi (National Center for Biotechnology Information GENBANK Identifier) number. In this table, the NCBI gi number which is associated (in the same row) with a given clone refers to the particular GENBANK sequence which is used in the sequence comparison. This entry is omitted when a clone is included solely due to its association with a particular cluster.

Method
The entry in the "Method" column of the table refers to the type of BLAST search that is used for the sequence comparison. "CLUSTER" is entered when the sequence comparison scores for a given clone fail to meet the minimum values required for significant similarity. In such cases, the clone is listed in the table solely as a result of its association with a given cluster for which sequences of one or more other member clones possess the required level of similarity.

Score
Each entry in the "Score" column of the table refers to the BLAST score that is generated by sequence comparison of the designated clone with the designated GENBANK sequence using the designated BLAST method. This entry is omitted when a clone is included solely due to its association with a particular cluster. If the program used to determine the hit is HMMSW then the score refers to HMMSW score.

P-Value
The entries in the P-Value column refer to the probability that such matches occur by chance.

% Ident
The entries in the "% Ident" column of the table refer to the percentage of identically matched nucleotides (or residues) that exist along the length of that portion of the sequences which is aligned by the BLAST comparison to generate the statistical scores presented. This entry is omitted when a clone is included solely due to its association with a particular cluster.

We claim:

1. A substantially purified nucleic acid molecule comprising the nucleic acid sequence of SEQ ID NO: 598 that encodes a maize tocopherol synthesis pathway enzyme or fragment thereof, wherein said maize tocopherol synthesis pathway enzyme is 4-hydroxyphenylpyruvate dioxygenase or fragment thereof.

2. A substantially purified nucleic acid molecule comprising the nucleic acid sequence of SEQ ID NO: 598 or the complement thereof.

3. A substantially purified nucleic acid molecule comprising a nucleic acid sequence having 90% identity to the nucleic acid sequence of SEQ ID NO: 598 or the complement thereof.

4. The substantially purified nucleic acid molecule according to claim 3, wherein the molecule comprises a nucleic acid sequence having 95% identity to the nucleic acid sequence of SEQ ID NO: 598 or the complement thereof.

5. The substantially purified nucleic acid molecule according to claim 3, wherein the molecule comprises a nucleic acid sequence having 98% identity to the nucleic acid sequence of SEQ ID NO: 598 or the complement thereof.

6. The substantially purified nucleic acid molecule according to claim 3, wherein the molecule comprises a nucleic acid sequence having 99% identity to the nucleic acid sequence of SEQ ID NO: 598 or the complement thereof.

* * * * *